US012746251B2

(12) United States Patent
Sommadossi et al.

(10) Patent No.: US 12,746,251 B2
(45) **Date of Patent: *Sep. 29, 2026**

(54) NiRAN INTERFERING DRUGS FOR SARS-CoV-2 MUTANT THERAPY

(71) Applicant: Atea Pharmaceuticals, Inc., Boston, MA (US)

(72) Inventors: Jean-Pierre Sommadossi, Boston, MA (US); Kai Lin, Belmont, MA (US); Adel Moussa, Burlington, MA (US); Bruno Canard, Marseilles (FR); Ashleigh Shannon, Marseilles (FR)

(73) Assignee: Atea Pharmaceuticals, Inc., Boston, MA (US)

( * ) Notice: Subject to any disclaimer, the term of this patent is extended or adjusted under 35 U.S.C. 154(b) by 561 days.

This patent is subject to a terminal disclaimer.

(21) Appl. No.: 18/132,300

(22) Filed: Apr. 7, 2023

(65) Prior Publication Data

US 2023/0364121 A1 Nov. 16, 2023

Related U.S. Application Data

(63) Continuation of application No. PCT/US2021/054294, filed on Oct. 8, 2021.

(60) Provisional application No. 63/236,151, filed on Aug. 23, 2021, provisional application No. 63/160,618, filed on Mar. 12, 2021, provisional application No. 63/135,494, filed on Jan. 8, 2021, provisional application No. 63/090,090, filed on Oct. 9, 2020.

(51) Int. Cl.
*A61K 31/7076* (2006.01)
*A61P 31/14* (2006.01)

(52) U.S. Cl.
CPC .......... *A61K 31/7076* (2013.01); *A61P 31/14* (2018.01)

(58) Field of Classification Search
None
See application file for complete search history.

(56) References Cited

U.S. PATENT DOCUMENTS

| | | | |
|---|---|---|---|
| 5,977,061 | A | 11/1999 | Holy et al. |
| 6,348,587 | B1 | 2/2002 | Schinazi et al. |
| 6,602,999 | B1 | 8/2003 | Kumar et al. |
| 6,660,721 | B2 | 12/2003 | Devos et al. |
| 6,777,395 | B2 | 8/2004 | Bhat et al. |
| 6,784,166 | B2 | 8/2004 | Devos et al. |
| 6,812,219 | B2 | 11/2004 | LaColla et al. |
| 6,908,924 | B2 | 6/2005 | Watanabe et al. |
| 6,911,424 | B2 | 6/2005 | Schinazi et al. |
| 6,914,054 | B2 | 7/2005 | Sommadossi et al. |
| 6,949,522 | B2 | 9/2005 | Otto et al. |
| 7,094,770 | B2 | 8/2006 | Watanabe et al. |
| 7,105,493 | B2 | 9/2006 | Sommadossi et al. |
| 7,105,499 | B2 | 9/2006 | Carroll et al. |
| 7,125,855 | B2 | 10/2006 | Bhat et al. |
| 7,138,376 | B2 | 11/2006 | Gosselin et al. |
| 7,148,206 | B2 | 12/2006 | Sommadossi et al. |
| 7,157,441 | B2 | 1/2007 | Sommadossi et al. |
| 7,163,929 | B2 | 1/2007 | Sommadossi et al. |
| 7,169,766 | B2 | 1/2007 | Sommadossi et al. |
| 7,192,936 | B2 | 3/2007 | LaColla et al. |
| 7,202,224 | B2 | 4/2007 | Eldrup et al. |
| 7,211,570 | B2 | 5/2007 | Schinazi et al. |
| 7,268,119 | B2 | 9/2007 | Cook et al. |
| 7,285,658 | B2 | 10/2007 | Cook et al. |
| 7,307,065 | B2 | 12/2007 | Schinazi et al. |
| 7,323,449 | B2 | 1/2008 | Olsen et al. |
| 7,339,054 | B2 | 3/2008 | Xu et al. |
| 7,365,057 | B2 | 4/2008 | LaColla et al. |
| 7,384,924 | B2 | 6/2008 | LaColla et al. |
| 7,388,002 | B2 | 6/2008 | Babu et al. |
| 7,429,571 | B2 | 9/2008 | Chand et al. |
| 7,429,572 | B2 | 9/2008 | Clark |
| 7,456,155 | B2 | 11/2008 | Sommadossi et al. |
| 7,495,006 | B2 | 2/2009 | Liotta et al. |
| 7,514,410 | B2 | 4/2009 | Babu et al. |
| 7,534,767 | B2 | 5/2009 | Butora et al. |
| 7,547,704 | B2 | 6/2009 | LaColla et al. |
| 7,560,434 | B2 | 7/2009 | Babu et al. |
| 7,560,550 | B2 | 7/2009 | Doring et al. |
| 7,582,618 | B2 | 9/2009 | Sommadossi et al. |
| 7,601,820 | B2 | 10/2009 | Wang et al. |

(Continued)

FOREIGN PATENT DOCUMENTS

| | | | |
|---|---|---|---|
| CN | 103435672 | A | 12/2013 |
| CN | 103980332 | A | 8/2014 |

(Continued)

OTHER PUBLICATIONS

U.S. Pat. No. 9,828,410, B2, U.S. Appl. No. 15/063,461, Sommadossi et al., Nov. 28, 2017.
U.S. Pat. No. 10,000,523, B2, U.S. Appl. No. 15/782,628, Sommadossi et al., Jun. 19, 2018.
U.S. Pat. No. 10,005,811, B2, U.S. Appl. No. 15/782,638, Sommadossi et al., Jun. 26, 2018.
U.S. Pat. No. 10,202,412, B2, U.S. Appl. No. 15/645,701, Sommadossi et al., Feb. 12, 2019.
U.S. Pat. No. 10,239,911, B2, U.S. Appl. No. 16/001,549, Sommadossi et al., Mar. 26, 2019.

(Continued)

*Primary Examiner* — Patrick T Lewis
(74) *Attorney, Agent, or Firm* — Knowles Intellectual Property Strategies, LLC

(57) ABSTRACT

Methods of treatment and prevention and assays to select optimal compounds for treating or preventing infections from severe acute respiratory syndrome (SARS)-related coronaviruses (SARS-CoV), such as SARS-CoV-2, that interfere with the activity of the nidovirus RdRp-associated nucleotidyltransferase (NiRAN) domain of non-structural protein 12 (nsp12). The invention establishes for the first time herein the foundational discovery of the mechanism of action of the NiRAN-domain, and how it can be used in pharmaceutical therapy against SARS-CoV infection, including a SARS-CoV-2 infection, or exposure.

28 Claims, 60 Drawing Sheets

Specification includes a Sequence Listing.

(56) References Cited

U.S. PATENT DOCUMENTS

| | | | |
|---|---|---|---|
| 7,608,597 | B2 | 10/2009 | Sommadossi et al. |
| 7,608,599 | B2 | 10/2009 | Klumpp et al. |
| 7,608,600 | B2 | 10/2009 | Storer et al. |
| 7,608,601 | B2 | 10/2009 | Devos et al. |
| 7,625,875 | B2 | 12/2009 | Gosselin et al. |
| 7,632,821 | B2 | 12/2009 | Butora et al. |
| 7,635,689 | B2 | 12/2009 | LaColla et al. |
| 7,638,502 | B2 | 12/2009 | Schinazi et al. |
| 7,652,001 | B2 | 1/2010 | Hostetler et al. |
| 7,662,798 | B2 | 2/2010 | LaColla et al. |
| 7,662,938 | B2 | 2/2010 | Schinazi et al. |
| 7,691,603 | B2 | 4/2010 | DeFrees |
| 7,713,941 | B2 | 5/2010 | Cook et al. |
| 7,718,790 | B2 | 5/2010 | Stuyver et al. |
| 7,749,983 | B2 | 7/2010 | Hostetler et al. |
| 7,772,208 | B2 | 8/2010 | Schinazi et al. |
| 7,824,851 | B2 | 11/2010 | Sommadossi et al. |
| 7,842,672 | B2 | 11/2010 | Boojamra et al. |
| RE42,015 | E | 12/2010 | Watanabe et al. |
| 7,879,815 | B2 | 2/2011 | MacCoss et al. |
| 7,902,202 | B2 | 3/2011 | Sommadossi et al. |
| 7,919,247 | B2 | 4/2011 | Stuyver et al. |
| 7,932,240 | B2 | 4/2011 | Dousson et al. |
| 7,951,789 | B2 | 5/2011 | Sommadossi et al. |
| 7,964,580 | B2 | 6/2011 | Sofia et al. |
| 7,973,013 | B2 | 7/2011 | Cho et al. |
| 7,994,139 | B2 | 8/2011 | Babu et al. |
| 8,008,264 | B2 | 8/2011 | Butler et al. |
| 8,012,941 | B2 | 9/2011 | Cho et al. |
| 8,012,942 | B2 | 9/2011 | Butler et al. |
| 8,071,567 | B2 | 12/2011 | Devos et al. |
| 8,071,568 | B2 | 12/2011 | Narjes et al. |
| 8,093,380 | B2 | 1/2012 | Wang et al. |
| 8,114,994 | B2 | 2/2012 | Liotta et al. |
| 8,114,997 | B2 | 2/2012 | Otto et al. |
| 8,119,607 | B2 | 2/2012 | Francom et al. |
| 8,133,870 | B2 | 3/2012 | Babu et al. |
| 8,148,349 | B2 | 4/2012 | Meppen et al. |
| 8,163,703 | B2 | 4/2012 | Babu et al. |
| 8,168,583 | B2 | 5/2012 | Schinazi et al. |
| 8,173,621 | B2 | 5/2012 | Du et al. |
| 8,193,372 | B2 | 6/2012 | Dousson et al. |
| 8,242,085 | B2 | 8/2012 | Babu et al. |
| 8,299,038 | B2 | 10/2012 | Sommadossi et al. |
| 8,318,682 | B2 | 11/2012 | Butler et al. |
| 8,324,179 | B2 | 12/2012 | Chen et al. |
| 8,334,270 | B2 | 12/2012 | Sofia et al. |
| 8,343,937 | B2 | 1/2013 | Sommadossi et al. |
| 8,362,068 | B2 | 1/2013 | Dousson et al. |
| 8,399,428 | B2 | 3/2013 | Wagner |
| 8,399,429 | B2 | 3/2013 | Jonckers et al. |
| 8,415,308 | B2 | 4/2013 | Cho et al. |
| 8,415,309 | B2 | 4/2013 | Francom et al. |
| 8,415,321 | B2 | 4/2013 | Schinazi et al. |
| 8,415,322 | B2 | 4/2013 | Clark |
| 8,431,588 | B2 | 4/2013 | Jonckers et al. |
| 8,440,813 | B2 | 5/2013 | Babu et al. |
| 8,455,451 | B2 | 6/2013 | Cho et al. |
| 8,470,834 | B2 | 6/2013 | Kwong et al. |
| 8,481,510 | B2 | 7/2013 | Jonckers et al. |
| 8,481,712 | B2 | 7/2013 | Bhat et al. |
| 8,481,713 | B2 | 7/2013 | Wang et al. |
| 8,492,539 | B2 | 7/2013 | Chun et al. |
| 8,501,699 | B2 | 8/2013 | Francom et al. |
| 8,507,460 | B2 | 8/2013 | Surleraux et al. |
| 8,541,434 | B2 | 9/2013 | Kwong et al. |
| 8,551,973 | B2 | 10/2013 | Bao et al. |
| 8,552,021 | B2 | 10/2013 | Jonckers et al. |
| 8,563,530 | B2 | 10/2013 | Chang et al. |
| 8,575,119 | B2 | 11/2013 | Wang et al. |
| 8,580,765 | B2 | 11/2013 | Sofia et al. |
| 8,609,627 | B2 | 12/2013 | Cho et al. |
| 8,618,076 | B2 | 12/2013 | Ross et al. |
| 8,629,263 | B2 | 1/2014 | Ross et al. |
| 8,633,309 | B2 | 1/2014 | Ross et al. |
| 8,637,475 | B1 | 1/2014 | Storer et al. |
| 8,642,756 | B2 | 2/2014 | Ross et al. |
| 8,658,616 | B2 | 2/2014 | McGuigan et al. |
| 8,673,926 | B2 | 3/2014 | Chu |
| 8,674,085 | B2 | 3/2014 | Sommadossi et al. |
| 8,680,071 | B2 | 3/2014 | Surleraux et al. |
| 8,691,788 | B2 | 4/2014 | Sommadossi et al. |
| 8,697,694 | B2 | 4/2014 | Arasappan et al. |
| 8,715,638 | B2 | 5/2014 | Kwong et al. |
| 8,716,262 | B2 | 5/2014 | Sofia et al. |
| 8,716,263 | B2 | 5/2014 | Chun et al. |
| 8,735,345 | B2 | 5/2014 | Porter et al. |
| 8,735,372 | B2 | 5/2014 | Du et al. |
| 8,735,569 | B2 | 5/2014 | Ross et al. |
| 8,742,101 | B2 | 6/2014 | Storer et al. |
| 8,759,318 | B2 | 6/2014 | Chamberlain et al. |
| 8,759,372 | B2 | 6/2014 | Roberts et al. |
| 8,759,510 | B2 | 6/2014 | Du et al. |
| 8,765,710 | B2 | 7/2014 | Sofia et al. |
| 8,772,474 | B2 | 7/2014 | Beigelman et al. |
| 8,802,840 | B2 | 8/2014 | Francom et al. |
| 8,815,829 | B2 | 8/2014 | Schinazi et al. |
| 8,816,074 | B2 | 8/2014 | Chu et al. |
| 8,841,275 | B2 | 9/2014 | Du et al. |
| 8,846,638 | B2 | 9/2014 | Or et al. |
| 8,846,896 | B2 | 9/2014 | Serebryany et al. |
| 8,853,171 | B2 | 10/2014 | Butler et al. |
| 8,859,595 | B2 | 10/2014 | Coats et al. |
| 8,859,756 | B2 | 10/2014 | Ross et al. |
| 8,871,737 | B2 | 10/2014 | Smith et al. |
| 8,871,785 | B2 | 10/2014 | Boojamra et al. |
| 8,877,731 | B2 | 11/2014 | Beigelman et al. |
| 8,877,733 | B2 | 11/2014 | Cho et al. |
| 8,889,159 | B2 | 11/2014 | Cleary et al. |
| 8,889,701 | B1 | 11/2014 | Ivachtchenko et al. |
| 8,895,531 | B2 | 11/2014 | Shi |
| 8,895,723 | B2 | 11/2014 | Serebryany et al. |
| 8,906,880 | B2 | 12/2014 | Du et al. |
| 8,912,321 | B2 | 12/2014 | Axt et al. |
| 8,921,384 | B2 | 12/2014 | Chu |
| 8,927,513 | B2 | 1/2015 | Manoharan et al. |
| 8,933,052 | B2 | 1/2015 | Jonckers et al. |
| 8,946,244 | B2 | 2/2015 | Chu et al. |
| 8,951,985 | B2 | 2/2015 | Surleraux et al. |
| 8,957,045 | B2 | 2/2015 | Sofia et al. |
| 8,957,046 | B2 | 2/2015 | Du et al. |
| 8,980,865 | B2 | 3/2015 | Wang et al. |
| 9,012,427 | B2 | 4/2015 | Blatt et al. |
| 9,012,428 | B2 | 4/2015 | Jonckers et al. |
| 9,045,520 | B2 | 6/2015 | Chun et al. |
| 9,061,041 | B2 | 6/2015 | Girijavallabhan et al. |
| 9,085,573 | B2 | 7/2015 | Du et al. |
| 9,085,599 | B2 | 7/2015 | Or et al. |
| 9,090,642 | B2 | 7/2015 | Cho et al. |
| 9,109,001 | B2 | 8/2015 | Parsy et al. |
| 9,139,604 | B2 | 9/2015 | Boojamra et al. |
| 9,156,872 | B2 | 10/2015 | Girijavallabhan et al. |
| 9,173,893 | B2 | 11/2015 | Cho et al. |
| 9,187,515 | B2 | 11/2015 | Mayes et al. |
| 9,192,621 | B2 | 11/2015 | Mayes et al. |
| 9,211,300 | B2 | 12/2015 | Mayes et al. |
| 9,243,025 | B2 | 1/2016 | Surleraux et al. |
| 9,249,174 | B2 | 2/2016 | Beigelman et al. |
| 9,339,541 | B2 | 5/2016 | Dousson et al. |
| 9,351,989 | B2 | 5/2016 | McGuigan et al. |
| 9,403,863 | B2 | 8/2016 | Surleraux et al. |
| 9,408,863 | B2 | 8/2016 | Verma et al. |
| 9,447,132 | B2 | 9/2016 | Deshpande et al. |
| 9,598,457 | B2 | 3/2017 | Smith et al. |
| 9,603,863 | B2 | 3/2017 | Blatt et al. |
| 9,603,864 | B2 | 3/2017 | Blatt et al. |
| 9,758,544 | B2 | 9/2017 | Beigelman et al. |
| 9,815,864 | B2 | 11/2017 | Beigelman et al. |
| 9,822,137 | B2 | 11/2017 | Dehaen et al. |
| 9,828,410 | B2 | 11/2017 | Sommadossi et al. |
| 9,890,188 | B2 | 2/2018 | Wang et al. |
| 10,000,523 | B2 | 6/2018 | Sommadossi et al. |
| 10,005,810 | B2 | 6/2018 | McGuigan et al. |
| 10,005,811 | B2 | 6/2018 | Sommadossi et al. |

(56) References Cited

U.S. PATENT DOCUMENTS

| | | | |
|---|---|---|---|
| 10,202,386 | B2 | 2/2019 | Biggadike et al. |
| 10,239,911 | B2 | 3/2019 | Sommadossi et al. |
| 10,519,186 | B2 | 12/2019 | Moussa et al. |
| 10,695,361 | B2 | 6/2020 | Clarke et al. |
| 12,084,473 | B2 | 9/2024 | Sommadossi et al. |
| 12,226,429 | B2 | 2/2025 | Sommadossi et al. |
| 12,458,656 | B2 | 11/2025 | Sommadossi et al. |
| 2002/0045599 | A1 | 4/2002 | Arimilli et al. |
| 2002/0058635 | A1 | 5/2002 | Averett |
| 2003/0087873 | A1 | 5/2003 | Stuyver et al. |
| 2004/0063658 | A1 | 4/2004 | Roberts et al. |
| 2004/0229839 | A1 | 11/2004 | Babu et al. |
| 2004/0259934 | A1 | 12/2004 | Olsen et al. |
| 2005/0038240 | A1 | 2/2005 | Connolly et al. |
| 2005/0203044 | A1 | 9/2005 | Zinnen |
| 2007/0004669 | A1 | 1/2007 | Carroll et al. |
| 2007/0265222 | A1 | 11/2007 | MacCoss et al. |
| 2008/0207554 | A1 | 8/2008 | Beigelman et al. |
| 2009/0156545 | A1 | 6/2009 | Hostetler et al. |
| 2009/0176732 | A1 | 7/2009 | Beigelman et al. |
| 2009/0181921 | A1 | 7/2009 | Blatt et al. |
| 2009/0318380 | A1 | 12/2009 | Sofia et al. |
| 2010/0137576 | A1 | 6/2010 | Stec et al. |
| 2010/0240604 | A1 | 9/2010 | Beigelman et al. |
| 2010/0249068 | A1 | 9/2010 | Beigelman et al. |
| 2010/0279969 | A1 | 11/2010 | Schinazi et al. |
| 2010/0331397 | A1 | 12/2010 | Beigelman et al. |
| 2011/0091943 | A1 | 4/2011 | Gallou et al. |
| 2011/0223659 | A1 | 9/2011 | Scholl et al. |
| 2011/0257121 | A1 | 10/2011 | Chang et al. |
| 2012/0070411 | A1 | 3/2012 | Beigelman et al. |
| 2012/0135951 | A1 | 5/2012 | Schinazi et al. |
| 2013/0064794 | A1 | 3/2013 | Surleraux et al. |
| 2013/0225636 | A1 | 8/2013 | Roberts et al. |
| 2013/0244966 | A1 | 9/2013 | Milne et al. |
| 2013/0315868 | A1 | 11/2013 | Mayes et al. |
| 2014/0038916 | A1 | 2/2014 | Wang et al. |
| 2014/0066395 | A1 | 3/2014 | Cho et al. |
| 2014/0112886 | A1 | 4/2014 | Moussa et al. |
| 2014/0212382 | A1 | 7/2014 | Schinazi et al. |
| 2014/0235566 | A1 | 8/2014 | Amblard et al. |
| 2015/0011481 | A1 | 1/2015 | Vilchez et al. |
| 2015/0011497 | A1 | 1/2015 | Beigelman et al. |
| 2015/0057243 | A1 | 2/2015 | Zhou et al. |
| 2015/0105341 | A1 | 4/2015 | Beigelman et al. |
| 2015/0150897 | A1 | 6/2015 | Denning et al. |
| 2015/0183818 | A1 | 7/2015 | Tran et al. |
| 2016/0002281 | A1 | 1/2016 | Mayes et al. |
| 2016/0220595 | A1 | 8/2016 | Liotta et al. |
| 2016/0257706 | A1 | 9/2016 | Sommadossi et al. |
| 2016/0271162 | A1 | 9/2016 | Moussa et al. |
| 2017/0022242 | A1 | 1/2017 | Herdewyn et al. |
| 2017/0029456 | A1 | 2/2017 | Dousson et al. |
| 2017/0275322 | A1 | 9/2017 | Oinho et al. |
| 2018/0009836 | A1 | 1/2018 | Sommadossi et al. |
| 2019/0153017 | A1 | 5/2019 | Sommadossi et al. |
| 2019/0201433 | A1 | 7/2019 | Sommadossi et al. |
| 2019/0255085 | A1 | 8/2019 | Clarke et al. |
| 2020/0087339 | A1 | 3/2020 | Moussa et al. |
| 2024/0226131 | A1 | 7/2024 | Sommadossi et al. |
| 2024/0261316 | A1 | 8/2024 | Sommadossi et al. |
| 2025/0082656 | A1 | 3/2025 | Moussa et al. |
| 2025/0109163 | A1 | 4/2025 | Moussa et al. |
| 2025/0243235 | A1 | 7/2025 | Sommadossi et al. |

FOREIGN PATENT DOCUMENTS

| | | | |
|---|---|---|---|
| CN | 105646629 | A | 6/2016 |
| CN | 106188192 | A | 12/2016 |
| EP | 547008 | A1 | 6/1993 |
| EP | 398231 | B1 | 7/1997 |
| WO | WO 1998/16184 | | 4/1998 |
| WO | WO 1998/52949 | A1 | 11/1998 |
| WO | WO 2001/009143 | A1 | 2/2001 |
| WO | WO 2001/90121 | A2 | 11/2001 |
| WO | WO 2001/92282 | A2 | 12/2001 |
| WO | WO 2002/32920 | A2 | 4/2002 |
| WO | WO 2003/033508 | A1 | 4/2003 |
| WO | WO 2003/039523 | A2 | 5/2003 |
| WO | WO 2003/062256 | A1 | 7/2003 |
| WO | WO 2003/093290 | A2 | 11/2003 |
| WO | WO 2004/002999 | A2 | 1/2004 |
| WO | WO 2004/003000 | A2 | 1/2004 |
| WO | WO 2004/014312 | A2 | 2/2004 |
| WO | WO 2004/052906 | A2 | 6/2004 |
| WO | WO 2004/074350 | A2 | 9/2004 |
| WO | WO 2004/091499 | A2 | 10/2004 |
| WO | WO 2004/106356 | A1 | 12/2004 |
| WO | WO 2005/000864 | A1 | 1/2005 |
| WO | WO 2005/020884 | A2 | 3/2005 |
| WO | WO 2005/021568 | A2 | 3/2005 |
| WO | WO 2005/084192 | A2 | 9/2005 |
| WO | WO 2005/090370 | A1 | 9/2005 |
| WO | WO 2006/012078 | A2 | 2/2006 |
| WO | WO 2006/063149 | A1 | 6/2006 |
| WO | WO 2006/063717 | A2 | 7/2006 |
| WO | WO 2006/094347 | A1 | 9/2006 |
| WO | WO 2006/102533 | A2 | 9/2006 |
| WO | WO 2006/121820 | A1 | 11/2006 |
| WO | WO 2006/130217 | A2 | 12/2006 |
| WO | WO 2007/022073 | A2 | 2/2007 |
| WO | WO 2007/112028 | A2 | 10/2007 |
| WO | WO 2007/130783 | A1 | 11/2007 |
| WO | WO 2008/012555 | A2 | 1/2008 |
| WO | WO 2008/048128 | A1 | 4/2008 |
| WO | WO 2008/062206 | A2 | 5/2008 |
| WO | WO 2008/095040 | A2 | 10/2008 |
| WO | WO 2009/001097 | A2 | 12/2008 |
| WO | WO 2009/003042 | A1 | 12/2008 |
| WO | WO 2009/067409 | A1 | 5/2009 |
| WO | WO 2009/086192 | A1 | 7/2009 |
| WO | WO 2009/086201 | A1 | 7/2009 |
| WO | WO 2009/129120 | A2 | 10/2009 |
| WO | WO 2010/081082 | A2 | 7/2010 |
| WO | WO 2010/091386 | A2 | 8/2010 |
| WO | WO 2010/108135 | A1 | 9/2010 |
| WO | WO 2010/145778 | | 12/2010 |
| WO | WO 2011/005595 | A1 | 1/2011 |
| WO | WO 2011/005860 | A2 | 1/2011 |
| WO | WO 2012/041965 | A1 | 4/2012 |
| WO | WO 2012/048013 | A2 | 4/2012 |
| WO | WO 2012/092484 | A2 | 7/2012 |
| WO | WO 2012/125900 | A1 | 9/2012 |
| WO | WO 2012/154321 | A1 | 11/2012 |
| WO | WO 2012/158811 | A2 | 11/2012 |
| WO | WO 2013/009737 | A1 | 1/2013 |
| WO | WO 2013/019874 | A1 | 2/2013 |
| WO | WO 2013/039855 | A1 | 3/2013 |
| WO | WO 2013/039920 | A1 | 3/2013 |
| WO | WO 2013/044030 | A1 | 3/2013 |
| WO | WO 2013/059735 | A1 | 4/2013 |
| WO | WO 2013/090420 | A2 | 6/2013 |
| WO | WO 2013/096680 | A1 | 6/2013 |
| WO | WO 2013/142125 | A1 | 9/2013 |
| WO | WO 2013/142157 | A1 | 9/2013 |
| WO | WO 2013/142159 | A1 | 9/2013 |
| WO | WO 2013/151975 | A1 | 10/2013 |
| WO | WO 2013/177219 | A1 | 11/2013 |
| WO | WO 2013/187978 | A1 | 12/2013 |
| WO | WO 2014/008236 | A1 | 1/2014 |
| WO | WO 2014/047117 | A1 | 3/2014 |
| WO | WO 2014/052638 | A1 | 4/2014 |
| WO | WO 2014/063019 | A1 | 4/2014 |
| WO | WO 2014/076490 | A1 | 5/2014 |
| WO | WO 2014/082935 | A1 | 6/2014 |
| WO | WO 2014/100498 | A1 | 6/2014 |
| WO | WO 2014/100505 | A1 | 6/2014 |
| WO | WO 2014/120981 | A1 | 8/2014 |
| WO | WO 2014/124430 | A1 | 8/2014 |
| WO | WO 2014/137930 | A1 | 9/2014 |
| WO | WO 2014/169278 | A1 | 10/2014 |
| WO | WO 2014/169280 | A2 | 10/2014 |
| WO | WO 2014/209979 | A1 | 12/2014 |
| WO | WO 2015/038596 | A1 | 3/2015 |

(56) References Cited

FOREIGN PATENT DOCUMENTS

| | | | |
|---|---|---|---|
| WO | WO 2015/053662 | A1 | 4/2015 |
| WO | WO 2015/081133 | A2 | 6/2015 |
| WO | WO 2015/095305 | A1 | 6/2015 |
| WO | WO 2015/158913 | A1 | 10/2015 |
| WO | WO 2016/041877 | A1 | 3/2016 |
| WO | WO 2016/100441 | A1 | 6/2016 |
| WO | WO 2016/100569 | A1 | 6/2016 |
| WO | WO 2016/144918 | A1 | 9/2016 |
| WO | WO 2016/145142 | A1 | 9/2016 |
| WO | WO 2018/013937 | A1 | 1/2018 |
| WO | WO 2018/048937 | A1 | 3/2018 |
| WO | WO 2019/200005 | A1 | 10/2019 |

OTHER PUBLICATIONS

U.S. Pat. No. 10,519,186, B2, U.S. Appl. No. 15/885,630, Moussa et al., Dec. 31, 2019.
U.S. Pat. No. 10,815,266, B2, U.S. Appl. No. 16/278,621, Sommadossi et al., Oct. 27, 2020.
U.S. Pat. No. 10,870,672, B2, U.S. Appl. No. 16/900,397, Sommadossi et al., Dec. 22, 2020.
U.S. Pat. No. 10,870,673, B2, U.S. Appl. No. 16/918,898, Sommadossi et al., Dec. 22, 2020.
U.S. Pat. No. 10,874,687, B2, U.S. Appl. No. 17/017,443, Sommadossi et al., Dec. 29, 2020.
U.S. Pat. No. 10,875,885, B2, U.S. Appl. No. 16/918,914, Sommadossi et al., Dec. 29, 2020.
U.S. Pat. No. 10,894,804, B2, U.S. Appl. No. 16/918,918, Moussa et al., Jan. 19, 2021.
U.S. Pat. No. 10,906,928, B2, U.S. Appl. No. 16/687,136, Moussa et al., Feb. 2, 2021.
U.S. Pat. No. 10,946,033, B2, U.S. Appl. No. 16/293,423, Sommadossi et al., Mar. 16, 2021.
U.S. Pat. No. 11,690,860, B2, U.S. Appl. No. 17/065,149, Sommadossi et al., Jul. 4, 2023.
U.S. Pat. No. 11,707,480, B2, U.S. Appl. No. 17/094,541, Sommadossi et al., Jul. 25, 2023.
U.S. Pat. No. 11,738,038, B2, U.S. Appl. No. 17/306,674, Sommadossi et al., Aug. 29, 2023.
U.S. Pat. No. 11,813,278, B2, U.S. Appl. No. 17/184,445, Sommadossi et al., Nov. 14, 2023.
U.S. Pat. No. 11,975,016, B2, U.S. Appl. No. 17/482,224, Sommadossi et al., May 7, 2024.
U.S. Pat. No. 12,006,340, B2, U.S. Appl. No. 18/100,448, Moussa et al., Jun. 11, 2024.
US, 2020/0179415, A1, U.S. Appl. No. 16/703,599, Sommadossi et al., Jun. 11, 2020.
US, 2020/0222442, A1, U.S. Appl. No. 16/821,850, Sommadossi et al., Jul. 16, 2020.
US, 2021/0009628, A1, U.S. Appl. No. 17/028,724, Sommadossi et al., Jan. 14, 2021.
US, 2021/0087217, A1, U.S. Appl. No. 17/118,314, Moussa et al., Mar. 25, 2021.
US, 2021/0277045, A1, U.S. Appl. No. 17/306,659, Moussa et al., Sep. 8, 2021.
US, 2022/0267366, A1, U.S. Appl. No. 17/306,643, Sommadossi et al., Aug. 25, 2022.
US, 2023/0049294, A1, U.S. Appl. No. 17/971,318, Moussa et al., Feb. 16, 2023.
US, 2023/0331751, A1, U.S. Appl. No. 18/111,316, Moussa et al., Oct. 19, 2023.
US, 2023/0365611, A1, U.S. Appl. No. 18/226,064, Moussa et al., Nov. 16, 2023.
US, 2024/0002426, A1, U.S. Appl. No. 18/100,452, Sommadossi et al., Jan. 4, 2024.
US, 2024/0148770, A1, U.S. Appl. No. 18/540,608, Sommadossi et al., May 9, 2024.
U.S. Appl. No. 18/206,921, Sommadossi et al., filed Jun. 7, 2023.
U.S. Appl. No. 18/225,452, Sommadossi et al., filed Jul. 24, 2023.
U.S. Appl. No. 18/368,959, Sommadossi et al., filed Sep. 15, 2023.
U.S. Appl. No. 18/592,037, Sommadossi et al., filed Feb. 29, 2024.
U.S. Appl. No. 18/739,149, Moussa et al., filed Jun. 10, 2024.
Atea Pharmaceuticals "Bemnifosbuvir (BEM, AT-527) a Potent Inhibitor of SARS-CoV-2 Variants of Concern (VOC), and a Promising Oral Antiviral with a High Resistance Barrier for Treatment of COVID-19 and other Coronaviruses Infections", ICAR 2023.
Bouvet et al. "In Vitro Reconstitution of SARS-Coronavirus mRNA Cap Methylation", PLoS Pathog. 6:e1000863. doi: 10.1371/journal.ppat.1000863, 2010.
Chen et al. "RNA based mNGS approach identifies a novel human coronavirus from twoindividual pneumonia cases in 2019 Wuhan outbreak", Emerg Microbes Infect., 9(1):313-319, Feb. 5, 2020.
Chen et al. "Structural Basis for Helicase-Polymerase Coupling in the SARS-CoV-2 Replication Transcription Complex", Cell 182,1-14, 2020.
Chowdhury et al. How the Novel coronavirus has Evolved, Dec. 10, 2020.
Devert, A. et al. "Primer-dependent and primer-independent initiation of double stranded RNAsynthesis by purified Arabidopsis RNA-dependent RNA polymerases RDR2and RDR6", PLoS One, 10(3):e0120100. doi:10.1371/journal.pone.0120100. PMID: 25793874; PMCID: PMC4368572, Mar. 20, 2015.
Duan et al. "The crystal structure of Zika virus NS5 reveals conserved drug targets", EMBO J. 36, 919-933, 2017.
Dwivedy et al. Manuscript, 2020.
Ferron et al. "Structural and molecular basis of mismatch correction and ribavirin excision from coronavirus RNA", Proc. Natl. Acad. Sci. U.S.A. 115, E162-E171. doi:10.1073/pnas.1718806115, 2018.
Godoy et al. "Crystal structure of Zika virus NS5 RNA-dependent RNA polymerase", Nat. Commun. 8, 14764, 2017.
Goodfellow et al. "Identification of a cis-Acting Replication Element within the Poliovirus Coding Region", J Virol., 74:4590-4600, 2000.
Hadfield et al. Nextstrain SARS-CoV-2 resources, 2018.
Hahn et al. Mutations in SARS-CoV-2 spike protein and RNA polymerase complex are associated with COVID-19 mortality risk, Nov. 17, 2020.
Hogan et al. Remdesivir Resistance in Transplant Recipients with Persistent Coronavirus Disease, CID, 2019.
Jordan PC, Liu C., Raynaud P, Lo MK, Spiropoulou CF, Symons JA, Beigelman L,Deval J. Initiation, extension, and termination of RNA synthesis by aparamyxovirus polymerase. PLoS Pathog., 14(2):e1006889. doi:10.1371/journal.ppat.1006889. PMID: 29425244; PMCID: PMC5823471, Feb. 9, 2018.
Kao et al. "De Novo Initiation of Viral RNA-Dependent RNA Synthesis", Virology 287:251-260, 2001.
Kirchdoerfer et al. "Structure of the SARS-CoV nsp12 polymerase bound to nsp7 and nsp8 co-factors", Nature Commun., 10:2342, 2019.
Lehmann et al. "Discovery of an essential nucleotidylating activity associated with a newly delineated conserved domain in the RNA polymerase-containing protein of all nidoviruses", Nucleic Acids Research, vol. 43, No. 17;8416-8434, Sep. 30, 2015.
Mohammadi et al. "Novel and emerging mutations of SARS-CoV-2: Biomedicalimplications", Biomed Pharmacother. 139: 111599, Jul. 2021.
Paul et al. "Identification of an RNA Hairpin in Poliovirus RNA That Serves as the Primary Template in the In Vitro Uridylylation of VPg", J Virol., 74:10359-10370, 2000.
Peng, Q. et al. "Structural and Biochemical Characterization of the nsp 12-nsp7-nsp8 Core Polymerase Complex from SARS-CoV2", Cell Rep. Jun. 16, 2020;31(11):107774. doi: 10.1016/j.celrep.2020.107774. Epub, PMID: 32531208; PMCID: PMC7260489, May 30, 2020.
Rieder et al. "Genetic and Biochemical Studies of Poliovirus cis-Acting Replication Element cre in Relation to VPg Uridylylation", J Virol., 74:10371-10380, 2000.
Riemersma et al. "Vaccinated and unvaccinated individuals have similar viral loads incommunities with a high prevalence of the SARS-CoV-2 delta variant", Jul. 31, 2021.

(56) References Cited

OTHER PUBLICATIONS

Rohayem et al. "Protein-Primed and De Novo Initiation of RNA Synthesis by Norovirus $3D^{pol}$", J Virol. Jul. 2006; 80(14):7060-7069, 2006.
Romano, M. et al. "A Structural View of SARS-CoV-2 RNA Replication Machinery: RNA Synthesis, Proofreading and Final Capping. Cells", 9(5):1267. doi: 10.3390/cells9051267. PMID:32443810; PMCID: PMC7291026, May 20, 2020.
Sawicki et al. "A Contemporary View of Coronavirus Transcription", Adv Exp Med Biol 380:499-506, 1995.
Snijder et al. "Unique and Conserved Features of Genome and Proteome of SARS-coronavirus, and Early Split-off From the Coronavirus Group 2 Lineage", J. Mol. Biol. 331,991-1004.doi: 10.1016/s0022-2836(03)00865-9, 2003.
Te Velthuis et al. "The SARS-coronavirus nsp7+nsp8 complex is a unique multimeric RNA polymerase capable of both de novo initiation and primer extension", Nucleic Acid Res., vol. 40(4):1737-1747, 2012.
Te Velthuis A.J. "Common and unique features of viral RNA-dependent polymerases", Cell Mol Life Sci. Nov. 2014;71(22):4403-20. doi: 10.1007/s00018-014-1695-z. Epub PMID: 25080879; PMCID: PMC4207942, Aug. 1, 2014.
Van Dijk A.A., Makeyev EV, Bamford DH. "Initiation of viral RNA-dependent RNA polymerization", J Gen Virol. 85(Pt 5):1077-1093. doi: 10.1099/vir.0.19731-0. PMID: 15105525, May 2004.
Wang et al. "Structural Basis for RNA Replication by the SARS-CoV-2 Polymerase", Cell 10.1016/j.cell.2020.05.034, Jul. 23, 2020.
Wang et al. "Characterizing SARS-CoV-2 Mutations in the United States", Jul. 24, 2020.
Wikipedia "Variants of SARS-CoV-2", Jan. 6, 2021.
Yin et al. "Structural Basis for the Inhibition of the RNA-Dependent RNA Polymerase from SARS-CoV-2 by Remdesivir", BioXriv., doi: 10.1126/science.abc1560, 2020.
Zhang, W.F. et al. "Novel Coronavirus Polymerase and Nucleotidyl-Transferase Structures: Potential to Target New Outbreaks", J Phys Chem Lett. 11(11):4430- 4435. doi: 10.1021/acs.jpclett.0c00571. Epub May 22, 2020. PMID: 32392072; PMCID: PMC7243427, Jun. 4, 2020.
Zhao et al. "Structure and function of the Zika virus full-length NS5 protein", Nat. Commun. 8, 14762, 2017.
Ziebuhr "The Coronavirus Replicase", Curr. Top. Microbiol. Immunol. 287, 57-94, 2005.
Agostini, Maria L. et al. "Coronavirus Susceptibility to the Antiviral Remdesivir (GS-5734) is Mediated by the Viral Polymerase and the Proofreading Exoribonuclease," American Society for Microbiology MBio., vol. 9 Issue 2, Mar. 6, 2018.
Ahmad, T. et al. "Cardiac dysfunction associated with a nucleotide polymerase inhibitor for treatment of hepatitis C" Hepatology, 62, 409, 2015.
Ahn et al. "Biochemical characterization of a recombinant SARS coronavirus nsp12 RNA-dependent RNA polymerase capable of copying viral RNA templates", Arch Virol., 157, 2095-2104, 2012.
Atea Pharmaceuticals Presentation, Jefferies Healthcare Conference, Jun. 8, 2022.
Berge, M.S. et al. "Pharmaceutical Salts" Journal of Pharmaceutical Sciences, 66, 1, 1977.
Berliba, et al. "Safety, Pharmacokinetics, and Antiviral Activity of AT-527, a Novel Purine Nucleotide Prodrug, in Hepatitis C Virus-Infected Subjects with or without Cirrhosis," Antimicrobial Agents and Chemotherapy, vol. 63, Issue 12, Dec. 2019.
Brown, Ariane J. et al. "Broad spectrum antiviral remdesivir inhibits human endemic and zoonotic deltacoronaviruses with a highly divergent RNA dependent RNA polymerase," Antiviral Research 169, Jun. 21, 2019.
Chang, W. et al. "Discovery of PSI-353661, a Novel Purine Nucleotide Prodrug for the Treatment of HCV Infection" ACS Med Chem Lett., 2, 130, 2011.
Clinical Trials—(NCT04252664) "A Trial of Remdesivir in Adults with Mild and Moderate COVID-19," Feb. 5, 2020.
Clinical Trial History of changes for study: NCT04396106 Safety and efficacy of AT-527 in subjects with moderate coronavirus disease (COVID-19), May 19, 2020.
Cretton-Scott, E. et al. "In vitro antiviral activity and pharmacology of idx184, a novel and potent inhibitor of HCV replication" (Abstract 588) J. Hepatol., 48, Supplement 2, S220, 2008.
Denison, Mark R. et al. "Coronaviruses an RNA proofreading machine regulates replication fidelity and diversity," RNA Biology 8:2, 270-279; Mar./Apr. 2011.
Freeman et al. 2-amino-9(3-azido-2,3-dideoxy-β-D-erythro-pentofuranosyl)-6-Substituted-9H-Purines: Synthesis and Anti-HIV Activity. Bioorganic and Medicinal Chemistry, 3(4): 447-448, 1995.
Gao et al. "Structure of the RNA-dependent RNA polymerase from COVID-19 virus", Science, 368(6492), 779-782, 2020.
Gilead Sciences Initiates Two Phase 3 Studies of Investigational Antiviral Remdesivir for the Treatment of COVID-19, U.S. FDA Grants Investigational New Drug Authorization to Study Remdesivir for the Treatment of COVID-19, Feb. 26, 2020.
Good, et al. "AT-527, a Double Prodrug of a Guanosine Nucleotide Analog, is a Potent Inhibitor of SARS-CoV-2 In Vitro and a Promising Oral Antiviral for Treatment of COVID19" Antimicrobial Agents and Chemotherapy, vol. 65, Issue 4, Apr. 2021.
Good, et al. "Preclinical evaluation of AT-527, a novel guanosine nucleotide prodrug with potent, pan-genotypic activity against hepatitis C virus," Plos One, https://doi.org/10.1371/journal.pone.0227104, Jan. 8, 2020.
Good, S. et al. "AT-337, AT-511, and its Salt Form, AT-527: Novel Potent and Selective Pan-genotypic Purine Nucleotide Prodrug Inhibitors of HCV Polymerase" presented at the AASLD 2017 Liver Meeting; Washington, D.C., Oct. 20-24, 2017.
Grein, J. et al. "Compassionate Use of Remdesivir for Patients with Severe Covid-19," The New England Journal of Medicine, Jun. 11, 2020.
Harris, Lynnette "Utah State University Antiviral Researchers at work on Coronavirus with NIH Support," Health & Wellness, Mar. 26, 2020.
Herman, B. et al. "Substrate mimicry: HIV-1 reverse transcriptase recognizes 6-modified-30-azido-20,30-dideoxyguanosine-50-triphosphates as adenosine analogs" Nucleic Acids Research 40, 381, 2012.
Hirayama, Noriaki, Handbook for Producing Organic Compound Crystals, pp. 17-23, 37-40, 45-51, and 57-65 and English partial translation, 2008.
Hoffman, M. et al., "SARS-CoV-2 Cell Entry Depends on ACE2 and TMPRSS2 and Is Blocked by a Clinically Proven Protease Inhibitor", Cell, 181(2), 271-280, 2020.
Holshue, Michelle L. et al. "First Case of 2019 Novel Coronavirus in the United States," The New England Journal of Medicine, 382; 929-936, Mar. 5, 2020.
Huang et al. "Impact of solid state properties on developability assessment of drug candidates" Advanced Drug Delivery Reviews, 56, 321, 2004.
Huang et al., "Clinical features of patients infected with 2019 novel coronavirus in Wuhan, China", Lancet, 395(10223), 497-506, 2020.
International Search Report and Written Opinion for PCT/US2021/054294, 11 pages, dated Feb. 23, 2021.
Krausslich et al. eds. Antiviral Strategies, Springer-Verlag Berlin Heidelberg, pp. 1-24, 2009.
Lau et al., "Severe acute respiratory syndrome coronavirus-like virus in Chinese horseshoe bats", PNAS, 102(39), 14040-14045, 2005.
Luan et al., "Spike protein recognition of mammalian ACE2 predicts the host range and an optimized ACE2 for SARS-CoV-2 infection", Biochem. Biophys. Res. Commun., 526(1), 165-169, 2020.
Luo, Shouqi et al. "4793: Lack of Reproductive and Developmental Toxicity for AT-527 (Bemnifosbuvir), an Oral Purine Nucleotide Prodrug for COVID-19 Infection", Poster board P857 Society of Toxicology Annual Meeting, Mar. 27, 2022.
Luo, Shouqi et al. "4794: Characterization of the Toxicity Profile of AT-527 (Bemnifosbuvir), a Novel Guanosine Nucleotide Prodrug with Antiviral Activity for COVID-19 Infection", Poster board P858 Society of Toxicology Annual Meeting, Mar. 27, 2022.

(56) References Cited

OTHER PUBLICATIONS

Mcguigan, C. et al. "Design, synthesis and evaluation of a novel double pro-drug: INX-08189. A new clinical candidate for hepatitis C virus" Bioorganic & Medicinal Chemistry Letters, 20, 4850, 2010.

Mcguigan, C. et al. "Dual pro-drugs of 2'-C-methyl guanosine monophosphate as potent and selective inhibitors of hepatitis C virus" Bioorganic & Medicinal Chemistry Letters, 21, 6007, 2011.

Mehellou, Youcef, et al. The ProTide Prodrug Technology: From the Concept to the Clinic—Miniperspective; Journal of Medicinal Chemistry, J. Med. Chem, 61, 2211-2226, 2018.

Murakami, E. et al. "Adenosine Deaminase-like Protein 1 (ADAL1): Characterization and Substrate Specificity in the Hydrolysis of N6- or O6-Substituted Purine or 2-Aminopurine Nucleoside Monophosphates" J Med Chem, 54, 5902, 2011.

Nguyen, Lien et al. International Journal of Biomedical Science: Chiral Drugs: An Overview; 20; 85-100, Jun. 2, 2006.

NIAID's Multi-Pronged Response to the COVID-2019 Outbreak, Allergy and Infectious Diseases, Feb. 19, 2020.

Owen, Dafydd R., et al. "An oral SARS-CoV-2 Mpro inhibitor clinical candidate for the treatment of COVID-19," Science 374, 1586-1593, Dec. 24, 2021.

Poordad et al. "Daclatasvir with Sofosbuvir and Ribavirin for Hepatitis C Virus Infection with Advanced Cirrhosis or Post-Liver Transplantation Recurrence" Hepatology, 63, 1493, 2016.

Pradere, U. et al. "Synthesis of 5'-Methylene-Phosphonate Furanonucleoside Prodrugs: Application to D-2'-Deoxy-2'-α-fluoro-2'-β-C-methyl Nucleosides" Organic Letters, 14, 4426, 2012.

Press Release, "Atea Pharmaceuticals Provides Update and Topline Results for Phase 2 MOONSONG Trial Evaluating AT-527 in the Outpatient Setting", Oct. 19, 2021.

Press Release, "Atea Pharmaceuticals Introduces New Strategic Clinical Development Program for AT-527 in COVID-19", Dec. 14, 2021.

Press Release, "Atea Pharmaceuticals Reports Nonclinical Bemnifosbuvir (AT-527) Toxicology Data at Society of Toxicology 61st Annual Meeting"; Mar. 28, 2022.

Press Release, "Atea to Advance Global Phase 3 Registrational Study of Bemnifosbuvir in High-Rish Non-Hospitalized Patients with COVID-19", Sep. 13, 2022.

Pruijssers, Andrea J. et al. Nucleoside analogues for the treatment of coronavirus infections, Current Opinion in Virology, 35:57-62, Apr. 2019.

Reddy, P. et al. "2'-Deoxy-2'-α-fluoro-2'-β-C-methyl 3',5'-cyclic phosphate nucleotide prodrug analogs as inhibitors of HCV NS5B polymerase: Discovery of PSI-352938" Bioorganic & Medicinal Chemistry Letters, 20, 7376, 2010.

Rest et al. "SARS associated coronavirus has a recombinant polymerase and coronaviruses have a history of host-shifting", Infect Genet Evol., 3(3), 219-225, 2003.

Rockman, Glenn "To accelerate innovation, the CDC should ease limits on which labs can handle the coronavirus," STAT News, Apr. 14, 2020.

Schoeman and Fielding, "Coronavirus envelope protein: current knowledge", Virology, 16(69), 1-22, 2019.

Serajuddin, A.T.M "Salt formation to improve drug solubility" Advanced Drug Delivery Reviews, 59, 603, 2007.

Shannon, Ashleigh, et al. "Remdesivir and SARS-CoV-2: Structural requirements at both nsp 12 RdRp and nsp14 Exonuclease active-sites," Antiviral Research, 178, Jun. 2020.

Shannon, Ashleigh et al. "A dual mechanism of action of AT-527 against SARS-CoV-2 polymerase" Nature Communications, 13, 621, Feb. 2, 2022.

Sheahan, Timothy P. et al. "Broad-spectrum antiviral GS-5734 inhibits both epidemic and zoonotic coronaviruses," Sci Transl. Med., 9(396), Jun. 28, 2017.

Smith, Everett C. et al. "Coronaviruses Lacking Exoribonuclease Activity Are Susceptible to Lethal Mutagenesis: Evidence for Proofreading and Potential Therapeutics," PLOS Pathogens, vol. 9 issues 8, Aug. 13, 2013.

Sofia, M.J. "Nucleotide Prodrugs for HCV Therapy," Antiviral Chemistry & Chemotherapy, 22, 23, 2011.

Stahl et al. "Handbook of Pharmaceutical Salts Properties, Selection, and Use", International Union of Pure and Applied Chemistry (IUPAC), (Chapters 6 and 7), 2002.

Subissi et al. "One severe acute respiratory syndrome coronavirus protein complex integrates processive RNA polymerase and exonuclease activities", Proc. Natl. Acad. Sci., 111(37), E3900-E3909, Sep. 2, 2014.

Tao, S. et al. Comparison of Three 2'-C-Methyl Guanosine Prodrugs for Hepatitis C including a Novel $^{2}$-D-2'-C-Me-2,6-Diaminopurine Ribonucleoside Phosphoramidate (RS-1389): Interspecies Hepatocyte and Human Cardiomyocyte Metabolism Profiles. The Liver Meeting, Boston, MA, USA, Nov. 6-11, 2014.

Wang, Manli et al. Remdesivir and chloroquine effectively inhibit the recently emerged novel coronavirus (2019-nCoV) in vitro, Cell Research, 30:269-271, Feb. 4, 2020.

Wu et al. "Ribavirin, viramidine and adenosine-deaminase-catalysed drug activation: implication for nucleoside prodrug design", Journal of Antimicrobial Chemotherapy, vol. 52:543-546, 2003.

Xu, Xiang, et al. "Molecular model of SARS coronavirus polymerase: implications for biochemical functions and drug design," Nucleic Acids Research, vol. 31, No. 24, 7117-7130, Dec. 15, 2003.

Yang et al. "Targeting the Endocytic Pathway and Autophagy Process as a Novel Therapeutic Strategy in COVID-19", Int. J. Biol. Sci., 16(10), 1724-1731, 2020.

Yoon et al. Design, Synthesis, and Anti-RNA Virus of 6'-Fluorinated-Aristeromycin Analogues Journal of Medicine Chemistry, vol. 62, p. 6346-6362, Jun. 7, 2019.

Zhang et al. "Synthesis and evaluation of 30-azido-20,30-dideoxypurine nucleosides as inhibitors of human immunodeficiency virus" Bioorganic and Medicinal Chemistry Letters, 20, 60, 2010.

Zhou et al. "A pneumonia outbreak associated with a new coronavirus of probable bat origin", Nature, 579, 270, 2020.

Zhou, L. et al. "β-D-2'-C-Methyl-2,6-diaminopurine Ribonucleoside Phosphoramidates are Potent and Selective Inhibitors of Hepatitis C Virus (HCV) and Are Bioconverted Intracellularly to Bioactive 2,6-Diaminopurine and Guanosine 5'-Triphosphate Forms" J Med Chem, 58, 3445, 2015.

Zhou, X. et al. "A Phase la Study of AT-527, a Novel Pan-Genotypic Purine Nucleotide Prodrug Inhibitor of Hepatitis C Virus (HCV)" presented at The Liver Meeting, Washington, D.C., Oct. 23, 2017.

Zhou, X. et al. "AT-527, a pan-genotypic purine nucleotide prodrug, exhibits potent antiviral activity in subjects with chronic hepatitis C" presented at The International Liver Congress, Paris, France, Apr. 13, 2018.

U.S. Appl. No. 19/350,713, Moussa, filed Oct. 6, 2025.

U.S. Appl. No. 19/350,774, Sommadossi et al., filed Oct. 6, 2025.

GTP 2' FCH3 2.85 ± 0.18
UTP 2'FCH3 1.62 ± 0.04
GTP 2'CH3 20.8 ± 1.7
UTP 2'CH3 6.10 ± 0.32

AT-511

AT-9010

STP 2.98 Å

NiRAN INTERFERING DRUGS FOR SARS-CoV-2 MUTANT THERAPY

STATEMENT OF RELATED APPLICATIONS

This application is a continuation of International Patent Application No. PCT/US2021/054294 filed in the U.S. Receiving Office on Oct. 8, 2021, which claims priority to provisional U.S. Provisional Application No. 63/090,090, filed Oct. 9, 2020, U.S. Provisional Application No. 63/135,494, filed Jan. 8, 2021, U.S. Provisional Application No. 63/160,618, filed Mar. 12, 2021, and U.S. Provisional Application No. 63/236,151, filed Aug. 23, 2021. The entirety of each of these applications is incorporated by reference herein.

FIELD OF THE INVENTION

The present invention provides compounds, methods, and compositions for the treatment or prevention of an infection from a mutant or resistant strain of severe acute respiratory syndrome (SARS)-related coronaviruses (SARS-CoVs), including SARS-CoV-2, with nidovirus RdRp-associated nucleotidyltransferase (NiRAN) domain of non-structural protein 12 (nsp12)-interfering drugs. The invention also provides assays and methods to select optimal compounds for treating or preventing infections from SARS-CoVs, including mutant forms of SARS-CoV-2, by interfering with the activity of the NiRAN-domain of non-structural protein 12 (nsp12).

INCORPORATION BY REFERENCE

The contents of the XML file named "12020-032WO1US1_ST26_2023-04-07" which was created on Apr. 7, 2023, and is 28.6 KB in size, are hereby incorporated by reference in their entirety.

BACKGROUND OF THE INVENTION

Since its emergence in December 2019, the novel severe acute respiratory syndrome coronavirus 2 (SARS-CoV-2) has infected almost 240 million people worldwide and killed almost 5 million people from the resulting disease COVID-19. SARS-CoV-2 is a coronavirus (CoV) (order Nidovirales, family Coronaviridae, subfamily Coronavirinae) which is an enveloped virus that is notable for its large single-strand, positive-sense RNA genome of approximately 26-32 kilobases. Related coronaviruses include severe acute respiratory syndrome coronavirus (SARS-CoV-1) and Middle East respiratory syndrome coronavirus (MERS-CoV). Compared to SARS-CoV-1 and MERS-CoV, however, SARS-CoV-2 exhibits a faster human-to-human transmission rate (Huang et al., (2020) Lancet 395, 497-506), making it particularly challenging to contain.

The complete genome of the SARS-CoV-2 virus was first reported on Jan. 23, 2020 (GenBank: MN988668.1—severe acute respiratory syndrome coronavirus 2 isolate 2019-nCoV WHU01, complete genome; see also Chen et al., RNA based mNGS approach identifies a novel human coronavirus from two individual pneumonia cases in 2019 Wuhan outbreak. Emerg Microbes Infect. 2020 Feb. 5; 9(1):313-319; considered herein as the wild type virus).

The replication of SARS-CoVs is controlled by a set of nonstructural proteins (nsps) encoded by open reading frame (ORF) 1a and ORF1ab in its genome, which are initially translated as polyproteins, followed by proteolysis cleavage for maturation (Ziebuhr, (2005) Curr. Top. Microbiol. Immunol. 287, 57-94). These proteins assemble into a multi-subunit polymerase complex to mediate transcription and replication of the viral genome. This not only requires the synthesis of new genomes from a full-length negative-stranded template, but also a process of discontinuous RNA synthesis to produce sub genome-length negative-stranded RNAs. The latter serve as templates to produce a nested set of sub genome mRNAs required to express the viral structural and accessory proteins from genes not accessible to ribosomes translating the viral genome RNA (Sawicki et al., (1995) Adv Exp Med Biol 380:499-506).

Nsp12 has been identified in SARS-CoVs as the primary catalytic subunit with RNA-dependent RNA polymerase (RdRp) activity (Ahn et al., (2012) Arch. Virol. 157, 2095-2104). Nsp12 on its own is capable of polymerase activity with low efficiency, however, the presence of nsp7 and nsp8 cofactors significantly enhances its polymerase activity (Subissi et al., (2014) PNAS USA 111, E3900-E3909). Thus, it is considered that the nsp12-nsp7-nsp8 subcomplex is the practical core component for accomplishing coronavirus RNA synthesis. It is also observed that the nsp12-nsp7-nsp8 complex can associate with nsp14, a bifunctional enzyme bearing 3'-5' exoribonuclease and RNA cap N7-guanine methyltransferase activities involved in replication fidelity and 5'-RNA capping, respectively (Subissi et al., (2014) PNAS USA E3900-E3909).

To achieve complete transcription and replication of the viral genome, several other nsp subunits are required to assemble into a holoenzyme complex, including nsp10 (cofactor of nsp16 and Nsp14), nsp13 (helicase, 5'-triphosphatase), nsp15 (NendoU, uridylate-specific endoribonuclease), and nsp16 (2'-O-ribose methyltransferase) (Romano et al., (2020) Cells 9,1267).

A number of vaccines are in development to reduce or prevent SARS-CoV-2 infections, and several have received Emergency Use Authorization (EUA) from the United States Food and Drug Administration (FDA). On Dec. 11, 2020, the FDA issued an EUA for Pfizer-BioNTech COVID-19 vaccine BNT162b2 in persons aged 16 years and older for prevention of COVID-19. On Dec. 18, 2020, the FDA issued an EUA for the Moderna TX, Inc. COVID-19 Vaccine mRNA-1272 for the prevention of COVID-19 in persons 18 years and older. Both the Pfizer and Moderna vaccines are mRNA vaccines that encode for the SARS-CoV-2 spike protein. On Feb. 27, 2021, the FDA issued a third EUA for Johnson & Johnson's COVID-19 Vaccine (JNJ-78436735) for the prevention of COVID-19 in persons 18 years of age and older. The J&J vaccine is a monovalent vaccine composed of a recombinant, replication-incompetent adenovirus type 26 (Ad26) vector, constructed to encode the SARS-CoV-2 spike (S) protein.

Recent mutations to the spike protein in SARS-CoV-2 variants have raised significant concerns about the effectiveness of current vaccines. These variants of interest/concern include Alpha (B.1.1.7; United Kingdom), Beta (B.1.351, B.1.351.2, and B1.351.3; South Africa), Gamma (P.1, P.1.1, P.1.2; Brazil), Delta (B.1.617.2, AY.1, AY.2, AY.3; India), Lambda (C.37; Peru), and Mu (B.1.621; Columbia). For example, in a small clinical trial, the Oxford-AstraZeneca vaccine was shown to have reduced effectiveness against the Beta variant due to the Beta variant's E484K mutation in the spike protein, which may render the vaccine less effective, resulting in potential escape mutants. More recently, increasing numbers of vaccinated individuals have been shown to be susceptible to "breakthrough" infections with the Delta variant, and potentially capable of transmitting the virus. See, e.g., Riemersma et al., Vaccinated and unvaccinated individuals have similar viral loads in communities with a high prevalence of the SARS-CoV-2 delta variant, Jul. 31, 2021; https://doi.org/10.1101/2021.07.31.21261387.

While much focus has been placed on spike mutations due to the mechanism of immuno-protection provided by current vaccines, a high rate of genetic variability and mutation has been shown in other proteins in SARS-CoV-2. See, e.g., Mohammadi, et al., Novel and emerging mutations of SARS-CoV-2: Biomedical implications. Biomed Pharmacother. 2021 July; 139: 111599. Such additional mutations, including those targeted by anti-viral drugs, raise further concerns about fleeting efficacy. Given the very recent emergence of SARS-CoV-2 and its rapid mutation, there is insufficient information to determine which drugs will remain effective after significant mutation of the virus. There is insufficient information to design new drugs to inhibit or prevent viral infection. Indeed, certain antiviral compounds that are active against other positive-sense RNA-dependent-RNA-polymerase containing viruses are insufficiently active against SARS-CoV-2 to progress to development. New methods and assays are needed to identify drugs for the optimal treatment or prevention of SARS-CoV-2, most notably, emerging mutant strains, and new methods of treatment are needed based on a new criterion for therapeutic and prophylactic treatment.

It is thus a goal of the present invention to provide compounds, compositions and methods of treatment or prevention of infection by mutant or resistant strains of SARS-CoV-2.

It is another object of the present invention to provide methods to identify and develop effective SARS-CoV-2 targeted therapeutics.

SUMMARY OF THE INVENTION

It has been unexpectedly discovered that the NiRAN-domain of nsp12 of severe acute respiratory syndrome (SARS)—related coronaviruses (SARS-CoVs) such as SARS-CoV-1 and SARS-CoV-2 plays a unique and fundamental role in viral RNA synthesis that is not shared with most other viruses. The present invention is based on the foundational discovery that the SARS-CoV-2 NiRAN-domain has an essential role in protein-primed RNA synthesis through a NiRAN-dependent protein-primed pathway wherein a tyrosine hydroxyl group of nsp8 is first covalently labeled with a uridine monophosphate (referred to as "UMPylation") by the transfer of UTP to nsp8 to yield UMP-nsp8, then further positioned to the poly(A) 3' end to prime (−)ssRNA strand synthesis (see FIG. 7H). This activity has been confirmed through experimental evidence, as exemplified in Examples 8-20 below (see also, FIGS. 5A, 5B, 6A, 13A, 13C and 13E). The UMPylation of nsp8 and resulting protein-primed genomic RNA synthesis pathway represents a previously unknown role for the NiRAN-domain. Importantly, by targeting the NiRAN-dependent pathway, the exonuclease activity of nsp14, which has rendered targeting strategies of RNA synthesis chain-termination ineffective, is bypassed. By targeting this highly conserved NiRAN-domain with NiRAN-domain mediated activity interfering agents, a powerful tool for treating SARS-CoVs, including SARS-CoV-2 variants that have mutated and/or developed resistance to other anti-viral agents, can be accomplished, without a significant risk of mutants being resistant to treatment.

Discovery of NiRAN Mechanism

Importantly, it has been discovered that the NiRAN-domain, whose function to date has been unknown, is involved in RNA synthesis in coordination with nsp8 for protein priming. As shown herein for the first time, nsp12 is able to specifically uridylate the RdRp cofactor nsp8, forming a UMP-nsp8 covalent intermediate which primes RNA synthesis from a poly(A) template, which is subsequently extended via the nsp12-nsp8-nsp7 minimal replication-transcription complex (RTC) (see FIG. 7H; pathway 1). This reaction is dependent on the CoV-unique, Nidovirus RdRp Associated Nucleotidylation (NiRAN)-domain, located on the N-terminus of nsp12, and thus represents a previously unknown activity for this domain.

Importantly, it has been found that disrupting this NiRAN-domain mediated activity using a compound capable of interfering with NiRAN's UMPylation of nsp8 significantly inhibits viral replication, and provides a powerful anti-coronavirus approach to treating SARS-related coronavirus infections. By targeting NiRAN's function, the invention establishes that genomic RNA synthesis can be permanently inhibited. Prior to this discovery, the unproven function and/or druggability of a number of the SARS-CoV-2 proteins made it particularly difficult to determine how to treat mutant forms of the virus—and which region was the best target for a therapeutic agent—which hindered the identification and/or development of potentially efficacious drugs.

Critically, this discovery confirms that compounds with a primary mechanism of disrupting NiRAN-domain mediated activity provide treatment or prevention of infection caused by mutant forms of the virus. Furthermore, because the NiRAN-domain is highly conserved, and mutations in the active region are likely fatal, the present strategy of targeting the NiRAN-domain in a SARS-CoV virus is unlikely to allow for the development of mutant strains capable of escaping the anti-viral effects of NiRAN-domain targeted compounds through the development of NiRAN mutations.

It is advantageous to have a compound that disrupts this important NiRAN-domain mediated activity over a compound that only acts through RNA chain termination during RNA replication, because the virus otherwise can escape the drug treatment by excising the incorporated drug from the growing polymerase with its 3',5'-exonuclease (nsp14).

The sequence of SARS-CoV-2 nsp12 protein is 932 amino acids in length. Similar to SARS-CoV-1, the nsp12 of SARS-CoV-2 contains a right-hand C-terminal RdRp domain (residues 366 to 920) and a nidovirus-specific N-terminal extension domain (residues 1-250) that adopts a nidovirus RdRp-associated nucleotidyltransferase (NiRAN) architecture (see FIG. 1) (Gao et al. Science 10.1126/science.abb7498 (2020)). The RdRp polymerase domain and NiRAN-domain are connected by an interface domain (residues A250 to R365). The NiRAN and interface domains represent an additional and unique feature of coronavirus RdRp compared with the polymerase subunit of other positive-sense RNA viruses such as flavivirus (Duan et al., (2017) EMBO J. 36, 919-933; Godoy et al., (2017) Nat. Commun. 8, 14764; Zhao et al., (2017) Nat. Commun. 8, 14762). The role of the unique NiRAN-domain of nsp12 in SARS-CoV-2 before this invention was unknown, as the prior proposed functions of the NiRAN-domain were complicated by the complexity of coronavirus replication, the uniqueness of the NiRAN-domain to coronaviruses, and the contradicting and dissimilar evolutionary, structural, and functional characteristics of domains from other viruses having the proposed functions of the SARS NiRAN-domain (see Lehmann (2015) Nucleic Acids Research, Volume 43, Issue 17, Pages 8416-8434). The exact mechanisms by which nsp12 initiates RNA replication, as well as the nature of its replication products, remained uncharacterized until now.

The present invention is based on the discovery of the importance of the protein-priming based initiation of the SARS-CoV-2 viral NiRAN-domain. Traditionally, viral RdRp had generally been classified into two main categories: a de novo (primer-independent) initiation and oligonucleotide primer-dependent initiation (Kao et al. 2001. Virology 287:251-260). However, specific mechanisms for within these broadly defined groups can vary considerably. In some viruses such as members of the Picornaviridae—e.g., poliovirus and foot-and-mouth disease virus—an additional mechanism of RNA synthesis termed "protein priming" RNA synthesis occurs in the absence of an RNA primer (see Rohayem et al., (2006) J Virol. 2006 July; 80(14): 7060-7069). In these viruses, initiation of RNA synthesis of genomic RNA relies upon uridylation and subsequent elongation of a viral protein, designated VPg (virion protein, genome-linked), in the presence of the polyadenylated genomic RNA. This "protein-primed" initiation occurs in Picornaviridae after the annealing of the elongated VPg-poly(U) to the poly(A) tail of the viral genome. In Picornaviridae such as poliovirus, VPg must undergo post-translational uridylation before it can act as a primer for replication. 3Dpol (the RdRp of poliovirus) is able to synthesize Vpg-pUpU-OH by using a polyA sequence within a stem-loop structure (cis-acting replication element) of 2C-ATPase as a template (see, e.g., Goodfellow et al., J Virol. 2000; 74:4590-4600; Paul et al., J Virol. 2000; 74:10359-10370; Rieder et al., J Virol. 2000; 74:10371-10380). Furthermore, a 5' terminal cloverleaf is required in cis to form the 3Dpol pre-initiation RNA replication complex involved in uridylating VPg.

Prior to this discovery, it was not known which mechanism SARS-CoV-2 uses to accomplish the synthesis of genomic RNA. It is now herein disclosed that the mechanism of SARS-CoV protein-primed RNA replication is accomplished via NiRAN-domain mediated protein priming in conjunction with nsp8, wherein nsp8 may be acting in a Vpg-like manner, and wherein the synthesized RNA is covalently bound to a protein. As shown herein, the NiRAN-domain transfers a uridine base to nsp8. The subsequent UMP-nsp8 complex promotes RNA synthesis via-base-pairing of the covalently bound UMP to the complementary base at the 3' end of the (+) RNA polyA template in the absence of a primer. Nucleotides are successively added to the product strand. The resulting final product is a (−) RNA strand with covalently attached nsp8. This nsp8-UMP protein primed strategy is specific to minus strand synthesis, templated from the poly(A) tail. Interfering with this pathway undergirds the present invention.

Nsp14 has been shown to excise 3'-terminal mismatched nucleotides from double-stranded (ds) RNA substrates, and provides a replication mismatch repair mechanism that serves to promote the fidelity of CoV RNA synthesis (Bouvet et al. (2010). PLoS Pathog. 6: e1000863. doi: 10.1371/journal.ppat.1000863). As described above, by targeting the NiRAN-domain and disrupting NiRAN-dependent protein primed RNA synthesis, the exon proofreading function provided by nsp14 that is essential for maintaining the natural fidelity of the coronavirus genome during replication is avoided. For example, it has been shown that nsp14 can efficiently excise ribavirin 5'-monophosphate, possibly explaining why this broad-spectrum antiviral drug is poorly active against CoVs (see Snijder et al. (2003). J. Mol. Biol. 331, 991-1004. doi: 10.1016/s0022-2836(03)00865-9; Ferron et al. (2018) Proc. Natl. Acad. Sci. U.S.A. 115, E162-E171. doi: 10.1073/pnas.1718806115). Because the exon proofreading function provided by nsp14 is capable of reversing a number of inhibitory mechanisms, targeting RNA synthesis through inhibition of NiRAN-domain mediated activity is a superior approach.

It is also shown herein that a parallel, NiRAN-independent de novo synthesis also occurs during CoV replication, wherein the SARS-CoV RTC synthesizes 5'-triphosphate dinucleotide primers to initiate RNA synthesis. As shown in Examples 13-15 and FIGS. 8A-B and 9A-9B the RdRp active site of nsp12, in conjunction with nsp7 and nsp8, drives synthesis of a pppNpN dinucleotide primer, preferably a pppGpU dinucleotide primer, in a NiRAN-independent manner, to prime (−)ssRNA synthesis from the genome 5'-end to start at the genome-poly(A) tail junction (see FIG. 7H; pathway 2). A conserved genomic RNA hairpin sequence at its junction with the poly(A) tail binds in the vicinity of the nsp12 RdRp active site to synthesize a pppGpU dinucleotide primer able to prime RNA synthesis of the complementary stand.

Treatment or Prevention of Infection caused by Mutant SARS-CoVs

As a result of this foundational discovery, it has now been determined that certain nucleotide drugs, including those of Formula I, including but not limited to Compounds 1, 2, 1A, 1B, 2A and 2B, uniquely act at the NiRAN-domain of SARS-related coronaviruses, which allows for the treatment of a host, including a human, infected or who may have been or may be exposed to, a mutant form of SARS-CoVs, including SARS-CoV-2, that does not have a disabling mutation in the NiRAN-domain, by administration of an effective amount of the compound or a pharmaceutically acceptable salt thereof of this compound, optionally in a pharmaceutically acceptable carrier. In another aspect, a compound of Formula II-VIII, or a pharmaceutically acceptable salt thereof, is used for the treatment of a host, including a human, infected or who may have been or may be exposed to, a mutant form of SARS-CoVs that does not have a disabling mutation in the NiRAN-domain, by administration of an effective amount of the compound or a pharmaceutically acceptable salt thereof of the compound of Formula II-VIII or its salt, optionally in a pharmaceutically acceptable carrier.

The NiRAN-domain of the equine arteritis virus has previously been shown to preferentially incorporate UTP over GTP during nucleotidylation (see Lehmann et al., Nucleic Acids Res. 2015 Sep. 30; 43(17): 8416-8434). However, it has surprisingly been discovered that certain guanosine-based nucleotides (e.g., AT-9010, which is the active 2'-fluoro-2'-C-methylguanosine-5'-triphosphate of AT-511 (Compound 1A) and AT-527 (Compound 2A) as described in Good et al., (2020) PLoS ONE 15(1): e0227104, and further described, for example, in U.S. Pat. Nos. 9,828,410 and 10,519,186, incorporated herein by reference) are preferentially incorporated by the NiRAN-domain, remain bound to the active site of the NiRAN-domain, and are capable of inhibiting transfer of UTP and GTP from the NiRAN-domain of nsp12 to nsp8 over both uridine-5'-triphosphate (UTP) and guanosine-5'-triphosphate (GTP) (see, e.g., Example 19; FIGS. 13A-C and 14A-C). For example, AT-9010 inhibits the transfer of UTP and GTP from nsp12 to nsp8 by 75% and 64%, respectively, when competing with UTP and GTP at an equimolar concentration (see, e.g., Example 8).

Thermal shift assays with nsp12 in the presence of $MgCl_2$ confirms that AT-9010 provides more thermodynamic stability than any other native nucleotide (Example 20; FIGS. 13F-H). Thermal shift assays with nsp12 in the presence of $MnCl_2$ confirms that AT-9010 provides more thermodynamic stability than any other native nucleotide (FIGS. 13F-H). Comparison of NiRAN and RdRp active-site mutants (K73A and SAA, respectively) shows that this stability increase is provided by AT-9010 binding preferentially into the NiRAN active-site, rather than the RdRp active-site. Both GTP- and AT-9010-nsp12 complexes show an increase in stability compared with UTP-bound complexes, and furthermore are able to bind in the NiRAN active-site in the presence of $MgCl_2$, as well as $MnCl_2$ (Examples 19-20; FIGS. 13A-C). Consistent with inhibition results, these results indicate that guanosine is the preferred base of the NiRAN active-site, and the 2'-fluoro-2'-C-methyl ribose modification of AT-9010 provides additional stability. Comparatively, the adenosine nucleotide Remdesivir and $^{m7}$GTP poorly inhibit transfer of UTP to nsp8 by nsp12 (see Example 19, FIGS. 13A-C), and indicates that guanosine-based nucleotides are likely the best candidates for NiRAN-based inhibition.

Comparatively, the uracil nucleotide sofosbuvir is about 5-fold less efficient at blocking nsp8 UMPylation by nsp12 compared to AT-9010, rendering such uracil nucleotide significantly less effective at generally inhibiting coronavirus viral replication (see, e.g., Example 2, Table 2A, Table 2B, Table 3A, Table 3B; Example 19). Furthermore, Remdesivir, which is referred to as an adenosine nucleotide but is in fact a pyrrolo[2,1-f][1,2,4]triazin-4-amine that does not metabolize to adenosine (or guanine), likely does not have NiRAN inhibitor activity given the preference of the NiRAN-domain for incorporating UTP and GTP to facilitate RNA synthesis. Remdesivir's assumed lack of NiRAN inhibitory activity may account for its limited efficacy, along with potential decreased binding to RdRp due to its unusual cyano 1'-substitution on the base or unusual pyrrolo[2,1-f][1,2,4]triazin-4-amine base.

SARS-CoV-2 is constantly mutating, which may increase virulence and transmission rates. The use of certain anti-viral drugs has been shown to lead to drug-resistant variants of viruses after prolonged treatment due to insufficient efficacy and the occurrence of mutation of a gene that encodes for the viral component targeted by the anti-viral drug. For example, the use of mutagenic agents, such as molnupiravir, which depend on the introduction of mutations into the viral genome for inhibition may result in the introduction of drug-induced mutations which may not be initially fatal to the virus, allowing the virus to continue to replicate while further accumulating additional mutations. Alternatively, in the case of SARS-related coronaviruses, the use of drugs which rely on RNA replication chain termination may allow for the excision of the terminating nucleotide via the exonuclease activity of nsp14, which may be replaced with an imperfect base-pair match during replacement, resulting in the accumulation of further mutations in the genomic viral sequence. Importantly, the compounds described herein may provide potent anti-viral activity against SARS-CoV-2 without inducing or driving additional mutations in the virus. For example, as shown in Example 27, AT-511 (Compound 1A) does not drive or induce further mutations in the virus compared to the mutational rate observed in the native viral population. Comparatively, as shown in Example 27, other anti-viral drugs targeting SARS-CoV-2 such as molnupiravir may result in increased mutagenesis.

Nonlimiting examples of SARS-CoV-2 mutations that are not in the NiRAN-domain that have been identified are provided in the Detailed Description of the Invention. The compounds of Formula I, as well as Formulas II-VII, or their pharmaceutically acceptable salt, optionally in a pharmaceutically acceptable carrier, can be used in medical therapy to treat or prevent a SARS-CoV-2 infection that bears one or more of these mutations, wherein the mutation is found either alone or in combination with other mutations. In general, it has been found that SARS-CoV-2 is prone to mutations over time, making this invention very important for healthcare solutions.

In non-limiting examples, the compounds of Formula I, as well as Formulas II-VIII, or their pharmaceutically acceptable salt, optionally in a pharmaceutically acceptable carrier, can be used in medical therapy to treat or prevent a SARS-CoV-2 variant, including, but not limited to (as defined by the World Health Organization (WHO)) Alpha (Pango lineage: B.1.1.7), Beta (Pango lineages: B.1.351, B.1.351.2, B.1.351.3), Gamma (Pango Lineages: P.1, P.1.1, P.1.2), Delta (Pango Lineages: B.1.617.2, AY.1, AY.2, AY.3), Mu (Pango Lineages: B.1.621, B.1.621.1), Eta (Pango Lineages: B.1.525), Iota (Pango Lineage: B.1.526), Kappa (Pango Lineage: B.1.617.1), Lambda (Pango Lineage: C.37), Epsilon (Pango Lineages: B.1.427, B.1.429), Zeta (Pango Lineage: P.2), and Theta (Pango Lineage: P.3). Additional SARS-CoV-2 variants targeted by the compounds and methods described herein include Pango Lineages, P.2, P.3, R.1, R.2, B.1.466.2, B.1.621, B.1.1.318, B.1.1.519, C.36.3, C.36.3.1, B.1.214.2, B.1.1.523, B.1.619, B.1.620, B.1.621, B.1.617.3.

In certain aspects, treatment of a human or host with a compound of Formula I-VIII with a mutant form of SARS-CoV-2 can be accomplished at substantially the same dose and treatment regimen as with wild-type virus (identified as GenBank: MN988668.1 on Jan. 23, 2020). In alternative embodiments, the selected compound or its pharmaceutically acceptable salt as described herein maintains at least 95%, at least 93%, at least 90% or at least 80 or 85% of the activity against the mutated or resistant SARS-CoV-2 virus in a treatment or prevention regime or as measured in an accepted in vitro assay.

In certain aspects, the compounds of Formula I, as well as Formulas II-VIII, or their pharmaceutically acceptable salt, optionally in a pharmaceutically acceptable carrier, can be used in combination or alternation with one or more additional active agents in a medical therapy to treat or prevent a SARS-CoV-2 variant or mutant. In some embodiments, the additional active agent is selected from, but not limited to, one or more of an additional anti-viral agent, an anti-inflammatory agent, or an immunosuppressive or immune-modulating agent. In some embodiments, the additional active agent is selected from, but not limited to, remdesivir, mavrilumab, molnupiravir, baricitinib, tocilizumab, siltuximab, sarilimab, asirivimab, imdevimab, dexamethasone, prednisone, methylprednisolone, hydrocortisone, bamlanivimab, etesevimab; molnupiravir, sofosbuvir, GC376, PF-07304814, PF-07321332, EDP-235, PBI-0451, ALG-097111, sotrovimab (VIR-7831), VIR-7832, BRII 196 BRII 198 ADG20, ADG10, or a combination thereof. In some embodiments, the additional active agent is molnupiravir. In some embodiments, the additional active agent is remdesivir. In some embodiments, the additional active agent is sofosbuvir. In some embodiments, the additional active agent is PF-07321332. In some embodiments, the additional active agent is EDP-235. In some embodiments, the additional active agent is PF-07304814. In some embodiments, the additional agent is casivirimab. In some embodiments, the additional active agent is imdevimab. In some embodiments, the additional agent is casivirimab and imdevimab. In some embodiments, the additional agent is REGN-COV2. In some embodiments, the additional agent is an antibody cocktail.

In some embodiments, the compound is Compound 2A, which is administered at a dose of between 500 mg and 1200 mg, once, twice, or three times a day. In some embodiments, the compound is Compound 2A, which is administered at a dose of at least 500 mg once, twice, or three times a day. In some embodiments, the compound is Compound 2A, which is administered at a dose of at least 550 mg once, twice, or three times a day. In some embodiments, the compound is Compound 2A, which is administered at a dose of at least 600 mg once, twice, or three times a day. In some embodiments, the compound is Compound 2A, which is administered at a dose of at least 650 mg once, twice, or three times a day. In some embodiments, the compound is Compound 2A, which is administered at a dose of at least 700 mg once, twice, or three times a day. In some embodiments, the compound is Compound 2A, which is administered at a dose of at least 750 mg once, twice, or three times a day. In some embodiments, the compound is Compound 2A, which is administered at a dose of at least 800 mg once, twice, or three times a day. In some embodiments, the compound is Compound 2A, which is administered at a dose of at least 850 mg once, twice, or three times a day. In some embodiments, the compound is Compound 2A, which is administered at a dose of at least 900 mg once, twice, or three times a day. In some embodiments, the compound is Compound 2A, which is administered at a dose of at least 950 mg once, twice, or three times a day. In some embodiments, the compound is Compound 2A, which is administered at a dose of at least 1000 mg once, twice, or three times a day. In some embodiments, the compound is Compound 2A, which is administered at a dose of at least 1050 mg once, twice, or three times a day. In some embodiments, the compound is Compound 2A, which is administered at a dose of at least 1100 mg once, twice, or three times a day. In some embodiments, the compound is Compound 2A, which is administered at a dose of at least 1150 mg once, twice, or three times a day.

In some embodiments, the compound is Compound 2A, which is administered at a dose of about 550 mg once, twice, or three times a day. In some embodiments, the compound is Compound 2A, which is administered at a dose of about 1100 mg once, twice, or three times a day.

In some embodiments, the compound is Compound 2A, which is administered at a dose of 2-275 mg doses two times, or three times a day. In some embodiments, the compound is Compound 2A, which is administered at a dose of 3-275 mg doses two times, or three times a day. In some embodiments, the compound is Compound 2A, which is administered at a dose of 4-275 mg doses two times, or three times a day.

In some embodiments, the administration of a compound described herein provide a shortened time to the alleviation of symptoms caused by a SARS-CoV virus. In some embodiments, the administration of a compound described herein provides a reduction in one or more of i) hospitalization, medically attended visits, and/or death. In some embodiments, the SARS-CoV infection is a SARS-CoV-2 variant infection. In some embodiments, the SARS-CoV infection is a SARS-CoV2 virus that is resistant to one or more anti-viral agents.

Assays and Methods to Identify Compounds that Interfere with the SARS-CoV NiRAN-Domain The fundamental discovery of this functional role of the NiRAN-domain allows for the screening and identification of compounds capable of inhibiting RNA synthesis mediated by the NiRAN-domain, by either i) directly inhibiting NiRAN function, or 2) using compounds that are incorporated by NiRAN and are capable of interrupting NiRAN-domain mediated protein primed RNA synthesis when transferred to NiRAN's obligate RNA synthesis partner nsp8, and the subsequent use of these NiRAN-domain mediated activity interfering compounds for the therapeutic treatment and prevention of COVID-19 and/or a SARS-CoV infection, including but not limited to a SARS-CoV-2 infection. The ability of a compound to inhibit NiRAN-domain mediated activity as described herein can be determined using an in vitro assay as described in the Examples herein, or similar in vitro assays known in the art, and is compared to a control wherein the compound is not present in the same assay.

Thus, another embodiment of the invention based on the discovery of the essential role of the NiRAN-domain in viral replication is the identification and use of a compound, for example a nucleotide, including a stabilized phosphate prodrug, such as a stabilized triphosphate, for example a phosphoramidate, thiophosphoramidate, or a phosphorothioate, that provides the 5'-monophosphate of the nucleoside), that efficiently disrupts NiRAN-domain mediated RNA synthesis activity and is thus able to treat the wild form, a mutant form that does not carry a disabling mutation in the NiRAN-domain, or a drug resistant form of a SARS-CoV virus, including, for example, SARS-CoV-2. This represents a significantly improved anti-viral strategy over compounds that are not capable of NiRAN inhibition but rely on other, non-exclusive inhibitory mechanisms such as mis-incorporation and mispairing, which are subject to the counteracting proofreading exonuclease activity of coronavirus nsp14.

Using the teachings herein, drugs for the treatment of COVID-19 and/or SARS-related coronavirus infections, including SARS-CoV-2, are selected that have advantageous properties for human treatment. The selection of compounds capable of inhibiting RNA synthesis through NiRAN-domain activity disruption provides a critical improvement in the state of the art on SARS-CoV therapeutic treatments, and overcomes challenges inherent with certain current SARS-CoV-2 treatment strategies.

By designing compounds that interfere with NiRAN-domain mediated RNA synthesis function that has been discovered as part of this invention, compounds can be selected for COVID-19 therapy and/or SARS-CoV infections that are fatal to the virus because the virus does not have an editing, or design around capability, if the NiRAN RNA synthesis role is disrupted. This creates a fundamentally new and powerful means of controlling SARS-CoV-2 and other SARS-related virus infections by targeting a unique region that has no known homologs, and greatly aids in identifying drugs that are specific and selective for SARS-related viruses, including SARS-CoV-2.

Therefore, in some embodiments, a method for the treatment or prevention of COVID-19 or a SARS-related coronavirus infection in a host, typically a human, in need thereof is provided that includes (i) selecting a compound whose dominant mechanism is the disruption of NiRAN-domain mediated protein-primed RNA synthesis over, or in addition to, a chain terminating inhibiting function of the RNA-dependent-RNA-polymerase (RdRp) or mismatch incorporation function and (ii) administering an effective amount of the drug to the host to treat or prevent the infection. In certain embodiments, the drug is a non-naturally occurring nucleotide, and in a specific embodiment, it is or is metabolized to a guanine triphosphate and/or monophosphate or a uridine triphosphate and/or monophosphate derivative, wherein the sugar moiety is non-naturally occurring, for example, as a sugar moiety species depicted independently in any of Formulas I-VIII. In some embodiments, the nucleotide has an alkyl and/or a halo (such as fluoro or chloro) moiety in the 2'-position of the sugar. In some embodiments, the nucleotide does not drive or induce further mutations in the targeted SARS-CoV virus, including a SARS-CoV-2 virus, compared to the mutational rate observed in the native viral population.

When the term guanine triphosphate is used below, it is intended to include any guanosine moiety that includes a sugar moiety species depicted independently in any of Formulas I-VIII.

Thus, the identification and use of a compound, for example a selected nucleotide that efficiently disrupts NiRAN-domain mediated RNA synthesis activity provides a significantly improved anti-viral strategy over compounds that are not capable of NiRAN inhibition but rely on other, non-exclusive inhibitory mechanisms such as mis-incorporation and mispairing, which are subject to the counteracting proofreading exonuclease activity of coronavirus nsp14.

As a result of the fundamental discovery herein, compounds capable of inhibiting NiRAN-domain mediated RNA synthesis activity can be identified through screening or designed and selected for their potential use for treating or preventing COVID-19 caused by SARS-CoV-2 or treating or preventing a SARS-related coronavirus infection, including mutant and variant forms of SARS-CoV-2.

Accordingly, in an aspect of the present invention, a method for the treatment or prevention of COVID-19 or a SARS-related coronavirus infection in a host, typically a human, in need thereof is provided that includes (i) selecting a nucleotide drug that exhibits a mechanism of action which is the disruption of NiRAN-domain mediated RNA synthesis and (ii) administering an effective amount of the drug to the host to treat or prevent the infection. In some aspects, the selected nucleotide inhibits transfer of native UTP and or GTP from nsp12 to nsp8 of at least about 50% over normal levels without the compound in vitro in equal molar concentrations of UTP and or GTP and the test compound. In some embodiments, the transfer of both UTP and GTP are inhibited by at least about 50%. In another embodiment, the transfer of UTP and/or GTP is inhibited by at least about 25%, 30%, 35%, 40%, 45%, 50%, 55%, 60%, 65%, 70%, 75%, 80%, 85%, 90%, or 95%, or greater. In some embodiments the transfer of UTP is inhibited by at least about 25%, 30%, 35%, 40%, 45%, 50%, 55%, 60%, 65%, 70%, 75%, 80%, 85%, 90%, or 95%, or greater. In some embodiments the transfer of GTP is inhibited by at least about 25%, 30%, 35%, 40%, 45%, 50%, 55%, 60%, 65%, 70%, 75%, 80%, 85%, 90%, or 95%, or greater. In some embodiments, the inhibition is measured using an in vitro assay, for example as described in Example 8, or an assay similar thereto. In some embodiments, the selected nucleotide inhibits or reduces NiRAN-domain mediated UMPylation of nsp8 by nsp12. In some embodiments, the selected nucleotide inhibits UMPylation by at least 25%, 30%, 35%, 40%, 45%, 50%, 55%, 60%, 65%, 70%, 75%, 80%, 85%, 90%, or 95%, or greater. In some embodiments, the inhibition is measured using an in vitro assay, for example as described in Examples 8-10, 17, and 19-20, or an assay similar thereto. In some embodiments, the selected nucleotide inhibits protein-primed RNA synthesis. In some embodiments, the selected nucleotide inhibits protein-primed RNA synthesis by at least 25%, 30%, 35%, 40%, 45%, 50%, 55%, 60%, 65%, 70%, 75%, 80%, 85%, 90%, or 95%, or greater. In some embodiments, the inhibition of protein-primed RNA synthesis is measured using an in vitro assay, for example as described in Examples 12, 19, and 20, or an assay similar thereto. In some embodiments, the selected nucleotide inhibits or reduces NiRAN-domain mediated primer independent RNA synthesis. In an alternative embodiment, the selected nucleotide inhibits nsp8 primase activity. In an alternative embodiment, the selected nucleotide inhibits nsp8 adenylase activity. In alternative embodiments, the selected nucleotide remains bound to the NiRAN active site and is not transferred to nsp8. In some embodiments, the selected nucleotide also inhibits or prevents the UMPylation by the NiRAN-domain of nsp9. In some embodiments, the COVID-19 or SARS-CoV related coronavirus infection in the host is caused by a mutant/variant form of SARS-CoV-2. In some embodiments, the nucleotide does not drive or induce further mutations in the targeted SARS-CoV virus, including a SARS-CoV-2 virus, compared to the mutational rate observed in the native viral population.

Accordingly, in another aspect of the present invention, a method for the treatment or prevention of COVID-19 and/or a SARS-related coronavirus infection in a host, typically a human, in need thereof is provided that includes (i) selecting a nucleotide drug that exhibits a dominant mechanism of action which is the disruption of NiRAN-domain mediated RNA synthesis over its RdRp chain terminating function and (ii) administering an effective amount of the drug to the host to treat or prevent the infection. In some aspects, the selected nucleotide inhibits transfer of native UTP and/or GTP from nsp12 to nsp8 of at least about 50% over normal level without the compound in vitro in equal molar concentrations of UTP and or GTP and the test compound. In some embodiments, the transfer of both UTP and GTP are inhibited by at least about 50%. In another embodiment, the transfer of UTP and/or GTP is inhibited by at least about at least about 25%, 30%, 35%, 40%, 45%, 50%, 55%, 60%, 65%, 70%, 75%, 80%, 85%, 90%, or 95%, or greater. In some embodiments, the transfer of UTP is inhibited by at least about 25%, 30%, 35%, 40%, 45%, 50%, 55%, 60%, 65%, 70%, 75%, 80%, 85%, 90%, or 95%, or greater. In some embodiments the transfer of GTP is inhibited by at least about 25%, 30%, 35%, 40%, 45%, 50%, 55%, 60%, 65%, 70%, 75%, 80%, 85%, 90%, or 95%, or greater. In some embodiments, the inhibition is measure using an in vitro assay, for example as described in Examples 8-12, 17, 19, or 20, or an assay similar thereto. In some embodiments, the selected nucleotide inhibits or reduces NiRAN-domain mediated UMPylation of nsp8 by nsp12 by at least about 25%, 30%, 35%, 40%, 45%, 50%, 55%, 60%, 65%, 70%, 75%, 80%, 85%, 90%, or 95%, or greater. In some embodiments, the selected nucleotide inhibits or reduces NiRAN-dependent protein-primed RNA synthesis initiation at least about 25%, 30%, 35%, 40%, 45%, 50%, 55%, 60%, 65%, 70%, 75%, 80%, 85%, 90%, or 95%, or greater. In some embodiments, the selected nucleotide inhibits or reduces NiRAN-domain mediated primer independent RNA synthesis by at least about at least about 25%, 30%, 35%, 40%, 45%, 50%, 55%, 60%, 65%, 70%, 75%, 80%, 85%, 90%, or 95%, or greater. In an alternative embodiment, the selected nucleotide inhibits nsp8 primase activity. In another alternative embodiment, the selected nucleotide inhibits nsp8 adenylase activity. In alternative embodiments, the selected nucleotide remains bound to the NiRAN active site and is not transferred to nsp8. In some embodiments, the selected nucleotide also inhibits or prevents the UMPylation by the NiRAN-domain of nsp9. In some embodiments, the COVID-19 or SARS-related coronavirus infection in the host is caused by a mutant/variant form of SARS-CoV-2. In some embodiments, the nucleotide does not drive or induce further mutations in the targeted SARS-CoV virus, including a SARS-CoV-2 virus, compared to the mutational rate observed in the native viral population.

In yet another aspect of the present invention, a method for the treatment or prevention of COVID-19 or SARS-related coronavirus infection in a host, typically a human, in need thereof is provided that includes (a) identifying and selecting a nucleotide capable of inhibiting NiRAN-domain mediated activity by assaying the compound's ability to: (i) prevent or decrease the binding of native UTP and/or GTP to the active region of NiRAN by at least 25% or more; (ii) prevent or decrease the binding of native UTP to the active UMPylation site of NiRAN (see, for example, Examples 8-10, 12, 17, 19-20) by at least 25% or more; iii) prevent or decrease the binding of native NTP to the active NMPylation site of NiRAN by at least 25% or more; iv) prevent or decrease the binding of native UTP and/or GTP to the invariant lysine residue K73 in the NiRAN-domain; by at least 25% or more (v) prevent or decrease native UTP and/or GTP from accessing the active site of the NiRAN-domain by at least 25% or more; (vi) prevent or decrease native UTP and/or GTP from accessing the active site of the NiRAN-domain by at least 25% or more, wherein the active site is a pocket lined with the following residues: K73, R74, H75, N79, E83, R116, N209, G214, D218, F219, and F222 (see e.g., Chen et al., 2020, Ce11182, 1-14); (vii) prevent or decrease native UTP and/or GTP from accessing the active site of the NiRAN-domain by at least 25% or more, wherein the active site is a pocket lined with the following residues: K50, R55 T120, N, 209, Y217; (viii) bind to the invariant lysine residue K73; (ix) bind to the active site pocket of the NiRAN-domain; (x) bind to the active site pocket of the NiRAN-domain, wherein the active site pocket is lined with the following residues: K73, R74, H75, N79, E83, R116, N209, G214, D218, F219, and F222; (xi) bind to the active site pocket of the NiRAN-domain, wherein the active site pocket is lined with the following residues: K50, R55 T120, N, 209, Y217; (xii) prevent the transfer of native UTP and/or GTP by the NiRAN-domain; by at least 25% or more (xiii) prevent the transfer of native GTP and/or UTP to nsp8 by at least 25% or more; or (xiv) prevent the initiation or completion of protein primed RNA synthesis by at least 25% or more; or combinations thereof, wherein the measurement is compared to a control wherein the compound is not present; and then (b) administering an effective amount of the selected nucleotide to the host in need thereof. In some embodiments, the COVID-19 or infection in the host is caused by a mutant/variant form of SARS-CoV-2. In some embodiments, the selected nucleotide inhibits NiRAN-domain mediated activity by at least 50% or more, for example, at least 50%, 55%, 60%, 65%, 70%, 75%, 80%, 85%, 90%, or 95%, or more compared to a control wherein the compound is not present. In alternative embodiments, the selected nucleotide remains bound to the NiRAN active site and is not transferred to nsp8. In some embodiments, the selected nucleotide also inhibits or prevents the UMPylation by the NiRAN-domain of nsp9. In some embodiments, the nucleotide does not drive or induce further mutations in the targeted SARS-CoV virus, including a SARS-CoV-2 virus, compared to the mutational rate observed in the native viral population. In some embodiments, the inhibition of NiRAN-domain mediated activity by the compound is determined using an in vitro assay as described herein, for example in Examples 8-12, 17, or 19-20, or an assay similar thereto.

In a further aspect of the present invention, a method for identifying a compound capable of inhibiting NiRAN-domain mediated activity in a SARS-CoV is provided comprising:

i. contacting the compound with a nsp12 protein of a SARS-CoV in the presence of UTP and/or GTP; and,
ii. measuring the binding of the compound, GTP, and/or UTP to the NiRAN-domain;

wherein a higher level of binding by the compound compared to GTP and/or UTP is indicative of a compound capable of inhibiting NiRAN-domain mediated activity. In some embodiments, the method provides contacting the compound and nsp12 in the presence of UTP. In some embodiments, the method provides contacting the compound and nsp12 in the presence of GTP. In some embodiments, the method provides contacting the compound and nsp12 in the presence of both UTP and GTP. In some embodiments, the method provides contacting the compound and nsp12 in the presence of GTP and/or UTP, wherein GTP and/or UTP are present in a greater concentration than the compound. In some embodiments, the method provides contacting the compound and nsp12 in the presence of GTP and/or UTP, wherein GTP and/or UTP are in equimolar concentrations with the compound. In some embodiments, a compound is identified as a compound capable of inhibiting the NiRAN-domain mediated activity if the compound binds the NiRAN-domain at about 1.25×, 1.5×, 1.75×, 2.0×, 2.25×, 2.5×, 2.75×, 3.0×, 3.25×, 3.5×, or greater than UTP and/or GTP compared to a control wherein the compound is not present. In some embodiments, a compound is identified as a compound capable of inhibiting the NiRAN-domain if the compound binds the NiRAN-domain at 1.5× or greater than GTP compared to when the compound is not present. In some embodiments, a compound is identified as a compound capable of inhibiting the NiRAN-domain if the compound binds the NiRAN-domain at 3.0× or greater than UTP compared to when the compound is not present. In some embodiments, the binding of the compound is determined using an in vitro assay, for example as described in Examples 8-10, 17, 19, or 20, or an assay similar thereto. In some embodiments, a NiRAN interfering compound identified as provided herein is administered to a subject to prevent or treat a SARS-CoV infection. In some embodiments, the SARS-related coronavirus viral infection is SARS-CoV-2. In some embodiments, the SARS-CoV-2 is a mutant/variant form of SARS-CoV-2. In some embodiments, a NiRAN interfering compound identified as provided herein is administered to a subject to prevent or treat COVID-19. In some embodiments, the NiRAN inhibitory compound administered to a subject to prevent or treat a SARS-CoV infection is a or is metabolized to a guanosine-based nucleotide analog. In some embodiments, the compound does not drive or induce further mutations in the targeted SARS-CoV virus, including a SARS-CoV-2 virus, compared to the mutational rate observed in the native viral population.

In another aspect of the present invention, a method for treating or preventing SARS-CoV infection in a host such as a human comprises (a) identifying a compound capable of inhibiting NiRAN-domain mediated activity comprising:

i. contacting the compound with a nsp12 protein and nsp8 protein of a SARS-related coronavirus in the presence of UTP; and, ii. determining whether the compound inhibits the UMPylation of nsp8;

and (b) administering an effective amount of the compound to a host in need thereof; wherein inhibition of UMPylation of nsp8 by the NiRAN-domain by at least 25% or more compared to a control wherein the compound is not present is indicative of a compound capable of inhibiting NiRAN-domain mediated activity. In some embodiments, the selected nucleotide inhibits UMPylation by at least 25%, 30%, 35%, 40%, 45%, 50%, 55%, 60%, 65%, 70%, 75%, 80%, 85%, 90%, or 95%, or greater. In some embodiments, the inhibition is measured using an in vitro assay, for example as described in Examples 8-10, 17, and 19-20, or an assay similar thereto. In some embodiments, the NiRAN inhibitory compound identified is administered to a subject to prevent or treat a SARS-CoV infection. In some embodiments, the SARS-related coronavirus viral infection is SARS-CoV-2. In some embodiments, the SARS-CoV-2 is a mutant/variant form of SARS-CoV-2. In some embodiments, the NiRAN inhibitory compound administered to a subject to prevent or treat a SARS-CoV infection is or is metabolized into a guanosine nucleotide. In some embodiments, the compound does not drive or induce further mutations in the targeted SARS-CoV virus, including a SARS-CoV-2 virus, compared to the mutational rate observed in the native viral population.

In another aspect of the present invention, a method for treating or preventing SARS-CoV infection in a host such as a human comprises (a) identifying a compound capable of inhibiting NiRAN-domain mediated activity comprising:

i. contacting the compound with a nsp12 protein and nsp8 protein of a SARS-related coronavirus in the presence of UTP and/or GTP; and, ii. determining whether the compound inhibits the nucleotidylation of nsp8;

and (b) administering an effective amount of the compound to a host in need thereof; wherein inhibition of nucleotidylation by the NiRAN-domain of at least 25% compared to a control wherein the compound is not present is indicative of a compound capable of inhibiting NiRAN-domain mediated activity. In some embodiments, the selected nucleotide inhibits nucleotidylation by at least 25%, 30%, 35%, 40%, 45%, 50%, 55%, 60%, 65%, 70%, 75%, 80%, 85%, 90%, or 95%, or greater. In some embodiments, the inhibition is measured using an in vitro assay, for example as described in Examples 8-10 and 19-20, or an assay similar thereto. In some embodiments, the method provides contacting the compound, nsp12, and nsp8 in the presence of UTP. In some embodiments, the method provides contacting the compound, nsp12, and nsp8 in the presence of GTP. In some embodiments, the method provides contacting the compound, nsp12, nsp8 in the presence of both UTP and GTP. In some embodiments, the method provides contacting the compound, nsp12, and nsp8 in the presence of GTP and/or UTP, wherein GTP and/or UTP are present in a greater concentration than the compound. In some embodiments, the method provides contacting the compound, nsp12, and nsp8 in the presence of GTP and/or UTP, wherein GTP and/or UTP are in equimolar concentrations with the compound. In some embodiments, the compound reduces nucleotidylation of nsp8 by at least 50%, 60%, 70%, 80%, 90%, 95%, 96%, 97%, 98%, or 99% or more compared to a control wherein the compound is not present. In some embodiments, the NiRAN inhibitory compound identified is administered to a subject to prevent or treat a SARS-CoV infection. In some embodiments, the SARS-related coronavirus viral infection is SARS-CoV-2. In some embodiments, the SARS-CoV-2 is a mutant/variant form of SARS-CoV-2. In some embodiments, the NiRAN inhibitory compound administered to a subject to prevent or treat a SARS-CoV infection is or is metabolized into a guanosine nucleotide. In some embodiments, the compound does not drive or induce further mutations in the targeted SARS-CoV virus, including a SARS-CoV-2 virus, compared to the mutational rate observed in the native viral population.

In yet another aspect of the present invention, a method for treating or preventing COVID 19 and/or a SARS-CoV infection is provided comprising (a) identifying a compound capable of inhibiting NiRAN-domain mediated activity in a SARS-related coronavirus comprising:

i. contacting the compound with a nsp12 and nsp8 protein of a SARS-related coronavirus in the presence of UTP and/or GTP; and, ii. determining whether the compound inhibits the transfer of UTP and/or GTP from nsp12 to nsp8;

and (b) administering an effective amount of the compound to a host in need thereof;

wherein inhibition of the transfer of UTP and/or GTP by the NiRAN-domain by at least 25% or more compared to a control wherein the compound is not present is indicative of a compound capable of inhibiting NiRAN-domain mediated activity. In some embodiments, the method provides contacting the compound and nsp12 and nsp8 in the presence of UTP. In some embodiments, the method provides contacting the compound and nsp12 and nsp8 in the presence of GTP. In some embodiments, the method provides contacting the compound and nsp12 and nsp8 in the presence of both UTP and GTP. In some embodiments, the method provides contacting the compound and nsp12 and nsp8 in the presence of GTP and/or UTP, wherein GTP and/or UTP are present in a greater concentration than the compound. In some embodiments, the method provides contacting the compound and nsp12 and nsp8 in the presence of GTP and/or UTP, wherein GTP and/or UTP are in equimolar concentrations with the compound. In some embodiments, a compound is identified as capable of inhibiting NiRAN-domain activity if the compound reduces transfer of GTP and/or UTP from nsp12 to nsp8 by at least 50%, 60%, 70%, 80%, 90%, 95%, 95%, 97%, 98%, 99% or more compared to a control wherein the compound is not present. In some embodiments, the inhibition is measured using an in vitro assay, for example as described in Examples 8-10, 17, and 19-20, or an assay similar thereto. In some embodiments, the NiRAN inhibitory compound identified is administered to a subject to prevent or treat a SARS-CoV infection. In some embodiments, the SARS-related coronavirus viral infection is SARS-CoV-2. In some embodiments, the SARS-CoV-2 is a mutant/variant form of SARS-CoV-2. In some embodiments, the NiRAN inhibitory compound administered to a subject to prevent or treat a SARS-CoV infection is or is metabolized into a guanosine nucleotide. In some embodiments, the compound does not drive or induce further mutations in the targeted SARS-CoV virus, including a SARS-CoV-2 virus, compared to the mutational rate observed in the native viral population.

In a further aspect of the present invention, a method for treating or preventing a SARS-CoV infection is provided that includes (a) identifying compounds capable of inhibiting protein primed RNA synthesis in a SARS-related coronavirus comprising:

i. contacting the compound with nsp12, nsp7, and nsp8 proteins of a SARS-related coronavirus in the presence of UTP and a poly(A) RNA template; and ii. determining whether the compound inhibits primer independent RNA synthesis on the poly(A) RNA template in the presence of UTP;

and (b) administering an effective amount of the compound to a host in need thereof; wherein the inhibition of primer independent RNA synthesis on the poly(A) RNA template in the presence of UTP by at least 25% or more compared to a control wherein the compound is not present is indicative of a compound capable of inhibiting primer independent RNA synthesis. In some embodiments, the method provides nsp12, nsp7, and nsp8 as a nsp12:nsp7-nsp8 complex. In some embodiments, the method provides nsp12, nsp7, and nsp8 as a nsp12:7L8:8 polymerase complex. In some embodiments, the method provides nsp12:7L8:8 polymerase complex in a 1:3:3 molar ratio. In some embodiments, nsp12, nsp7, and nsp8 polymerase complex is in a 1:3:6 molar ratio. In some embodiments, nsp12:7L8:8 polymerase complex is in a 1:3:6 molar ratio. In some embodiments, a compound is identified as capable of inhibiting primer independent RNA synthesis if the compound reduces primer independent RNA synthesis of the poly(A) RNA template by at least 50%, 60%, 70%, 80%, 90%, 95%, 96%, 97%, 98%, 99% or more compared to a control wherein the compound is not present. In some embodiments, the NiRAN inhibitory compound identified is administered to a subject to prevent or treat a SARS-CoV infection. In some embodiments, the SARS-related coronavirus viral infection is SARS-CoV-2. In some embodiments, the SARS-CoV-2 is a mutant/variant form of SARS-CoV-2. In some embodiments, the NiRAN inhibitory compound administered to a subject to prevent or treat a SARS-CoV infection is or is metabolized to a guanosine nucleotide.

In a following aspect, a method of treating or preventing a SARS-CoV infection in a host is provided that comprises: (a) identifying a compound capable of inhibiting SARS-CoV replication in a subject is provided, comprising:

i. selecting a nucleotide;

ii. screening the nucleotide to determine whether the compound inhibits the NiRAN-domain mediated activity of the virus; and (b) administering an effective amount of the compound to a host in need thereof;

wherein the compound is determined to inhibit NiRAN activity if it inhibits by at least 25% or more compared to a control wherein the compound is not present one or more of: a) NiRAN-domain mediated nsp8 UMPylation; b) NiRAN-domain mediated nucleotidylation of nsp8; c) inhibits transfer of UMP from the NiRAN-domain of nsp12 to nsp8; d) inhibits the transfer of a nucleotide from the NiRAN-domain of nsp12 to nsp8; e) NiRAN-domain mediated protein primed RNA synthesis; f) preferentially binds to the NiRAN-domain of nsp12 over native UTP and GTP; g) preferentially binds to the NiRAN-domain at least about 3-fold over native UTP when assayed in a 1:1 ratio; h) preferentially binds to the NiRAN-domain at least about 1.5-fold over native GTP when assayed in a 1:1 ratio; i) binds the invariant lysine residue K73 in the NiRAN-domain; or a combination thereof. In some embodiments, the NiRAN inhibitory compound is a selected guanosine nucleotide. In some embodiments, the NiRAN inhibitory compound is a stabilized phosphate prodrug. In some embodiments, the NiRAN-domain mediated inhibiting compound identified is administered to a subject to prevent or treat a SARS-CoV infection. In some embodiments, the SARS-related coronavirus viral infection is SARS-CoV-2. In some embodiments, the SARS-CoV-2 is a mutant/variant form of SARS-CoV-2. In alternative embodiments, the compound remains bound to the NiRAN active site and is not transferred to nsp8. In some embodiments, the compound also inhibits or prevents the UMPylation by the NiRAN-domain of nsp9. In some embodiments, the NiRAN inhibitory compound administered to a subject to prevent or treat a SARS-CoV infection is or is metabolized to a selected guanosine nucleotide. In some embodiments, the compound does not drive or induce further mutations in the targeted SARS-CoV virus, including a SARS-CoV-2 virus, compared to the mutational rate observed in the native viral population. In some embodiments, a compound is identified as capable of inhibiting NiRAN mediated activity if the compound inhibits NiRAN-domain mediated activity by at least 50%, 60%, 70%, 80%, 90%, 95%, 95%, 97%, 98%, 99% or more compared to a control wherein the compound is not present.

In a following aspect, a method of treating or preventing a SARS-CoV infection in a host is provided that comprises: (a) identifying a compound capable of inhibiting SARS-CoV infection in a subject is provided, comprising:

i. selecting a nucleotide;

ii. screening the nucleotide to determine whether the compound inhibits NiRAN-domain mediated protein primed RNA synthesis; and (b) administering an effective amount of the compound to a host in need thereof;

wherein the compound is determined to inhibit NiRAN-domain mediated protein primed RNA synthesis, and thus capable of inhibiting SARS-CoV infection, if it inhibits by at least 25% or more NiRAN-domain mediated protein primed RNA synthesis compared to a control wherein the compound is not present. In some embodiments, a compound is identified as capable of inhibiting NiRAN mediated protein primed RNA synthesis if the compound inhibits NiRAN-domain mediated protein primed RNA synthesis by at least 50%, 60%, 70%, 80%, 90%, 95%, 95%, 97%, 98%, 99% or more compared to a control wherein the compound is not present. In some embodiments, the SARS-related coronavirus viral infection is SARS-CoV-2. In some embodiments, the SARS-CoV-2 is a mutant/variant form of SARS-CoV-2. In some embodiments, the compound administered to a subject to prevent or treat a SARS-CoV infection is a selected guanosine nucleotide.

In another aspect, a method for treating or preventing a SARS-CoV infection in a subject is provided comprising:

i) determining whether the subject has a SARS-CoV infection;

ii) identifying a compound having NiRAN inhibitory activity, wherein a compound that inhibits NiRAN-domain mediated activity by at least 25% or more compared to a control wherein the compound is not present is indicative of a compound having NiRAN inhibitory activity; and, iii) administering to the subject an effective amount of the NiRAN inhibitory compound.

In some embodiments, the NiRAN inhibitory compound inhibits NiRAN mediated activity nsp8 UMPylation. In some embodiments, the NiRAN inhibitory compound inhibits NiRAN mediated activity nsp8 nucleotidylation. In some embodiments, the NiRAN inhibitory compound inhibits transfer of a nucleotide from the NiRAN-domain of nsp12 to nsp8. In some embodiments, the NiRAN inhibitory compound inhibits NiRAN-domain mediated protein primed RNA synthesis. In some embodiments, the NiRAN inhibitory compound inhibits protein primed RNA synthesis and RdRP-mediated de novo primer-independent RNA synthesis. In some embodiments, the NiRAN inhibitory compound inhibits protein primed RNA synthesis and primer-dependent RNA chain extension. In some embodiments, the NiRAN inhibitory compound preferentially binds to the NiRAN-domain of nsp12 over native UTP and GTP. In some embodiments, the NiRAN inhibitory compound preferentially binds to the NiRAN-domain at least about 3-fold over native UTP when assayed in a 1:1 ratio. In some embodiments, the NiRAN inhibitory compound preferentially binds to the NiRAN-domain at least about 1.5-fold over native GTP when assayed in a 1:1 ratio. In some embodiments, the NiRAN inhibitory compound binds the invariant lysine residue K73 in the NiRAN-domain. In some embodiments, the NiRAN inhibitory compound is a selected nucleotide. In some embodiments, the NiRAN inhibitory compound is a selected guanosine nucleotide. In some embodiments, the NiRAN inhibitory compound is a stabilized phosphate prodrug. In some embodiments, the SARS-related coronavirus viral infection is SARS-CoV-2. In some embodiments, the SARS-CoV-2 is a mutant/variant form of SARS-CoV-2. In some embodiments, the NiRAN inhibitory compound administered to a subject to prevent or treat a SARS-CoV infection is a selected guanosine nucleotide.

Also provided herein is a method of inhibiting NiRAN-domain activity in a SARS-CoV comprising contacting the coronavirus with a NiRAN interfering compound, wherein the NiRAN interfering compound acts by a) inhibiting NiRAN mediated nsp8 UMPylation; b) inhibiting NiRAN mediated nsp8 nucleotidylation; c) inhibiting transfer of a nucleotide from the NiRAN-domain of nsp12 to nsp8; d) inhibiting NiRAN-domain mediated protein primed RNA synthesis; e) preferentially binding to the NiRAN-domain of nsp12 over native UTP and GTP; f) preferentially binding to the NiRAN-domain at least about 3-fold over native UTP when assayed in a 1:1 ratio; g) preferentially binding to the NiRAN-domain at least about 1.5-fold over native GTP when assayed in a 1:1 ratio; or h) binding the invariant lysine residue K73 in the NiRAN-domain; or a combination thereof.

In some embodiments, the NiRAN-inhibitory compound is capable of also inhibiting NiRAN-independent de novo dinucleotide synthesis. In some embodiments, the compound is capable of inhibiting a SARS-CoV viral RTC (nsp12:nsp7L8:nsp8) from synthesizing a 5' triphosphate dinucleotide primer. In some embodiments, the dinucleotide primer is pppGpU. In some embodiments, the NiRAN-inhibitory compound is capable of inhibiting poly(U) synthesis from a heteropolymeric RNA corresponding to the last 20 nucleotides of the 3'-end of the SARS-CoV genome (ST20) in the presence of a poly(A) tail template and pppNpN dinucleotide, for example, a pppGpU dinucleotide The NiRAN interfering compounds described herein or identified by the methods described herein can be used to treat or prevent SARS-CoV infections, including SARS-CoV-2 infections in a human, and disorders caused thereby, including but not limited to drug resistant and multidrug resistant forms of the virus and related disease states, conditions, or complications of the viral infection, including pneumonia, such as 2019 novel coronavirus-infected pneumonia (NCIP), acute lung injury (ALI), and acute respiratory distress syndrome (ARDS). Additional non-limiting complications caused by SARS-CoV-2 that can be treated or prevented using the NiRAN-interfering compounds described herein include hypoxemic respiratory failure, acute respiratory failure (ARF), acute liver injury, acute cardiac injury, acute kidney injury, septic shock, disseminated intravascular coagulation, blood clots, multisystem inflammatory syndrome, chronic fatigue, rhabdomyolysis, and cytokine storm.

The NiRAN interfering compounds or their pharmaceutically acceptable salts as described herein can be administered in addition to the current standard of care for patients suffering from a SARS-CoV, e.g., COVID-19 patients, or in combination or alternation with any other compound or therapy that the healthcare provider deems beneficial to the patient, as described in more detail below. The combination and/or alternation therapy can be preventative, therapeutic, adjunctive, or palliative.

DETAILED DESCRIPTION OF THE INVENTION

Figure 1:
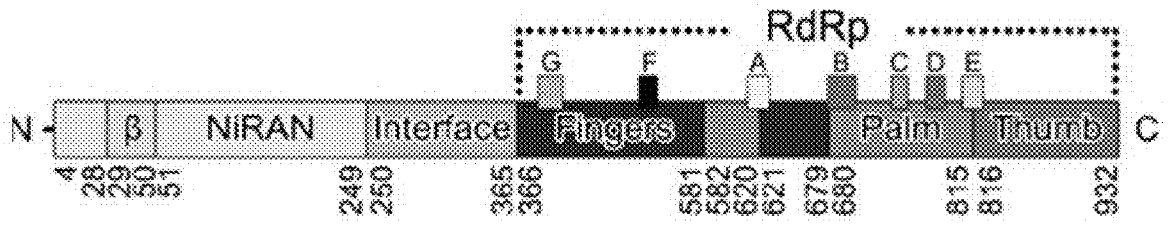
FIG. 1 Diagram of SARS-CoV-2 nsp12 with conserved motifs in each domain (adapted from Gao et al., Structure of the RNA-dependent RNA polymerase from COVID-19. Science 10.1126/science.abb7498 (2020).

Severe Acute Respiratory Syndrome coronavirus type 2 (SARS-CoV-2) is a human pathogen of the Coronaviridae (CoV) family, order Nidovirales, responsible for the ongoing pandemic which has so far resulted in over 2.5 million fatalities (https://covid19.who.int/). This has prompted large-scale, global research efforts. Much remains to be learned regarding the specific mechanisms directing CoV replication and transcription of viral RNA, of direct importance for appropriate antiviral strategies.

Having ~30,000 nt, the CoV positive-sense RNA (+RNA) genome is approximately three-times larger than that of significant human pathogenic+RNA viruses such as dengue, zika and poliovirus. This size difference reflects the acquisition of novel domains, many of which remain poorly characterized despite being potential candidates for CoV-specific drug targets. The viral genome is principally comprised of two-large open reading frames, Orfla and Orflab, which are translated to yield 16 non-structural proteins (nspl-nsp16) responsible for viral replication and genome maintenance (Hartenian et al. J Biol Chem. 2020 Sep. 11; 295(37): 12910-12934). Among these is the viral RNA-dependent-RNA polymerase (RdRp, nsp12), which associates with two small cofactor proteins, nsp7 and nsp8, to form the minimal replication-transcription complex (RTC) capable of RNA synthesis (Subissi et al. Proc Natl Acad Sci USA. 2014 Sep. 16; 111(37): E3900-E3909; Kirchdoerfer et al., (2019) Nat Commun. May 28; 10(1):2342). The 3' end of the CoV genome specifies a nested set of subgenomic mRNAs which are translated to yield structural and accessory proteins.

Once expressed in the target cell, the viral RdRp and associated proteins must diligently initiate viral RNA synthesis at precise termini to ensure all the genetic information is copied. RNA viruses have evolved a diverse range of initiation strategies, often dictated by subtle structural variations in the RdRp. Initiation is commonly divided into two main categories; de novo (primer-independent), and primer-dependent. However, specific mechanisms within these broadly defined groups can vary considerably. In the case of CoVs, the mechanism for initiation of RNA synthesis is poorly understood and controversial. The viral protein nsp8 has been considered in this process, since it has been reported to synthesize short priming oligonucleotides (Imbert et al., A second, non-canonical RNA-dependent RNA polymerase in SARS coronavirus. EMBO J. 2006 Oct. 18; 25(20):4933-42), as well as performing adenosine-specific terminal transferase (Tvarogova et al. J Virol. 2019 May 29; 93(12): e00291-19), and primer-extension activity (Te Velthuis et al. Nucleic Acids Res. 2012 February; 40(4): 1737-47). On a structural level, the CoV RdRp is related to "small-thumb" RNA polymerases, such as those of Picornaviridae (Peersen. Virus Res. 2017 Apr. 15; 234: 4-20). These polymerases prime RNA synthesis through a 'protein-primed' mechanism (Paul et al. Virus Res. 2015 Aug. 3; 206: 12-26), whereby a tyrosine hydroxyl group of a small viral peptide, known as VPg (Viral Protein genome-linked) is first covalently labeled with a uridine monophosphate (referred to as UMPylation). The VPg-pU is then extended to a dinucleotide and used to prime RNA synthesis, yielding genomic RNA which remains covalently linked to the viral VPg. Notably, the N-terminus of CoV nsp12 (just upstream of the RdRp) contains a Nidovirus-specific domain known as the NiRAN, which has been shown to mediate the covalent transfer of nucleotide monophosphates (NMP) to various viral cofactor proteins (Lehmann et al., Nucleic Acids Research, Volume 43, Issue 17, 30 Sep. 2015, Pages 8416-8434; Slanina et al., PNAS Feb. 9, 2021 118 (6) e2022310118; Conti et al., (2020) doi: https://doi.org/10.1101/2020.10.07.330324).

Certain nucleotides are metabolized by cellular kinases into active 5'-triphosphate forms which compete with native nucleotide triphosphates (NTP) for incorporation into the viral RNA by the RdRp. Upon incorporation, these nucleotides cause either chain-termination of RNA synthesis, or act as mutagenic nucleotides lethally altering the genetic make-up of the virus. However, CoVs stand out among RNA viruses for possessing an RNA-repair 3'-to-5' exonuclease (ExoN, nsp14) able to excise mismatched bases as well as chain terminating nucleotides (Minskaia et al., PNAS 2006 Mar. 28; 103(13):5108-13; Eckerle et al., J Virol 81: 12135-12144; Eckerle et al., (2010) PLOS Pathogens 6(5): e1000896; Bouvet et al., PNAS Jun. 12, 2012 109 (24) 9372-9377; Ferron PNAS. 2018 Jan. 9; 115(2): E162-E171), generally compromising the efficacy of these drugs.

The present invention is based on the fundamental discovery of the role of the NiRAN-domain of SARS-CoV in the initiation of viral RNA synthesis, and the ability of this domain to be targeted by certain nucleotides to inhibit viral replication. It is now discovered and established that the CoV nsp7-(nsp8)2-nsp12 minimal RTC can initiate RNA synthesis through two distinct pathways; one protein-primed and mediated by the NiRAN-domain through the UMPylation of nsp8, and the other through de novo synthesis of dinucleotide primers in a NiRAN-independent fashion. The inhibition of both NiRAN transferase activity and de novo synthesis is accomplished AT-9010, the active triphosphate of the prodrug AT-527 (Compound 2A), as well as other nucleotides that act on NiRAN in a similar way. The discoveries allow for the development of methods for identifying compounds useful to treat SARS-CoV-2 infections, including SARS-CoV-2 mutant strains that may be resistant, or prone to developing resistance, to current treatments.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

"Alkyl" is a straight chain or branched saturated aliphatic hydrocarbon group. In certain embodiments, the alkyl is $C_1$-$C_2$, $C_1$-$C_3$, $C_1$-$C_4$, $C_1$-$C_5$, or $C_1$-$C_6$ (i.e., the alkyl chain can be 1, 2, 3, 4, 5, or 6 carbons in length). The specified ranges as used herein indicate an alkyl group with length of each member of the range described as an independent species. For example, $C_1$-$C_6$ alkyl as used herein indicates an alkyl group having from 1, 2, 3, 4, 5, or 6 carbon atoms and is intended to mean that each of these is described as an independent species and $C_1$-$C_4$alkyl as used herein indicates an alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane and 2,3-dimethylbutane.

"Cycloalkyl" is a saturated mono-cycle hydrocarbon ring system. Non-limiting examples of cycloalkyl groups include cyclopropyl, cyclobutyl, cyclopentyl, and cyclohexyl.

"Haloalkyl" is an alkyl group in which one or more of the hydrogen atoms are replaced with a halogen (e.g., mono-haloalkyl, di-haloalkyl, and tri-haloalkyl). Non-limiting examples include chloromethyl, fluoromethyl, difluoromethyl, trifluoromethyl, 1-chloro-2-fluoromethyl, and 2-fluoroisobutyl. A haloalkyl may be further substituted.

"Aryl" indicates aromatic groups containing only carbon in the aromatic ring or rings. In some embodiments, the aryl groups contain 1 to 3 separate or fused rings and is 6 to about 14 or 18 ring atoms, without heteroatoms as ring members. Aryl groups include, for example, phenyl and naphthyl, including 1-naphthyl and 2-naphthyl. In some embodiments, aryl groups are pendant. An example of a pendant ring is a phenyl group substituted with a phenyl group. In some embodiments, the aryl group is optionally substituted as described above. In some embodiments, aryl groups include, for example, dihydroindole, dihydrobenzofuran, isoindoline-1-one and indolin-2-one.

"Aryl(alkyl)-" is an alkyl group as described herein substituted with an aryl group as described herein. Examples include benzyl, 2-phenyl(alkyl), 3-phenyl(alkyl), and napthyl(alkyl).

"Heteroaryl" refers to a stable monocyclic, bicyclic, or multicyclic aromatic ring which contains from 1 to 3, or in some embodiments from 1, 2, or 3 heteroatoms selected from N, O, S, B, and P (and typically selected from N, O, and S) with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B or P with remaining ring atoms being carbon. In some embodiments, the only heteroatom is nitrogen. In some embodiments, the only heteroatom is oxygen. In some embodiments, the only heteroatom is sulfur. Monocyclic heteroaryl groups typically have from 5 or 6 ring atoms. When the total number of S and O atoms in the heteroaryl group exceeds 1, these heteroatoms are not adjacent to one another. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl.

The term "heteroalkyl" refers to an alkyl or haloalkyl moiety as defined herein wherein a $CH_2$ group is either replaced by one or more heteroatoms or a carbon atom is substituted with one or more heteroatoms for example, an amine, carbonyl, carboxy, oxo, thio, phosphate, phosphonate, nitrogen, phosphorus, silicon, or boron. In some embodiments, the only heteroatom is nitrogen. In some embodiments, the only heteroatom is oxygen. In some embodiments, the only heteroatom is sulfur. In some embodiments, "heteroalkyl" is used to indicate a heteroaliphatic group (cyclic, acyclic, substituted, unsubstituted, branched or unbranched) having 1-6 carbon atoms.

Unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting.

A "patient" or "host" or "subject" is a human or non-human animal in need of treatment or prevention of a SARS-CoV infection. Typically, the host is a human. A "patient" or "host" or "subject" also refers to, for example, a mammal, primate (e.g., human), cow, sheep, goat, horse, dog, cat, rabbit, rat, mice, bird and the like.

The term "prophylactic" or "preventative" when used refers to the administration of an active NiRAN inhibitory compound to prevent, reduce the likelihood of an occurrence or a reoccurrence of a SARS-CoV infection such as SARS-CoV-1 or SARS-CoV-2, or to minimize a new infection relative to infection that would occur without such treatment. The present invention includes both treatment and prophylactic or preventative therapies. In some embodiments, the active NiRAN inhibitory compound is administered to a host who has been exposed to and is thus at risk of contracting a SARS-CoV infection such as SARS-CoV-1 or SARS-CoV-2. In another alternative embodiment, a method to prevent transmission is provided that includes administering an effective amount of one of the compounds described herein to humans for a sufficient length of time prior to exposure to crowds that can be infected, including during travel or public events or meetings, including for example, up to 3, 5, 7, 10, 12, 14 or more days prior to a communicable situation.

The terms "coadminister," "coadministration," or "in combination" are used to describe the administration of a NiRAN interfering compound in combination with at least one other antiviral active agent. The timing of the coadministration is best determined by the medical specialist treating the patient. It is sometimes desired that the agents are administered at the same time. Alternatively, the drugs selected for combination therapy are administered at different times to the patient. Of course, when more than one viral or other infection or other condition is present, the present compounds may be combined with other agents to treat that other infection or condition as required.

NiRAN interfering compounds identified through the methods described herein can be administered to a subject as a pharmaceutically acceptable salt thereof. A "pharmaceutically acceptable salt" is an ionic form of the disclosed compound in which the parent compound is modified to an inorganic and organic, acid or base addition salt thereof without undue toxicity. The salts of the present compounds can be synthesized from the parent compound with a basic or acidic moiety by known chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds may optionally be provided in the form of a solvate.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the salts and the quaternary ammonium salts of the parent compound formed, for example, from inorganic or organic acids that are not unduly toxic. For example, acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

The compound can be delivered in any molar ratio of salt that delivers the desired result. For example, the compound can be provided with less than a molar equivalent of a counter ion, such as in the form of a hemi-sulfate salt. Alternatively, the compound can be provided with more than a molar equivalent of counter ion, such as in the form of a di-sulfate salt. Non-limiting examples of molar ratios of the compound to the counter ion include 1:0.25, 1:0.5, 1:1, and 1:2.

Compounds to Treat or Prevent Infection by Mutant or Resistant Forms of SARS-Related Coronaviruses, Including SARS-CoV-2

In one aspect, the invention disclosed herein includes a method to disrupt NiRAN function in a coronavirus or for the treatment or prevention of a mutant or resistant form of the SARS-CoV-2 virus in a host, for example a human, in need thereof comprising administering an effective amount of a compound of Formula I or a pharmaceutically acceptable salt thereof:

Formula I

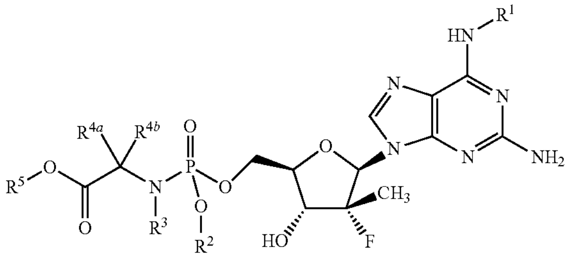

wherein $R^1$ is selected from $C_1$-$C_6$alkyl, $C_3$-$C_6$cycloalkyl, and —$C(O)C_1$-$C_6$alkyl;

$R^2$ is hydrogen, $C_{1-6}$alkyl (including methyl, ethyl, propyl, and isopropyl), $C_{3-7}$cycloalkyl, aryl (including phenyl and napthyl), aryl($C_1$-$C_4$alkyl)-, heteroaryl, or heteroalkyl;

$R^3$ is hydrogen or $C_{1-6}$alkyl (including methyl, ethyl, propyl, and isopropyl);

$R^{4a}$ and $R^{4b}$ are independently selected from hydrogen, $C_{1-6}$alkyl (including methyl, ethyl, propyl, and isopropyl), and $C_{3-7}$cycloalkyl; and $R^5$ is hydrogen, $C_{1-6}$alkyl (including methyl, ethyl, propyl, and isopropyl), $C_{1-6}$haloalkyl, $C_{3-7}$cycloalkyl, aryl($C_1$-$C_4$alkyl)-, aryl, heteroaryl, or heteroalkyl.

In certain embodiments, $R^1$ is not $C_1$-$C_6$alkyl. In certain embodiments, $R^1$ is not methyl. In certain embodiments, $R^2$ is not aryl. In certain embodiments, $R^2$ is not phenyl. In certain embodiments, $R^3$ is not hydrogen. In certain embodiments, $R^{4a}$ and $R^{4b}$ are not selected from hydrogen and $C_{1-6}$alkyl. In certain embodiments, $R^{4a}$ and $R^{4b}$ are not selected from hydrogen and methyl. In certain embodiments, $R^5$ is not $C_{1-6}$alkyl. In certain embodiments, $R^5$ is not isopropyl.

Non-limiting examples of a compound of Formula I include Compound 1 and Compound 2. In some embodiments, the compounds are administered as the S-enantiomer, such as Compound 1A. In some embodiments, the compounds are administered as the R-enantiomer, such as Compound 1B. In some embodiments, a compound of Formula I is Compound 2, Compound 2A, or Compound 2B.

Compound 1

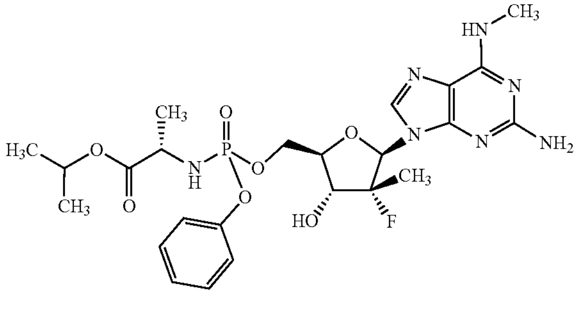

-continued

Compound 2

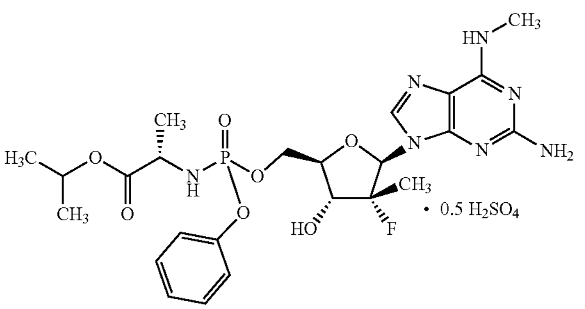

Compound 1A

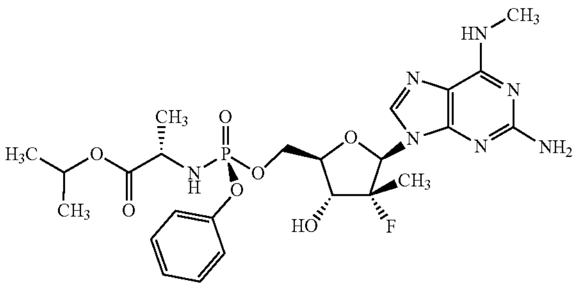

Compound 1B

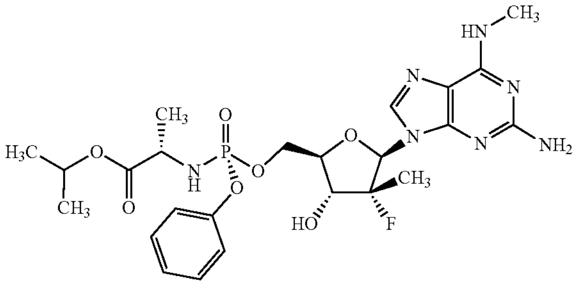

Compound 2A

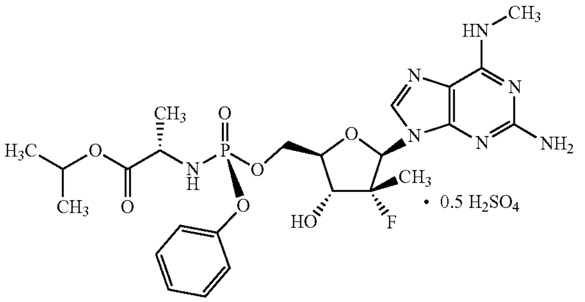

Compound 2B

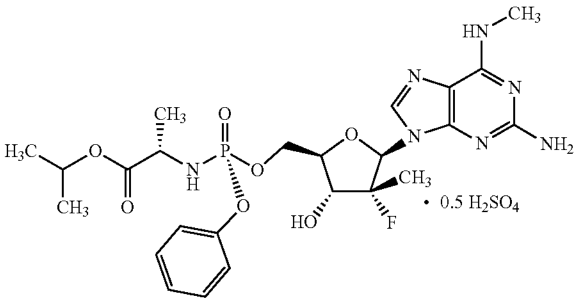

Alternative configurations of Compound 1 or a pharmaceutically acceptable salt thereof that can be used include:

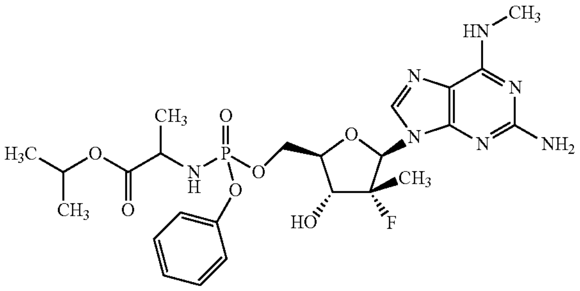
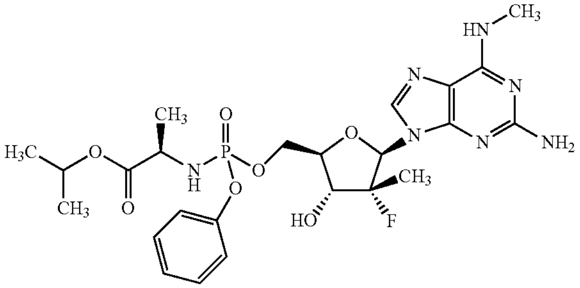
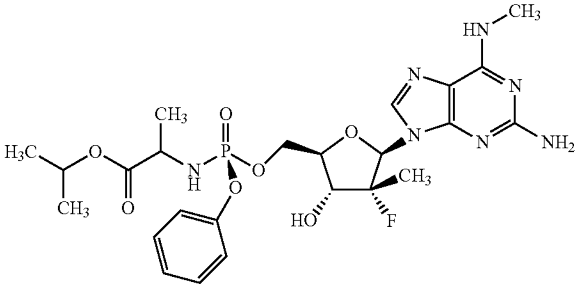
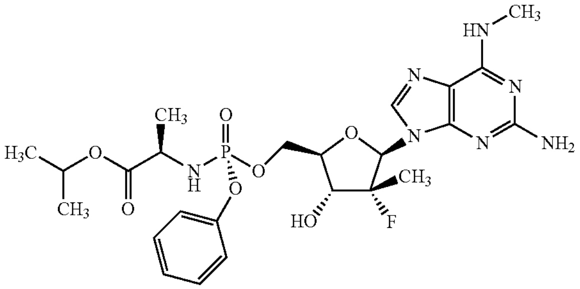
Alternative configurations of Compound 2 that can be used include:
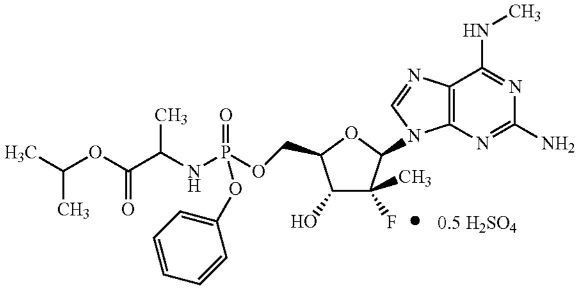
-continued
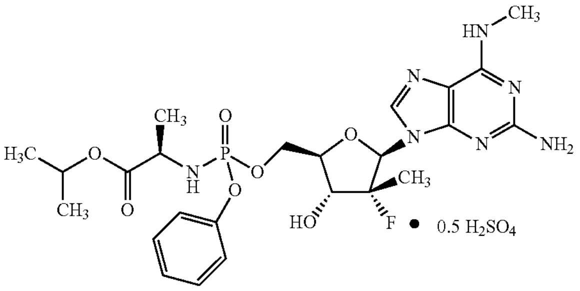
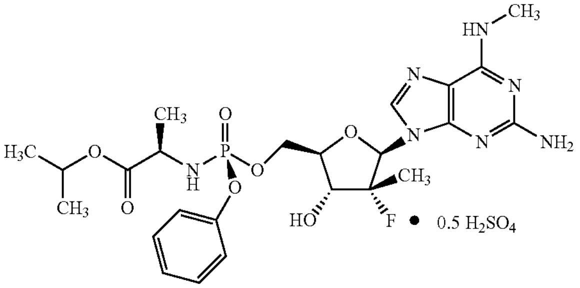
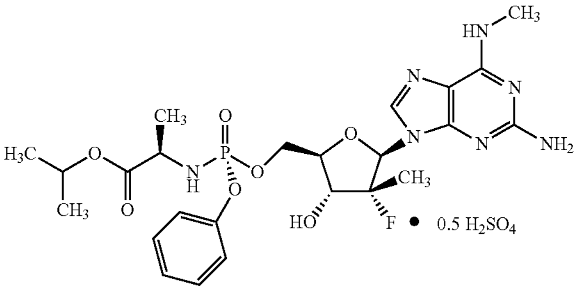
Non-limiting examples of a compound of Formula I include:
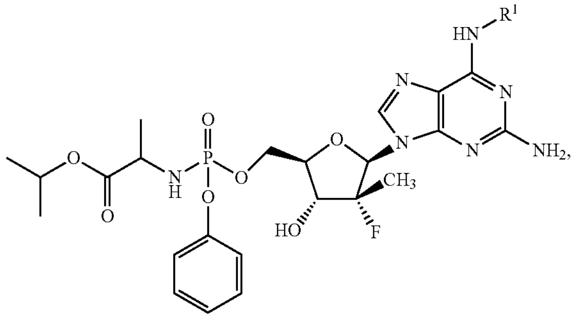
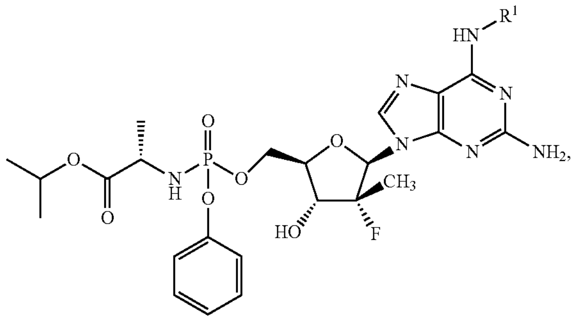

-continued
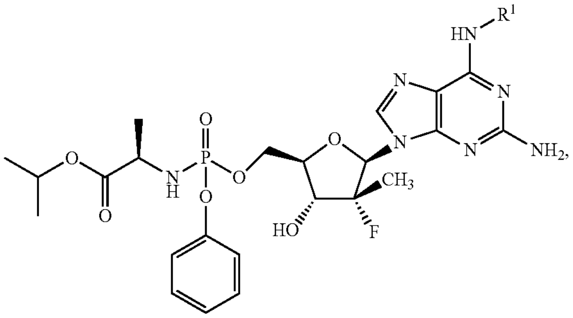
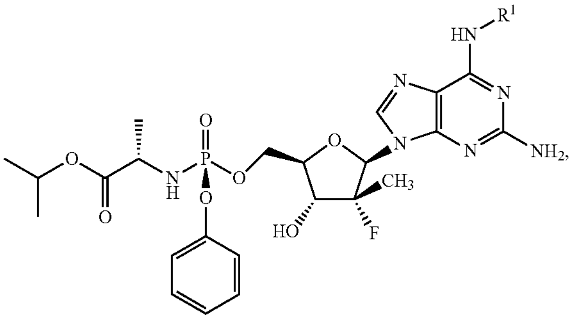
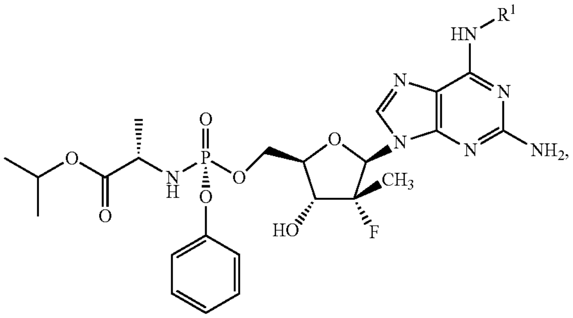
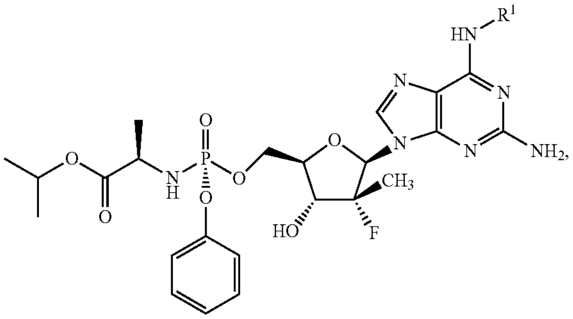
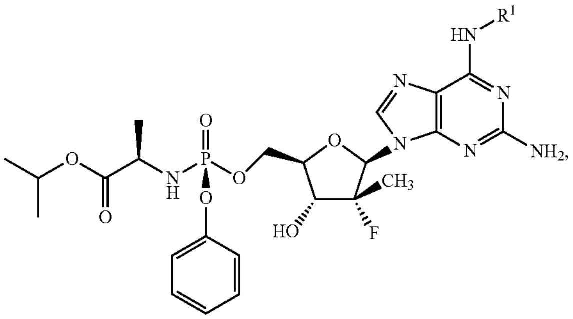
-continued
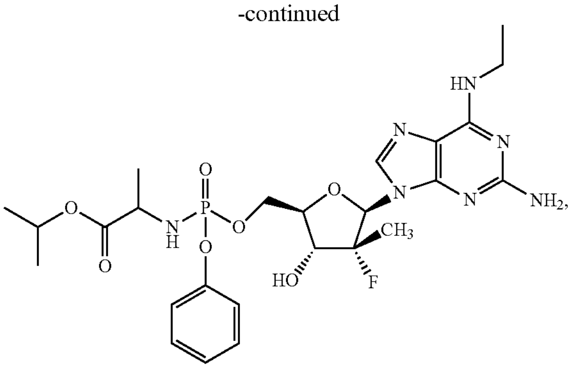
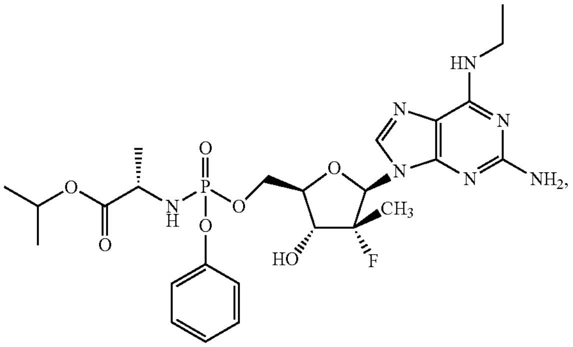
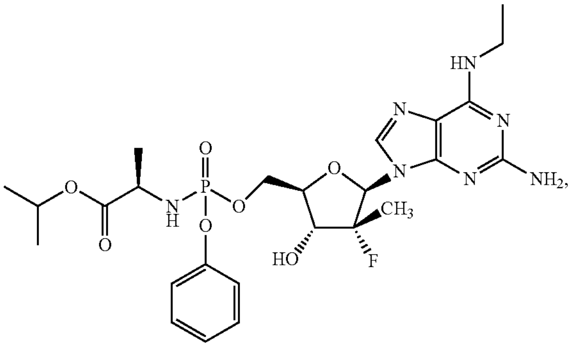
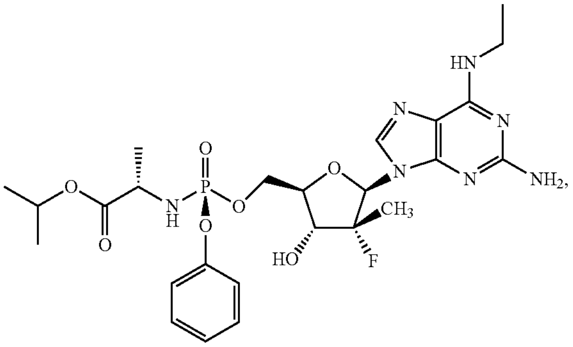
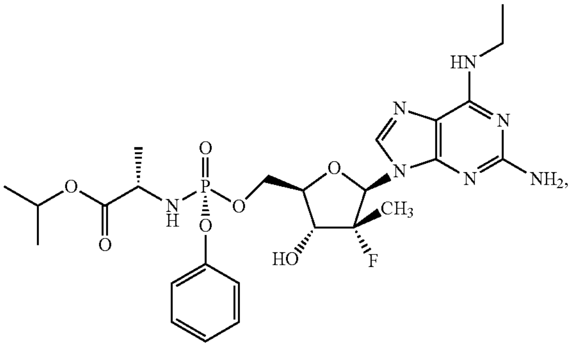

-continued
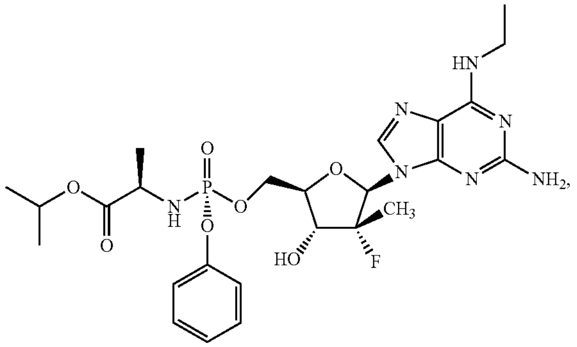
,
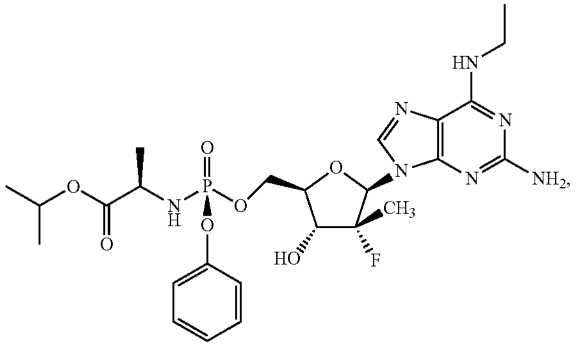
,
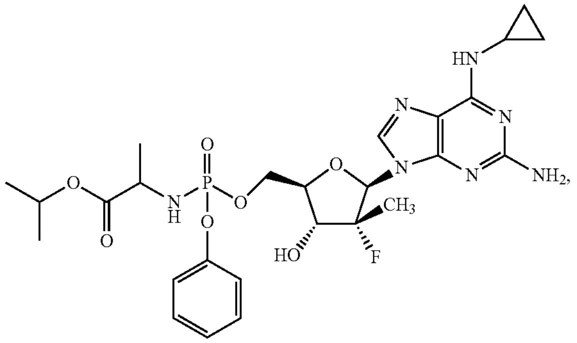
,
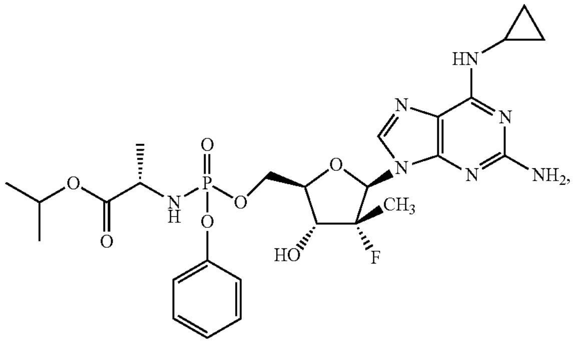
,
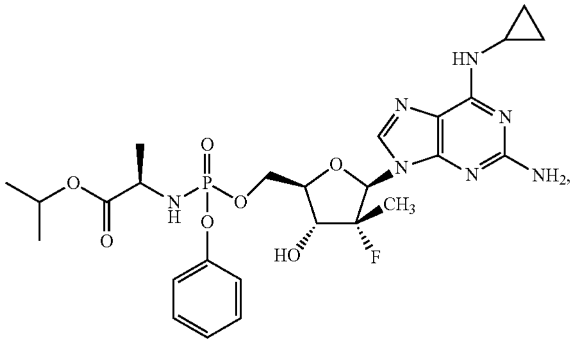
,
-continued
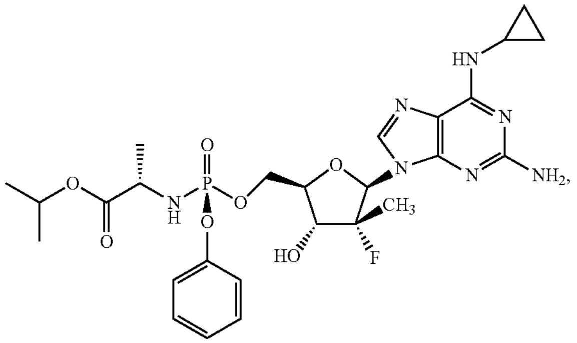
,
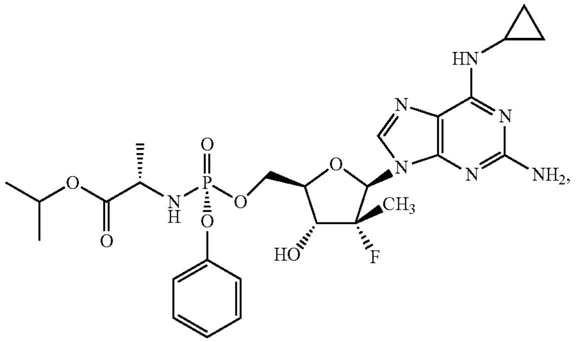
,
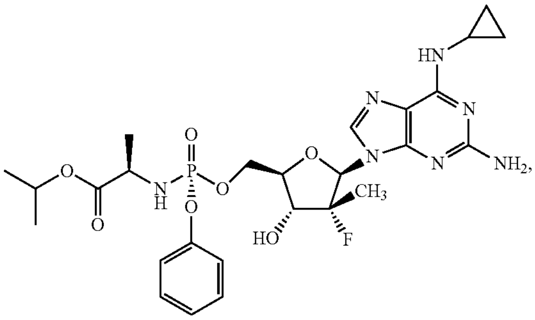
, and
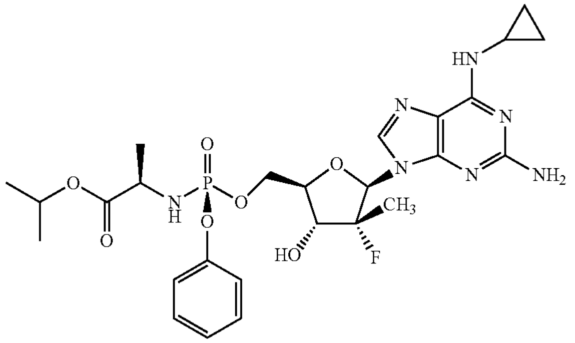
or a pharmaceutically acceptable salt thereof.

Additional non-limiting examples of a compound of Formula I include:
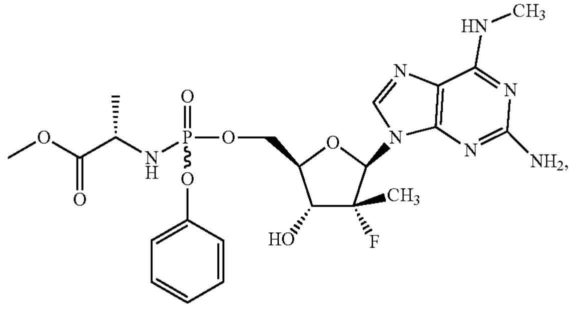
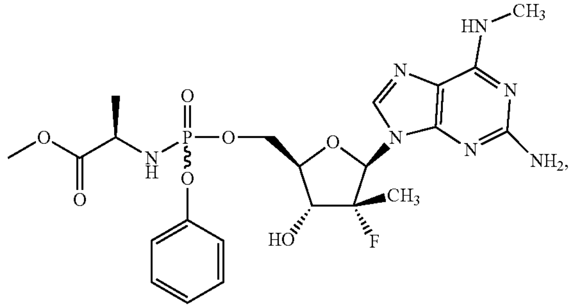
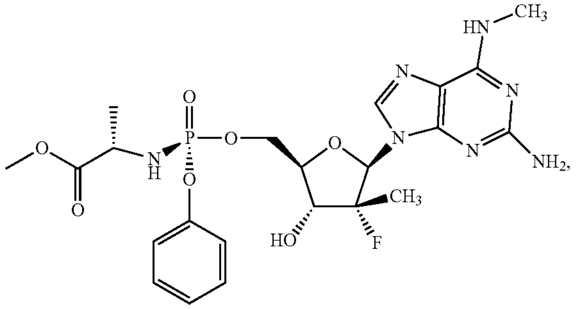
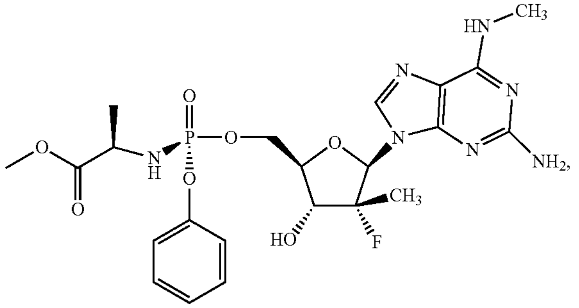
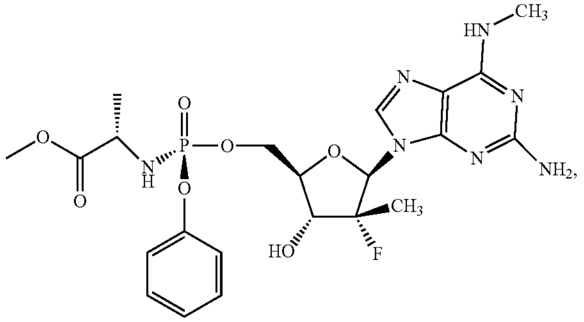
-continued
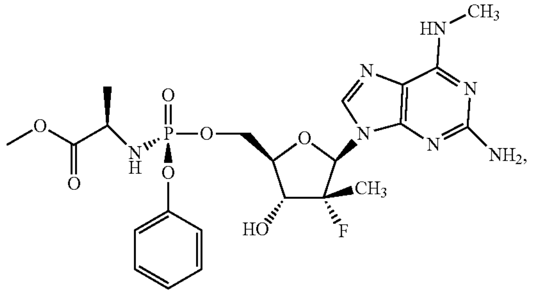
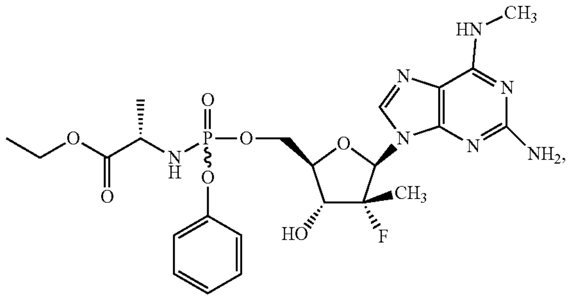
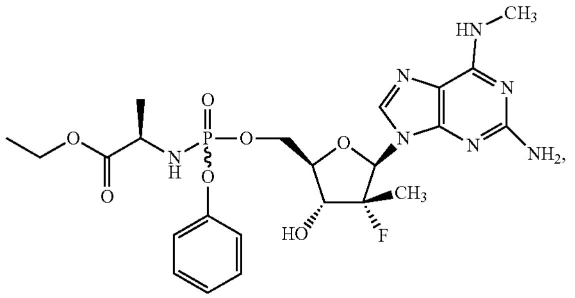
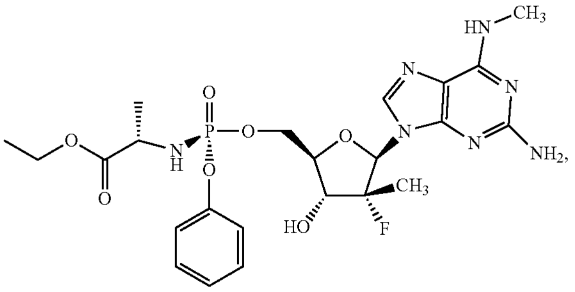
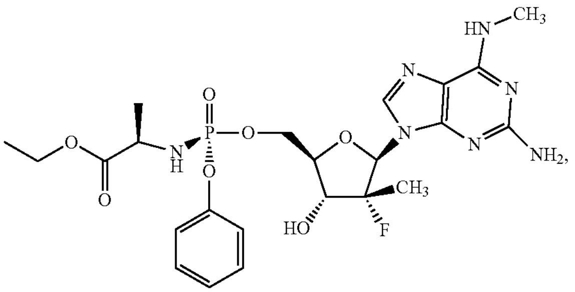

-continued
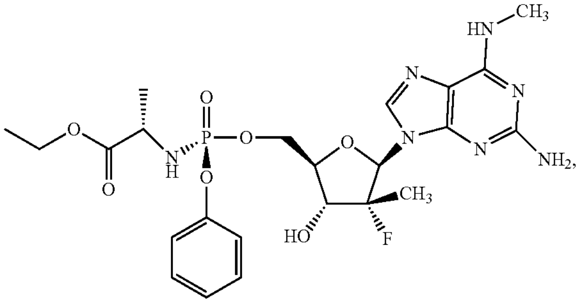
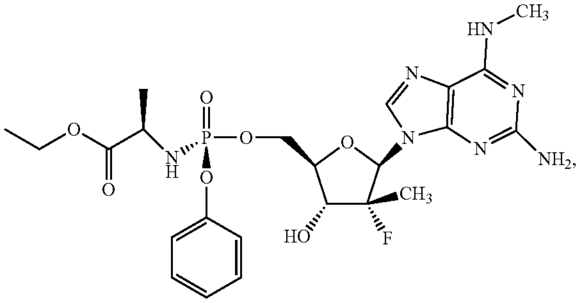
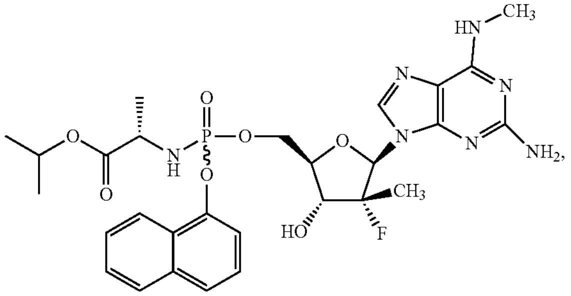
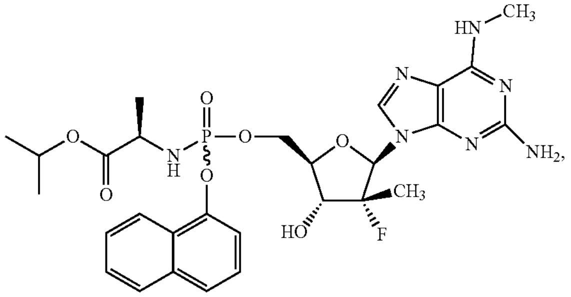
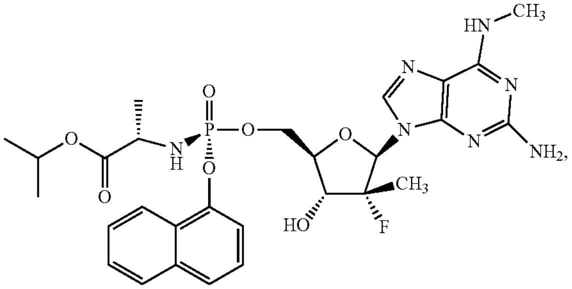
-continued
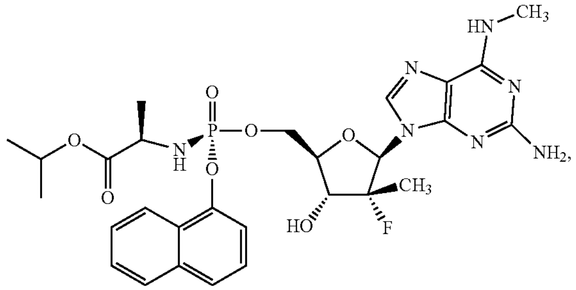
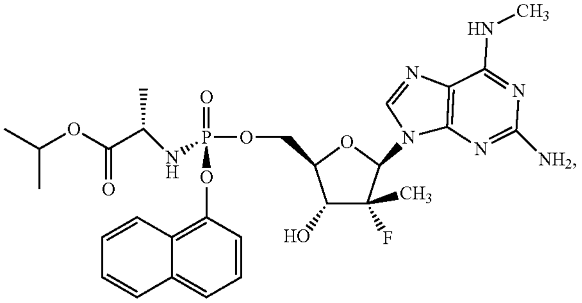
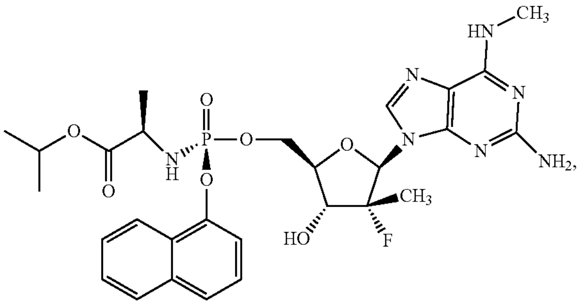
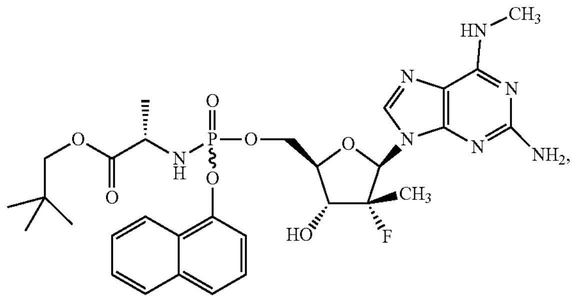
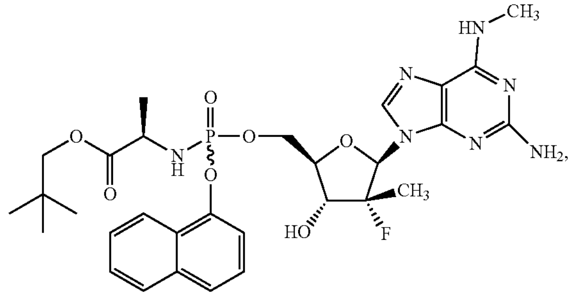

-continued
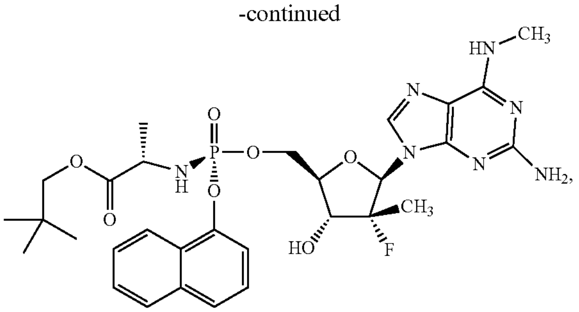
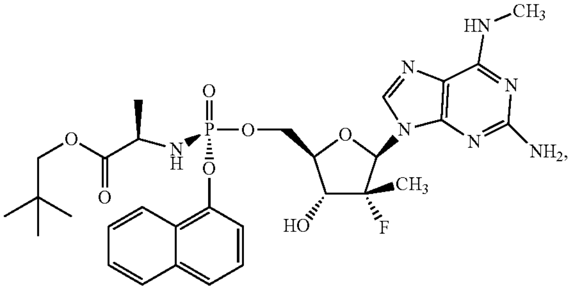
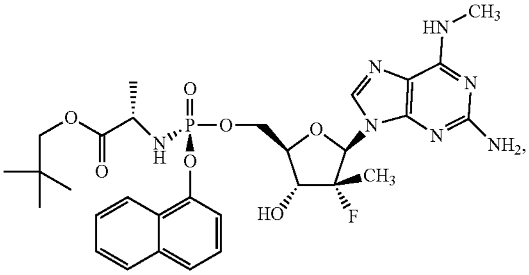
and
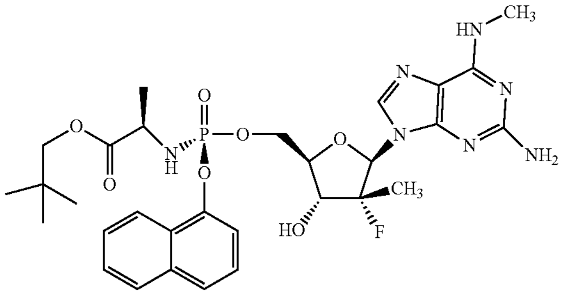
or a pharmaceutically acceptable salt thereof.
Additional non-limiting examples of compounds of Formula I include:
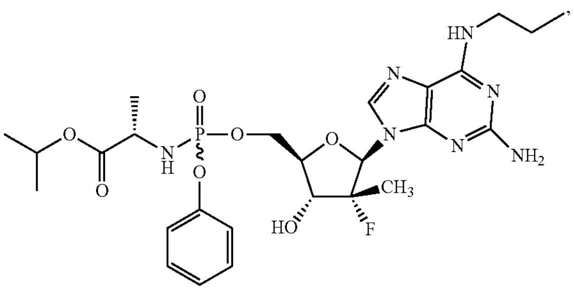
-continued
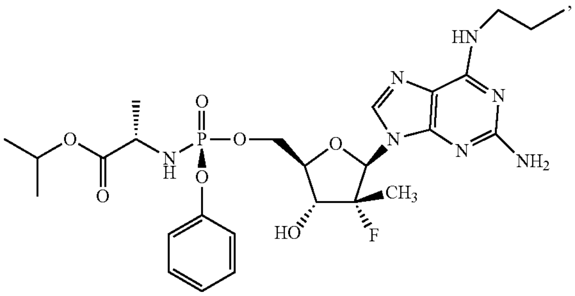
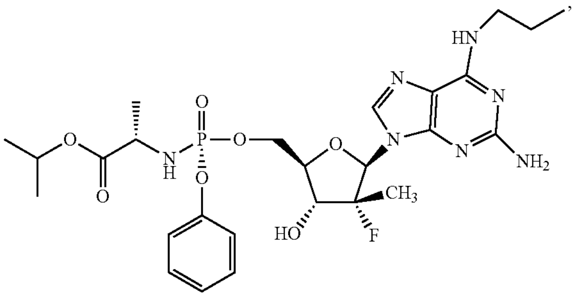
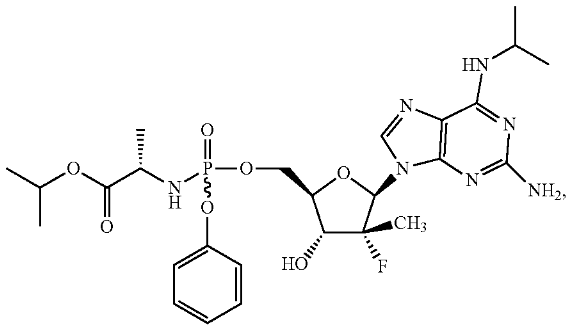
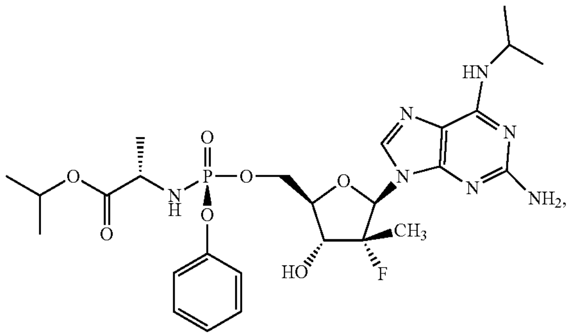
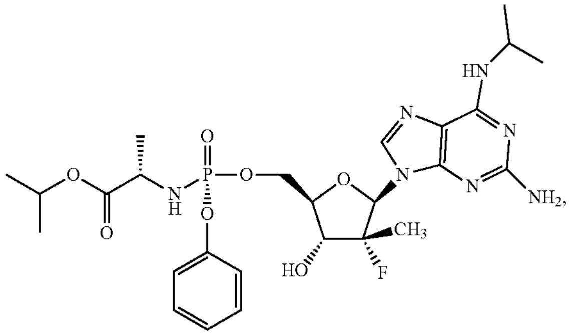

-continued
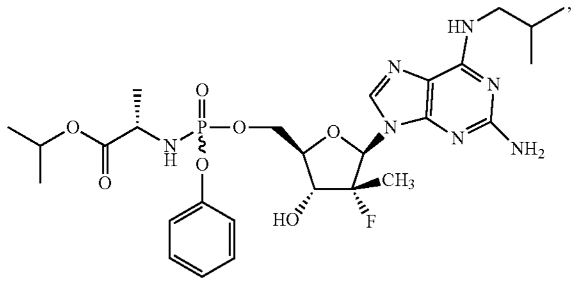
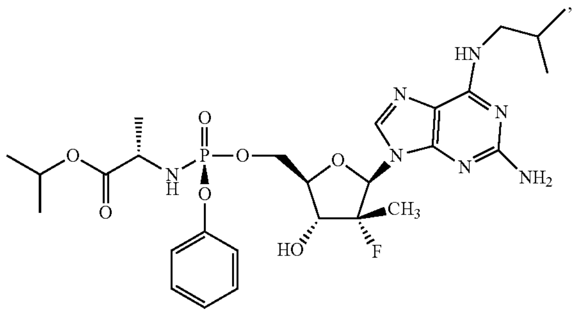
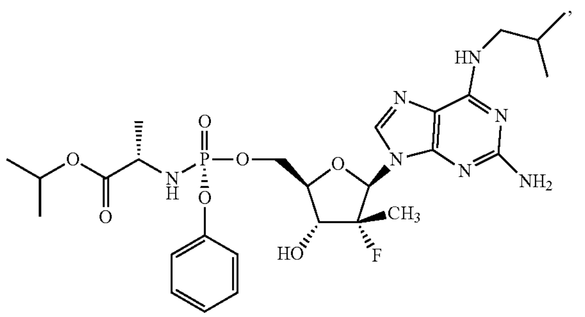
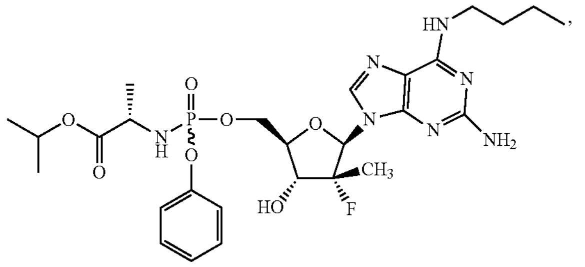
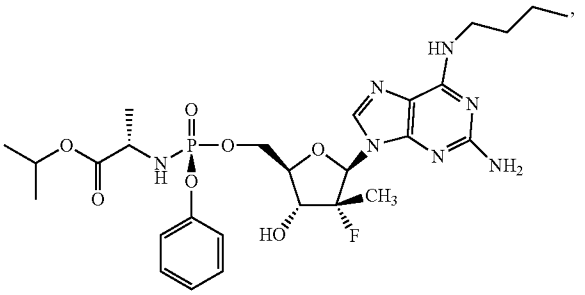
-continued
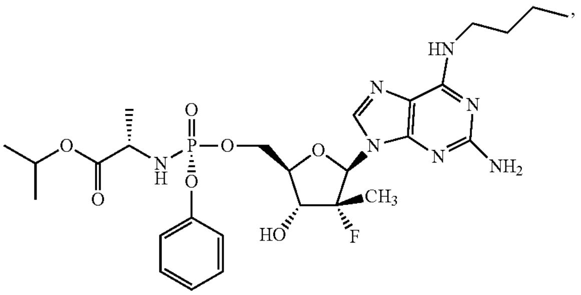
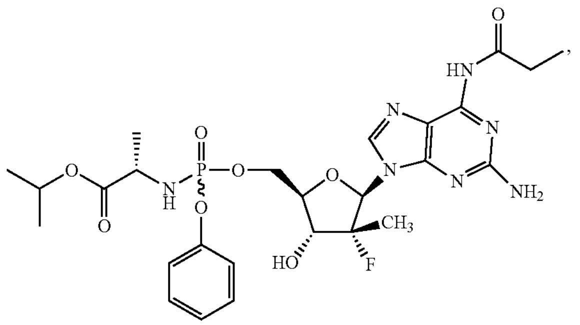
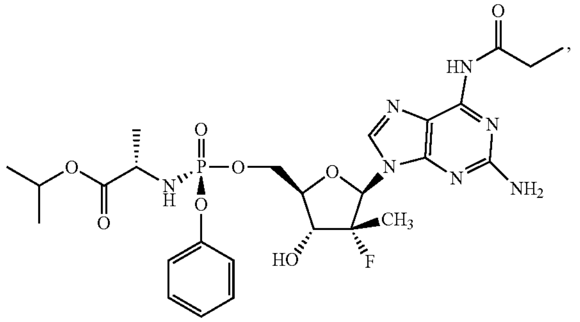
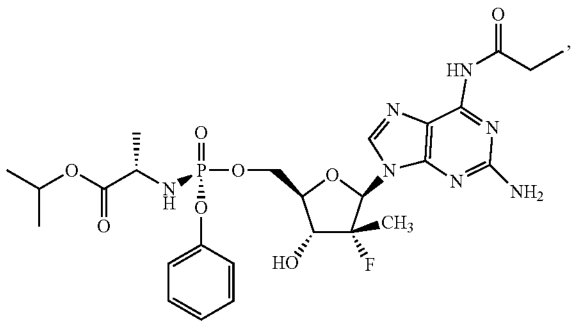
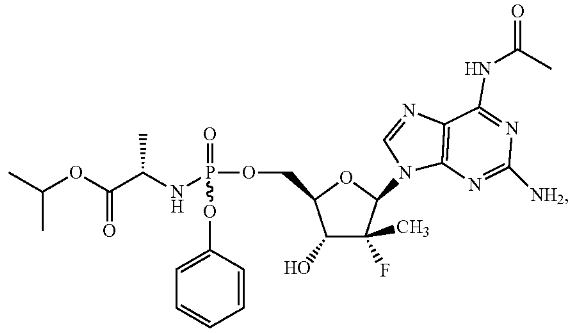

-continued

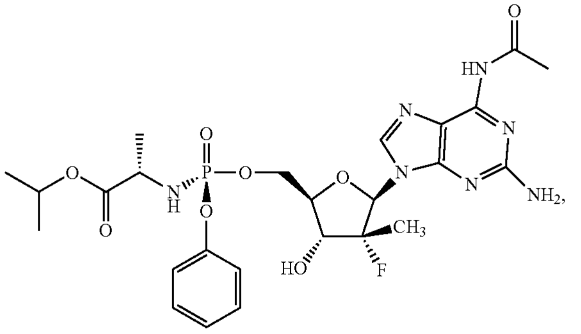

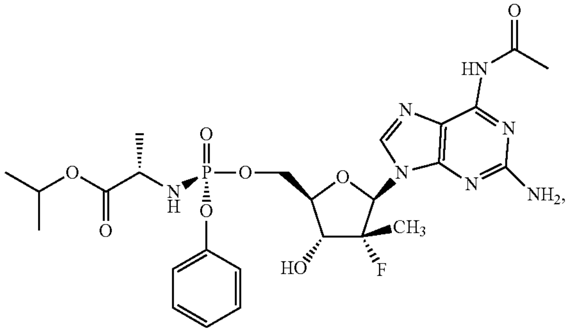

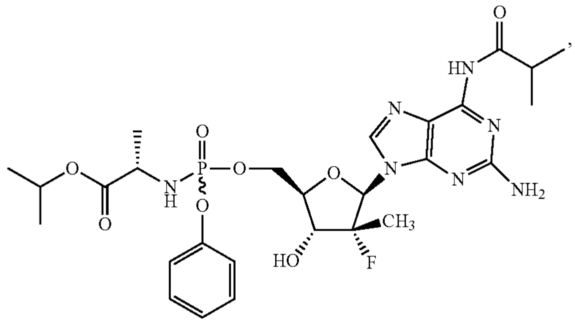

,

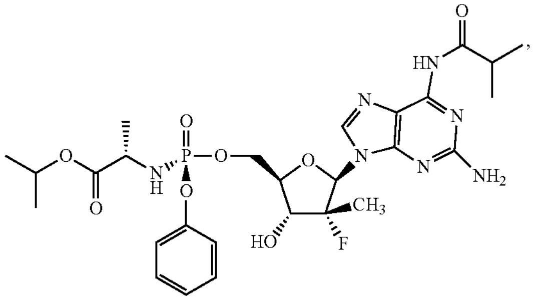

, and

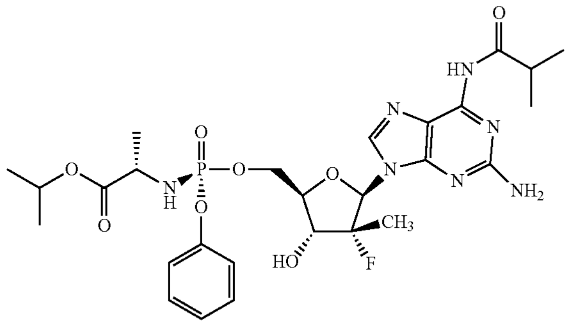 [SMILES: CC(C)OC(=O)[C@H](C)N[P@@](=O)(OC[C@H]1O[C@@H](n2cnc3c(NC(=O)C(C)C)nc(N)nc32)[C@](C)(F)[C@@H]1O)Oc1ccccc1]

or a pharmaceutically acceptable salt thereof.

The present invention also includes the use of an effective amount of a compound of Formula II to disrupt NiRAN function in a coronavirus or to treat or prevent a mutant or resistant form of the SARS-CoV-2 virus in a host in need thereof:

Formula II

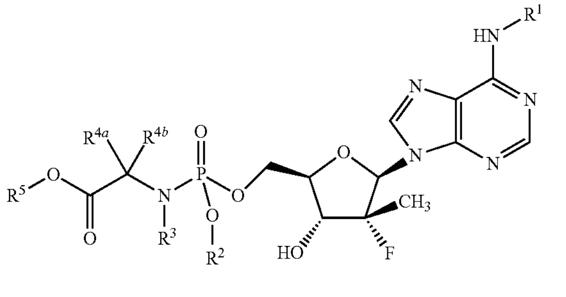

or a pharmaceutically acceptable salt thereof, wherein:

$R^1$ is selected from $C_1$-$C_6$alkyl, $C_3$-$C_6$cycloalkyl, and —C(O)$C_1$-$C_6$alkyl;

$R^2$ is hydrogen, $C_{1-6}$alkyl (including methyl, ethyl, propyl, and isopropyl), $C_{3-7}$cycloalkyl, aryl (including phenyl and napthyl), aryl($C_1$-$C_4$alkyl)-, heteroaryl, or heteroalkyl;

$R^3$ is hydrogen or $C_{1-6}$alkyl (including methyl, ethyl, propyl, and isopropyl);

$R^{4a}$ and $R^{4b}$ are independently selected from hydrogen, $C_{1-6}$alkyl (including methyl, ethyl, propyl, and isopropyl), and $C_{3-7}$cycloalkyl; and $R^5$ is hydrogen, $C_{1-6}$alkyl (including methyl, ethyl, propyl, and isopropyl), $C_{1-6}$haloalkyl, $C_{3-7}$cycloalkyl, aryl ($C_1$-$C_4$alkyl)-, aryl, heteroaryl, or heteroalkyl.

Non-limiting examples of a compound of Formula II include Compound 3 and Compound 4. In some embodiments, the compounds are administered as the S-enantiomer, such as Compound 3A and Compound 4A. In some embodiments, the compounds are administered as the R-enantiomer, such as Compound 3B or Compound 4B.

Compound 3

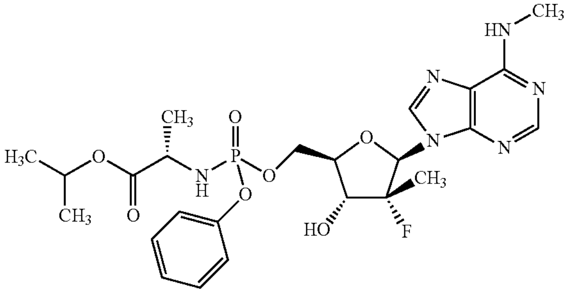

Compound 4

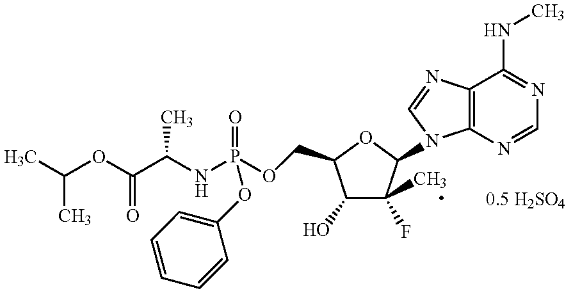

-continued
Compound 3A
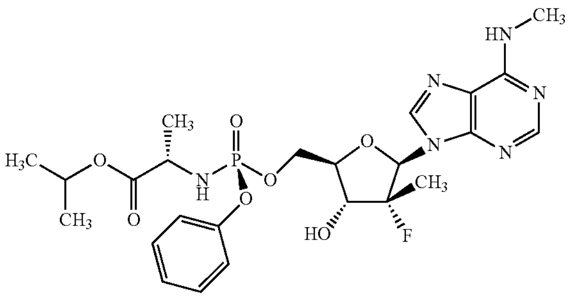
Compound 3B
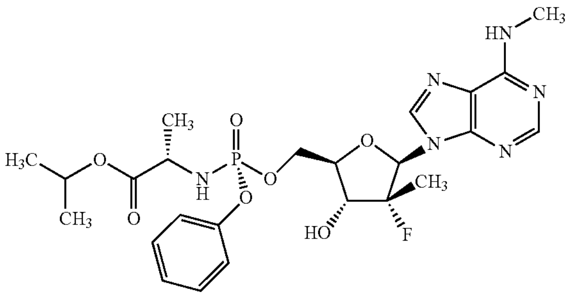
Compound 4A
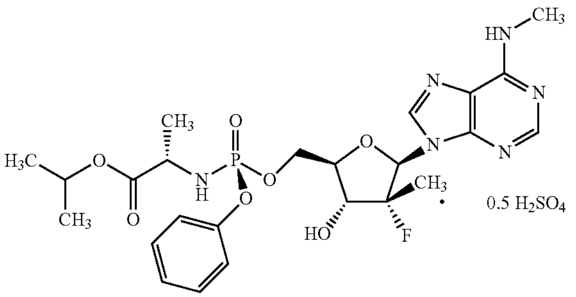
Compound 4B
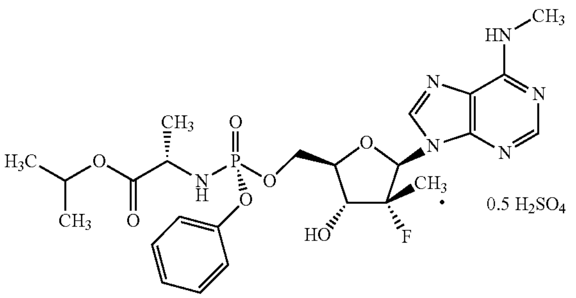
Alternative configurations of Compound 3 or a pharmaceutically acceptable salt thereof include:
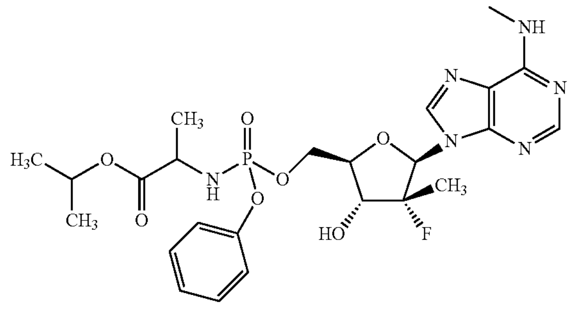
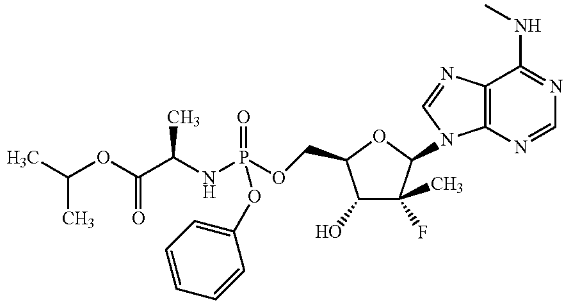
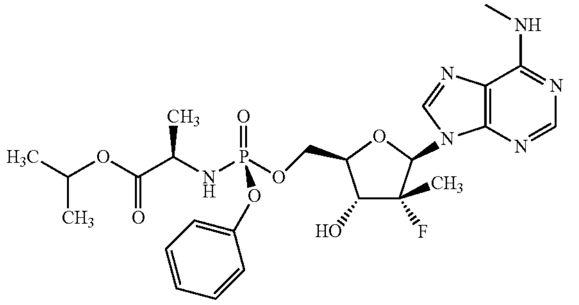
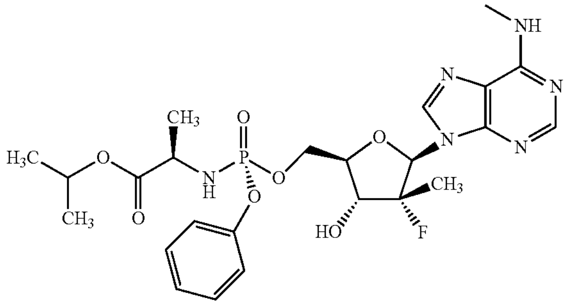
Additional alternative configurations of Compound 4 include:
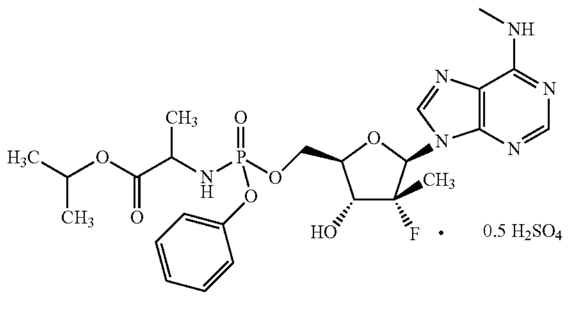

-continued
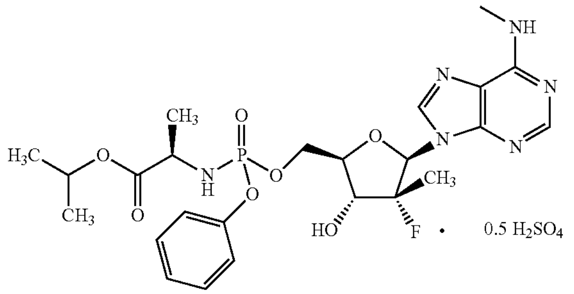
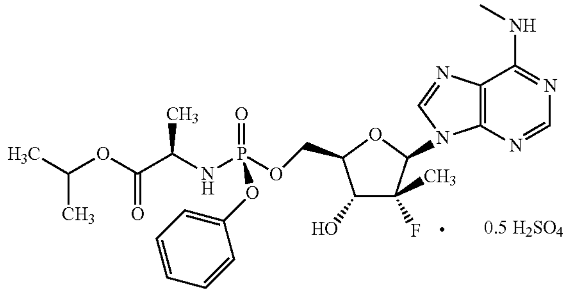
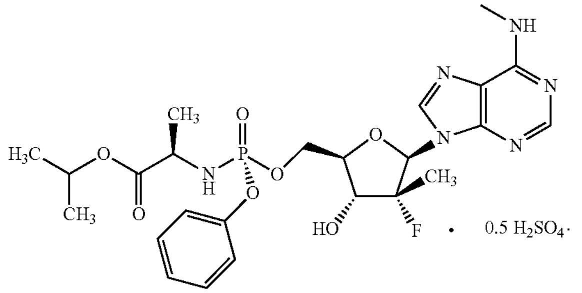
Non-limiting examples of a compound of Formula II include:
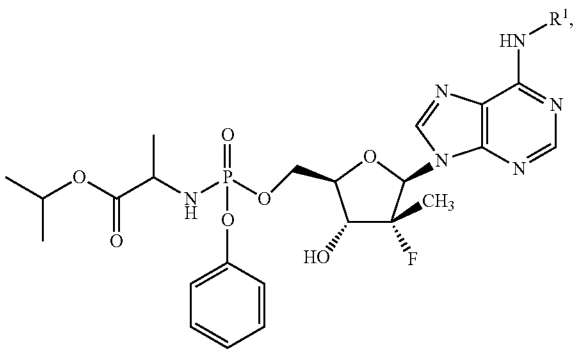
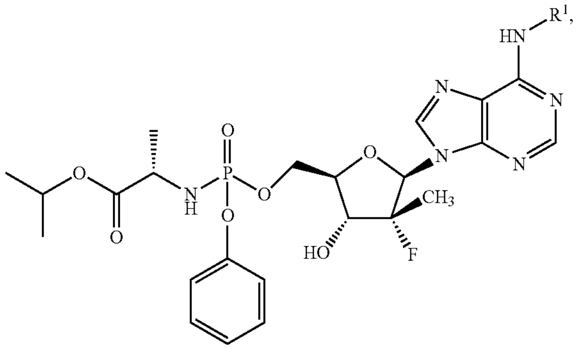
-continued
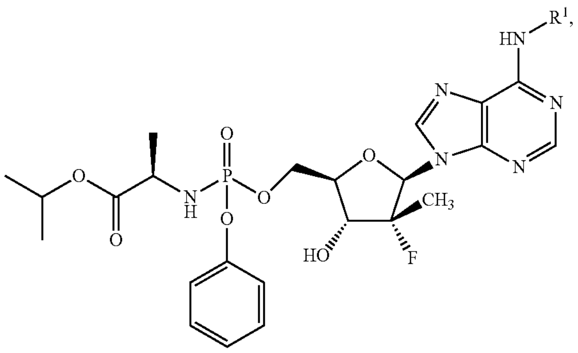
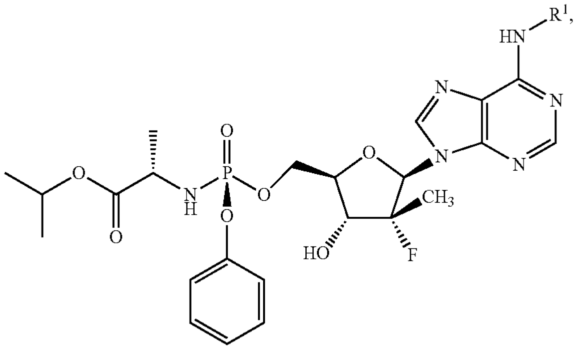
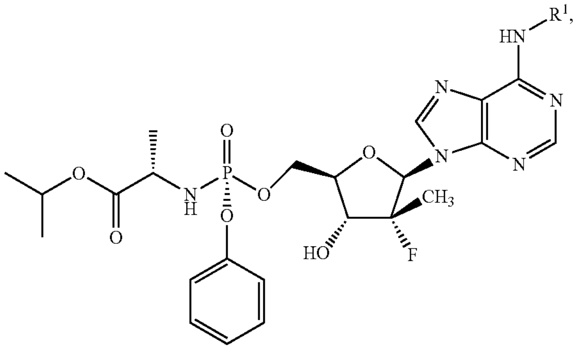
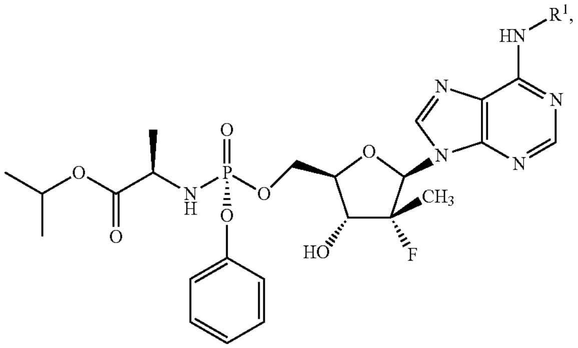

-continued
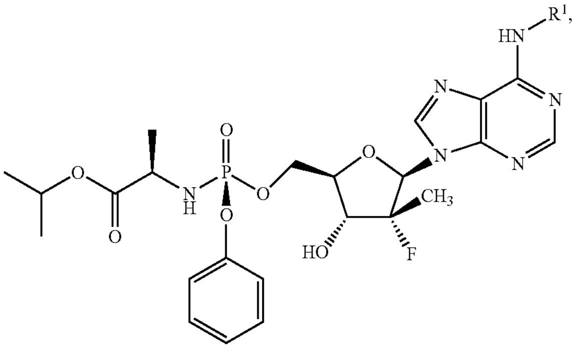
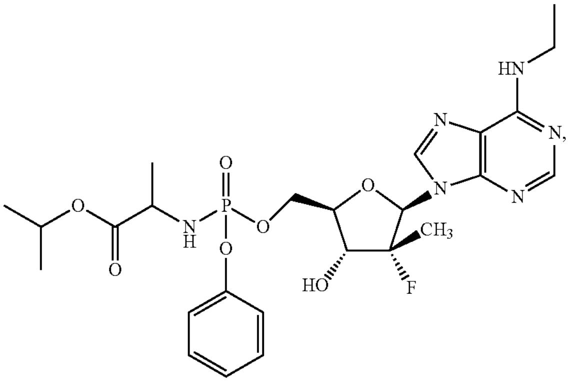
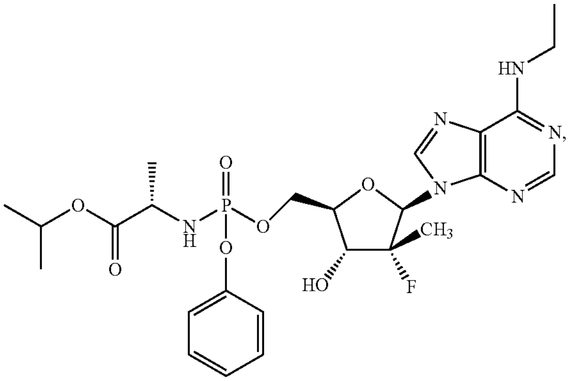
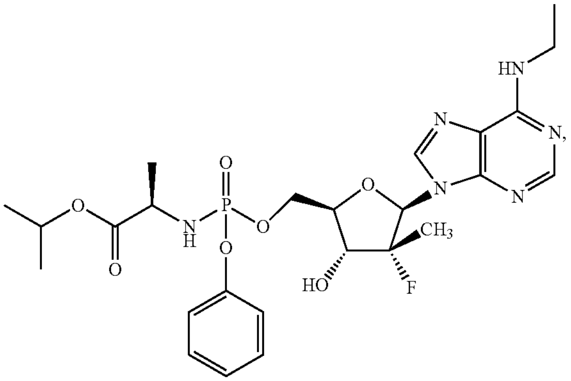
-continued
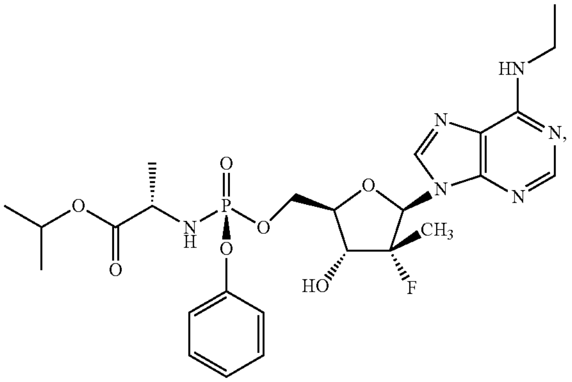
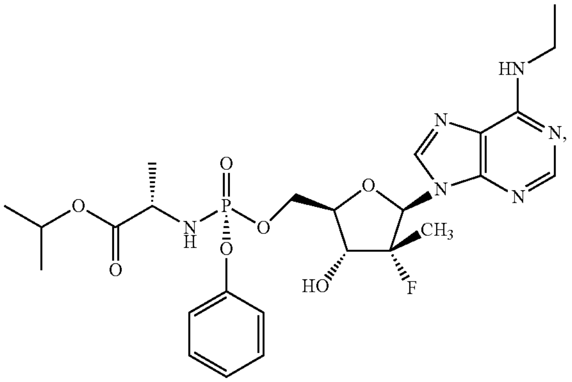
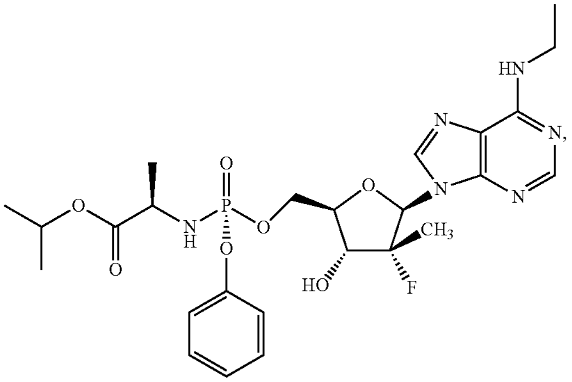
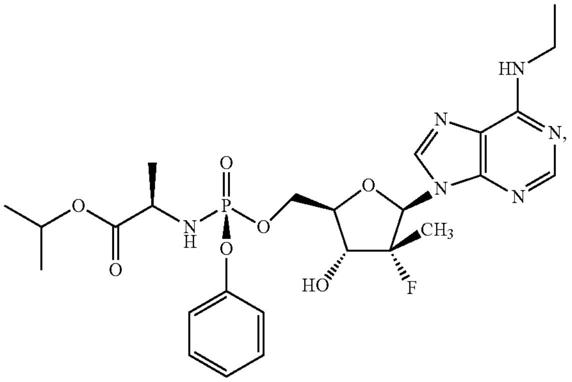

-continued
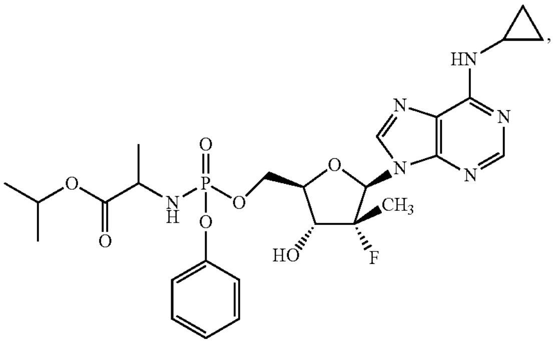
,
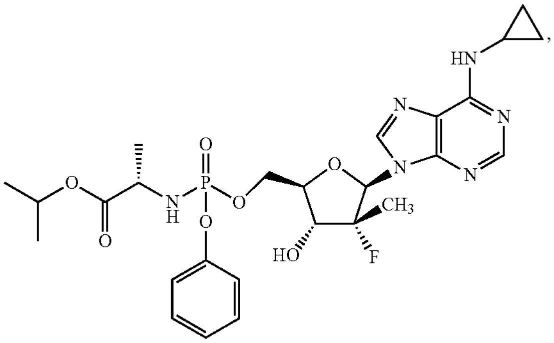
,
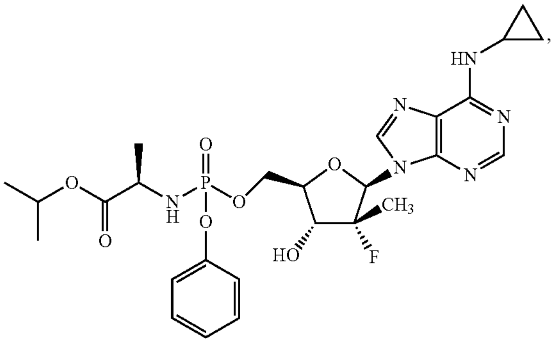
,
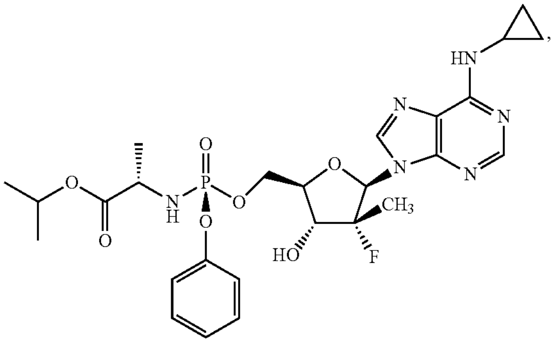
,
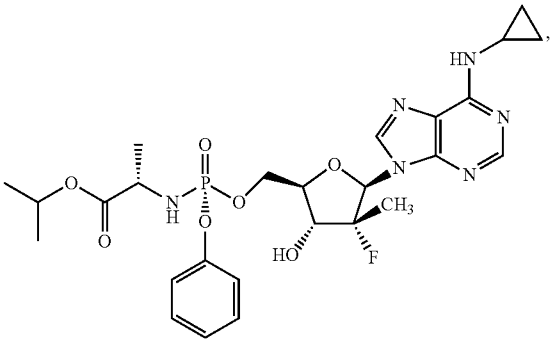
,
-continued
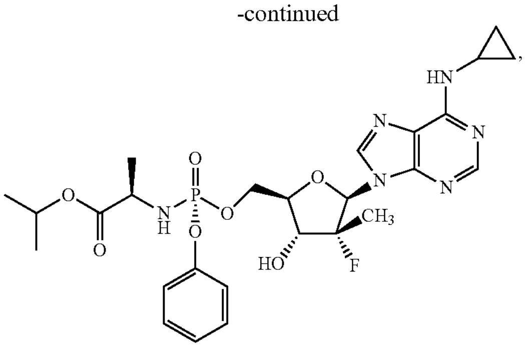
, and
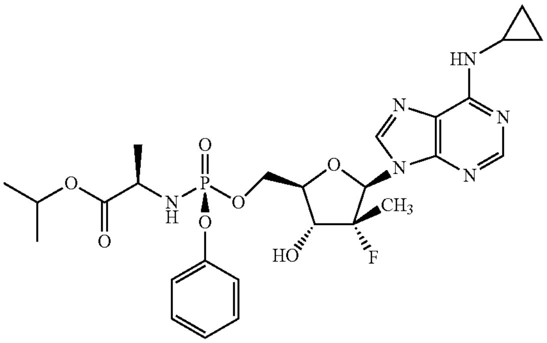
or a pharmaceutically acceptable salt thereof.
Additional non-limiting examples of a compound of Formula II include:
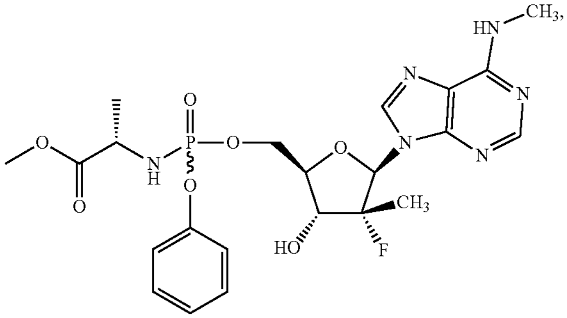
,
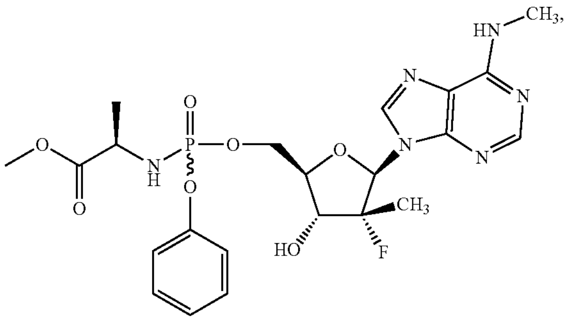
, -continued
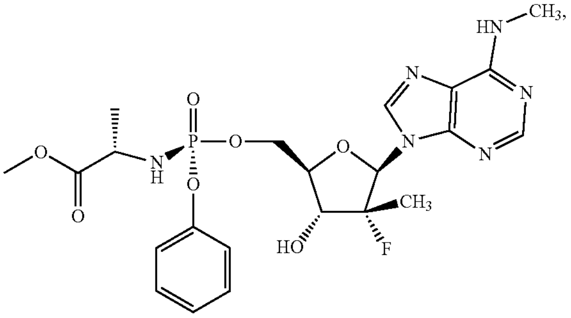
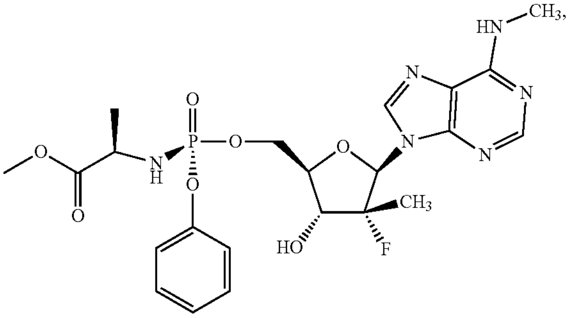
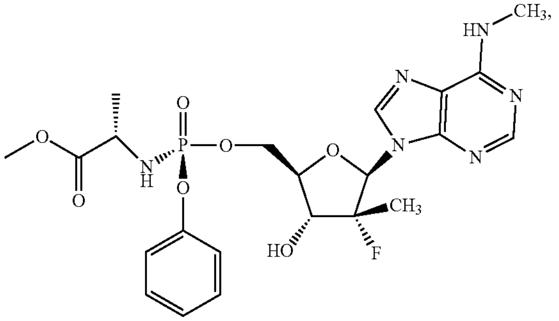
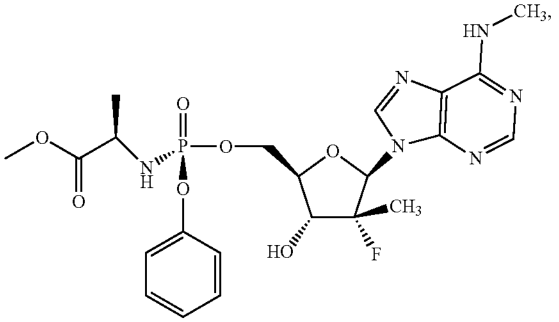
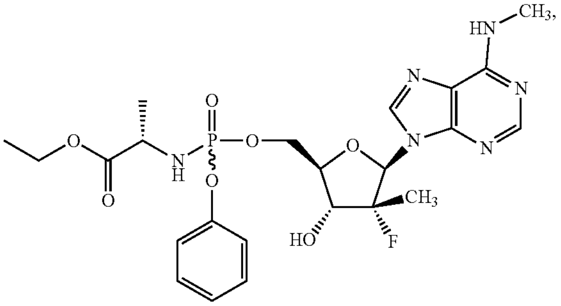
-continued
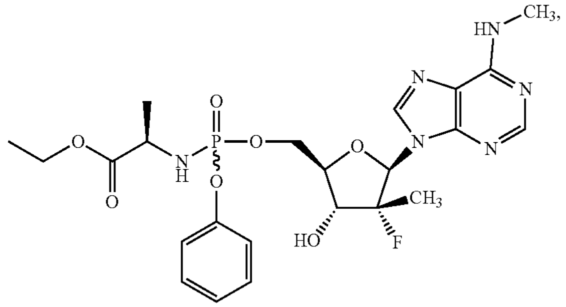
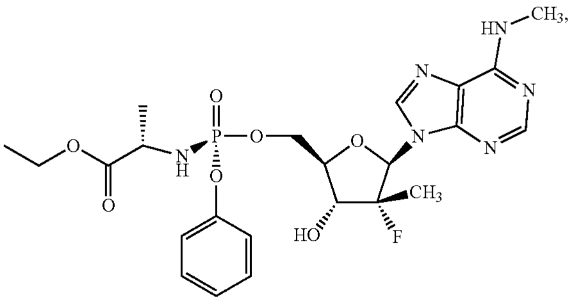
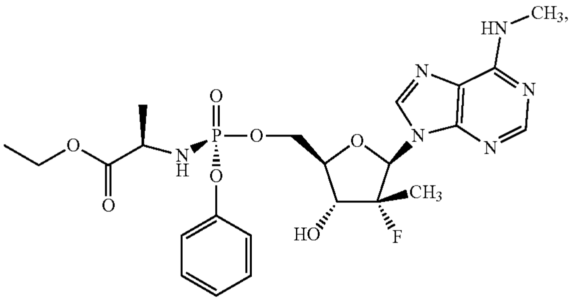
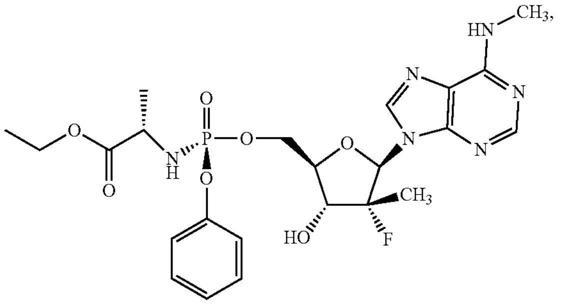
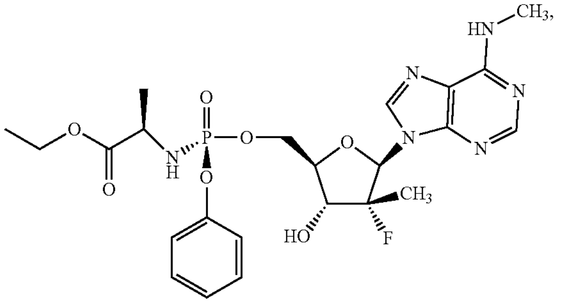

-continued
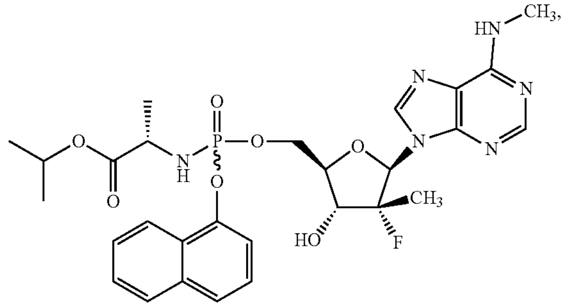
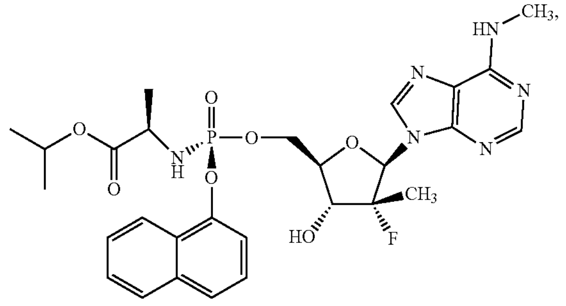
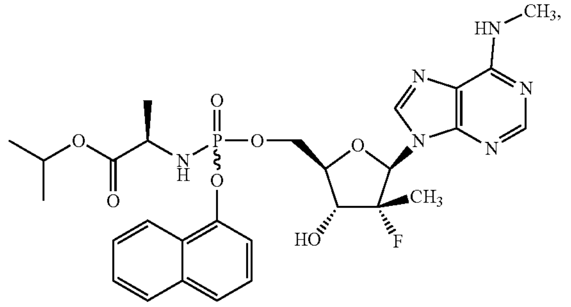
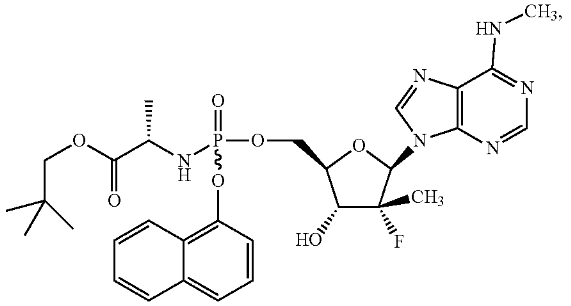
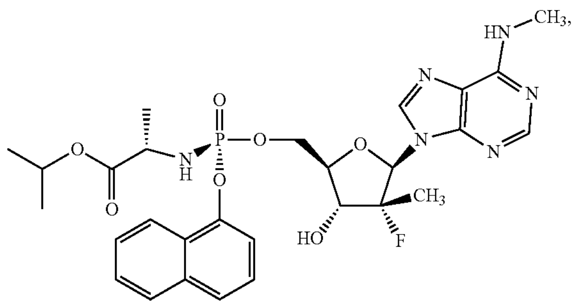
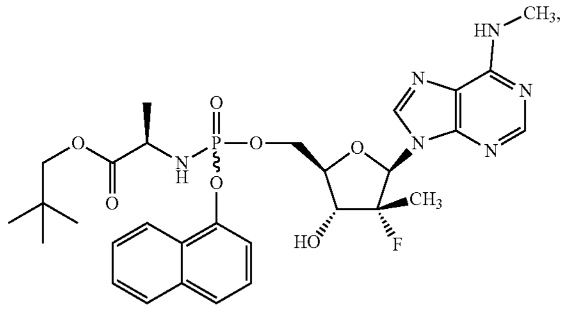
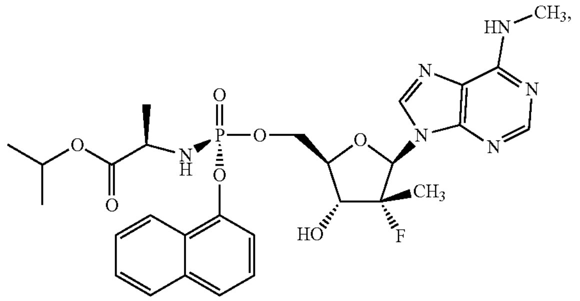
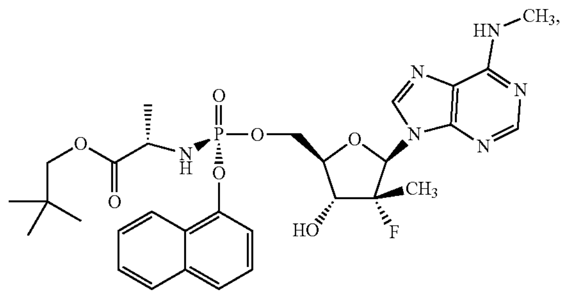
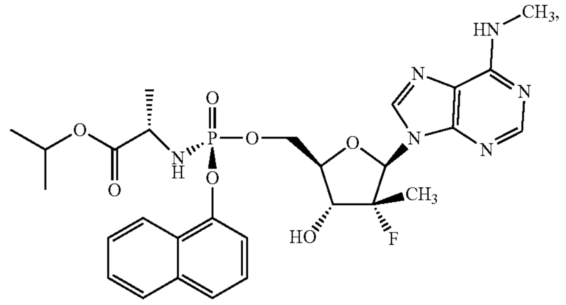
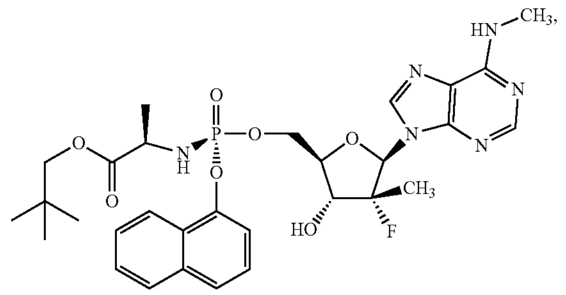
-continued -continued
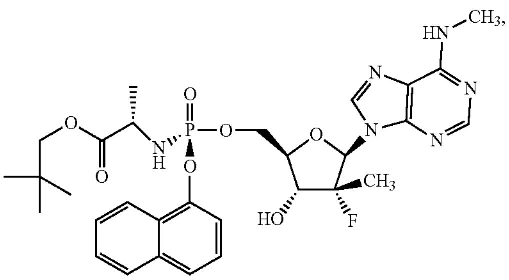
, and
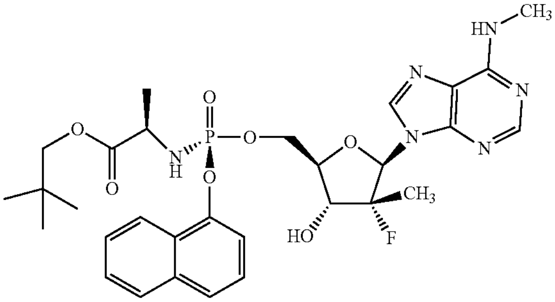
or a pharmaceutically acceptable salt thereof.
Additional non-limiting examples of compounds of Formula II include:
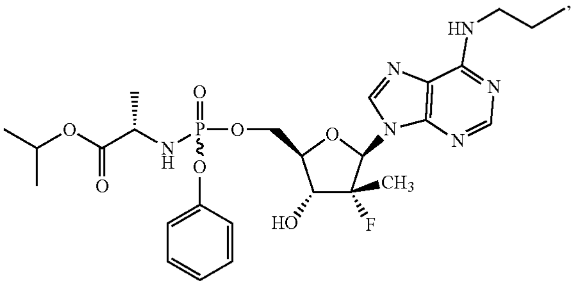
,
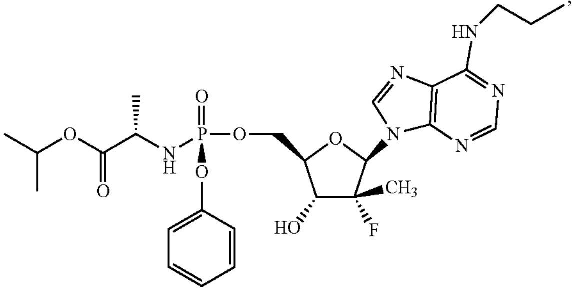
,
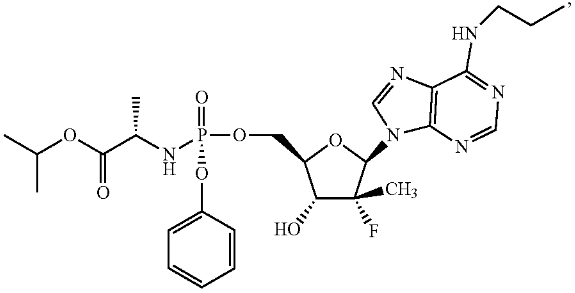
,
-continued
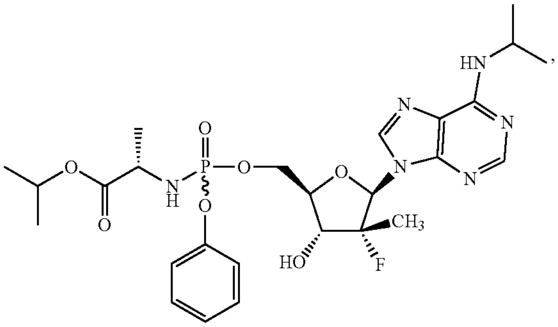
,
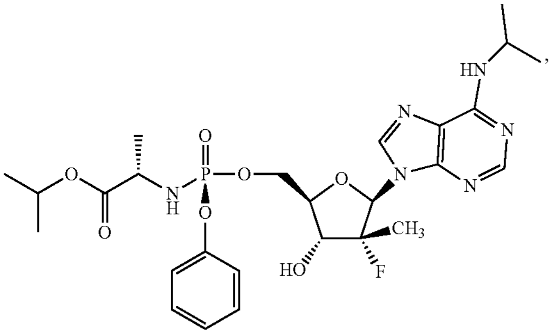
,
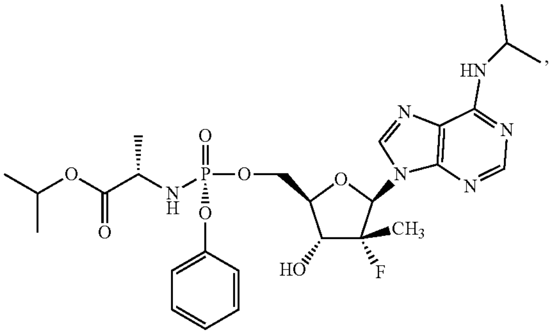
,
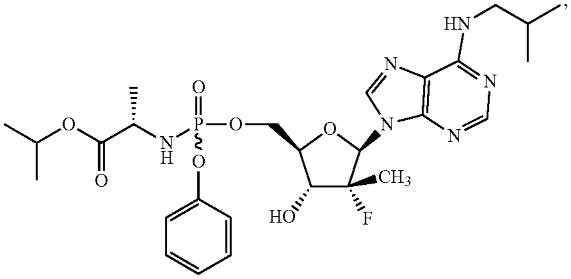
,
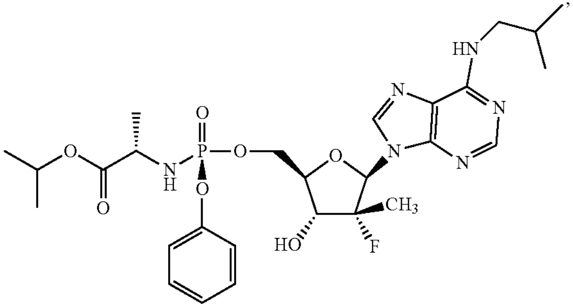
, -continued
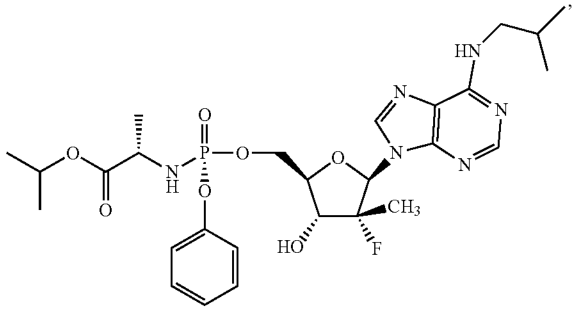
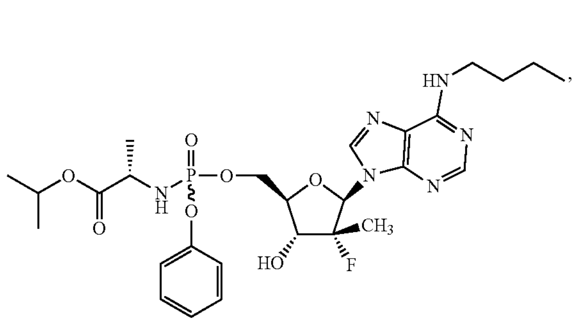
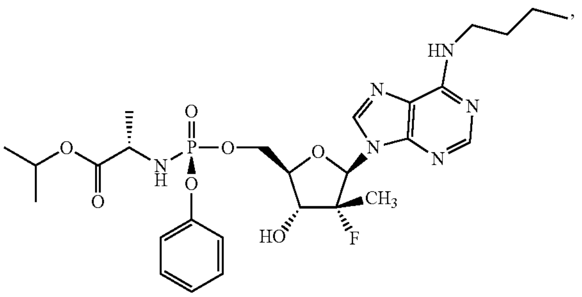
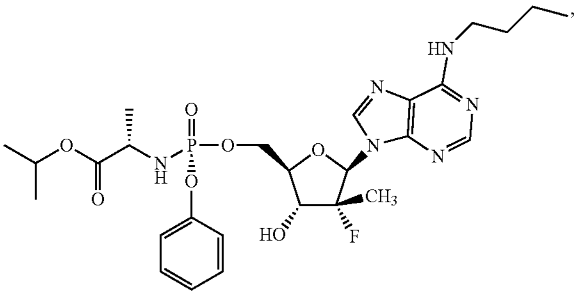
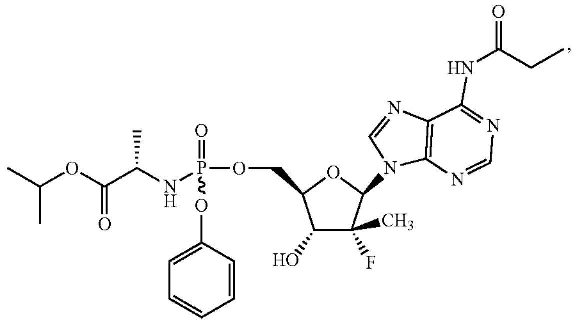
-continued
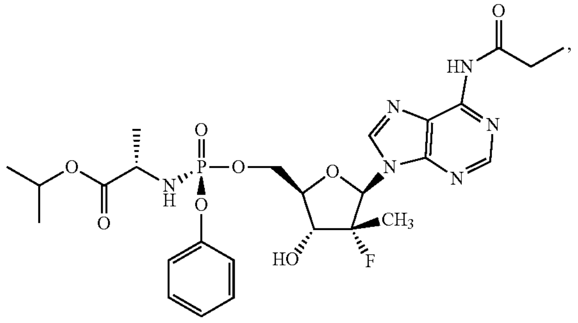
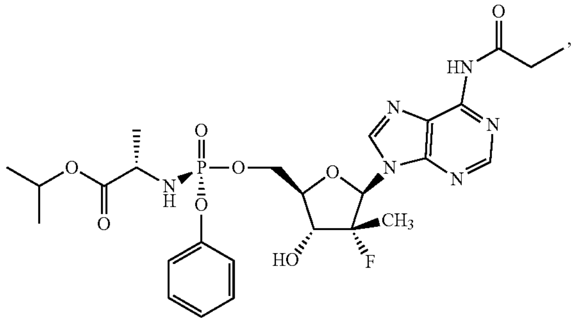
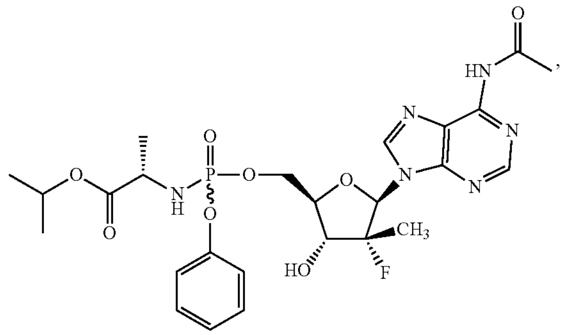
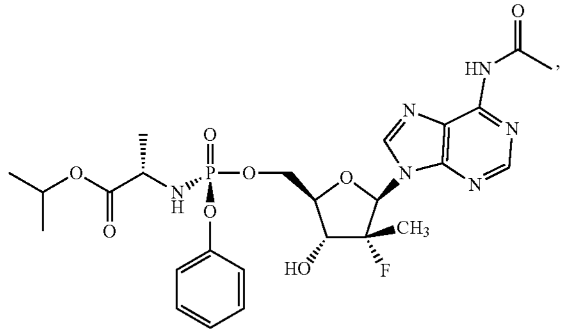
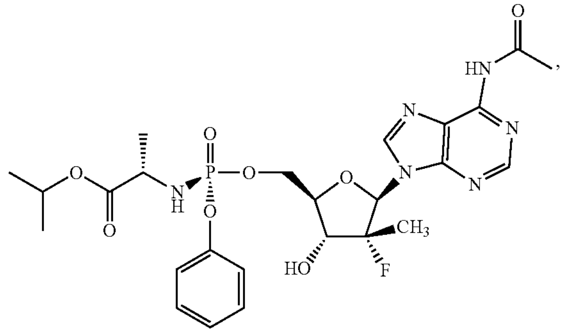

-continued

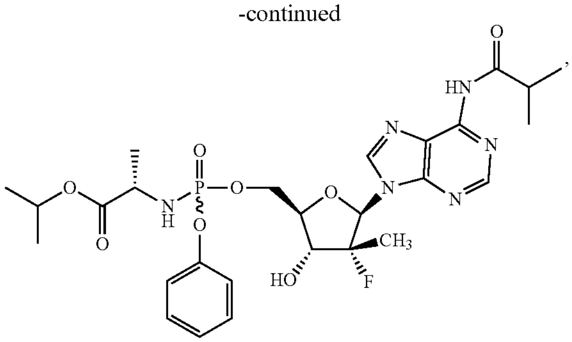

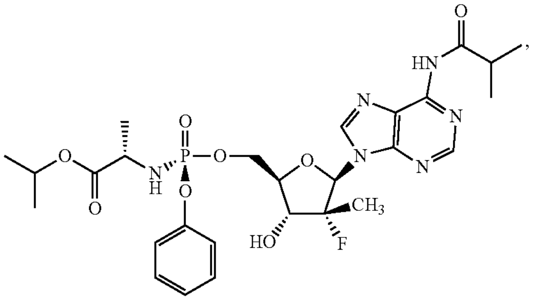

and

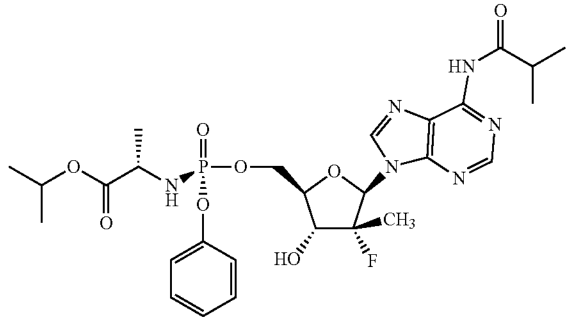 [SMILES: CC(C)OC(=O)[C@H](C)N[P@@](=O)(OC[C@H]1O[C@@H](n2cnc3c(NC(=O)C(C)C)ncnc32)[C@](C)(F)[C@@H]1O)Oc1ccccc1]

or a pharmaceutically acceptable salt thereof.

The present invention also includes the use of an effective amount of a compound of Formula III to disrupt NiRAN function in a coronavirus or to treat a mutant or resistant form of the SARS-CoV-2 virus in a host in need thereof:

Formula III

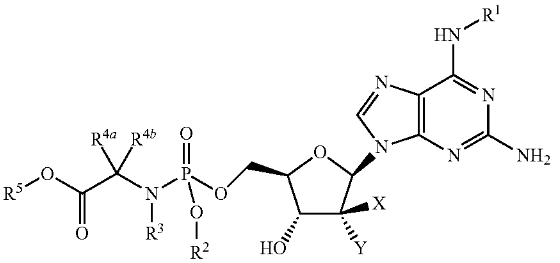

or a pharmaceutically acceptable salt thereof, wherein:

$R^1$ is selected from $C_1$-$C_6$alkyl, $C_3$-$C_6$cycloalkyl, and —C(O)$C_1$-$C_6$alkyl;

$R^2$ is hydrogen, $C_{1-6}$alkyl (including methyl, ethyl, propyl, and isopropyl), $C_{3-7}$cycloalkyl, aryl (including phenyl and napthyl), aryl($C_1$-$C_4$alkyl)-, heteroaryl, or heteroalkyl;

$R^3$ is hydrogen or $C_{1-6}$alkyl (including methyl, ethyl, propyl, and isopropyl);

$R^{4a}$ and $R^{4b}$ are independently selected from hydrogen, $C_{1-6}$alkyl (including methyl, ethyl, propyl, and isopropyl), and $C_{3-7}$cycloalkyl; and $R^5$ is hydrogen, $C_{1-6}$alkyl (including methyl, ethyl, propyl, and isopropyl), $C_{1-6}$haloalkyl, $C_{3-7}$cycloalkyl, aryl ($C_1$-$C_4$alkyl)-, aryl, heteroaryl, or heteroalkyl;

X is selected from F, $C_1$, $C_1$-$C_3$haloalkyl (including $C_{1-3}$fluoroalkyl and $C_{1-3}$chloroalkyl, such as $CH_2F$, $CHF_2$, $CF_3$, $CH_2CF_3$, $CH_2CHF_2$, $CH_2CH_2F$, $CF_2CH_3$, $CF_2CF_3$, and $CH_2C_1$), $C_2$-$C_4$alkenyl, $C_2$-$C_4$alkynyl, and $C_1$-$C_3$hydroxyalkyl; and Y is Cl or F.

In some embodiments, the compound of Formula III to disrupt NiRAN function in a coronavirus or to treat or prevent a mutant or resistant form of the SARS-CoV-2 virus in a host in need thereof is a compound of Formula IIIa:

Formula IIIa

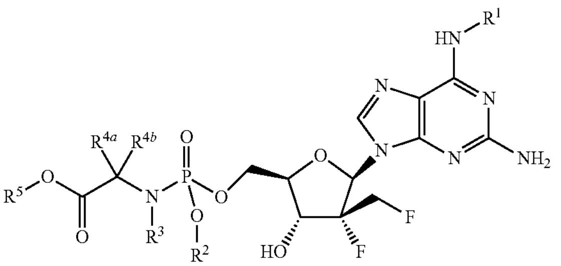

or a pharmaceutically acceptable salt thereof.

In some embodiments of Formula IIIa, $R^1$ is methyl.

In some embodiments of Formula IIIa, $R^1$ is cyclopropyl.

In some embodiments of Formula IIIa, $R^2$ is phenyl.

In some embodiments of Formula IIIa, $R^2$ is napthyl.

In some embodiments of Formula IIIa, $R^{4a}$ is hydrogen and $R^{4b}$ is methyl.

In some embodiments of Formula IIIa, $R^5$ is isopropyl.

In some embodiments of Formula IIIa, the compound is the $S_p$-isomer and the phosphoramidate is in the L-configuration.

In some embodiments of Formula IIIa, the compound is the $R_p$-isomer and the phosphoramidate is in the L-configuration.

In some embodiments of Formula IIIa, the pharmaceutically acceptable salt is the hemi-sulfate salt.

Non-limiting examples of a compound of Formula IIIa include:

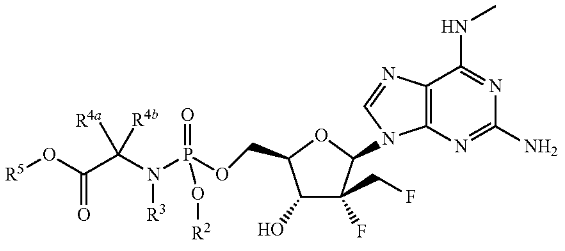

-continued
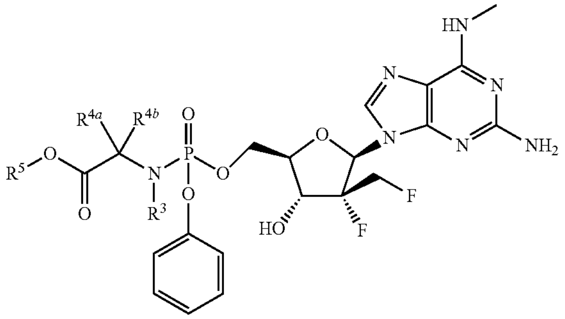
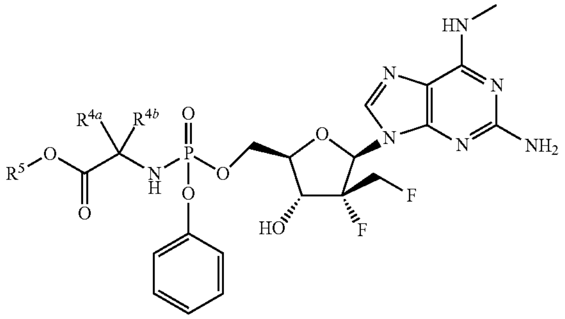
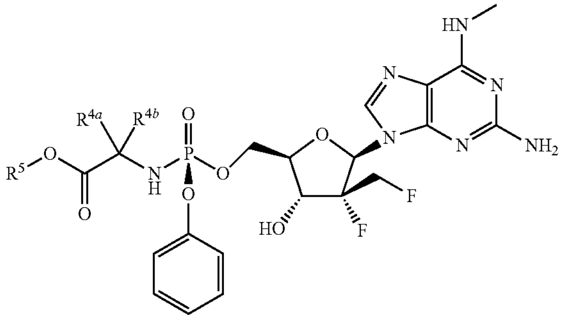
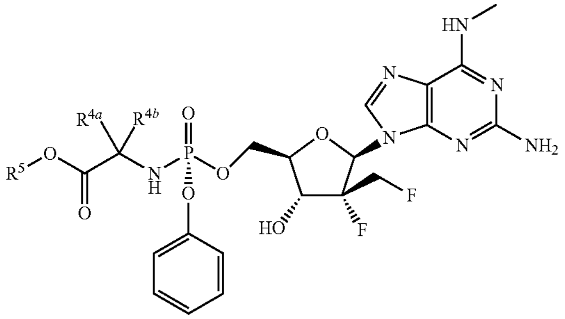
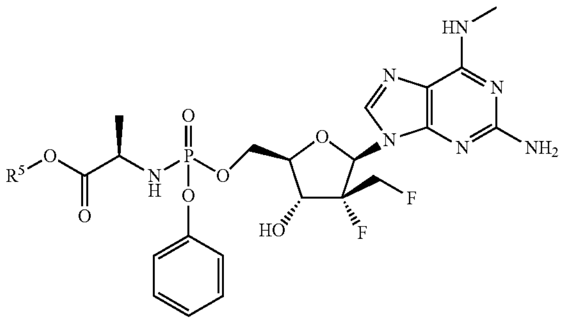
-continued
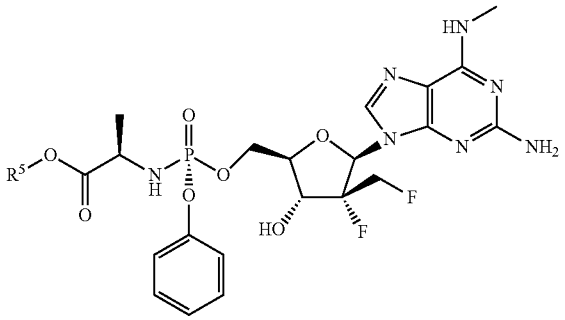
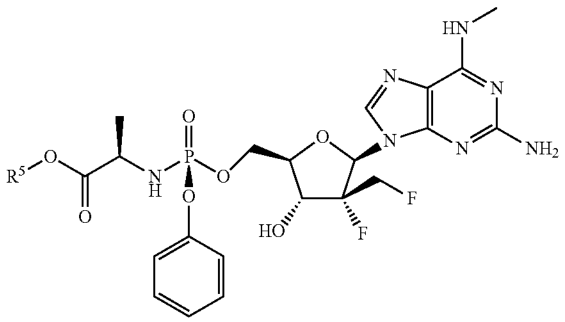
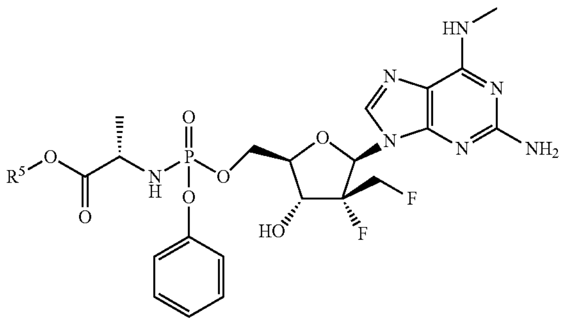
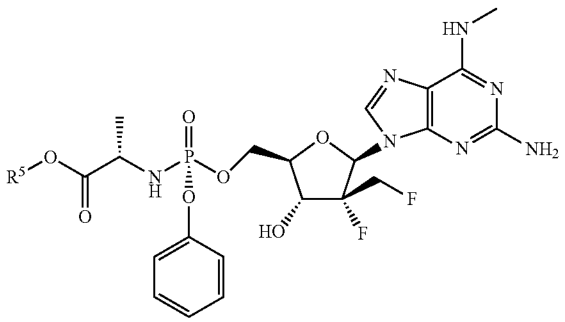
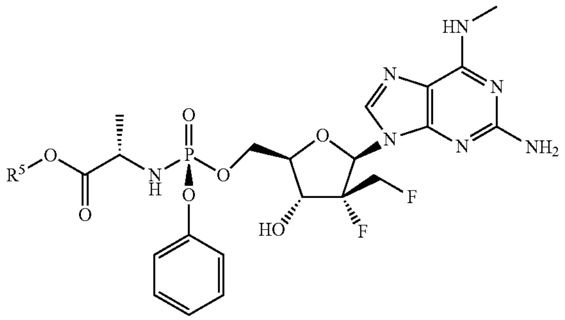

-continued
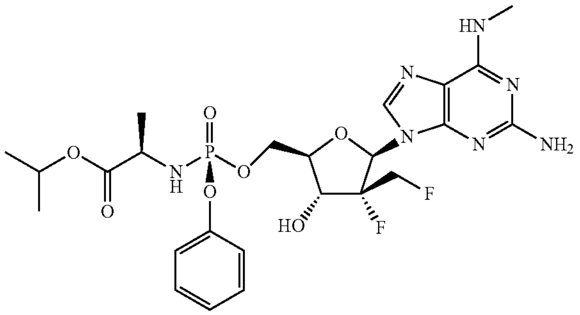
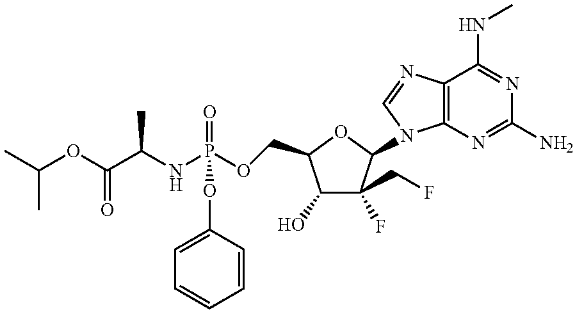
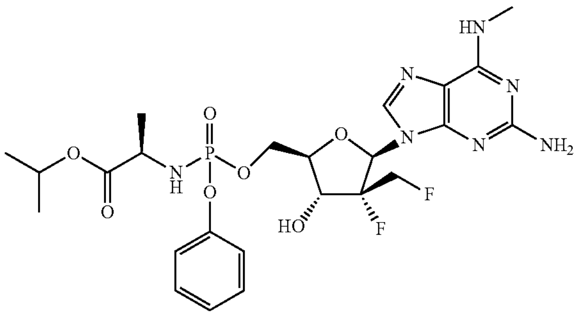
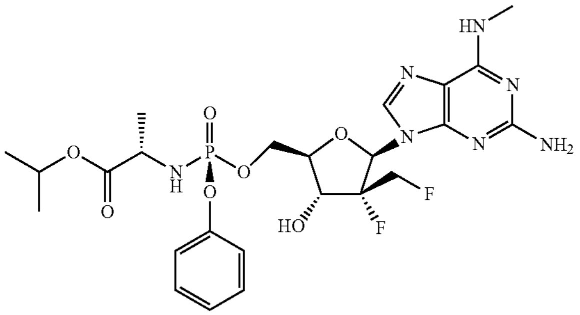
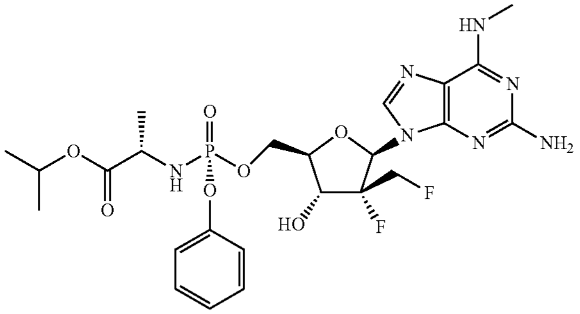
-continued
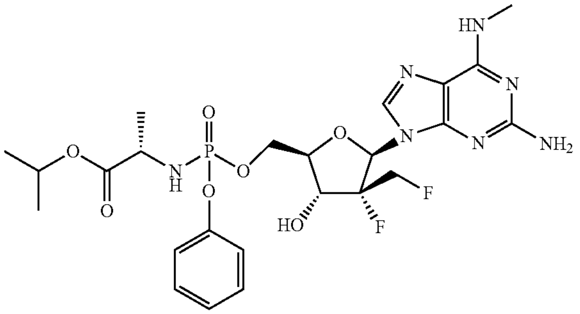
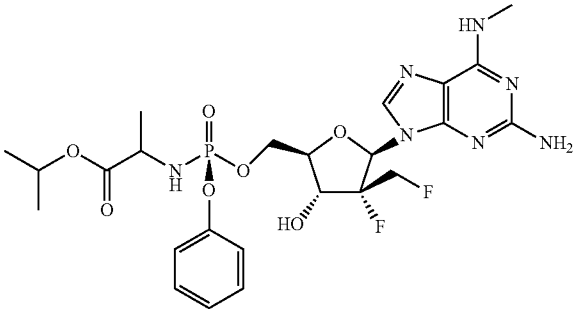
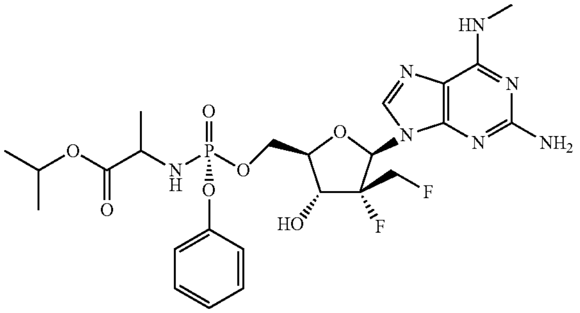
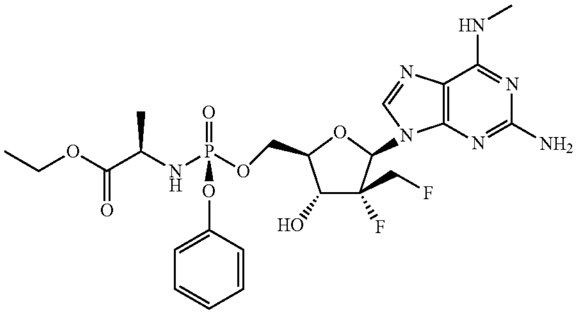
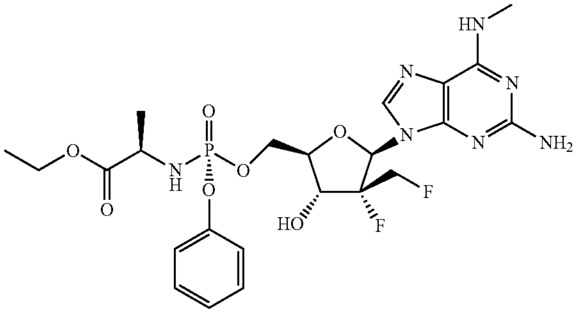

-continued
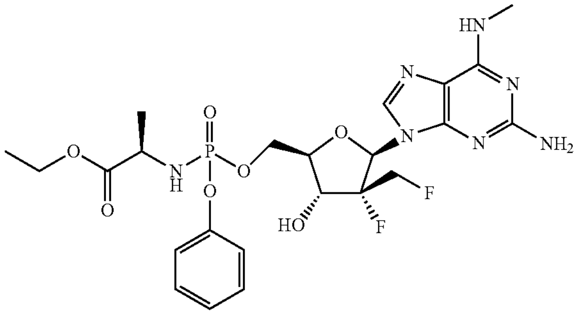
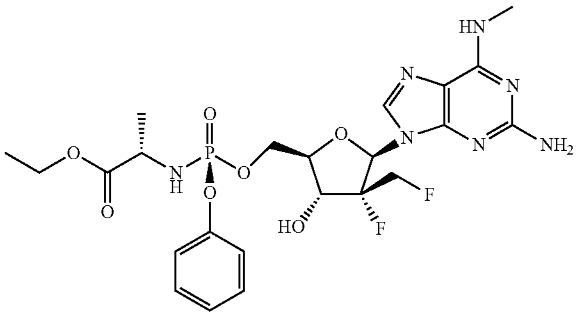
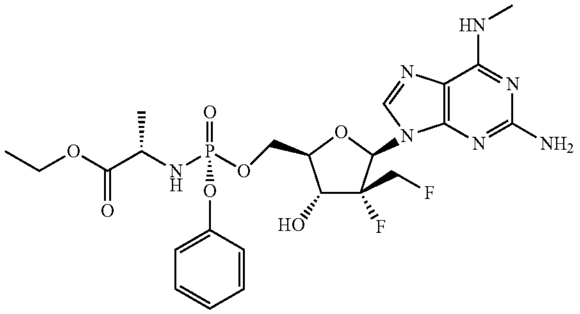
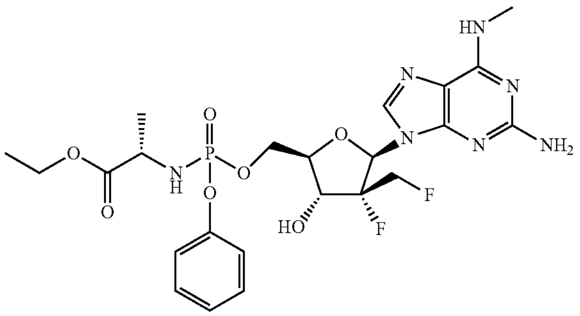
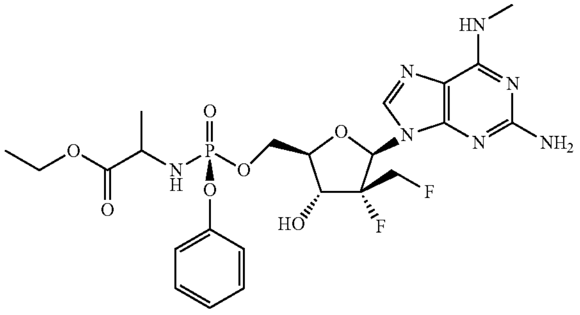
-continued
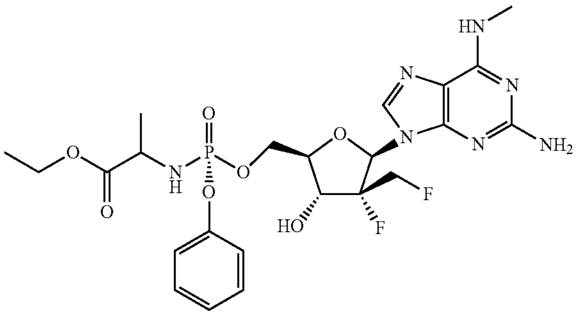
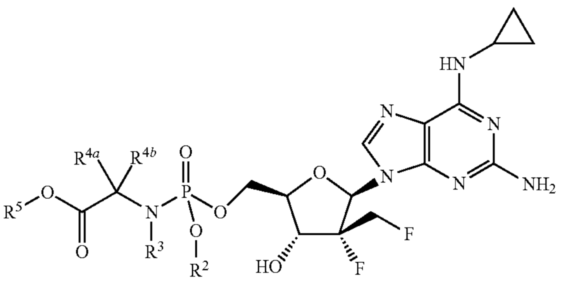
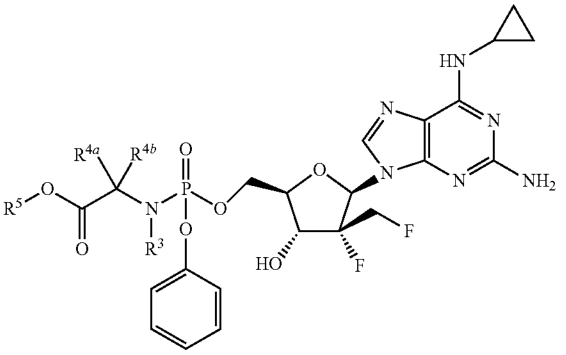
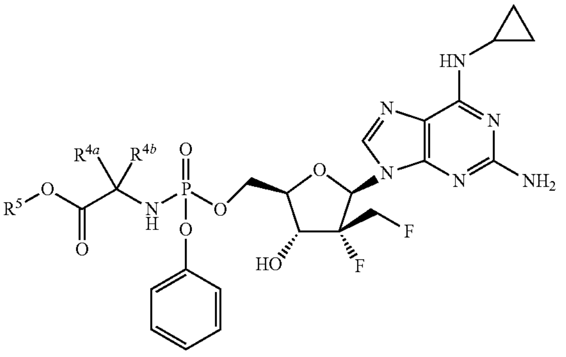
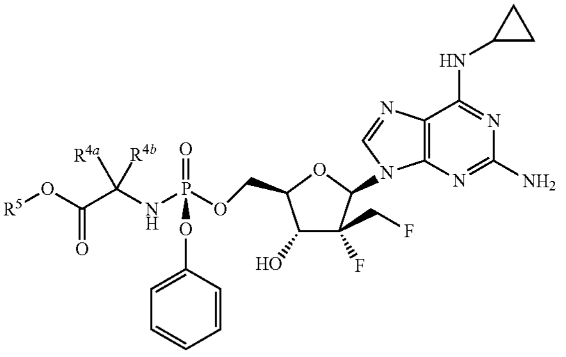

-continued
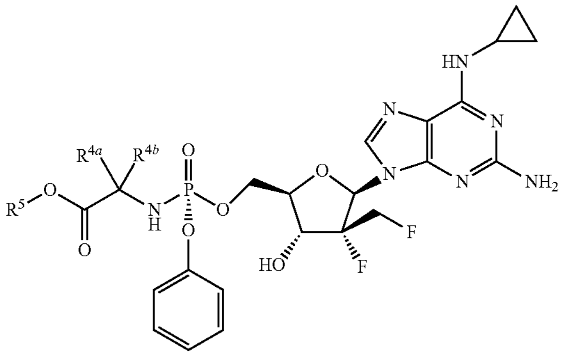
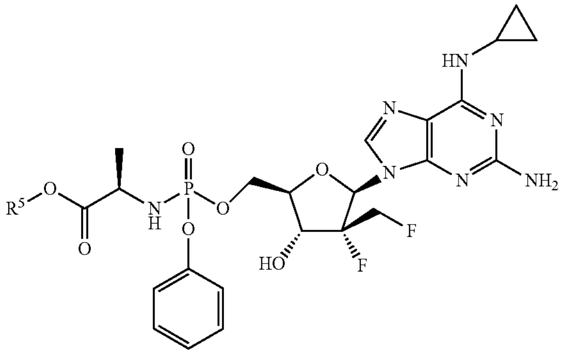
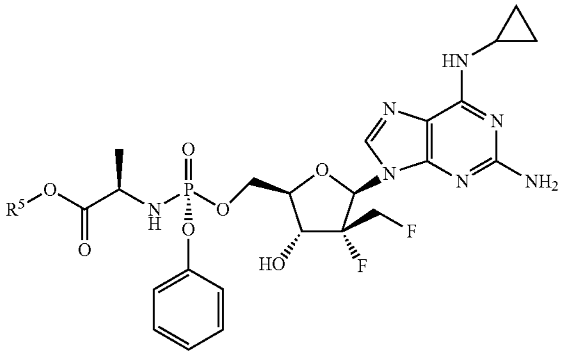
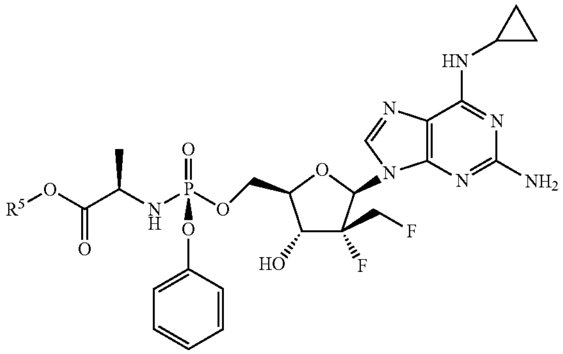
-continued
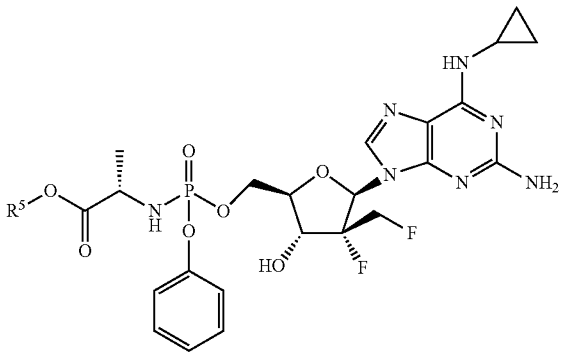
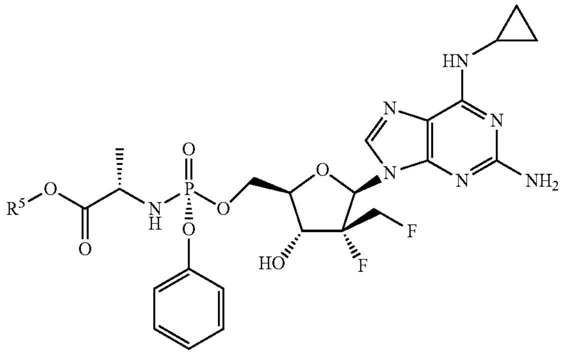
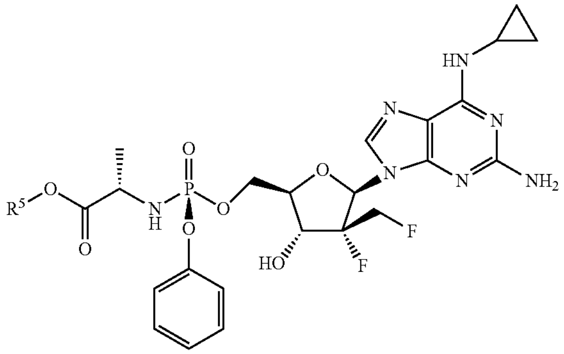
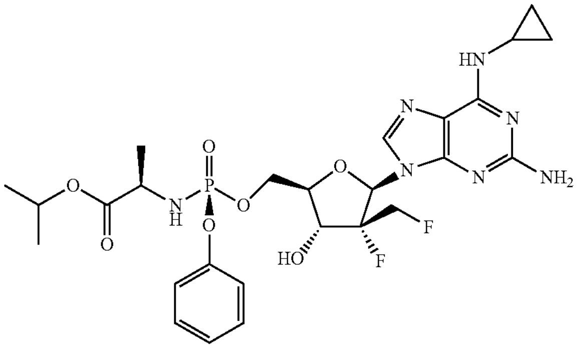

-continued
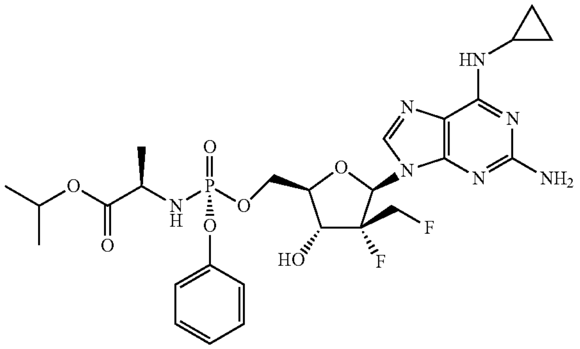
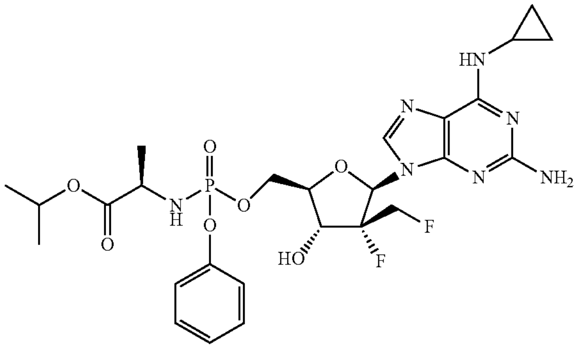
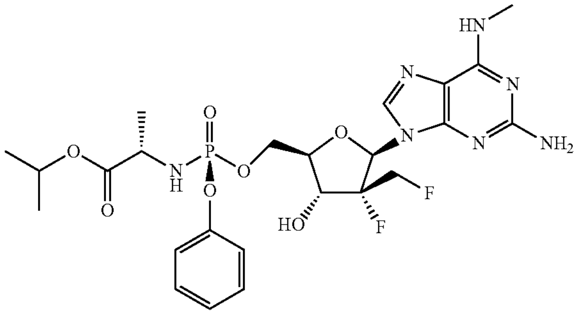
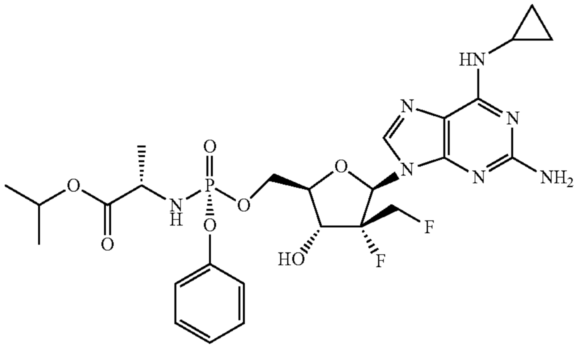
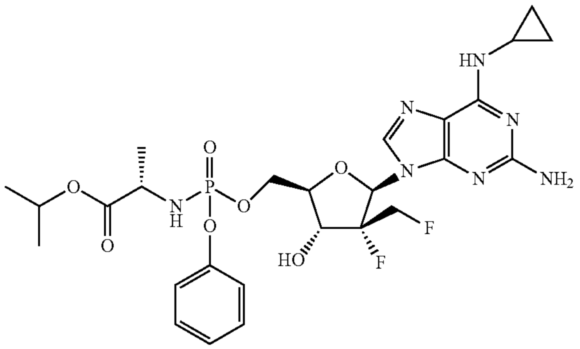
-continued
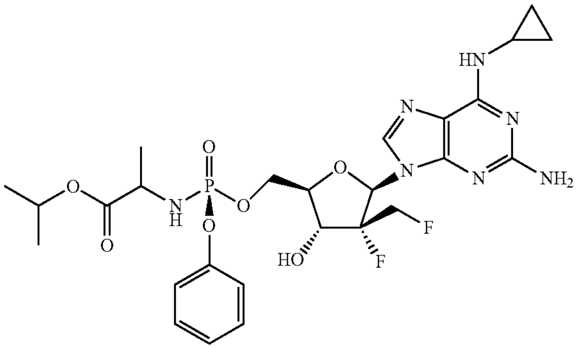
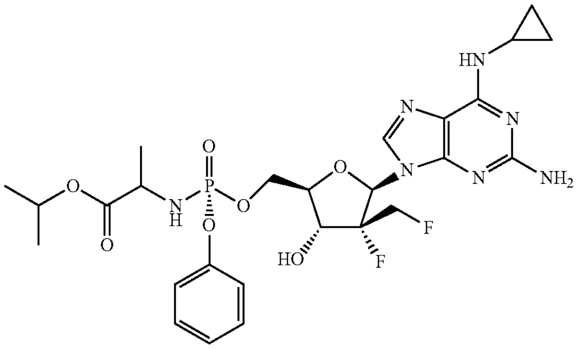
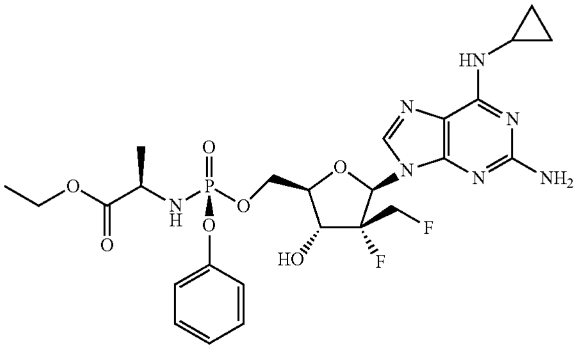
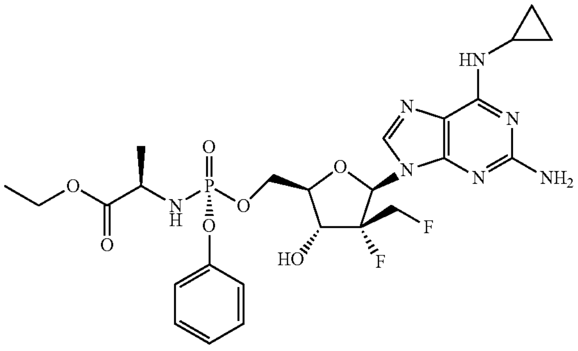

-continued
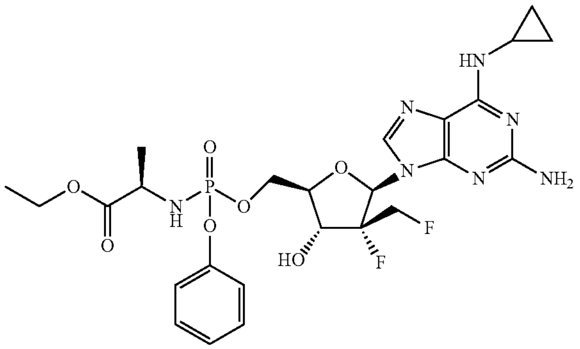
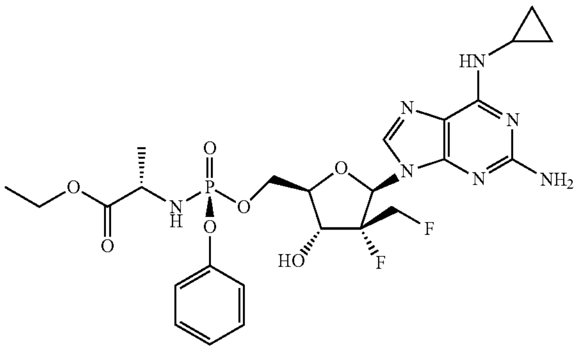
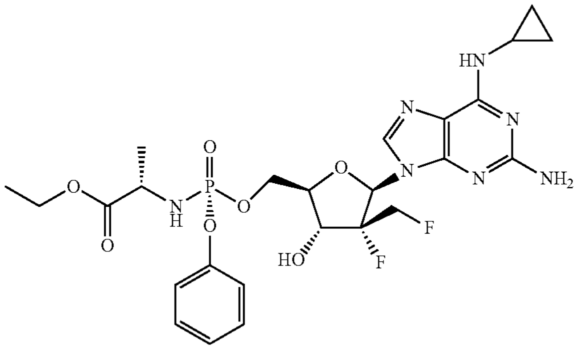
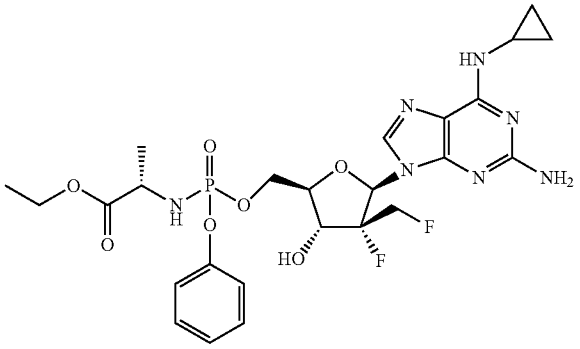
-continued
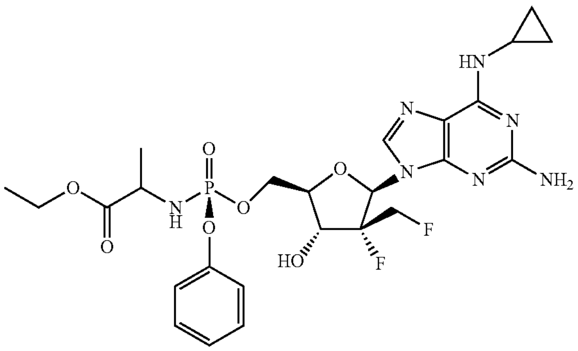
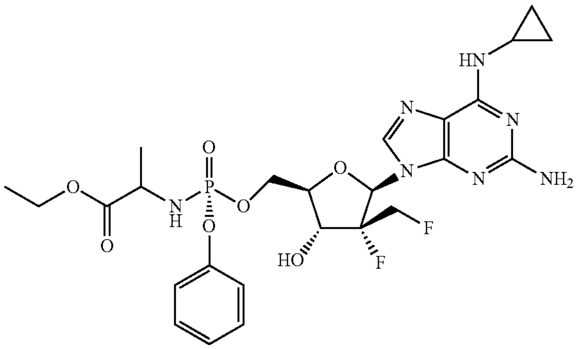
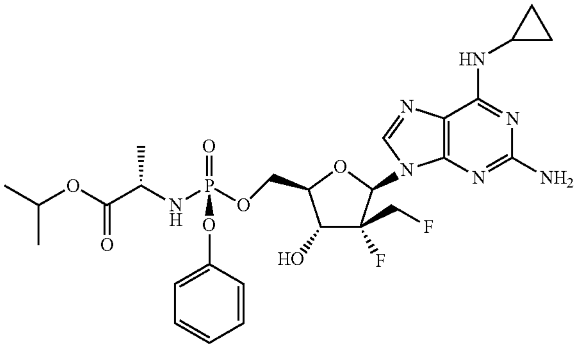
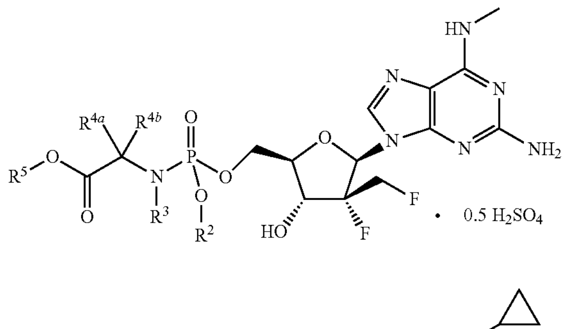
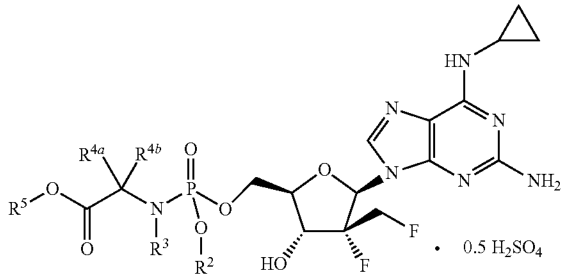

-continued

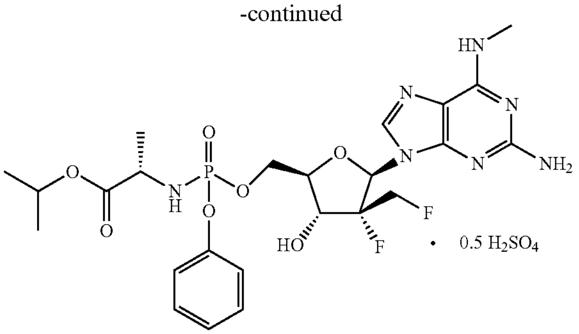

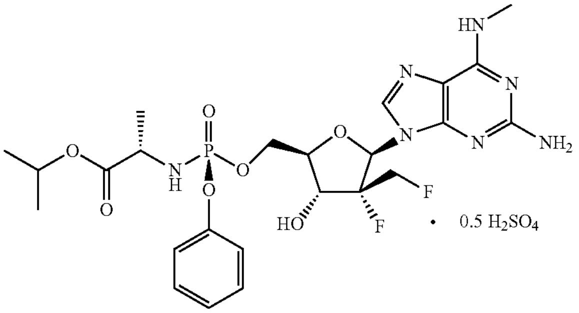

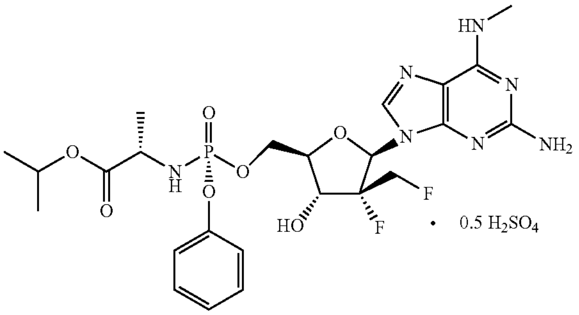

In some embodiments, the compound of Formula III to disrupt NiRAN function in a coronavirus or to treat or prevent a mutant or resistant form of the SARS-CoV-2 virus in a host in need thereof is a compound of Formula IIIb:

Formula IIIb

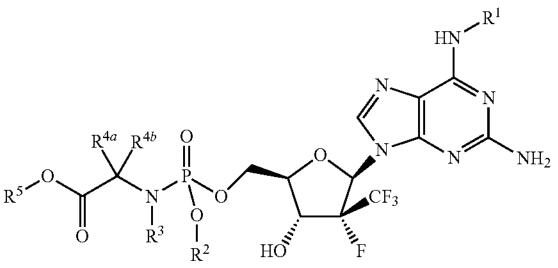

or a pharmaceutically acceptable salt thereof.

In some embodiments of Formula IIIb, $R^1$ is methyl.

In some embodiments of Formula IIIb, $R^1$ is cyclopropyl.

In some embodiments of Formula IIIb, $R^2$ is phenyl.

In some embodiments of Formula IIIb, $R^2$ is napthyl.

In some embodiments of Formula IIIb, $R^{4a}$ is hydrogen and $R^{4b}$ is methyl.

In some embodiments of Formula IIIb, $R^5$ is isopropyl.

In some embodiments of Formula IIIb, the compound is the $S_p$-isomer and the phosphoramidate is in the L-configuration.

In some embodiments of Formula IIIb, the compound is the $R_p$-isomer and the phosphoramidate is in the L-configuration.

In some embodiments of Formula IIIb, the pharmaceutically acceptable salt is the hemi-sulfate salt.

Non-limiting examples of a compound of Formula IIIb include:

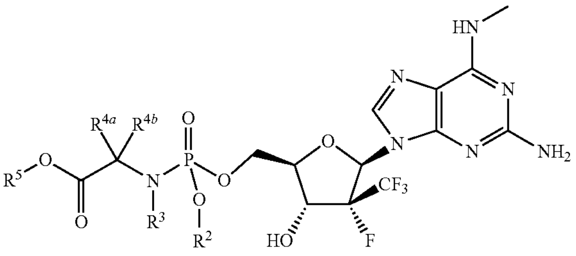

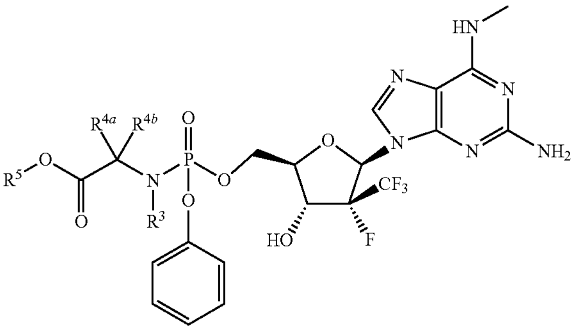

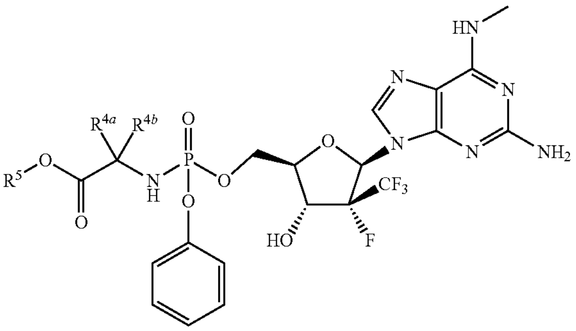

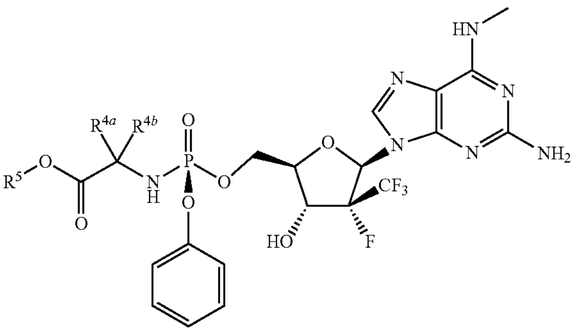

-continued
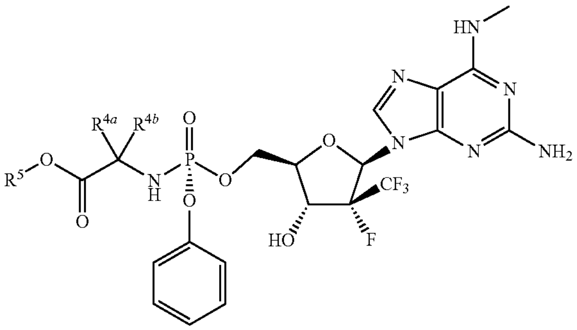
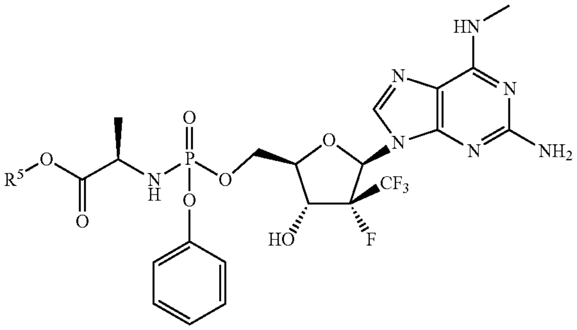
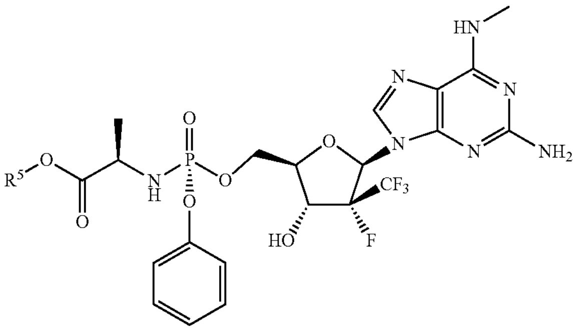
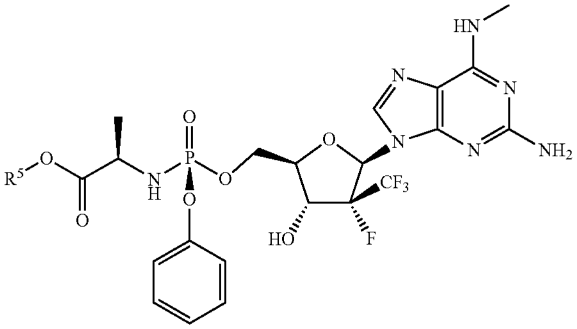
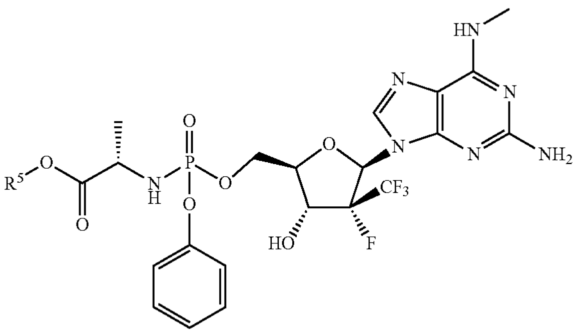
-continued
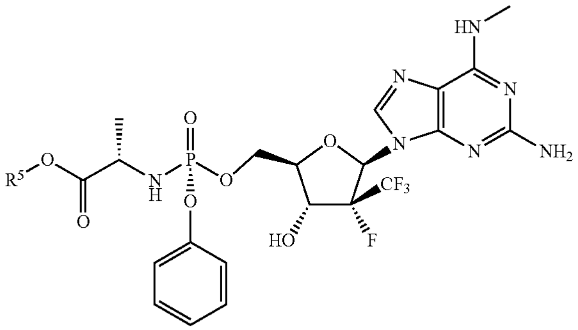
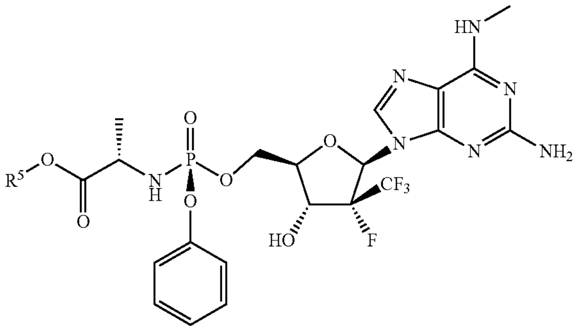
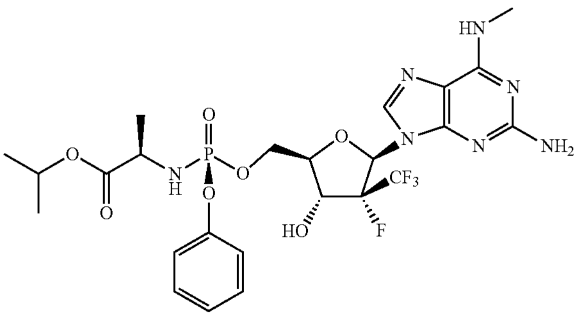
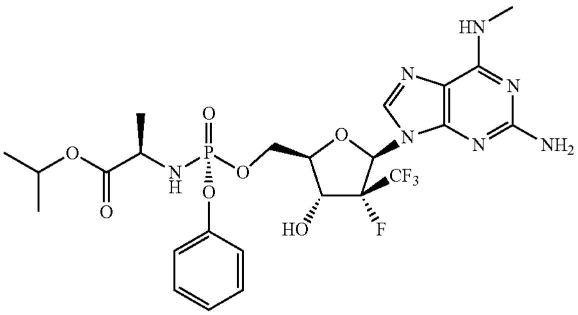
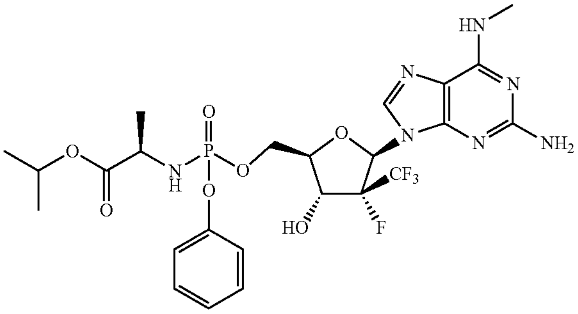

-continued
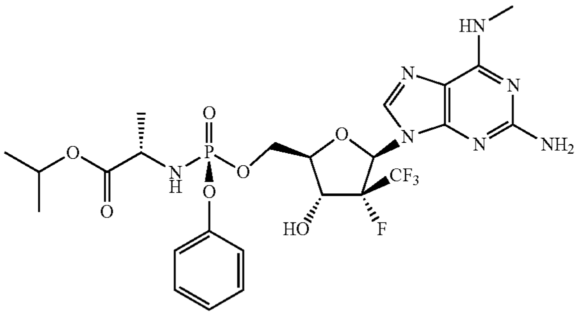
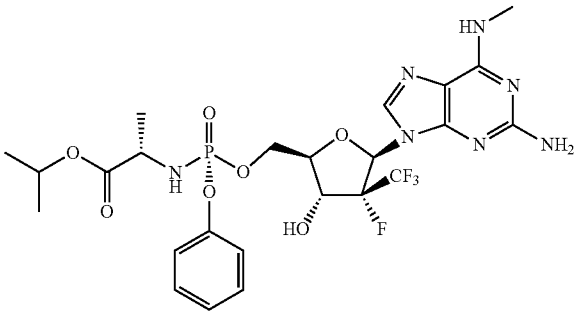
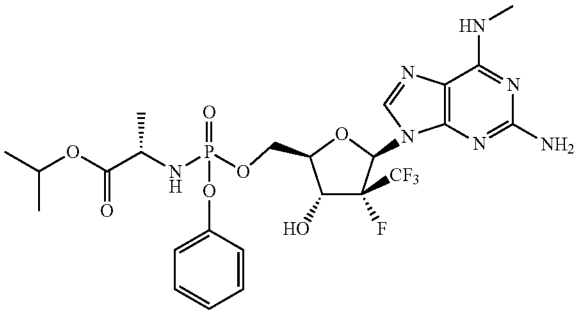
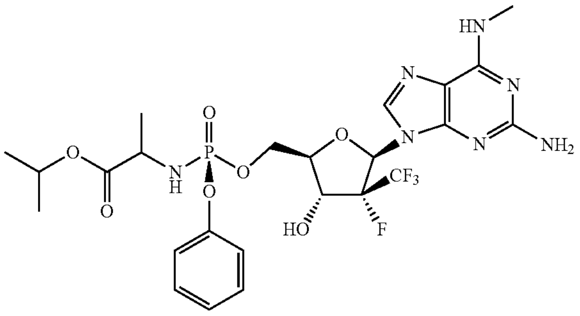
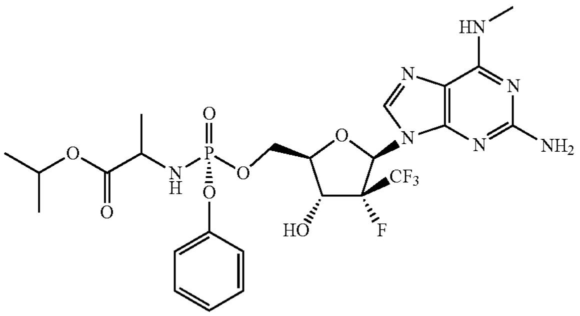
-continued
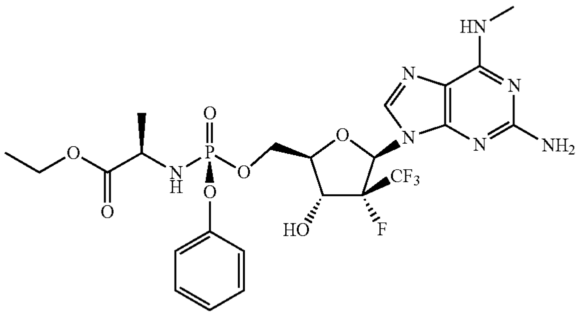
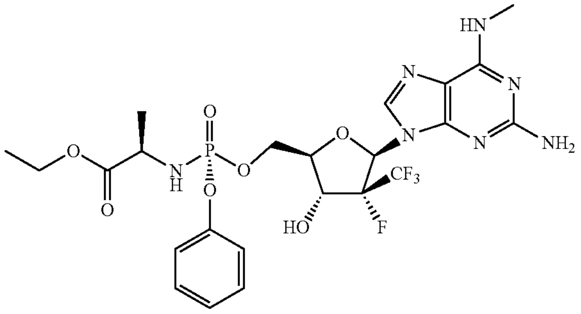
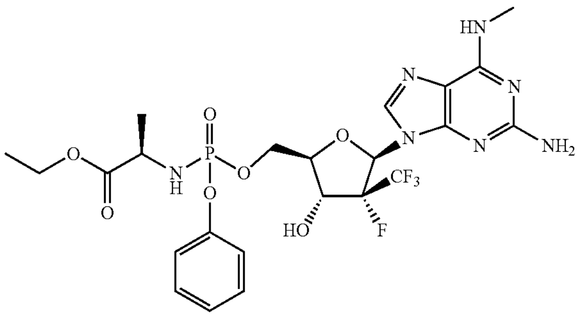
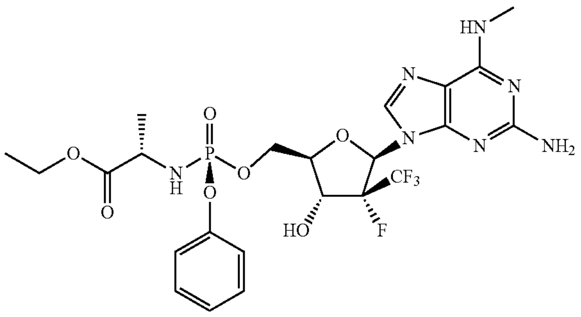
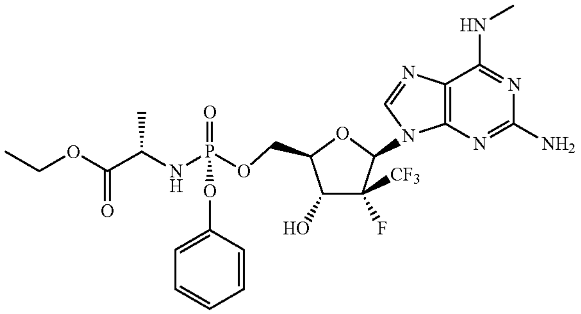

-continued
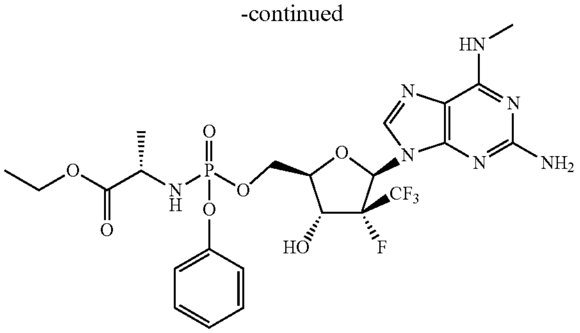
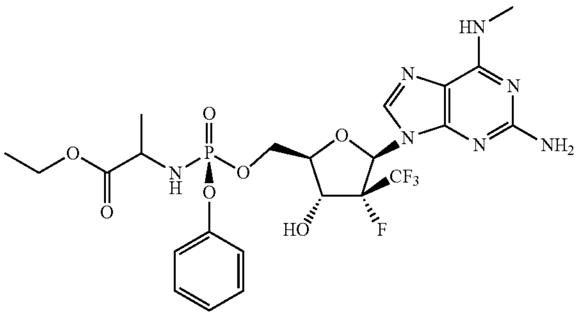
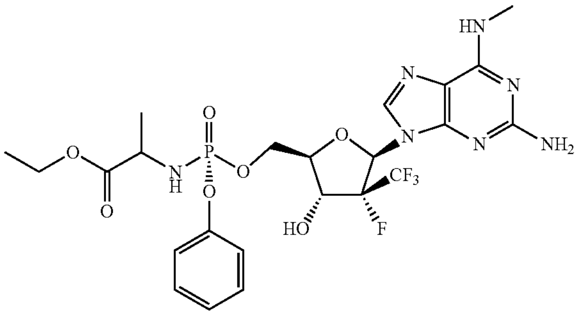
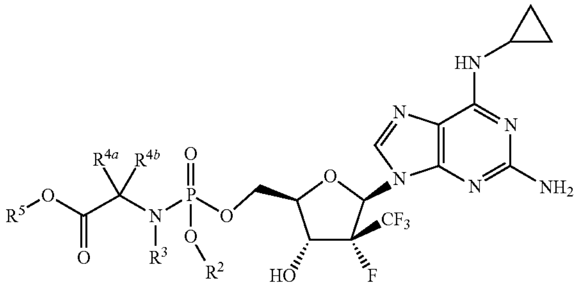
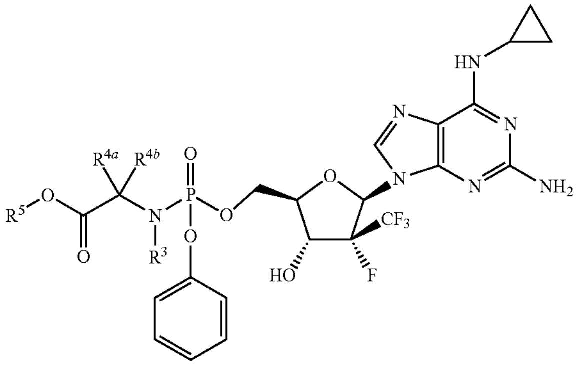
-continued
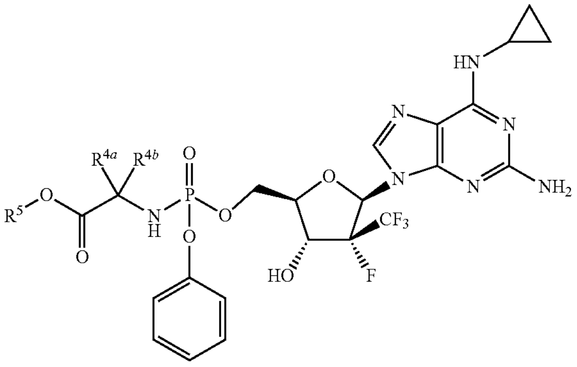
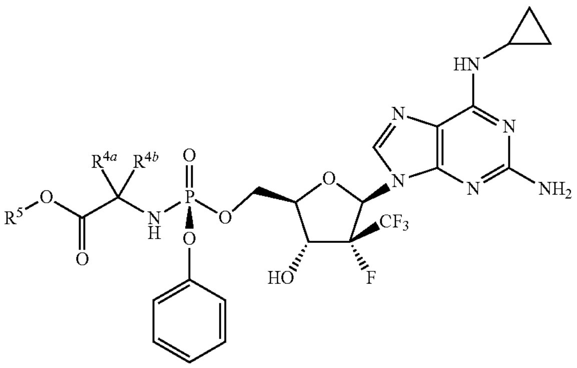
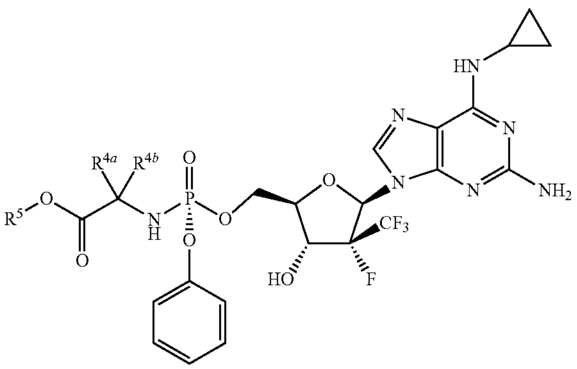
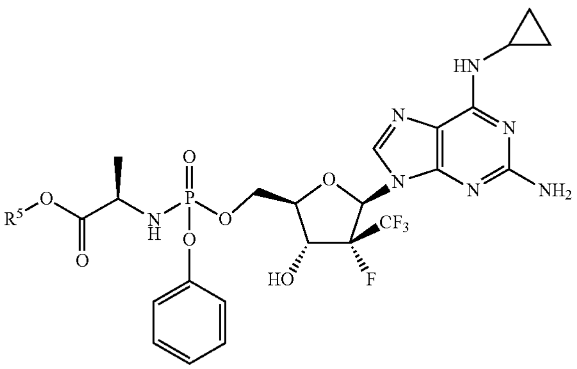

-continued
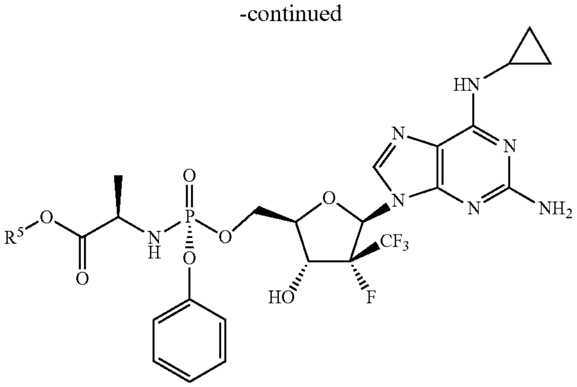
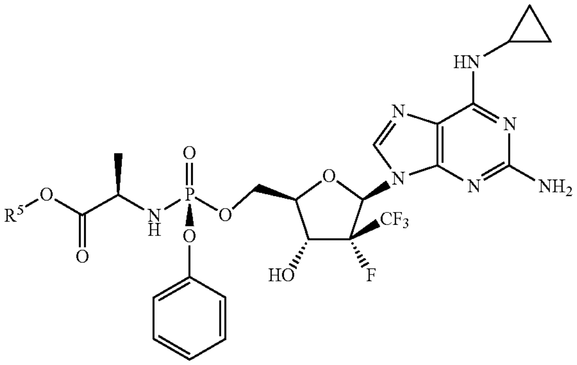
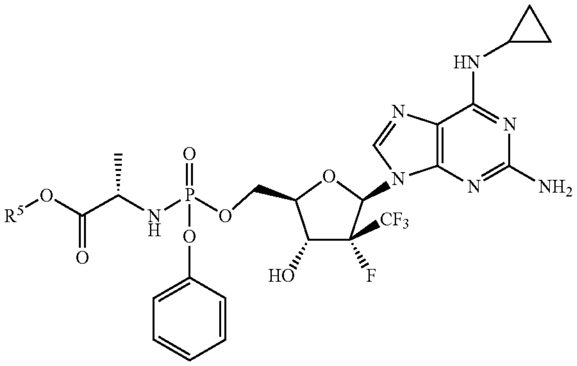
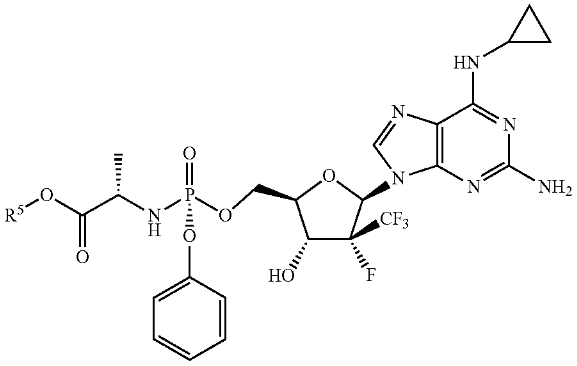
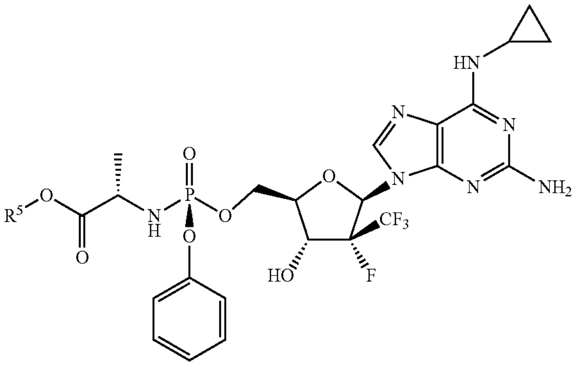
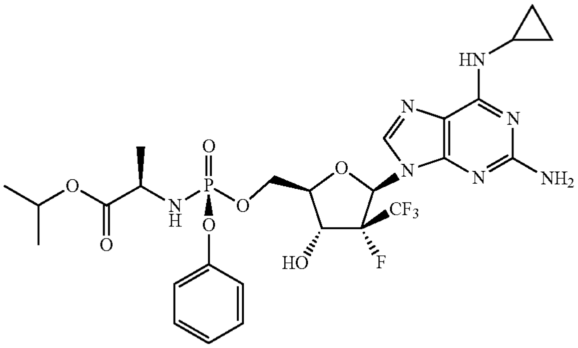
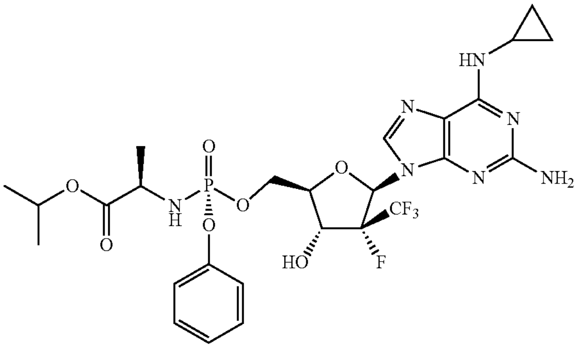
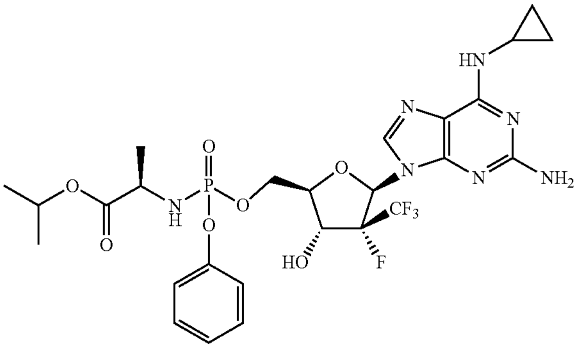
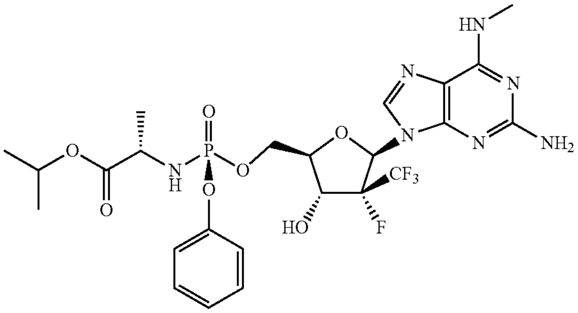

-continued
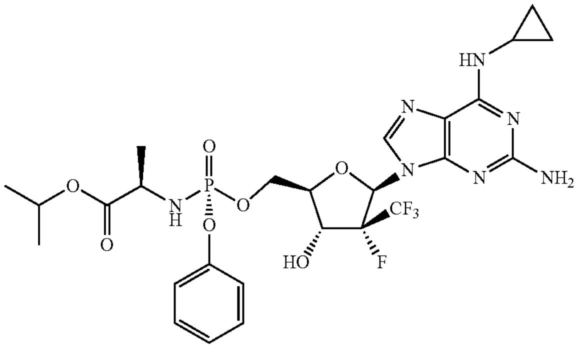
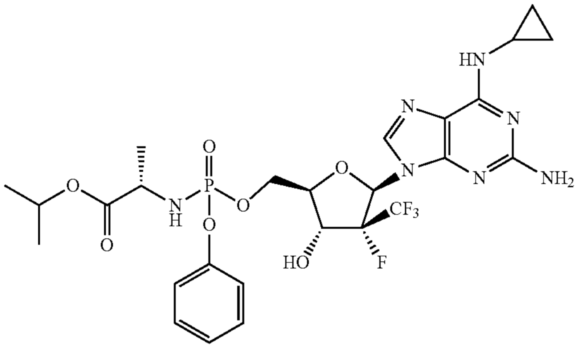
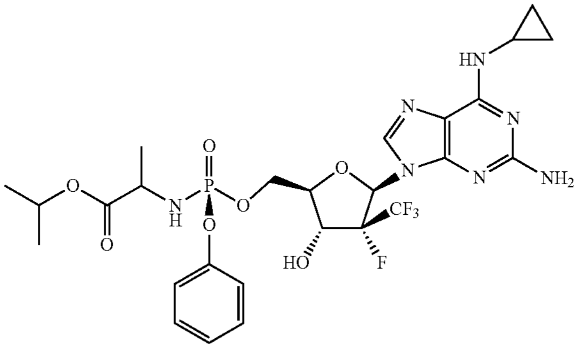
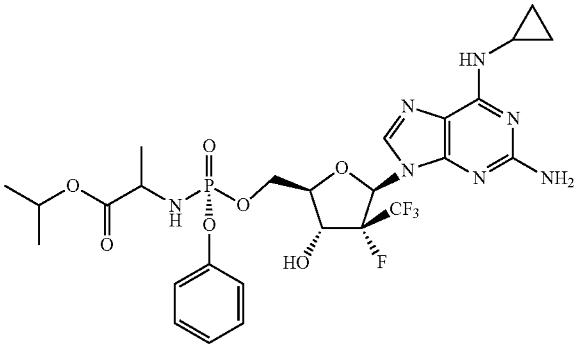
-continued
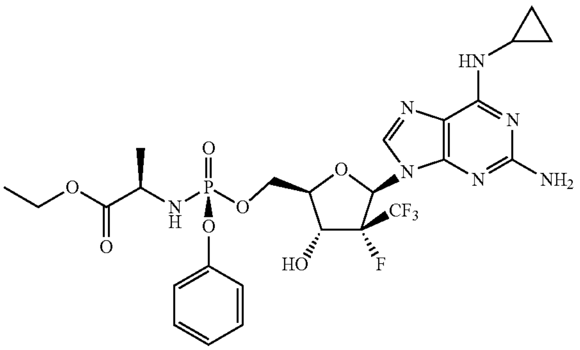
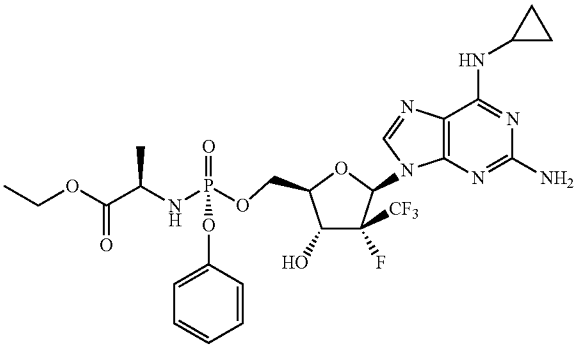
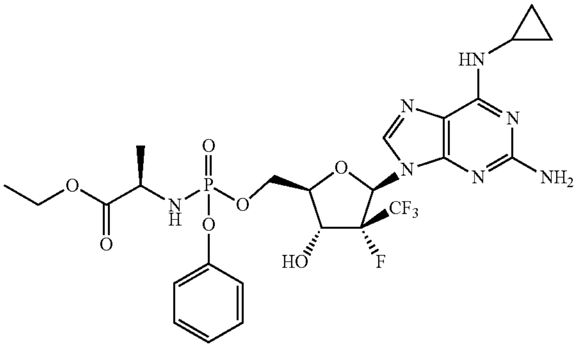
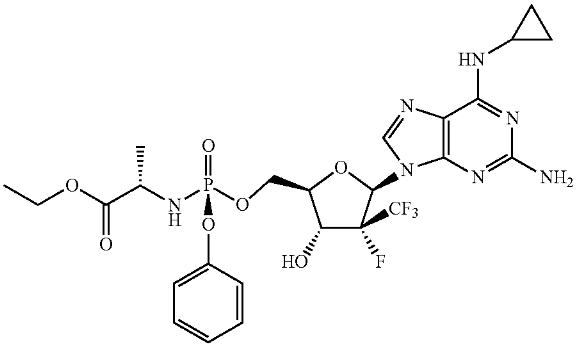

-continued
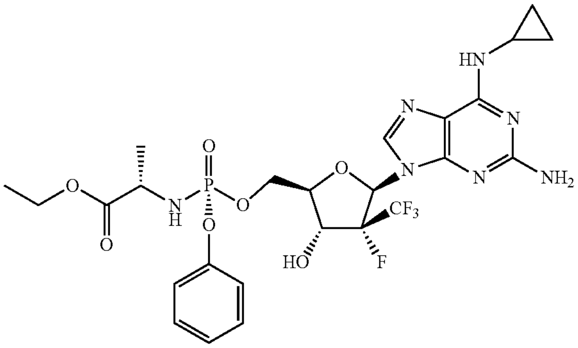
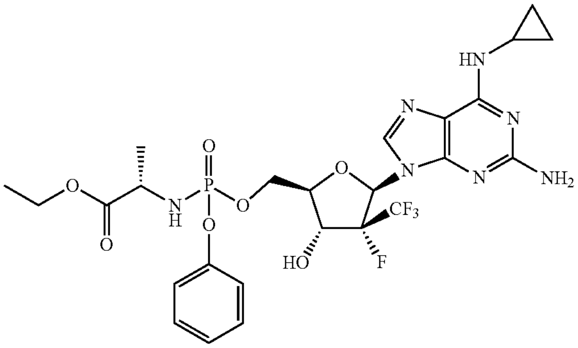
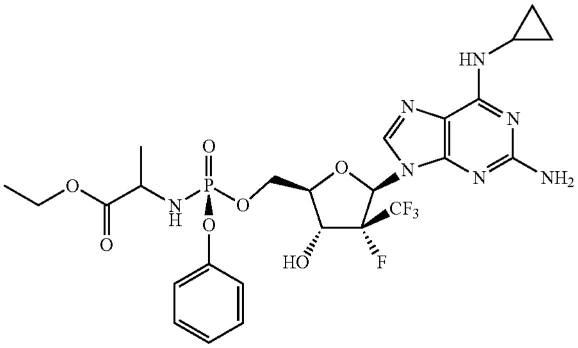
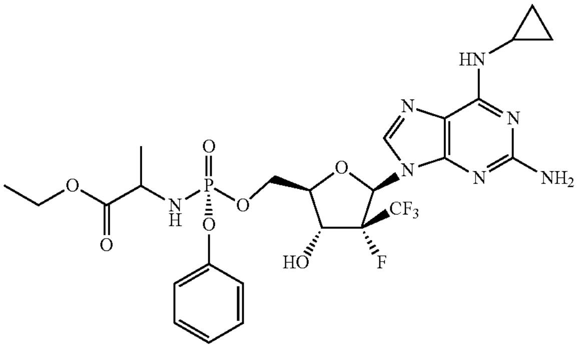
-continued
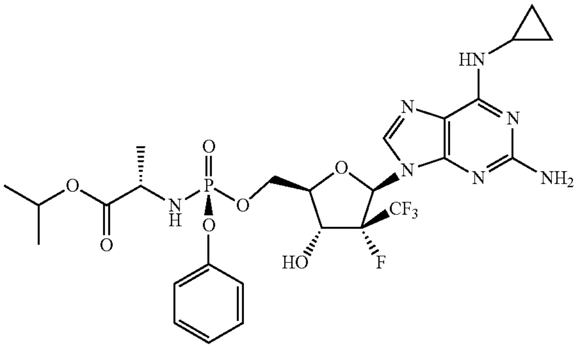
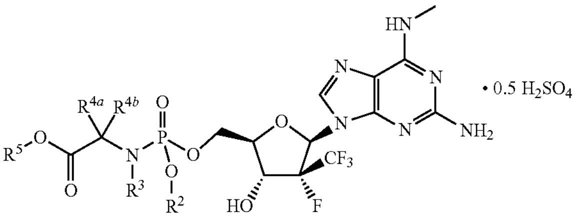
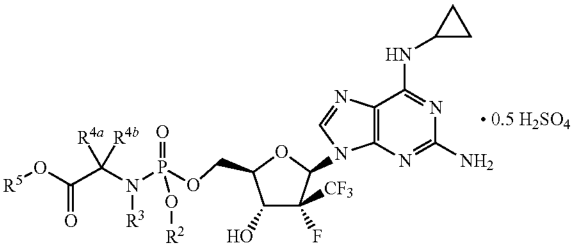
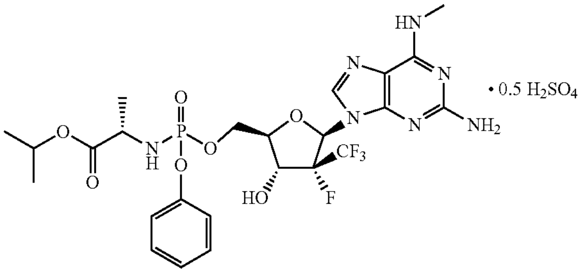
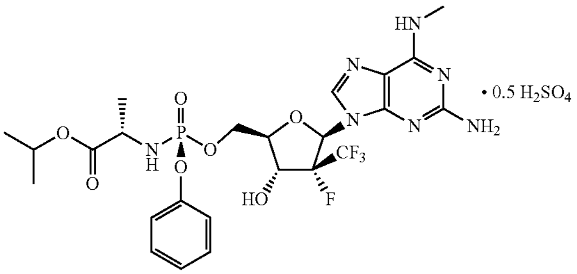
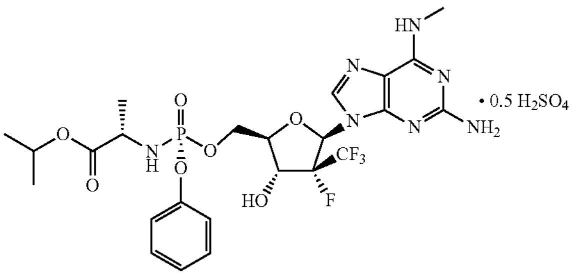
In some embodiments, the compound of Formula III to disrupt NiRAN function in a coronavirus or to treat or prevent a mutant or resistant form of the SARS-CoV-2 virus in a host in need thereof is a compound of Formula IIIc:

Formula IIIc

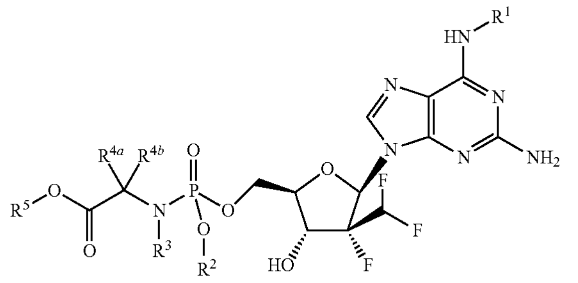

or a pharmaceutically acceptable salt thereof.

In some embodiments of Formula IIIc, $R^1$ is methyl.

In some embodiments of Formula IIIc, $R^1$ is cyclopropyl.

In some embodiments of Formula IIIc, $R^2$ is phenyl.

In some embodiments of Formula IIIc, $R^2$ is napthyl.

In some embodiments of Formula IIIc, $R^{4a}$ is hydrogen and $R^{4b}$ is methyl.

In some embodiments of Formula IIIc, $R^5$ is isopropyl.

In some embodiments of Formula IIIc, the compound is the $S_p$-isomer and the phosphoramidate is in the L-configuration.

In some embodiments of Formula IIIc, the compound is the $R_p$-isomer and the phosphoramidate is in the L-configuration.

In some embodiments of Formula IIIc, the pharmaceutically acceptable salt is the hemi-sulfate salt.

Non-limiting examples of a compound of Formula IIIc include:

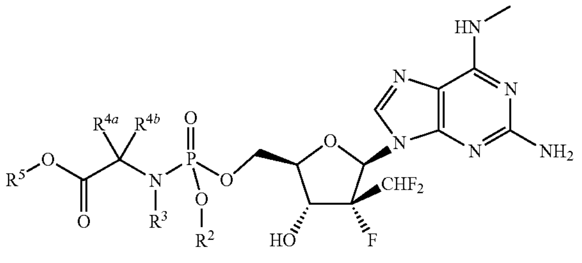

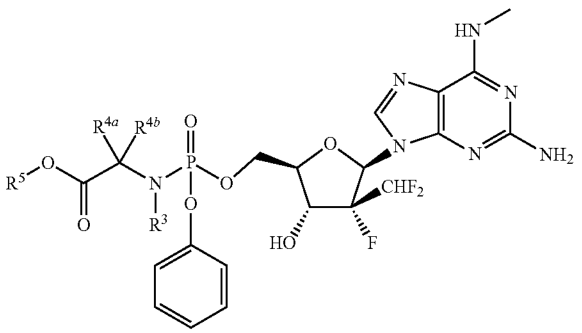

-continued

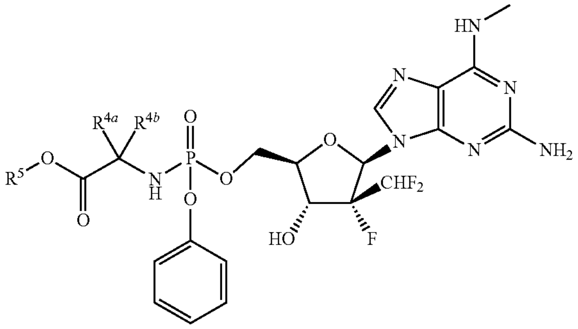

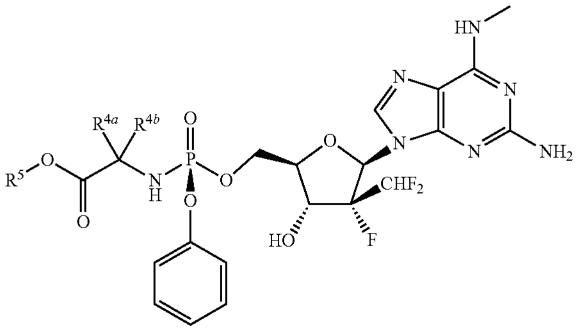

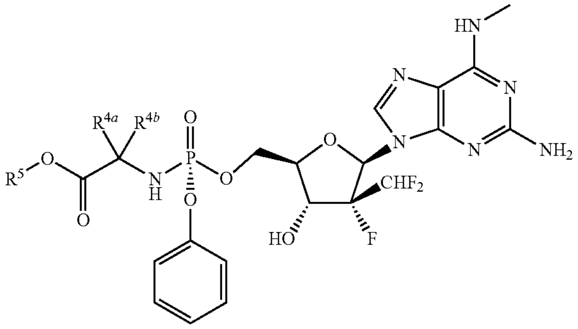

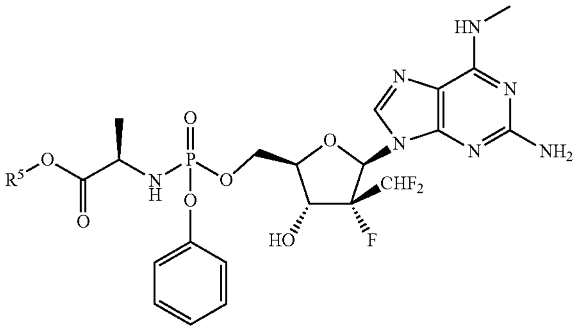

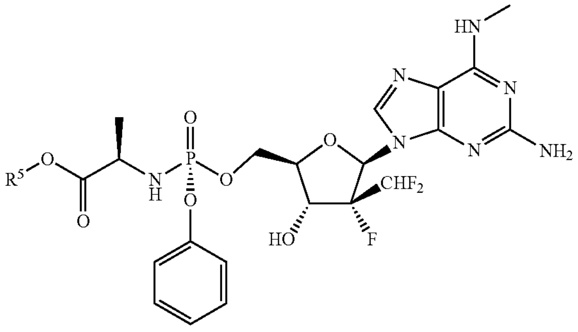

-continued
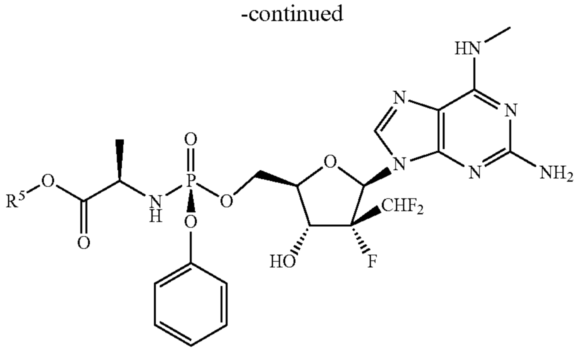
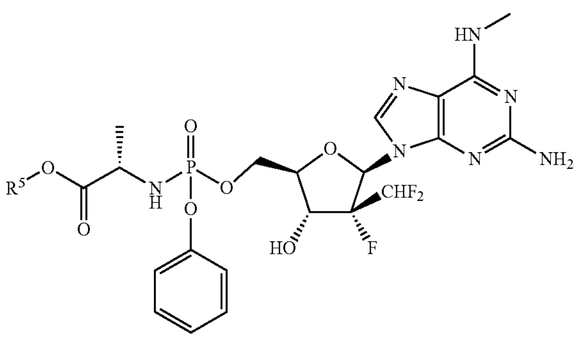
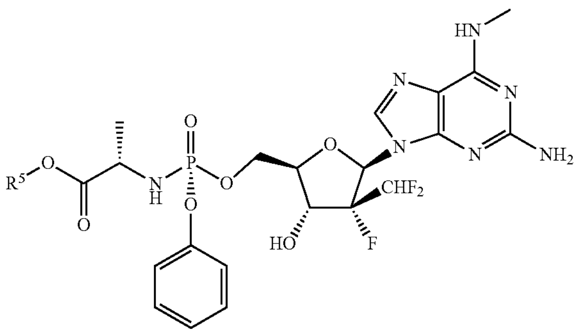
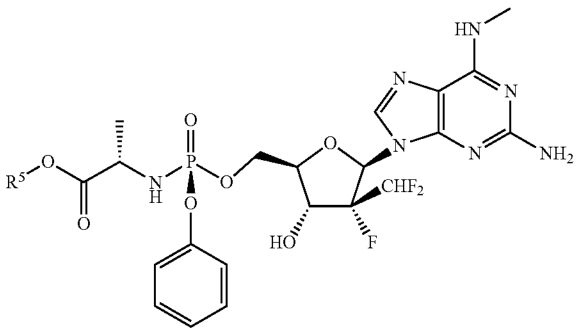
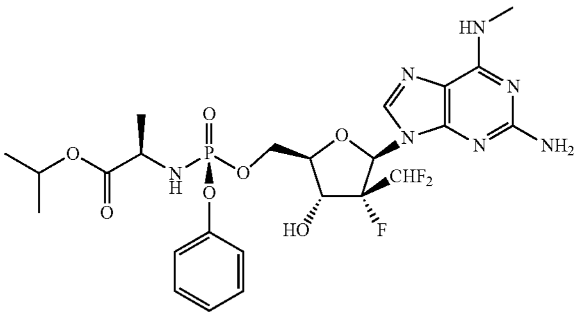
-continued
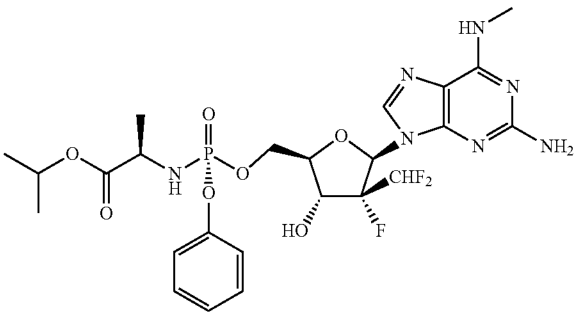
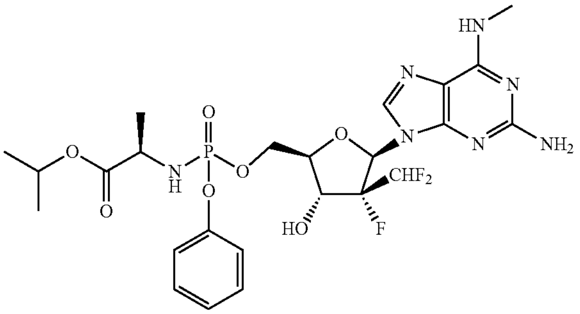
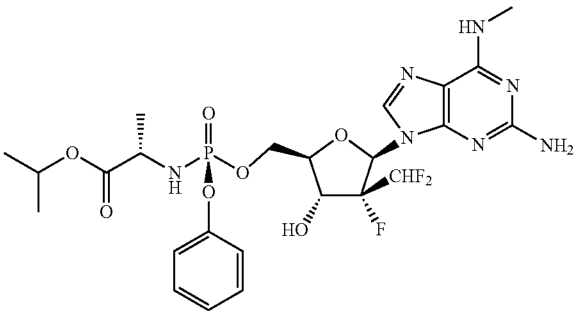
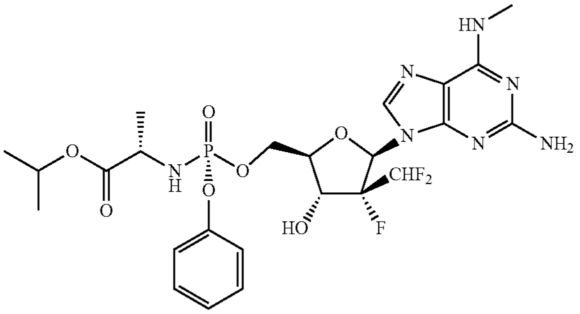
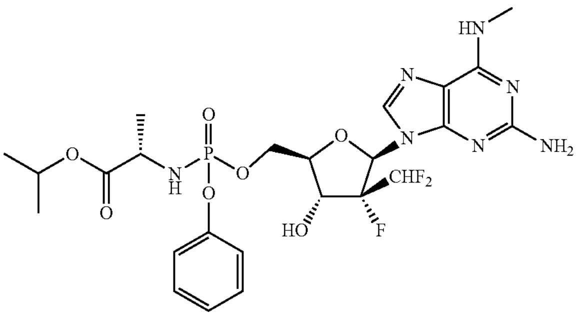

-continued
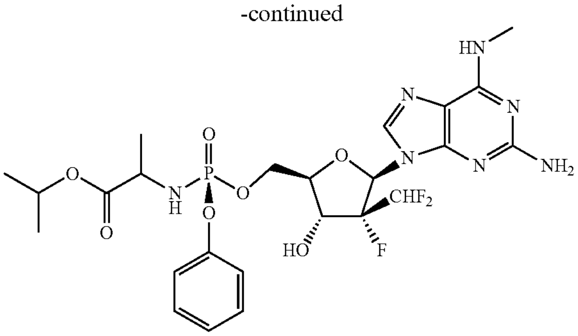
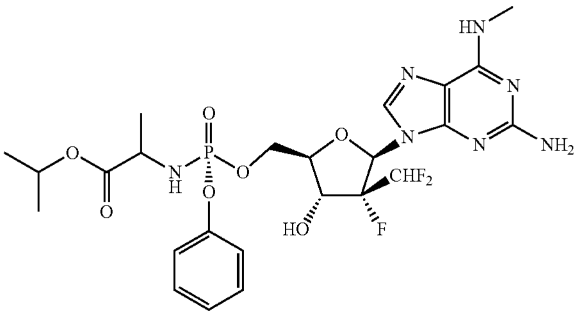
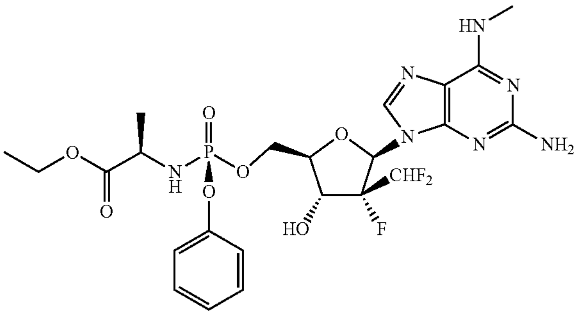
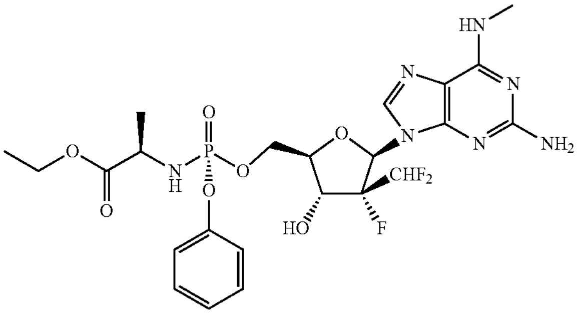
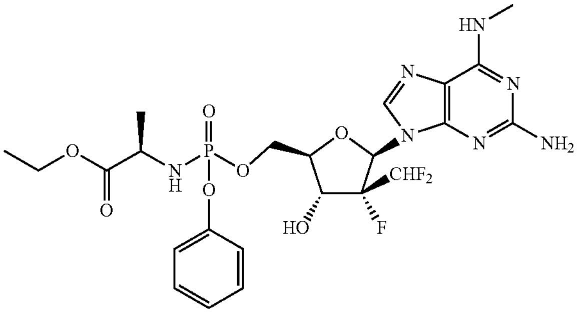
-continued
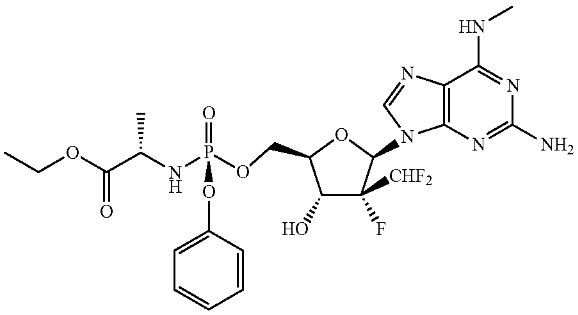
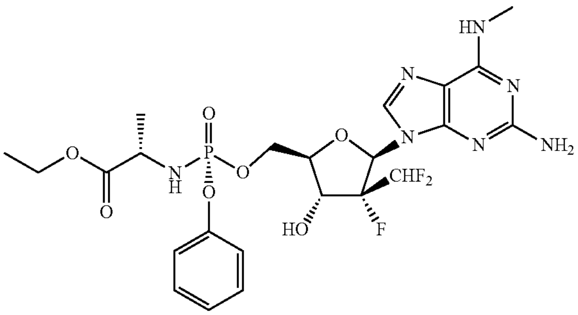
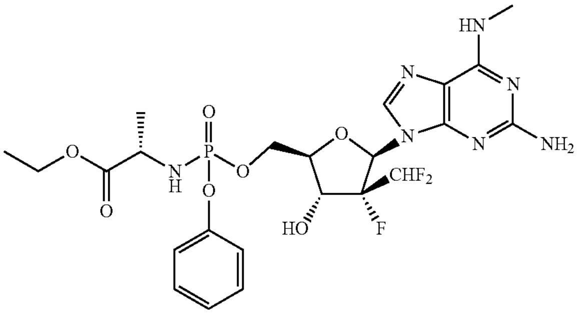
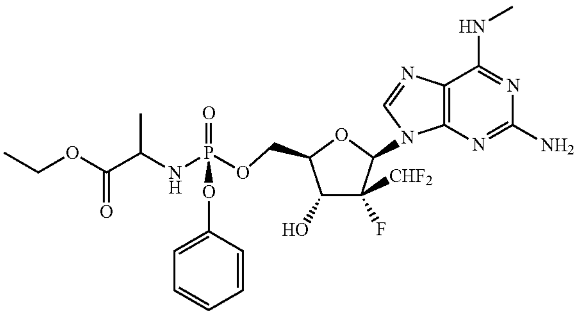
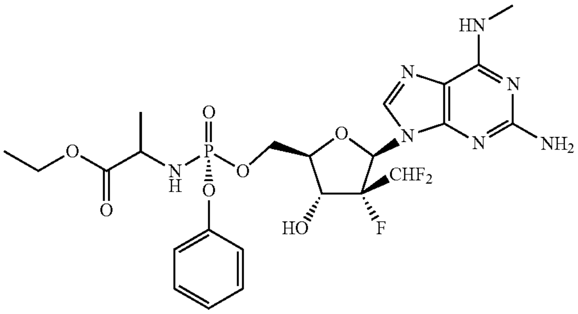

-continued
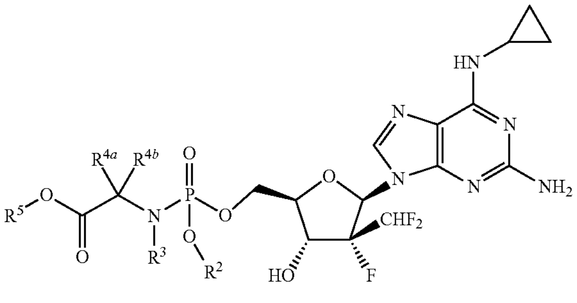
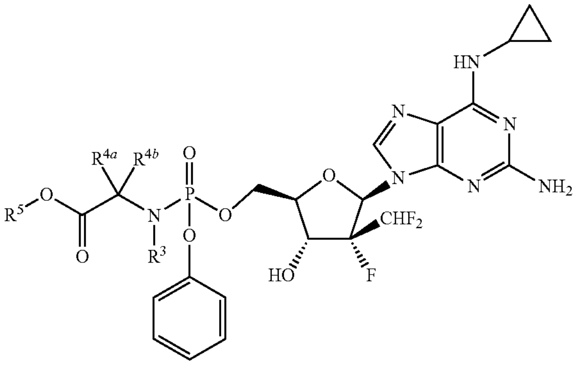
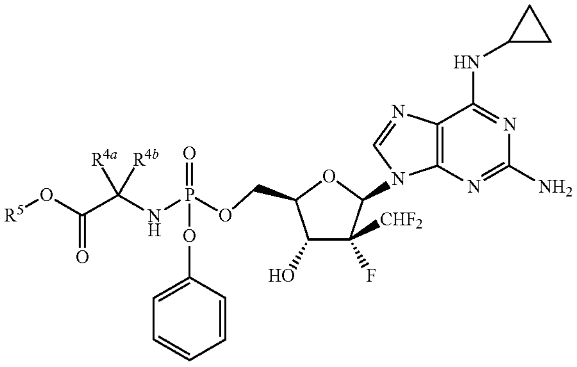
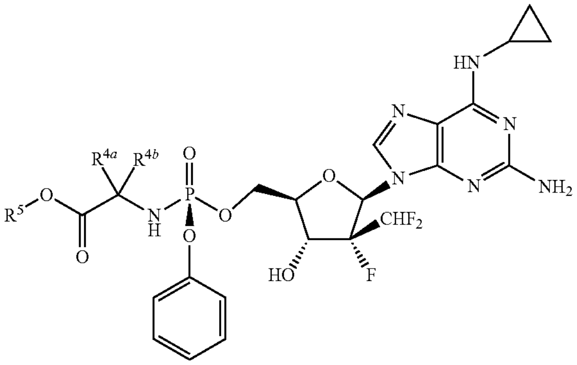
-continued
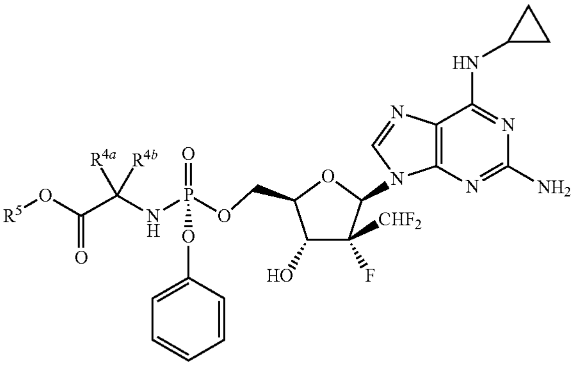
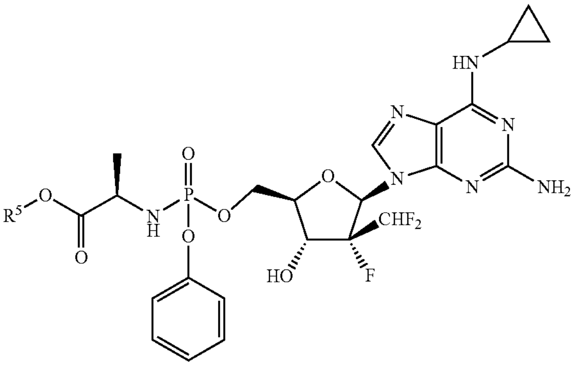
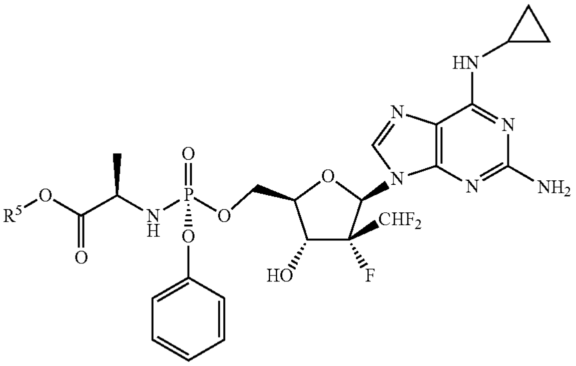
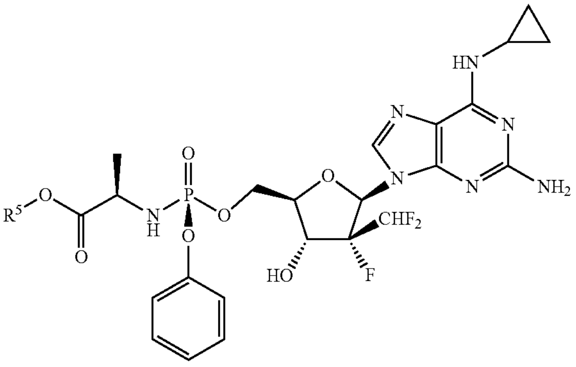

-continued
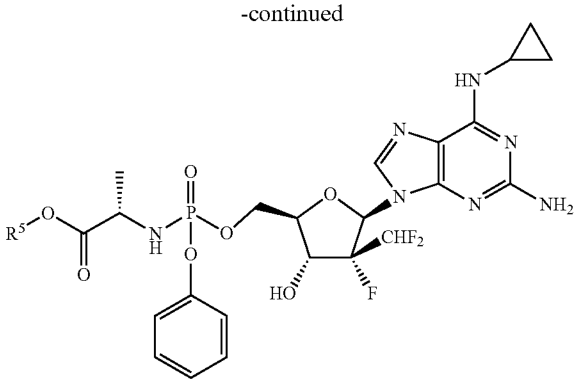
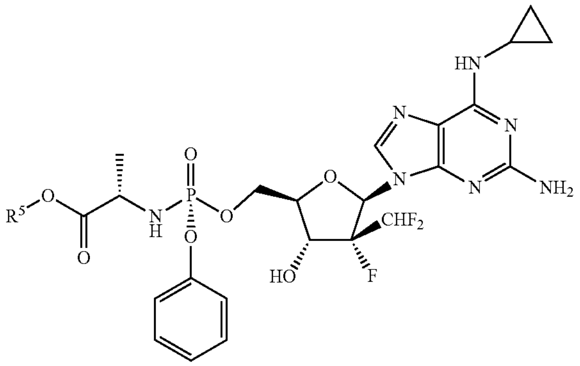
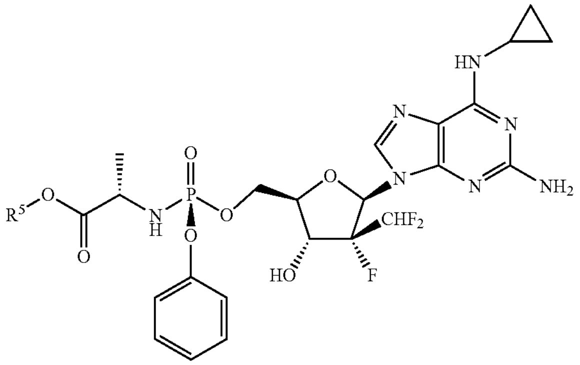
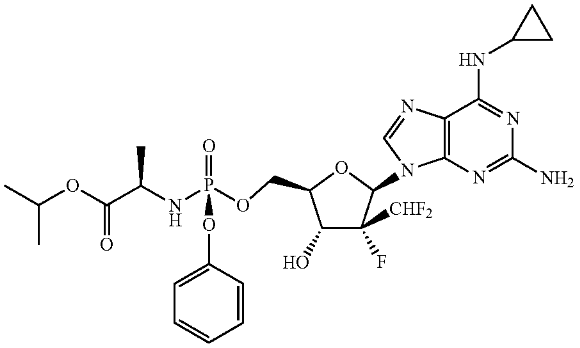
-continued
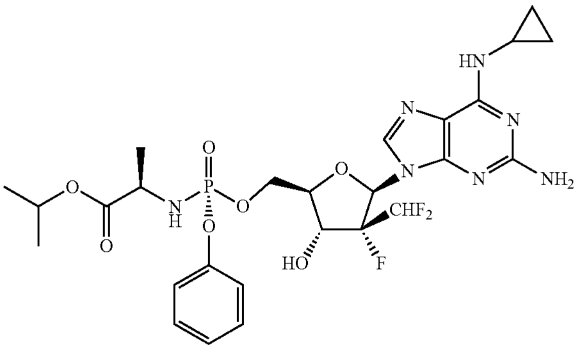
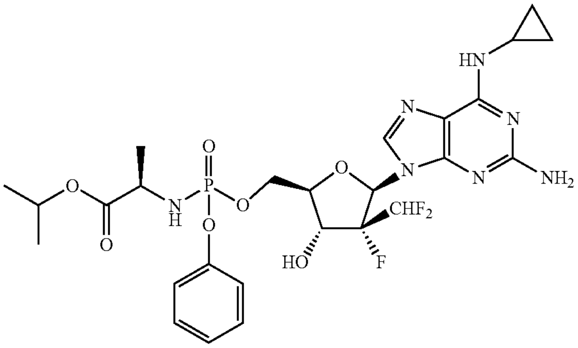
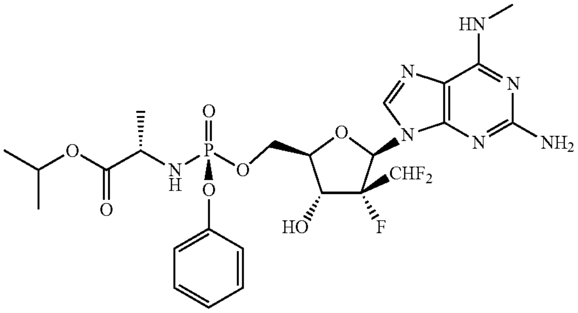
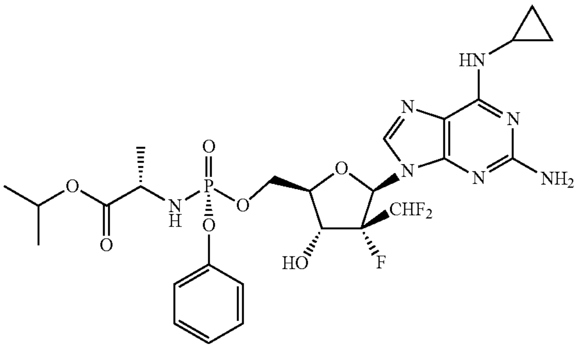
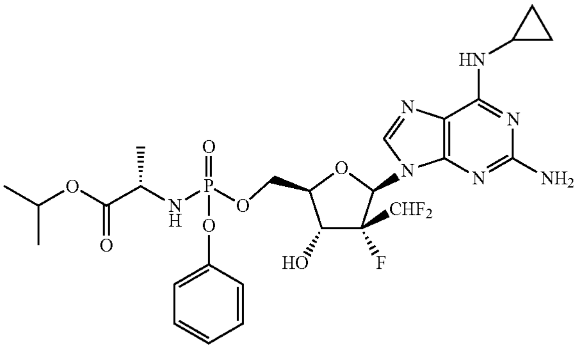

-continued
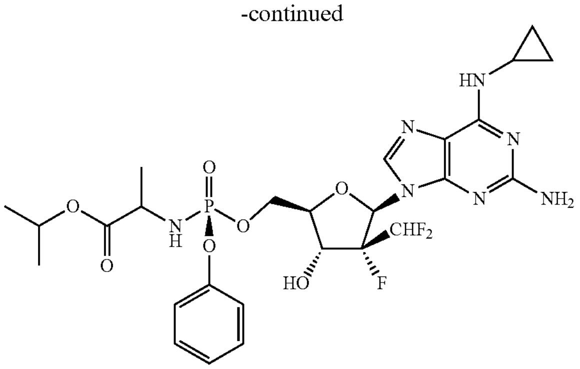
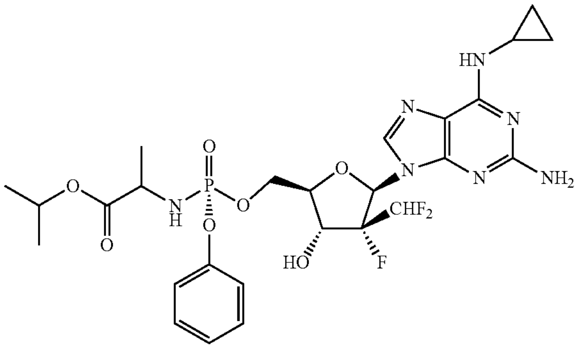
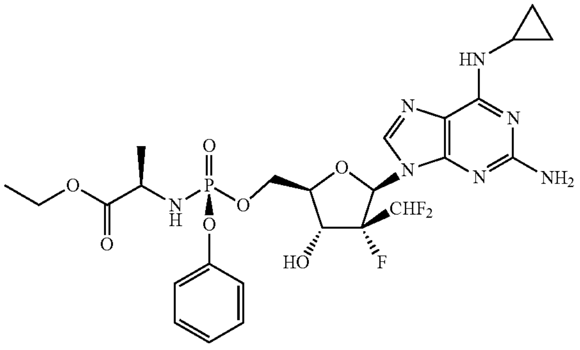
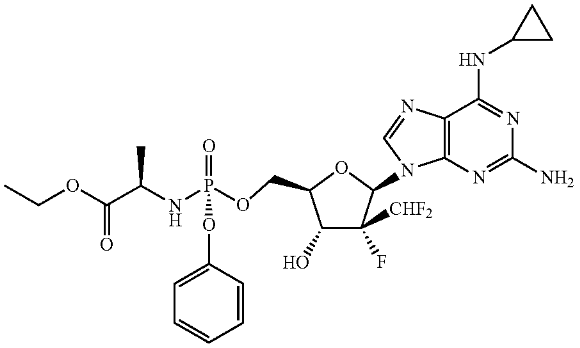
-continued
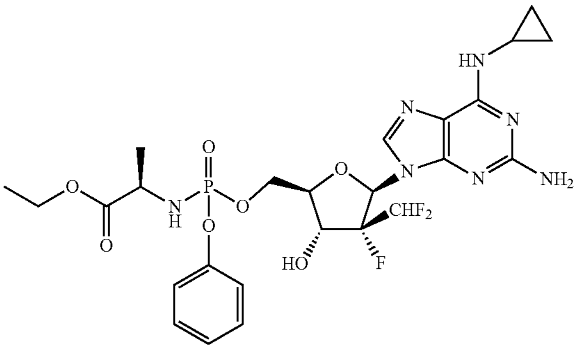
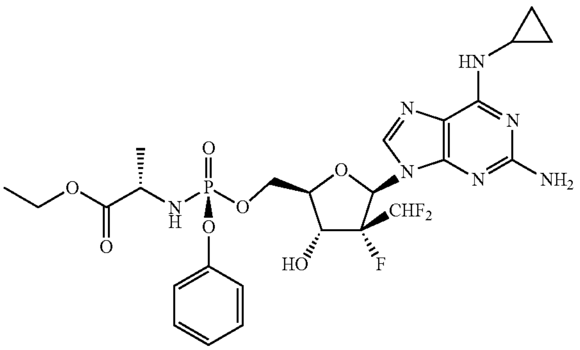
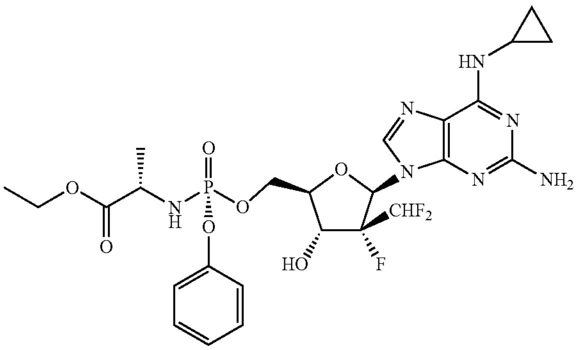
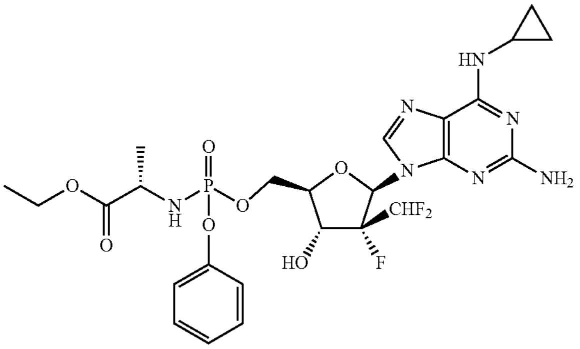

-continued

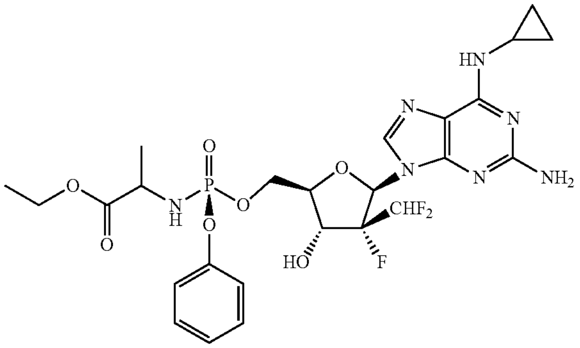

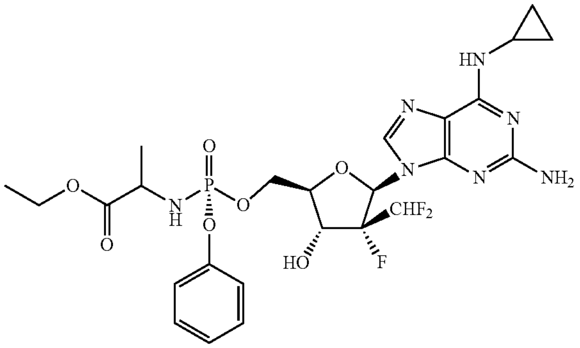

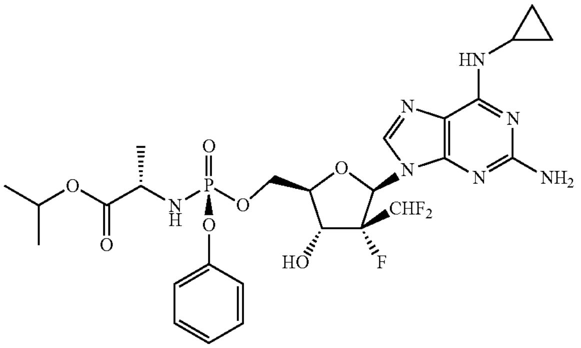

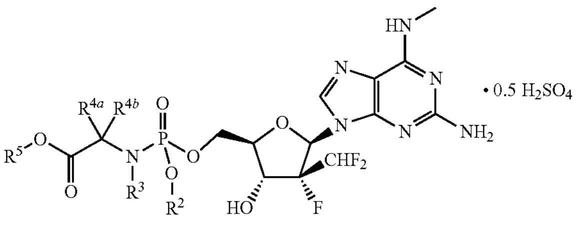

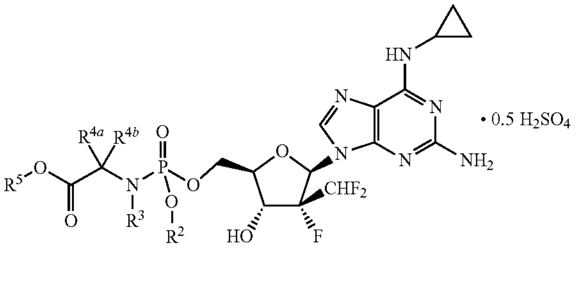

-continued

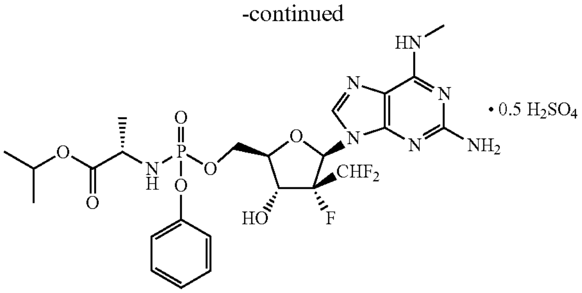

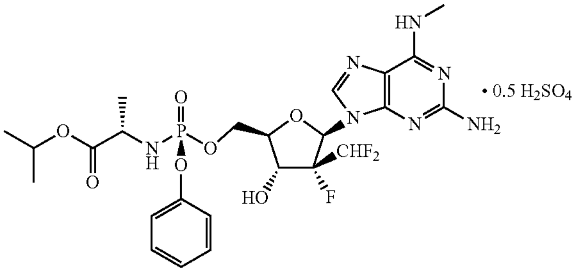

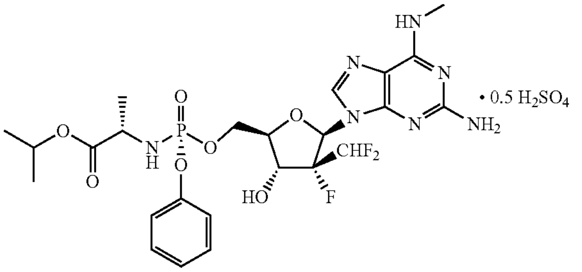

In some embodiments, the compound of Formula III to disrupt NiRAN function in a coronavirus or to treat or prevent a mutant or resistant form of SARS-CoV-2 virus in a host in need thereof is a compound of Formula IIId:

Formula IIId

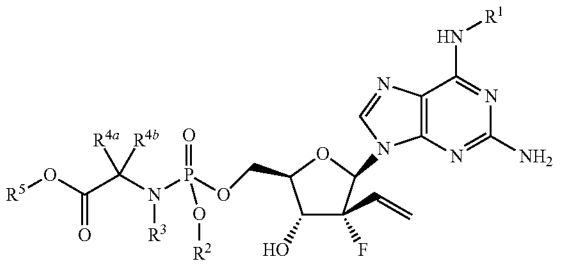

or a pharmaceutically acceptable salt thereof.

In some embodiments of Formula IIId, $R^1$ is methyl.

In some embodiments of Formula IIId, $R^1$ is cyclopropyl.

In some embodiments of Formula IIId, $R^1$ is phenyl.

In some embodiments of Formula IIId, $R^2$ is napthyl.

In some embodiments of Formula IIId, $R^{4a}$ is hydrogen and $R^{4b}$ is methyl.

In some embodiments of Formula IIId, $R^5$ is isopropyl.

In some embodiments of Formula IIId, the compound is the $S_p$-isomer and the phosphoramidate is in the L-configuration.

In some embodiments of Formula IIId, the compound is the $R_p$-isomer and the phosphoramidate is in the L-configuration.

In some embodiments of Formula IIId, the pharmaceutically acceptable salt is the hemi-sulfate salt.

Non-limiting examples of a compound of Formula IIId include:
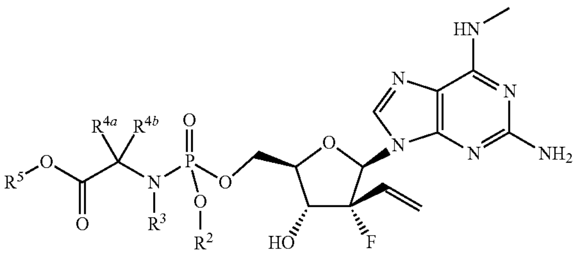
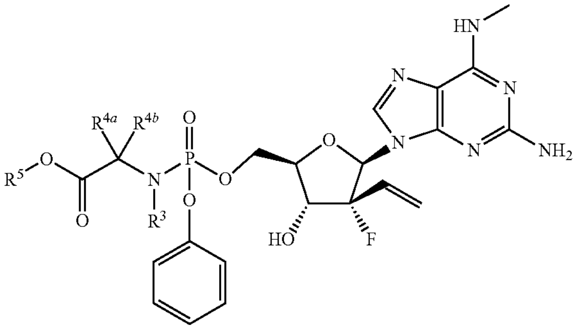
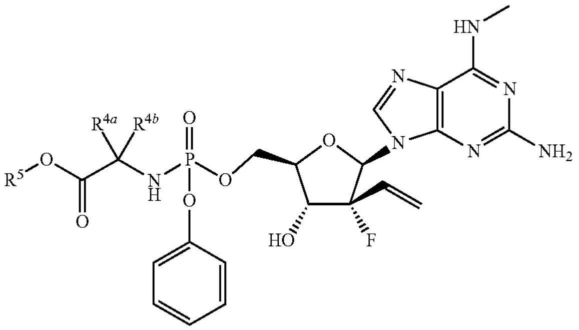
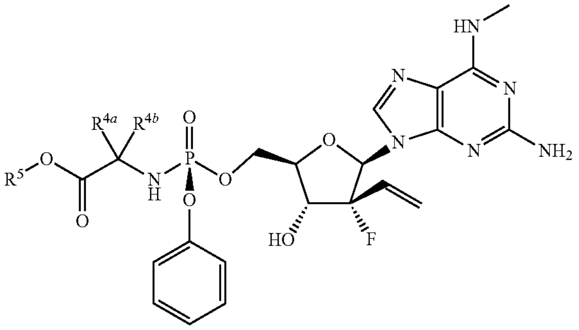
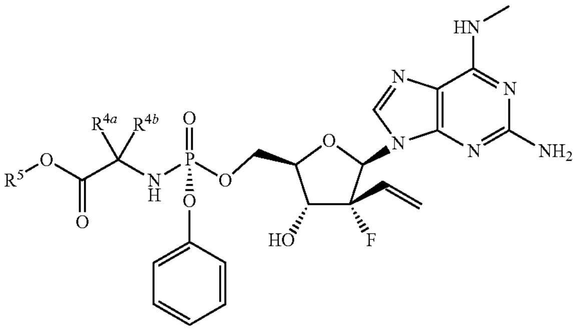
-continued
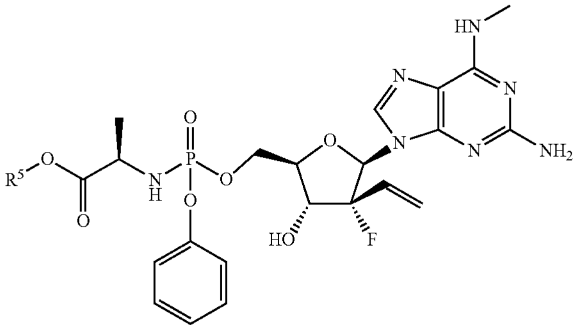
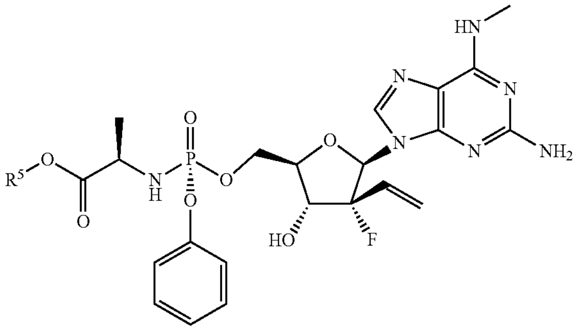
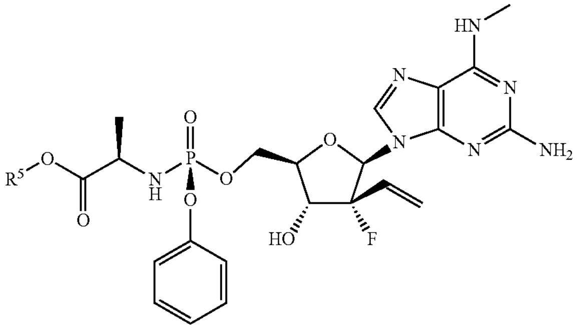
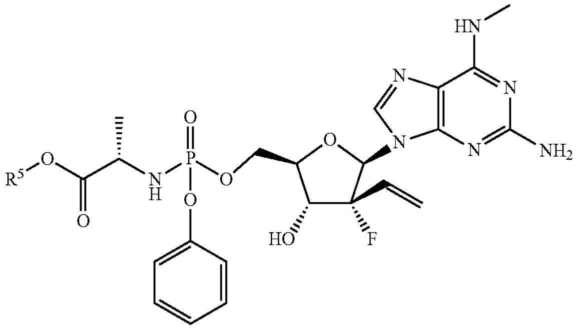
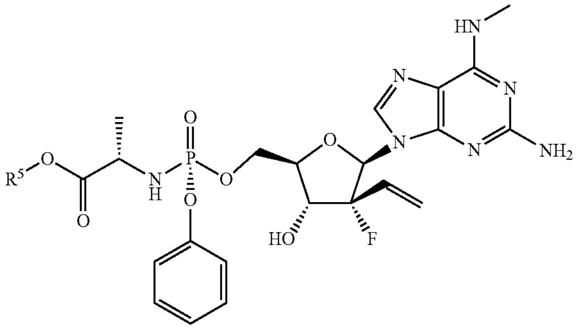

-continued
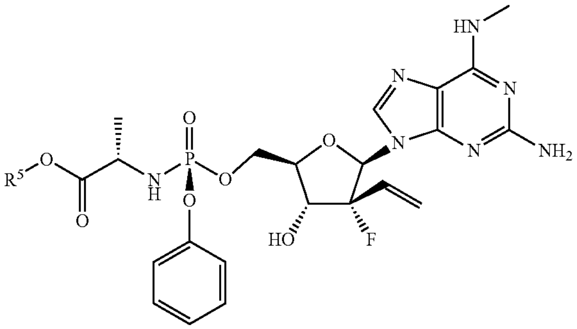
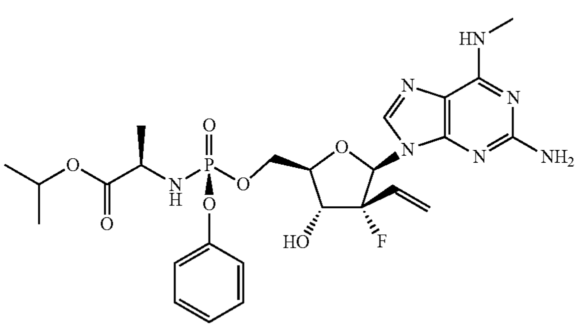
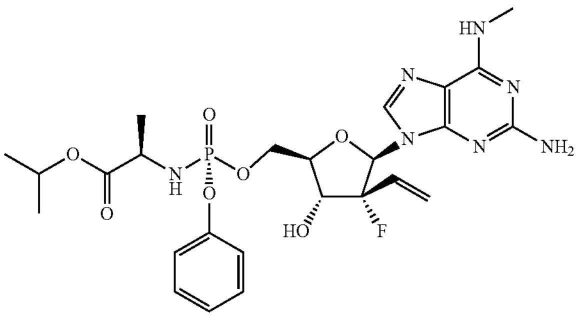
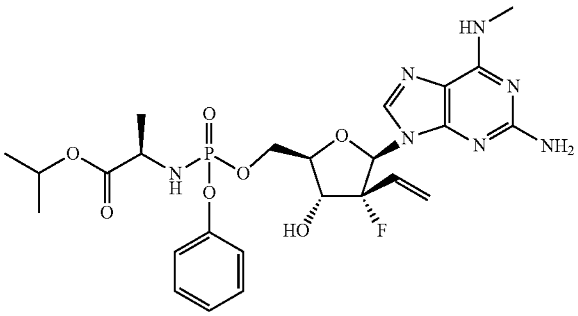
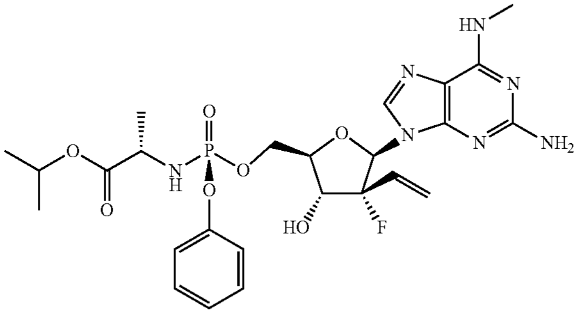
-continued
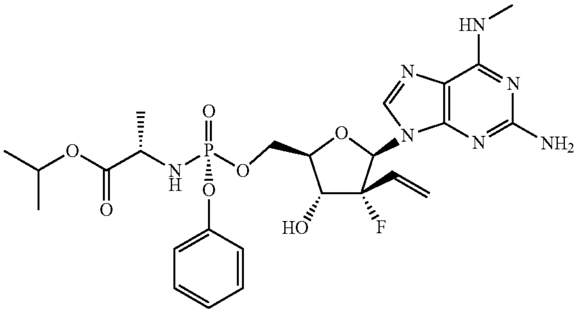
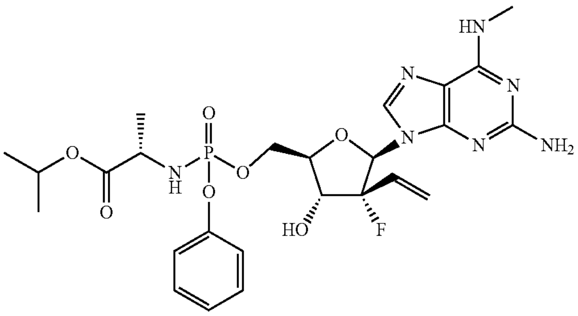
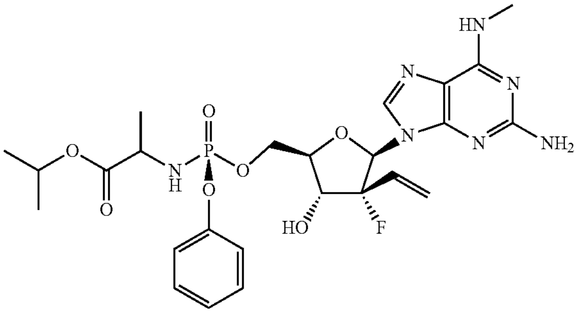
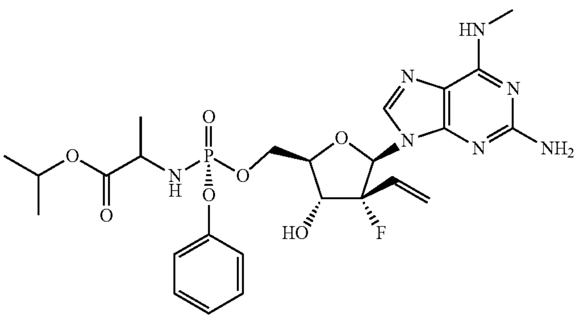
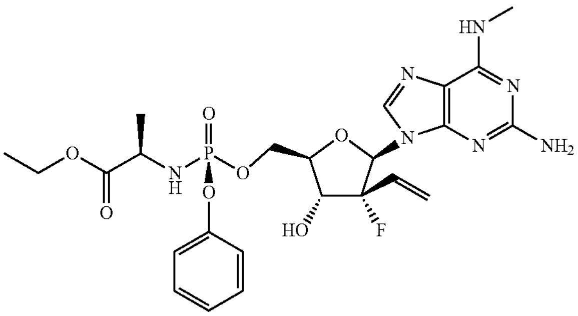

-continued
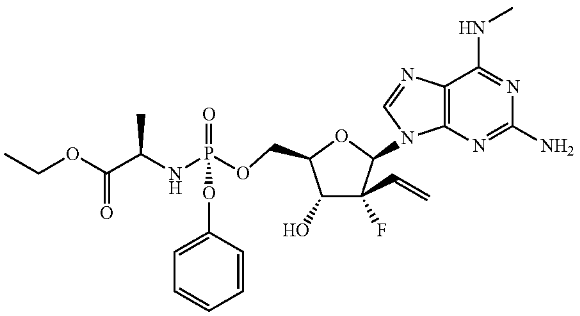
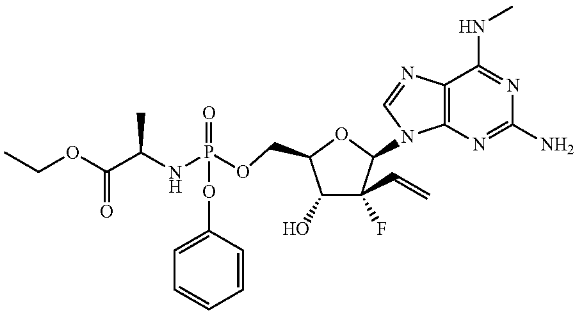
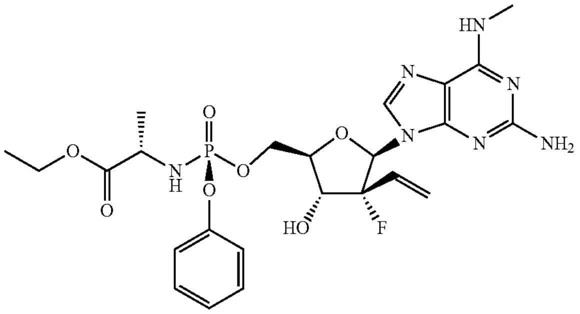
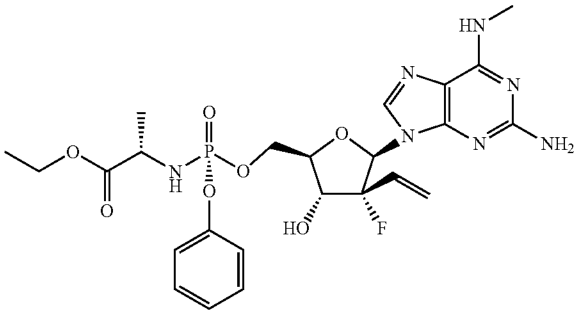
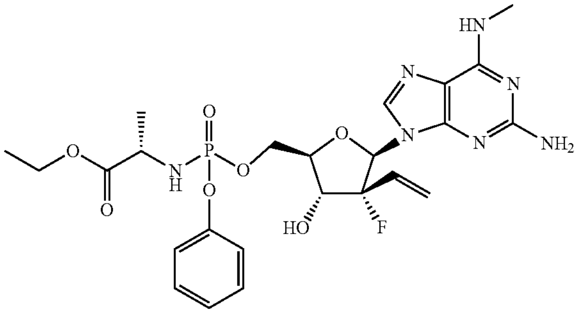
-continued
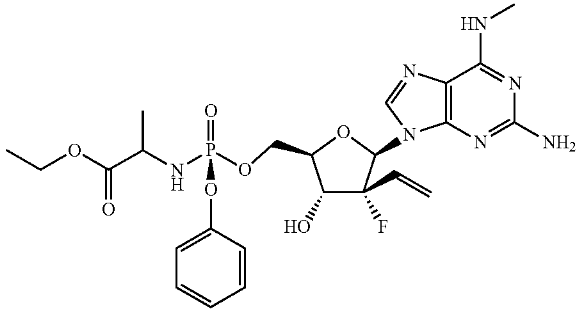
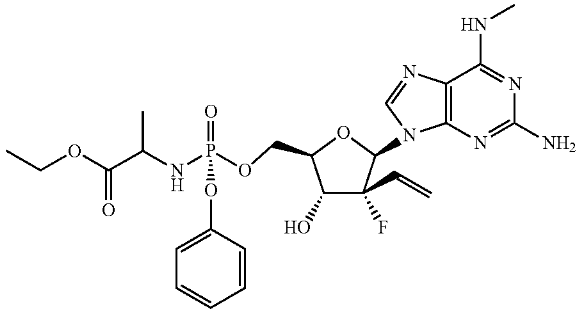
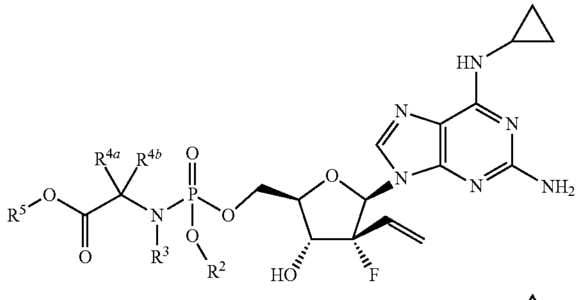
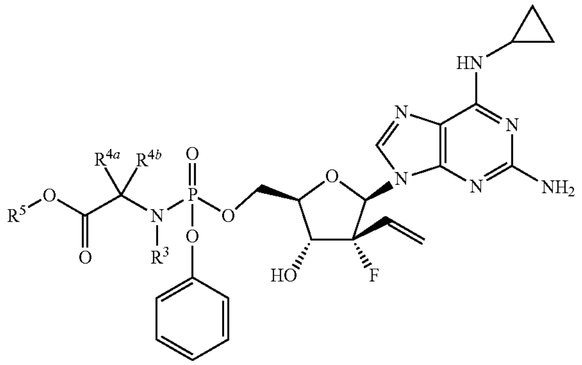
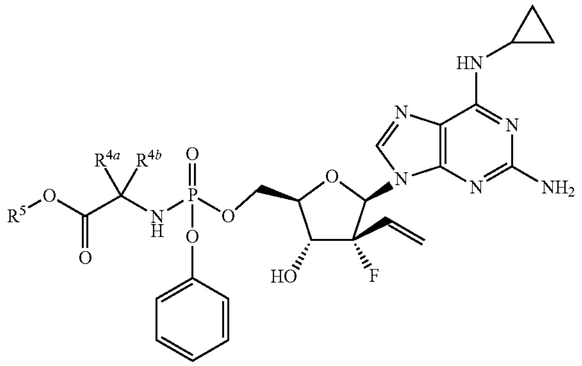

-continued
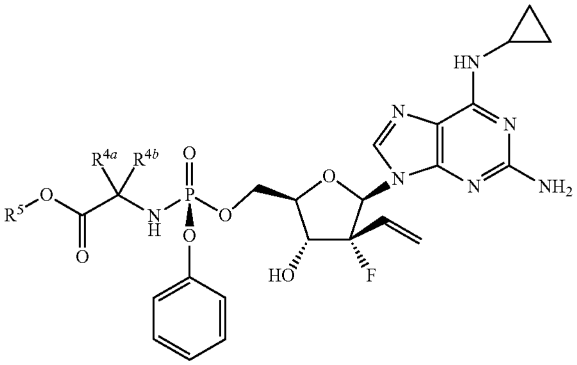
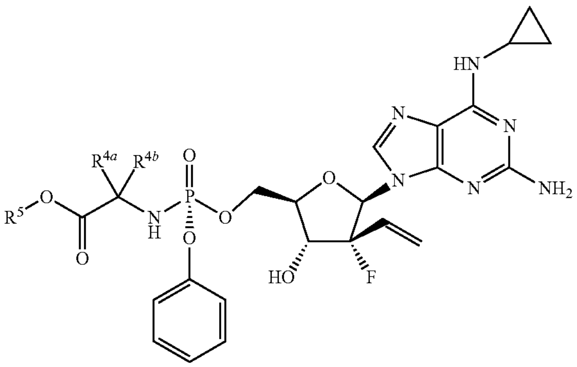
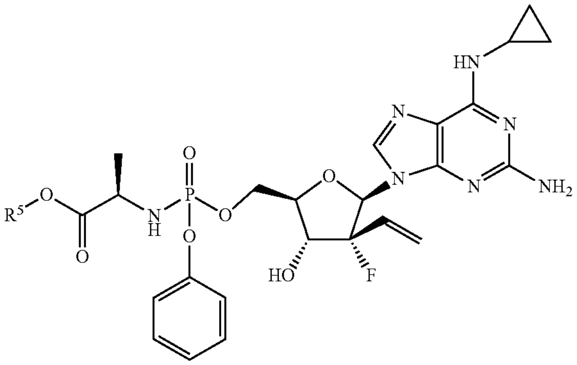
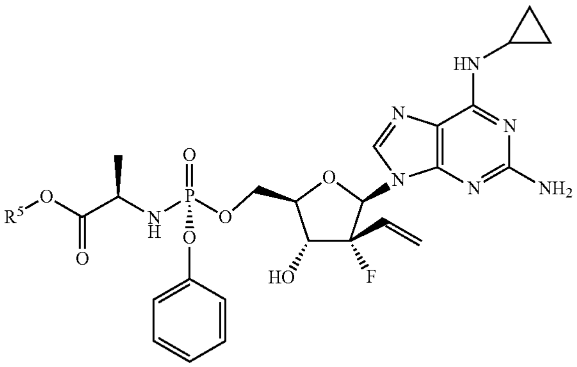
-continued
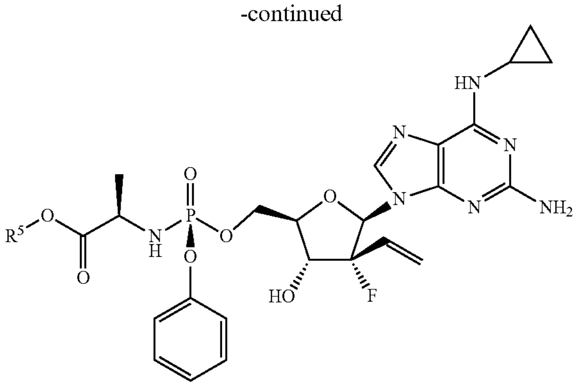
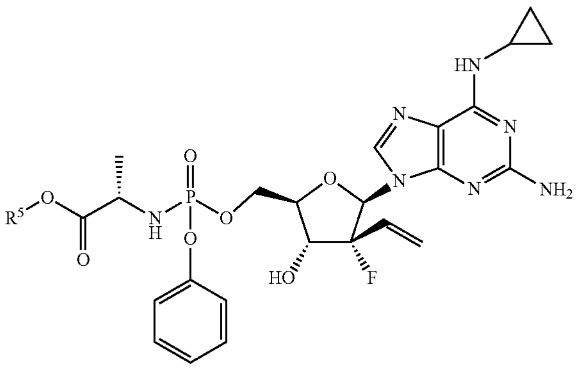
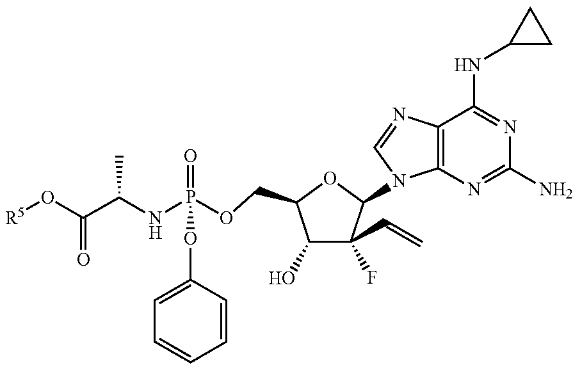
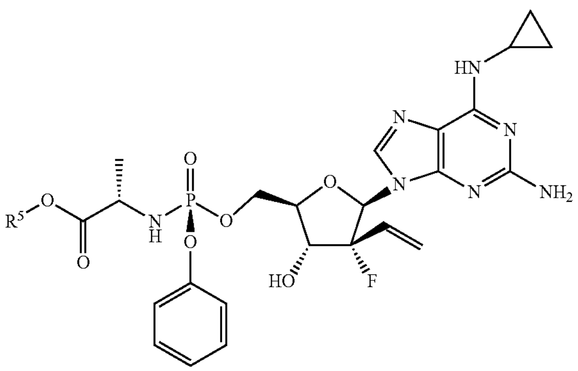

-continued
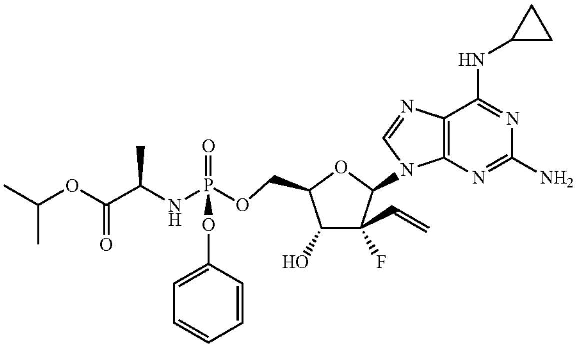
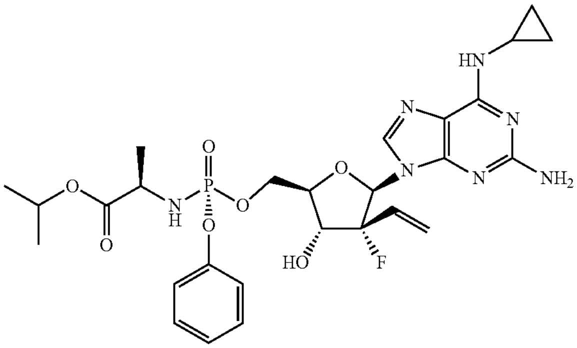
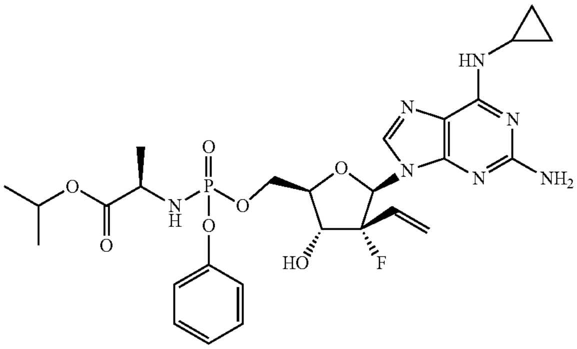
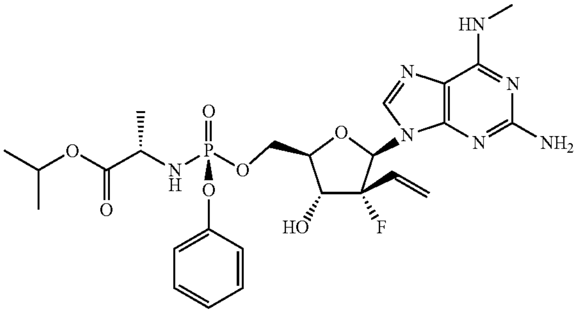
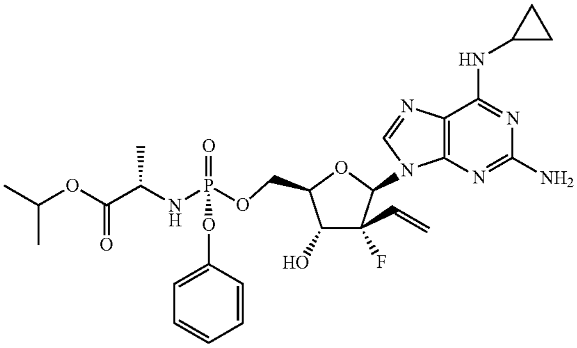
-continued
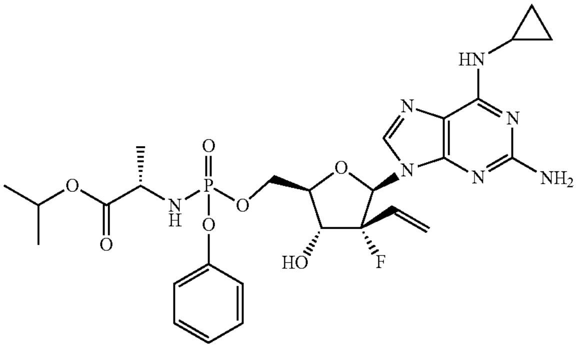
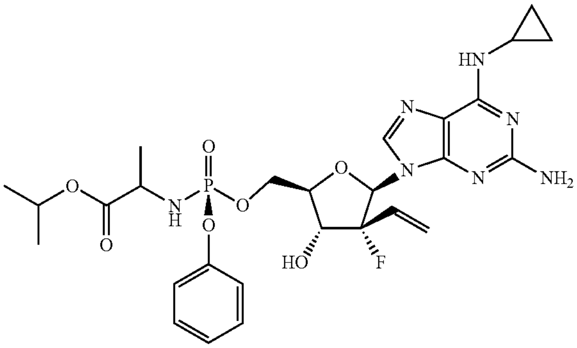
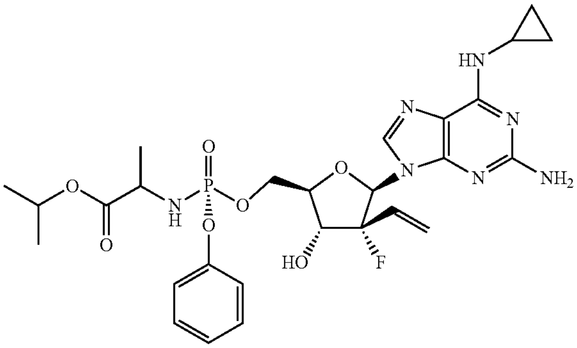
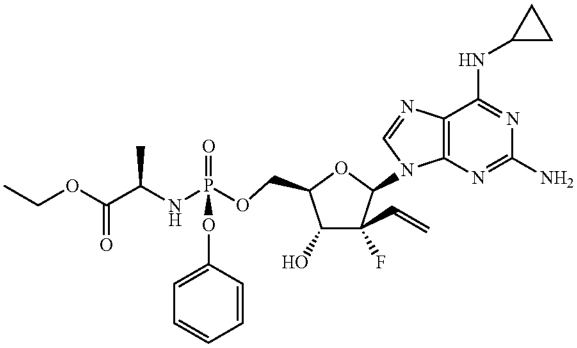

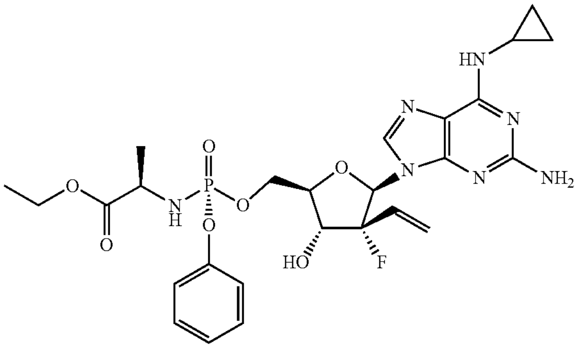
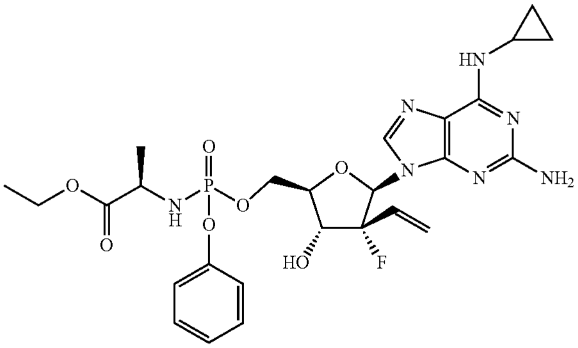
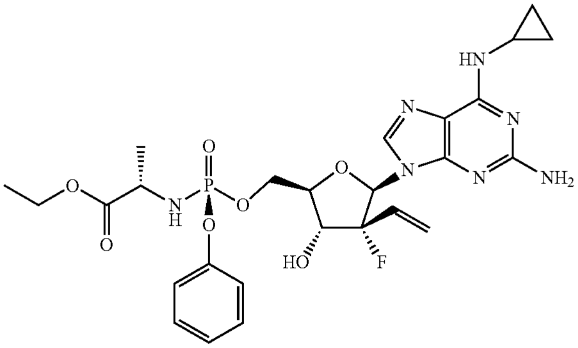
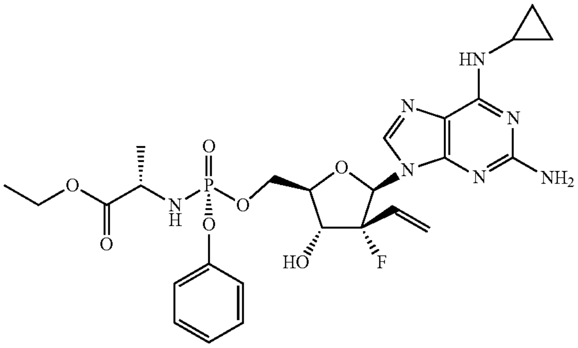
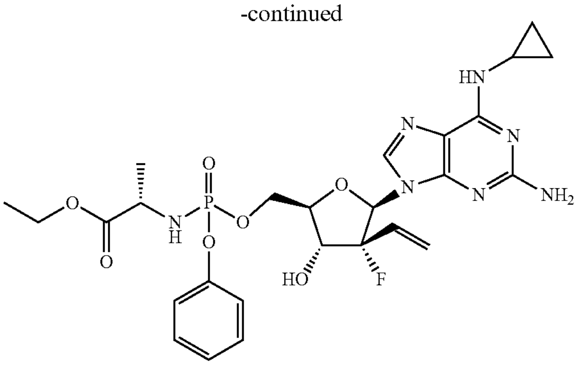
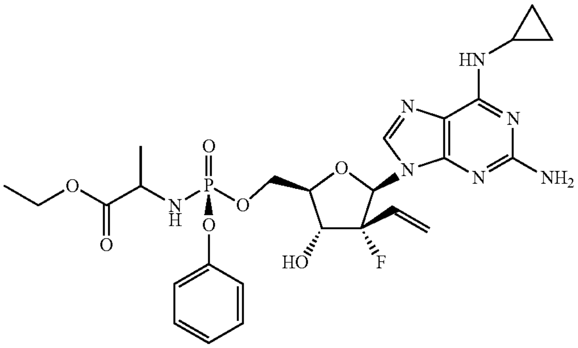
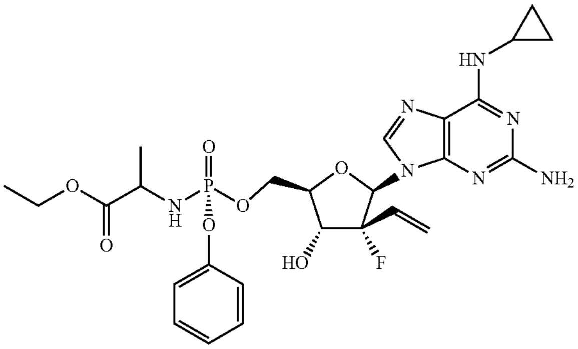
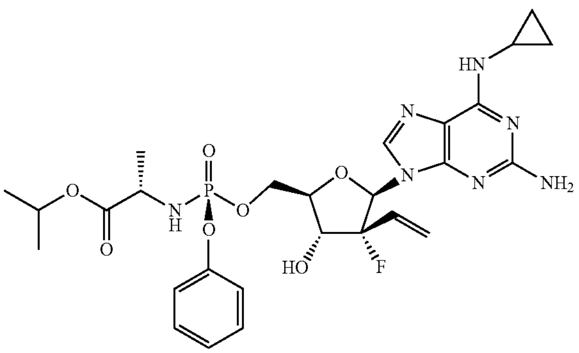
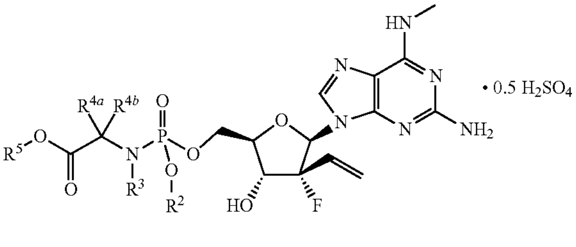

-continued

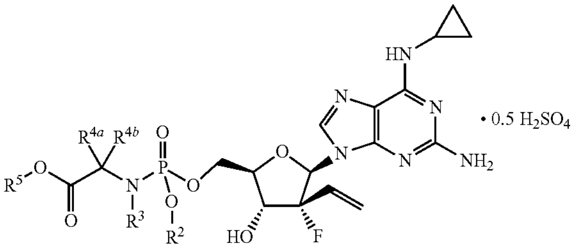

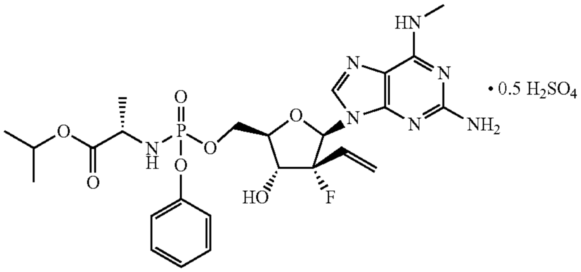

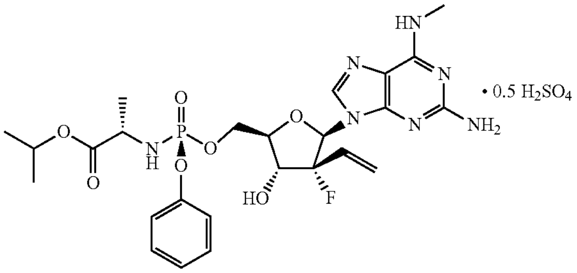

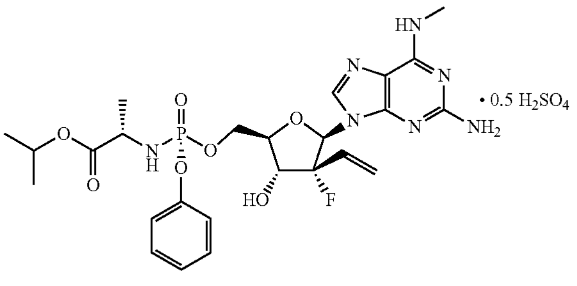

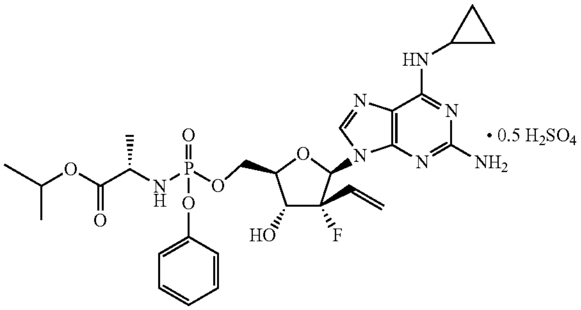

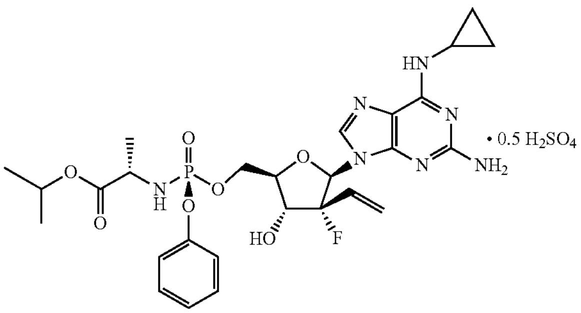

-continued

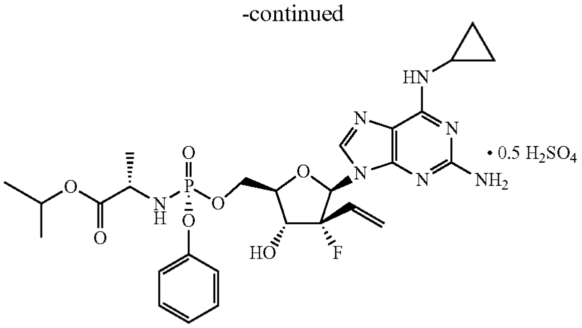

In some embodiments, the compound of Formula III to disrupt NiRAN function in a coronavirus or to treat or prevent a mutant or resistant form of the SARS-CoV-2 virus in a host in need thereof is a compound of Formula IIIe:

Formula IIIe

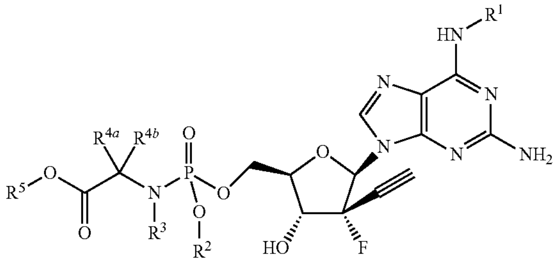

or a pharmaceutically acceptable salt thereof.

In some embodiments of Formula IIIe, $R^1$ is methyl.

In some embodiments of Formula IIIe, $R^1$ is cyclopropyl.

In some embodiments of Formula IIIe, $R^2$ is phenyl.

In some embodiments of Formula IIIe, $R^2$ is napthyl.

In some embodiments of Formula IIIe, $R^{4a}$ is hydrogen and $R^{4b}$ is methyl.

In some embodiments of Formula IIIe, $R^5$ is isopropyl.

In some embodiments of Formula IIIe, the compound is the $S_p$-isomer and the phosphoramidate is in the L-configuration.

In some embodiments of Formula IIIe, the compound is the $R_p$-isomer and the phosphoramidate is in the L-configuration.

In some embodiments of Formula IIIe, the pharmaceutically acceptable salt is the hemi-sulfate salt.

Non-limiting examples of a compound of Formula IIIe include:

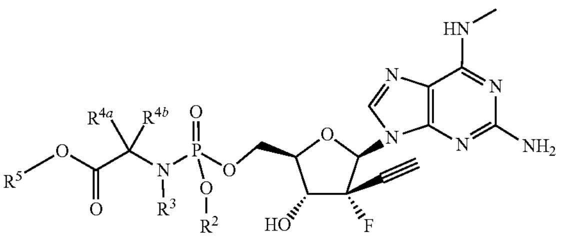

-continued
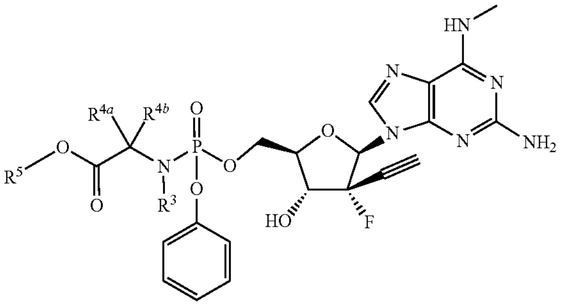
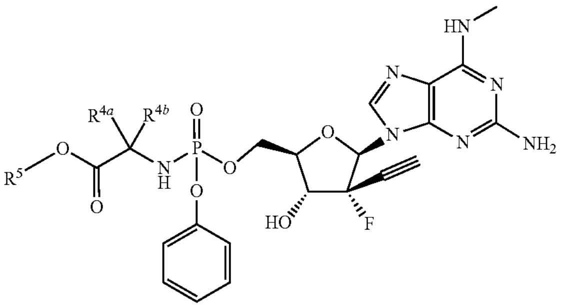
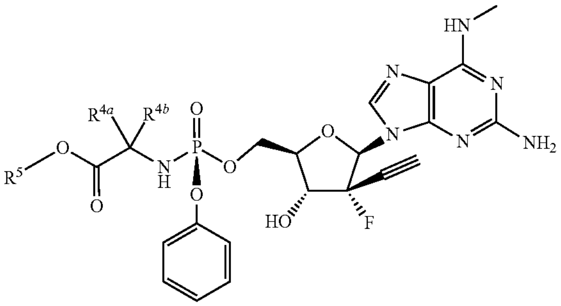
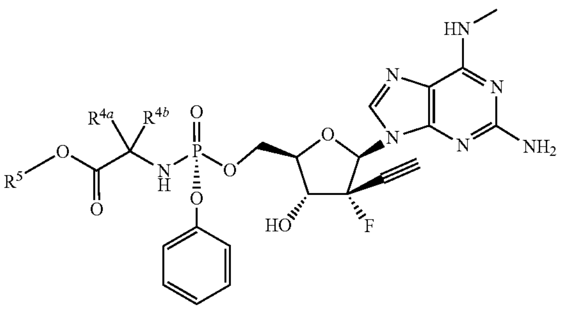
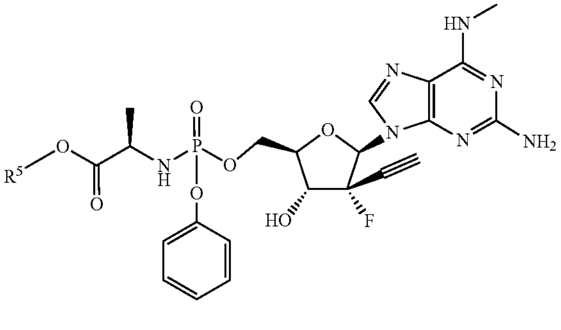
-continued
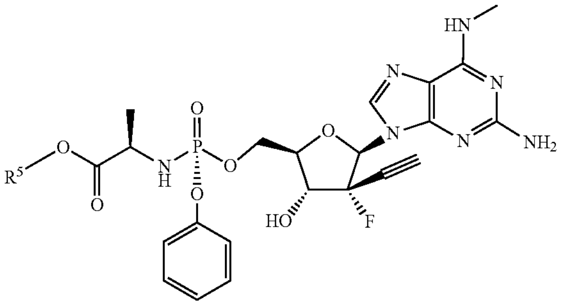
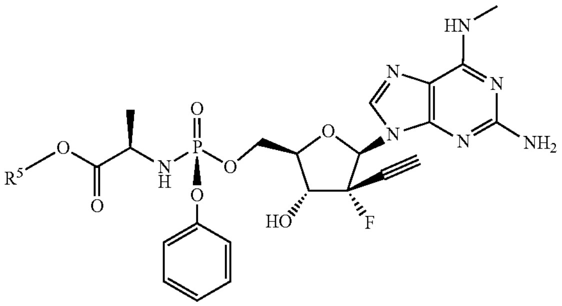
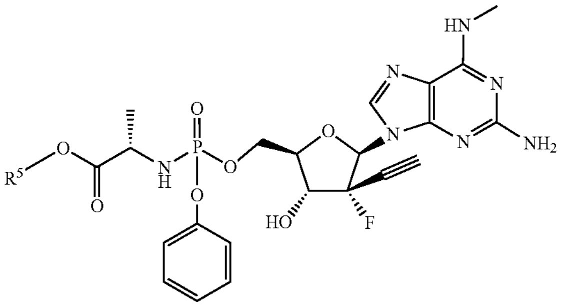
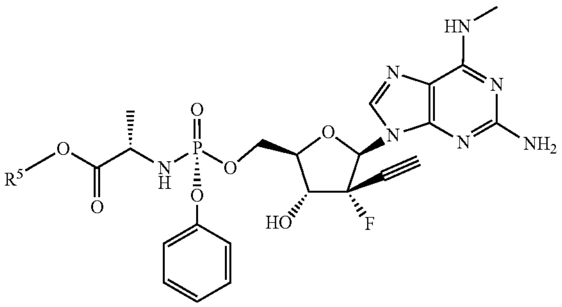
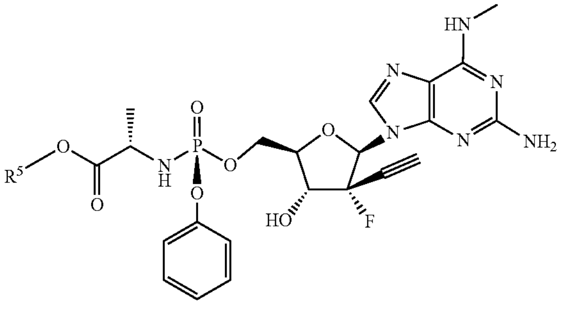

-continued
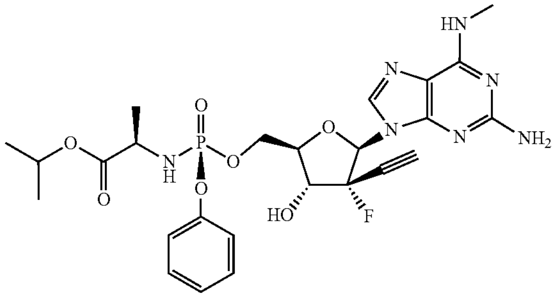
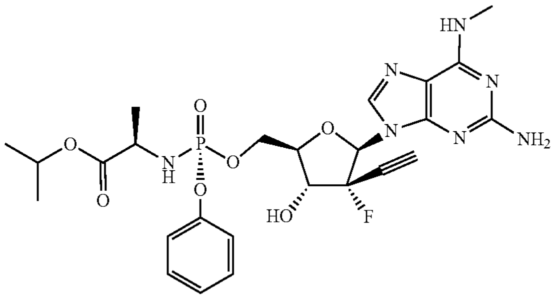
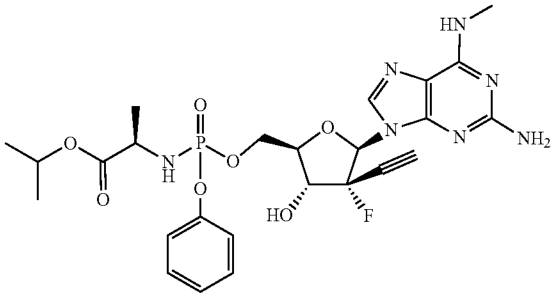
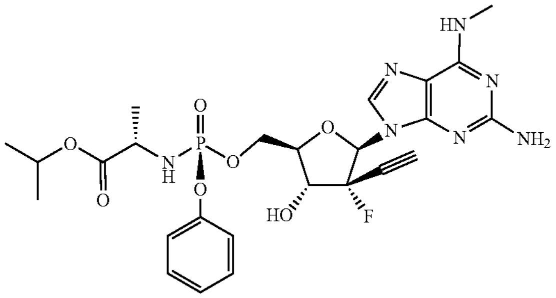
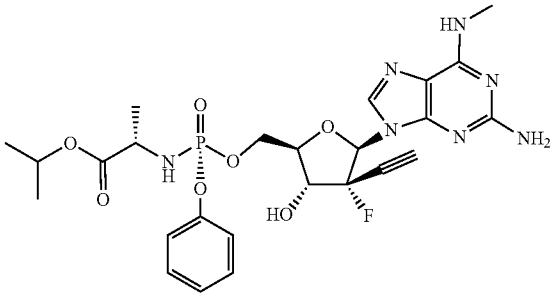
-continued
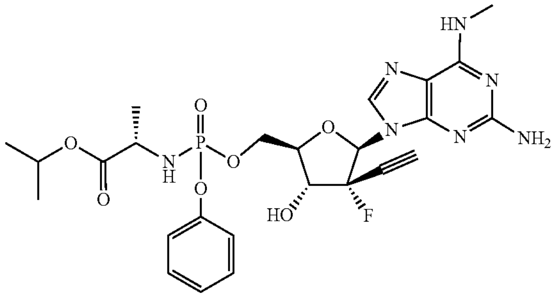
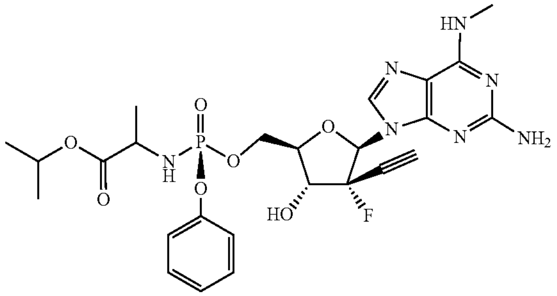
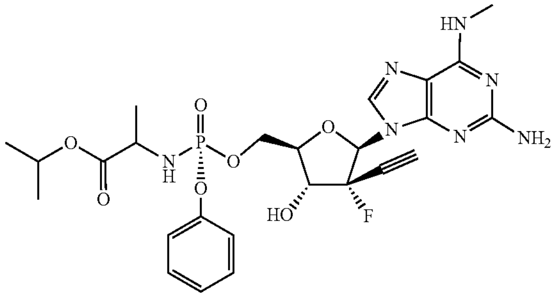
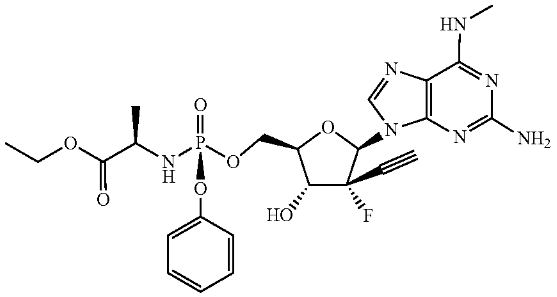
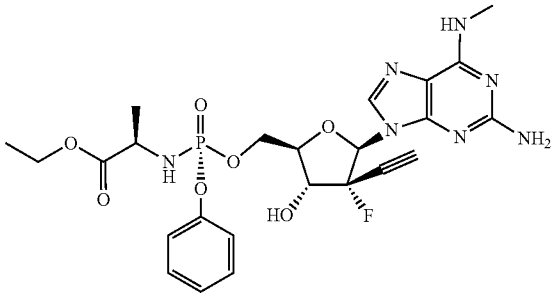

-continued
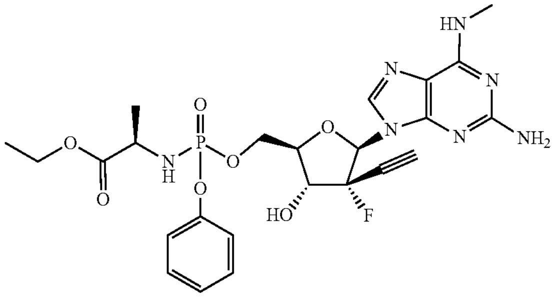
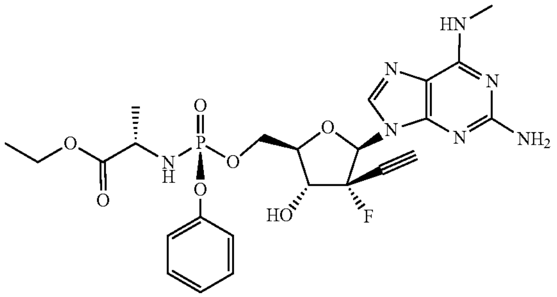
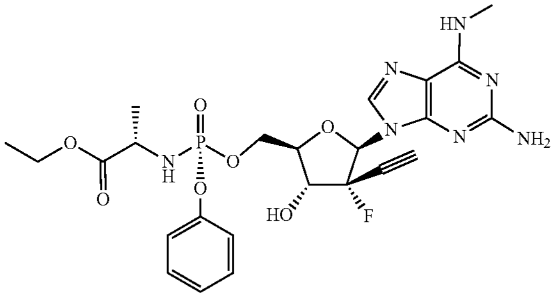
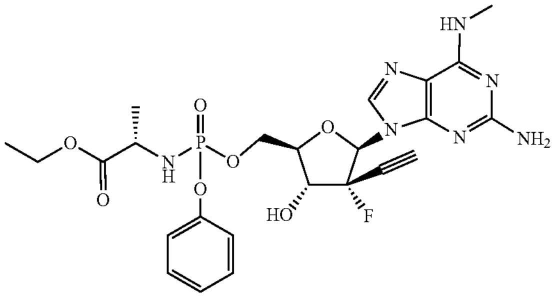
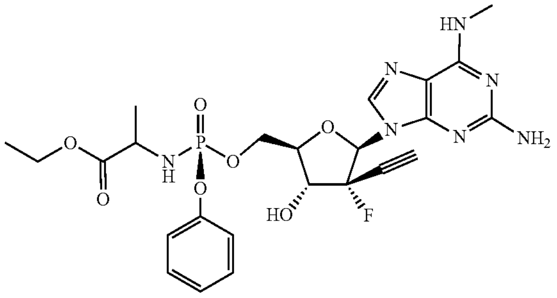
-continued
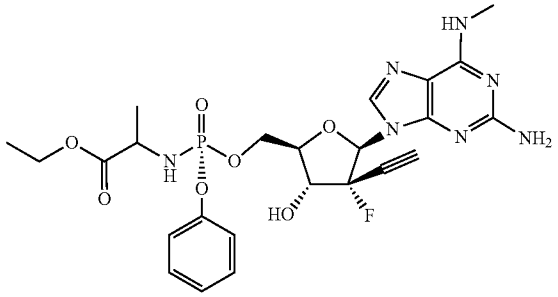
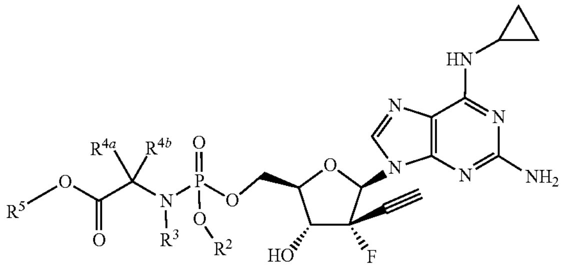
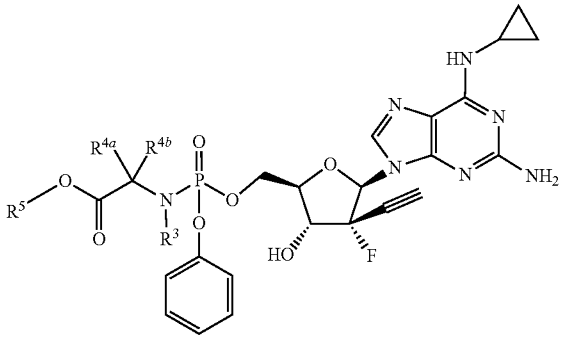
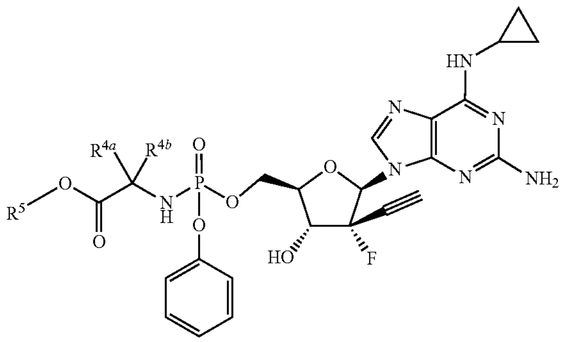
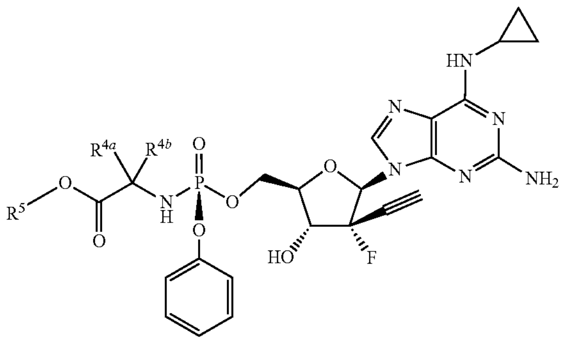

-continued
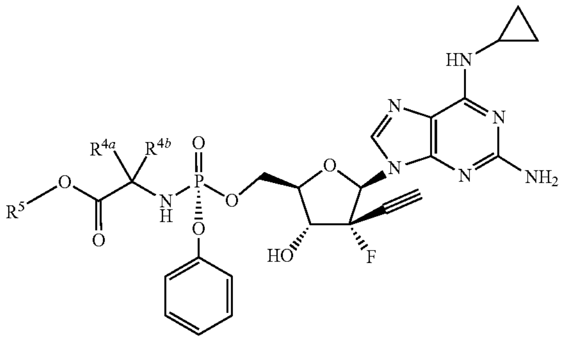
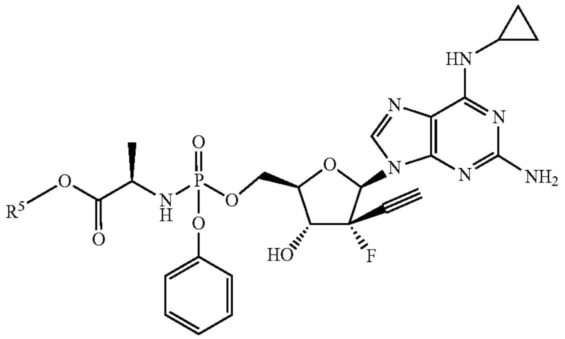
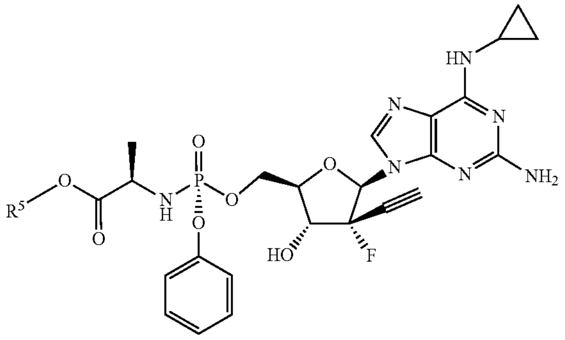
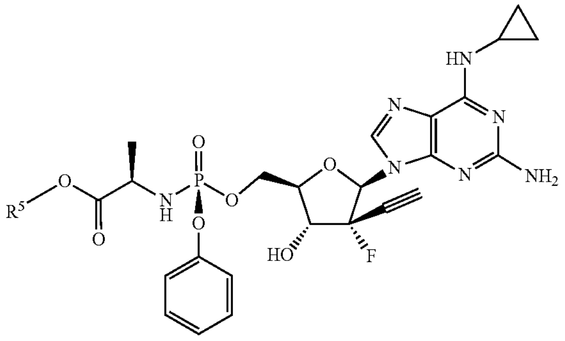
-continued
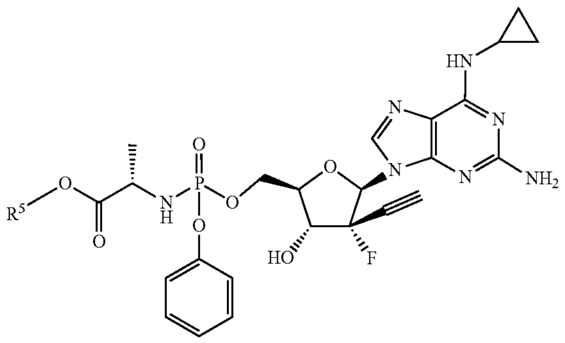
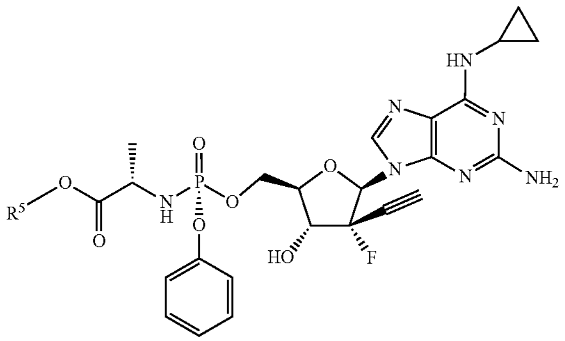
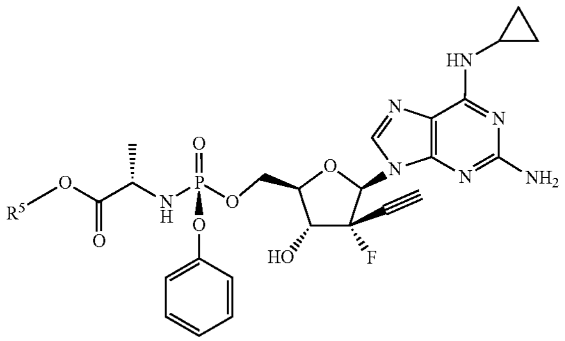
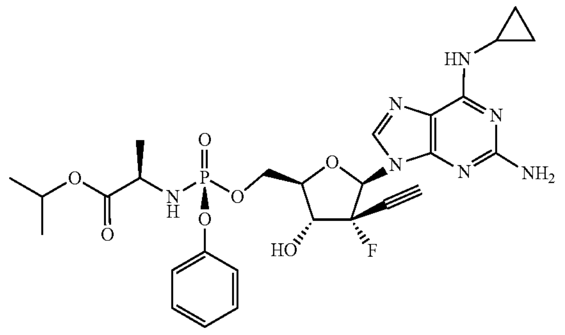

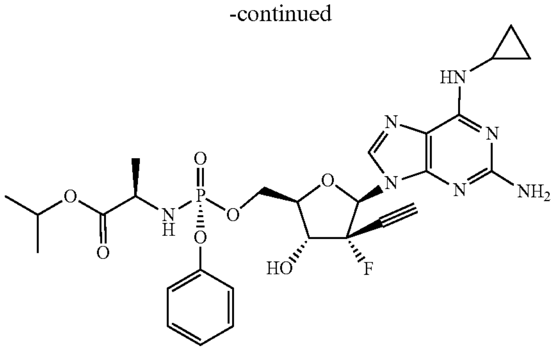
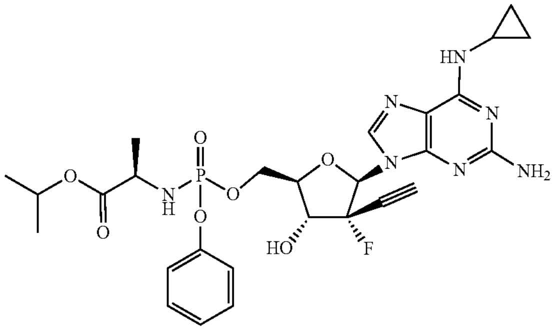
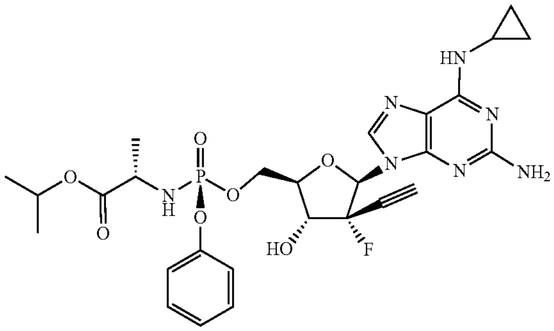
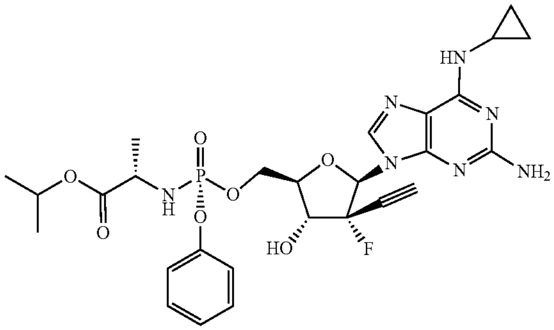
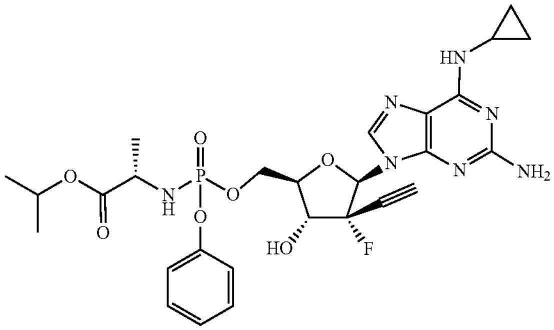
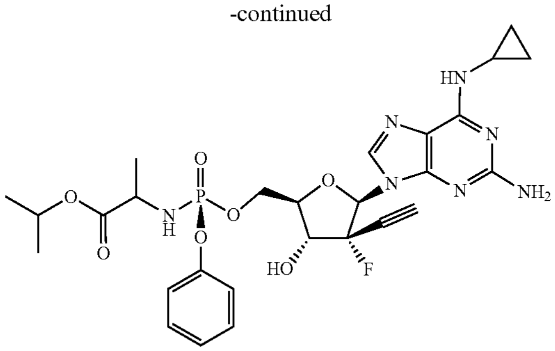
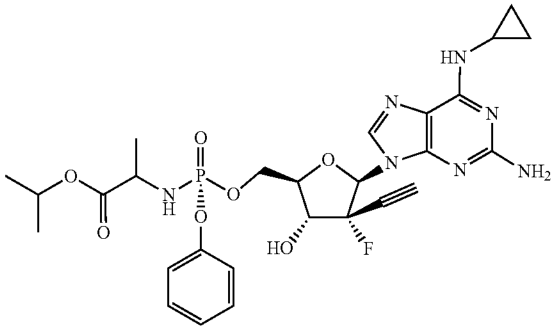
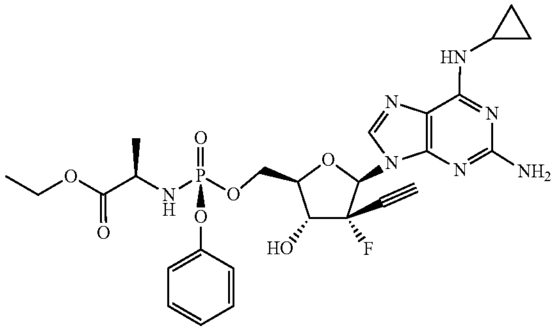
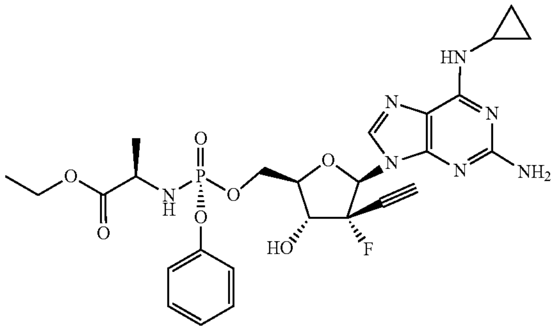
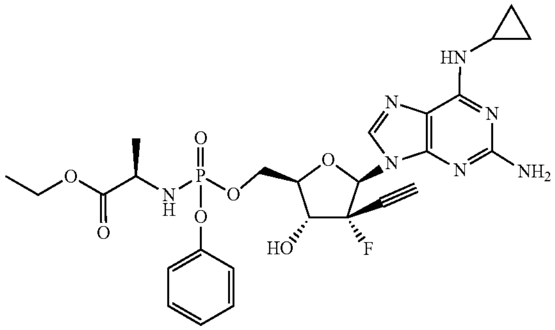

-continued
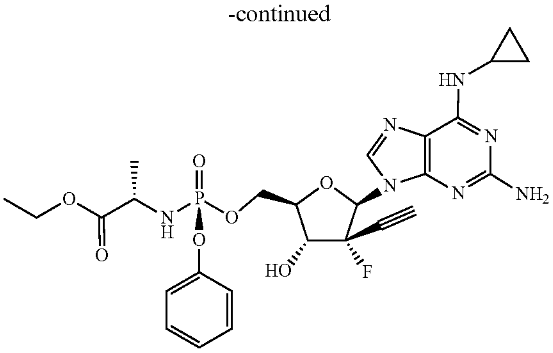
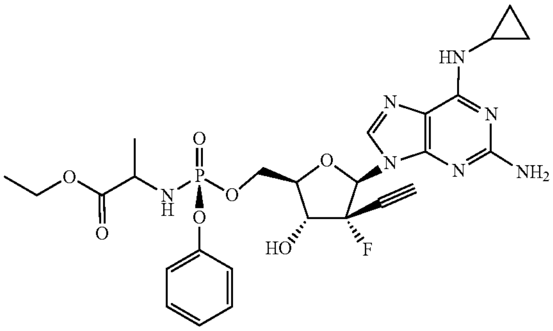
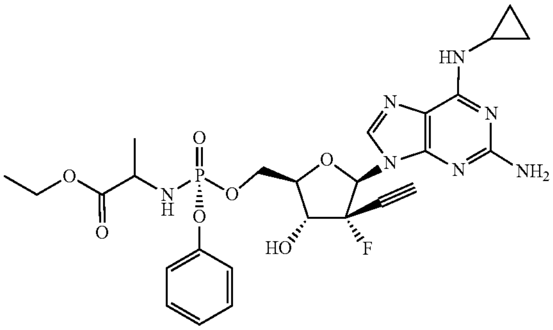
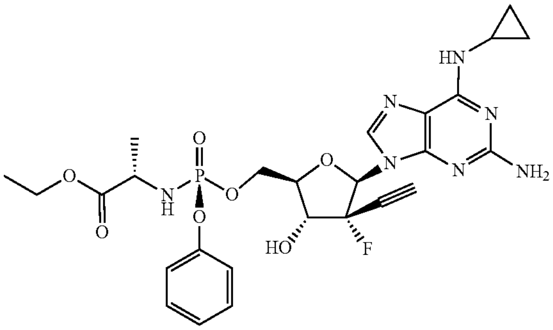
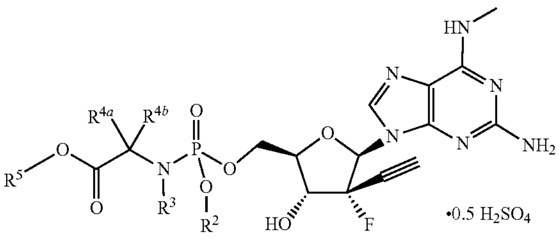
•0.5 $H_2SO_4$
-continued
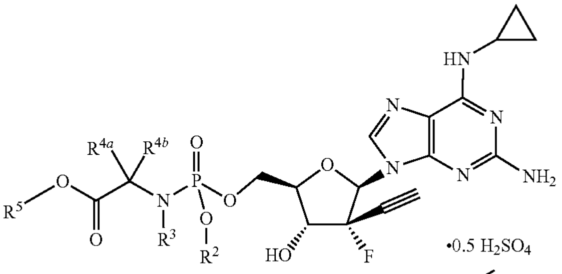
•0.5 $H_2SO_4$
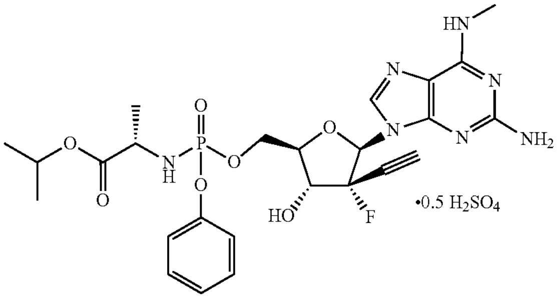
•0.5 $H_2SO_4$
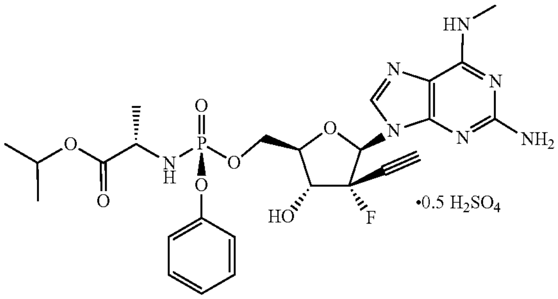
•0.5 $H_2SO_4$
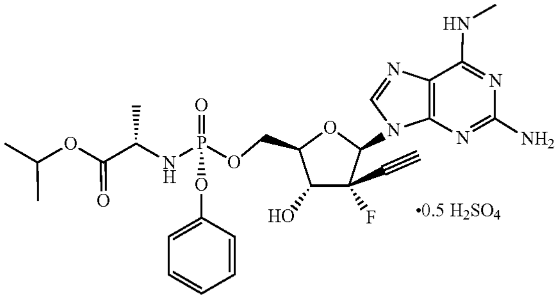
•0.5 $H_2SO_4$
In some embodiments, the compound of Formula III to disrupt NiRAN function in a coronavirus or to treat or prevent a mutant or resistant form of the SARS-CoV-2 virus in a host in need thereof is a compound of Formula IIIf:
Formula IIIf
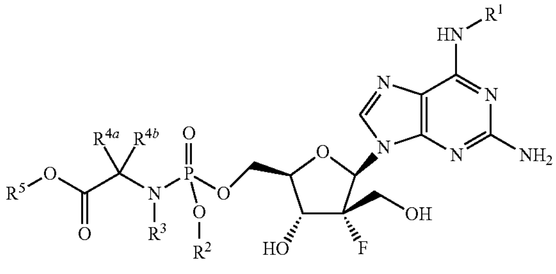
or a pharmaceutically acceptable salt thereof.

In some embodiments of Formula IIIf, $R^1$ is methyl.

In some embodiments of Formula IIIf, $R^1$ is cyclopropyl.

In some embodiments of Formula IIIf, $R^2$ is phenyl.

In some embodiments of Formula IIIf, $R^2$ is napthyl.

In some embodiments of Formula IIIf, $R^{4a}$ is hydrogen and $R^{4b}$ is methyl.

In some embodiments of Formula IIIf, $R^5$ is isopropyl.

In some embodiments of Formula IIIf, the compound is the $S_p$-isomer and the phosphoramidate is in the L-configuration.

In some embodiments of Formula IIIf, the compound is the $R_p$-isomer and the phosphoramidate is in the L-configuration.

In some embodiments of Formula IIIf, the pharmaceutically acceptable salt is the hemi-sulfate salt.

Non-limiting examples of a compound of Formula Tiff include:

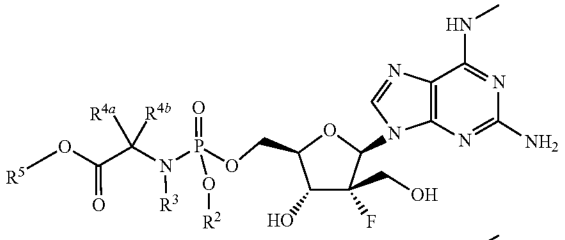

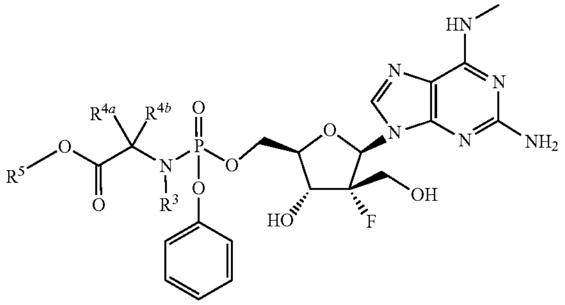

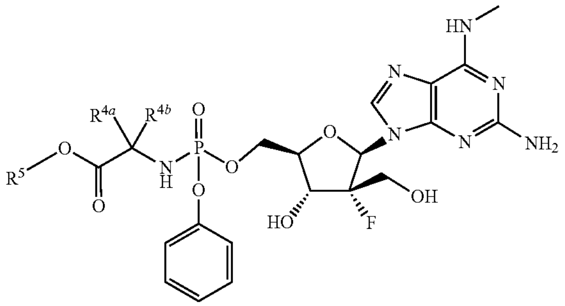

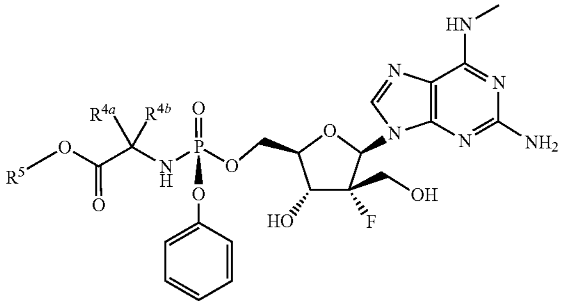

-continued

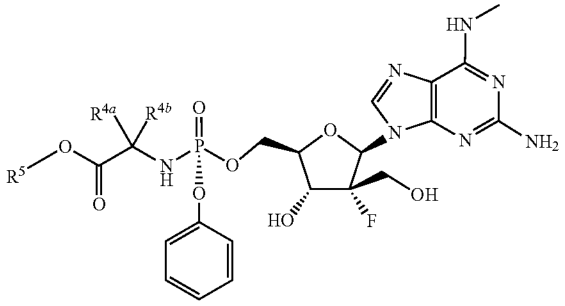

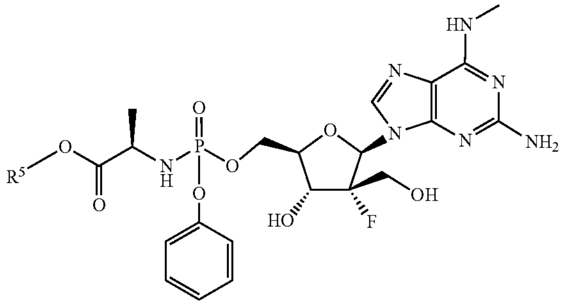

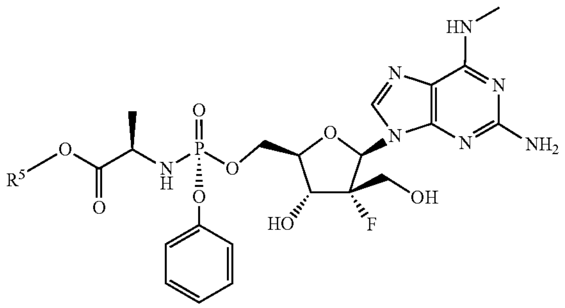

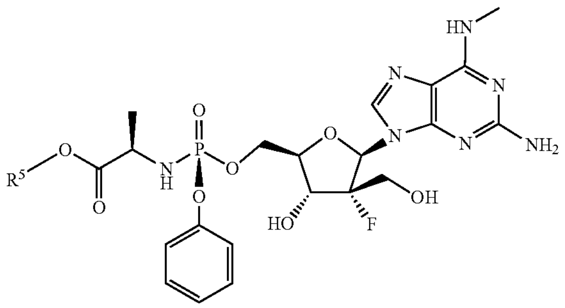

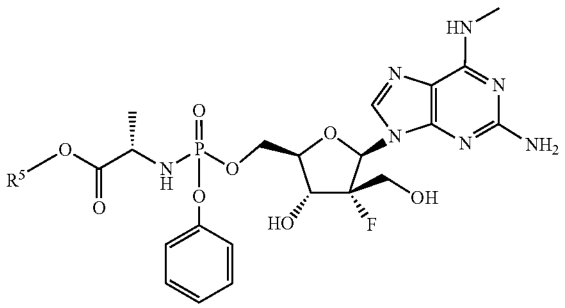

-continued
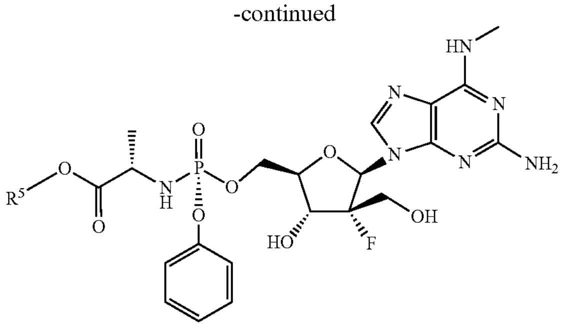
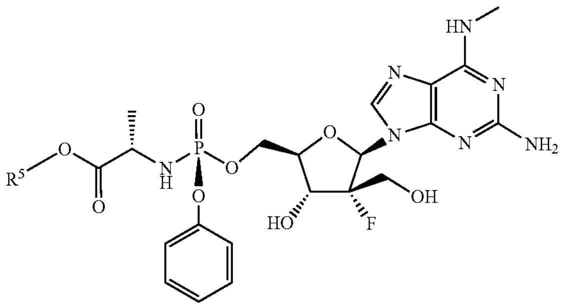
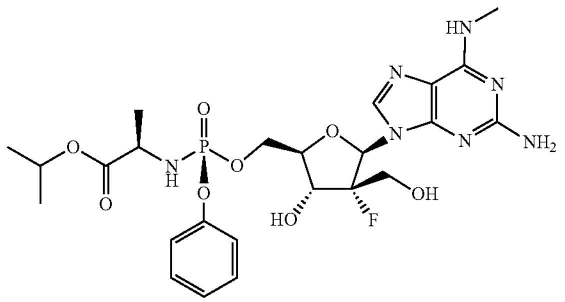
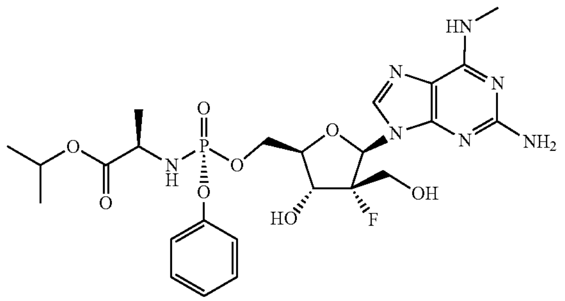
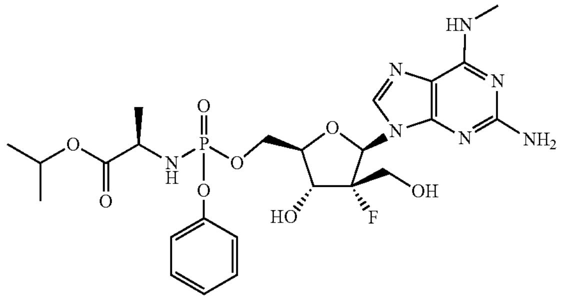
-continued
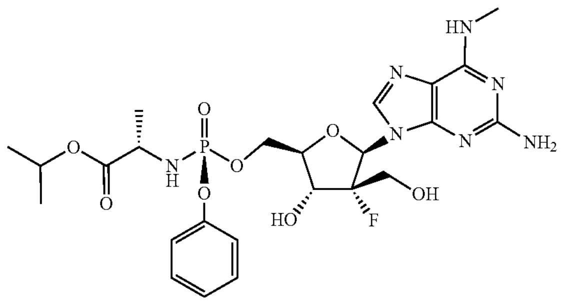
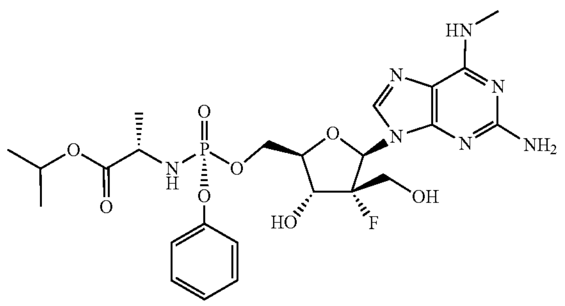
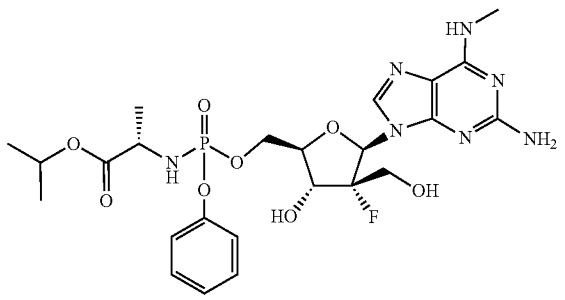
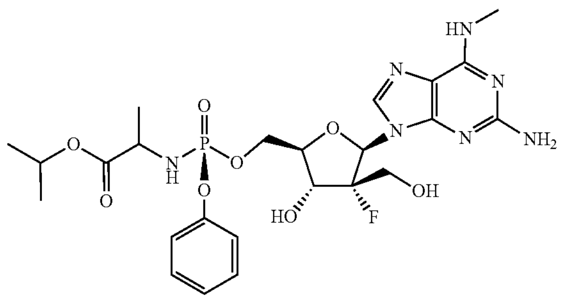
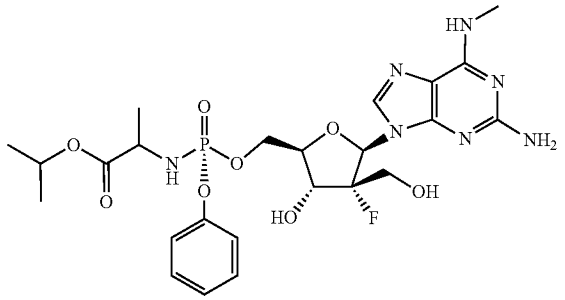

-continued
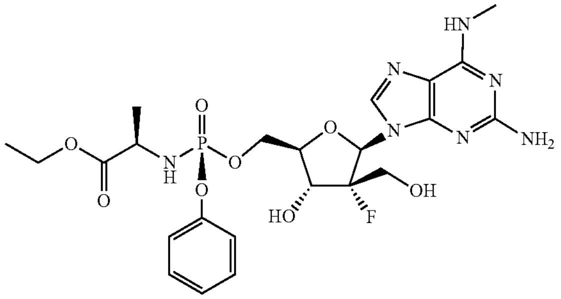
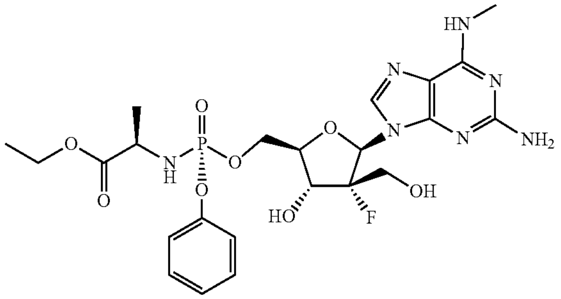
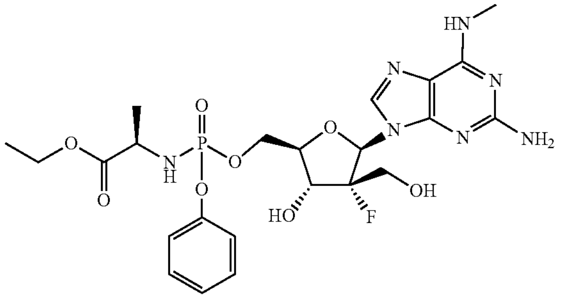
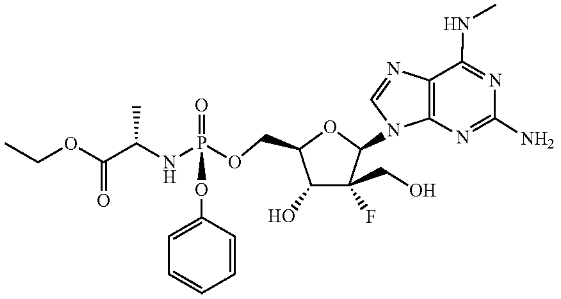
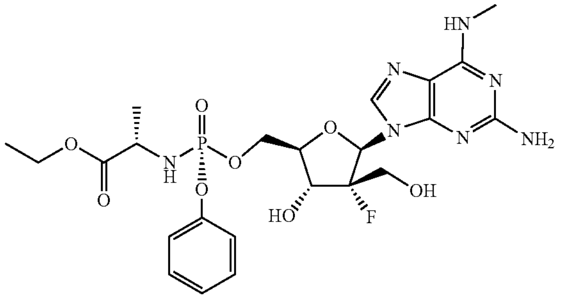
-continued
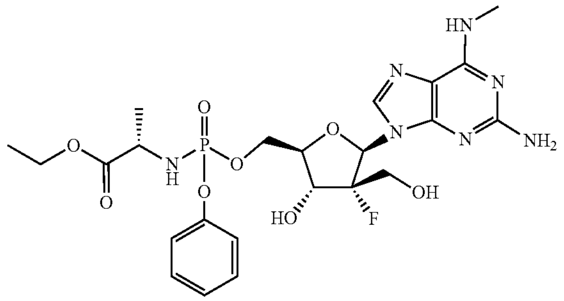
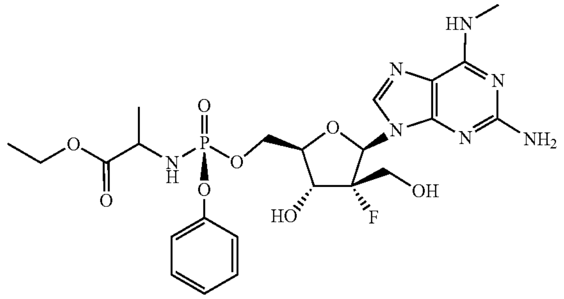
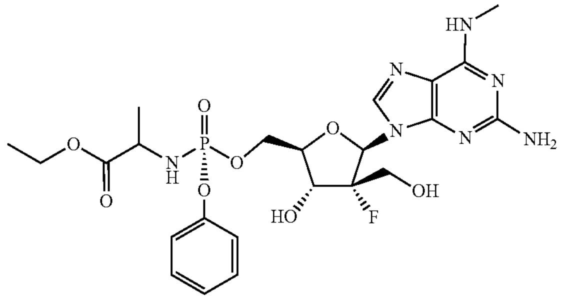
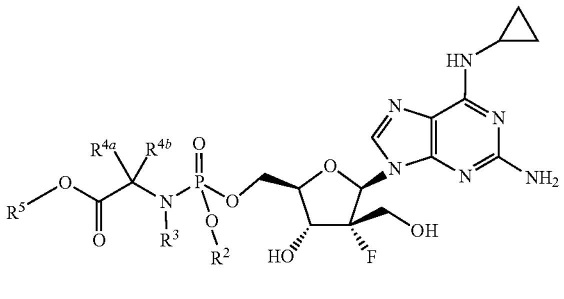
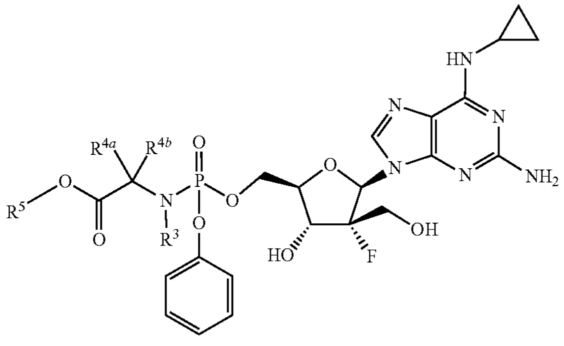

-continued
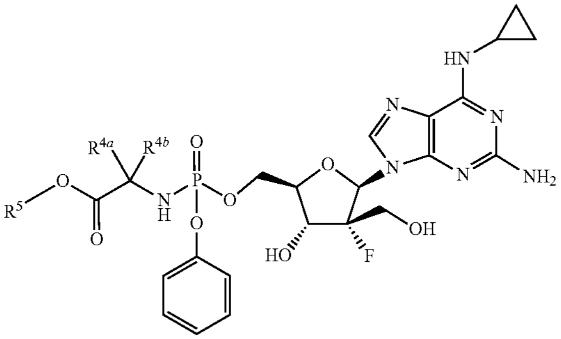
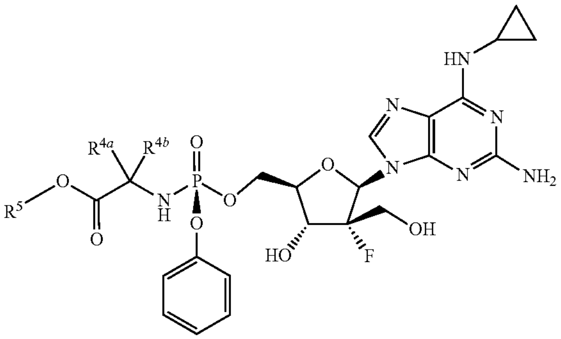
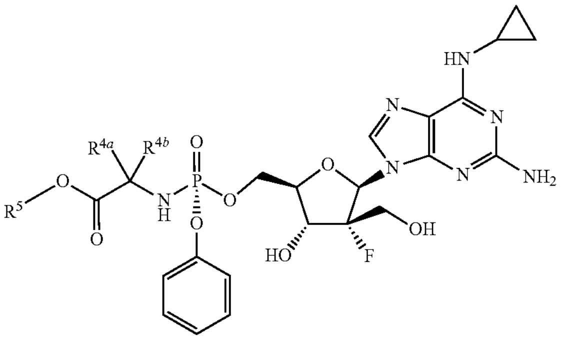
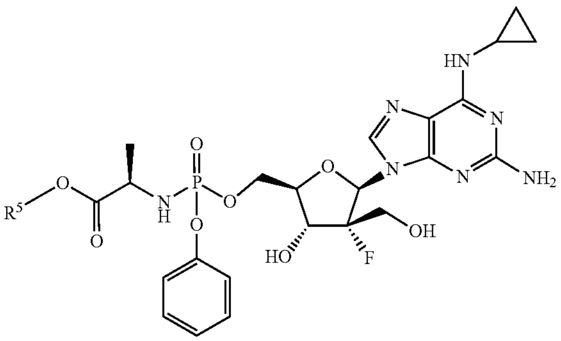
-continued
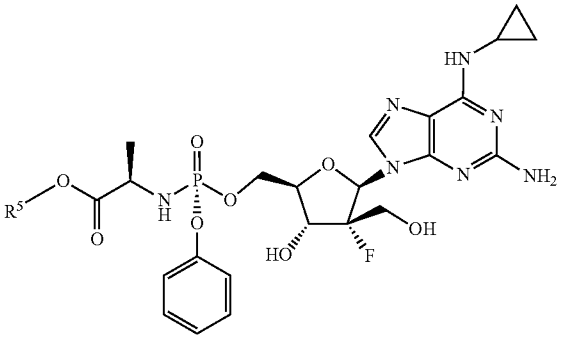
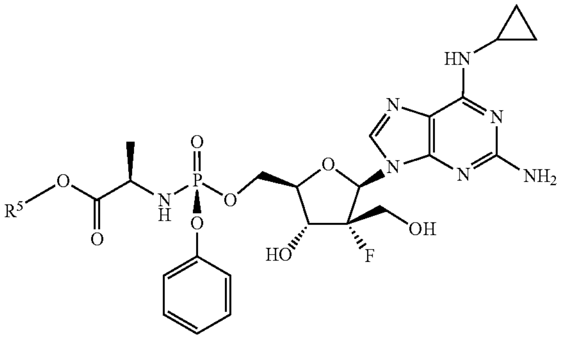
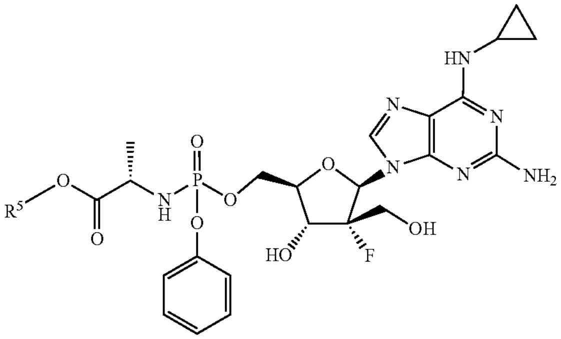
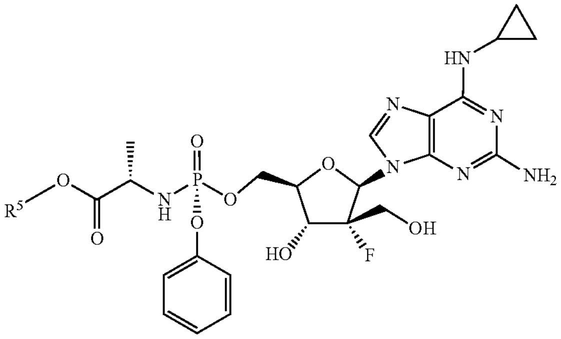

-continued
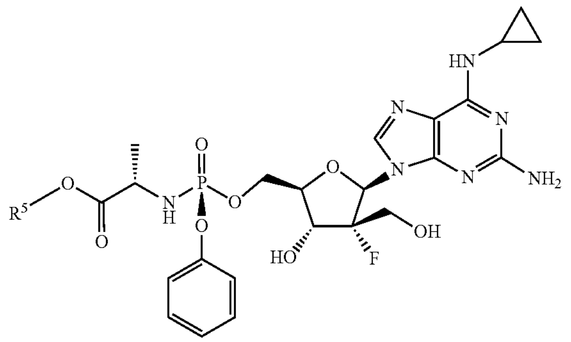
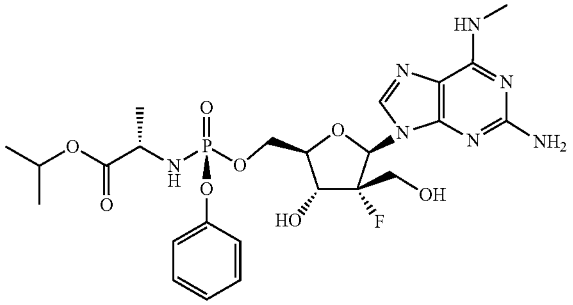
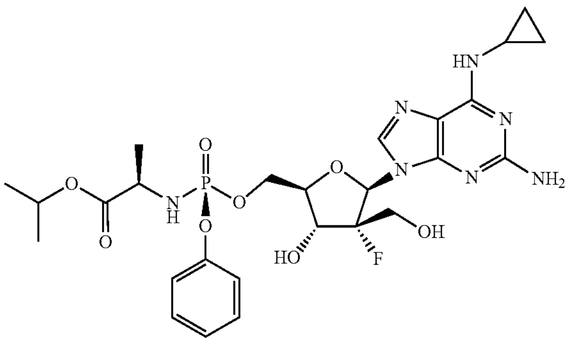
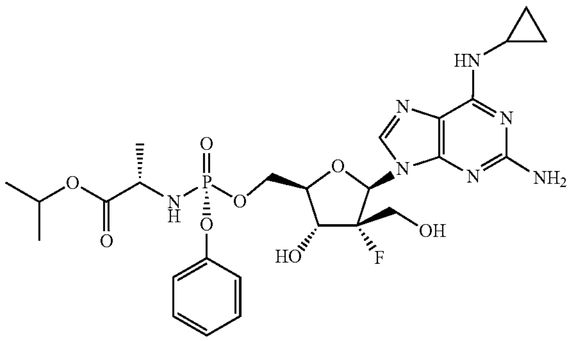
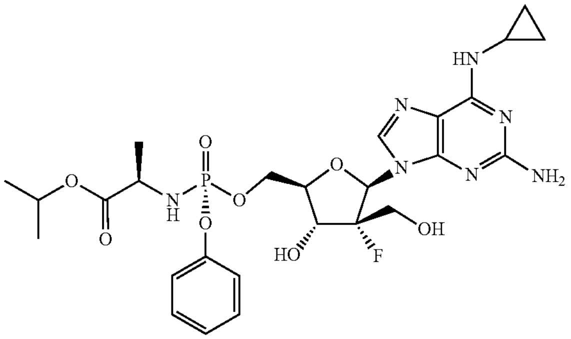
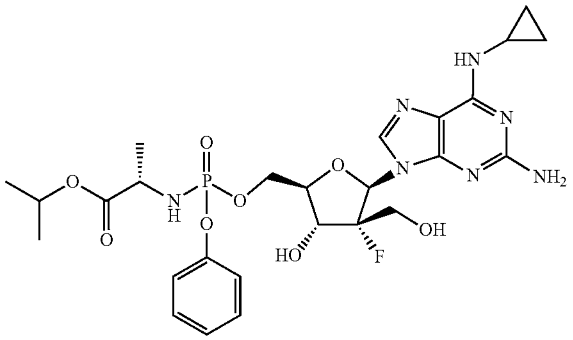
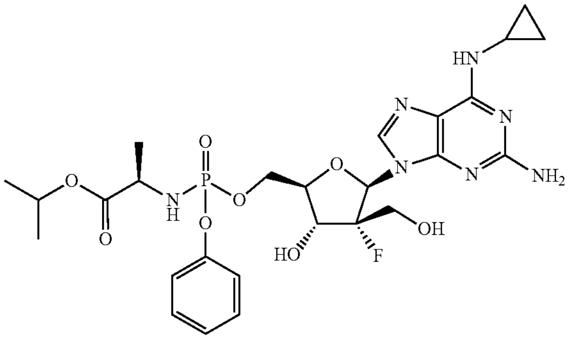
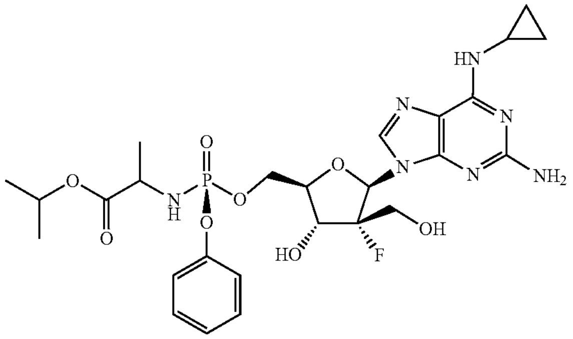

-continued
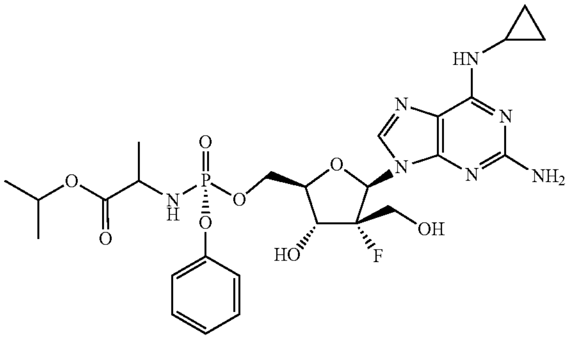
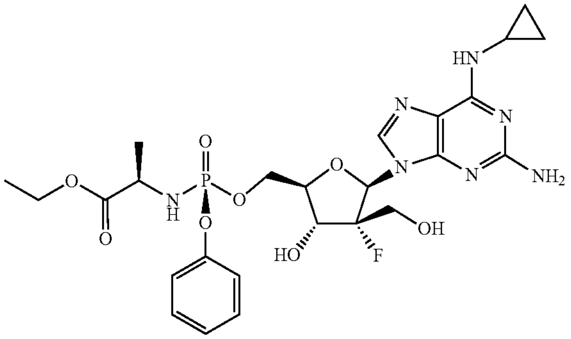
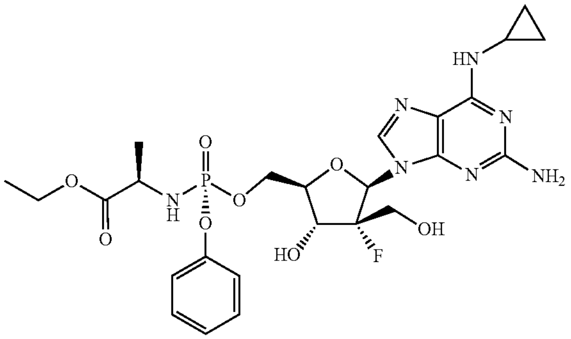
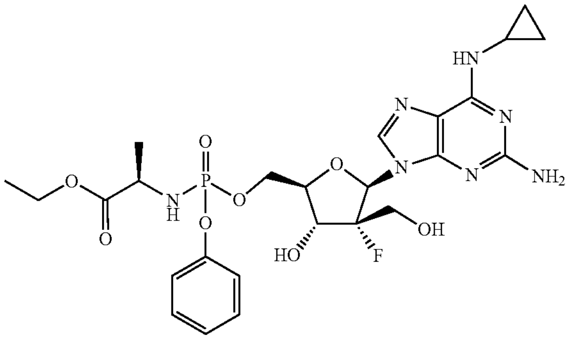
-continued
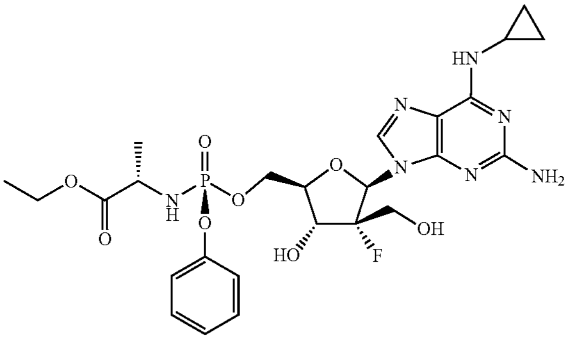
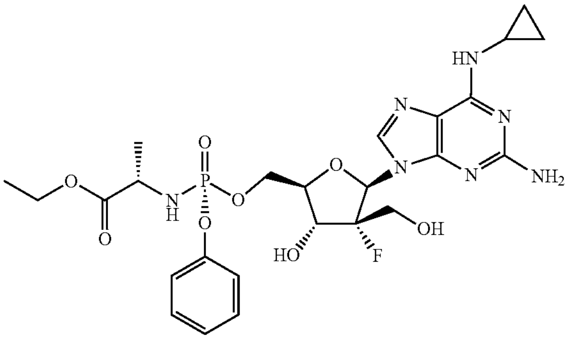
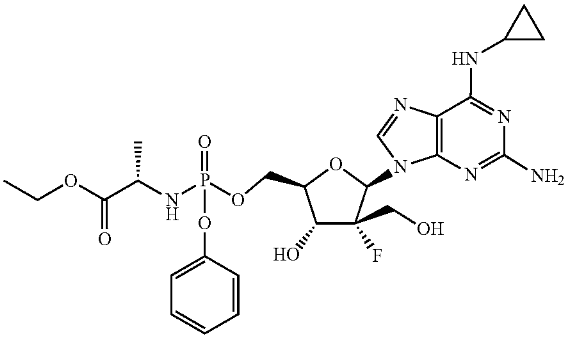
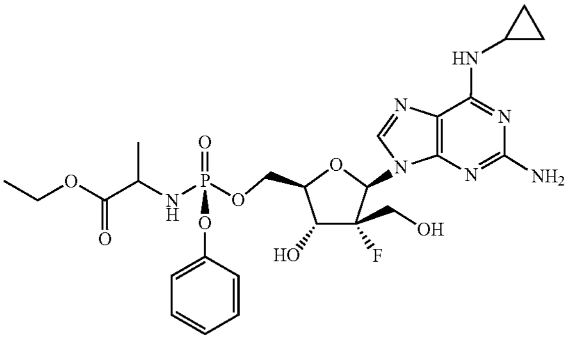

-continued
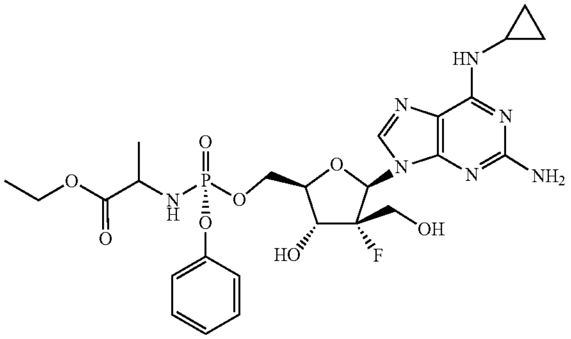
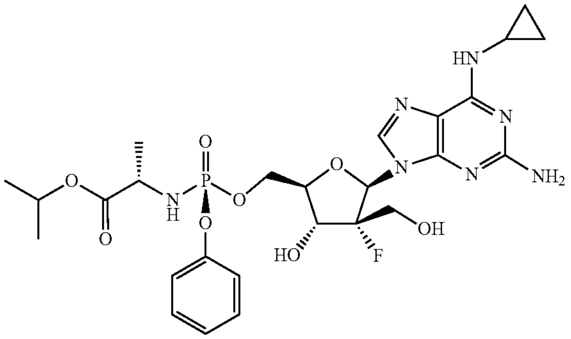
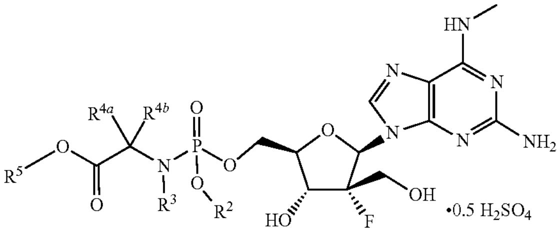
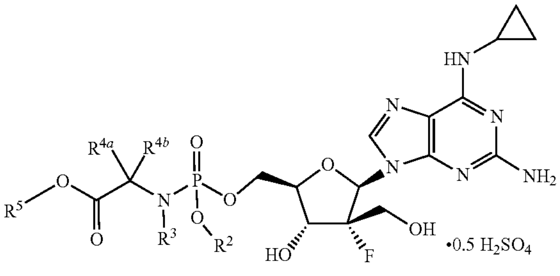
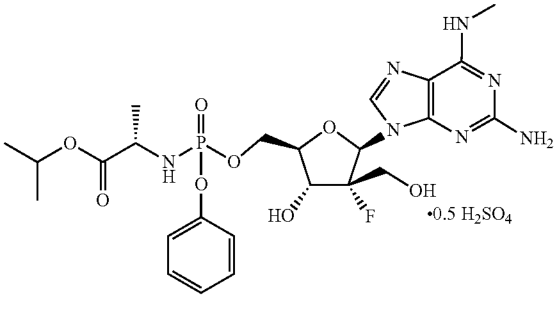
-continued
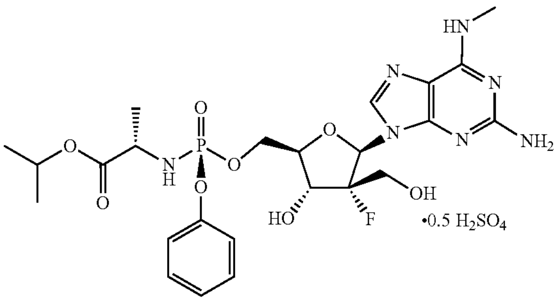
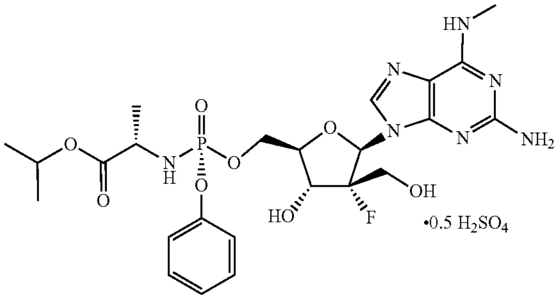
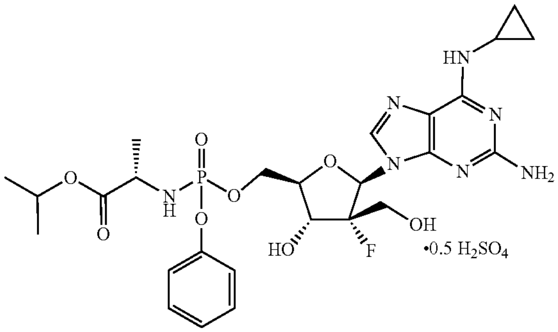
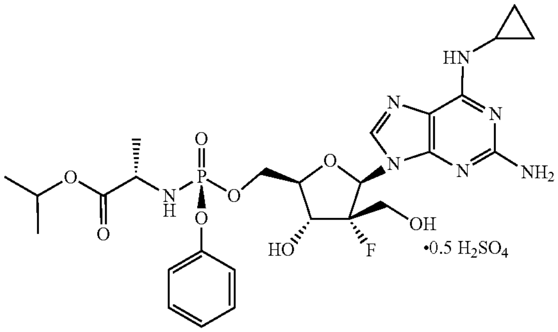
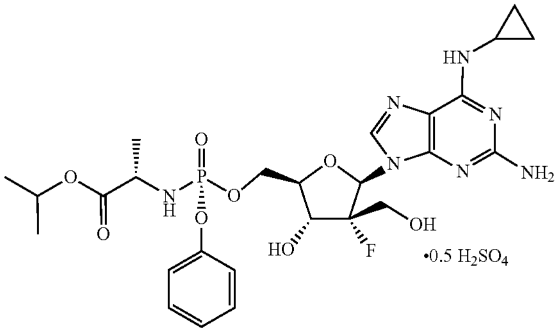

In some embodiments, the compound of Formula III to disrupt NiRAN function in a coronavirus or to treat or prevent a mutant or resistant form of the SARS-CoV-2 virus in a host in need thereof is a compound of Formula IIIg:

Formula IIIg

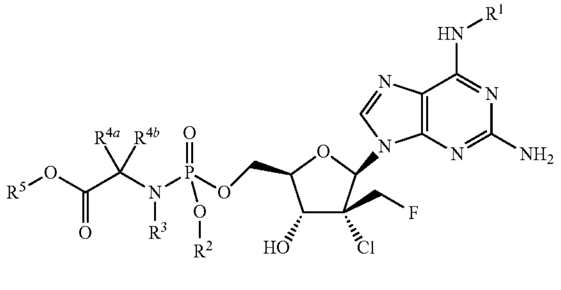

or a pharmaceutically acceptable salt thereof.

In some embodiments of Formula IIIg, $R^1$ is methyl.

In some embodiments of Formula IIIg, $R^1$ is cyclopropyl.

In some embodiments of Formula IIIg, $R^2$ is phenyl.

In some embodiments of Formula IIIg, $R^2$ is napthyl.

In some embodiments of Formula IIIg, $R^{4a}$ is hydrogen and $R^{4b}$ is methyl.

In some embodiments of Formula IIIg $R^5$ is isopropyl.

In some embodiments of Formula IIIg the compound is the $S_p$-isomer and the phosphoramidate is in the L-configuration.

In some embodiments of Formula IIIg the compound is the $R_p$-isomer and the phosphoramidate is in the L-configuration.

Non-limiting examples of a compound of Formula IIIg include:

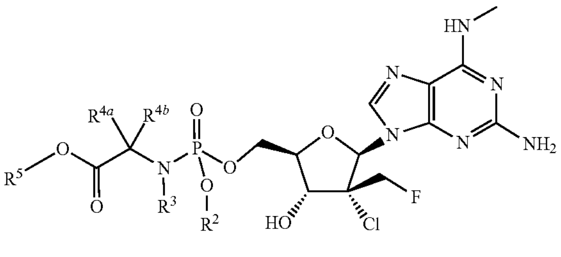

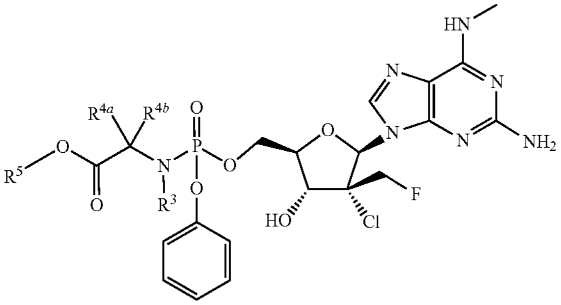

-continued

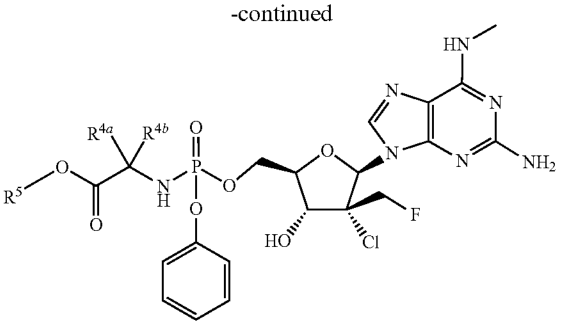

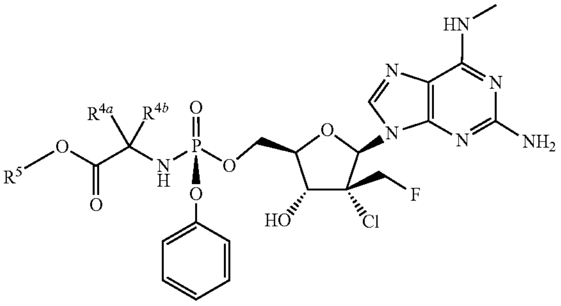

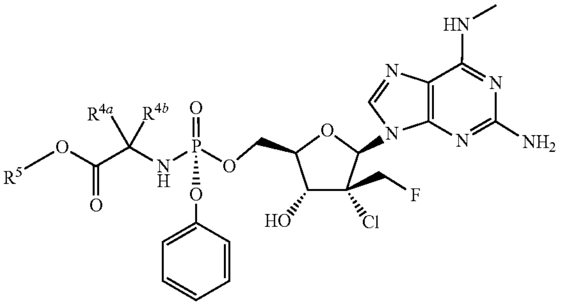

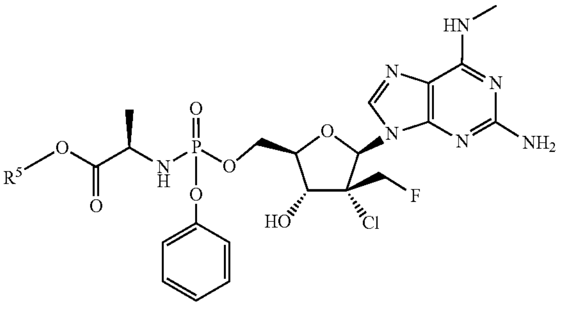

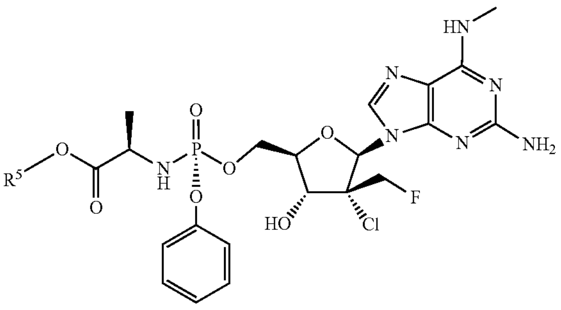

-continued
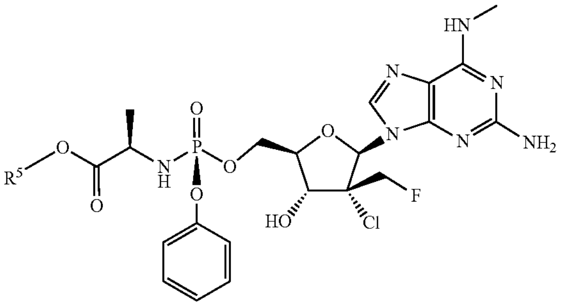
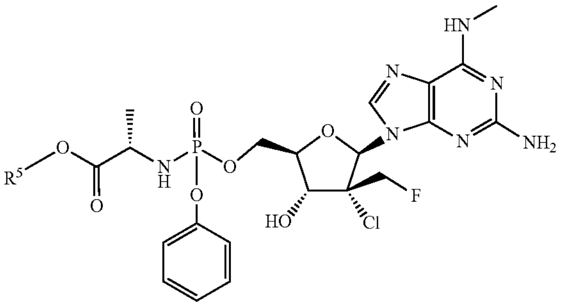
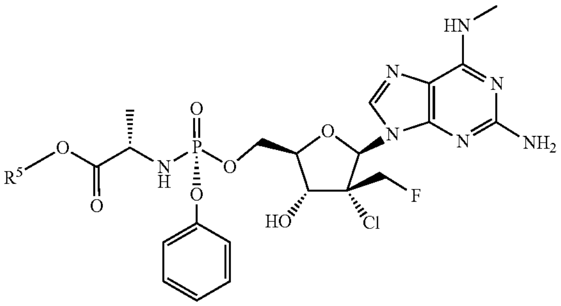
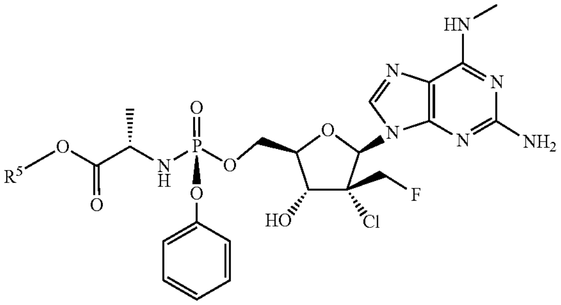
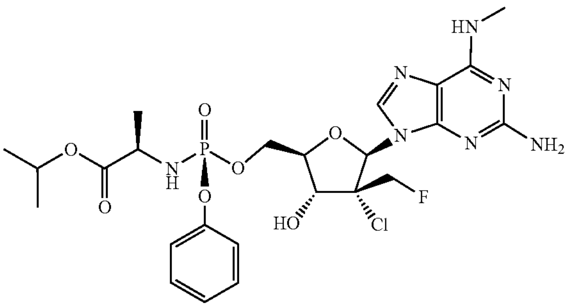
-continued
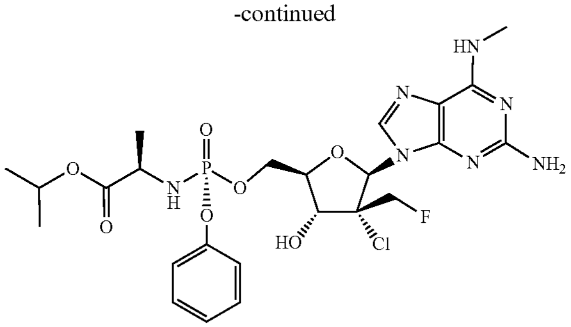
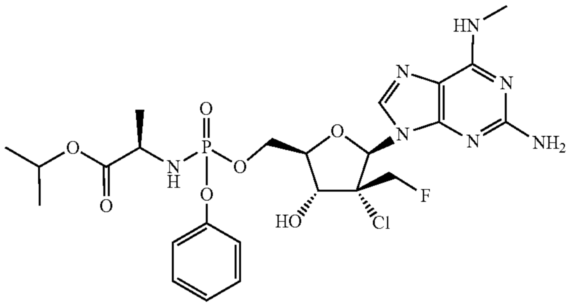
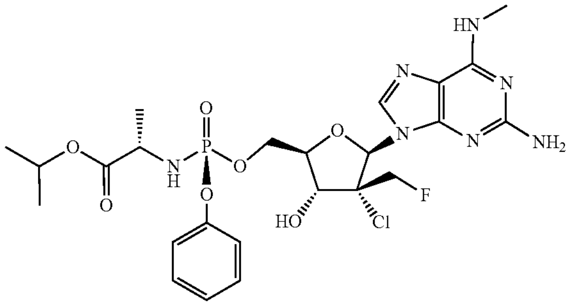
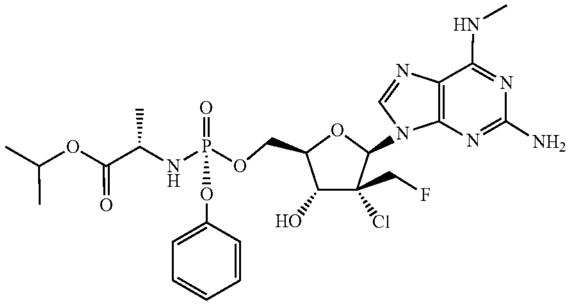
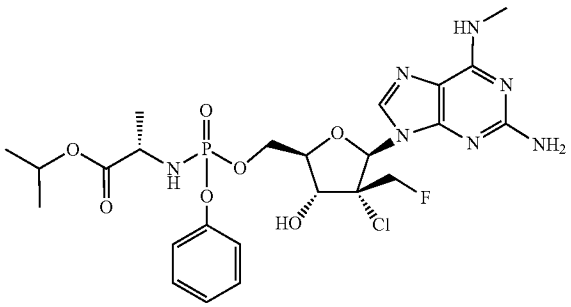

-continued
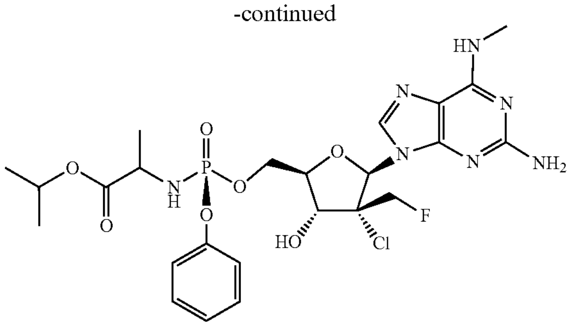
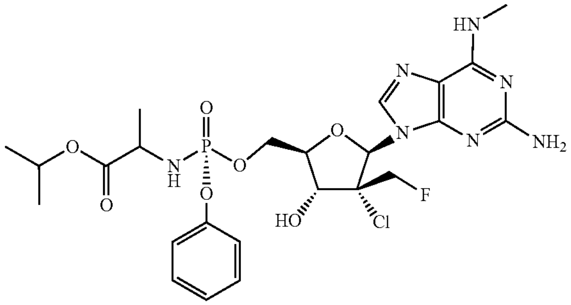
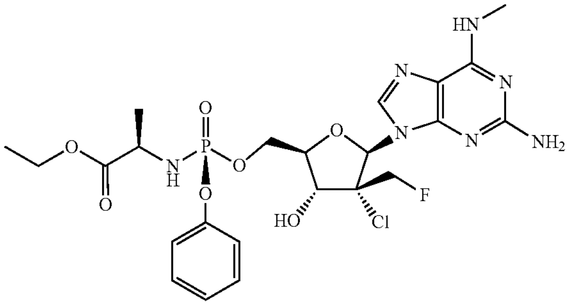
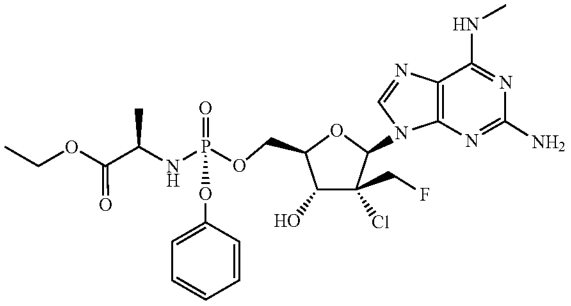
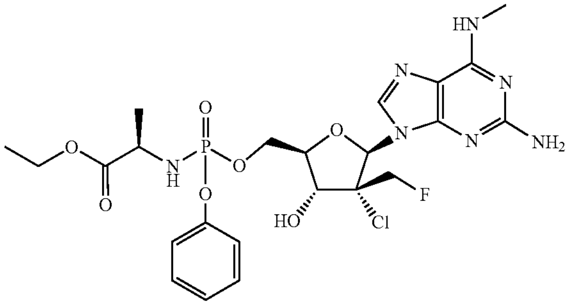
-continued
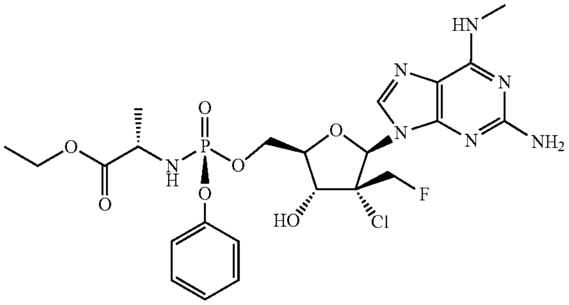
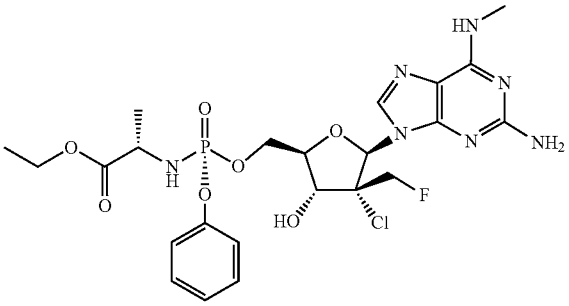
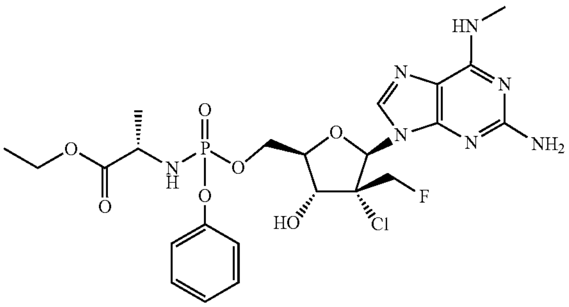
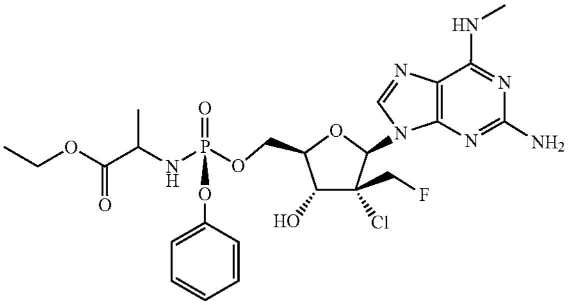
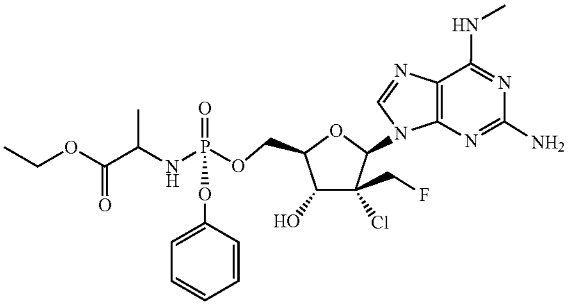

-continued
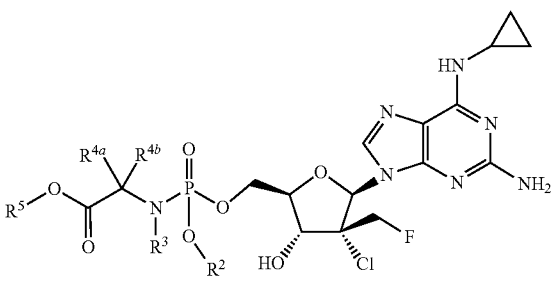
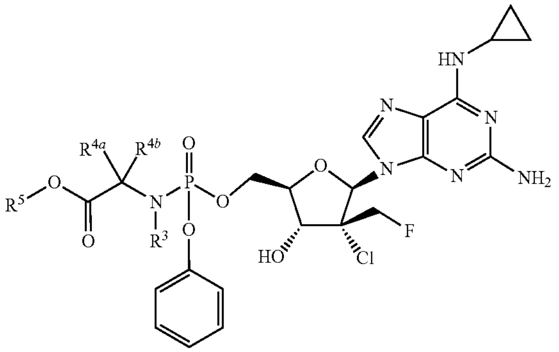
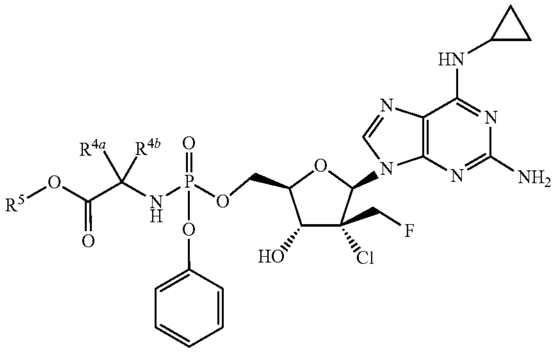
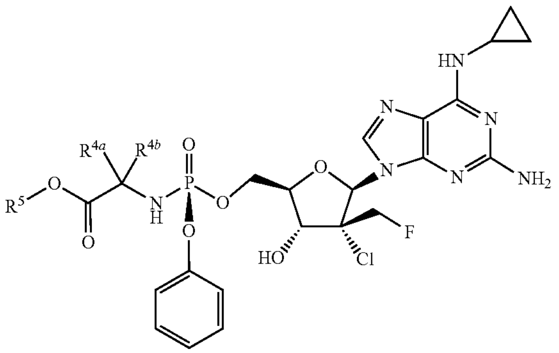
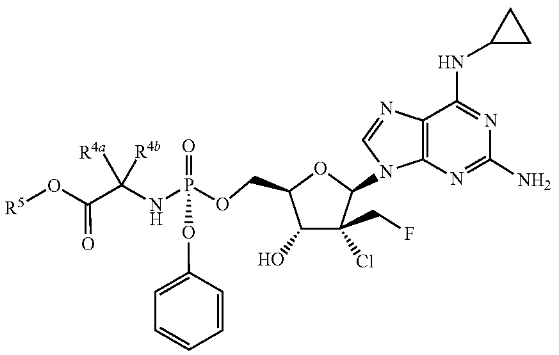
-continued
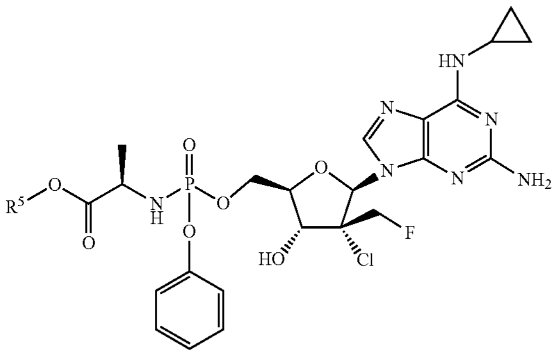
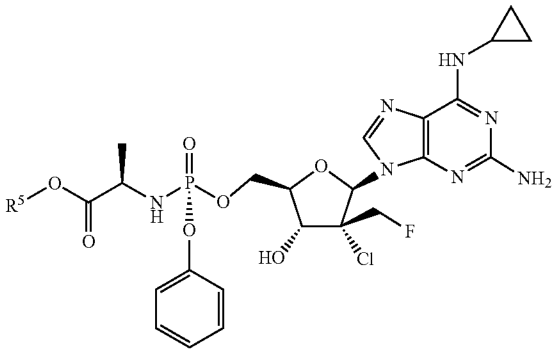
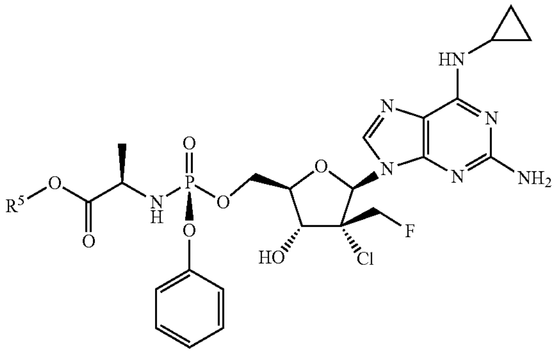
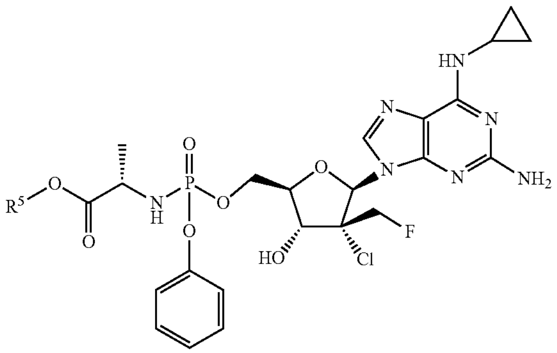

-continued
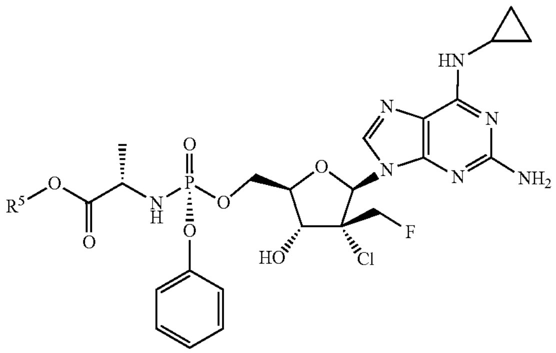
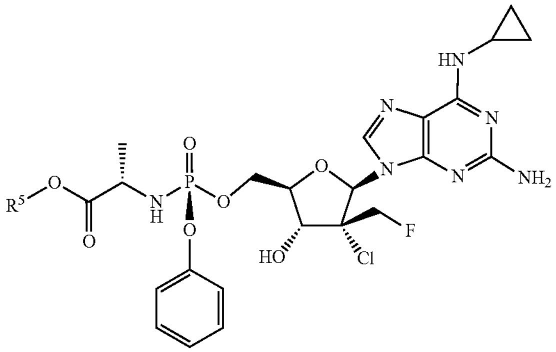
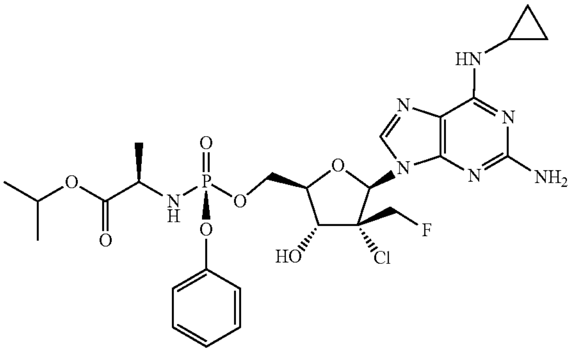
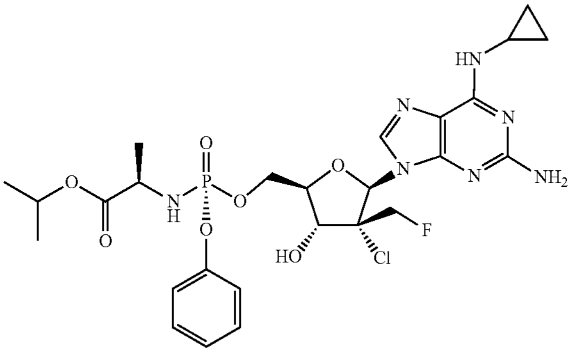
-continued
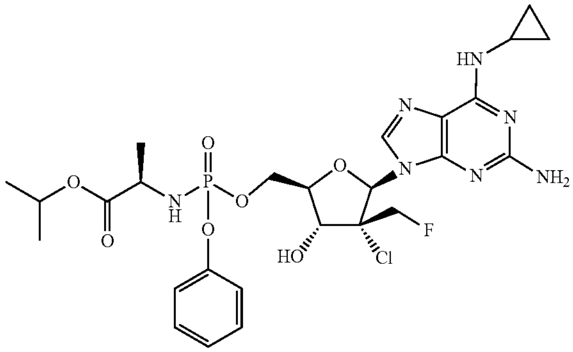
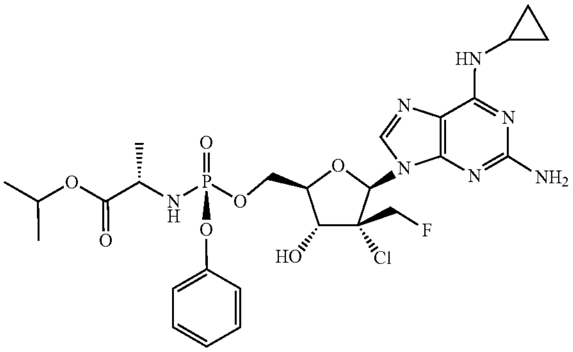
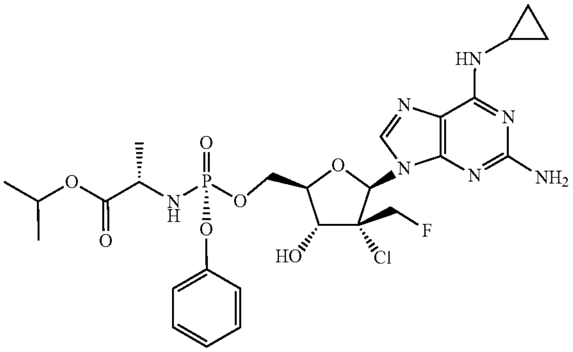
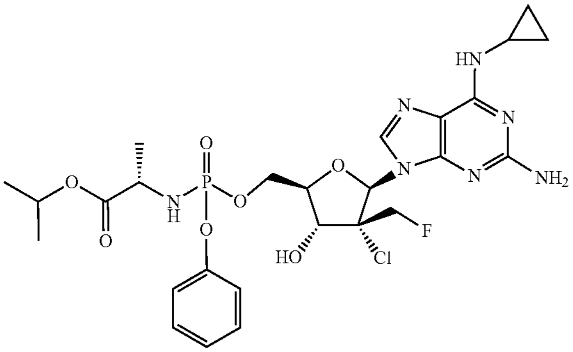

-continued
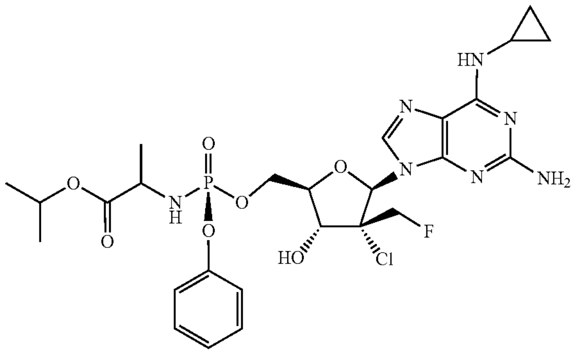
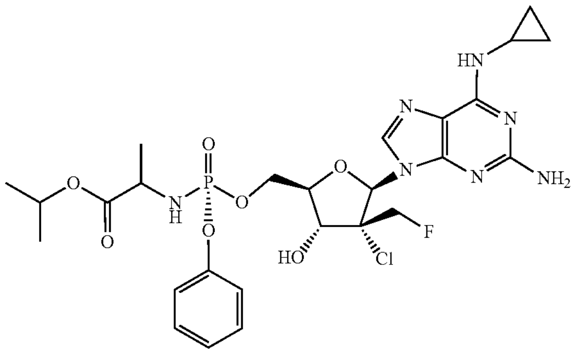
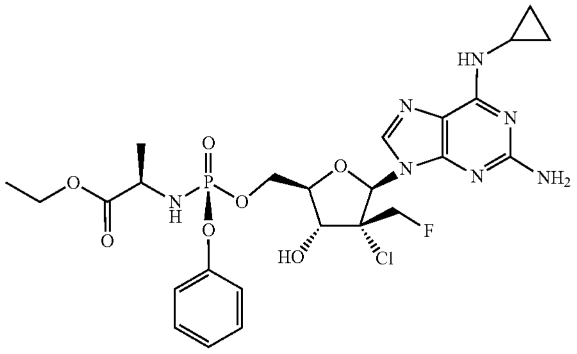
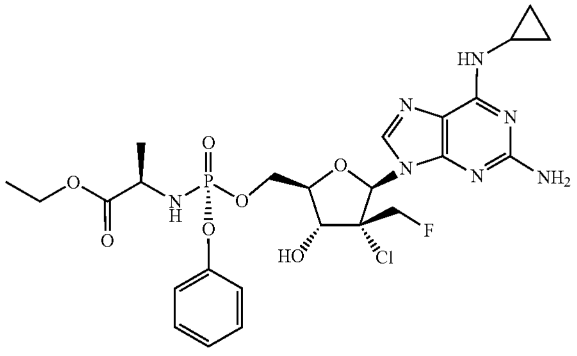
-continued
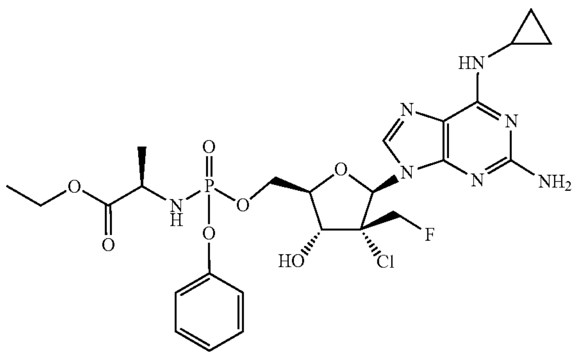
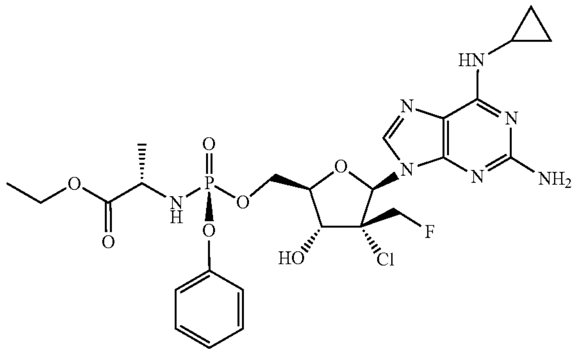
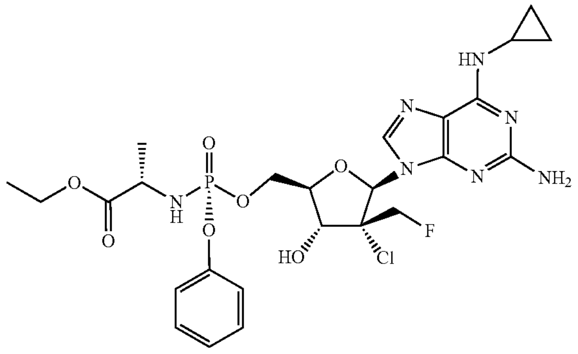
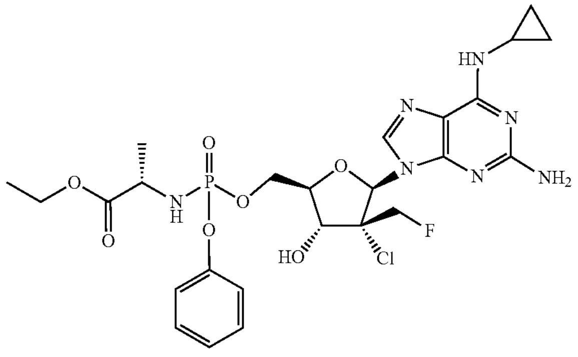

-continued

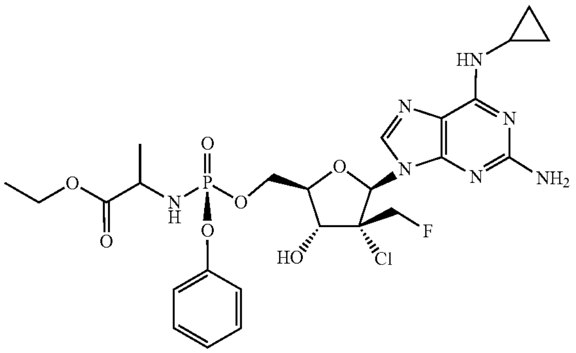

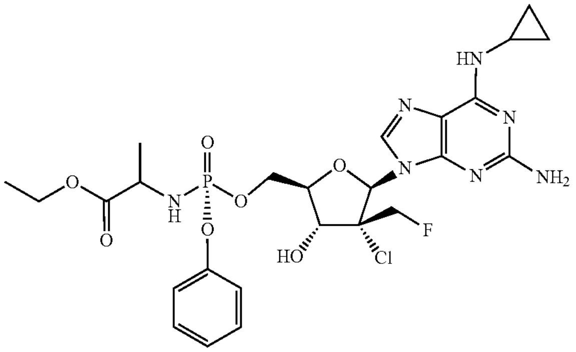

In some embodiments, the compound of Formula III to disrupt NiRAN function in a coronavirus or to treat or prevent a mutant or resistance form of SARS-CoV-2 virus is a compound of Formula IIIh:

Formula IIIh

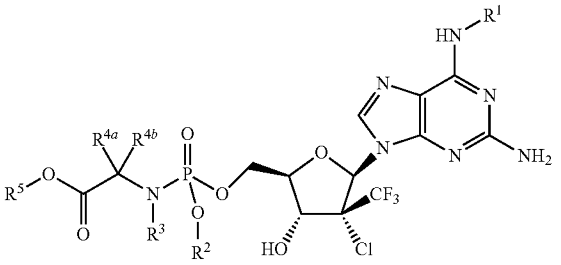

or a pharmaceutically acceptable salt thereof.

In some embodiments of Formula IIIh, $R^1$ is methyl.

In some embodiments of Formula IIIh, $R^1$ is cyclopropyl.

In some embodiments of Formula IIIh, $R^2$ is phenyl.

In some embodiments of Formula IIIh, $R^2$ is napthyl.

In some embodiments of Formula IIIh, $R^{4a}$ is hydrogen and $R^{4b}$ is methyl.

In some embodiments of Formula IIIh, $R^5$ is isopropyl.

In some embodiments of Formula IIIh, the compound is the $S_p$-isomer and the phosphoramidate is in the L-configuration.

In some embodiments of Formula IIIh, the compound is the $R_p$-isomer and the phosphoramidate is in the L-configuration.

Non-limiting examples of a compound of Formula IIIh include:

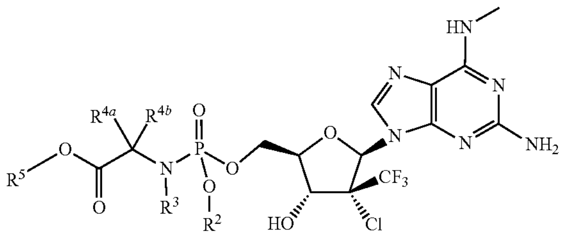

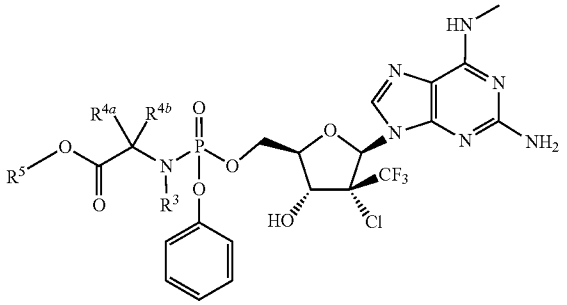

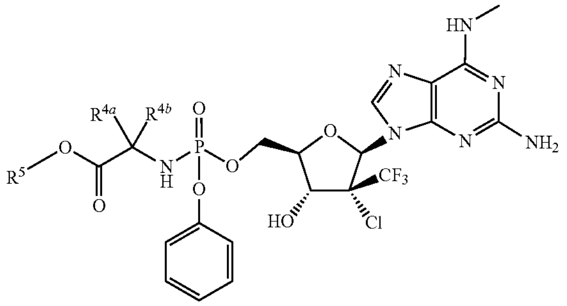

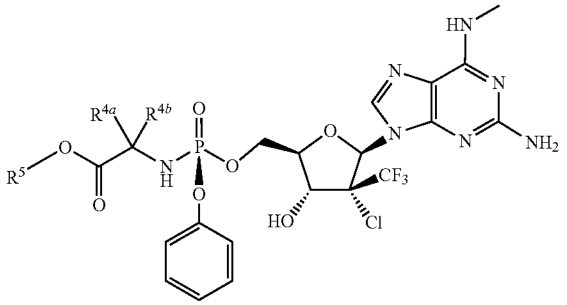

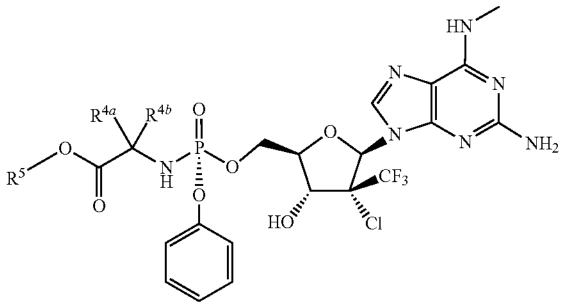

-continued
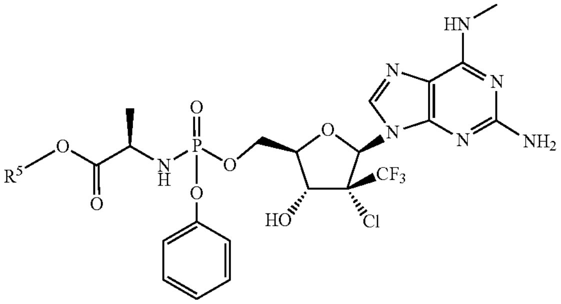
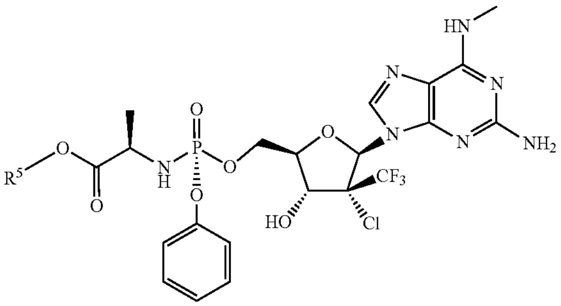
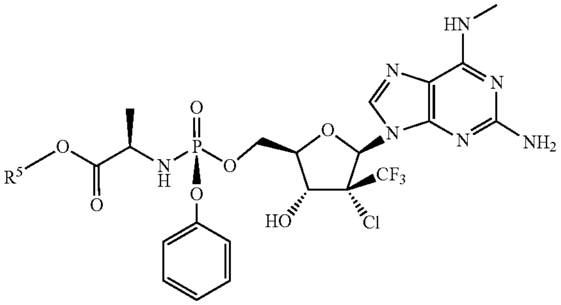
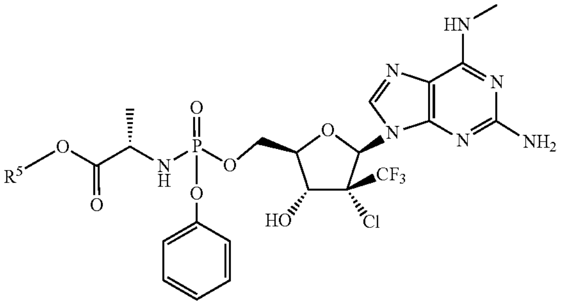
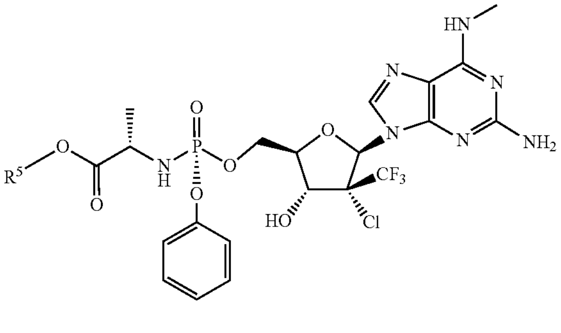
-continued
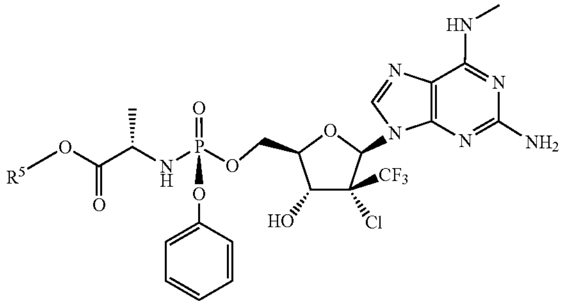
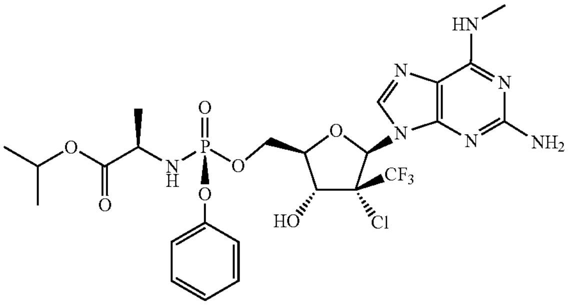
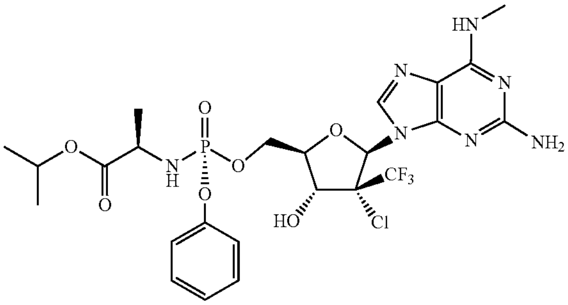
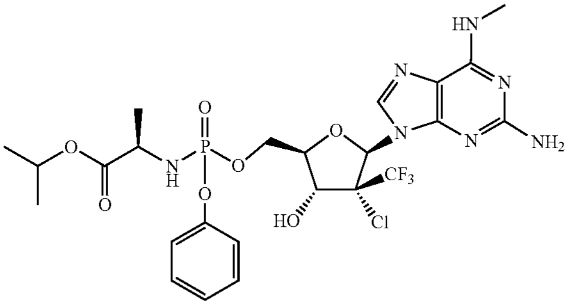
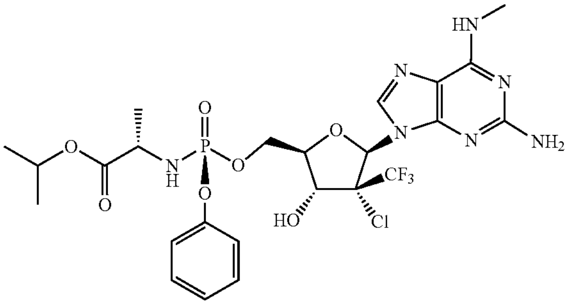

-continued
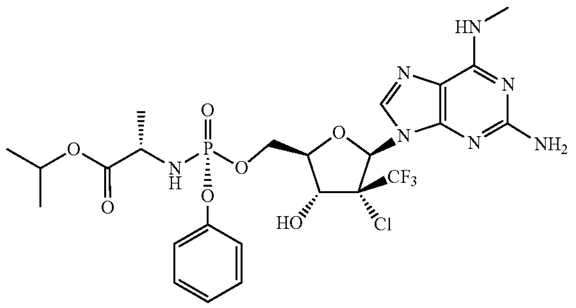
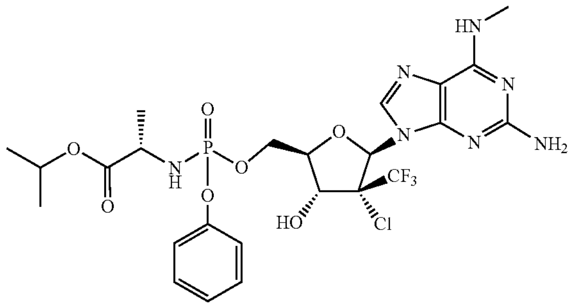
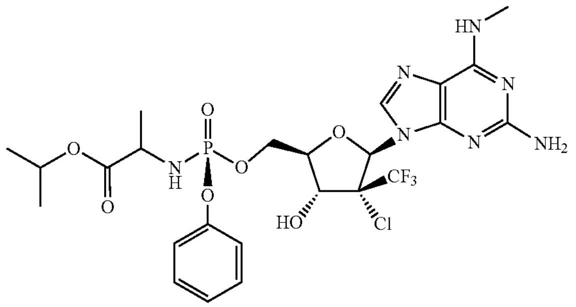
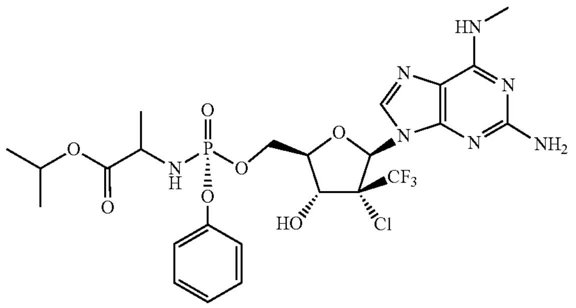
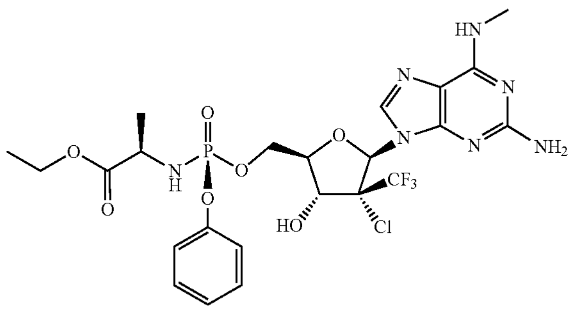
-continued
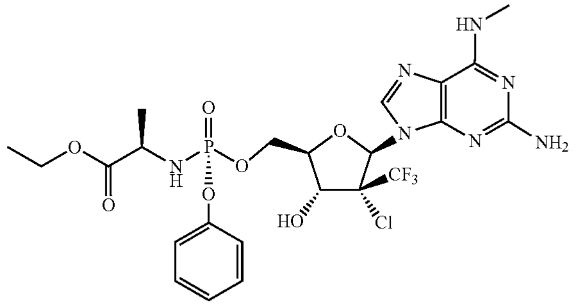
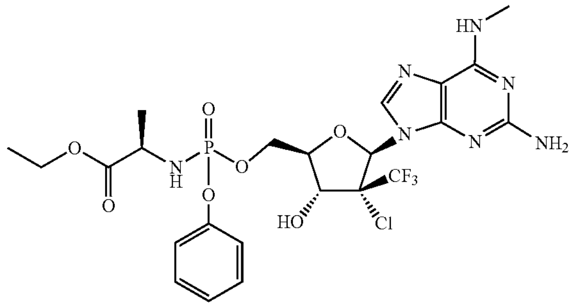
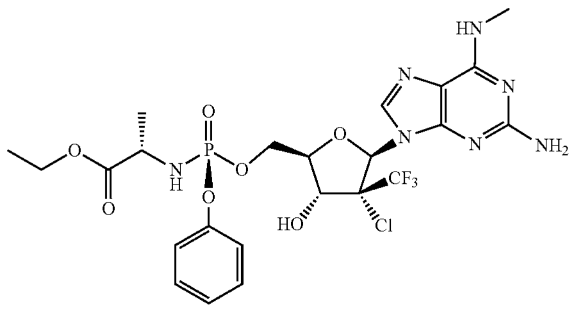
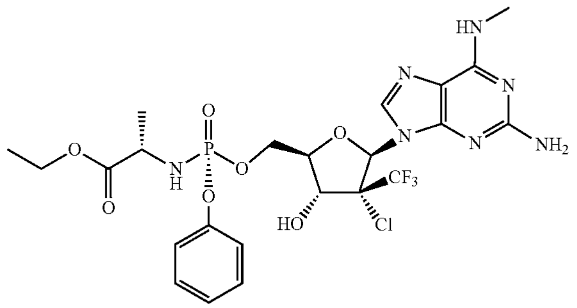
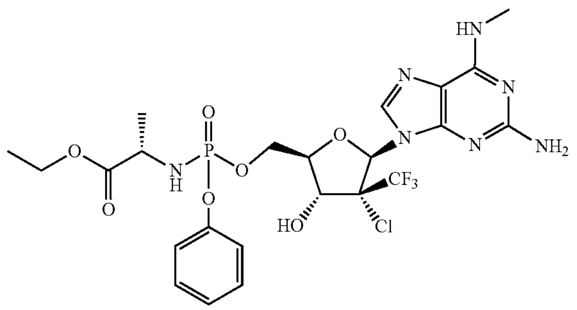

-continued
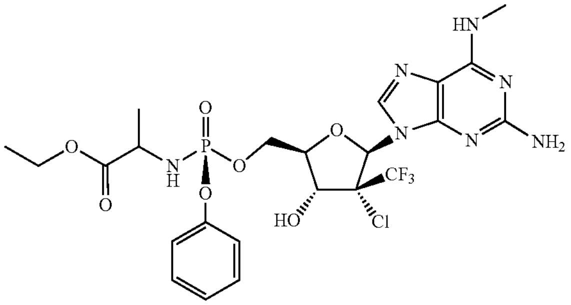
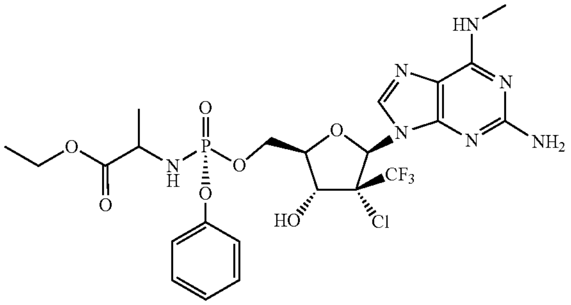
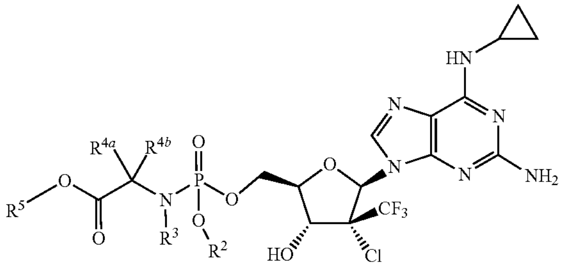
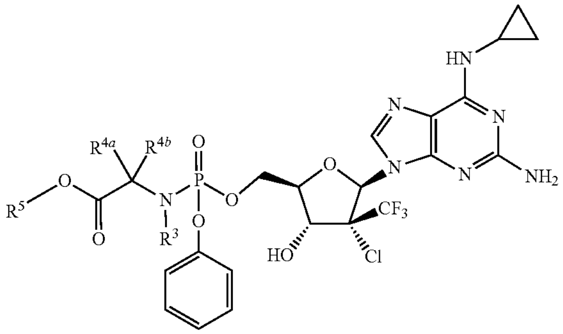
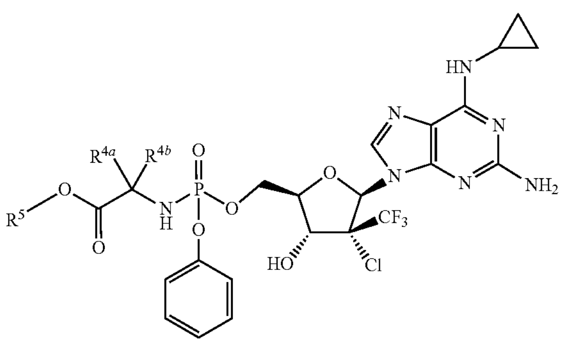
-continued
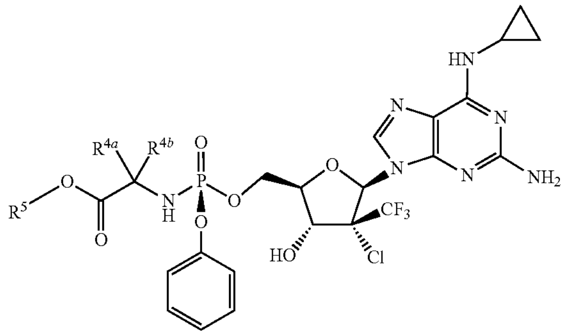
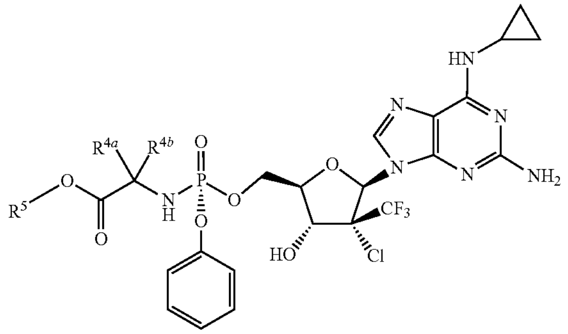
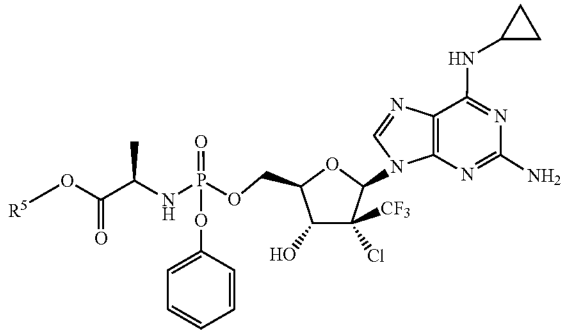
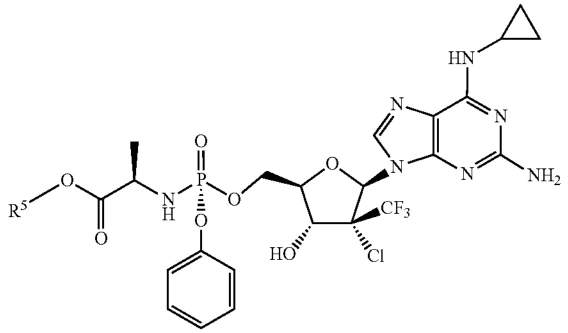
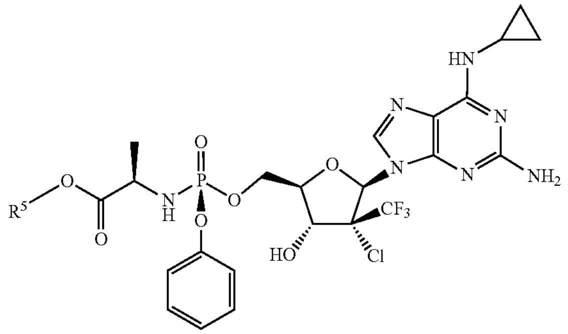

-continued
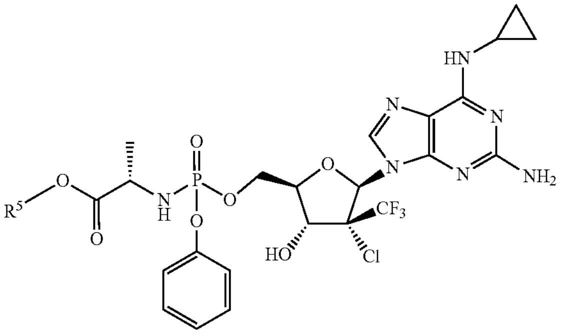
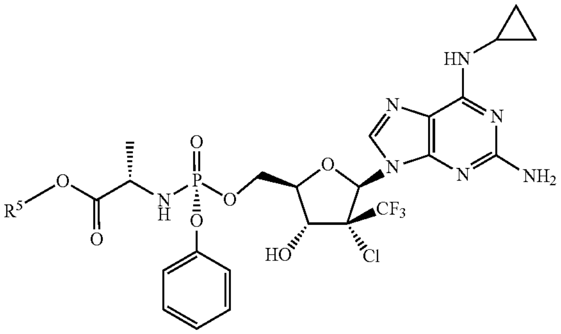
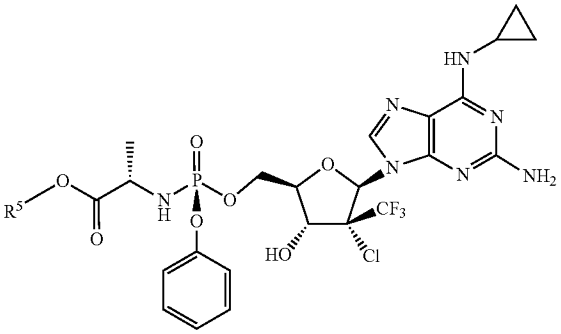
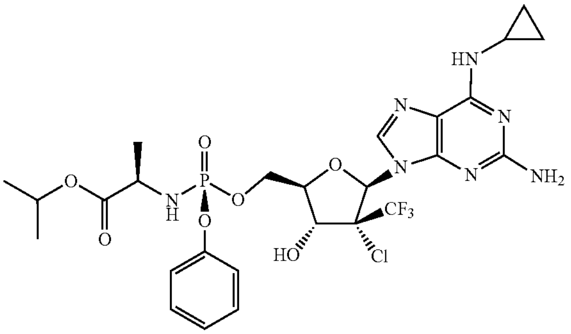
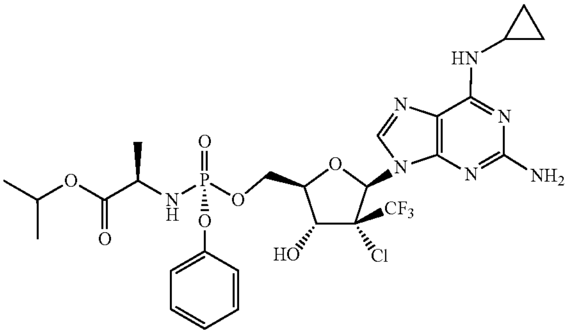
-continued
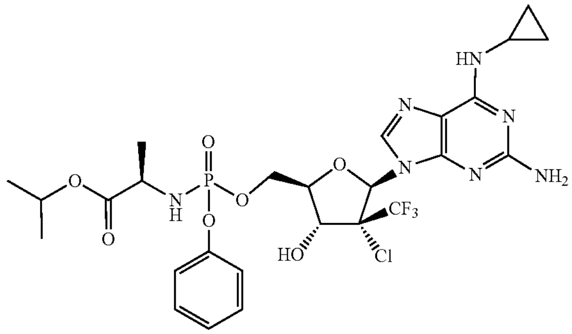
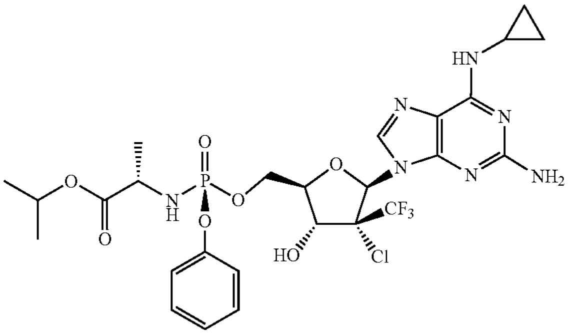
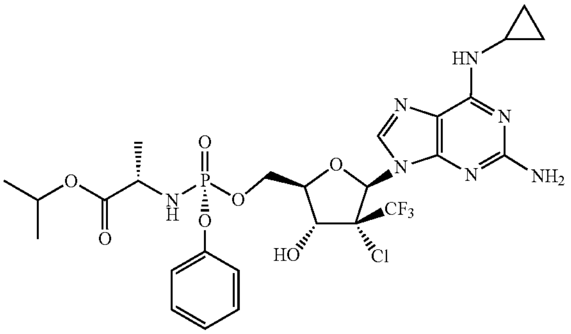
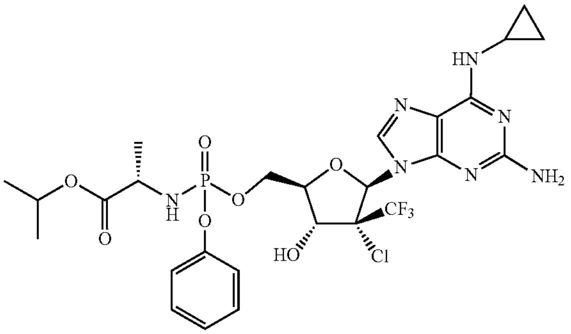
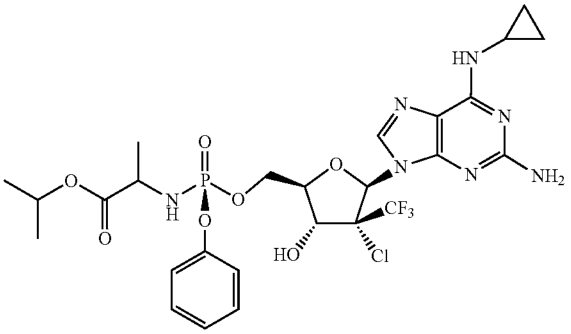

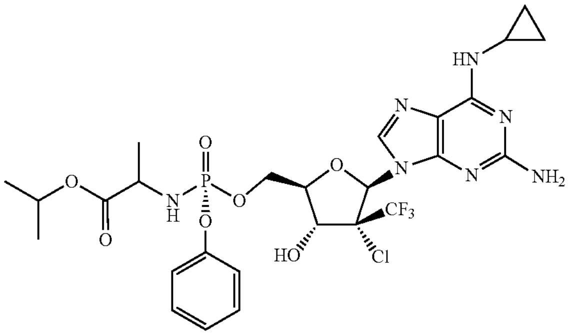
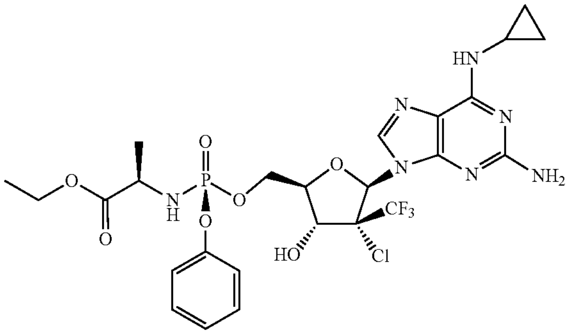
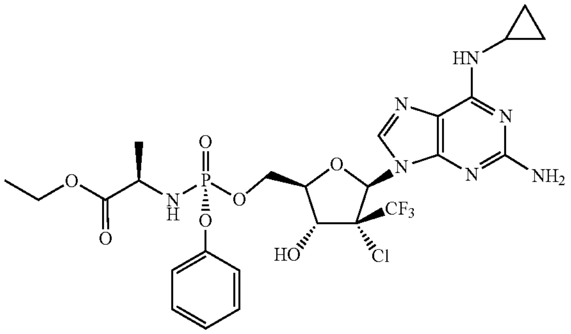
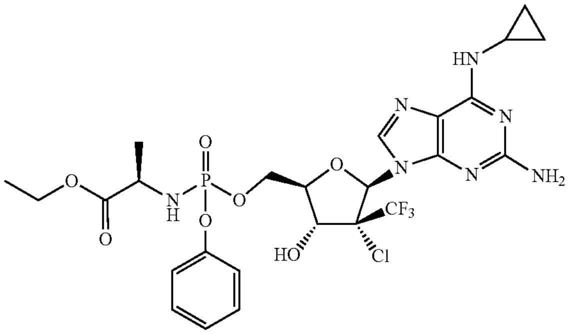
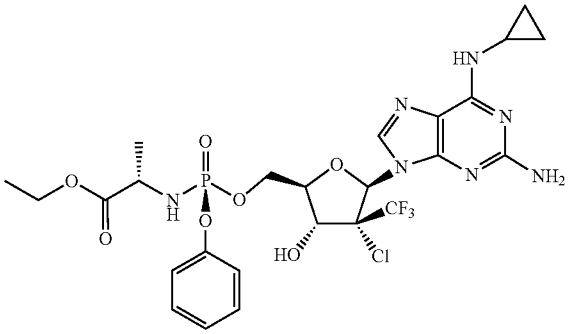
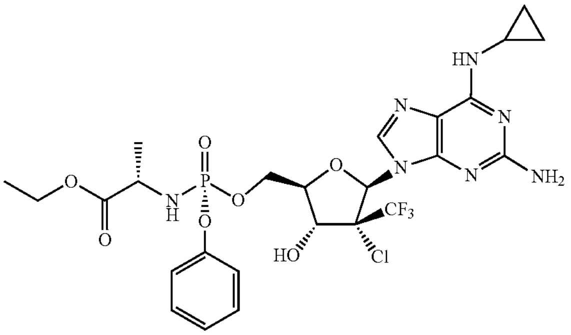
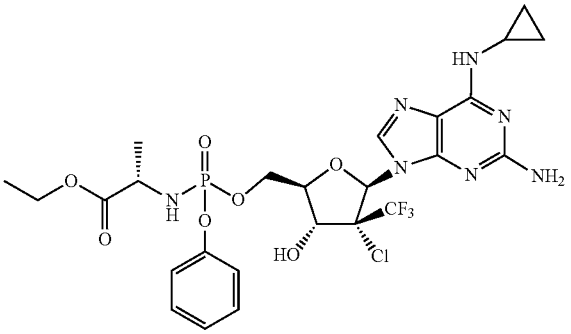
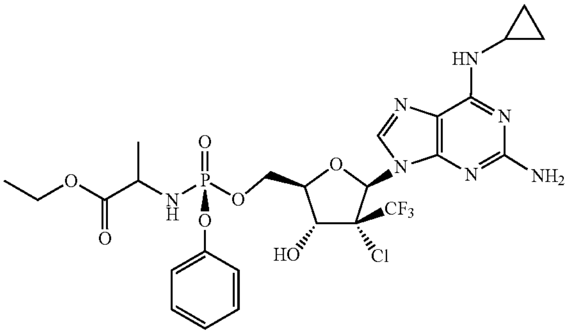
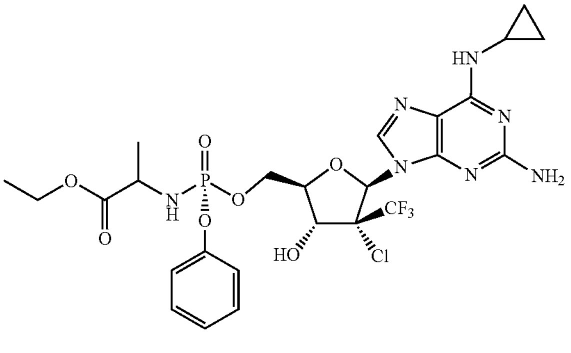

In some embodiments, the compound of Formula III to disrupt NiRAN function in a coronavirus or to treat or prevent a mutant or resistance form of the SARS-CoV-2 virus is a compound of Formula IIIi:

Formula IIIi

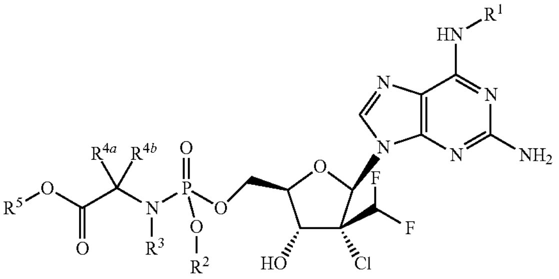

or a pharmaceutically acceptable salt thereof.

In some embodiments of Formula IIIi, $R^1$ is methyl.

In some embodiments of Formula IIIi, $R^1$ is cyclopropyl.

In some embodiments of Formula IIIi, $R^1$ is phenyl.

In some embodiments of Formula IIIi, $R^1$ is napthyl.

In some embodiments of Formula IIIi, $R^{4a}$ is hydrogen and $R^{4b}$ is methyl.

In some embodiments of Formula IIIi, $R^5$ is isopropyl.

In some embodiments of Formula IIIi the compound is the $S_p$-isomer and the phosphoramidate is in the L-configuration.

In some embodiments of Formula IIIi, the compound is the $R_p$-isomer and the phosphoramidate is in the L-configuration.

In some embodiments of Formula IIIi, the pharmaceutically acceptable salt is the hemi-sulfate salt.

Non-limiting examples of a compound of Formula IIIi include:

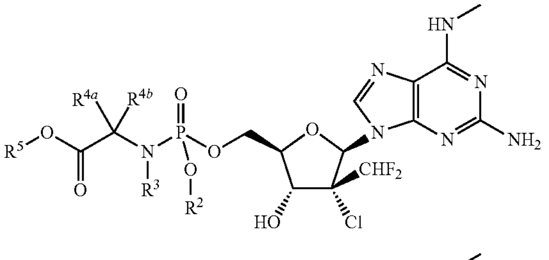

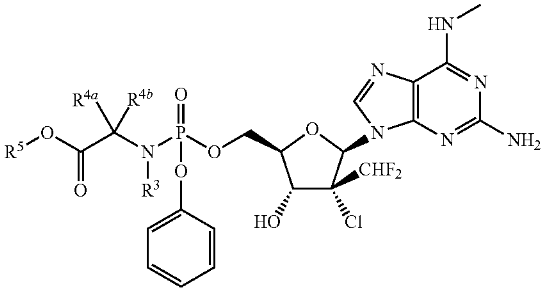

-continued

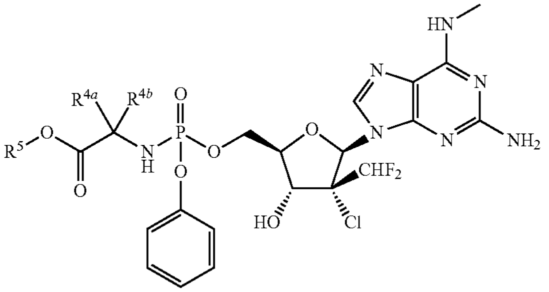

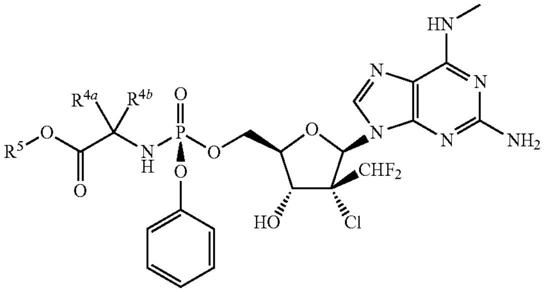

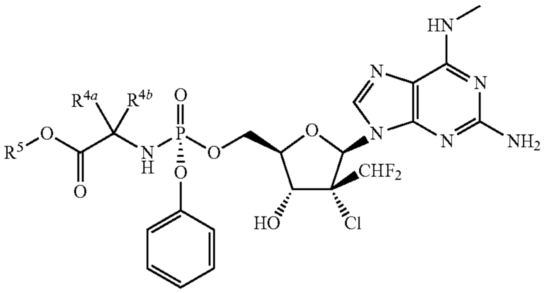

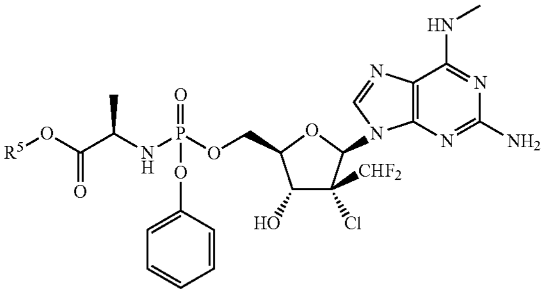

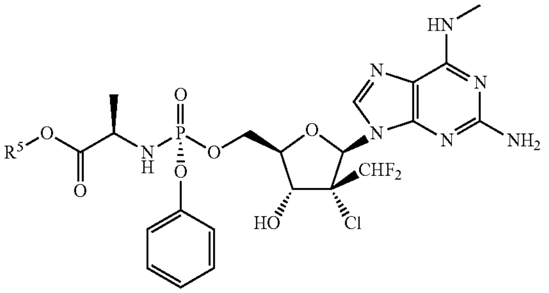

-continued
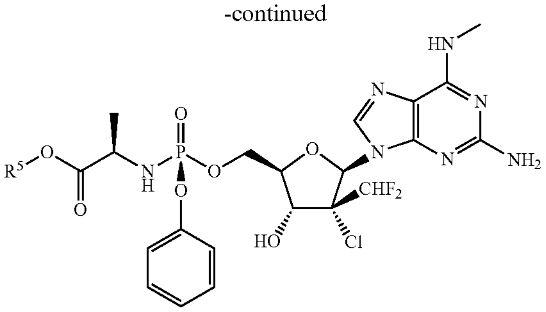
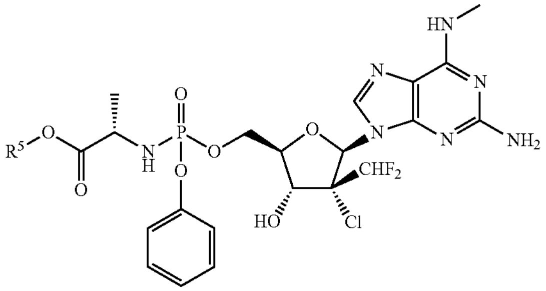
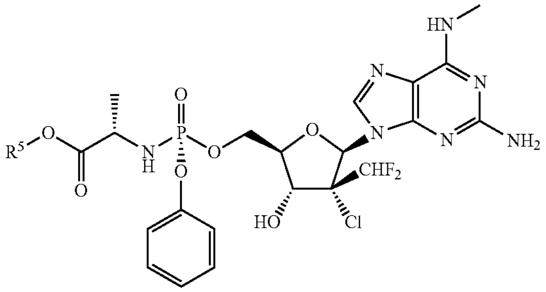
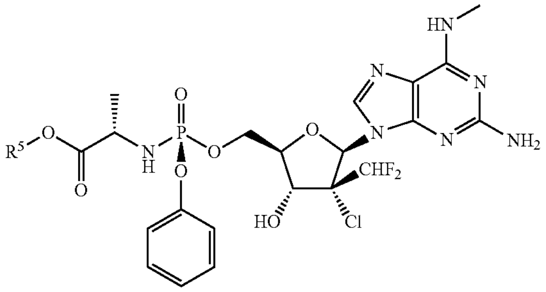
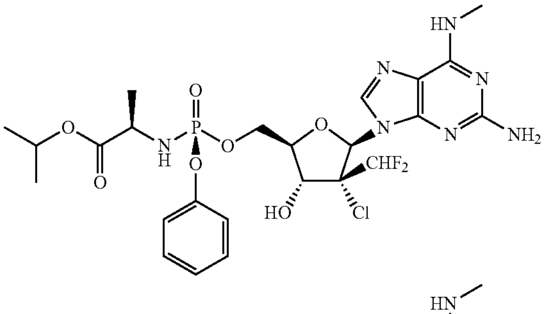
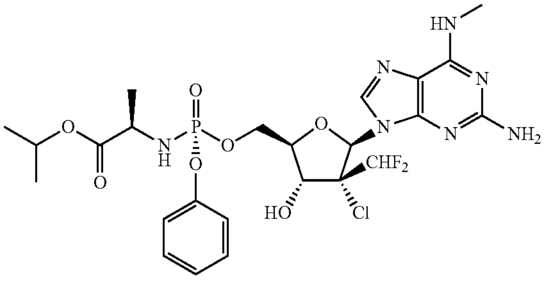
-continued
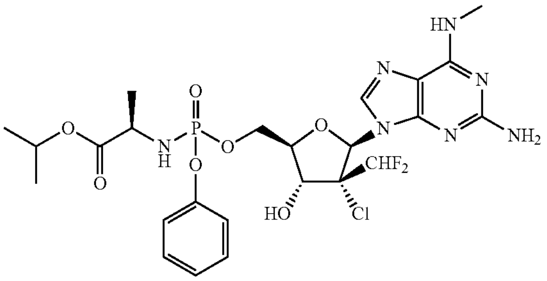
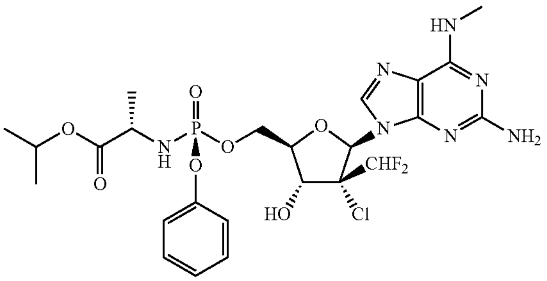
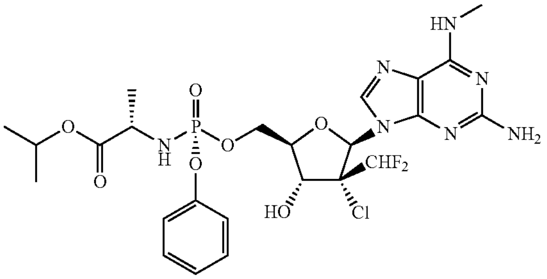
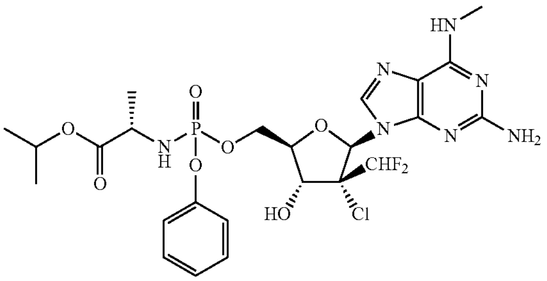
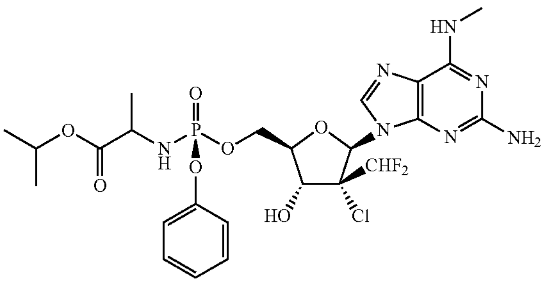
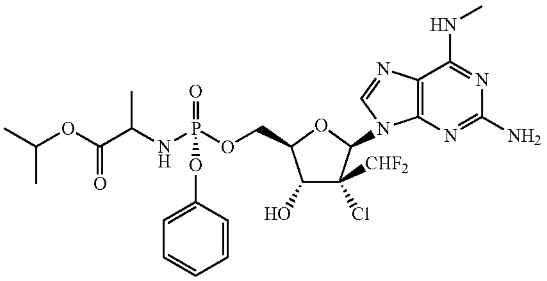

-continued
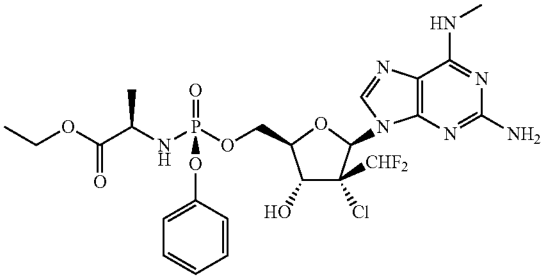
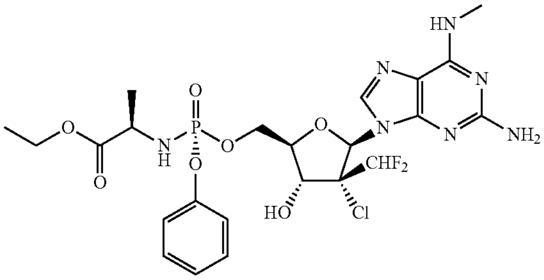
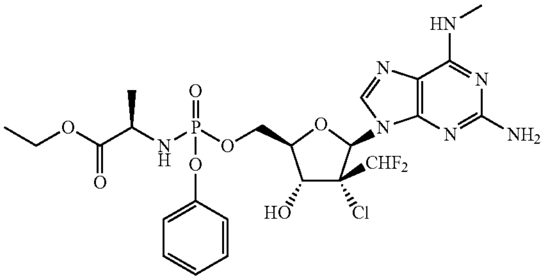
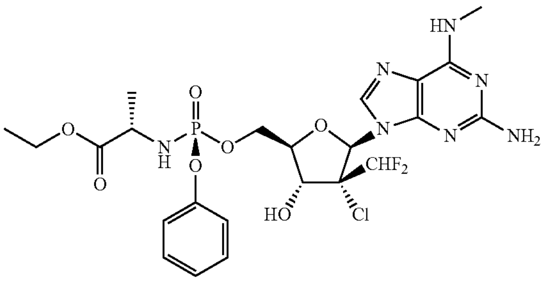
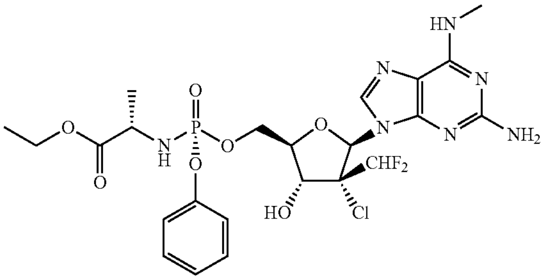
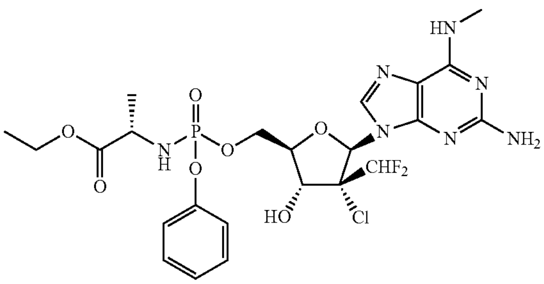
-continued
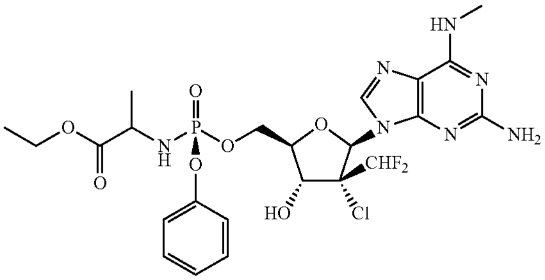
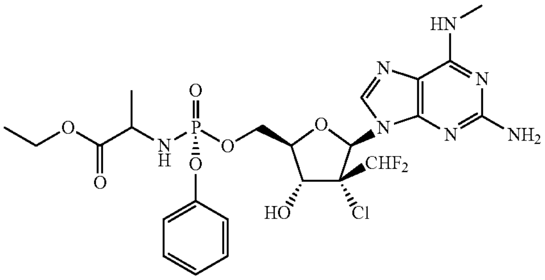
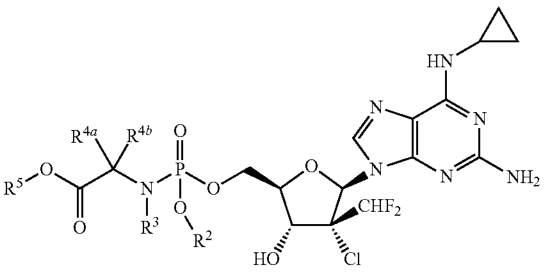
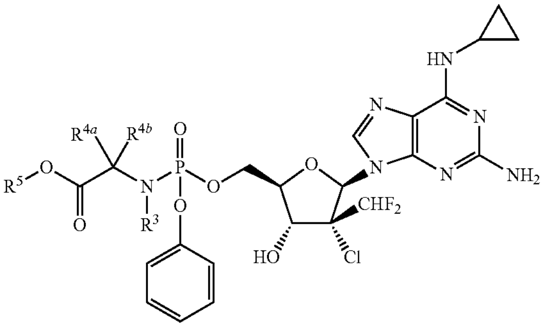
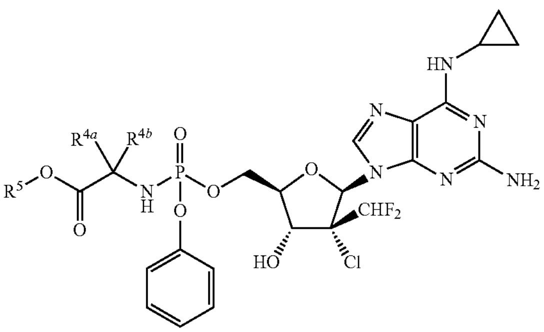

-continued
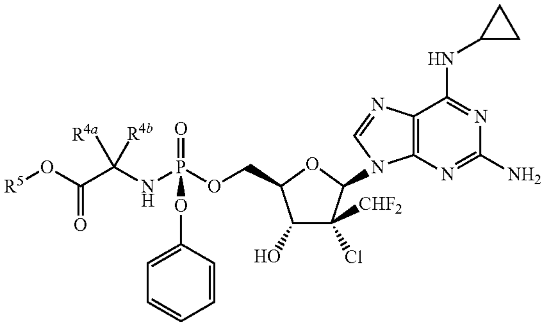
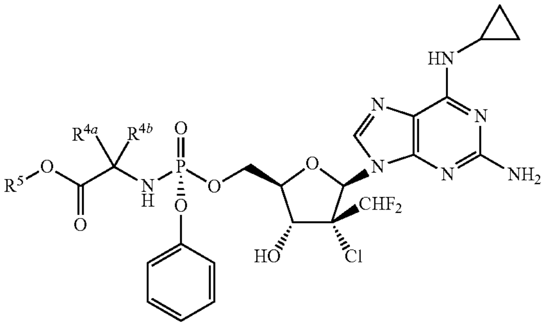
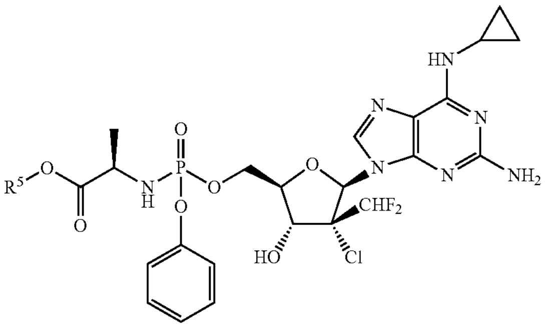
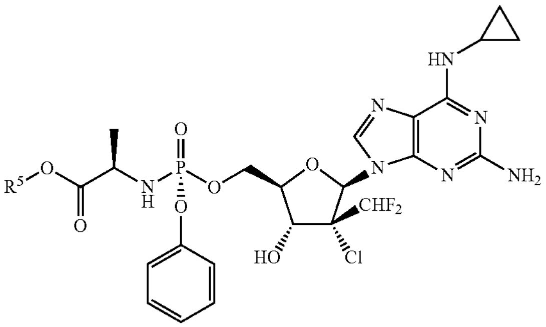
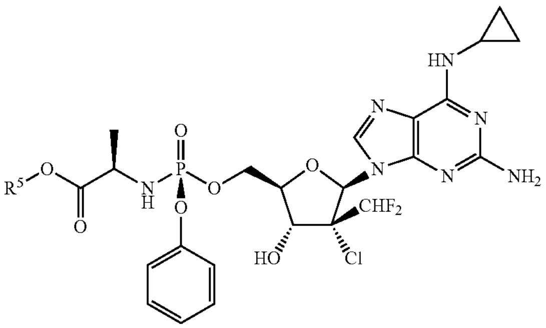
-continued
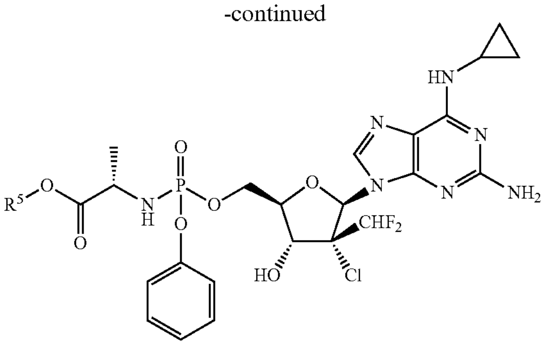
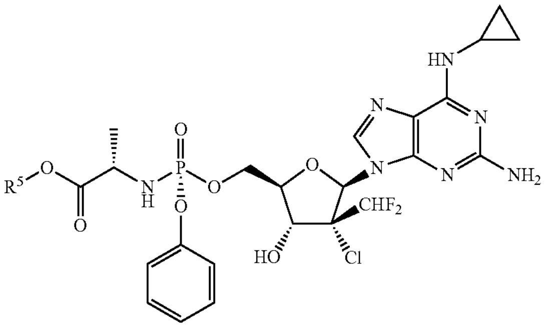
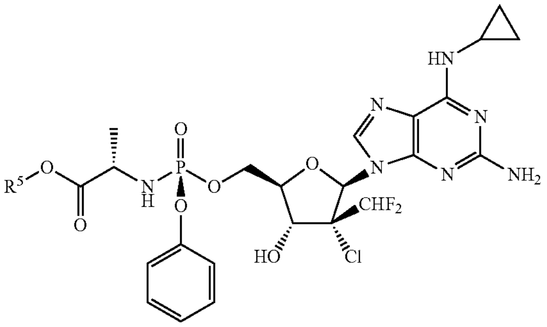
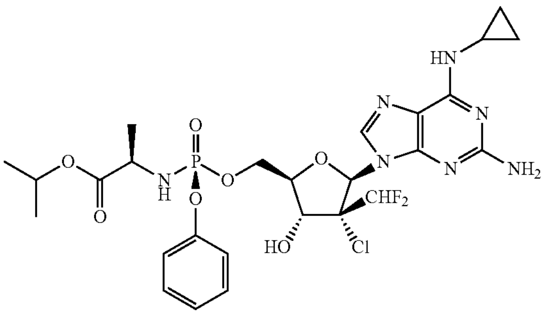
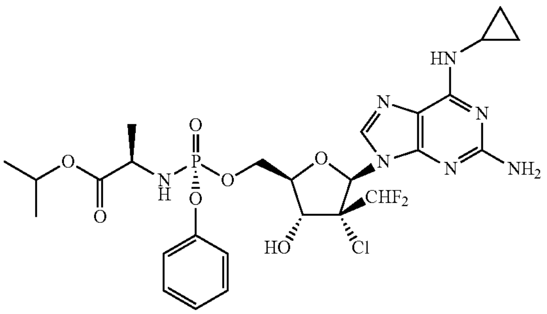

-continued
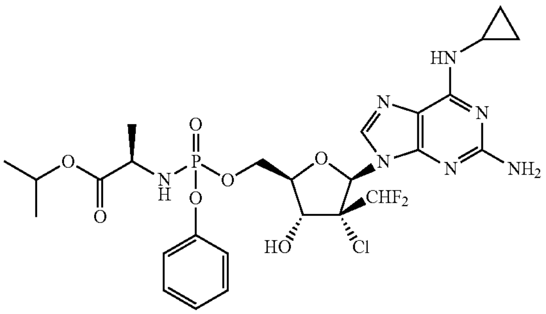
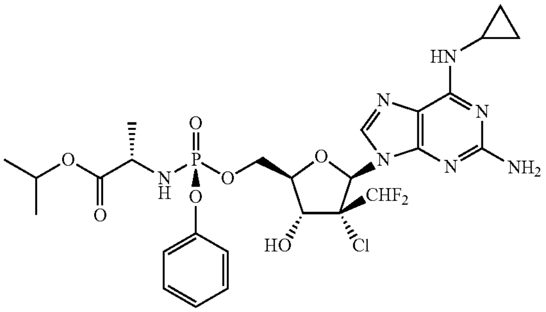
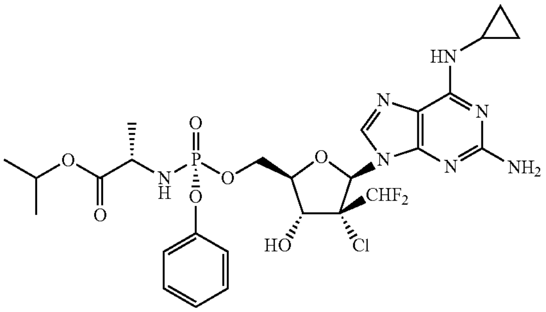
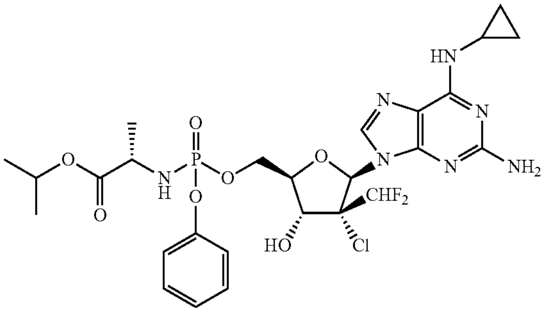
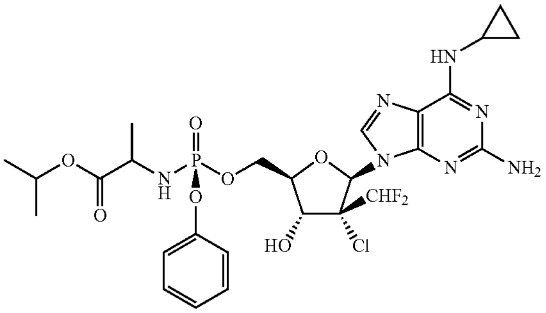
-continued
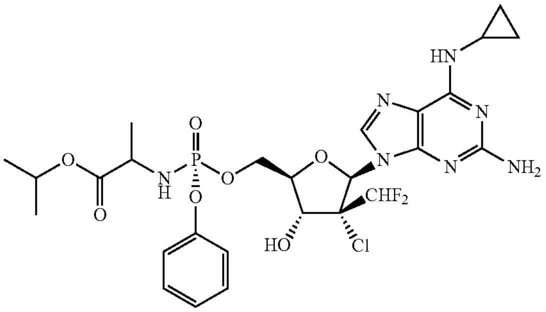
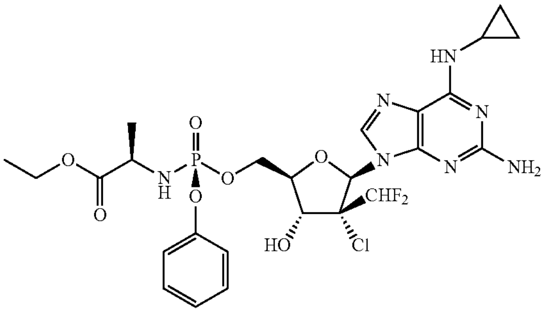
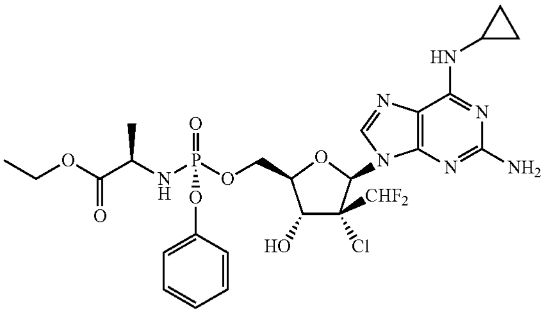
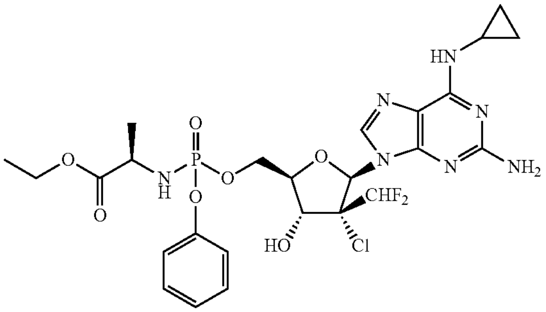
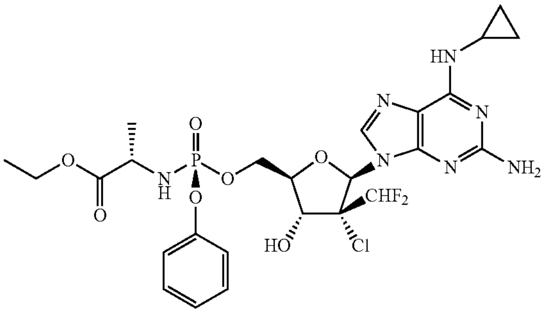

-continued

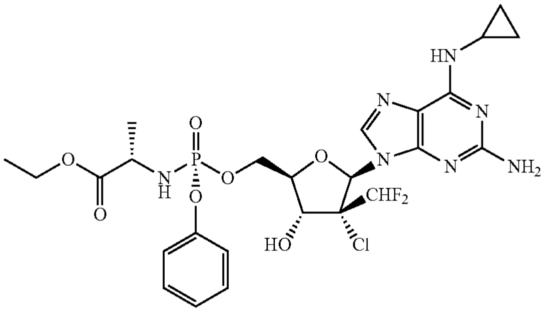

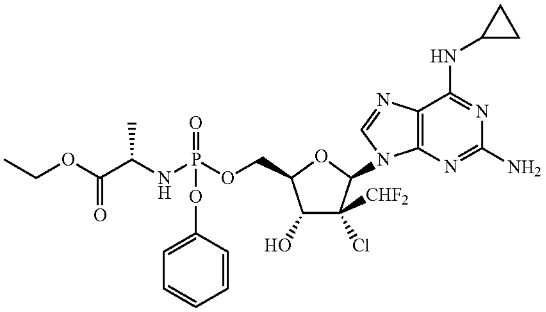

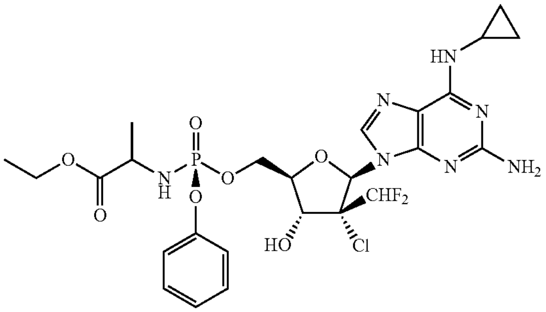

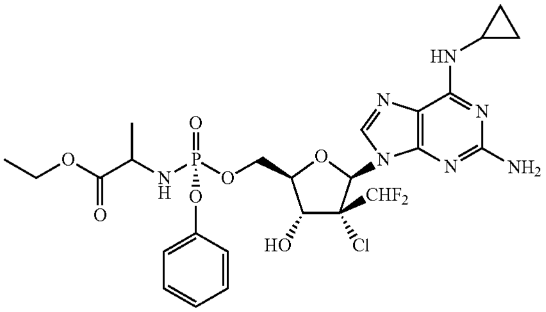

In some embodiments, the compound of Formula III to disrupt NiRAN function in a coronavirus or to treat or prevent a mutant or resistance form of the SARS-CoV-2 virus a compound of Formula IIIj:

Formula IIIj

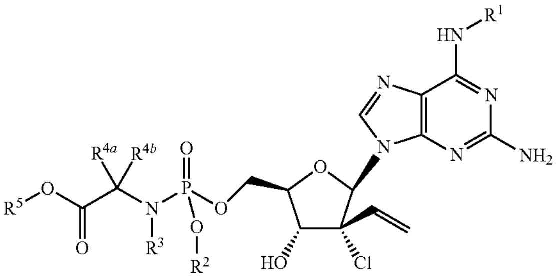

or a pharmaceutically acceptable salt thereof.

In some embodiments of Formula IIIj, $R^1$ is methyl.

In some embodiments of Formula IIIj, $R^1$ is cyclopropyl.

In some embodiments of Formula IIIj, $R^1$ is phenyl.

In some embodiments of Formula IIIj, $R^2$ is napthyl.

In some embodiments of Formula IIIj, $R^{4a}$ is hydrogen and $R^{4b}$ is methyl.

In some embodiments of Formula IIIj, $R^5$ is isopropyl.

In some embodiments of Formula IIIj, the compound is the $S_p$-isomer and the phosphoramidate is in the L-configuration.

In some embodiments of Formula IIIj, the compound is the $R_p$-isomer and the phosphoramidate is in the L-configuration.

In some embodiments of Formula IIIj, the pharmaceutically acceptable salt is the hemi-sulfate salt.

Non-limiting examples of a compound of Formula IIIj include:

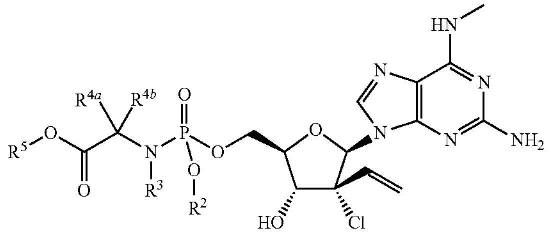

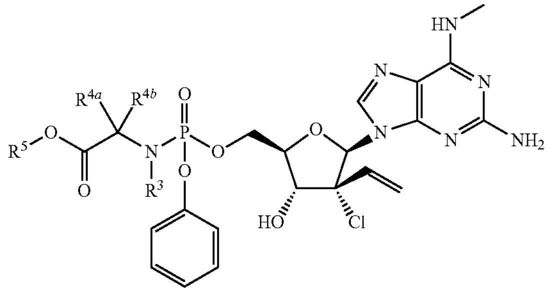

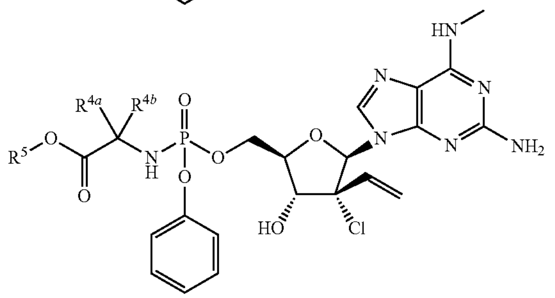

-continued
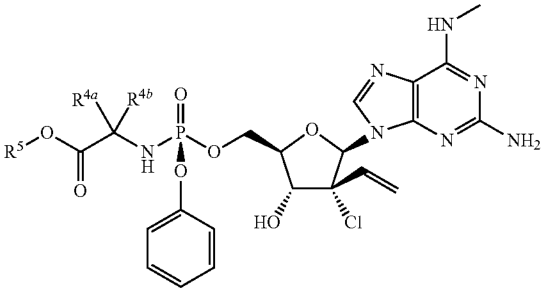
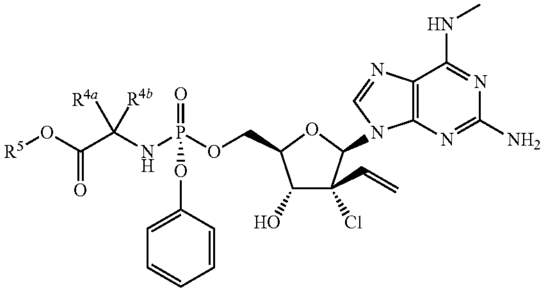
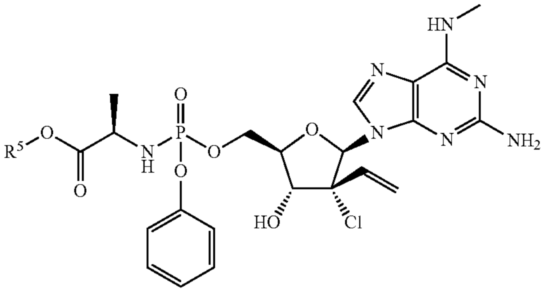
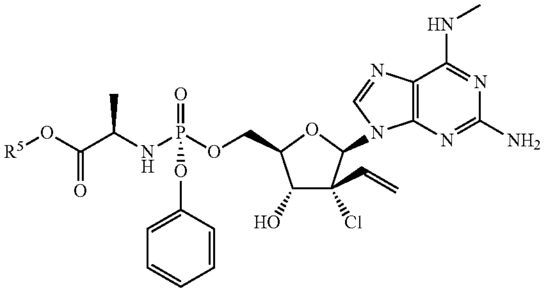
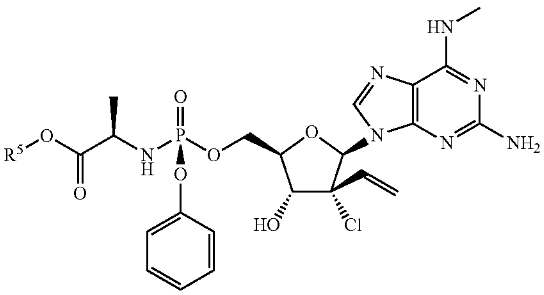
-continued
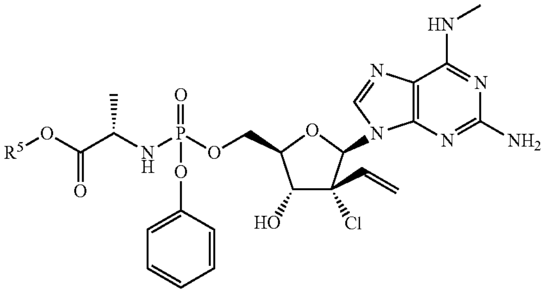
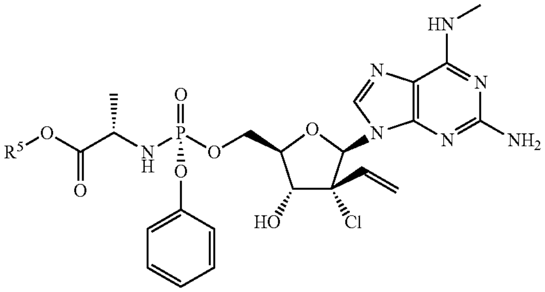
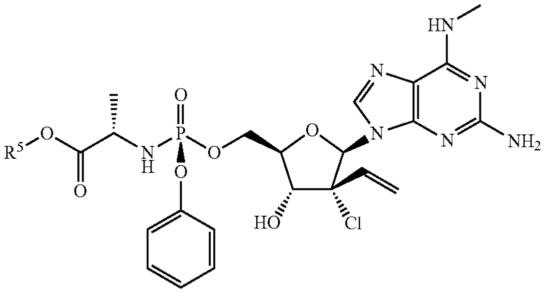
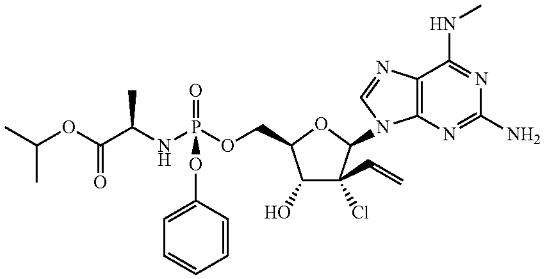
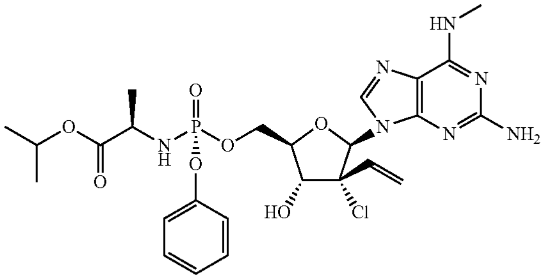
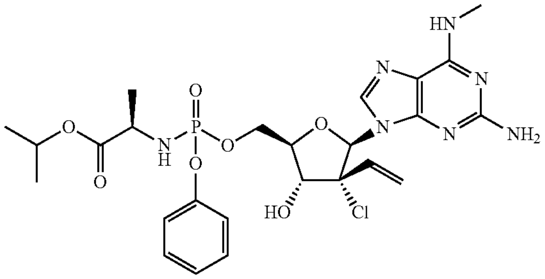

-continued
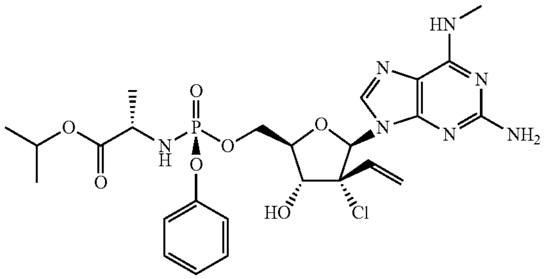
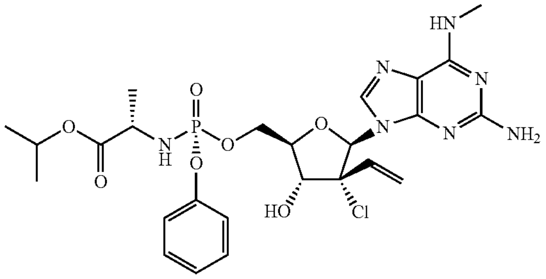
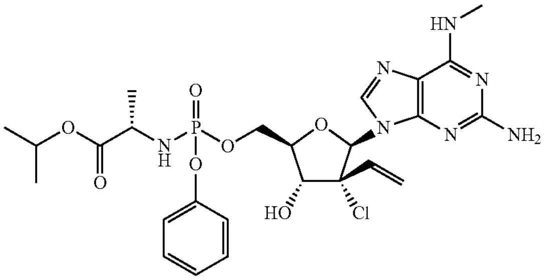
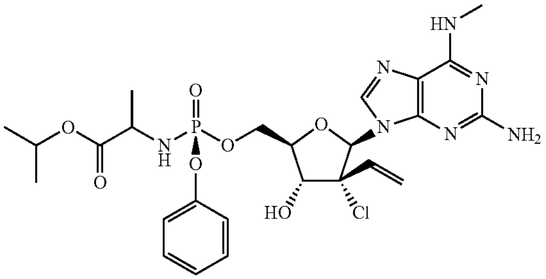
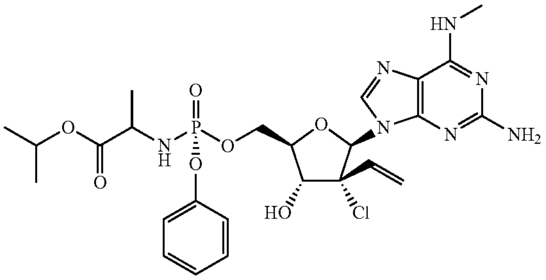
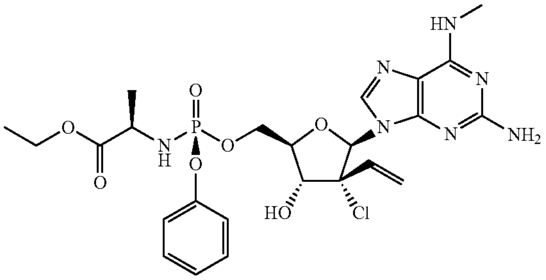
-continued
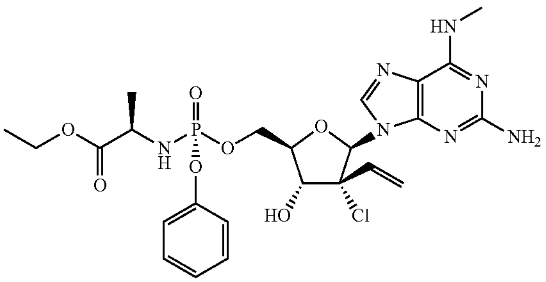
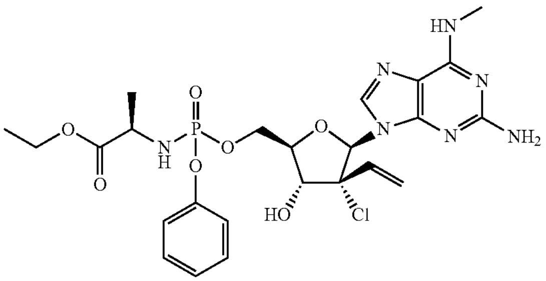
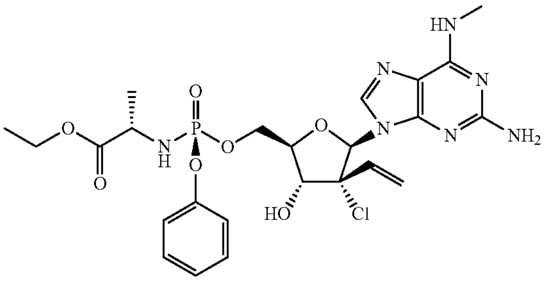
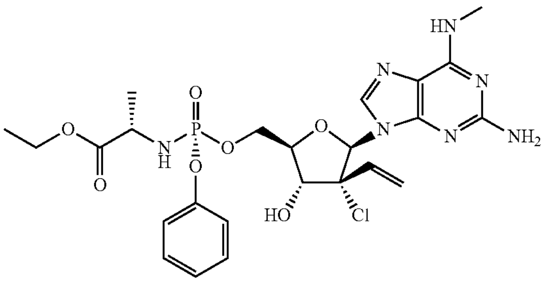
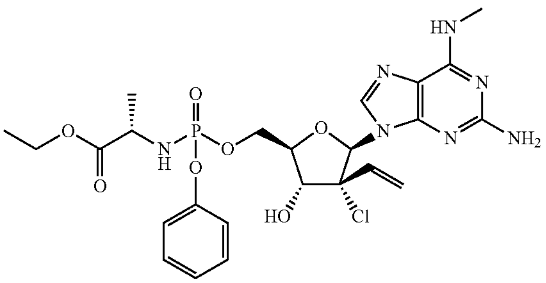
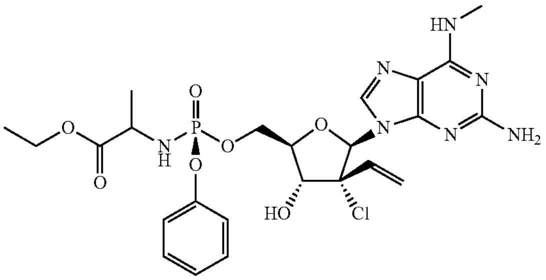

-continued
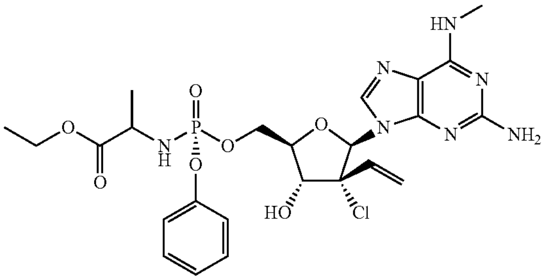
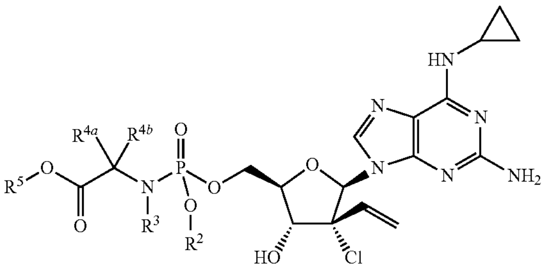
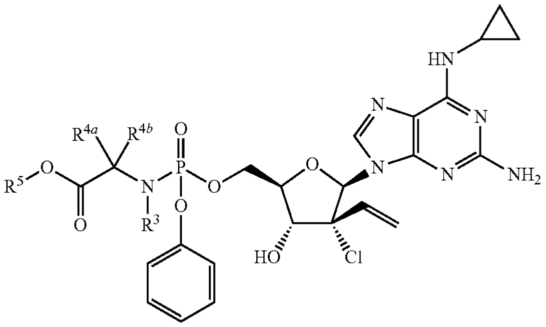
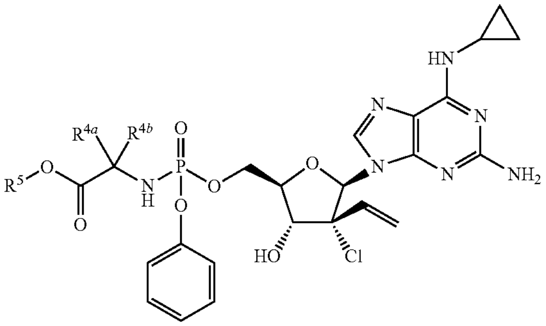
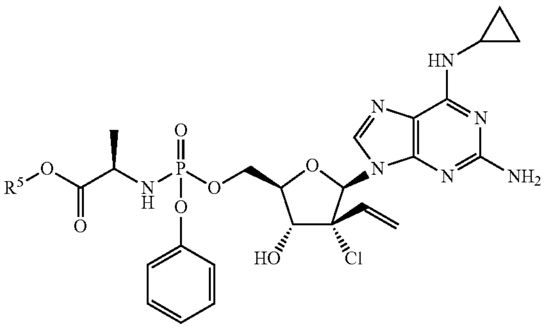
-continued
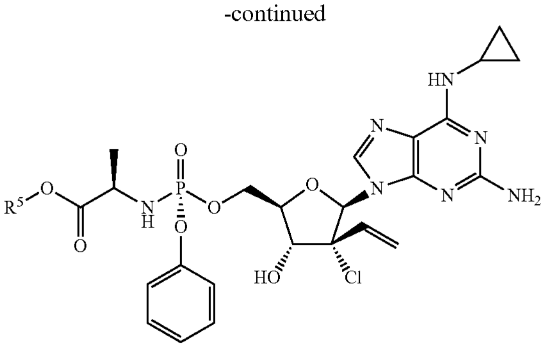
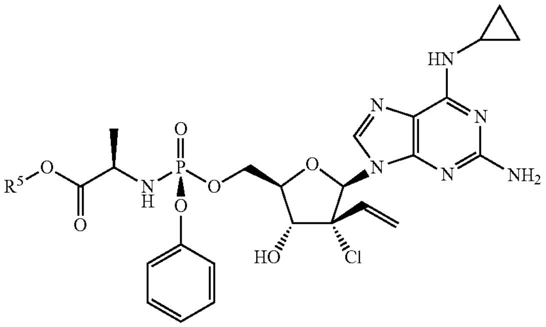
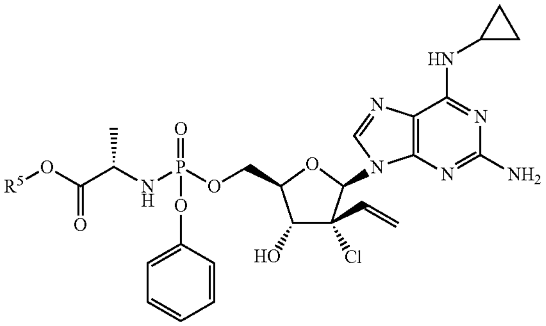
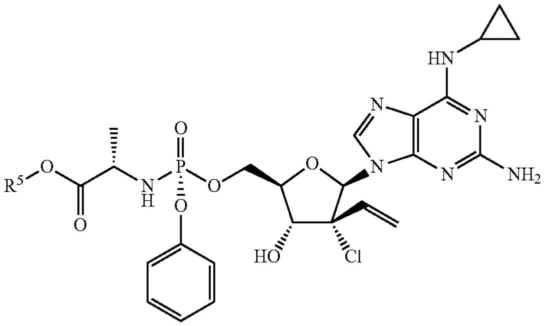
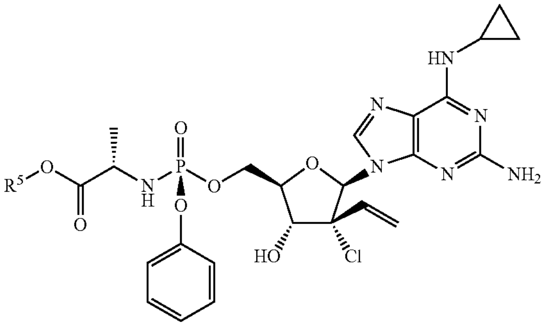

In some embodiments, the compound of Formula III to disrupt NiRAN function in a coronavirus or to treat or prevent a mutant or resistant form of the SARS-CoV-2 is a compound of Formula IIIk:

Formula IIIk

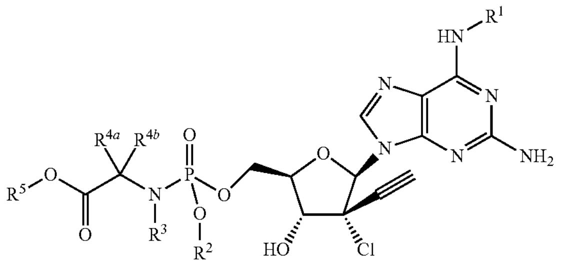

or a pharmaceutically acceptable salt thereof.

In some embodiments of Formula IIIk, $R^1$ is methyl.

In some embodiments of Formula IIIk, $R^1$ is cyclopropyl.

In some embodiments of Formula IIIk, $R^2$ is phenyl.

In some embodiments of Formula IIIk, $R^2$ is napthyl.

In some embodiments of Formula IIIk, $R^{4a}$ is hydrogen and $R^{4b}$ is methyl.

In some embodiments of Formula IIIk, $R^5$ is isopropyl.

In some embodiments of Formula IIIk, the compound is the $S_p$-isomer and the phosphoramidate is in the L-configuration.

In some embodiments of Formula IIIk, the compound is the $R_p$-isomer and the phosphoramidate is in the L-configuration.

In some embodiments of Formula IIIk, the pharmaceutically acceptable salt is the hemi-sulfate salt.

Non-limiting examples of a compound of Formula IIIk include:

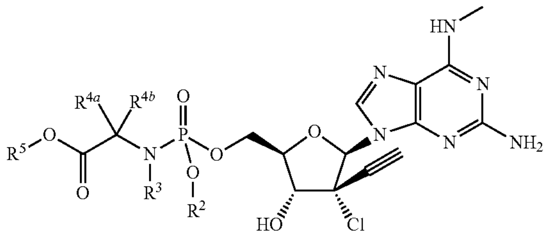

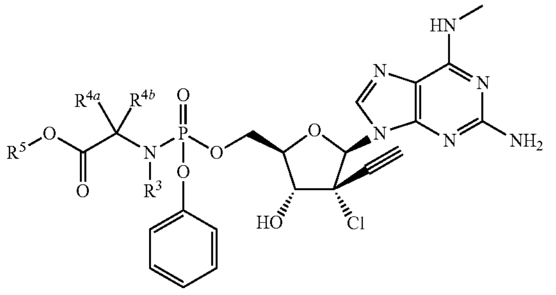

-continued

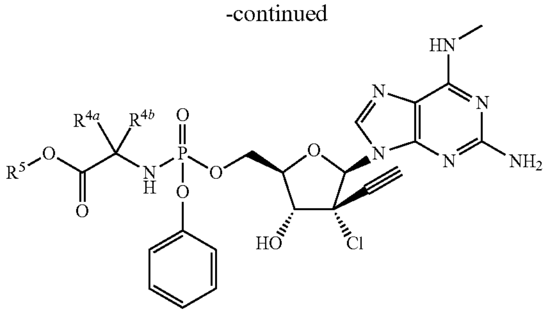

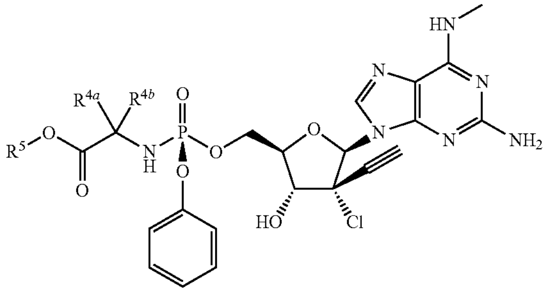

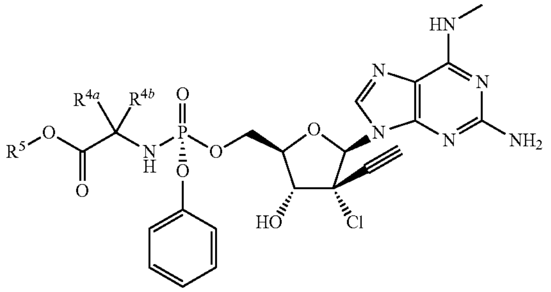

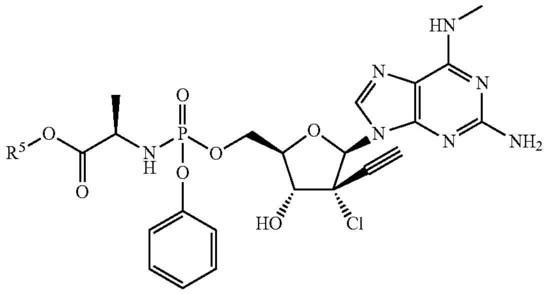

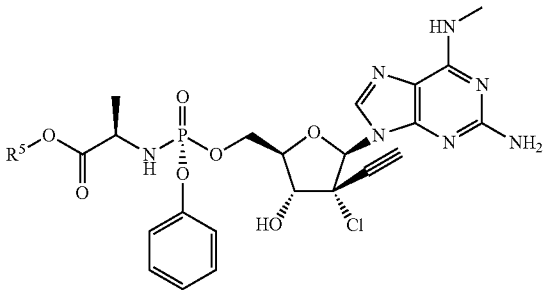

-continued
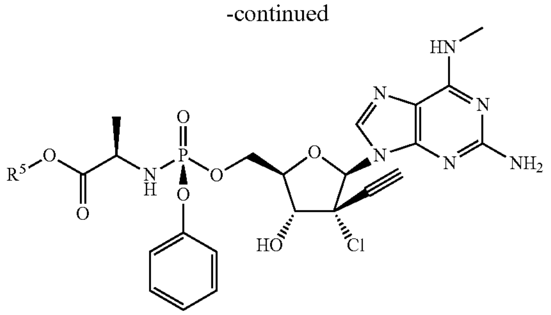
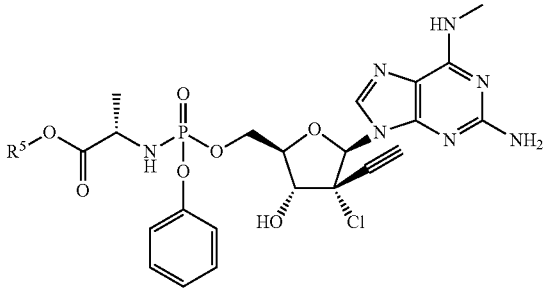
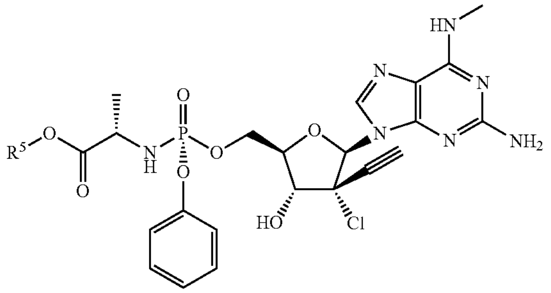
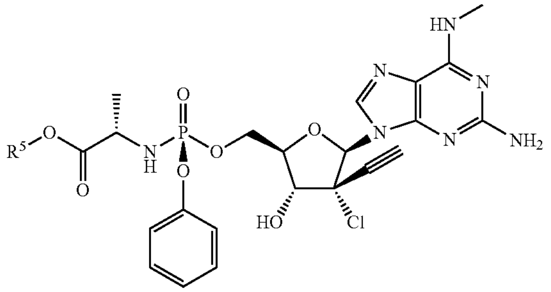
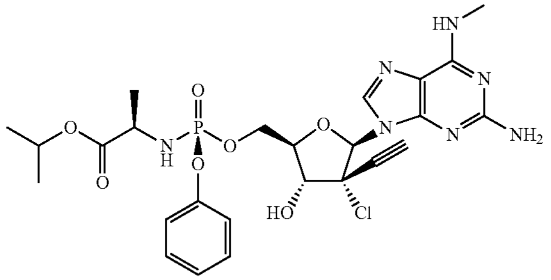
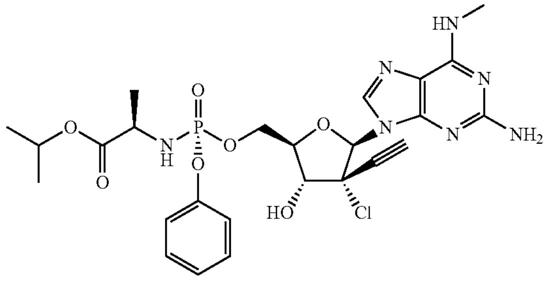
-continued
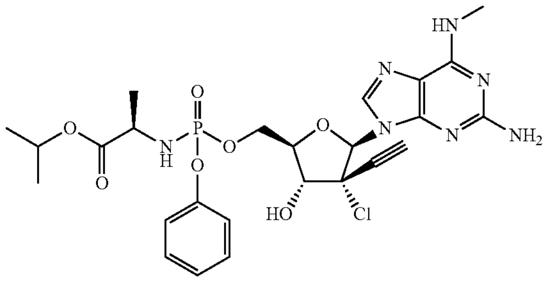
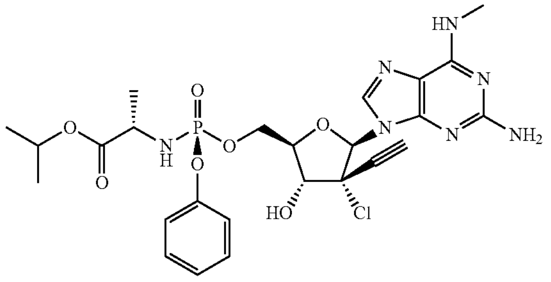
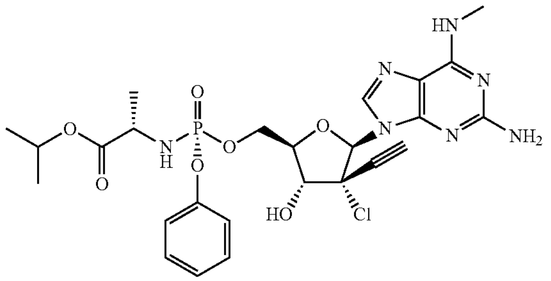
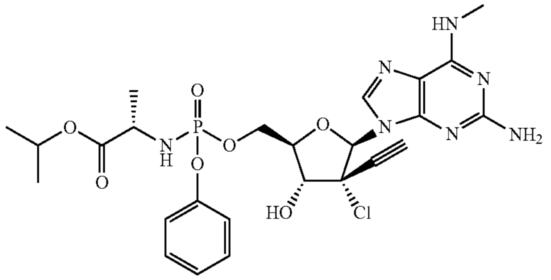
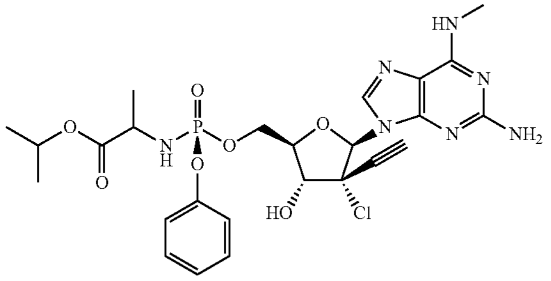
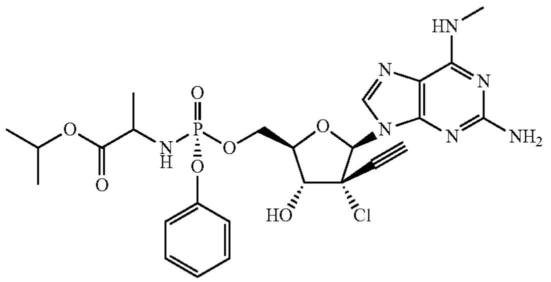

-continued
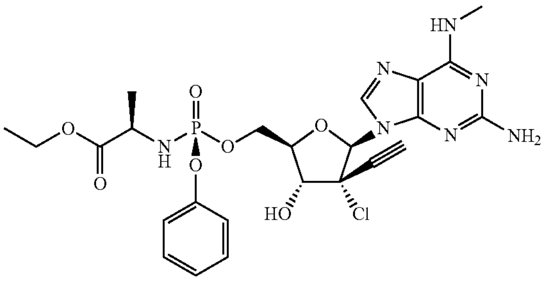
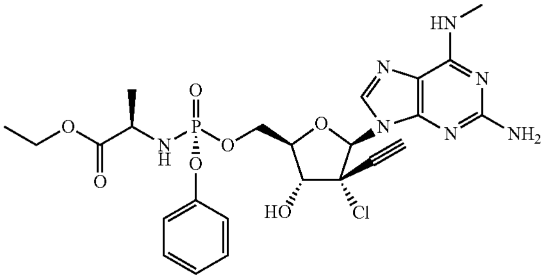
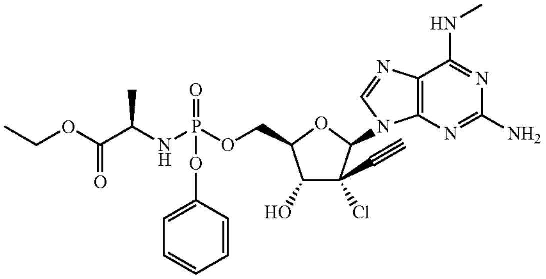
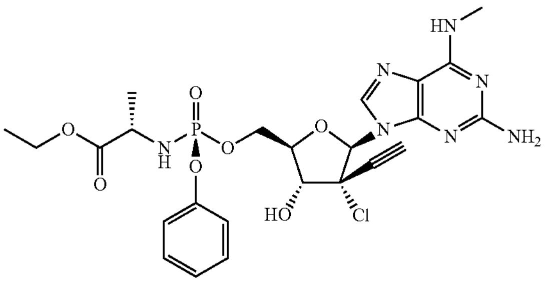
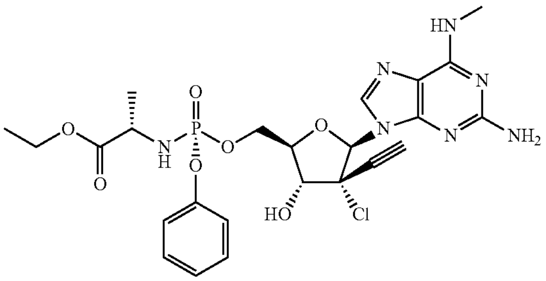
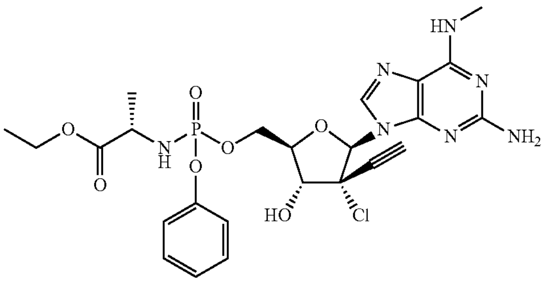
-continued
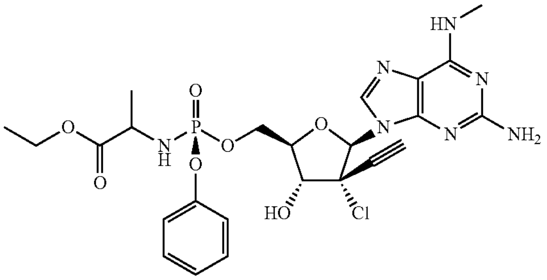
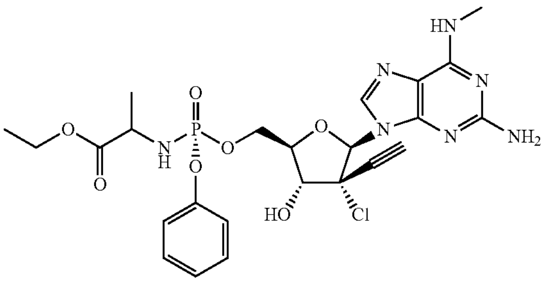
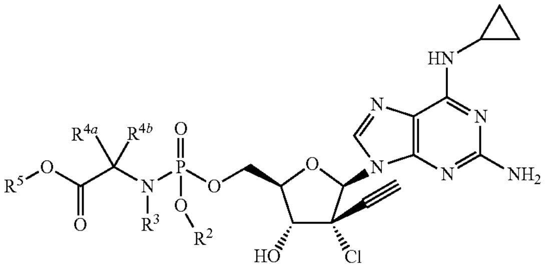
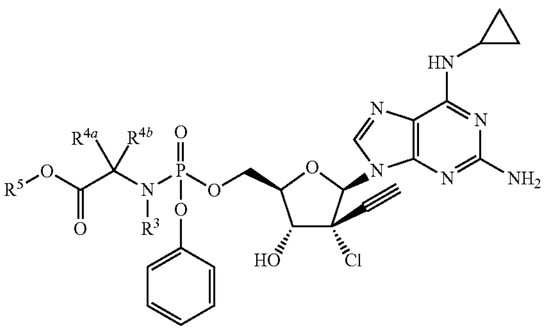
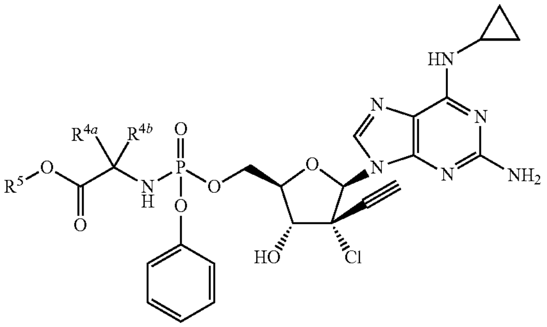

-continued

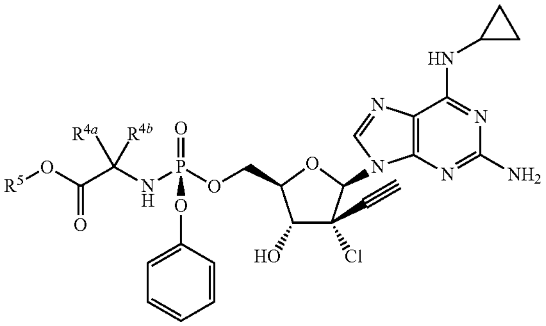

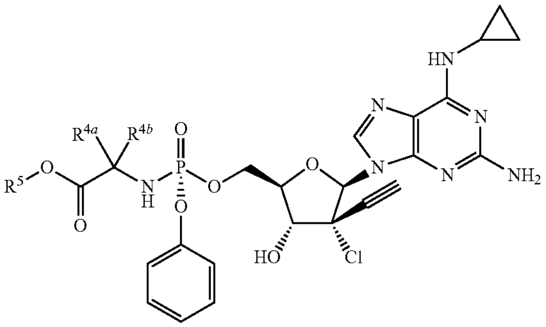

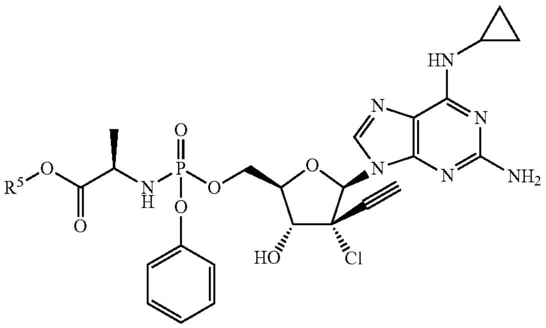

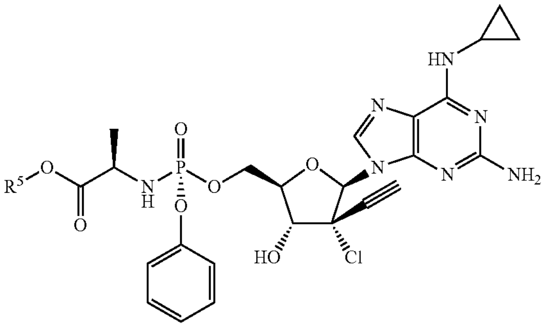

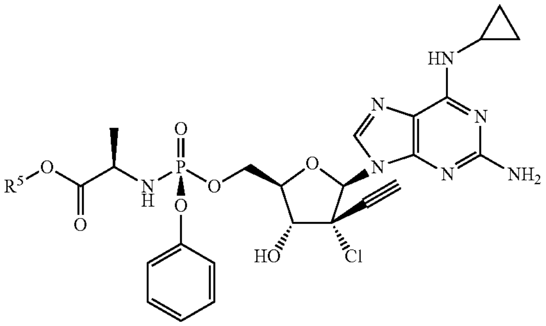

-continued

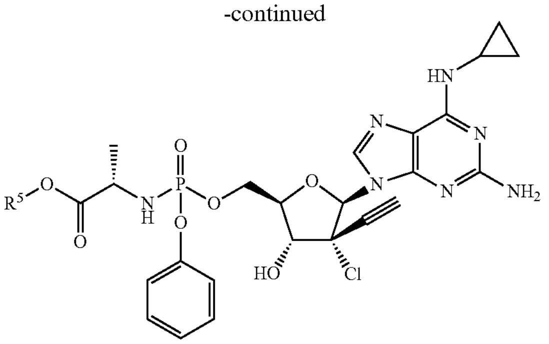

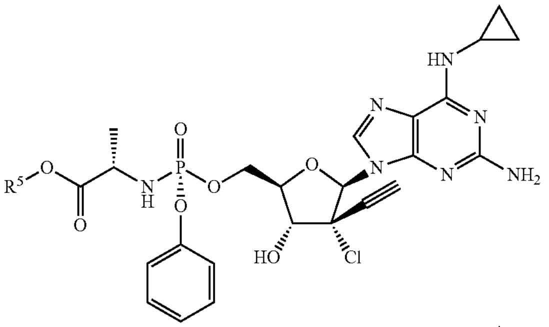

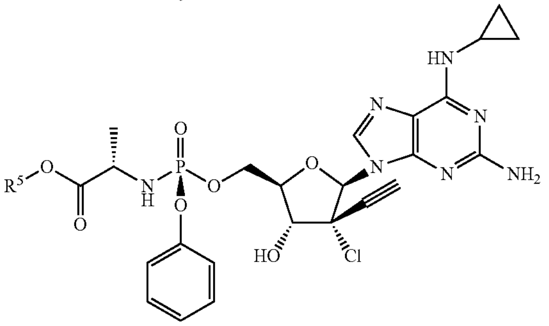

In some embodiments, the compound of Formula III to disrupt NiRAN function in a coronavirus or to treat or prevent a mutant or resistant form of the SARS-CoV-2 virus is a compound of Formula IIII:

Formula IIII

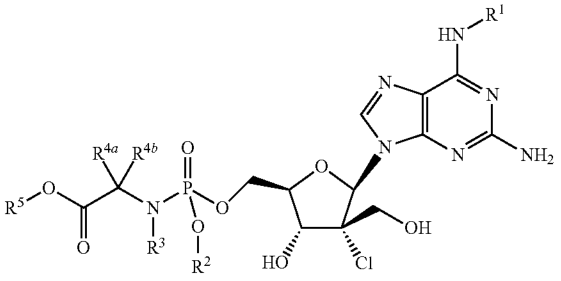

or a pharmaceutically acceptable salt thereof.

In some embodiments of Formula IIII, $R^1$ is methyl.

In some embodiments of Formula IIII, $R^1$ is cyclopropyl.

In some embodiments of Formula IIII, $R^1$ is phenyl.

In some embodiments of Formula IIII, $R^1$ is napthyl.

In some embodiments of Formula IIII, $R^{4a}$ is hydrogen and $R^{4b}$ is methyl.

In some embodiments of Formula IIII, $R^5$ is isopropyl.

In some embodiments of Formula IIIl, the compound is the $S_p$-isomer and the phosphoramidate is in the L-configuration.

In some embodiments of Formula IIIl, the compound is the $R_p$-isomer and the phosphoramidate is in the L-configuration.

In some embodiments of Formula IIIl, the pharmaceutically acceptable salt is the hemi-sulfate salt.

Non-limiting examples of a compound of Formula IIIl include:

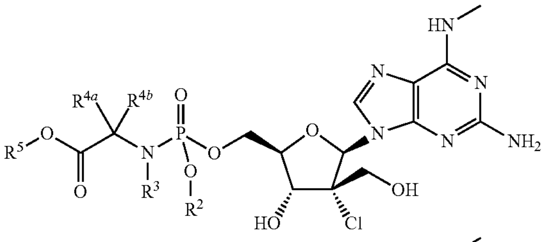

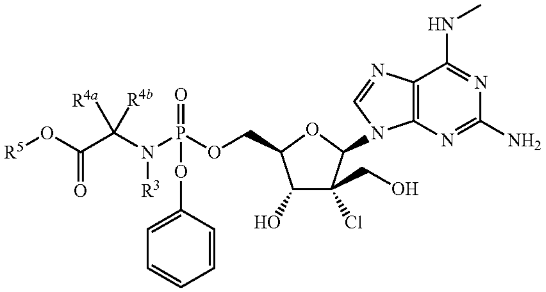

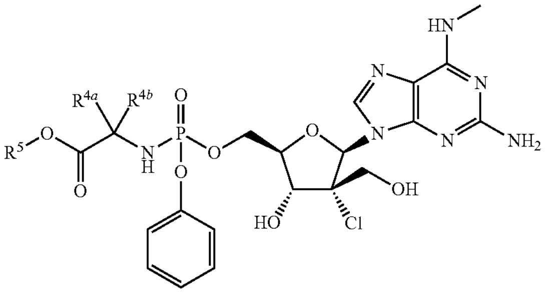

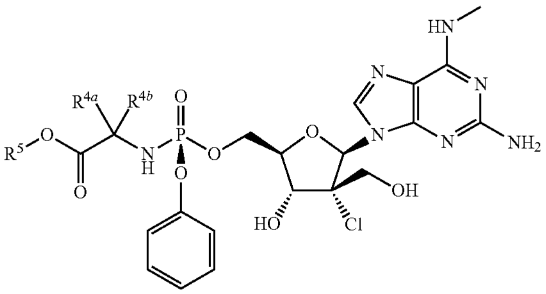

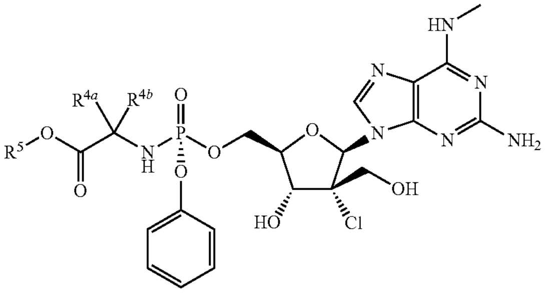

-continued

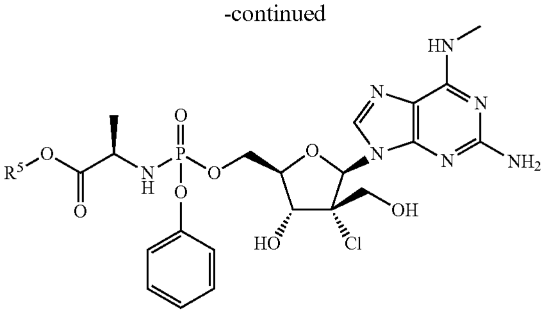

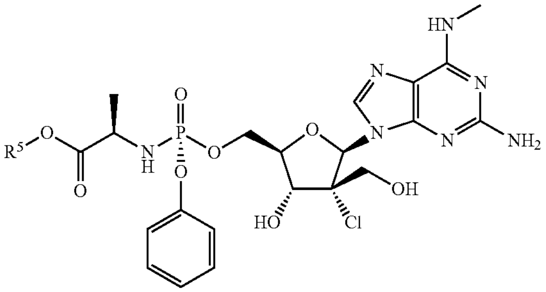

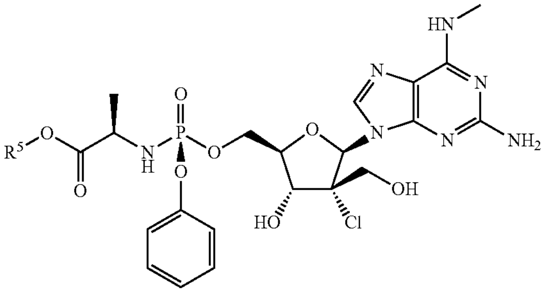

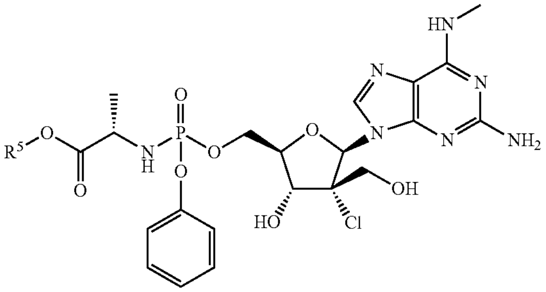

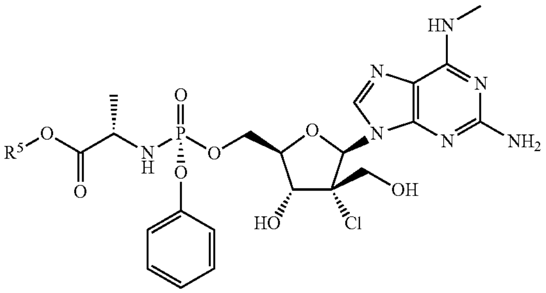

-continued
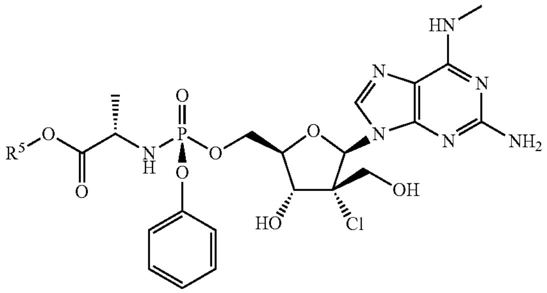
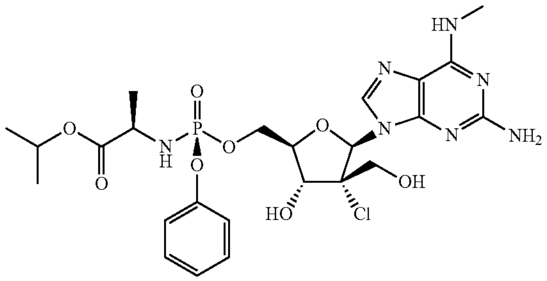
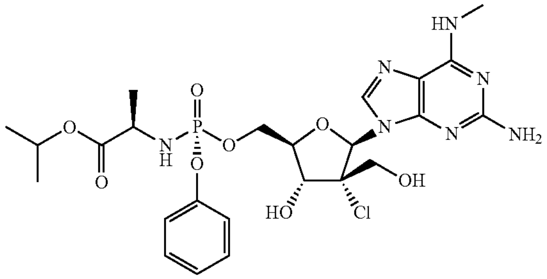
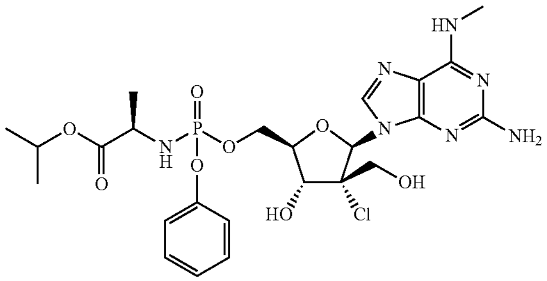
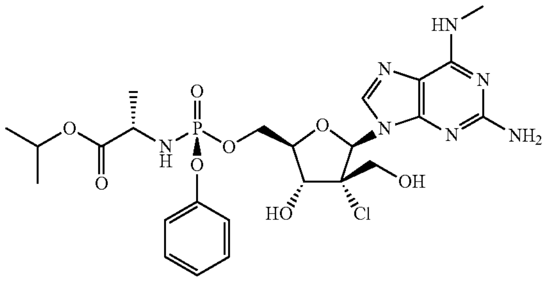
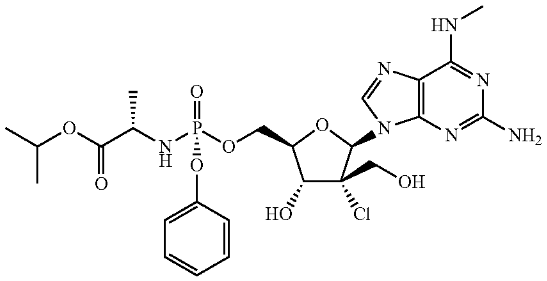
-continued
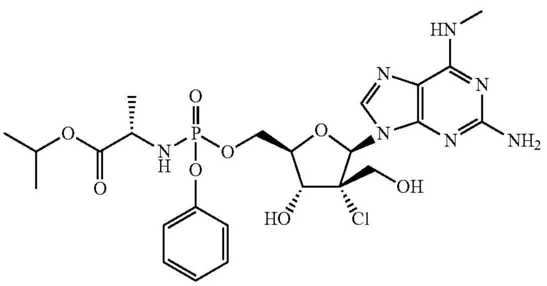
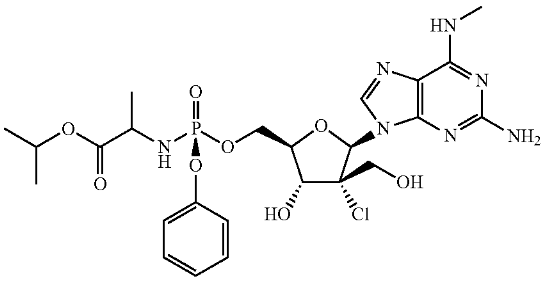
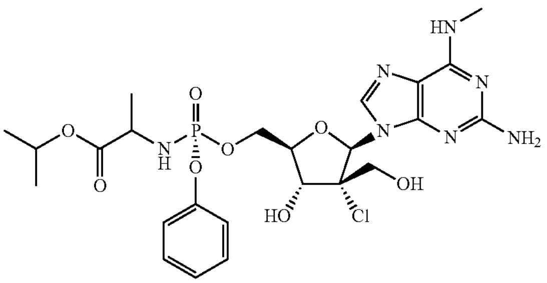
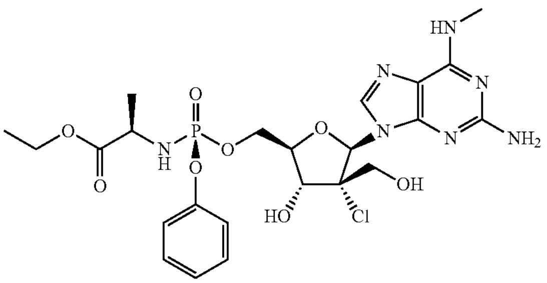
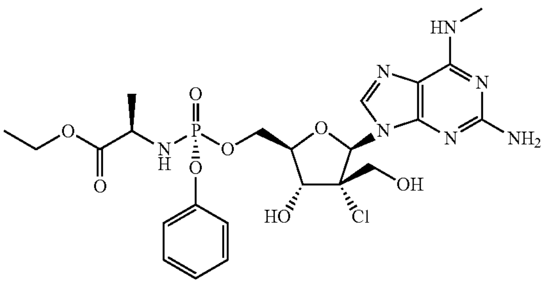
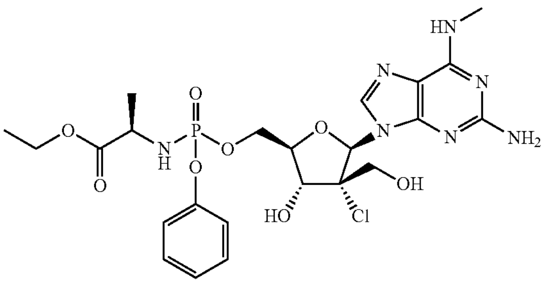

-continued
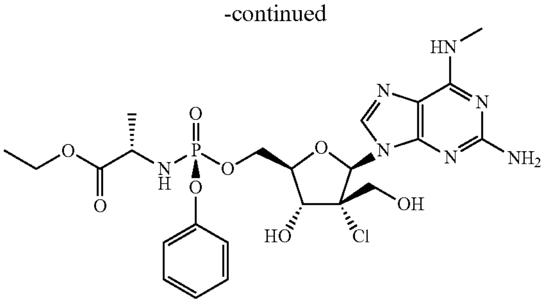
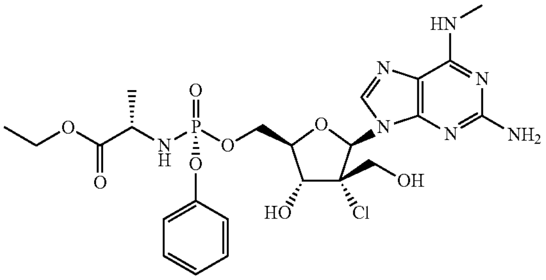
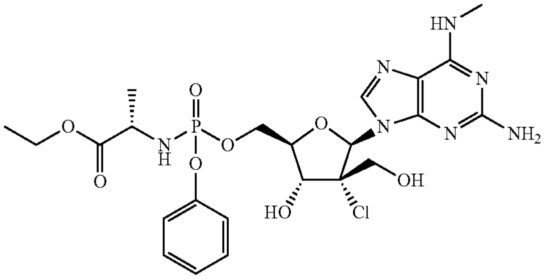
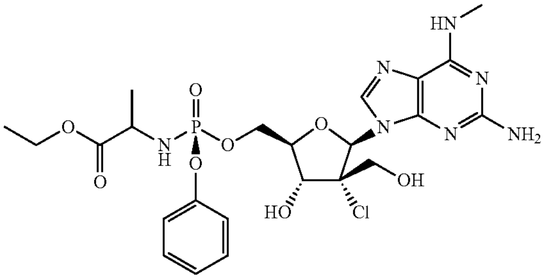
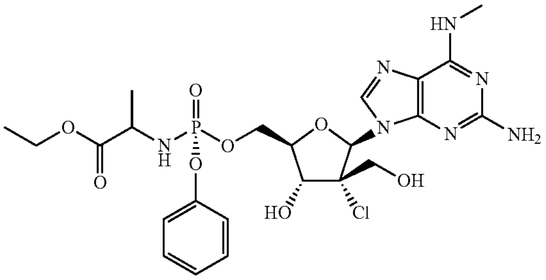
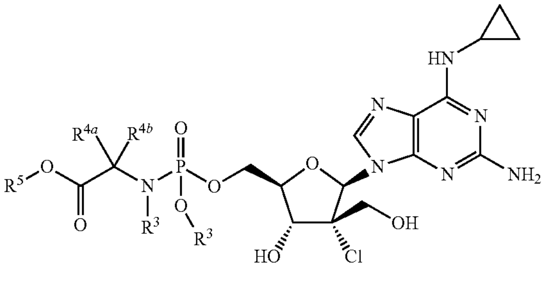
-continued
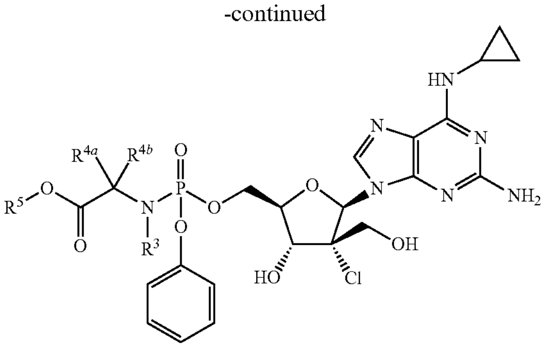
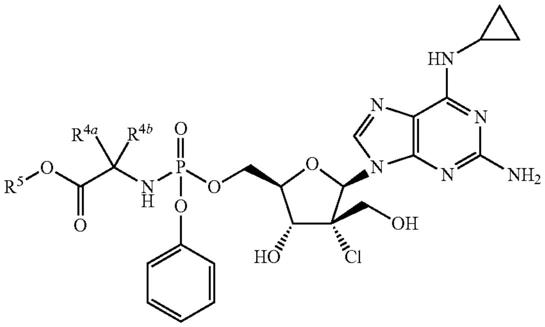
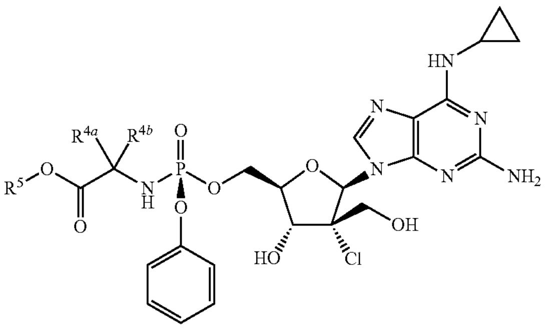
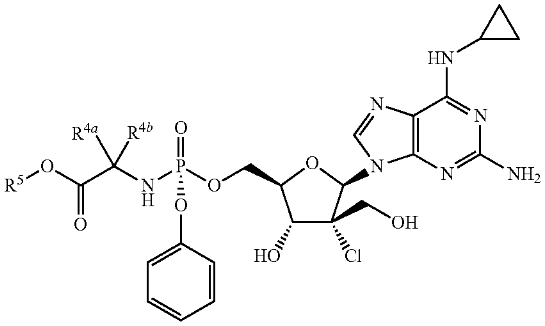
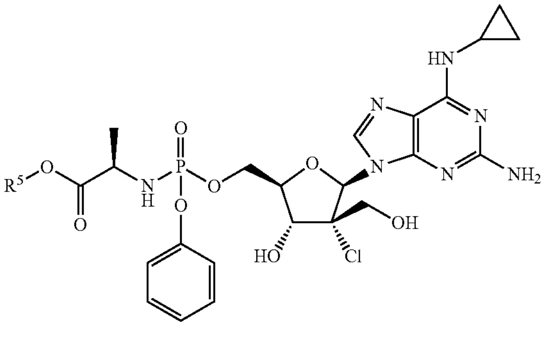

-continued

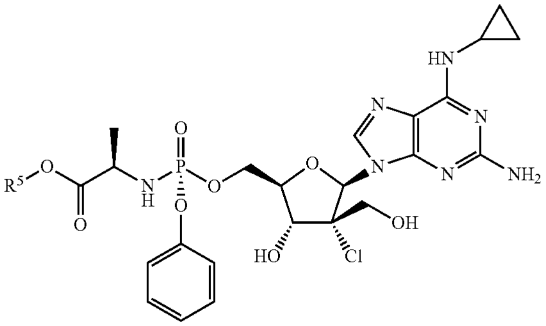

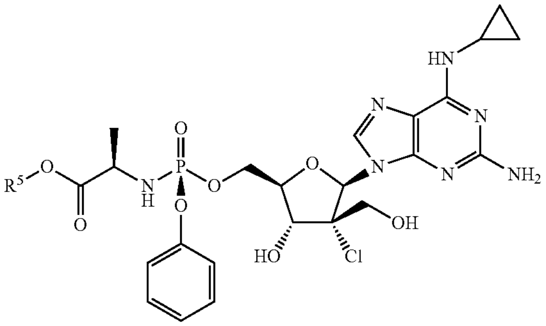

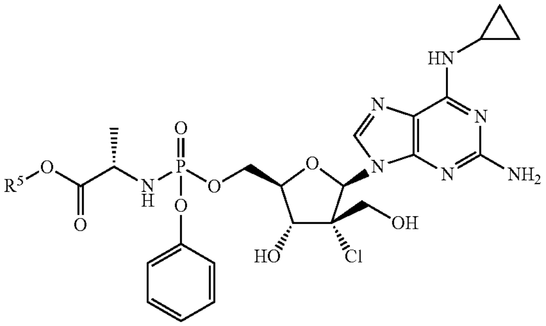

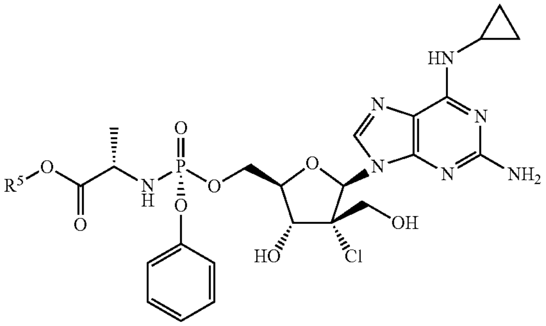

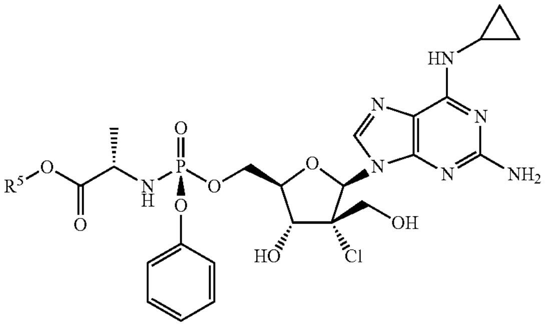

In some embodiments, the compound of Formula III to disrupt NiRAN function in a coronavirus or to treat or prevent a mutant or resistant form of the SARS-CoV-2 virus is a compound of Formula IIIm, Formula IIIn, Formula IIIo, or Formula IIIp:

Formula IIIm

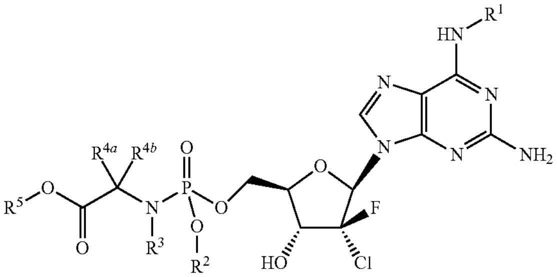

Formula IIIn

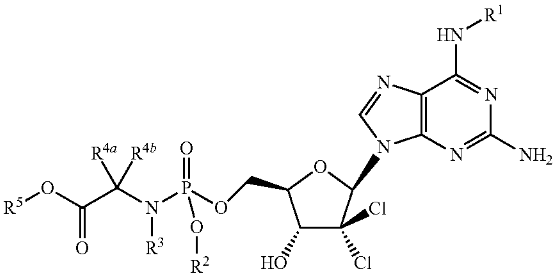

Formula IIIo

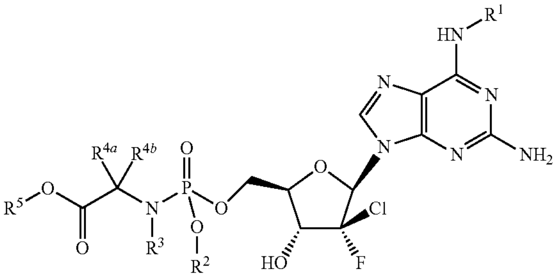

Formula IIIp

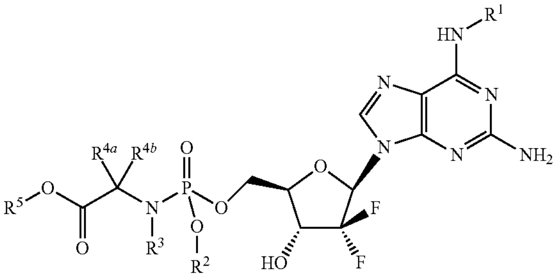

or a pharmaceutically acceptable salt thereof.

In some embodiments of Formula IIIm, Formula IIIn, Formula IIIo, or Formula IIIp, $R^1$ is methyl.

In some embodiments of Formula IIIm, Formula IIIn, Formula IIIo, or Formula IIIp, $R^1$ is cyclopropyl.

In some embodiments of Formula IIIm, Formula IIIn, Formula IIIo, or Formula IIIp, $R^2$ is phenyl.

In some embodiments of Formula IIIm, Formula IIIn, Formula IIIo, or Formula IIIp, $R^2$ is napthyl.

In some embodiments of Formula IIIm, Formula IIIn, Formula IIIo, or Formula IIIp, $R^{4a}$ is hydrogen and $R^{4b}$ is methyl.

In some embodiments of Formula IIIm, Formula IIIn, Formula IIIo, or Formula IIIp, $R^5$ is isopropyl.

In some embodiments of Formula IIIm, Formula IIIn, Formula IIIo, or Formula IIIp, the compound is the $S_p$-isomer and the phosphoramidate is in the L-configuration.

In some embodiments of Formula IIIm, Formula IIIn, Formula IIIo, or Formula IIIp, the compound is the $R_p$-isomer and the phosphoramidate is in the L-configuration.

In some embodiments of Formula IIIm, Formula IIIn, Formula IIIo, or Formula IIIp, the pharmaceutically acceptable salt is the hemi-sulfate salt.

In some embodiments of Formula IIIp, X is F, Y is F, $R^1$ is methyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IIIp, X is F, Y is F, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IIIp, X is F, Y is F, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IIIp, X is F, Y is F, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IIIo, X is $C_1$, Y is F, $R^1$ is methyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IIIo, X is $C_1$, Y is F, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IIIo, X is $C_1$, Y is F, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IIIo, X is $C_1$, Y is F, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IIIn, X is $C_1$, Y is $C_1$, $R^1$ is methyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IIIn, X is $C_1$, Y is $C_1$, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IIIn, X is $C_1$, Y is $C_1$, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IIIn, X is $C_1$, Y is $C_1$, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IIIm, X is F, Y is $C_1$, $R^1$ is methyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IIIm, X is F, Y is $C_1$, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IIIm, X is F, Y is $C_1$, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IIIm, X is F, Y is $C_1$, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

Non-limiting examples of a compound of Formula IIIm, Formula IIIn, Formula IIIo, or Formula IIIp include

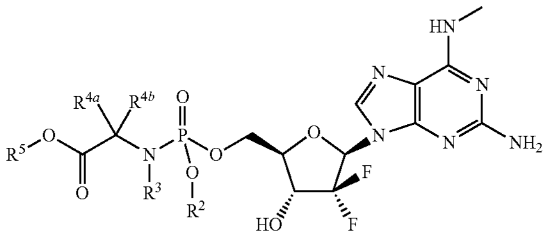

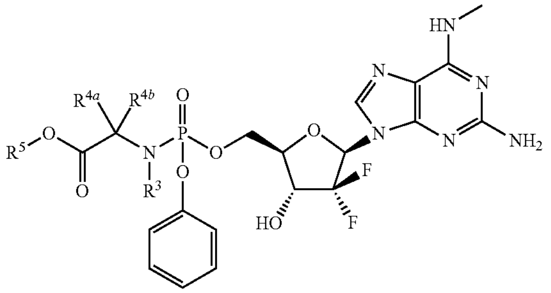

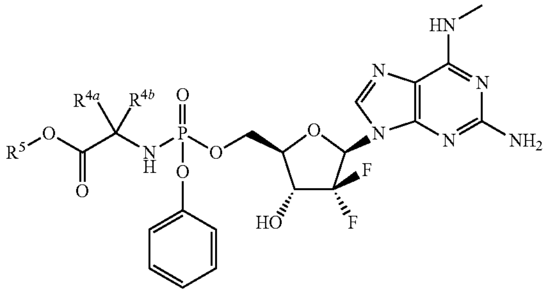

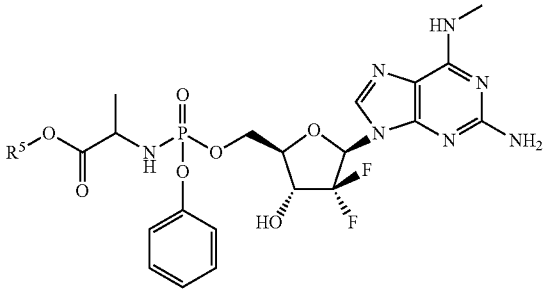

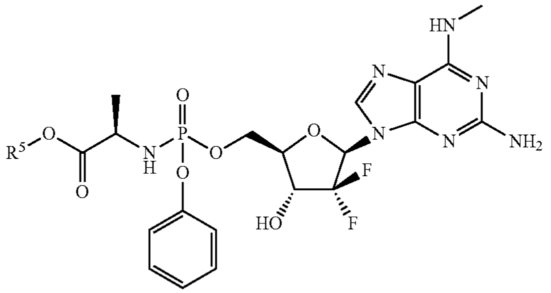

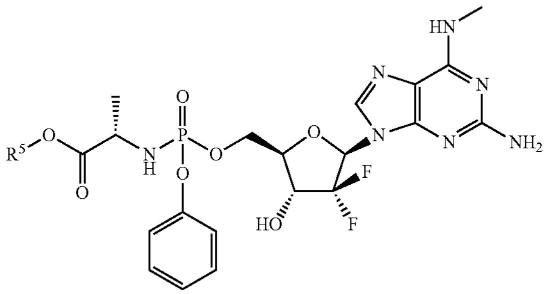

-continued
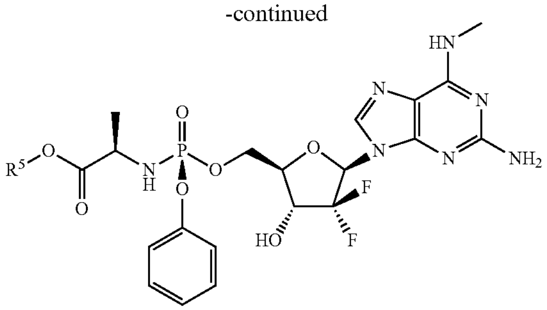
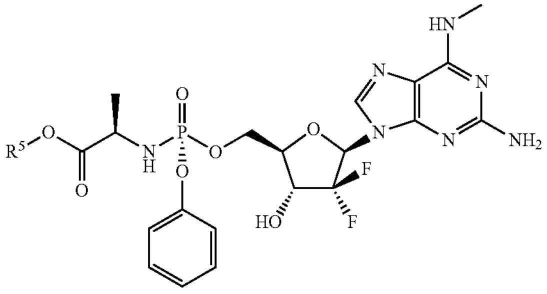
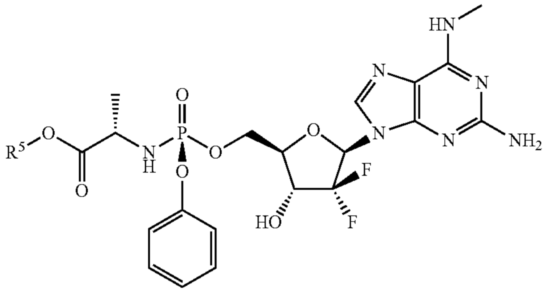
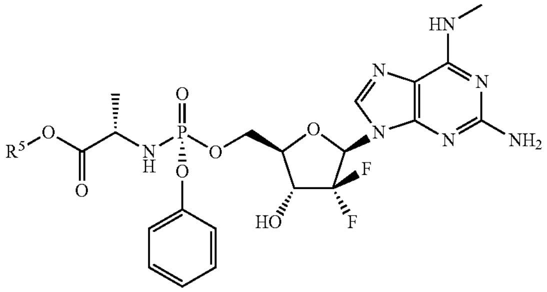
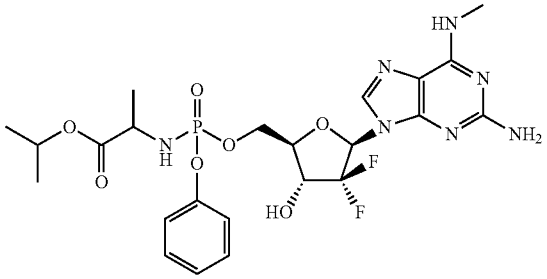
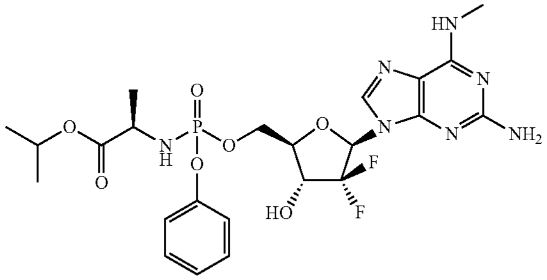
-continued
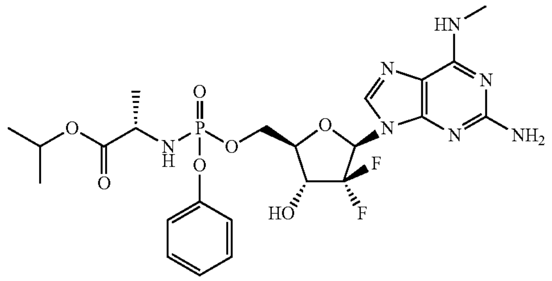
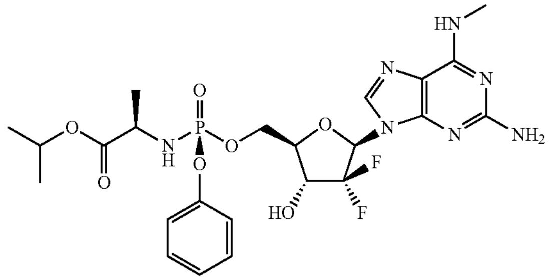
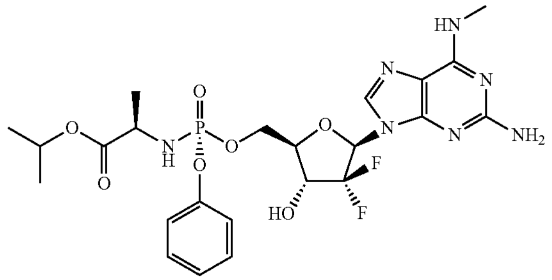
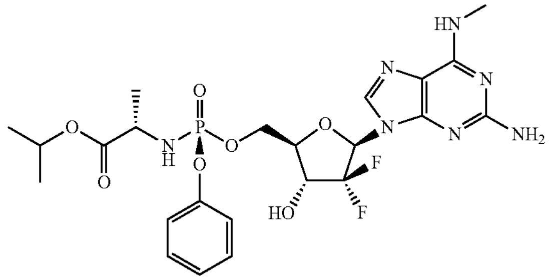
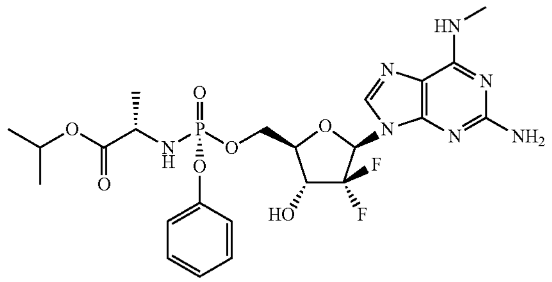
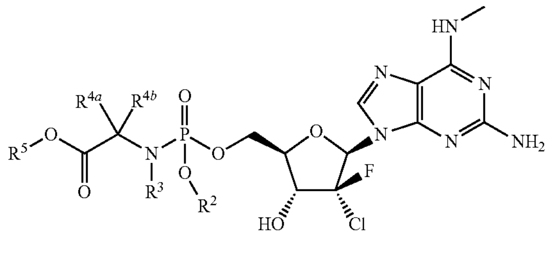

-continued
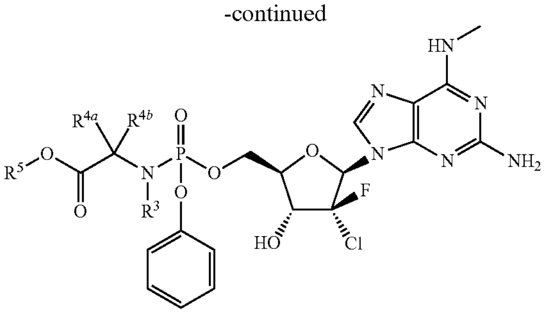
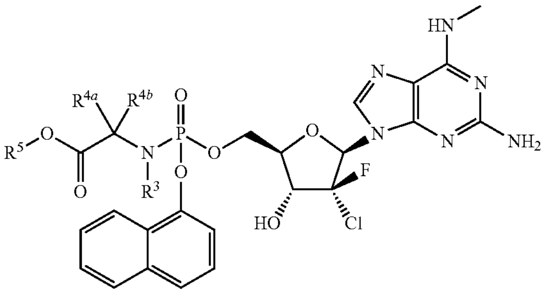
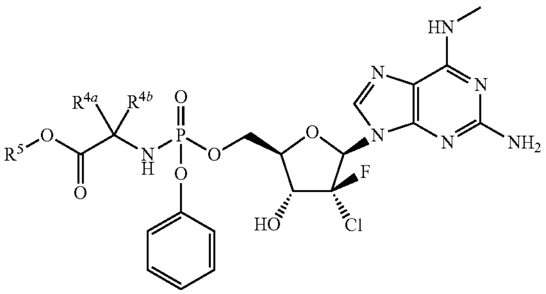
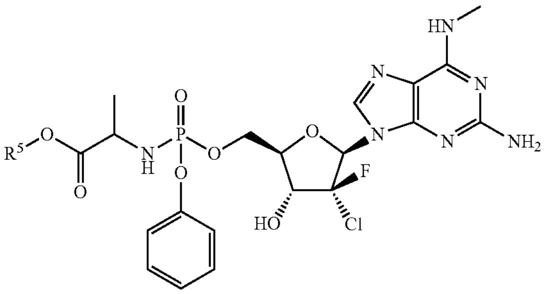
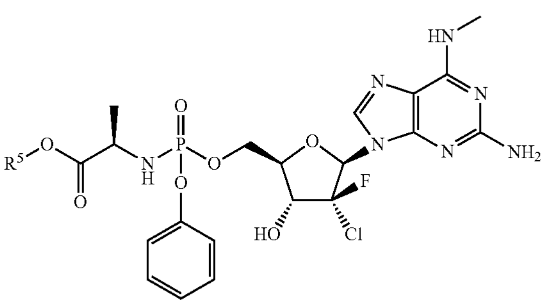
-continued
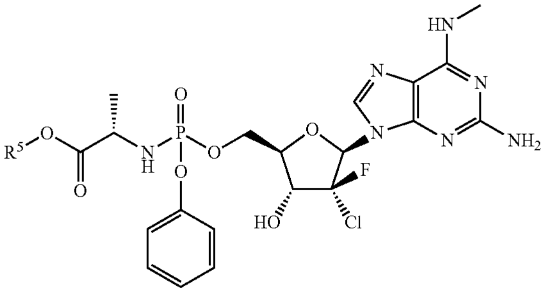
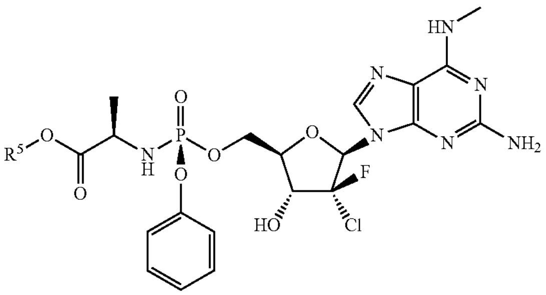
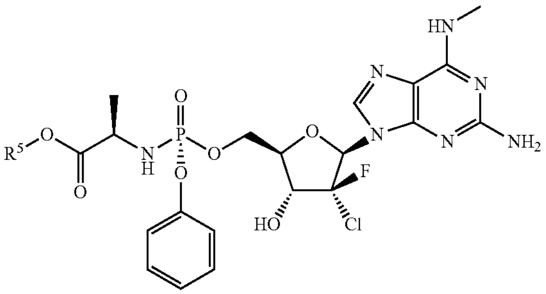
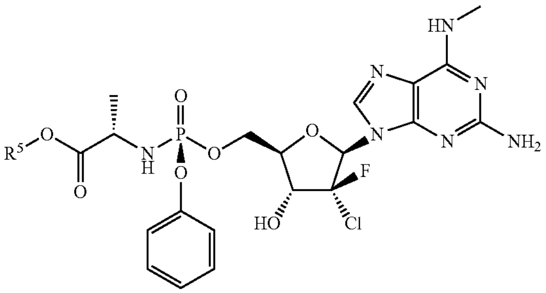
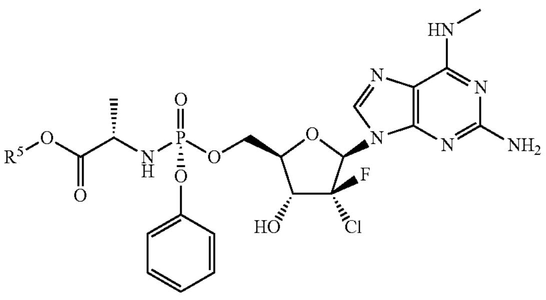

-continued
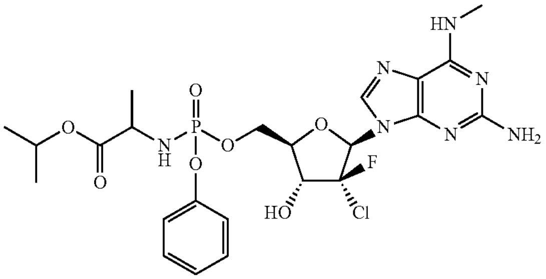
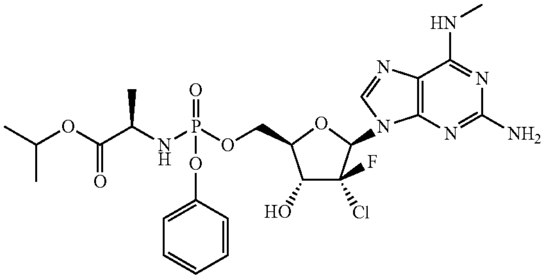
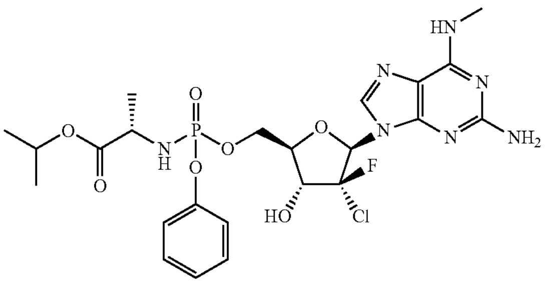
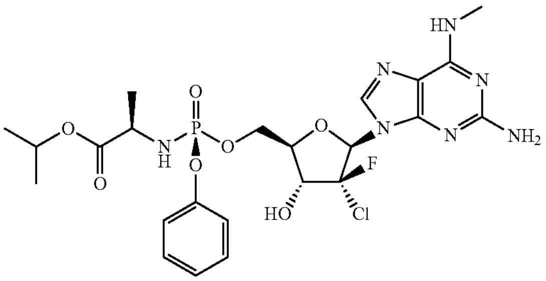
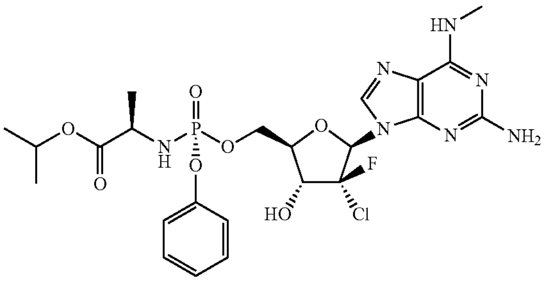
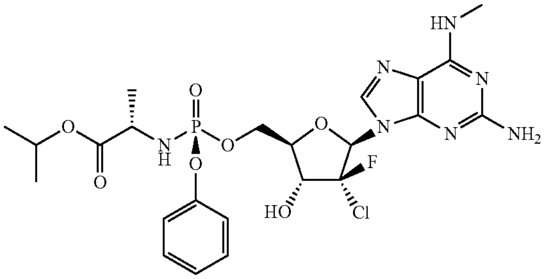
-continued
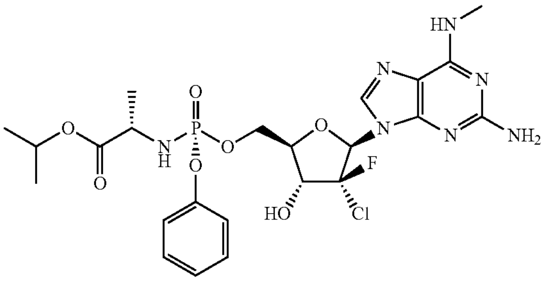
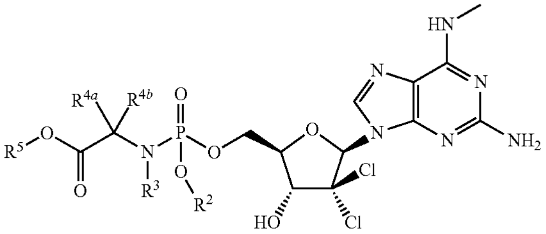
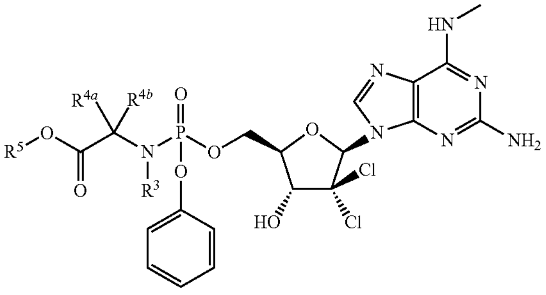
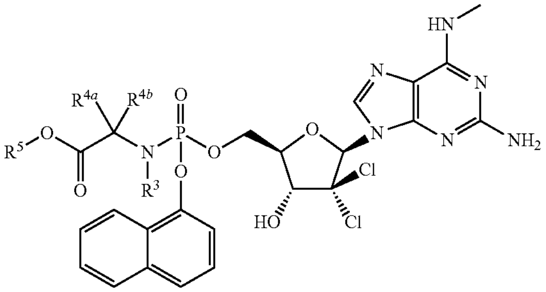
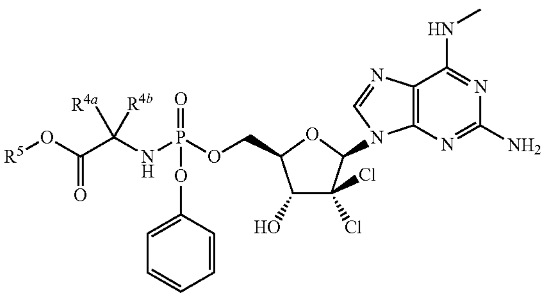
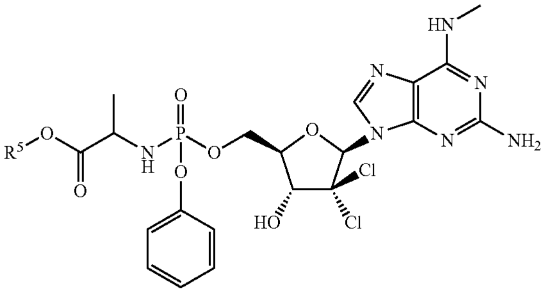

-continued
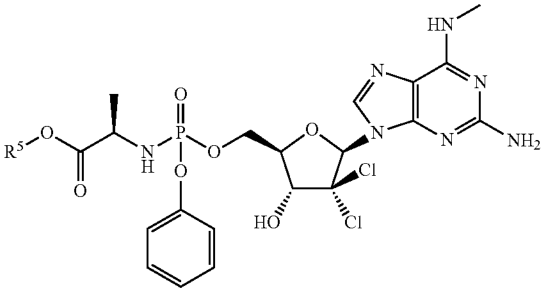
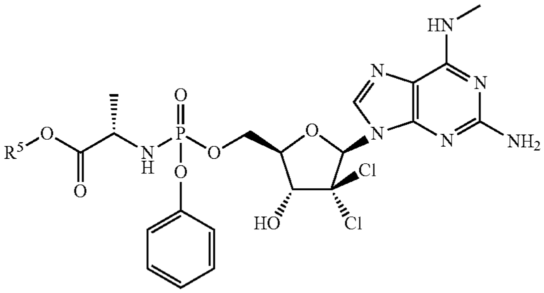
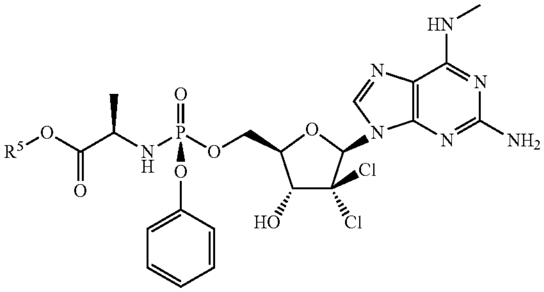
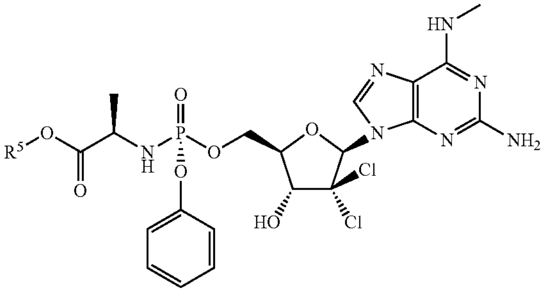
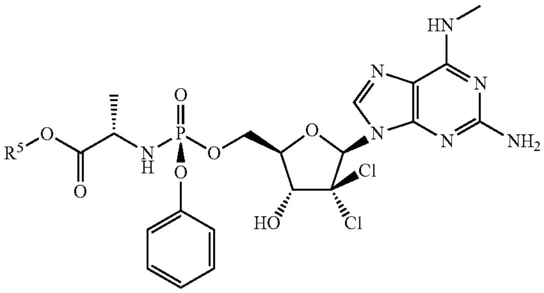
-continued
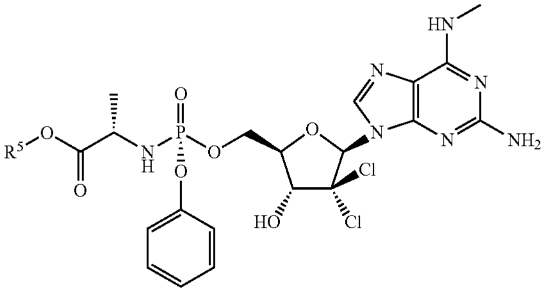
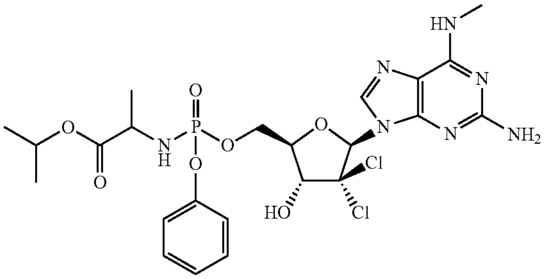
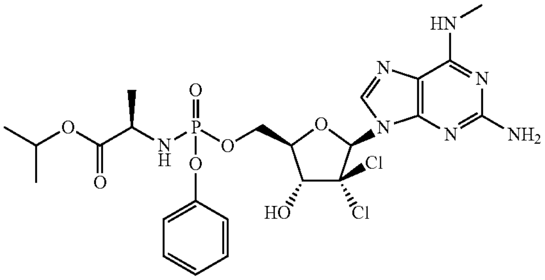
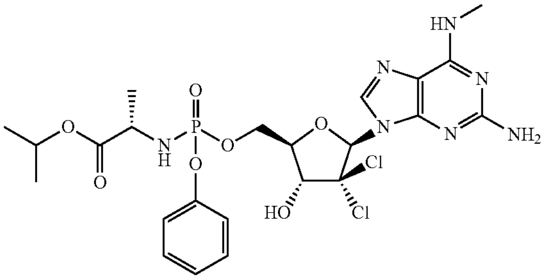
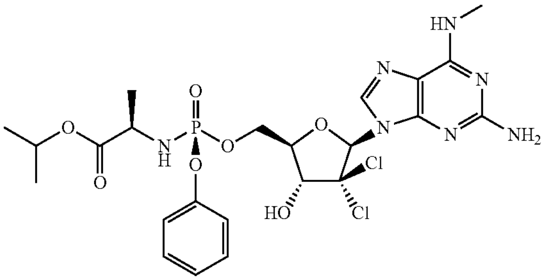
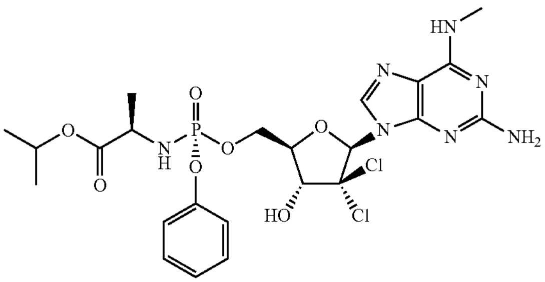

-continued
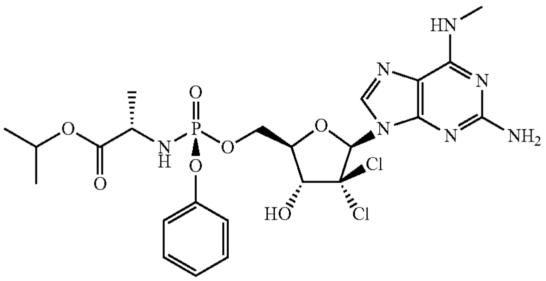
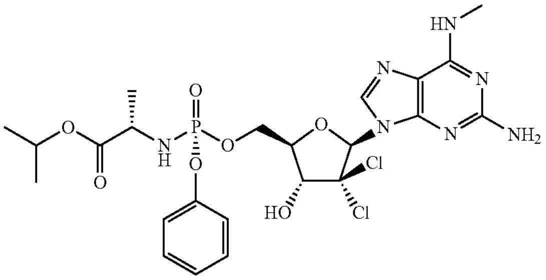
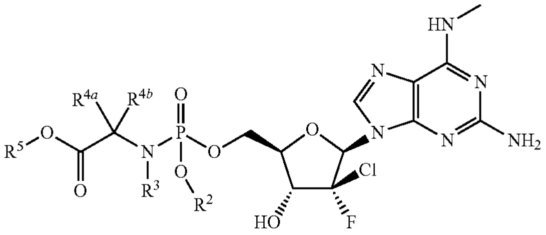
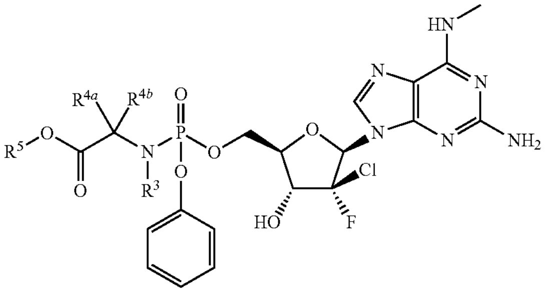
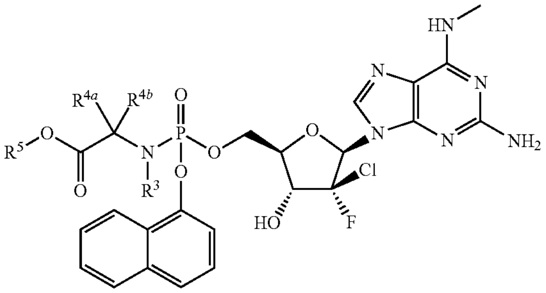
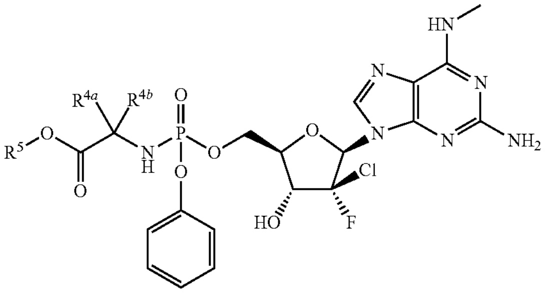
-continued
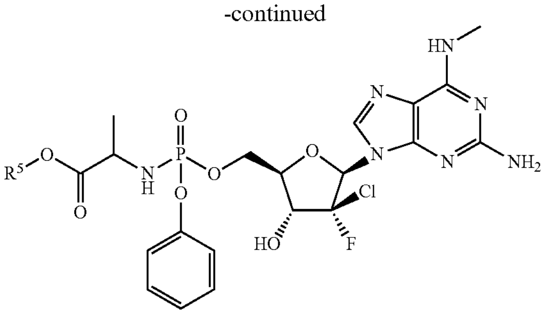
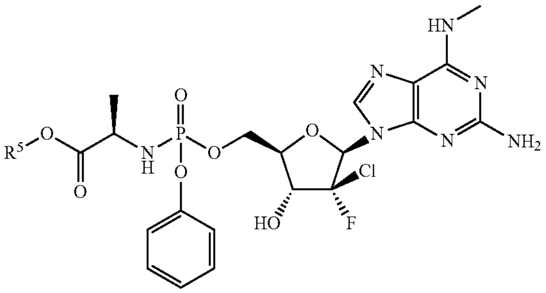
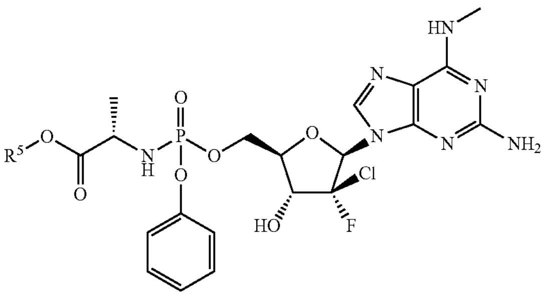
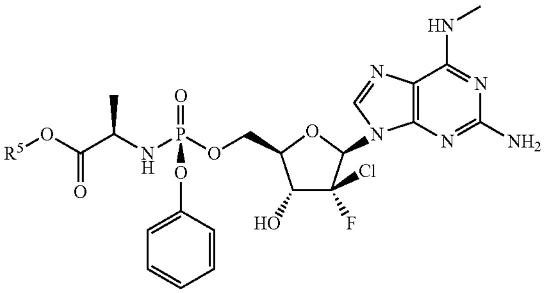
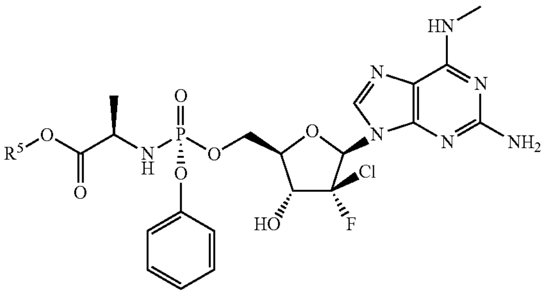

-continued

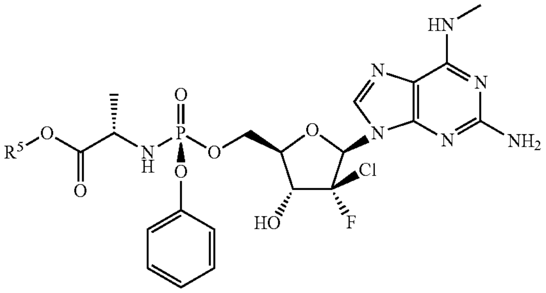

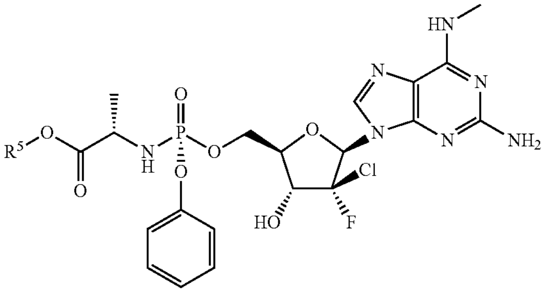

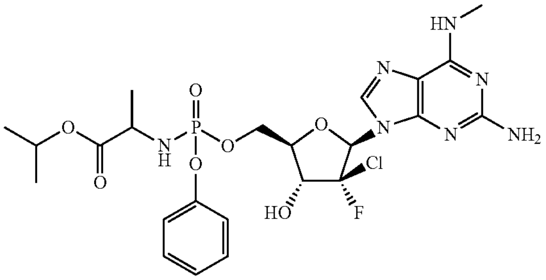

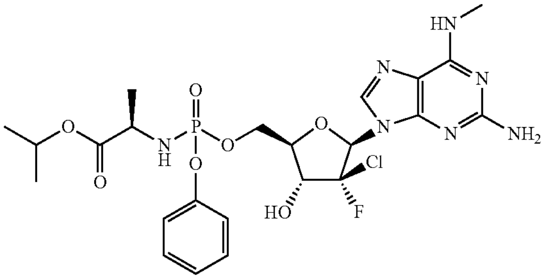

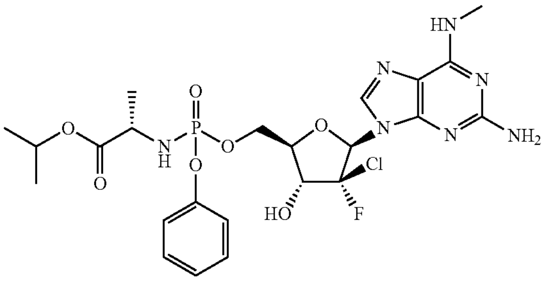

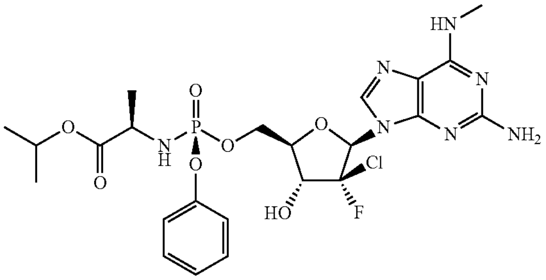

-continued

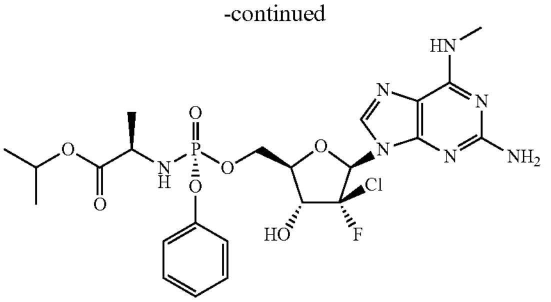

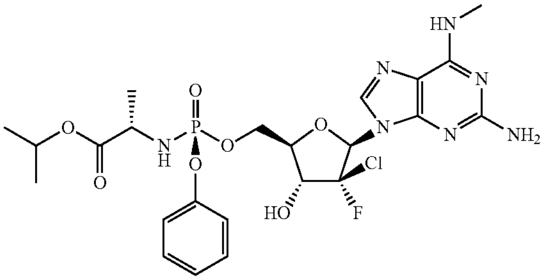

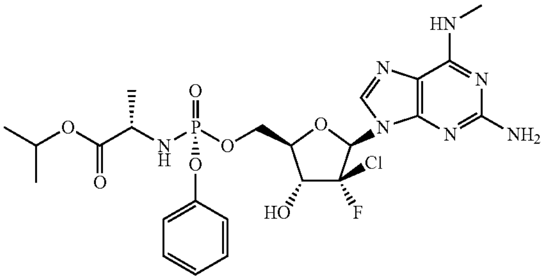

The present invention also includes the use of a compound of Formula IV to disrupt NiRAN function in a coronavirus or to treat or prevent a mutant or resistant form of SARS-CoV-2 in a host in need thereof as described herein:

Formula IV

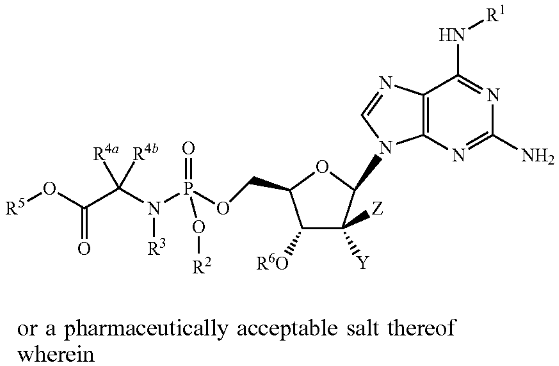

or a pharmaceutically acceptable salt thereof wherein $R^6$ is selected from hydrogen, —C(O)$R^{6A}$, —C(O)O$R^{6A}$, $C_{1-6}$alkyl, —$CH_2$—O—$R^{6A}$;

$R^{6A}$ is selected from hydrogen, $C_{1-6}$alkyl, $C_1$-$C_6$haloalkyl (for example, —$CHCl_2$, —$CCl_3$, —$CH_2Cl$, —$CF_3$, —$CHF_2$, —$CH_2F$), aryl, aryl($C_{1-6}$alkyl)- wherein the aryl group is optionally substituted with a substituent selected from alkoxy, hydroxy, nitro, bromo, chloro, fluoro, azido, and haloalkyl;

$R^7$ is $NH_2$, H, or —$NR^8R^9$;

$R^8$ and $R^9$ are independently selected from hydrogen, $C_{1-6}$alkyl, —C(O)$R^{6A}$, and —C(O)O$R^{6A}$;

Y is selected from F and Cl;

Z is selected from methyl, $C_1$-$C_3$haloalkyl (including $C_{1-3}$fluoroalkyl and $C_{1-3}$chloroalkyl, such as $CH_2F$, $CHF_2$, $CF_3$, $CH_2CF_3$, $CH_2CHF_2$, $CH_2CH_2F$, $CF_2CH_3$, $CF_2CF_3$, and $CH_2C_1$), $C_2$-$C_4$alkenyl, $C_2$-$C_4$alkynyl, $C_1$-$C_3$hydroxyalkyl, and halogen (including Cl and F), or in an alternative embodiment, Z is $C_{1-6}$alkyl; and $R^1$, $R^2$, $R^3$, $R^{4a}$, $R^{4b}$, and $R^5$ are as defined herein.

Non-limiting examples of $R^6$ include

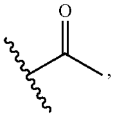, 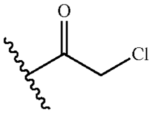, 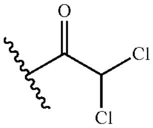,

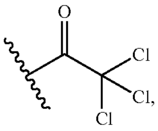 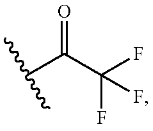 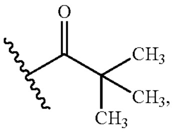

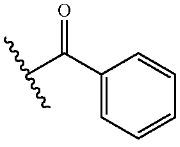, 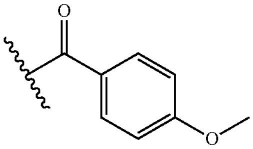,

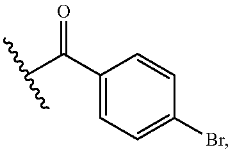 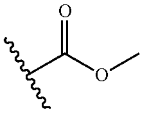,

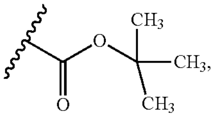 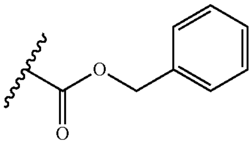,

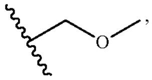, 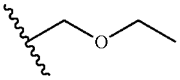,

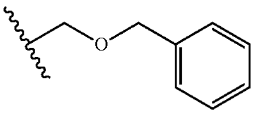, 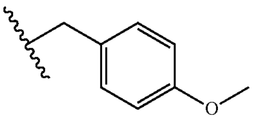

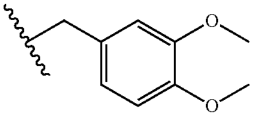 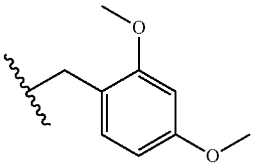

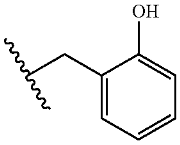 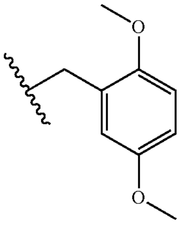

-continued

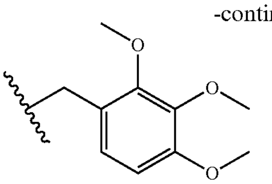 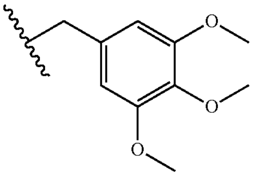

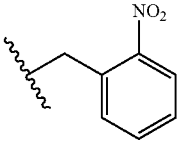 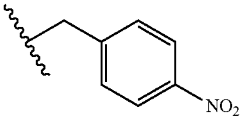

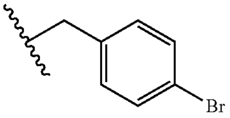 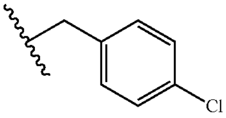

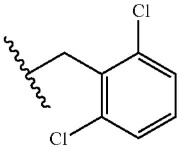 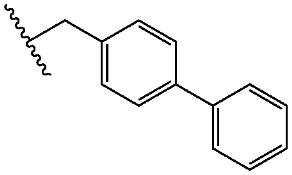

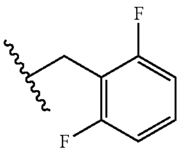 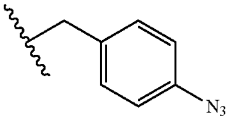

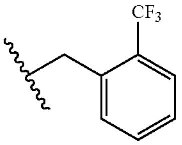 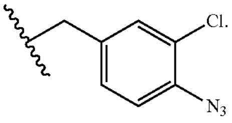

In some embodiments of Formula IV, Z is $CH_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $CH_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $CH_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $CH_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is $CH_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $CH_3$, Y is F, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CH_3$, Y is F, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $CH_3$, Y is F, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CF_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $CF_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $CF_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $CF_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is $CF_3$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $CF_3$, Y is F, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CF_3$, Y is F, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $CF_3$, Y is F, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $C_1$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $C_1$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $C_1$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $C_1$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is $C_1$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $C_1$, Y is F, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $C_1$, Y is F, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $C_1$, Y is F, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CH_2F$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $CH_2F$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $CH_2F$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $CH_2F$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is $CH_2F$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $CH_2F$, Y is F, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CH_2F$, Y is F, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $CH_2F$, Y is F, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CHCH_2$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $CH_2CH_2$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $CH_2CH_2$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $CH_2CH_2$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is $CH_2CH_2$, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $CHCH_2$, Y is F, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CHCH_2$, Y is F, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $CHCH_2$, Y is F, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is CCH, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is CCH, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is CCH, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is CCH, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is CCH, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is CCH, Y is F, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is CCH, Y is F, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is CCH, Y is F, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is F, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is F, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is F, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is F, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is F, Y is F, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is F, Y is F, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is F, Y is F, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is F, Y is F, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CH_3$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $CH_3$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $CH_3$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $CH_3$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is $CH_3$, Y is $C_1$, $R^1$ is methyl, $R^1$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $CH_3$, Y is $C_1$, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CH_3$, Y is $C_1$, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $CH_3$, Y is $C_1$, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CF_3$, Y is $C_1$, $R^1$ is methyl, $R^1$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $CF_3$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $CF_3$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $CF_3$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is $CF_3$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $CF_3$, Y is $C_1$, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CF_3$, Y is $C_1$, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $CF_3$, Y is $C_1$, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $C_1$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $C_1$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $C_1$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $C_1$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^1$ is $NHC(O)R^{6A}$.

In some embodiments of Formula IV, Z is $C_1$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $C_1$, Y is $C_1$, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $C_1$, Y is $C_1$, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $C_1$, Y is $C_1$, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CH_2F$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $CH_2F$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $CH_2F$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $CH_2F$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is $CH_2F$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $CH_2F$, Y is $C_1$, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CH_2F$, Y is $C_1$, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $CH_2F$, Y is $C_1$, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CHCH_2$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is $CH_2CH$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is $CH_2CH$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is $CH_2CH$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^1$ is $NHC(O)R^{6A}$.

In some embodiments of Formula IV, Z is $CH_2CH$, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is $CHCH_2$, Y is $C_1$, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is $CHCH_2$, Y is $C_1$, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is $CHCH_2$, Y is $C_1$, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is CCH, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NH_2$.

In some embodiments of Formula IV, Z is CCH, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is H.

In some embodiments of Formula IV, Z is CCH, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NR^8R^9$.

In some embodiments of Formula IV, Z is CCH, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)R^{6A}$.

In some embodiments of Formula IV, Z is CCH, Y is $C_1$, $R^1$ is methyl, $R^2$ is aryl, $R^3$ is hydrogen, $R^{4a}$ is hydrogen, $R^{4a}$ is $C_1$-$C_4$alkyl, $R^5$ is $C_1$-$C_6$alkyl, and $R^7$ is $NHC(O)OR^{6A}$.

In some embodiments of Formula IV, Z is CCH, Y is $C_1$, $R^1$ is methyl, $R^2$ is aryl, $R^3$ is hydrogen, $R^{4a}$ is hydrogen, $R^{4a}$ is methyl, and $R^5$ is $C_1$-$C_6$alkyl.

In some embodiments of Formula IV, Z is CCH, Y is $C_1$, $R^1$ is cyclopropyl, $R^2$ is aryl, $R^3$ is hydrogen, $R^{4a}$ is hydrogen, $R^{4a}$ is $C_1$-$C_4$alkyl, and $R^5$ is $C_1$-$C_6$alkyl.

In some embodiments of Formula IV, Z is CCH, Y is $C_1$, $R^1$ is cyclopropyl, $R^2$ is aryl, $R^3$ is hydrogen, $R^{4a}$ is hydrogen, $R^{4a}$ is methyl, and $R^5$ is $C_1$-$C_6$alkyl.

Non-limiting examples of a compound of Formula IV include

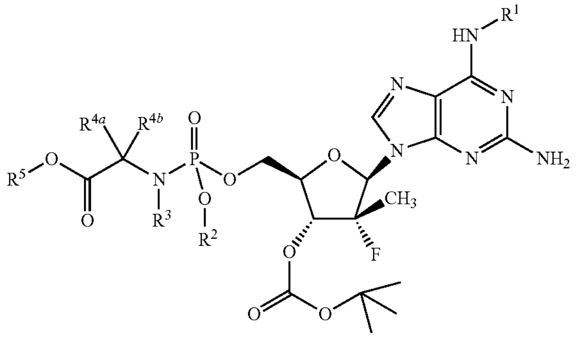

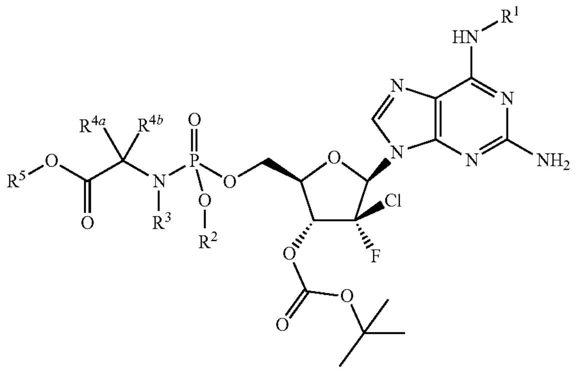

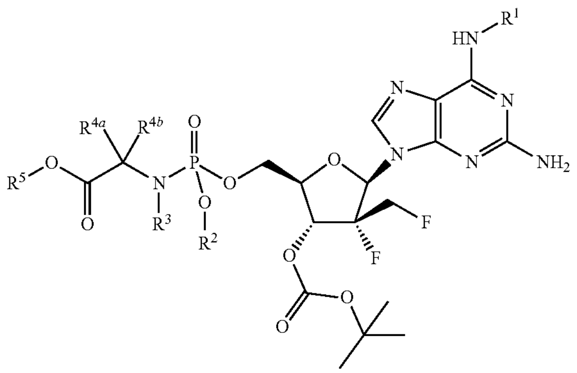

-continued

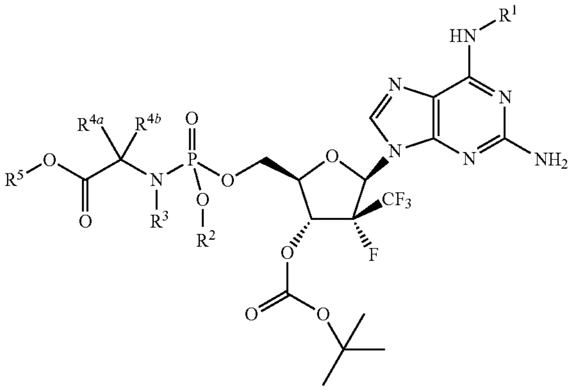

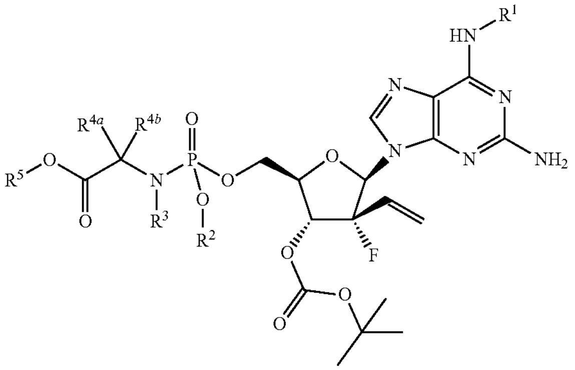

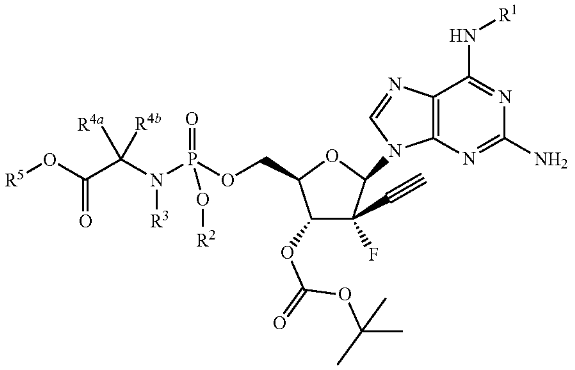

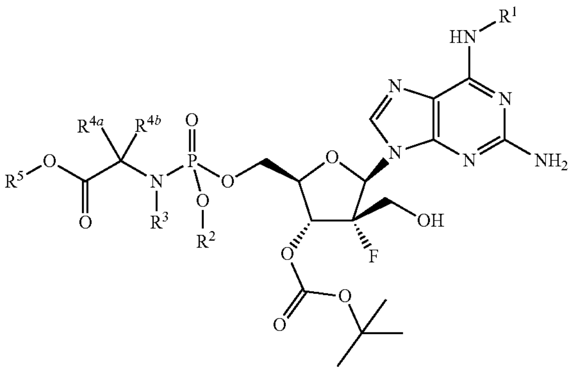

-continued
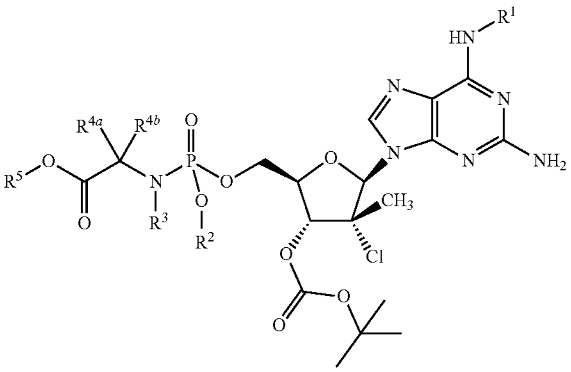
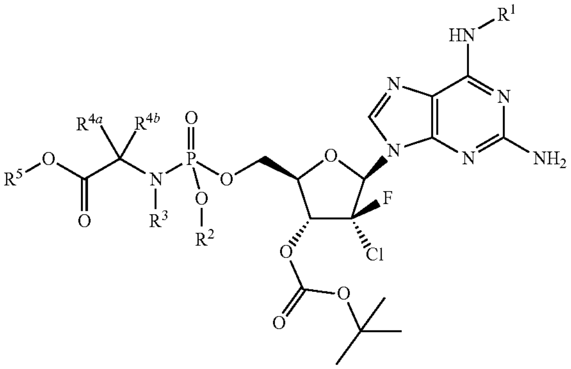
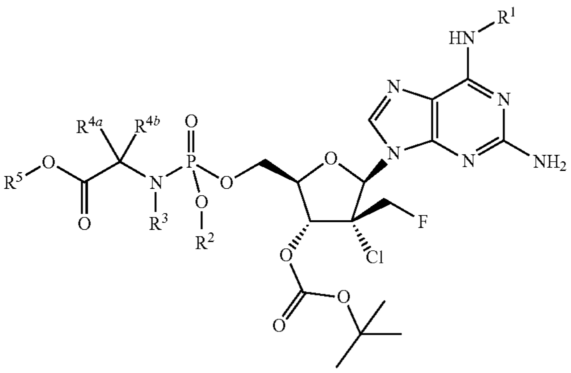
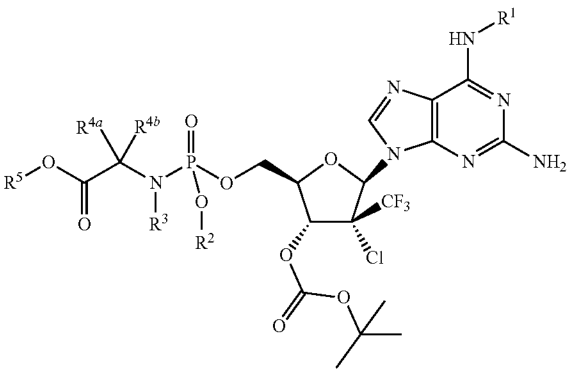
-continued
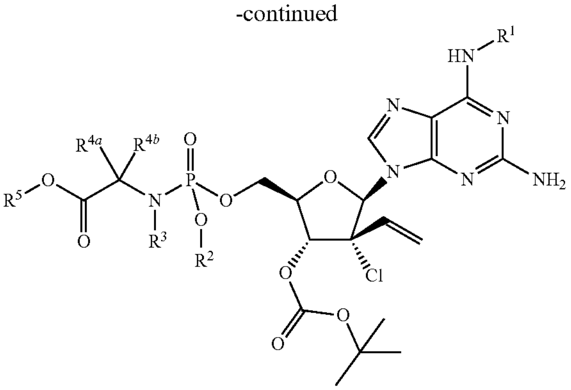
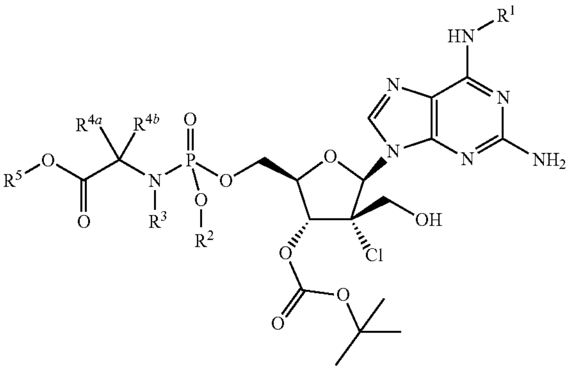
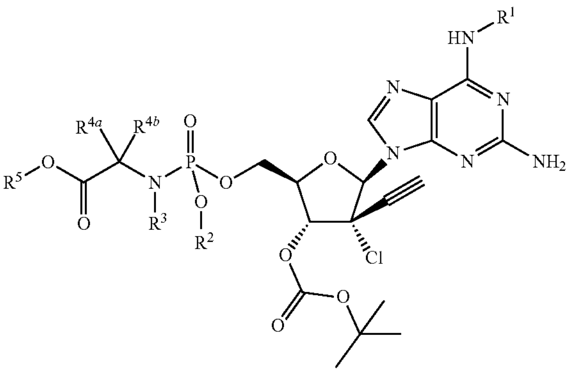
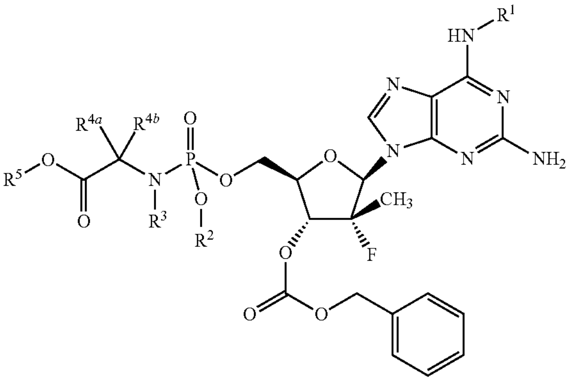

-continued
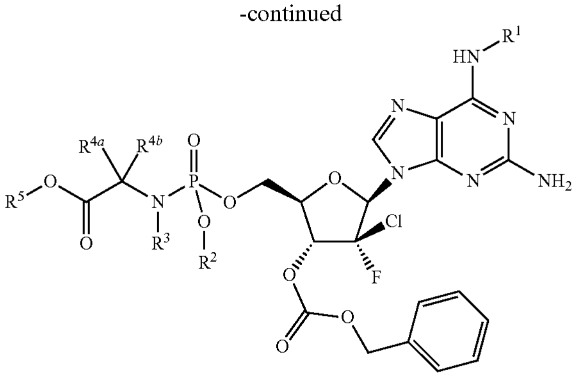
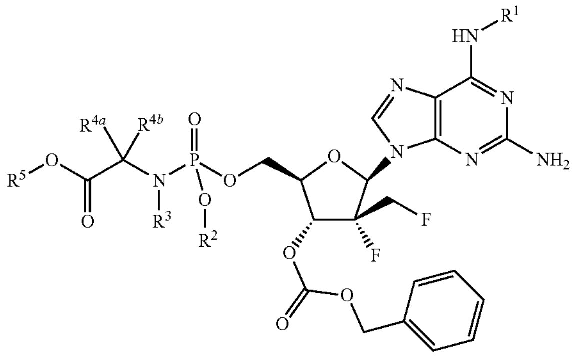
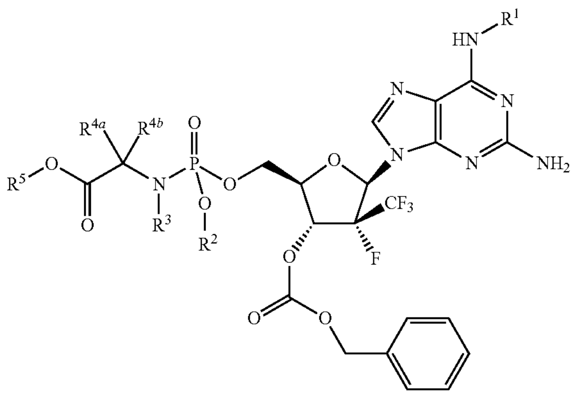
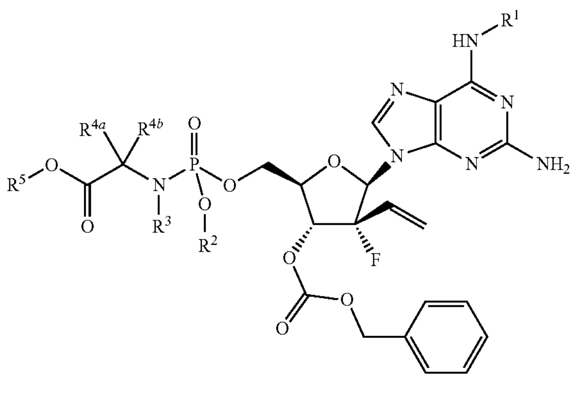
-continued
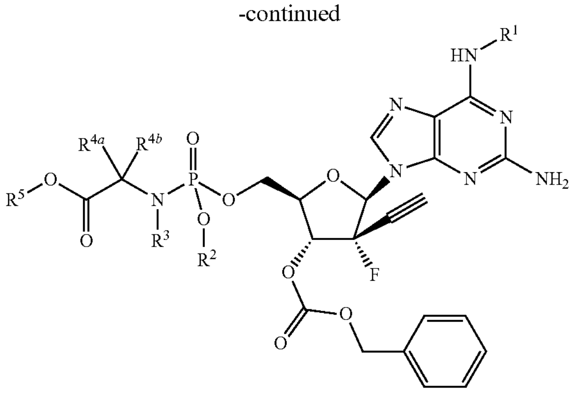
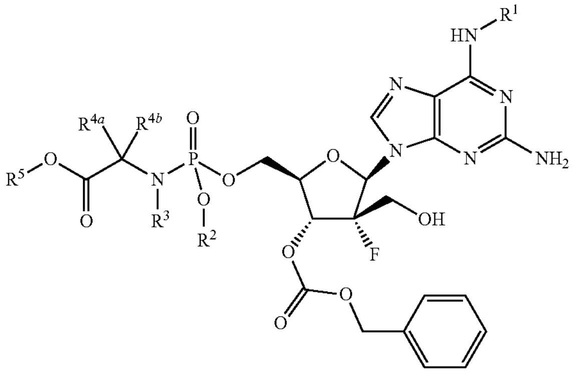
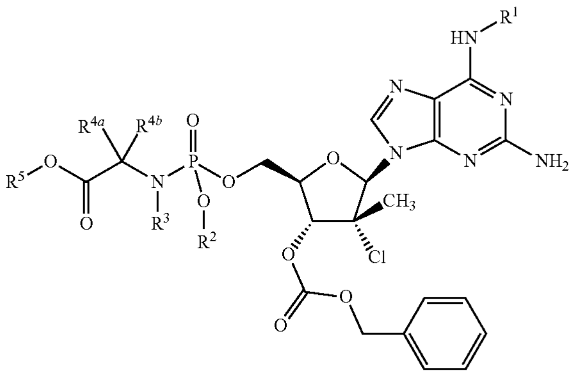
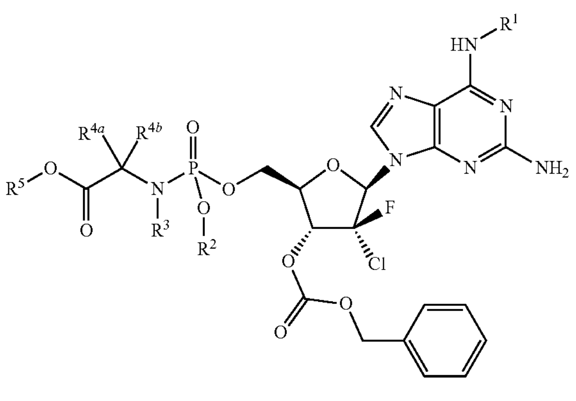

-continued
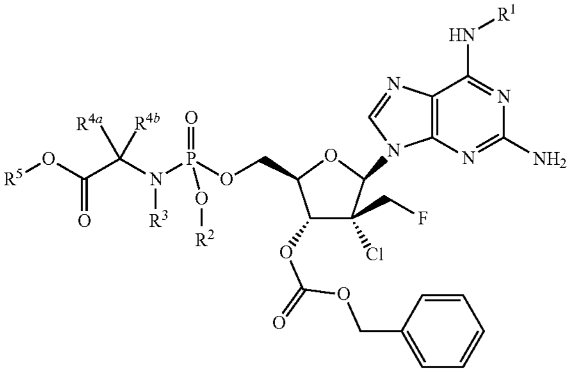
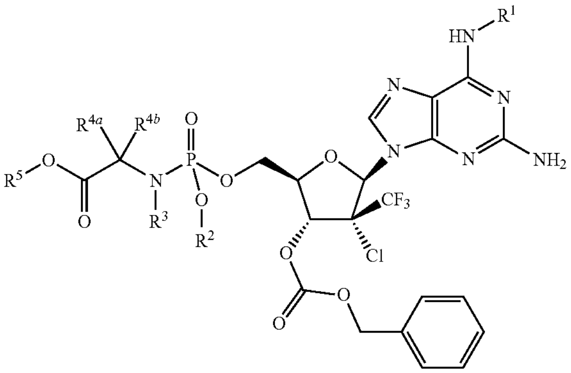
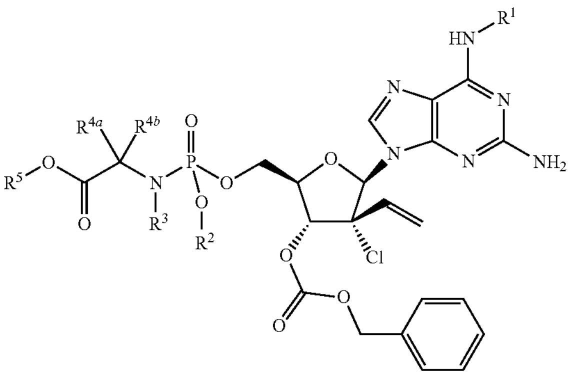
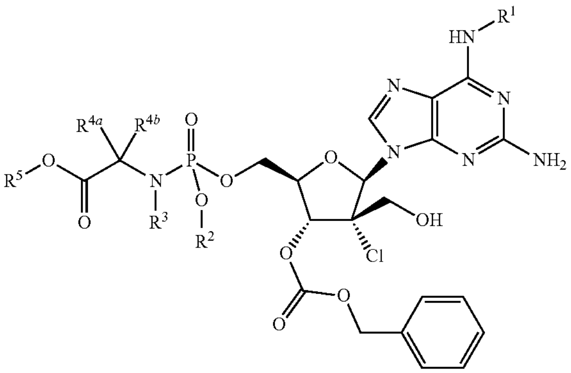
-continued
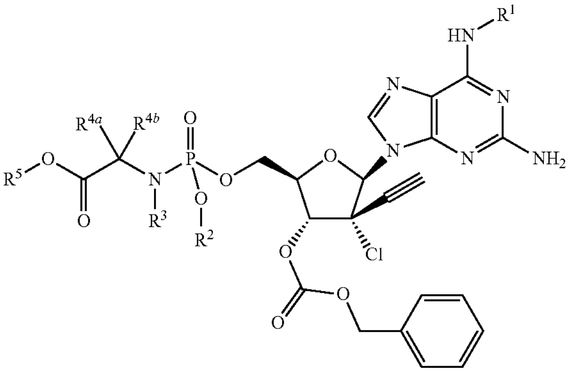
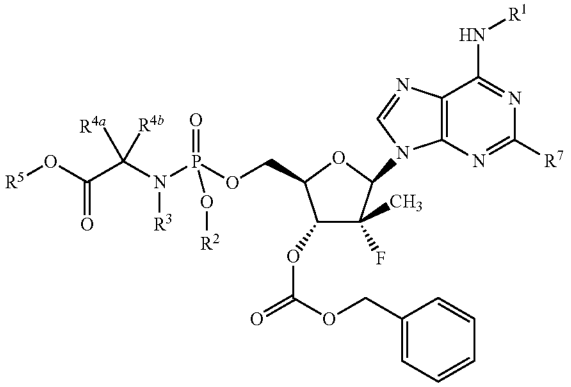
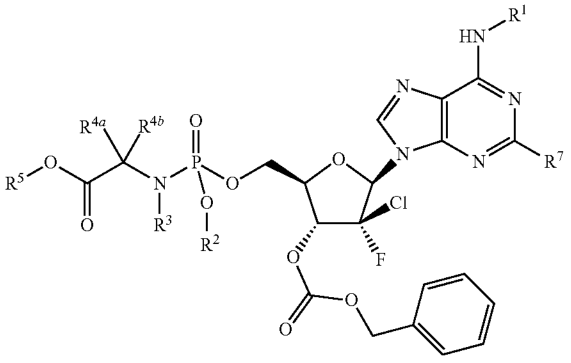
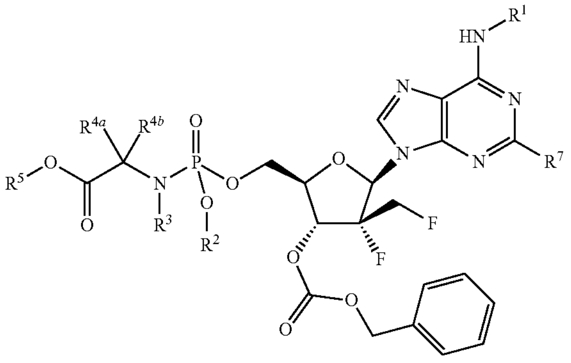

-continued
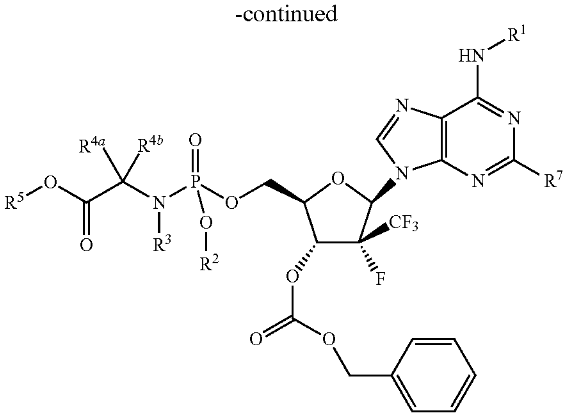
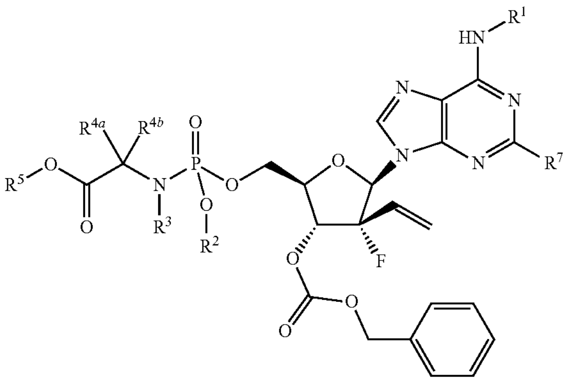
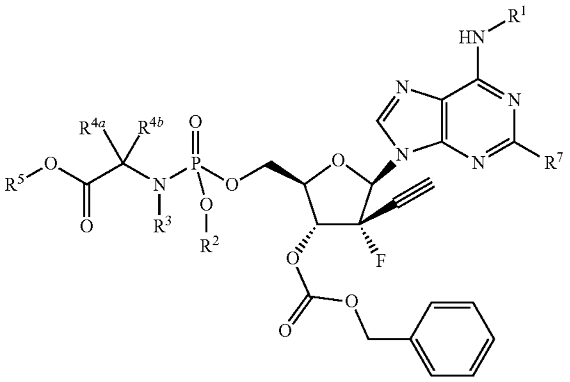
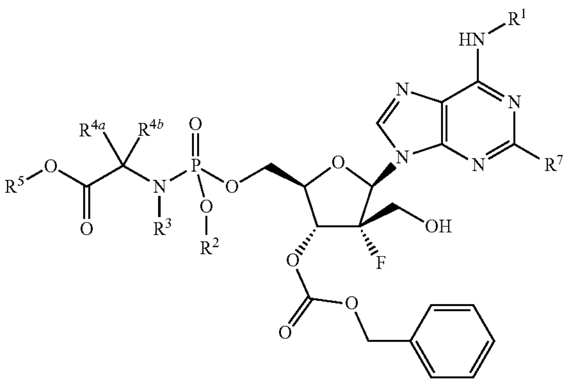
-continued
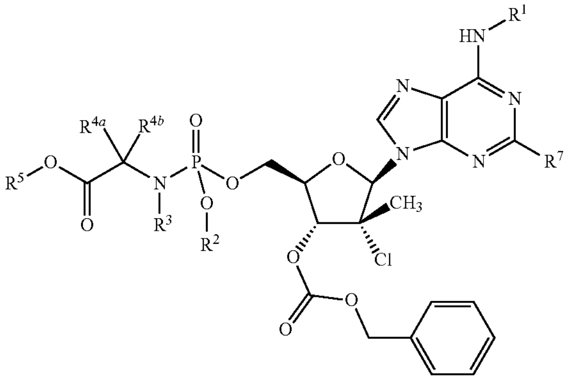
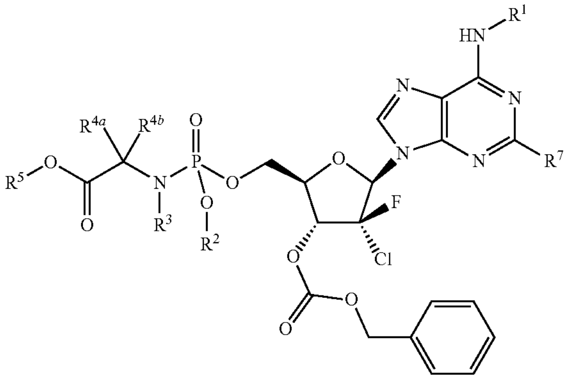
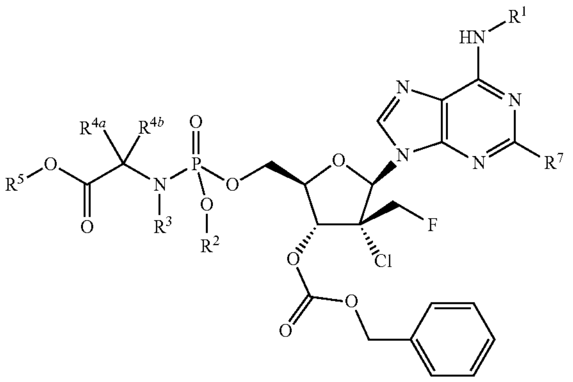
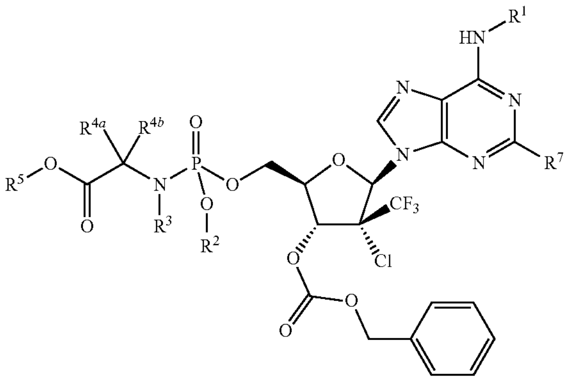

-continued
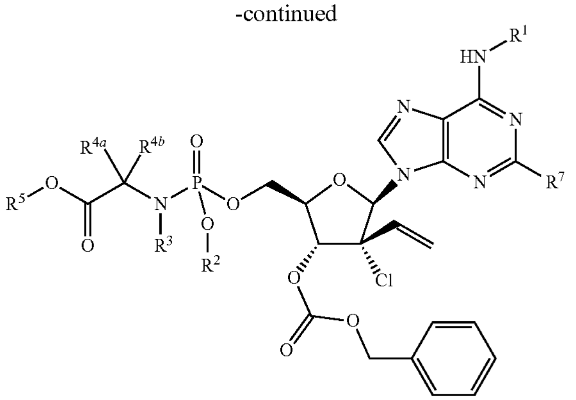
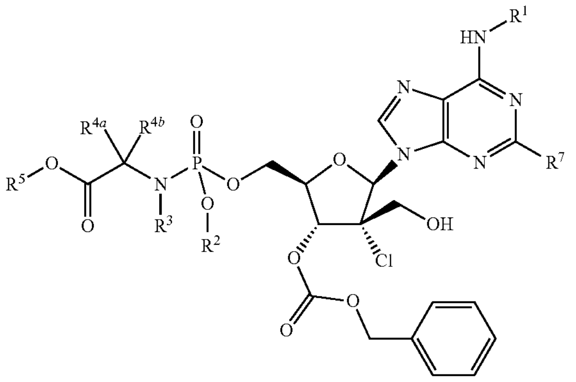
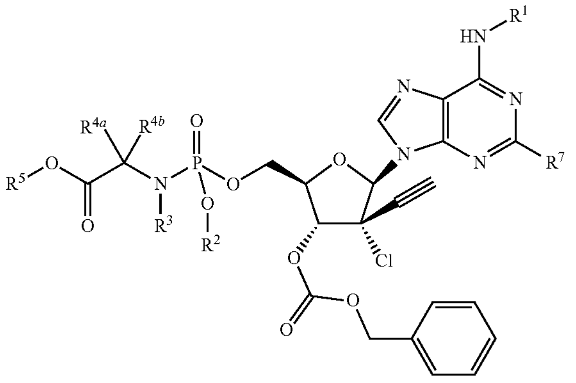
Additional non-limiting examples of a compound of Formula IV include:
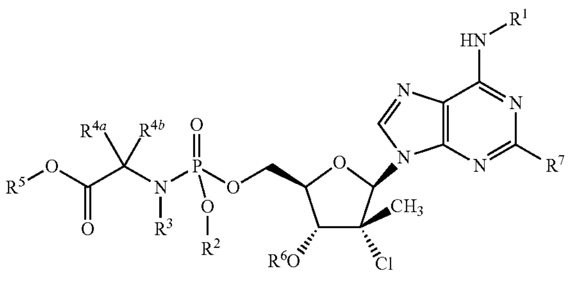
-continued
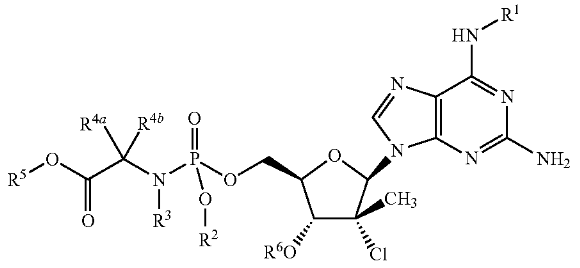
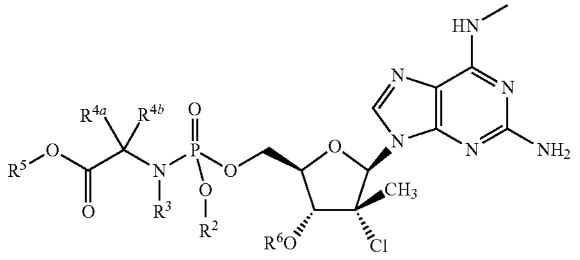
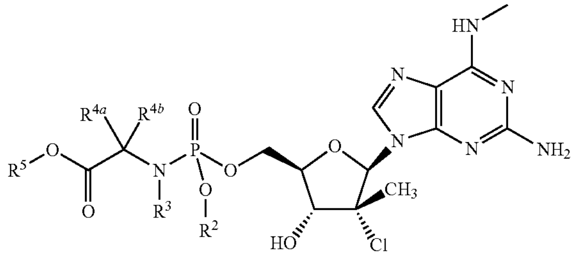
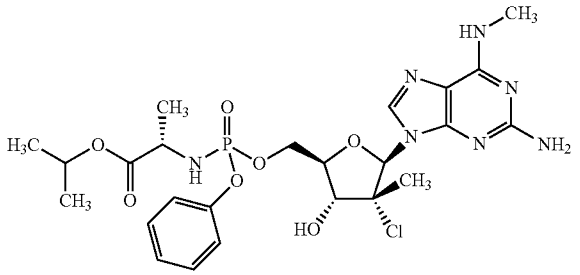
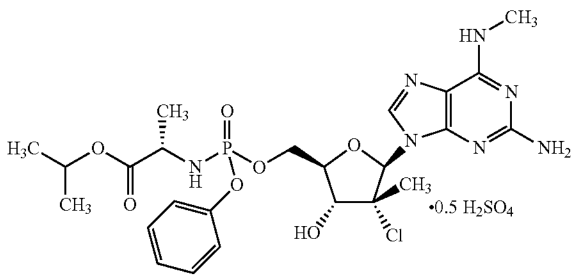
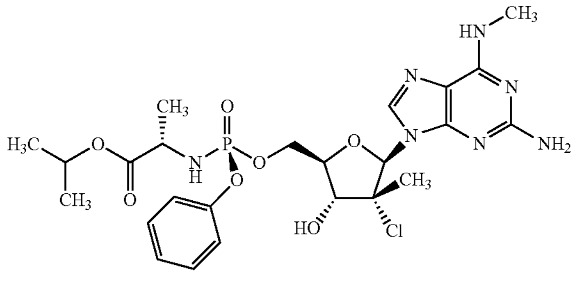

-continued

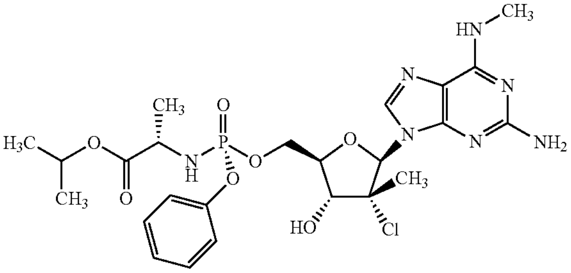

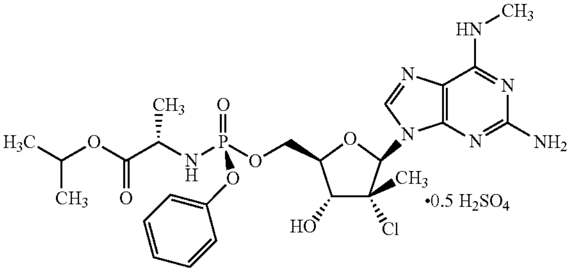

$\cdot 0.5\ H_2SO_4$

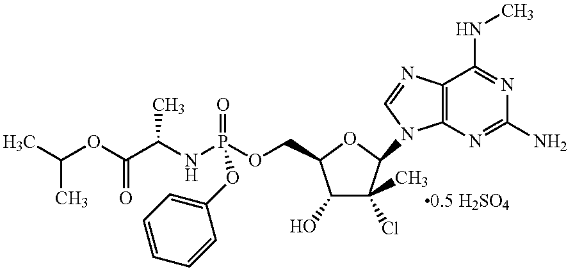

$\cdot 0.5\ H_2SO_4$

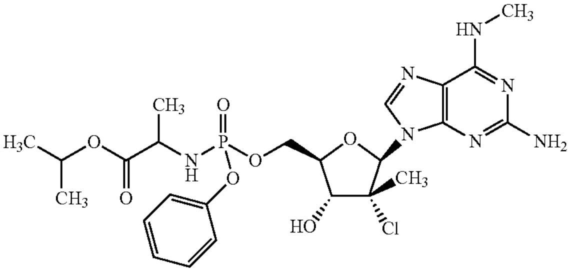

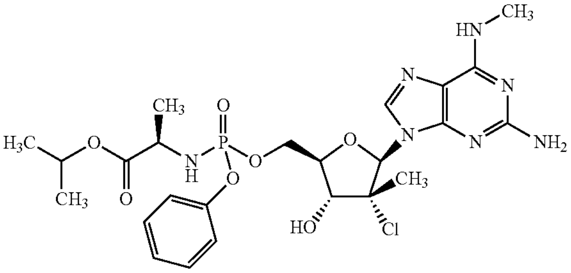

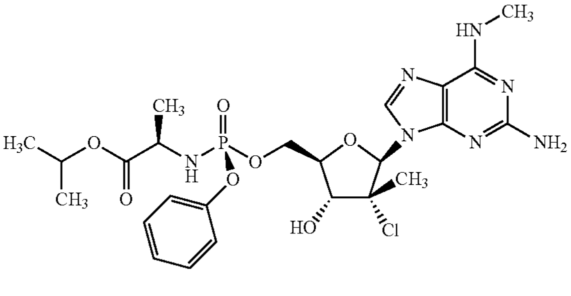

-continued

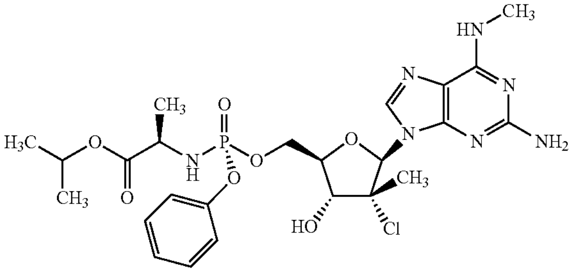

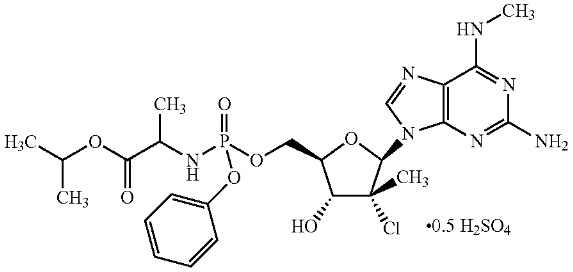

$\cdot 0.5\ H_2SO_4$

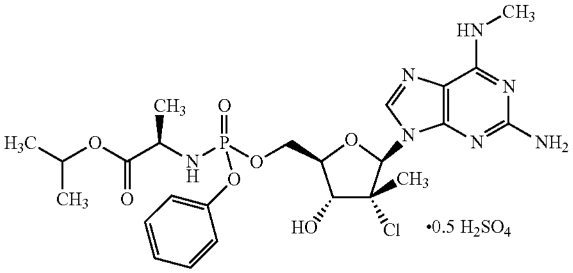

$\cdot 0.5\ H_2SO_4$

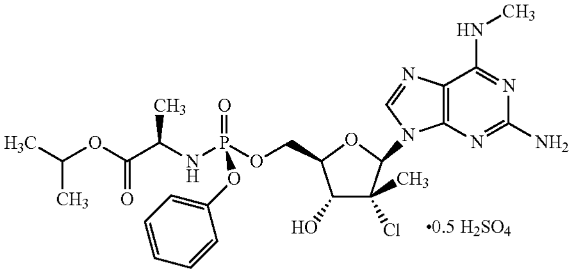

$\cdot 0.5\ H_2SO_4$

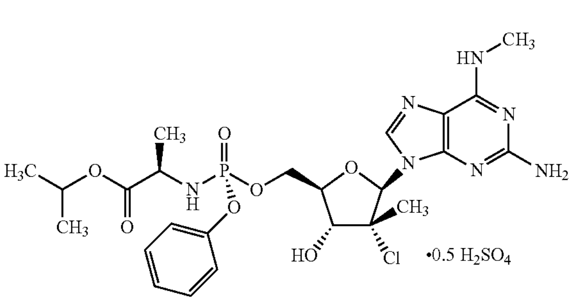

$\cdot 0.5\ H_2SO_4$

The present invention also includes the use of a compound of Formula V, Formula VI, or Formula VI wherein $R^{10}$ is a monophosphate, a diphosphate, a triphosphate, or $R^{10A}$ wherein $R^{10A}$ is a stabilized phosphate prodrug that metabolizes in vivo to a monophosphate, diphosphate, or triphosphate to disrupt NiRAN function in a coronavirus or to treat or prevent a mutant or resistant form of SARS-CoV-2 disease in a host in need thereof as described herein:

Formula V

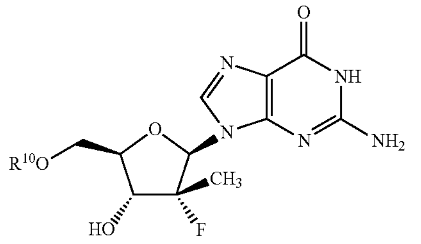

Formula VI

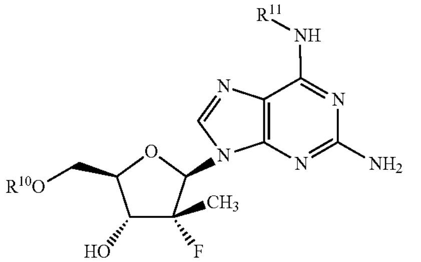

Formula VII

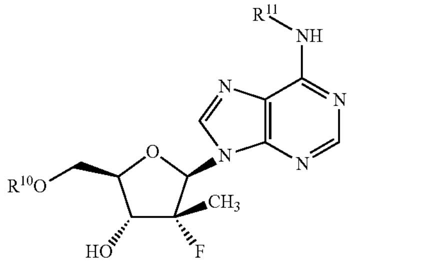

wherein $R^{10}$ is selected from

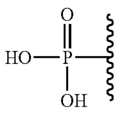,

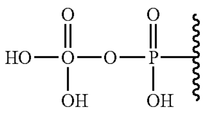,

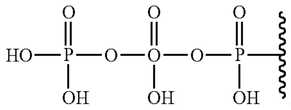, and $R^{10A}$;

$R^{10A}$ is a stabilized phosphate prodrug that metabolizes in vivo to a monophosphate, diphosphate, or triphosphate;

$R^{11}$ is selected from hydrogen and $R^1$; and $R^1$ is selected from $C_1$-$C_6$alkyl, $C_3$-$C_6$cycloalkyl, and —$C(O)C_1$-$C_6$alkyl.

The present invention also includes the use of a compound of Formula VIII to disrupt NiRAN function in a coronavirus or to treat or prevent a mutant or resistant form of SARS-CoV-2 in a host in need thereof as described herein:

Formula VIII

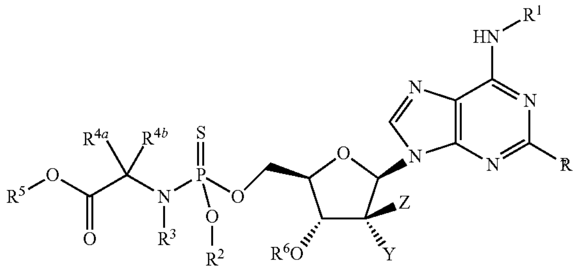

or a pharmaceutically acceptable salt thereof:

wherein $R^1$ is selected from $C_1$-$C_6$alkyl, $C_3$-$C_6$cycloalkyl, and —$C(O)C_1$-$C_6$alkyl;

$R^2$ is hydrogen, $C_{1-6}$alkyl (including methyl, ethyl, propyl, and isopropyl), $C_{3-7}$cycloalkyl, aryl (including phenyl and napthyl), aryl($C_1$-$C_4$alkyl)-, heteroaryl, or heteroalkyl;

$R^3$ is hydrogen or $C_{1-6}$alkyl (including methyl, ethyl, propyl, and isopropyl);

$R^{4a}$ and $R^{4b}$ are independently selected from hydrogen, $C_{1-6}$alkyl (including methyl, ethyl, propyl, and isopropyl), and $C_{3-7}$cycloalkyl; and $R^5$ is hydrogen, $C_{1-6}$alkyl (including methyl, ethyl, propyl, and isopropyl), $C_{1-6}$haloalkyl, $C_{3-7}$cycloalkyl, aryl ($C_1$-$C_4$alkyl)-, aryl, heteroaryl, or heteroalkyl.

$R^6$ is selected from hydrogen, —$C(O)R^{6A}$, —$C(O)OR^{6A}$, $C_{1-6}$alkyl, —$CH_2$—O—$R^{6A}$;

$R^{6A}$ is selected from hydrogen, $C_{1-6}$alkyl, $C_1$-$C_6$haloalkyl (for example, —$CHCl_2$, —$CCl_3$, —$CH_2Cl$, —$CF_3$, —$CHF_2$, —$CH_2F$), aryl, aryl($C_{1-6}$alkyl)- wherein the aryl group is optionally substituted with a substituent selected from alkoxy, hydroxy, nitro, bromo, chloro, fluoro, azido, and haloalkyl;

$R^7$ is $NH_2$, H, or —$NR^8R^9$;

$R^8$ and $R^9$ are independently selected from hydrogen, $C_{1-6}$alkyl, —$C(O)R^{6A}$, and —$C(O)OR^{6A}$;

Y is selected from F and Cl; and

Z is selected from $C_{1-4}$alkyl (including methyl), $C_1$-$C_3$haloalkyl (including $C_{1-3}$fluoroalkyl and $C_{1-3}$chloroalkyl, such as $CH_2F$, $CHF_2$, $CF_3$, $CH_2CF_3$, $CH_2CHF_2$, $CH_2CH_2F$, $CF_2CH_3$, $CF_2CF_3$, and $CH_2C_1$), $C_2$-$C_4$alkenyl, $C_2$-$C_4$alkynyl, $C_1$-$C_3$hydroxyalkyl, and halogen (including $C_1$ and F).

In certain embodiments, $R^1$ is not $C_1$-$C_6$alkyl. In certain embodiments, $R^1$ is not methyl. In certain embodiments, $R^2$ is not aryl. In certain embodiments, $R^2$ is not phenyl. In certain embodiments, $R^3$ is not hydrogen. In certain embodiments, $R^{4a}$ and $R^{4b}$ are not selected from hydrogen and $C_{1-6}$alkyl. In certain embodiments, $R^{4a}$ and $R^{4b}$ are not selected from hydrogen and methyl. In certain embodiments, $R^5$ is not $C_{1-6}$alkyl. In certain embodiments, $R^5$ is not isopropyl.

Non-limiting examples of a compound of Formula VIII include:

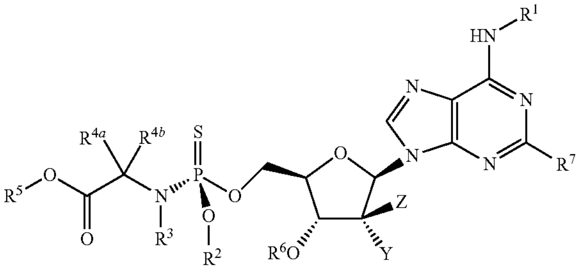

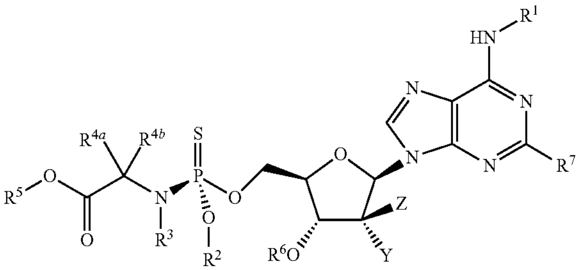

In one embodiment, the compound of Formula VIII to disrupt NiRAN function in a coronavirus or to treat or prevent a mutant or resistant form of the SARS-CoV-2 virus in a host in need thereof is a compound of Formula VIIIa or a pharmaceutically acceptable salt thereof:

Formula VIIIa

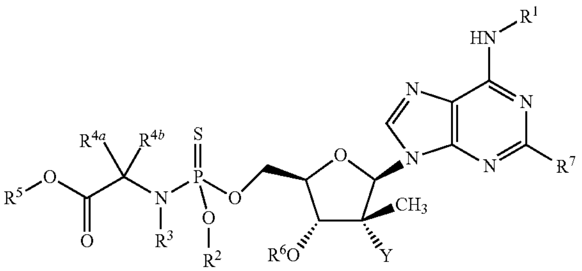

Non-limiting examples of compounds of Formula VIII include, but are not limited to:

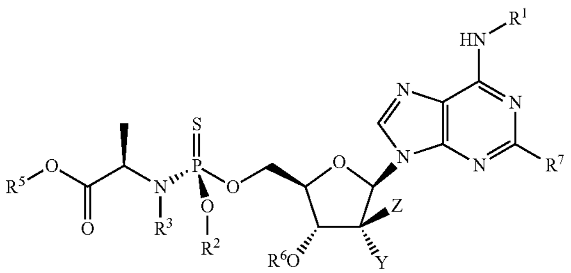

-continued

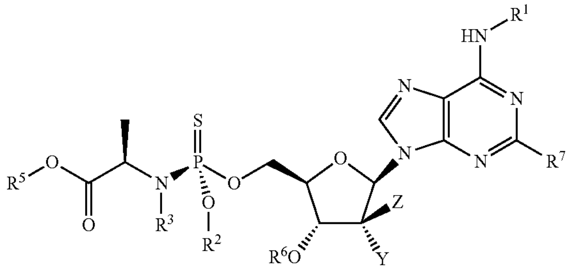

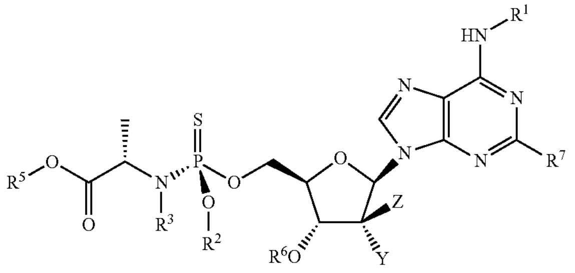

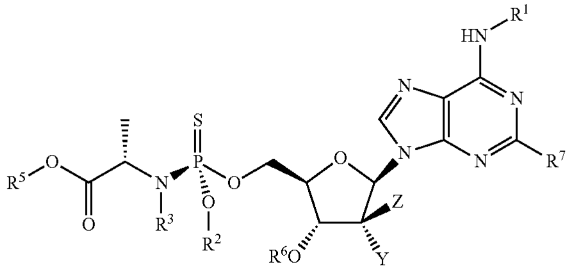

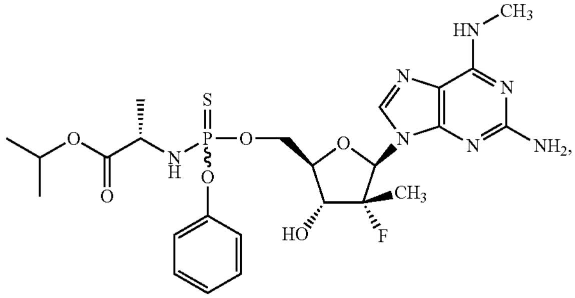
,

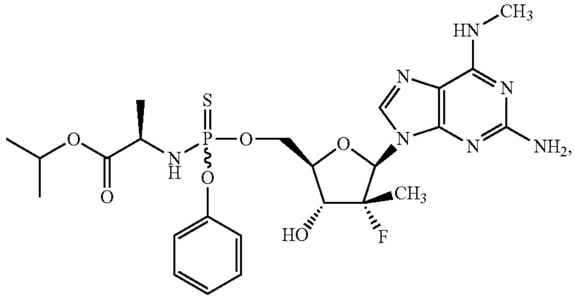
,

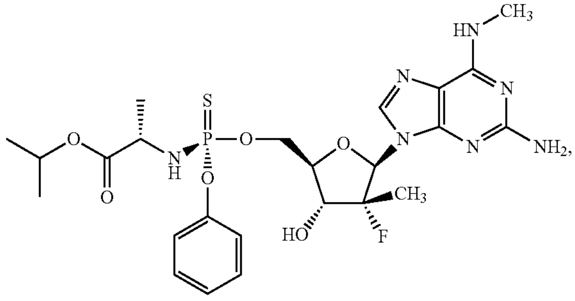
,

-continued
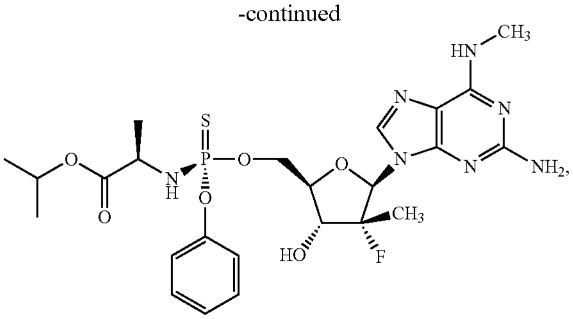
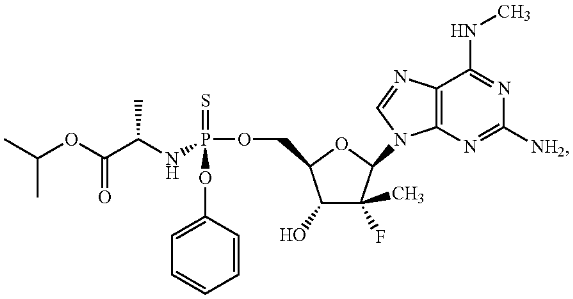
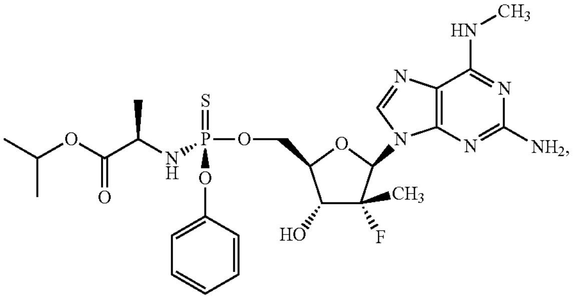
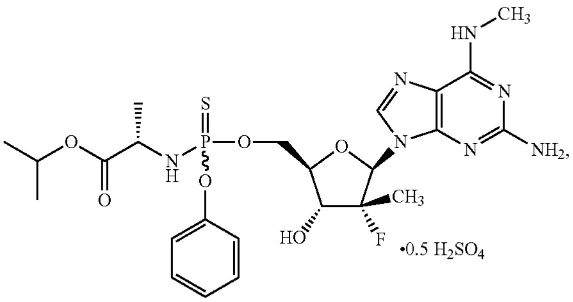
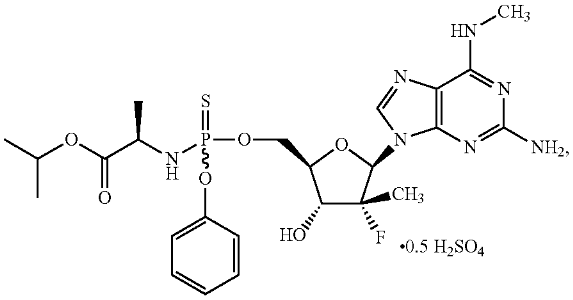
-continued
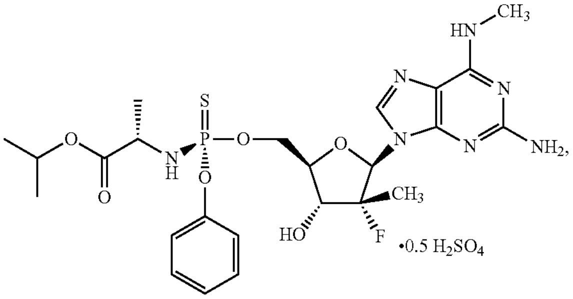
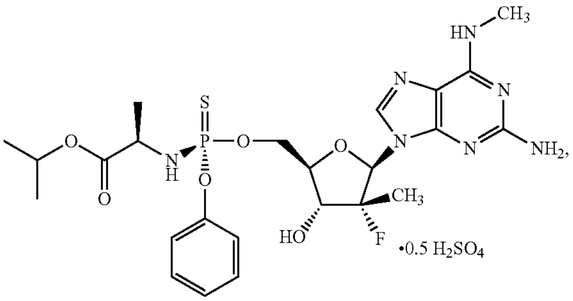
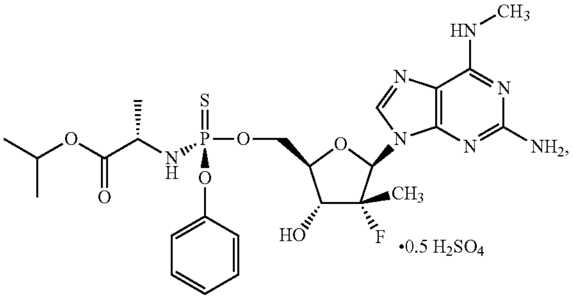
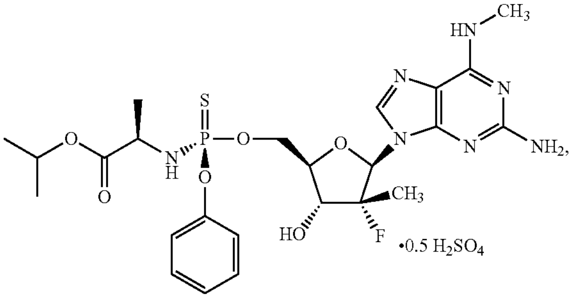
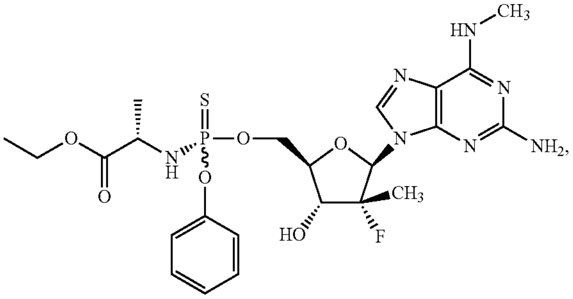

-continued
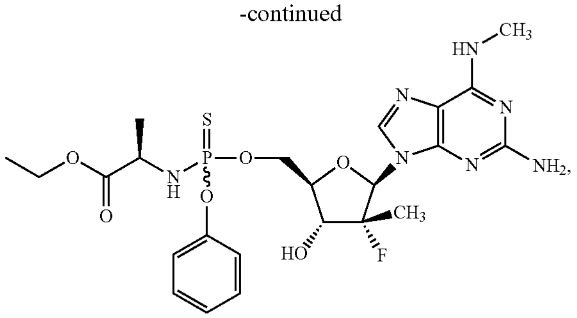
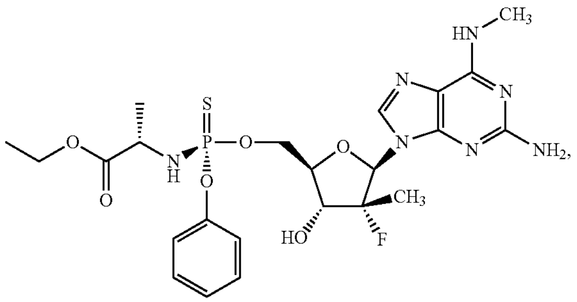
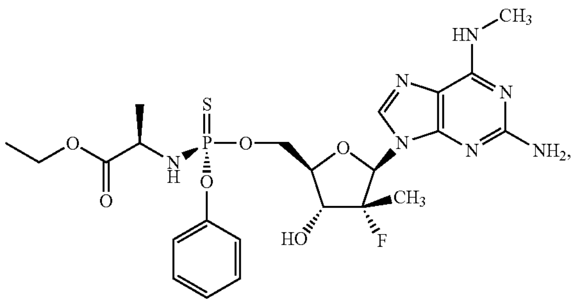
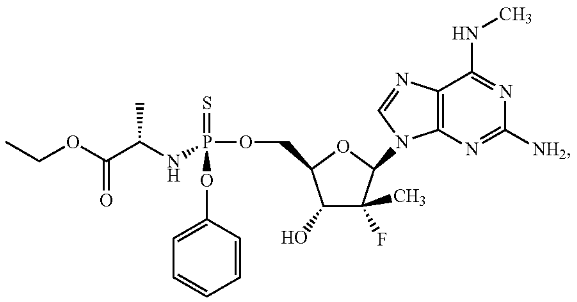
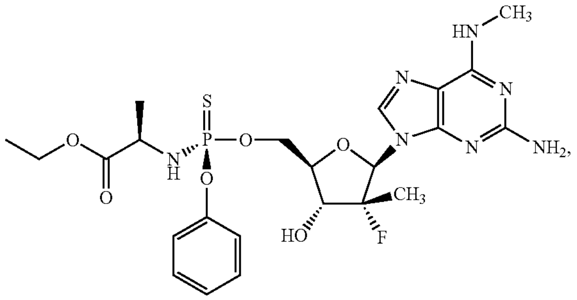
-continued
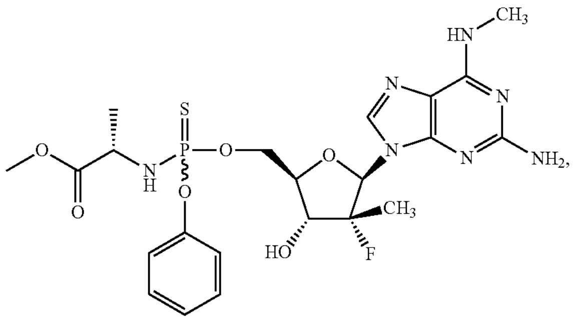
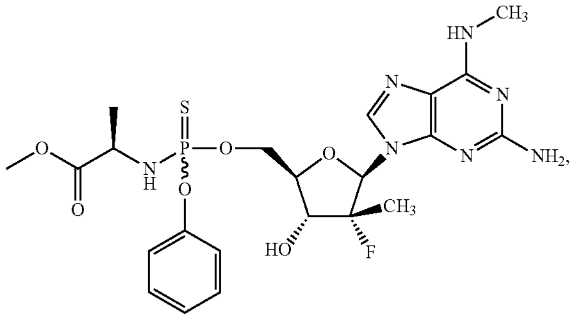
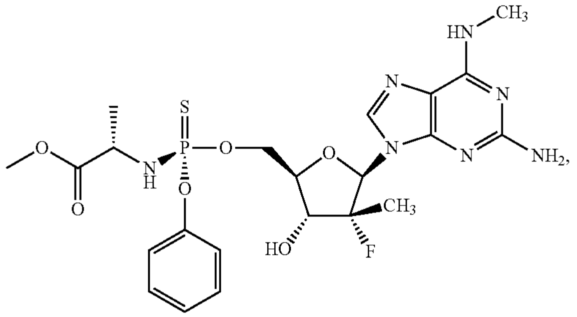
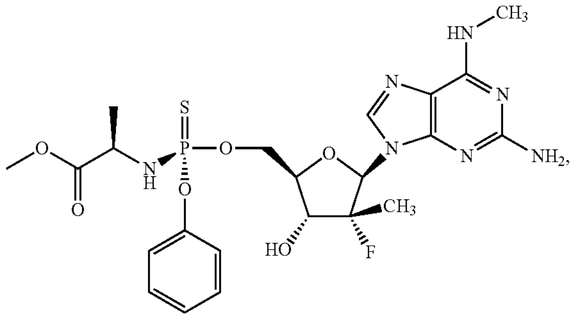
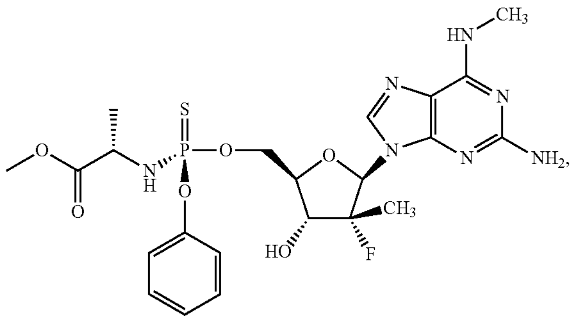

-continued
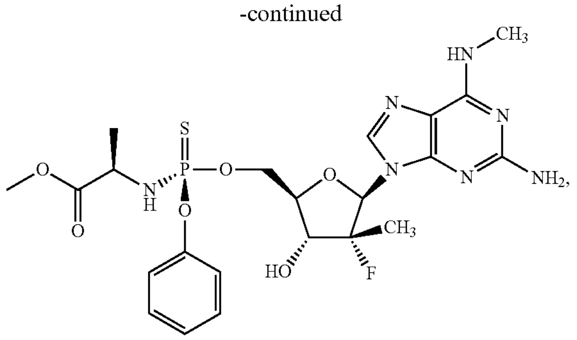
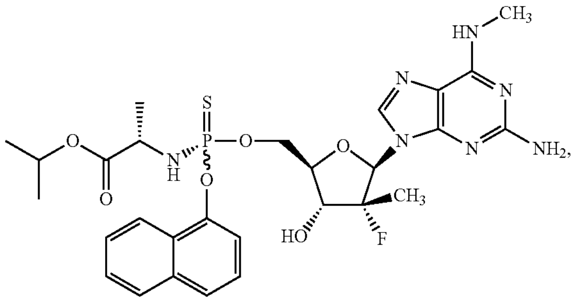
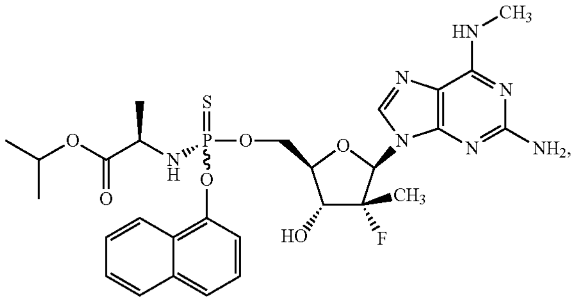
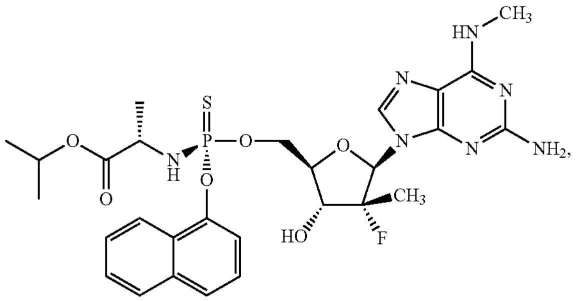
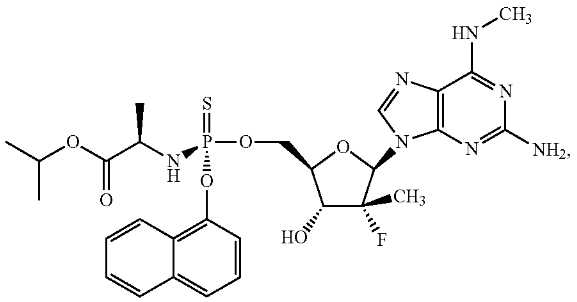
-continued
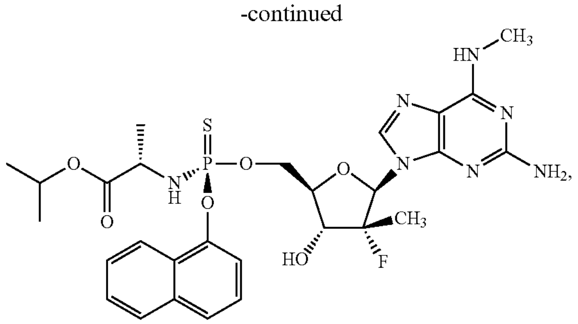
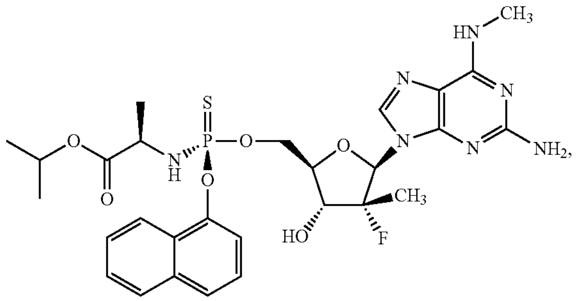
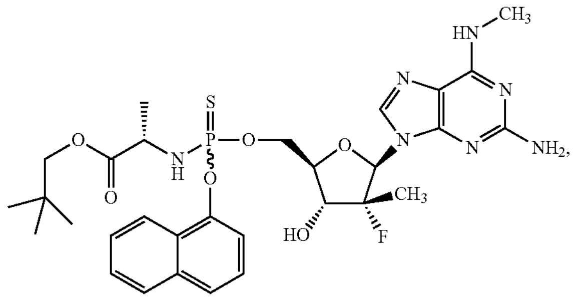
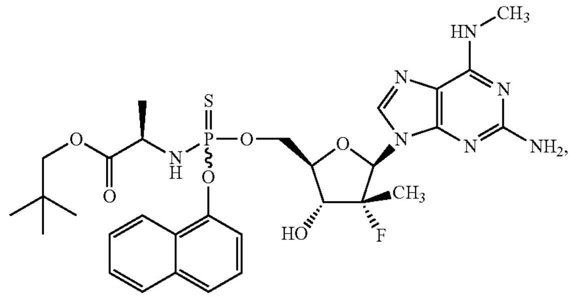
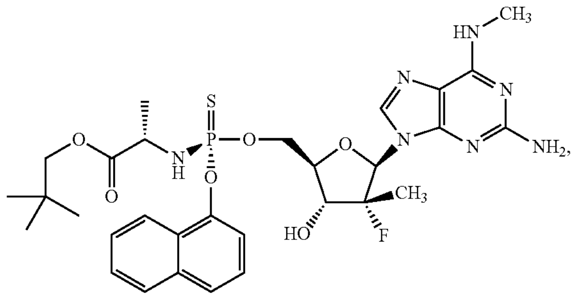

-continued
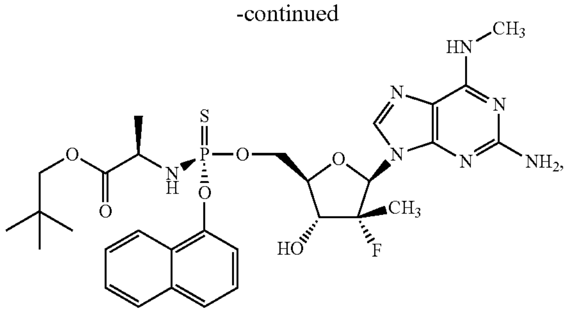
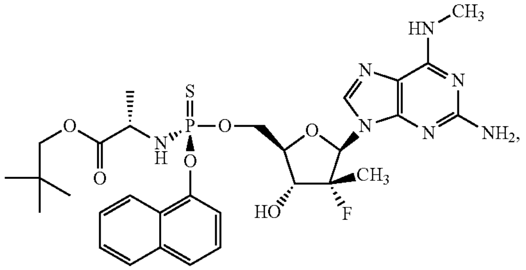
and
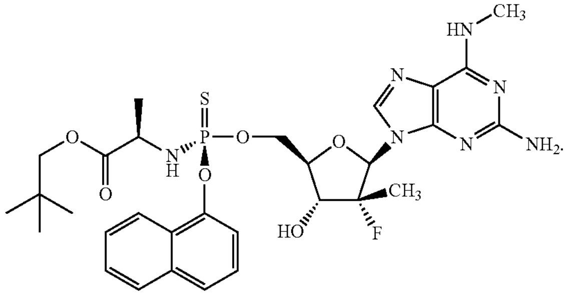
Additional non-limiting examples of compounds of Formula VIII include, but are not limited to:
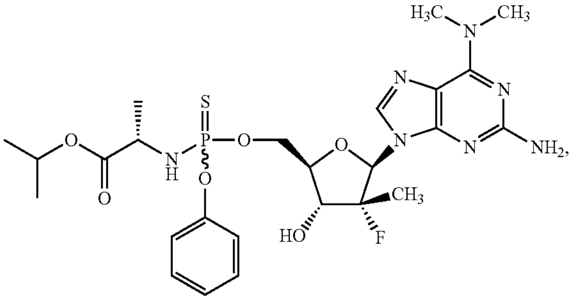
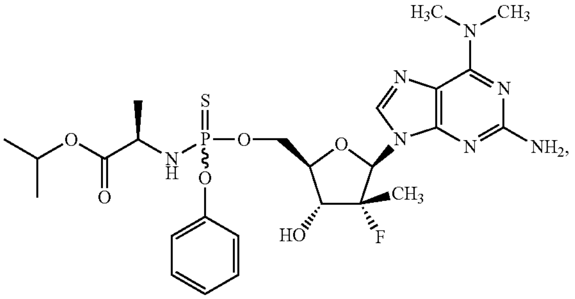
-continued
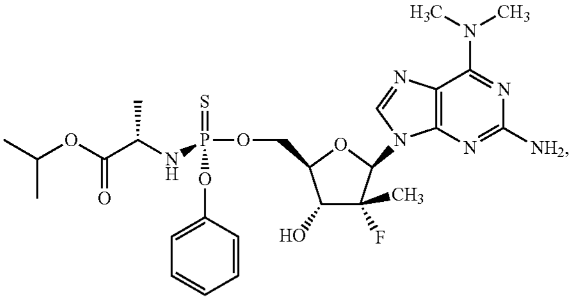
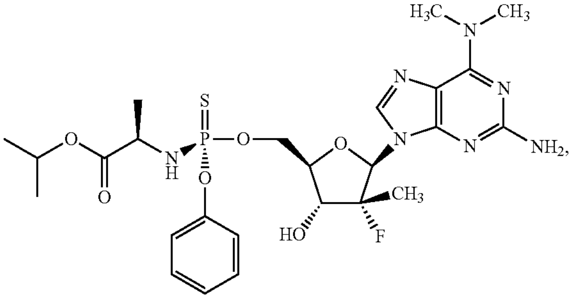
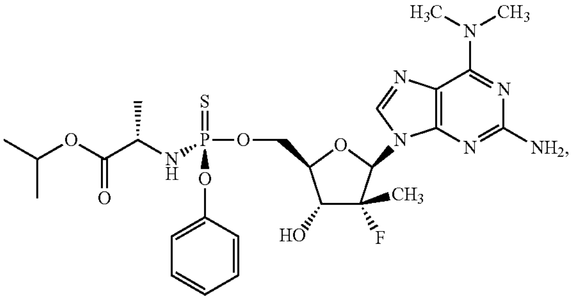
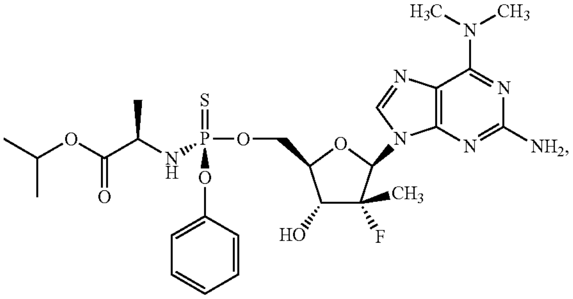
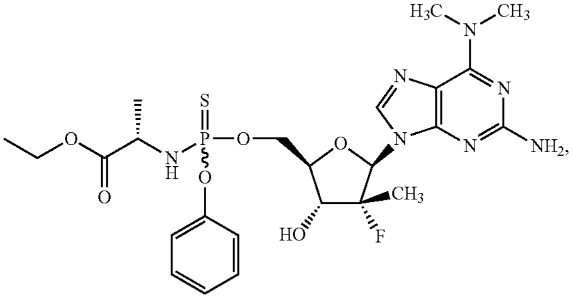

-continued
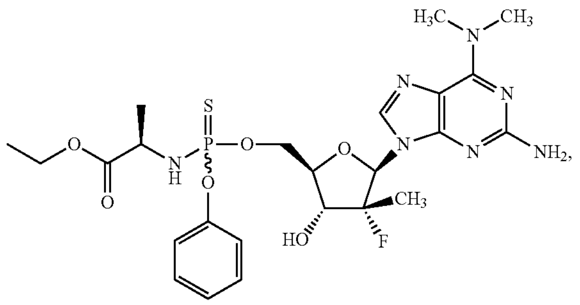
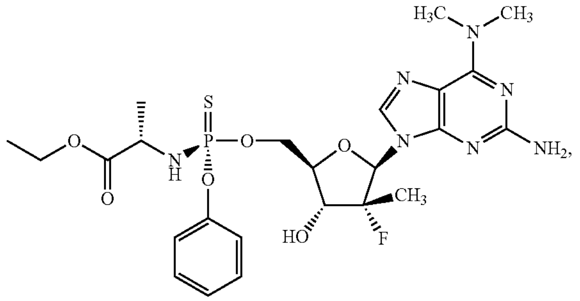
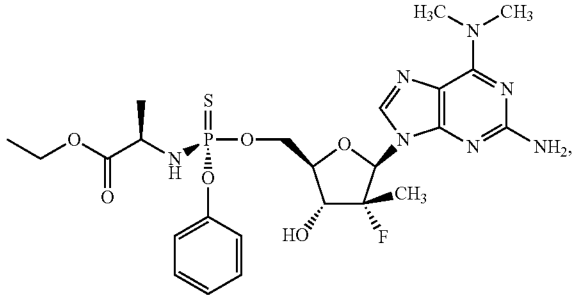
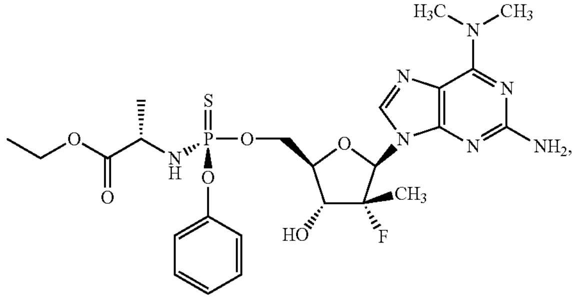
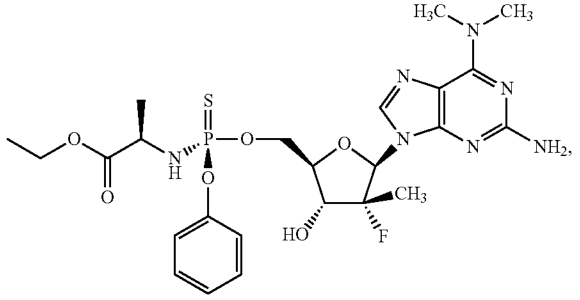
-continued
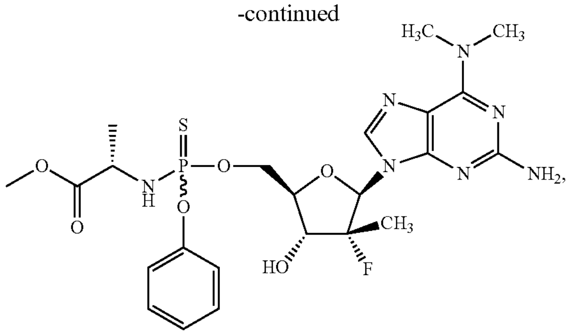
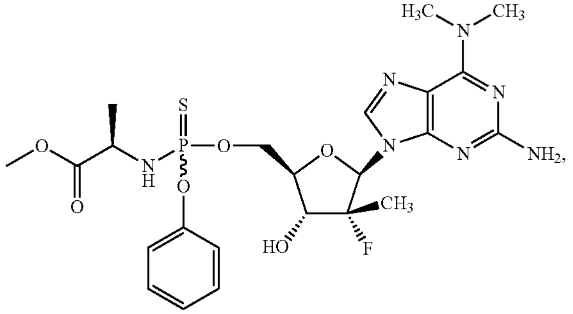
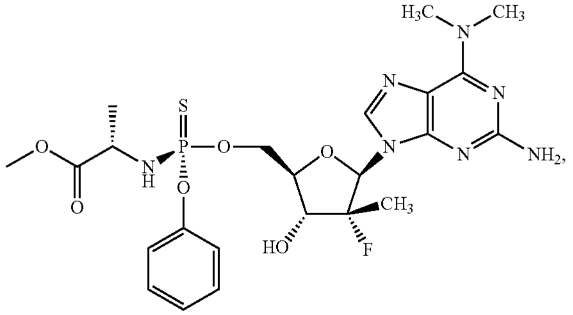
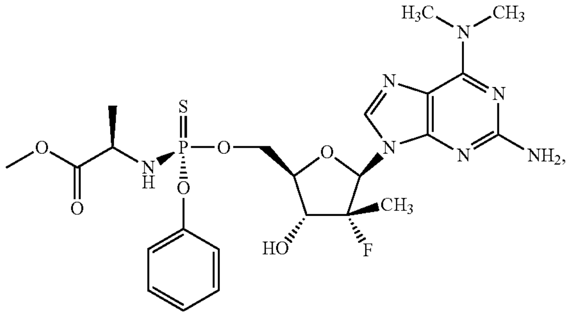
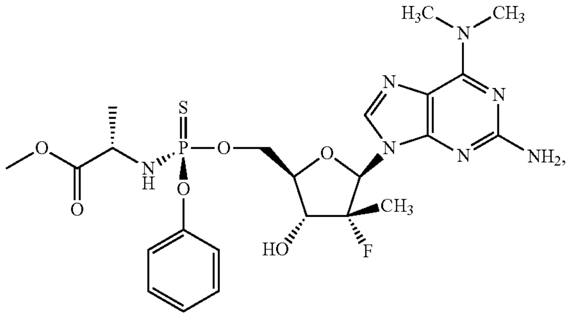

-continued
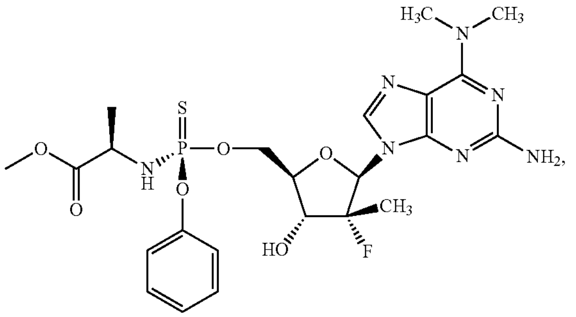
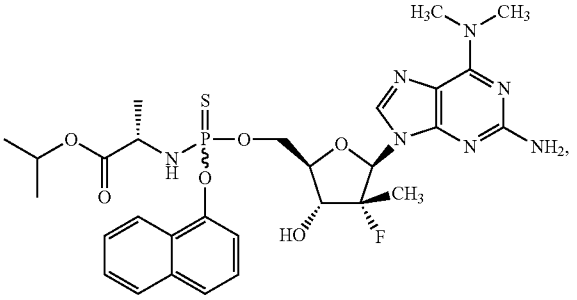
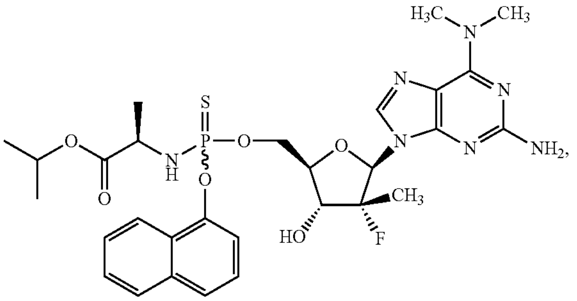
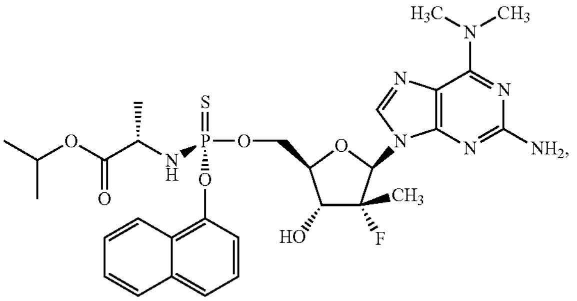
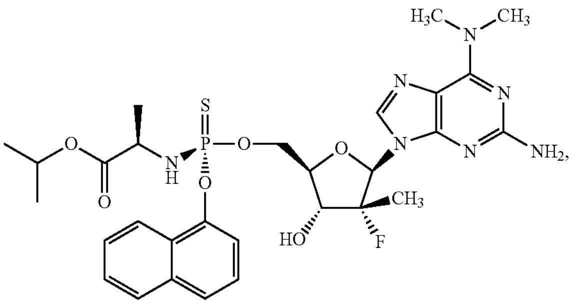
-continued
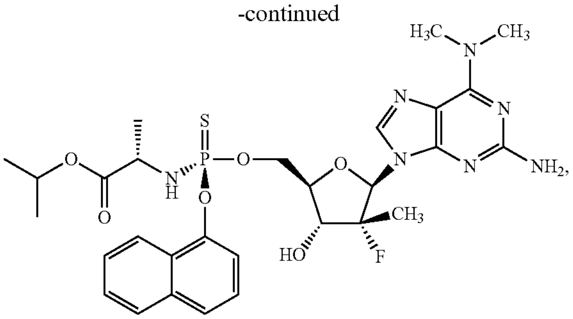
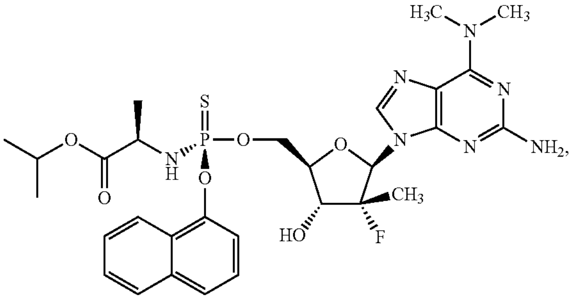
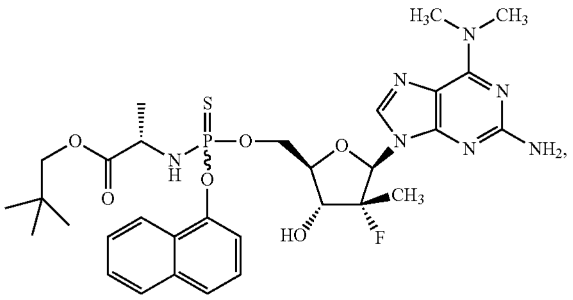
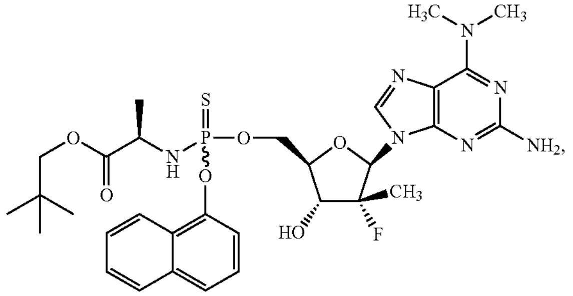
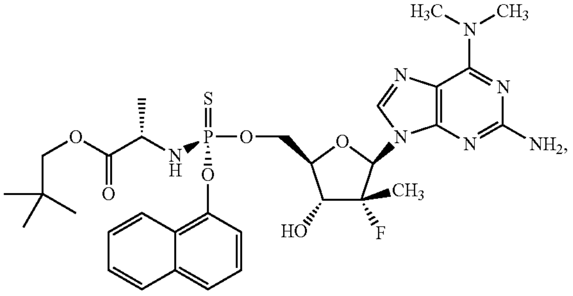

-continued

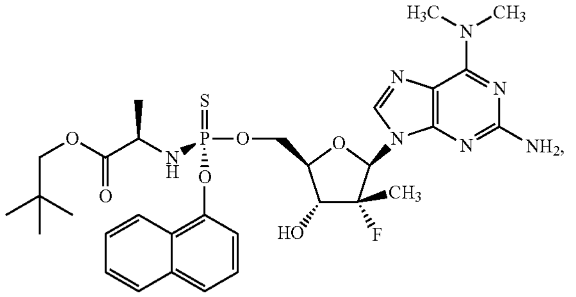

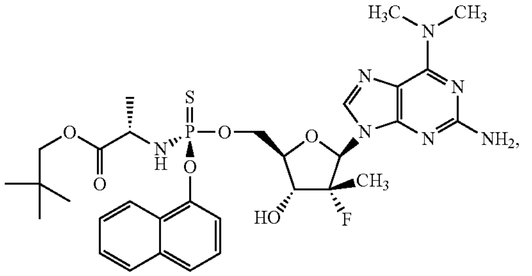

and

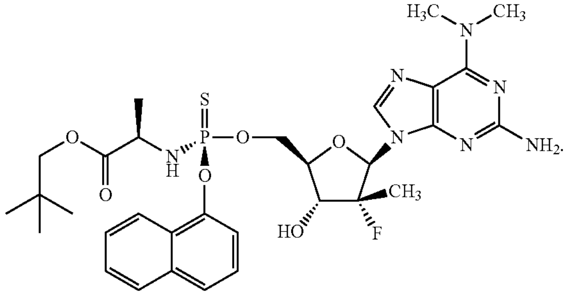

In one embodiment, the compound of Formula VIII to disrupt NiRAN function in a coronavirus or to treat or prevent a mutant or resistant form of the SARS-CoV-2 virus in a host in need thereof is a compound of Formula VIIIb or a pharmaceutically acceptable salt thereof:

Formula VIIIb

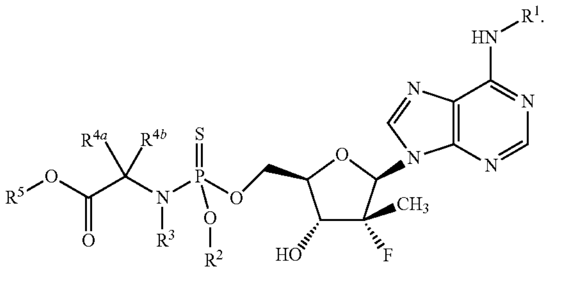

In one embodiment, the compound of Formula VIII to treat or prevent a mutant or resistant form of the SARS-CoV-2 virus in a host in need thereof is a compound of Formula VIIIc or a pharmaceutically acceptable salt thereof:

Formula VIIIc

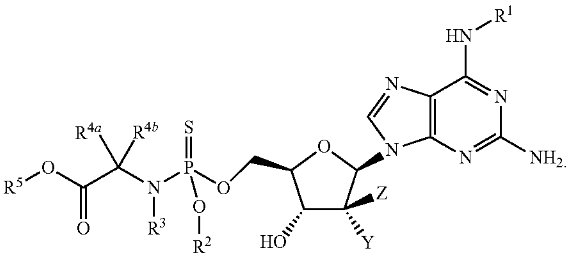

Non-limiting examples of a compound of Formula VIIIc include:

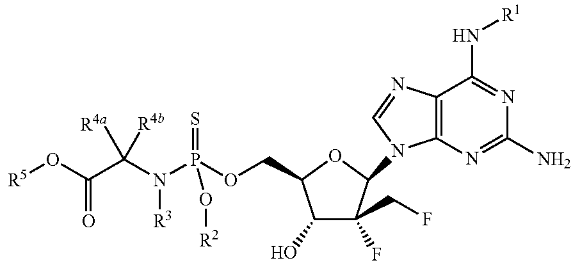

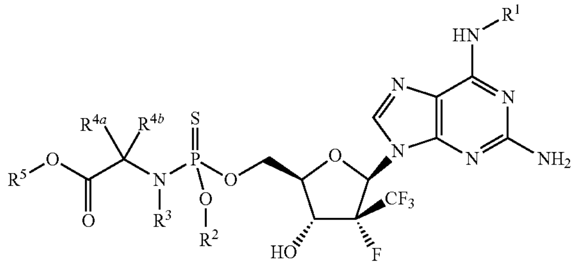

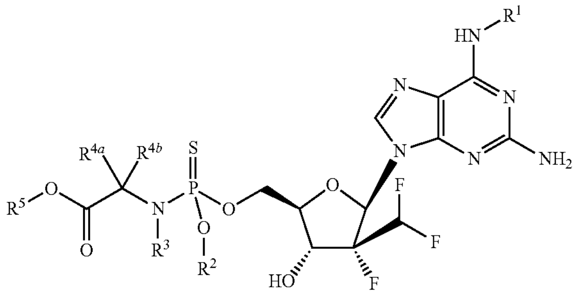

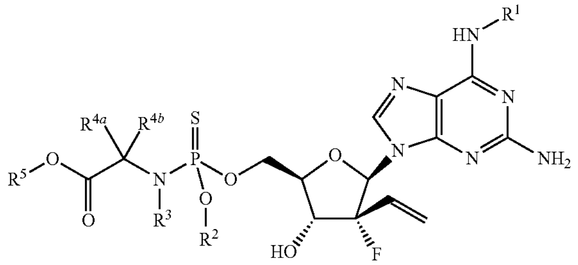

-continued
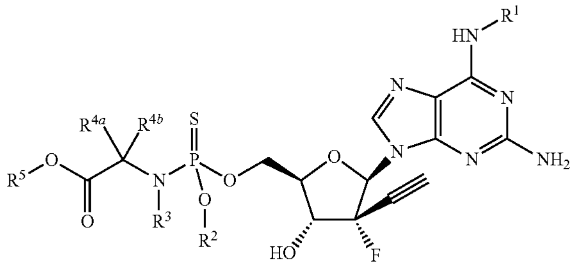
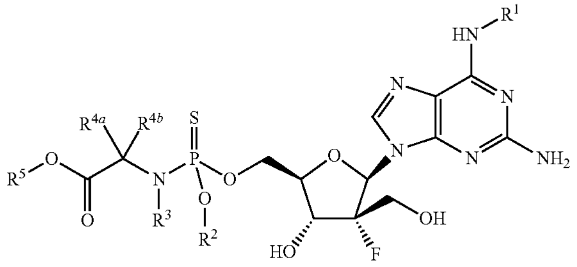
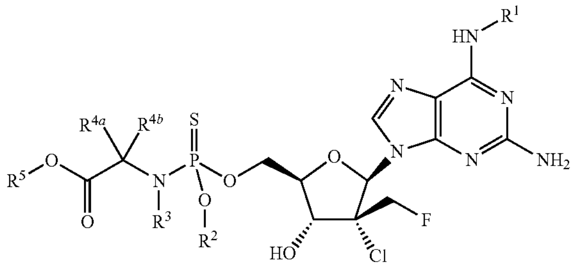
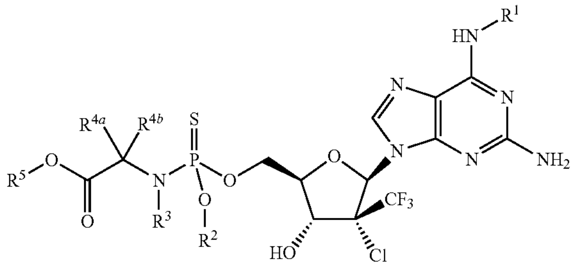
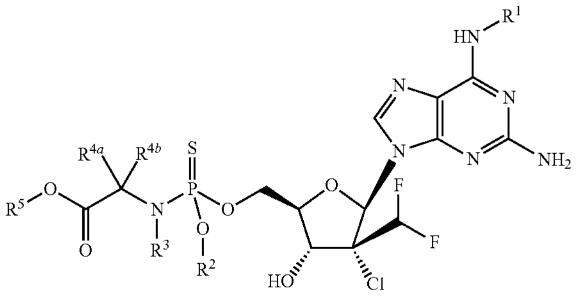
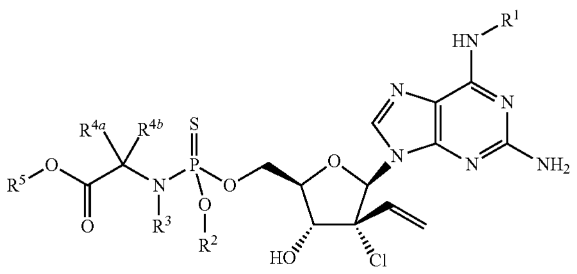
-continued
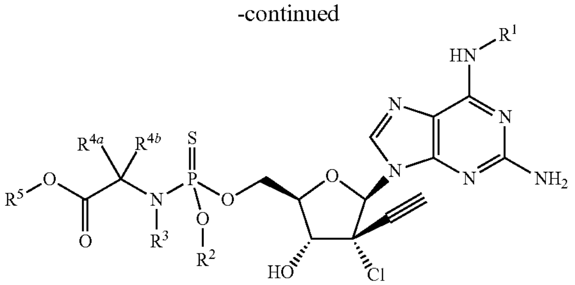
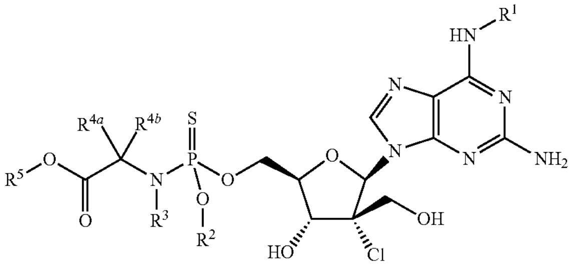
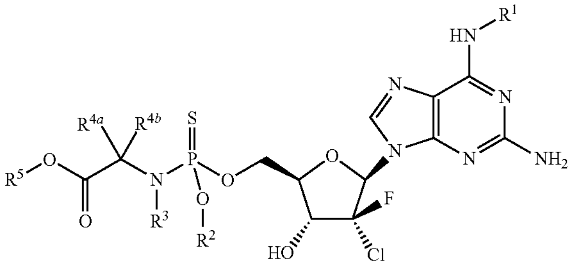
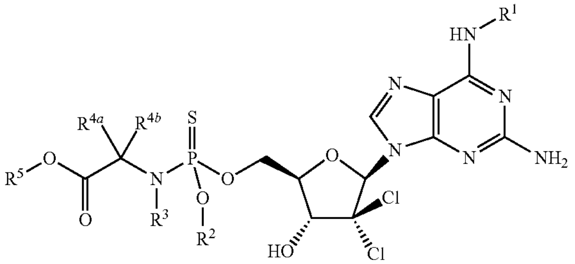
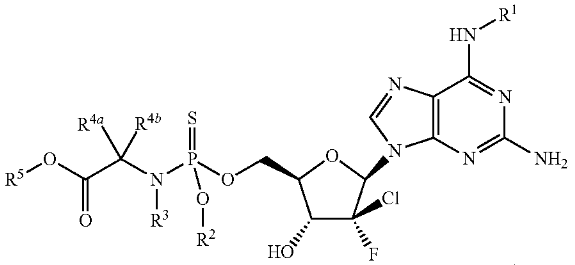
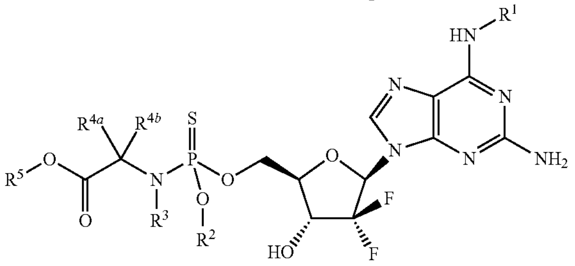
Compounds of Formula VIII can be synthesized according to the procedures described in U.S. Pat. Nos. 8,895,723 and 8,871,737 assigned to Alios Biopharma. For example, a general synthesis is shown below using a representative compound of the present invention:

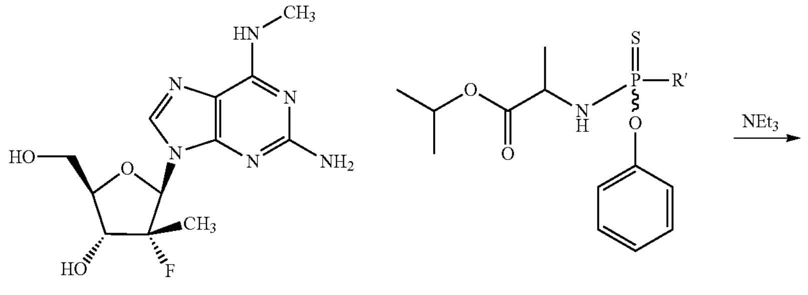

A B

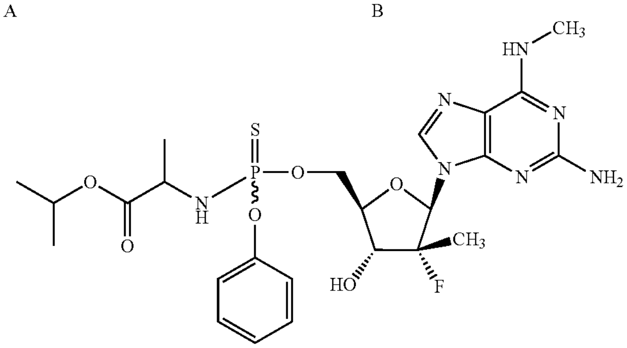

wherein R' is selected from Cl, Br, I, tosylate, mesylate, trifluoroacetate, trifluorosulfonate, or an aryloxide substituted with at least one electron withdrawing group, including, but are not limited to, 2-nitrophenoxide, 4-nitrophenoxide, 2,4-dinitrophenoxide, pentafluorophenoxide, 2-chloro-4-nitrophenoxide; 2,4-dichlorophenoxide; and 2,4,6-trichlorophenoxide.

A variety of methods can be used in the reaction between a compound of Formula (A) and a compound of Formula (B). In some embodiments, a compound of Formula (A) can be coupled to a compound of Formula (B) using a base, an acid or a Grignard reagent. In some embodiments, to facilitate the coupling, a Grignard reagent can be used. Suitable Grignard reagents are known to those skilled in the art and include, but are not limited to, alkylmagnesium chlorides and alkylmagnesium bromides. In some embodiments, the Grignard reagent can have the general formula of $R^X$—MgBr or $R^X$—MgCl, wherein $R^X$ can be an optionally substituted alkyl or an optionally substituted aryl. In some embodiments, a reaction between a compound of Formula (A) and a compound of Formula (B) can be conducted in the presence of a base. For example, a compound of Formula (B) can be added to a mixture of a compound of Formula (A) and a base.

Examples of bases include, but are not limited to, an optionally substituted amine base, such as an alkylamine (including mono-, di- and tri-alkylamines (for example, monoethylamine, diethylamine and triethylamine)), optionally substituted pyridines (such as collidine) and optionally substituted imidazoles (for example, N-methylimidazole)). In some embodiments, a reaction between a compound of Formula (A) and a compound of Formula (B) can be conducted in the presence of N-methylimidazole. In some embodiments, a reaction between a compound of Formula (A) and a compound of Formula (B) can be conducted in the presence of an acid. Example of a suitable acid is trifluoromethanesulfonic acid.

In some embodiments, a base, such as N-methyl imidazole (NMI), can displace the chloride of a compound of Formula (B) to form an intermediate. This intermediate can react with a compound of Formula (A) to form a compound of Formula VIII of the present invention. When the base is NMI, a compound of Formula (C) can be formed, wherein the counterion is a chloride anion.

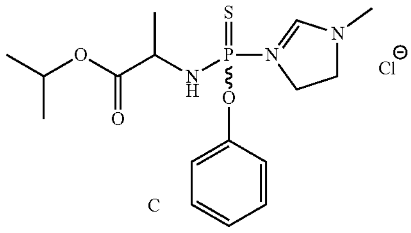

C

In some embodiments, the reaction between a compound of Formula (B) and a base, such as NMI, can provide a diastereomeric mixture of a compound of Formula Sp-C and a compound of Formula Rp-C:

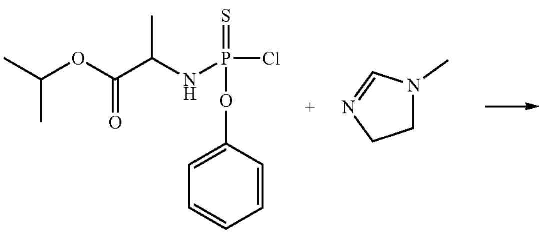

B

-continued

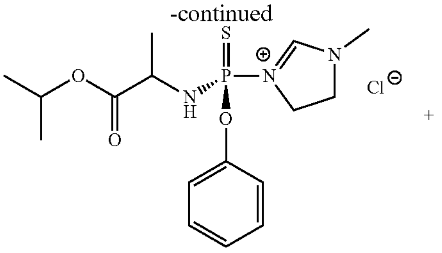

Sp-C

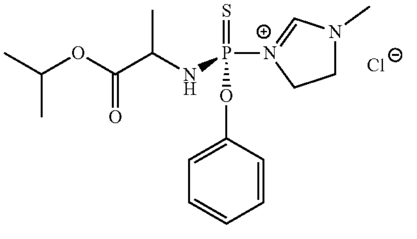

Rp-C

In some embodiments, the reaction between a compound of Formula (B) and a base can provide a compound of Formula (C) that can be enriched in one diastereomer, for example, the (S)-diastereomer with respect to the phosphorous (Compound Sp-C). In some embodiments, a reaction between a compound of Formula (B) and a base (such as NMI) as described herein can provide a compound of Formula (C) that can be ≥60%, ≥75%, ≥90% enriched in the (S)-diastereomer with respect to the phosphorous. In some embodiments, a reaction between a compound of Formula (B) and a base (such as NMI) as described herein can provide a diastereomeric mixture with a diastereomeric ratio of 2 or more:1 of a compound of Formula Sp-C to a compound of Formula Rp-C. In other embodiments, the reaction between a compound of Formula (B) and a base can provide a compound of Formula (C) that can be enriched in the (R)-diastereomer with respect to the phosphorous (Compound Rp-C). In other embodiments, a reaction between a compound of Formula (B) and a base (such as NMI) as described herein can provide a compound of Formula (C) that can be ≥60%, ≥75%, ≥90% enriched in the (R)-diastereomer with respect to the phosphorous. In other embodiments, a reaction between a compound of Formula (B) and a base (such as NMI) as described herein can provide a diastereomeric mixture with a diastereomeric ratio of 2 or more:1 of a compound of Formula Rp-C to a compound of Formula Sp-C.

In one embodiment, a reaction between a compound of Formula (B) and a base (such as NMI) as described herein can provide a compound of Formula (C) that can be ≥90% enriched in the (R)-diastereomer with respect to the phosphorous. In this embodiment, the Rp-C will react with Compound A to afford a compound of Formula VIII enriched with Sp-stereochemistry. For example, the general reaction is shown below using a representative compound of the present invention:

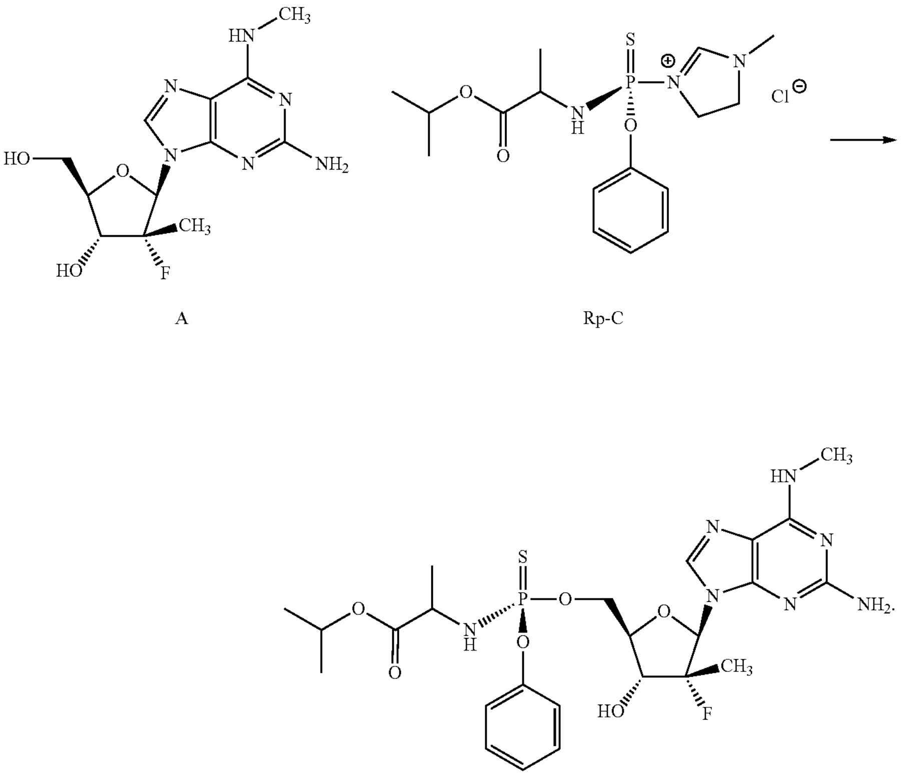

A

Rp-C

Sp-C

Alternatively, a compound of Formula VIII with no stereochemistry at the phosphorus can be separated using conventional methods, such as preparatory HPLC, to afford the Rp- and Sp-isomers:

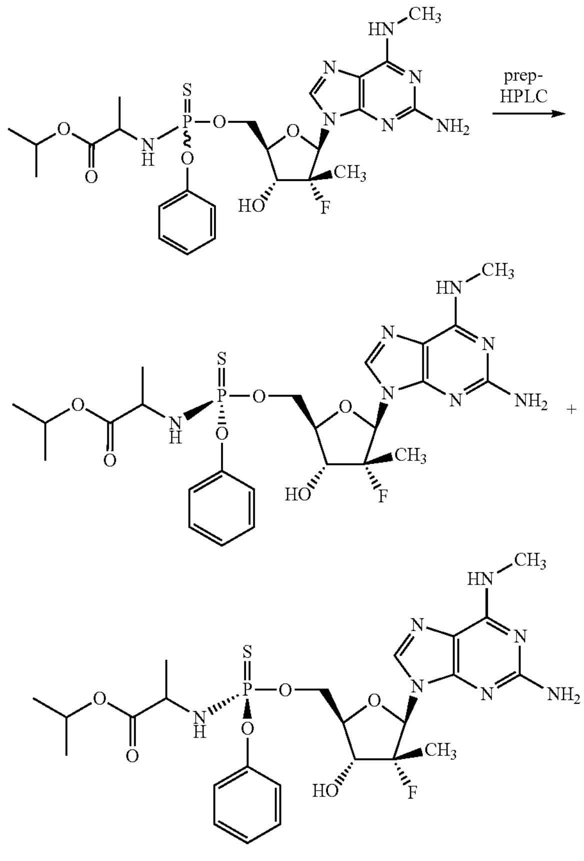

Treatment or Prevention of Mutated or Resistant forms of SARS-CoV-2

The complete genome of the SARS-CoV-2 virus was first reported on Jan. 23, 2020 (GenBank: MN988668.1—severe acute respiratory syndrome coronavirus 2 isolate 2019-nCoV WHU01, complete genome; see also Chen et al., RNA based mNGS approach identifies a novel human coronavirus from two individual pneumonia cases in 2019 Wuhan outbreak. Emerg Microbes Infect. 2020 Feb. 5; 9(1):313-319), and generally forms the basis for identifying the mutational rate for SARS-CoV-2. SARS-CoV-2, like other SARS-related coronaviruses, has shown a high mutation rate, and this mutation rate drives SARS-related coronavirus evolution and genome variability, thereby potentially enabling SARS-related coronaviruses such as SARS-CoV-2 to escape host immunity and to develop drug resistance.

Importantly, many of the initial treatments targeting SARS-CoV-2 were derived based on the initially reported genetic sequence, including the approved vaccines BNT162b2 (Pfizer, Inc. and BioNTech), mRNA-1273 (Moderna TX, Inc.), Regeneron antibodies, and convalescent plasma, and many early anti-viral drug candidates were assayed via drug-target site modeling and/or biological assays developed using the initially reported protein amino-acid sequences. Since the original report of the SARS-CoV-2 genomic sequence, a large number of SARS-CoV-2 variants have been identified, which may potentially affect the therapeutic efficacy of various treatments. For example, the large number of mutations recently identified in the structural spike protein has raised concerns that vaccine strategies could be rendered less effective due to mutational escape.

The accumulation of mutations in SARS-related coronaviruses such as SARS-CoV-2 may be several-fold. Like other RNA viruses, the mutation rate in SARS-related coronaviruses is substantially higher than DNA viruses, and the rate of mutation accumulation in RNA viruses can occur at six orders of magnitude greater than the rate of mutation of host cells. In addition, exposure to certain anti-viral drugs can result in the further enhancement of viral mutation accumulation due to the induction of mutations caused by the drug itself. For example, the use of mutagenic agents which depend on the introduction of mutations into the viral genome for inhibition may result in the introduction of drug-induced mutations which may not be initially fatal to the virus, allowing the virus to continue to replicate while further accumulating additional mutations. Alternatively, in the case of SARS-related coronaviruses, the use of drugs which rely on RNA replication chain termination may allow for the excision of the terminating nucleotide via the exonuclease activity of nsp14, which may be replaced with an imperfect base-pair match during replacement, resulting in the accumulation of further mutations in the genomic viral sequence.

The development of mutations, either naturally or drug-induced, can create a major obstacle to antiviral therapy. Mutagenic events which cause changes to drug target regions are common mechanism for the development of drug resistance to previously effective drugs (see Pucci et al., 5.17—Recent Epidemiological Changes in Infectious Diseases, Editor(s): Samuel Chackalamannil, David Rotella, Simon E. Ward, Comprehensive Medicinal Chemistry III, Elsevier, 2017, Pages 511-552).

It is difficult to predict mutational effects on drug effectiveness in non-target regions or in other viral proteins which may affect interaction between a drug and its orthosteric target site. For example, a mutation in the non-targeted domain of a protein may induce a slight structural change to a target site in that same protein which, while not negatively affecting the activity of protein in the virus, may reduce the effectiveness of drugs targeting the orthosteric binding region. Furthermore, a mutation in a different protein may affect the drug targeting orthosteric binding region due to allosteric protein-protein interactions during complex formation, which have been shown to be capable of generating allosteric perturbations through the interaction of protein structures from allosteric to orthosteric sites via propagation of an allosteric wave, leading to fine tuning of the conformational dynamics of the orthosteric site (see, e.g., Lu et al., Emergence of allosteric drug-resistance mutations: new challenges for allosteric drug discovery, Drug Discovery Today, Volume 25, Issue 1, 2020, Pages 177-184). This is especially true where a targeted domain is within a protein that actively interacts with multiple proteins, as occurs with the nsp12 protein, which interacts in complex formation with nsp7, nsp8, and multiple other non-structural and structural proteins during viral replication. There is insufficient information about SARS-related coronaviruses such as SARS-CoV-2 and their steric interactions as they mutate in various positions on the genome to be able to predict whether there will be a loss of drug efficacy against mutant strains.

By targeting the highly conserved region of the NiRAN-domain of nsp12, the impact of naturally-evolving mutants in acquiring resistance to NiRAN targeting agents is significantly reduced and therapeutic efficacy can be maintained. Furthermore, by targeting the NiRAN-domain for replication inhibition, the mechanisms associated with drug-induced mutagenesis are not relied on or implicated, thus reducing the potential for developing drug-induced viral mutants.

In some aspects, a method of treating or preventing a SARS-related coronavirus infection in a host, typically a human, in need thereof is provided by administering to the host an effective amount of a selected nucleotide drug that exhibits a mechanism of action which is the disruption of NiRAN-domain mediated RNA synthesis, wherein the SARS-related coronavirus infection is caused by a viral variant that has development a natural or drug-induced mutation. In some embodiments, the SARS-related coronavirus is SARS-CoV-2. In some embodiments, the viral variant has developed an acquired resistance to an anti-viral drug that does not rely on a mechanism of action which is the disruption of NiRAN-domain mediated RNA synthesis.

In some embodiments, the SARS-related coronavirus viral variant has a natural mutation or drug-induced mutation in a viral protein selected from an envelope (E) protein, membrane (M) protein, spike (S) protein, nsp1, nsp2, nsp3, nsp4, nsp5, nsp 6, nsp7, nsp8, nsp9, nsp10, nsp12, nsp13, nsp14, nsp15, nsp16, ORF1ab, ORF3a, ORF6, ORF7a, ORF7b, ORF8, and ORF10. In some embodiments, the viral variant has a mutation which results in the acquired resistance to one or more anti-viral drugs.

In some embodiments, the variant strain is a SARS-CoV-2 virus which has a deletion of the spike protein amino acids H69 and V70.

In some embodiments, the variant strain is a SARS-CoV-2 virus which has a spike protein amino acid substitution D614G.

In some embodiments, the variant strain is a SARS-CoV-2 virus which has a deletion of the spike protein amino acid Y144.

In some embodiments, the variant strain is a SARS-CoV-2 virus which has a spike protein amino acid substitution N501Y.

In some embodiments, the variant strain is a SARS-CoV-2 virus which has a spike protein amino acid substitution A570D.

In some embodiments, the variant strain is a SARS-CoV-2 virus which has a spike protein amino acid substitution P681H.

In some embodiments, the variant strain is a SARS-CoV-2 virus which has a spike protein amino acid substitution T716I.

In some embodiments, the variant strain is a SARS-CoV-2 virus which has a spike protein amino acid substitution S982A.

In some embodiments, the variant strain is a SARS-CoV-2 virus which has a spike protein amino acid substitution D1118H.

In some embodiments, the variant strain is a SARS-CoV-2 virus which has a premature stop codon mutation Q27stop in the protein product of ORFS.

In some embodiments, the variant strain is a SARS-CoV-2 virus which has a spike protein amino acid substitution K417N.

In some embodiments, the variant strain is a SARS-CoV-2 virus which has a spike protein amino acid substitution E484K.

In some embodiments, the variant strain is a SARS-CoV-2 virus which has a spike protein amino acid substitution K417N.

In some embodiments, the variant strain is a SARS-CoV-2 virus which has a spike protein amino acid substitution D215G.

In some embodiments, the variant strain is a SARS-CoV-2 virus which has a spike protein amino acid substitution A701V.

In some embodiments, the variant strain is a SARS-CoV-2 virus which has a spike protein amino acid substitution L18F.

In some embodiments, the variant strain is a SARS-CoV-2 virus which has a spike protein amino acid substitution R246I.

In some embodiments, the variant strain is a SARS-CoV-2 virus which has a spike protein deletion at amino acids 242-244

In some embodiments, the variant strain is a SARS-CoV-2 virus which has a spike protein amino acid substitution Y453F.

In some embodiments, the variant strain is a SARS-CoV-2 virus which has a spike protein amino acid substitution I692V.

In some embodiments, the variant strain is a SARS-CoV-2 virus which has a spike protein amino acid substitution M1229I.

In some embodiments, the variant strain is a SARS-CoV-2 virus which has a spike protein amino acid substitution N439K.

In some embodiments, the variant strain is a SARS-CoV-2 virus which has a spike protein amino acid substitution A222V.

In some embodiments, the variant strain is a SARS-CoV-2 virus which has a spike protein amino acid substitution S477N.

In some embodiments, the variant strain is a SARS-CoV-2 virus which has a spike protein amino acid substitution A376T.

In some embodiments, the variant strain is a SARS-CoV-2 virus which has a nsp12 protein amino acid substitution P323L.

In some embodiments, the variant strain is a SARS-CoV-2 virus which has a nsp12 protein amino acid substitution Y455I.

In some embodiments, the variant strain is a SARS-CoV-2 virus which has a Orf8 protein amino acid substitution R52I.

In some embodiments, the variant strain is a SARS-CoV-2 virus which has an ORF8 protein amino acid substitution Y73C.

In some embodiments, the variant strain is a SARS-CoV-2 virus which has a nucleocapsid (N) protein amino acid substitution D3L.

In some embodiments, the variant strain is a SARS-CoV-2 virus which has a nucleocapsid (N) protein amino acid substitution S235F.

In some embodiments, the variant strain is a SARS-CoV-2 virus which has a ORF1ab protein amino acid substitution T1001I.

In some embodiments, the variant strain is a SARS-CoV-2 virus which has a ORF1ab protein amino acid substitution A1708D.

In some embodiments, the variant strain is a SARS-CoV-2 virus which has a ORF1ab protein amino acid substitution 12230T.

In some embodiments, the variant strain is a SARS-CoV-2 virus which has a ORF1ab protein amino acid SGF 3675-3677 deletion.

In some embodiments, the variant strain is a SARS-CoV-2 virus which has a nsp12 protein amino acid substitution S861X, wherein X is any amino acid.

In some embodiments, the variant strain is a SARS-CoV-2 virus which has a nsp12 protein amino acid substitution F480V.

In some embodiments, the variant strain is a SARS-CoV-2 virus which has a nsp12 protein amino acid substitution V557L.

In some embodiments, the variant strain is a SARS-CoV-2 virus which has a nsp12 protein amino acid substitution D484Y.

In some embodiments, the variant strain is a SARS-CoV-2 virus which has a nsp12 protein amino acid substitution E802D.

In some embodiments, the variant strain is a SARS-CoV-2 virus which has a nsp12 protein amino acid substitution E802A.

In some embodiments, the SARS-CoV-2 has a nsp12 protein amino acid substitution F480X, wherein X=any amino acid.

In some embodiments, the SARS-CoV-2 has a nsp12 protein amino acid substitution V557X, wherein X=any amino acid.

In some embodiments, the SARS-CoV-2 has a nsp12 protein amino acid substitution D484X, wherein X=any amino acid.

In some embodiments, the SARS-CoV-2 has a nsp12 protein amino acid substitution P323L and a spike protein amino acid substitution D614G.

In some embodiments, the SARS-CoV-2 has a nsp2 protein amino acid substitution T85I and a ORF3a amino acid substitution Q57H.

In some embodiments, the SARS-CoV-2 has a nsp13 protein amino acid substitution P504L and Y541C.

In some embodiments, the SARS-CoV-2 has K417T, E484K, and N501Y mutations in the spike protein.

In some embodiments, the variant strain is a SARS-CoV-2 virus which includes a deletion of the spike protein amino acids 69-70, deletion of the spike protein amino acid Y144, the spike protein amino acid substitution N501Y, the spike protein amino acid substitution A570D, the spike protein amino acid substitution D614G, the spike protein amino acid substitution P681H, the spike protein amino acid substitution T716I, the spike protein amino acid substitution S982A, the spike protein amino acid substitution D1118H, and a premature stop codon mutation (Q27stop) in the protein product of ORFS.

In some embodiments, the variant strain is a SARS-CoV-2 virus which includes amino acid substitutions in the spike protein of N501Y, K417N, E484K, D80A, D215G, L18F, and R246I in the spike protein, and amino acid deletion at amino acids 242-244 of the spike protein.

In some embodiments, the variant strain is a SARS-CoV-2 variant strain and is selected from SARS-CoV-2 clade O, S, L, V, G, GH, or GR as described by Alm et al., "Geographical and temporal distribution of SARS-CoV-2 clades in the WHO European Region, January to June 2020". Euro Surveillance: Bulletin European Sur les Maladies Transmissibles=European Communicable Disease Bulletin. 25 (32).

In some embodiments, the variant strain is a SARS-CoV-2 variant strain and is selected from SARS-CoV-2 clade G614, S84, V251, 1378 or D392 as described by Guan et al., A genetic barcode of SARS-CoV-2 for monitoring global distribution of different clades during the COVID-19 pandemic. Int J Infect Dis. 2020 November; 100: 216-223.

In some embodiments, the variant strain is a SARS-CoV-2 variant strain and is selected from SARS-CoV-2 clade 19A, 19B, 20A, or 20C as described by Nextstrain: Genomic epidemiology of novel coronavirus—Global sub-sampling. Available from: https://nextstrain.org/ncov.

In some embodiments, the variant strain is a SARS-CoV-2 variant strain and is selected from SARS-CoV-2 lineage A, B, B.1, B.1.1, or B.1.177 as described by Rambaut et al., Phylogenetic Assignment of Named Global Outbreak LINeages (pangolin). San Francisco: GitHub. Available from: https://github.com/cov-lineages/pangolin; Rambaut et al. A dynamic nomenclature proposal for SARS-CoV-2 lineages to assist genomic epidemiology. Nat Microbiol. 2020 November; 5(11):1403-1407; Rambaut et al. SARS-CoV-2 lineages. Available from: https://cov-lineages.org/.

In some embodiments, the variant strain is a SARS-CoV-2 and is the "Cluster 5" variant, which includes the spike protein amino acid substitution D614G.

In some embodiments, the variant strain (as defined by the World Health Organization (WHO)) is the Alpha variant (Pango lineage: B.1.1.7).

In some embodiments, the variant strain (as defined by the World Health Organization (WHO)) is the Beta variant (Pango lineages: B.1.351, B.1.351.2, B.1.351.3).

In some embodiments, the variant strain (as defined by the World Health Organization (WHO)) is the Gamma variant (Pango Lineages: P.1, P.1.1, P.1.2).

In some embodiments, the variant strain (as defined by the World Health Organization (WHO)) is the Delta variant (Pango Lineages: B.1.617.2, AY.1, AY.2, AY.3).

In some embodiments, the variant strain (as defined by the World Health Organization (WHO)) is the Eta variant (Pango Lineages: B.1.525).

In some embodiments, the variant strain (as defined by the World Health Organization (WHO)) is the Iota variant (Pango Lineage: B.1.526).

In some embodiments, the variant strain (as defined by the World Health Organization (WHO)) is the Kappa variant (Pango Lineage: B.1.617.1).

In some embodiments, the variant strain (as defined by the World Health Organization (WHO)) is the Lambda variant (Pango Lineage: C.37).

In some embodiments, the variant strain (as defined by the World Health Organization (WHO)) is the Epsilon variant (Pango Lineages: B.1.427, B.1.429).

In some embodiments, the variant strain (as defined by the World Health Organization (WHO)) is the Zeta variant (Pango Lineage: P.2).

In some embodiments, the variant strain (as defined by the World Health Organization (WHO)) is the Theta variant (Pango Lineage: P.3).

In some embodiments, the variant strain (as defined by the World Health Organization (WHO)) is the Mu variant (Pango Lineage: B.1.621).

Additional SARS-CoV-2 variants targeted by the compounds and methods described herein include Pango Lineages P.2, P.3, R.1, R.2, B.1.466.2, B.1.1.318, B.1.1.519, C.36.3, C.36.3.1, B.1.214.2, B.1.1.523, B.1.617.3, B.1.619, B.1.620, B.1.621, A.23.1 (+E484K), A.27, A.28, C.16, B.1.351 (+P384L), B.1351 (+E516Q), B.1.1.7 (+L452R), B.1.1.7 (+S494P), C.36 (+L452R), AT.1, B.1.526.1, B.1.526.2, B.1.1.318, B.1.1.519, AV.1, P.1 (+P681H), B.1.671.2 (+K417N), and C.1.2.

In some embodiments, the variant strain is a SARS-CoV-2 variant strain and is VUI 202012/01 (Variant Under Investigation, year 2020, month 12, variant 01) (also known as B.1.1.7 lineage and 20B/501Y.V1), which has been defined by multiple spike protein changes including deletion of the spike protein amino acids 69-70, deletion of the spike protein amino acid Y144, the the spike protein amino acid substitution D614G, the spike protein amino acid substitution P681H, the spike protein amino acid substitution T716I, the spike protein amino acid substitution S982A, the spike protein amino acid substitution D1118H, and a premature stop codon mutation (Q27stop) in the protein product of ORFS.

In some embodiments, the variant strain is a SARS-CoV-2 variant strain and is the B.1.351 lineage variant (also known as 501.V2, 20C/501Y.V2), which includes several mutations in the receptor-binding domain (RBD) in the spike protein: N501Y, K417N, and E484K, which allows the virus to attach more easily to human cells, as well as amino acid substitution D80A in the spike protein, an amino acid substitution D215G in the spike protein, an amino acid substitution A701V in the spike protein, an amino acid substitution L18F in the spike protein, an amino acid substitution R246I in the spike protein, and amino acid deletion at amino acids 242-244 of the spike protein.

In some embodiments, the variant strain is a SARS-CoV-2 variant strain and is the B.1.1.207 lineage variant, which includes a P681H mutation in the spike protein.

In some embodiments, the variant strain is a SARS-CoV-2 variant strain and is the P.1 lineage variant, which includes K417T, E484K, and N501Y mutations in the spike protein.

In some embodiments, the variant strains are a SARS-CoV-2 variant strain and is the B.1.427/B1.428 variant, which includes a L452R mutation in the spike protein.

In some embodiments, the variant strain is a SARS-CoV-2 variant strain and is the Danish mink variant which includes an amino acid deletion of H69 and V70 in the spike protein, and an amino acid substitution Y453F in the spike protein.

In some embodiments, the variant strain is a SARS-CoV-2 variant strain and is the Danish mink cluster 5 variant, which includes an amino acid deletion of H69 and V70 in the spike protein, an amino acid substitution Y453F in the spike protein, an amino acid substitution I692V in the spike protein, and an amino acid substitution M1229I in the spike protein.

In some embodiments, the variant strain is a SARS-CoV-2 variant strain and includes an amino acid deletion of H69 and V70 in the spike protein, and an amino acid substitution N439K in the spike protein.

In some embodiments, the variant strain is a SARS-CoV-2 variant strain and is the Nexstrain cluster 20A.EU1 variant, which includes an amino acid substitution A222V in the spike protein.

In some embodiments, the variant strain is a SARS-CoV-2 variant strain and is the Nexstrain cluster 20A.EU2 variant, which includes an amino acid substitution S477N in the spike protein, and an amino acid substitution A376T in the nucleocapsid protein.

In some embodiments, the variant strain is a SARS-CoV-2 variant strain and has one or more of the following mutations selected from: an amino acid substitution T1001I in the protein product of ORF1ab; an amino acid substitution A1708D in the protein product of ORF1a; an amino acid substitution 12230T in the protein product of ORF1ab; a deletion of amino acids SGF at 3675-3677 in the protein product of ORF1ab; an amino acid substitution G251V in the protein product of ORF3a; an amino acid substitution S24L in the protein product of ORF8; an amino acid substitution R52I in the protein product of ORF8; an amino acid substitution Y73C in the protein product of ORF8; an amino acid substitution L84S in the protein product of ORF8; an amino acid substitution P323L in the nsp12 domain; an amino acid substitution Y455I in the nsp12 domain; an amino acid substitution Q57H in the protein product of ORF3a; an amino acid substitution $R^{27C}$ in nsp2; an amino acid substitution V198I in nsp2; an amino acid substitution T851 in nsp2; an amino acid substitution P585S in nsp2; an amino acid substitution I559V in nsp2; an amino acid substitution M33I in nsp4; an amino acid substitution G15S in nsp5; an amino acid substitution L37F in nsp6; an amino acid substitution Y541C in nsp13; an amino acid substitution P504L in nsp13; an amino acid substitution S477N in the spike protein; an amino acid substitution N439K in the spike protein; an amino acid substitution N501Y in the spike protein; an amino acid substitution Y453F in the spike protein; an amino acid substitution K417N in the spike protein; an amino acid substitution E484K in the spike protein; an amino acid substitution A222V in the spike protein; an amino acid substitution S98F in the spike protein; an amino acid substitution D80Y in the spike protein; an amino acid substitution A626S in the spike protein; an amino acid substitution V1122L in the spike protein; an amino acid substitution A570D in the spike protein; an amino acid substitution P681H in the spike protein; an amino acid substitution V1122L in the spike protein; an amino acid substitution T716I in the spike protein; an amino acid substitution S982A in the spike protein; an amino acid substitution D1118H in the spike protein; an amino acid substitution E583D in the spike protein; an amino acid substitution V483A in the spike protein; an amino acid substitution Q675R in the spike protein; an amino acid substitution A344S in the spike protein; an amino acid substitution T345S in the spike protein; an amino acid substitution R346K in the spike protein; an amino acid substitution A348S in the spike protein; an amino acid substitution A348T in the spike protein; an amino acid substitution N354K in the spike protein; an amino acid substitution S359N in the spike protein; an amino acid substitution V367F in the spike protein; an amino acid substitution V382L in the spike protein; an amino acid substitution P384L in the spike protein; an amino acid substitution P384S in the spike protein; an amino acid substitution T385S in the spike protein; an amino acid substitution V395I in the spike protein; an amino acid substitution R403K in the spike protein; an amino acid substitution D405V in the spike protein; an amino acid substitution Q414P in the spike protein; an amino acid substitution Q414E in the spike protein; an amino acid substitution I418V in the spike protein; an amino acid substitution L441I in the spike protein; an amino acid substitution R457K in the spike protein; an amino acid substitution K458Q in the spike protein; an amino acid substitution P463 S in the spike protein; an amino acid substitution A475V in the spike protein; an amino acid substitution G476S in the spike protein; an amino acid substitution T478A in the spike protein; an amino acid substitution P479L in the spike protein; an amino acid substitution V483A in the spike protein; an amino acid substitution F490L in the spike protein; an amino acid substitution Q493L in the spike protein; an amino acid substitution A520S in the spike protein; an amino acid substitution L5F in the spike protein; an amino acid substitution P521R in the spike protein; an amino acid substitution A522S in the spike protein; an amino acid substitution A831V in the spike protein; an amino acid substitution D839Y in the spike protein; an amino acid substitution D839N in the spike protein; an amino acid substitution D839E in the spike protein; an amino acid substitution L8V in the spike protein; an amino acid substitution L8W in the spike protein; an amino acid substitution H49Y in the spike protein; a deletion of amino acid H69 in the spike protein; a deletion of amino acid V70 in the spike protein; a deletion of amino acid Y144 in the spike protein; an amino acid substitution D3L in the nucleocapsid protein; an amino acid substitution S253F in the nucleocapsid protein; an amino acid substitution RG203KR in the nucleocapsid protein; an amino acid substitution G214C in the nucleocapsid protein; an amino acid substitution S194L in the nucleocapsid protein; an amino acid substitution F377L in the nsp14 protein; an amino acid substitution K1186R in nsp3; or an amino acid substitution A58T in nsp3.

In some embodiments, the SARS-CoV-2 variant contains a L452R mutation in the spike protein.

In some embodiments, the SARS-CoV-2 variant contains one or more of the following mutations in the envelope (E) protein: S68F; L73F; P71L; S55F; R69I; T9I; V24M; D72H; T301; S68C; V75L; V58F; V75F; or L21F; and combinations thereof.

In some embodiments, the SARS-CoV-2 variant contains one or more of the following mutations in the membrane (M) protein: T175M; D3G; V23L; W31C; A2V; V70F; W75L; M109I; I52T; L46F; V70I; D3Y; K162N; H125Y; K15R; D209Y; R146H; R158C; L87F; A2S; A69S; S214I; T2081; L124F; or S4F; and combinations thereof.

In some embodiments, the SARS-CoV-2 variant contains one or more of the following mutations in the nucleocapsid (N) protein: RG203KR; S194L; S197L; P13L; D103Y; S1931; S188L; I292T; S202N; D401Y; S190I; D22G; A208G; T2051; S183Y; S33I; D81Y; T393I; A119S; D377Y; S37P; T247I; A156S; D128Y; P199L; R195I; P207L; E62V; R209T; T362I; G18C; T24N; R185C; S180I; M234I; Q9H; P383L; A35S; P383S; D348H; K374N; R32H; S327L; G179C; G238C; A55S; S190G; H300Y; A119V; D144Y; L139F; P199S; P344S; P6L; R203K; P364L; R209I; S188P; A35V; K387N; P122L; R191C; R195K; T391I; A252S; Q418L; T271I; T325I; G18V; L161F; Q289H; R203S; P162L; D340N; K373N; P168Q; A211V; D3L; G212V; K370N; P151L; T334I; A359S; G34W; P67T; R203M; D144N; R191L; S232I; D402Y; P168S; S187L; T366I; A152S; A381T; N140T; T198I; A251V; A398V; A90S; D348Y; D377G; G204R; G243C; G34E; Q229H; R185L; T24I; T379I; A134V; N196I; P365S; Q384H; R276I; S235F; D216A; M210I; M322I; P20S; Q389H; R209 deletion; or V246I; and combinations thereof.

In some embodiments, the SARS-CoV-2 variant contains one or more of the following mutations in the nsp1 protein: M85; D75E; G82 deletion; V84 deletion; P80 deletion; H83 deletion; V86 deletion; H81 deletion; E87 deletion; L88 deletion; K141 deletion;A79 deletion;V89 deletion; V56I; R124C; D75G; A90 deletion; Y118C; D139N; Y136 deletion; G30D; R24C; D139Y; E37K; H45Y; H110Y; G52S; I71V; D156 deletion; A76T; E37D; S135 deletion; S166G; A138T; F157 deletion; G49C; M85I; or D144A; and combinations thereof.

In some embodiments, the SARS-CoV-2 variant contains one or more of the following mutations in the nsp10 protein: D64E; P136S; A104V; A32V; T12I; T111I; P84S; T51I; I55V; T102I; or T51A; and combinations thereof.

In some embodiments, the SARS-CoV-2 variant contains one or more of the following mutations in the nsp12 protein: P323L; T141I; A449V; S434F; M666I; H613Y; S647I; M380I; E922D; M629I; G774S; M6011; E436G; N491S; Q822H; A443V; T85I; A423V; M463I; T26I; A656T; M668I; T8061; T276M; T801N; V588L; K267N; V880I; K718R; L514F; F415S; T252N; Y38H; E744D; H752Q; I171V; S913L; A526V; A382V; G228C; P94L; E84K; K59N; P830S; T9081; P21S; D879Y; G108D; K780N; R279S; D258Y; T259I; K263N; D284Y; Q292H; T293I; N297S; V299F; D304Y; T319I; F321L; P328S; V330E; I333T; G337C; T344I; Y346H; L351P; V354L; Q357H; E370G; L372F; A400S; T4021; V405F; V410I; D418N; K426N; K430N; V435F; Q444H; D445G; A448V; R457C; P461T; C464F; I466V; V473F; K478N; D481G; D517G; D523N; A529V; P537S; S549N; A555V; C563F; M566I; A581T; G584V; A585T; G596S; T6041; S6071; D608G; V6091; M615V; W617L; M629V; I632V; L636F; L638F; A639V; T643I; T644M; L648F; V667I; A699S; N713S; H725; N734T; D736N; V737F; T739I; V742M; N743S; M756I; L758I; A771V; L775V; A777T; K780T; F793L; T801I; T803A; H810Y; G823C; D825Y; V827A; Y828H; V848L; T870I; K871R; N874D; Q875R; E876D; H882Y; H892Y; D901Y; M9061; N909D; T912N; P918S; E919D; A923T; F480V; V557L; D484Y; E802D, E802A; or S433G; and combinations thereof.

In some embodiments, the SARS-CoV-2 variant contains one or more of the following mutations in the nsp13 protein: Y541C; P504L; A18V; R392C; P47L; S485L; L297P; H290Y; T127I; L176F; V1931; V570L; D260Y; V49I; Q518H; S468L; A598V; D204Y; S74L; T588I; G206C; V226L; V348L; M576I; A302D; P53S; T481M; K524N; A338V; P419S; V479F; P77L; V169F; N124S; P78S; S80G; V496L; A4V; T413I; A296S; A368S; K460R; L297F; P172S; A302S; P402S; T530I; L428F; P504S; A368V; D458Y; P364S; S74P; T416A; A568V; M474I; S166L; S350L; D344N; E341D; I432T; L581F; S38L; T250I; Y253H; A509V; E244D; H164Y; S74A; T141I; V356F; E319D; E365D; G170S; L526F; R155C; or Y396C; and combinations thereof.

In some embodiments, the SARS-CoV-2 variant contains one or more of the following mutations in the nsp14 protein: A320V; F233L; T250I; V182L; A225V; R289C; A274S; P24L; 1150T; S374A; H26Y; L177F; L157F; T16I; A482V; P297S; V120A; S255I; P203L; A23 deletion; K311N; M72I; V290F; F431L; K349N; M58I; P140S; R205C; T193A; L409F; P443S; Y260C; D345G; E204D; R163C; R81K; T524I; T1131; T31I; L493F; A119V; D345Y; M5011; A360V; A371V; T2061; V287F; A360S; I74T; M315I; P142L; or Q343K; and combinations thereof.

In some embodiments, the SARS-CoV-2 variant contains one or more of the following mutations in the nsp15 protein: V320L; A217V; V22L; V172L; D219N; P205S; V127F; Q19H; M218 deletion; A92V; D282G; I252V; T33I; G129S; L331F; A81V; V69L; S312F; T325I; A171V; R206S; D272Y; D87N; S288F; K109R; P270S; P65S; D267Y; D128Y; E215I; T144I; S261L; S287L; T112I; E260K; P205L; S161I; V66L; D39Y; or T114A; or combinations thereof.

In some embodiments, the SARS-CoV-2 variant contains one or more of the following mutations in the nsp16 protein: S33R; K160R; P134S; Q28K; T195I; V78G; T35I; G265V; K249N; A204S; K182N; R287I; A188S; A116V; T1401; L111F; M270T; R216N; A188V; A34V; D108N; L163F; L163H; M171; T91M; A226S; G77R; L126F; N298L; R216S; T48I; Q238H; or R279K; and combinations thereof.

In some embodiments, the SARS-CoV-2 variant contains one or more of the following mutations in the nsp2 protein: T85I P585S; I559V; D268; G212D; V198I; H237R; F10L; G339S; T1661; R27C; L271F; S211F; P91S; G199E; T371I; A336V; 1120F; S122F; A476V; S138L; V480A; T388I; T634I; P129S; R218C; I188T; T1701; P568L; E574A; I367V; H208Y; S99F; T429I; A306V; M405V; P129L; R222C; T44I; Q275H; R380C; A360V; A361V; G115C; L353F; H237Y; L462F; E261G; R4C; S263F; T573I; A318V; G262V; P624L; S430L; T422I; A357S; I100V; E272G; L400F; A192V; D464A; E172D; G262S; L501F; S369F; E172K; G465S; K219R; A411V; A522V; H194Y; S32L; F437L; P181S; P446L; G115V; H532Y; N92H; P13S; A159V; A184S; A306S; I273T; L274F; P13L; R370H; T223I; T590I; E453D; H145Y; K618N; S301F; T153M; V244I; V530I; A127V; L24F; P191L; Q182L; S196L; S248G; S378F; T1391; T434I; A205V; A375V; A411S; C51Y; F300L; M135T; P568S; Q496H; S348P; T412I; T528I; T547I; V447F; or V577I; and combinations thereof.

In some embodiments, the SARS-CoV-2 variant contains one or more of the following mutations in the nsp3 protein: A58T; T1198K; T428I; P153L; S1197R; D218E; S1424F; A1431V; S1285F; P74L; Q1884H; P1326L; L1221F; P141S; P1103S; S126L; Y916H; L557F; E391D; A1311V; 5650F; P1103L; Y952H; P3405; A534V; P17875; L1791F; N15875; S371N; K1693N; G282V; P278S; T1335I; A1711V; K19R; A994D; K1325R; P822L; K412N; A465V; T10041; T8081; G489D; S1699F; M1436V; 51265R; V1768G; A231V; M951I; K384N; T12881; Q966H; R1614K; T1036I; T1306I; A1179V; P395L; N1785D; P679L; S166G; A1769V; T181I; L1718F; P822S; T1022I; A1381V; A602T; 11720V; K837N; T73I; A1033V; S1204; C1223Y; P389L; T398A; M1441I; M494I; T13031; T181A; P1228L; R1135K; V267F; A1883V; A655V; S1296F; T686I; L198I; P1403A; L781F; T1046A; A1215V; E374D; I205 deletion; V477F; E324K; 1707V; P109L; P1558L; P74S; S1212L; 51807F; T819I; T864I; H1000Y; P340L; S697F; T1189I; A480V; D729Y; K1771R; S1717L; T749I; M829I; Q172R; T1482I; A1395V; I385T; M560I; S1206L; S1699P; T1269I; T779I; V13151; V1795F; V325F; A1892V; A579V; E493G; H1274Y; S1467F; T10631; T350I; V61F; A1736V; K1804N; R646W; T583I; T611I; V1243I; V190I; A41V; H290Y; H295Y; H342Y; L1244F; Q128H; V16731; A1305V; A15265; E948K; L72F; P1255; P402T; A1766V; D1214N; E1271D; G1440D; G283D; K1211N; K902N; K945N; L18395; L312F; N12635; P12925; 51670F; S743A; T771I; V1936I; A1262V; A1321V; A358V; A41T; C55Y; G12735; K463E; K497Q; P10445; R30K; S1375F; S1682F; T1331; T13481; 4651; T1830I; T237I; V1248L; A225V; A496V; G1217R; I1816T; L956I; N1369T; N506S; P1535; P2L; T12751; T1459I; V1234M; E595D; F90L; G15855; H1307Y; 11409V; L1034V; L1328F; L292F; N1264; P1326T; S1197G; T1456I; T64I; T7031; T720I; T820I; V1229F; V234I; A1279V; A333V; A545; D1121G; D1761N; E731D; I1672T; I789V; K1037R; K487N; L142F; N1177H; P1228S; P723S; Q180H; Q474R; Q940L; 5370L; T11801; T275I; T422I; T526I; T724I; V1434G; or V207L; or combinations thereof.

In some embodiments, the SARS-CoV-2 variant contains one or more of the following mutations in the nsp4 protein: F308Y; T295I; M33I; A307V; A457V; G309C; L360F; A231V; H313Y; K399E; V20F; 5137L; S34F; A380V; H470Y; T2041; S336L; L264F; L438F; M33L; 5209F; C296S; L475I; G79V; T327N; T350I; L206F; M324I; E230G; L436 deletion; T237I; T492I; A260V; A446V; M458I; 5395G; 5481L; H36Y; T73I; L323F; L349F; S59F; T214I; or T601; and combinations thereof.

In some embodiments, the SARS-CoV-2 variant contains one or more of the following mutations in the nsp5 protein: G15S; D248E; K90R; L89F; A266V; P1085; A70T; A129V; T45I; G715; L75F; A191V; L220F; N274D; L67F; P241L; K236R; V157L; K61R; P184S; S62Y; T21I; L50F; P108L; S254F; T93I; A255V; A94V; P132S; A234V; A260V; R60C; P96L; V247F; or T199I; and combinations thereof.

In some embodiments, the SARS-CoV-2 variant contains one or more of the following mutations in the nsp6 protein: L37F; G277S; A46V; L75F; F37 deletion; T10I; V149F; L260F; Q208H; M83I; A136V; V1451; N156D; M86I; Y153C; G188V; L230I; F34 deletion; I189V; R233H; V114A; L33F; A287V; H11Y; A287T; A51V; G188S; I162T; M126V; M183I; N40Y; 5104; F35L; M58L; or V84F; and combinations thereof.

In some embodiments, the SARS-CoV-2 variant contains one or more of the following mutations in the nsp7 protein: S25L; S26F; L71F; S15T; M75I; or N78S; and combinations thereof.

In some embodiments, the SARS-CoV-2 variant contains one or more of the following mutations in the nsp8 protein: M129I; I156V; T1451; R51C; T1231; L95F; T89I; P133S; S41F; K37N; T141M; V34F; R51L; A14T; A74V; 1107V; A16V; P10S; A194V; D30G; A152V; or T1871; and combinations thereof.

In some embodiments, the SARS-CoV-2 variant contains one or more of the following mutations in the nsp9 protein: T77I; T109I; L42F; T34I; T19I; M101V; T62I; or T19K; and combinations thereof.

In some embodiments, the SARS-CoV-2 variant contains one or more of the following mutations in the protein product of ORF10: L17P; A28V; P10S; I4L; S23F; R24C; *39Q; Q29 stop; Y14C; R20I; or A8V; and combinations thereof.

In some embodiments, the SARS-CoV-2 variant contains one or more of the following mutations in the protein product of ORF3a: Q57H; G251V; V13L; G196V; A54S; A99V; H93Y; T14I; L46F; Q185H; T1751; Q213K; L108F; K61N; Y264C; A72S; T1511; A23S; G224C; K67N; S171L; W69L; H78Y; K136E; L86F; W131C; L147F; 558N; Y91H; I63T; D155Y; G172C; P240L; Y189C; W131R; KN136NY; T223I; G100C; 5195Y; V112F; W131L; G44V; D27H; G174C; K21N; S165F; L65F; T229I; T89I; S74F; A99S; G254R; H204N; K75N; F43L; L53F; Q38P; S26L; S40L; M260I; V256 deletion; K16N; Q218R; S253P; V163L; W69C; A23V; L41F; L106F; V55F; V88A; A99D; E239D; L52F; T24I; A31T; D27Y; I186V; L73F; P104L; D22Y; F114V; L95F; P240S; P42L; T268M; or T32I; and combinations thereof.

In some embodiments, the SARS-CoV-2 variant contains one or more of the following mutations in the protein product of ORF6: I33T; W27L; D53G; F22 deletion; P57L; D61Y; D61L; K42N; D53Y; H3Y; I32T; or R20S; or combinations thereof.

In some embodiments, the SARS-CoV-2 variant contains one or more of the following mutations in the protein product of ORF7a: S81L; ABT; L96F; A50V; V104F; Q62 stop; S83L; E16D; T14I; T28I; V93F; G38V; H47Y; T39I; T120S; Q62 deletion; Q62L; S37T; V104; P34S; P99L; T120I; V108L; H73Y; V24F; V29L; A13T; or LSF; or combinations thereof.

In some embodiments, the SARS-CoV-2 variant contains one or more of the following mutations in the protein product of ORF7b: C41F; T401; A43V; L11F; S31L; C41 deletion; H42; H42L; SSL; L20F; L32F; E33 stop; A15S; or F13 deletion; and combinations thereof.

In some embodiments, the SARS-CoV-2 variant contains one or more of the following mutations in the protein product of ORFS: E110 stop; G66 deletion; S69L; T11I; F104L; F120L; G8R; P38S; D119E; I10S; or I39V; and combinations thereof.

In some embodiments, the SARS-CoV-2 variant contains one or more of the following mutations in the spike protein: D614G; D936Y; P1263L; LSF; N439K; R21I; D839Y; L54F; A879S; L18F; F1121L; R847K; T478I; A829T; Q675H; S477N; H49Y; T29I; G769V; G1124V; V1176F; K1073N; P479S; S1252P; Y145 deletion; E583D; R214L; A1020V; Q1208H; D215G; H146Y; S98F; T95I; G1219C; A846V; I197V; R102I; V367F; T572I; A1078S; A831V; P1162L; T73I; A845S; G1219V; H245Y; L8V; Q675R; S254F; V483A; Q677H; D138H; D80Y; M1237T; D1146H; E654D; H655Y; SSOL; S939F; S943P; G485R; Q613H; T76I; V341I; M153I; S221L; T859I; W258L; L242F; P681L; V289I; A520S; V1104L; V1228L; L176F; M1237I; T3071; T716I; L141; M1229I; A1087S; P26S; P330S; P384L; R765L; S940F; T323I; V826L; E1202Q; L1203F; L611F; V615I; A262S; A522V; A688V; A706V; A892S; E554D; Q836H; T1027I; T22I; A222V; A27S; A626V; C1247F; K1191N; M731I; P26L; S1147L; S1252F; S255F; V1264L; V308L; D80A; I670L; P251L; P631S; *1274Q; A344S; A771S; A879T; D1084Y; D253G; H1101Y; L1200F; Q14H; Q239K; A623V; D215Y; E1150D; G476S; K77M; M177I; P812S; S704L; T51I; T547I; T791I; V1122L; Y145H; D574Y; G142D; G181V; I834T; N370S; P812L; S12F; T791P; V90F; W152L; A292S; A570V; A647S; A845V; D1163Y; G181R; L84I; L938F; P1143L; P809S; R78M; T1160I; V1133F; V213L; V615F; A831V; D839Y; D839N; D839E; S943P; P1263L; or V622F; and combinations thereof.

In some embodiments, the targeted SARS-CoV-2 variant targeted for treatment comprises at least the following mutations in the spike (S) protein: N501Y, D614G, and P681H.

In some embodiments, the targeted SARS-CoV-2 variant targeted for treatment comprises at least the following mutations in the spike (S) protein: E484K, N501Y, D614G, and P681H.

In some embodiments, the targeted SARS-CoV-2 variant targeted for treatment comprises at least the following mutations in the spike (S) protein: K417N, E484K, N501Y, D614G, and A701V.

In some embodiments, the targeted SARS-CoV-2 variant targeted for treatment comprises at least the following mutations in the spike (S) protein: K417T, E484K, N501Y, D614G, and H655Y.

In some embodiments, the targeted SARS-CoV-2 variant targeted for treatment comprises at least the following mutations in the spike (S) protein: L452R, T478K, D614G, and P681R.

In some embodiments, the targeted SARS-CoV-2 variant targeted for treatment comprises at least the following mutations in the spike (S) protein: E484K, D614G, and Q677H.

In some embodiments, the targeted SARS-CoV-2 variant targeted for treatment comprises at least the following mutations in the spike (S) protein: E484K, N501Y, D614G, and P681H.

In some embodiments, the targeted SARS-CoV-2 variant targeted for treatment comprises at least the following mutations in the spike (S) protein: L452R, E484Q, D614G, and P681R.

In some embodiments, the targeted SARS-CoV-2 variant targeted for treatment comprises at least the following mutations in the spike (S) protein: S477N, E484K, D614G, and P681H.

In some embodiments, the targeted SARS-CoV-2 variant targeted for treatment comprises at least the following mutations in the spike (S) protein: R346K, E484K, N501Y, D614G, and P681H.

In some embodiments, the targeted SARS-CoV-2 variant targeted for treatment comprises at least the following mutations in the spike (S) protein: L452Q, F490S, and D614G.

In some embodiments, the targeted SARS-CoV-2 variant targeted for treatment comprises at least the following mutations in the spike (S) protein: L452R, E484Q, D614G, and P681R.

In some embodiments, the targeted SARS-CoV-2 variant targeted for treatment comprises at least the following mutations in the spike (S) protein: Q414K, N450K, ins214TDR, and D614G.

In some embodiments, the targeted SARS-CoV-2 variant targeted for treatment comprises at least the following mutations in the spike (S) protein: V367F, E484K, and Q613H.

In some embodiments, the targeted SARS-CoV-2 variant targeted for treatment comprises at least the following mutations in the spike (S) protein: L452R, N501Y, A653V, and H655Y.

In some embodiments, the targeted SARS-CoV-2 variant targeted for treatment comprises at least the following mutations in the spike (S) protein: E484K, N501T, and H655Y.

In some embodiments, the targeted SARS-CoV-2 variant targeted for treatment comprises at least the following mutations in the spike (S) protein: L452R, and D614G.

In some embodiments, the targeted SARS-CoV-2 variant targeted for treatment comprises at least the following mutations in the spike (S) protein: P384L, K417N, E484K, N501Y, D614G, and A701V.

In some embodiments, the targeted SARS-CoV-2 variant targeted for treatment comprises at least the following mutations in the spike (S) protein: K417N, E484K, N501Y, E516Q, D614G, and A701V.

In some embodiments, the targeted SARS-CoV-2 variant targeted for treatment comprises at least the following mutations in the spike (S) protein: L452R, N501Y, D614G, and P681H.

In some embodiments, the targeted SARS-CoV-2 variant targeted for treatment comprises at least the following mutations in the spike (S) protein: S494P, N501Y, D614G, and P681H.

In some embodiments, the targeted SARS-CoV-2 variant targeted for treatment comprises at least the following mutations in the spike (S) protein: L452R, D614G, and Q677H.

In some embodiments, the targeted SARS-CoV-2 variant targeted for treatment comprises at least the following mutations in the spike (S) protein: E484K, D614G, N679K, and ins679GIAL.

In some embodiments, the targeted SARS-CoV-2 variant targeted for treatment comprises at least the following mutations in the spike (S) protein: E484K, D614G, and A701V.

In some embodiments, the targeted SARS-CoV-2 variant targeted for treatment comprises at least the following mutations in the spike (S) protein: L452R, and D614G.

In some embodiments, the targeted SARS-CoV-2 variant targeted for treatment comprises at least the following mutations in the spike (S) protein: S477N, and D614G.

In some embodiments, the targeted SARS-CoV-2 variant targeted for treatment comprises at least the following mutations in the spike (S) protein: E484K, D614G, and P681H.

In some embodiments, the targeted SARS-CoV-2 variant targeted for treatment comprises at least the following mutations in the spike (S) protein: E484K, and D614G.

In some embodiments, the targeted SARS-CoV-2 variant targeted for treatment comprises at least the following mutations in the spike (S) protein: T478K, and D614G.

In some embodiments, the targeted SARS-CoV-2 variant targeted for treatment comprises at least the following mutations in the spike (S) protein: N439K, E484K, D614G, and P681H.

In some embodiments, the targeted SARS-CoV-2 variant targeted for treatment comprises at least the following mutations in the spike (S) protein: D614G, E484K, H655Y, K417T, N501Y, and P681H.

In some embodiments, the targeted SARS-CoV-2 variant targeted for treatment comprises at least the following mutations in the spike (S) protein: L452R, T478K, D614G, P681R, and K417N.

In some embodiments, the targeted SARS-CoV-2 variant targeted for treatment comprises at least the following mutations in the spike (S) protein: D614G, E484K, H655Y, N501Y, N679K, and Y449H.

In some embodiments, the targeted SARS-CoV-2 variant targeted for treatment comprises at least the following mutations in the spike (S) protein: T19R, T951, G142D, E156del, F157del, R158G, L452R, T478K, D614G, P681R, and D950N.

In some embodiments, the targeted SARS-CoV-2 variant targeted for treatment comprises at least the following mutations in the spike (S) protein: T19R, V70F, T951, G142D, E156del, F157del, R158G, A222V, W258L, K417N, L452R, T478K, D614G, P681R, and D950N.

Treatment of Anti-Viral Drug Resistant SARS-CoV-2 Strains

In some aspects, a method of treating or preventing a SARS-related coronavirus in a host, typically a human, in need thereof is provided by administering to a host in need thereof an effective amount of a selected nucleotide drug that exhibits a mechanism of action which is the disruption of NiRAN-domain mediated RNA synthesis, wherein the SARS-related coronavirus is caused by a variant strain of SARS-related coronavirus that has developed an acquired resistance to one or more anti-viral drugs. In some embodiments, the SARS-related coronavirus is SARS-CoV-2.

In some embodiments, the variant strain has developed a resistance to an anti-viral drug selected from remdesivir, molnupiravir, levovir (clevidine), galidesivir, ribavirin, ritonavir, asc09 (Ascletis), favilavir, favipiravir, T-705, lopinavir, maraviroc, sofosbuvir, darunavir, umifenovir, neurosivir, tenofovir, emtricitabine, oseltamivir, atazanavir, daclatasvir, AB001 (Agastiya Biotech), GC376 (Anivie Lifesciences), ISR-50 (ISR Immune System Regulation), slv213 (Selva Therapeutics), or vicromax (Viralclear Pharmaceuticals).

In some embodiments, the variant strain has developed a resistance to remdesivir. In some embodiments, the variant strain is a SARS-CoV-2 variant strain. In some embodiments, the SARS-CoV-2 has a nsp12 amino acid substitution S861X, wherein X=any amino acid. In some embodiments, the SARS-CoV-2 has a nsp12 protein amino acid substitution F480X, wherein X=any amino acid. In some embodiments, the SARS-CoV-2 has a nsp12 protein amino acid substitution V557X, wherein X=any amino acid. In some embodiments, the SARS-CoV-2 has a nsp12 protein amino acid substitution D484X, wherein X=any amino acid. In some embodiments, the SARS-CoV-2 has a nsp12 protein amino acid substitution F480V. In some embodiments, the SARS-CoV-2 has a nsp12 protein amino acid substitution V557L. In some embodiments, the SARS-CoV-2 has a nsp12 protein amino acid substitution D484Y. In some embodiments, the SARS-CoV-2 has a nsp12 protein amino acid substitution E802D. In some embodiments, the SARS-CoV-2 has a nsp12 protein amino acid substitution E802A. Remdesivir (VEKLURY®; Gilead Sciences) is generally referred to as an adenosine analog but is in fact a pyrrolo [2,1-f] [1,2,4]triazine—amine that does not metabolize to adenosine (or guanosine), and is believed to act as a delayed chain terminator (Eastman et al. (May 2020). "Remdesivir: A Review of Its Discovery and Development Leading to Emergency Use Authorization for Treatment of COVID-19". ACS Central Science. 6 (5): 672-683. Remdesivir has the structure:

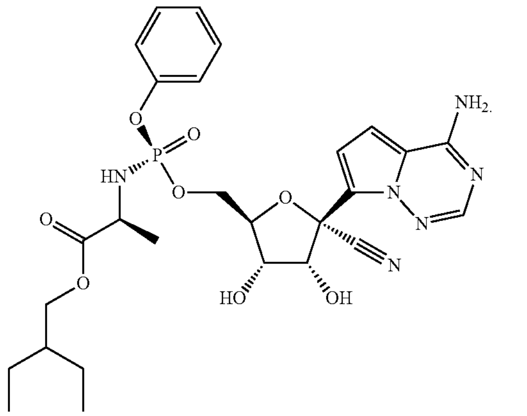 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

Remdesivir has been approved for the treatment of Covid-19 in humans in the United States, however it shows only marginal activity. Previous studies indicate that mutations in nsp12, for example at Ser861, are capable of reducing the activity of remdesivir (Gordon et al. (2020). Remdesivir is a direct-acting antiviral that inhibits RNA-dependent RNA polymerase from severe acute respiratory syndrome coronavirus 2 with high potency. J Biol Chem295, 6785-6797).

In some embodiments, the variant strain has developed a resistance to molnupiravir. In some embodiments, the variant strain is a SARS-CoV-2 variant strain. Molnupiravir (also known as MK-4482 and EIDD-2801) was developed by Emory University and Drug Innovation Ventures at Emory (DRIVE) and is currently in clinical trials sponsored by Merck for the treatment of SARS-CoV-2 infection. Molnupiravir is a prodrug of the synthetic nucleoside derivative N4-hydroxycytidine having the structure:

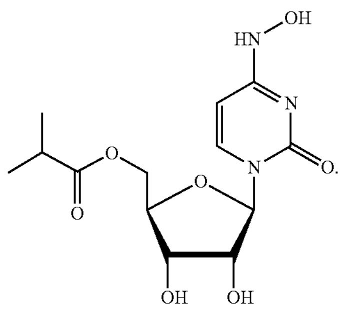

Molnupiravir was first generally described in WO 2002/032920 (pg. 28).

Molnupiravir is believed to exert its antiviral action through introduction of viral error catastrophe during viral RNA replication likely by causing C-to-U and G-to-A transition mutations following incorporation of the agent during replication (see, e.g., Toots et al. (October 2019). "Characterization of orally efficacious influenza drug with high resistance barrier in ferrets and human airway epithelia". Science Translational Medicine. 11 (515): eaax5866). In light of its mechanism of action, however, significant safety concerns regarding mutagenic effects of molnupiravir in humans have been raised, which caused Pharmasset to originally abandon the development of the active ingredient of molnupiravir in 2003 after discovering its mutagenic properties. In May 2020, Rick Bright, former head of the Biomedical Advanced Research and Development Authority (BARDA) filed a whistleblower complaint with the United States Government raising safety concerns over the use of the drug. In response, Merck acknowledged that the drug is AMES test positive, which is common biological assay used to assess the mutagenic potential of chemical compounds (see Mortelmans K, Zeiger E (November 2000). "The Ames Salmonella/microsome mutagenicity assay". Mutation Research. 455 (1-2): 29-60). A positive test indicates that the chemical is mutagenic and therefore may act as a carcinogen.

In some embodiments, the variant strain has developed a resistance to levovir (clevidine), a nucleoside analog. In some embodiments, the variant strain is a SARS-CoV-2 variant strain.

In some embodiments, the variant strain has developed a resistance to galidesivir (BioCryst Pharmaceuticals), an adenosine analog. In some embodiments, the variant strain is a SARS-CoV-2 variant strain.

In some embodiments, the variant strain has developed a resistance to ribavirin, guanosine (ribonucleic) analog. In some embodiments, the variant strain is a SARS-CoV-2 variant strain.

In some embodiments, the variant strain has developed a resistance to ritonavir (Norvir), a protease inhibitor. In some embodiments, the variant strain is a SARS-CoV-2 variant strain.

In some embodiments, the variant strain has developed a resistance to asc09 (Ascletis), a protease inhibitor. In some embodiments, the variant strain is a SARS-CoV-2 variant strain.

In some embodiments, the variant strain has developed a resistance to favilavir. In some embodiments, the variant strain is a SARS-CoV-2 variant strain.

In some embodiments, the variant strain has developed a resistance to favipiravir (Avigan). In some embodiments, the variant strain is a SARS-CoV-2 variant strain.

In some embodiments, the variant strain has developed a resistance to lopinavir, a protease inhibitor. In some embodiments, the variant strain is a SARS-CoV-2 variant strain.

In some embodiments, the variant strain has developed a resistance to maraviroc (Selzentry), a CCR % receptor antagonist. In some embodiments, the variant strain is a SARS-CoV-2 variant strain.

In some embodiments, the variant strain has developed a resistance to sofosbuvir, a derivatized uridine nucleotide. In some embodiments, the variant strain is a SARS-CoV-2 variant strain.

In some embodiments, the variant strain has developed a resistance to darunavir, a protease inhibitor. In some embodiments, the variant strain is a SARS-CoV-2 variant strain.

In some embodiments, the variant strain has developed a resistance to umifenovir (Arbidol), a viral membrane formation inhibitor. In some embodiments, the variant strain is a SARS-CoV-2 variant strain.

In some embodiments, the variant strain has developed a resistance to neurosivir. In some embodiments, the variant strain is a SARS-CoV-2 variant strain.

In some embodiments, the variant strain has developed a resistance to tenofovir. In some embodiments, the variant strain is a SARS-CoV-2 variant strain.

In some embodiments, the variant strain has developed a resistance to emtricitabine. In some embodiments, the variant strain is a SARS-CoV-2 variant strain.

In some embodiments, the variant strain has developed a resistance to oseltamivir (Tamiflu). In some embodiments, the variant strain is a SARS-CoV-2 variant strain.

In some embodiments, the variant strain has developed a resistance to atazanavir, a protease inhibitor. In some embodiments, the variant strain is a SARS-CoV-2 variant strain.

In some embodiments, the variant strain has developed a resistance to daclatasvir, a protease inhibitor. In some embodiments, the variant strain is a SARS-CoV-2 variant strain.

In some embodiments, the variant strain has developed a resistance to AB001 (Agastiya Biotech). In some embodiments, the variant strain is a SARS-CoV-2 variant strain.

In some embodiments, the variant strain has developed a resistance to GC376 (Anivie Lifesciences). In some embodiments, the variant strain is a SARS-CoV-2 variant strain.

In some embodiments, the variant strain has developed a resistance to ISR-50 (ISR Immune System Regulation). In some embodiments, the variant strain is a SARS-CoV-2 variant strain.

In some embodiments, the variant strain has developed a resistance to slv213 (Selva Therapeutics). In some embodiments, the variant strain is a SARS-CoV-2 variant strain.

In some embodiments, the variant strain has developed a resistance to vicromax (Viralclear Pharmaceuticals). In some embodiments, the variant strain is a SARS-CoV-2 variant strain.

In some embodiments, the variant strain has developed a resistance to vicromax (Viralclear Pharmaceuticals). In some embodiments, the variant strain is a SARS-CoV-2 variant strain.

In some embodiments, the variant strain has developed a resistance to boceprevir (Victrelis). In some embodiments, the variant strain is a SARS-CoV-2 variant strain.

In some embodiments, the variant strain has developed a resistance to GC-376. In some embodiments, the variant strain is a SARS-CoV-2 variant strain.

In some embodiments, the variant strain has developed a resistance to calpain inhibitor II. In some embodiments, the variant strain is a SARS-CoV-2 variant strain.

In some embodiments, the variant strain has developed a resistance to calpain inhibitor XII. In some embodiments, the variant strain is a SARS-CoV-2 variant strain.

In some embodiments, the variant strain has developed a resistance to PF-07304814. In some embodiments, the variant strain is a SARS-CoV-2 variant strain.

In some embodiments, the variant strain has developed a resistance to PF-07321332. In some embodiments, the variant strain is a SARS-CoV-2 variant strain.

In some embodiments, the variant strain has developed a resistance to EDP-235. In some embodiments, the variant strain is a SARS-CoV-2 variant strain.

In some embodiments, the variant strain has developed a resistance to PBI-0451. In some embodiments, the variant strain is a SARS-CoV-2 variant strain.

In some embodiments, the variant strain has developed a resistance to ALG-097111. In some embodiments, the variant strain is a SARS-CoV-2 variant strain.

In some embodiments, the variant strain has developed a resistance to sotrovimab (VIR-7831). In some embodiments, the variant strain is a SARS-CoV-2 variant strain.

In some embodiments, the variant strain has developed a resistance to VIR-7832. In some embodiments, the variant strain is a SARS-CoV-2 variant strain.

In some embodiments, the variant strain has developed a resistance to BRII-196. In some embodiments, the variant strain is a SARS-CoV-2 variant strain.

In some embodiments, the variant strain has developed a resistance to BRII-198. In some embodiments, the variant strain is a SARS-CoV-2 variant strain.

In some embodiments, the variant strain has developed a resistance to ADG20. In some embodiments, the variant strain is a SARS-CoV-2 variant strain.

In some embodiments, the variant strain has developed a resistance to ADG10. In some embodiments, the variant strain is a SARS-CoV-2 variant strain.

In some embodiments, the variant strain has developed a resistance to casirivimab, imdevimab, or both casirivimab and imdevimab. In some embodiments, the variant strain is a SARS-CoV-2 variant strain.

In some embodiments, the variant has developed a resistance to REGN-COV2. In some embodiments, the variant strain is a SARS-CoV-2 variant strain.

Assays and Methods to determine other Advantageous Drugs for the Treatment or Prevention of SARS-CoV-2

In some embodiments, the present invention provides a method for identifying an advantageous compound which selectively binds to or inhibits NiRAN-domain mediated activity of the nsp12 protein of a SARS-related coronavirus for use in a therapy described herein. The ability of a compound to inhibit NiRAN-domain mediated activity as described herein can be determined using an in vitro assay as described in the Examples herein, or similar in vitro assays known in the art, and is compared to a control wherein the compound is not present in the same assay.

In a primary embodiment, the compound is a selected nucleotide, for example a compound of Formula I-VIII. As used herein a selected nucleotide or nucleoside is a non-naturally occurring nucleotide, for example a species independently selected from Formulas I-VIII, that can be metabolized to a monophosphate, diphosphate or triphosphate active form. In certain embodiments, the sugar moiety of the nucleotide has a 2'-methyl group. In certain embodiments, the sugar moiety of the nucleotide has both a 2'-methyl group and a 2'-fluoro, 2'-hydroxyl or 2'-chloro group.

Assays to detect binding of compounds to NiRAN, nsp8 or nsp12, are described herein in, for example, Examples 8, 10, 11, 12, 17, and 19. Other assays are known in the art, for example as described in McFedries, et al, Methods for the Elucidation of Protein-Small Molecule Interactions. Chemistry & Biology (2013); Vol. 20(5):667-673; Pollard, A Guide to Simple and Informative Binding Assays, Mol. Biol. Cell (2010) Vol. 21, 4061— 4067, both incorporated herein by reference in their entirety.

Methods used for identifying compounds that binds to the NiRAN-domain of the nsp12 protein may be labeled ligand binding assays or label-free ligand binding assays.

In competitive binding assays, the compound can be labelled. Free compound is separated from that present in a complex and the amount of free (i.e., uncomplexed) label is a measure of the binding of the compound being tested to nsp12.

In some embodiments, the binding assay is a labeled ligand binding assay. In some embodiments, the labeled ligand-binding assay is a fluorescent ligand binding assay. In some embodiments, the labeled ligand-binding assay is a radioligand binding assay. In some embodiments, the labeled ligand-binding assay is a bioluminescent binding assay using nanoluciferase. Compounds are screened to determine their ability to interact or bind to the NiRAN-domain of the nsp12 protein of a SARS-related coronavirus. For example, a labeled compound is contacted with nsp12 protein and then an assay is performed to detect binding of the compound to the NiRAN-domain of the nsp12 protein using the labeled ligand to detect its binding to a target. Free compound is separated from that present in a binding complex and the amount of free (i.e., uncomplexed) label is a measure of the binding of the compound being tested to nsp12

In some embodiments, the binding assay is a label-free ligand binding assay. Nonlimiting examples of label-free ligand binding assays include surface plasmon resonance (SPR), plasmon-waveguide resonance (PWR), SPR imaging for affinity-based biosensors, nanofluidic fluorescence microscopy (NFM), whispering gallery microresonator (WGM), resonant waveguide grating (RWG), and biolayer interferometry biosensor (BIB). Compounds are screened to determine their ability to interact or bind to the NiRAN-domain of the nsp12 protein of a SARS-related coronavirus. For example, a compound is contacted with a nsp12 protein and then an assay is performed to detect binding of the compound to the NiRAN-domain of the nsp12 protein using the changes in light or electromagnetic waves to detect the binding kinetics to the target.

Additionally, the assay may measure the binding between the active pocket of the NiRAN-domain of nsp12 and the compound being tested. Thus, the present invention provides methods of identifying compounds comprising contacting a compound with nsp12 protein and assaying for the binding of the active pocket of the NiRAN-domain and the compound. In some embodiments, binding of the compound to the active pocket, wherein the active site pocket is lined with the following residues: K73, R74, H75, N79, E83, R116, N209, G214, D218, F219, and F222, is indicative of a compound capable of inhibiting NiRAN-domain activity. In some embodiments, binding of the compound to the active pocket, wherein the active site pocket is lined with the following residues: K50, R55 T120, N, 209, Y217.

In some embodiments, the assay further comprises:

i. contacting the compound with the nsp12 protein in the presence of UTP and/or GTP; and, ii. measuring the binding of the compound, GTP, and/or UTP to the NiRAN-domain;

wherein a higher level of binding by the compound compared to GTP and UTP is indicative of a compound capable of inhibiting NiRAN-domain mediated activity.

In some embodiments, the assay further comprises:

i. contacting the compound with the nsp12 protein in the presence of UTP and/or GTP; and, ii. measuring the binding of the compound, GTP, and/or UTP to the NiRAN-domain;

wherein a higher level of binding by the compound compared to GTP and UTP is indicative of a compound capable of inhibiting NiRAN-domain mediated activity. In such competitive binding assays, nsp12, UTP or GTP can be labelled. Free nsp12 is separated from that present in a complex and the amount of free (i.e., uncomplexed) label is a measure of the binding of the compound being tested to nsp12 or its interference with binding of UTP or GTP. In some embodiments, the GTP or UTP is radiolabeled with [$\alpha$-$P^{32}$]. In some embodiments, the GTP or UTP is fluorescently labeled. In some embodiments, the compound contacts nsp12 in the presence of labeled UTP. In some embodiments, the compound contacts nsp12 in the presence of labeled GTP. In some embodiments, the compound contacts nsp12 in the presence of both labeled UTP and GTP. In some embodiments, the compound contacts nsp12 in the presence of labeled GTP and/or UTP, wherein labeled GTP and/or UTP are present in a greater concentration than the compound. In some embodiments, the compound contacts nsp12 in the presence of labeled GTP and/or UTP, wherein GTP and/or UTP are in equimolar concentrations with the compound. In some embodiments, the compound binds the NiRAN-domain at about 1.25×, 1.5×, 1.75×, 2.0×, 2.25×, 2.5×, 2.75×, 3.0×, 3.25×, 3.5×, or greater than UTP and/or GTP compared to a control wherein the compound is not present.

In the methods above, the amount of nsp12 and nsp12: compound contained in a solution may be measured using, for example, nsp12 labeled with biotin, a radioisotope, a fluorophore, a chromophore, or a chemiluminescent moiety. For example, the amount of the biotin-labeled nsp12 may be measured by using a protein capable of binding to the biotin with high affinity such as avidin, streptavidin, or a variant protein thereof (hereinafter referred to as the avidins) such that avidins are labeled with the radioisotope, the fluorophore, the luminophore, or the enzyme, which can be easily detected, and bound to the biotin-labeled compound. The radioactive substance may be measured using a common radiation measuring apparatus such as a scintillation counter, a gamma counter, or a GM meter. The fluorophore, the chromophore, and the luminophore may be measured using a fluorescence measuring apparatus, an absorptiometer, and a luminescence measuring apparatus respectively. The amount of the enzyme-labeled compound can be easily measured using a compound that is converted by the enzyme to a chromogenic, fluorescent, or luminescent compound.

In some embodiments, the present invention provides a method for identifying compounds capable of inhibiting NiRAN-domain mediated activity in a SARS-related coronavirus comprising:

i. contacting the compound with a nsp12 protein and nsp8 of a SARS-related coronavirus in the presence of UTP; and, ii. determining whether the compound inhibits the UMPylation of nsp8;

wherein prevention of UMPylation of nsp8 by the NiRAN-domain is indicative of a compound capable of inhibiting NiRAN-domain mediated activity. Methods of measuring UMPylation are described in Example 19.

In some embodiments, the present invention provides a method for identifying compounds capable of inhibiting NiRAN-domain mediated activity in a SARS-related coronavirus comprising:

i. contacting the compound with a nsp12 protein and nsp8 of a SARS-related coronavirus in the presence of UTP and/or GTP; and, ii. determining whether the compound inhibits the nucleotidylation of nsp8;

wherein prevention of nucleotidylation nsp8 by the NiRAN-domain is indicative of a compound capable of inhibiting NiRAN-domain mediated activity. In some embodiments, the compound contacts nsp12 and nsp8 in the presence of UTP. In some embodiments, the compound contacts nsp12 and nsp8 in the presence of GTP. In some embodiments, the compound contacts nsp12 and nsp8 in the presence of both UTP and GTP. In some embodiments, the compound contacts nsp12 and nsp8 in the presence of GTP and/or UTP, wherein GTP and/or UTP are present in a greater concentration than the compound. In some embodiments, the compound contacts nsp12 and nsp8 in the presence of GTP and/or UTP, wherein GTP and/or UTP are in equimolar concentrations with the compound. In some embodiments, the compound reduces nucleotidylation of nsp8 by at least 50%, 60%, 70% or more compared to a control wherein the compound is not present.

Methods of measuring nucleotidylation are described in Lehmann et al., Nucleic Acids Res. 2015 Sep. 30; 43(17): 8416-8434. An example of a nucleotidylation assay that can identify inhibitors of nucleotidylation is described in, for example, Example 8.

In some embodiments, the present invention provides a method for identifying compounds capable of inhibiting NiRAN-domain mediated activity in a SARS-related coronavirus comprising:

i. contacting the compound with a nsp12 and nsp8 protein of a SARS-related coronavirus in the presence of UTP and/or GTP; and, ii. determining whether the compound inhibits the transfer of UTP and/or GTP from nsp12 to nsp8;

wherein inhibition of the transfer of UTP and/or GTP by the NiRAN-domain is indicative of a compound capable of inhibiting NiRAN-domain mediated activity. In some embodiments, the compound contacts nsp12 and nsp8 in the presence of UTP. In some embodiments, the compound contacts nsp12 and nsp8 in the presence of GTP. In some embodiments, the compound contacts nsp12 and nsp8 in the presence of both UTP and GTP. In some embodiments, the compound contacts nsp12 and nsp8 in the presence of GTP and/or UTP, wherein GTP and/or UTP are present in a greater concentration than the compound. In some embodiments, the compound contacts nsp12 and nsp8 in the presence of GTP and/or UTP, wherein GTP and/or UTP are in equimolar concentrations with the compound. In some embodiments, the compound reduces transfer of GTP and/or UTP from nsp12 to nsp8 by at least 50%, 60%, 70%, or more compared to a control wherein the compound is not present.

In some embodiments, the present invention provides a method of identifying compounds capable of neutralizing the ability of nsp12 to label nsp8 with radioactively labeled GTP or UTP. For example, the assay may measure the amount of labeled GTP or NTP on nsp8 by nsp12-NiRAN in the presence of the compound. A reduction in the amount of labeled nsp8 identifies a compound that is capable of competing with GTP or UTP and neutralizes the ability of nsp12 to label nsp8. An example of an assay that can identify compounds capable of neutralizing the ability of nsp12 to label nsp8 is described in, for example, Example 19 and FIGS. 13A-3E.

In some embodiments, the present invention provides a method for identifying compounds capable of inhibiting NiRAN-domain mediated protein primed RNA synthesis in a SARS-related coronavirus comprising:

i. contacting the compound with a nsp12, nsp7, and nsp8 protein of a SARS-related coronavirus in the presence of UTP and a poly(A) RNA template; and ii. determining whether the compound inhibits primer independent RNA synthesis on the poly(A) RNA template in the presence of UTP;

wherein the inhibition of primer independent RNA synthesis on the poly(A) RNA template in the presence of UTP is indicative of a compound capable of inhibiting primer independent RNA synthesis. In some embodiments, the nsp12, nsp7, and nsp8 is provided as a nsp12:7L8:8 polymerase complex. In some embodiments, nsp12:7L8:8 polymerase complex is in a 1:3:3 molar ratio. In some embodiments, nsp12, nsp7 and nsp8 polymerase complex is in a 1:3:6 molar ratio. In some embodiments, the compound reduces primer independent RNA synthesis of the poly(A) RNA template by at least 50% or more compared to a control wherein the compound is not present.

In one non-limiting illustrative example, the primer independent RNA synthesis assay can be performed with fixed concentrations of poly(A) RNA template and labeled UTP in the presence of the nsp12:7L8:8 polymerase complex with or without the compound. Without the compound, the nsp12:7L8:8 polymerase complex will synthesize a poly(U) strand from the poly(A) RNA template. The presence of the synthesis products can be measured and is indicative of a functioning nsp12:7L8:8 polymerase complex. When the assay is performed with a compound capable of inhibiting de novo RNA synthesis, the nsp12:7L8:8 polymerase complex will be unable to synthesize the poly(U) strand from the poly(A) RNA template in the presence of labeled UTP. This result is indicative of a compound capable of inhibiting primer independent RNA synthesis. This type of assay and results are shown in Example 7 and FIG. 4.

It should be noted that the methods for identifying the compounds above are considered to be illustrative and not restrictive.

In some embodiments, the compound is also capable of inhibiting the replication/transcription complex nsp12:nsp7:nsp8 dinucleotide primer pppUpU-mediated NiRAN-independent de novo protein synthesis. Accordingly, a compound capable of inhibiting NiRAN-domain mediated UMPylation of nsp8 by nsp12 and/or capable of inhibiting NiRAN-domain mediated protein primed RNA synthesis is further screened to determine its ability to inhibit RNA-initiation at the RdRp active site. In some embodiments, the compound is further capable of inhibiting de novo NiRAN-independent initiation of RNA synthesis. In some embodiments, the compound is further capable of RNA extension chain termination.

In some embodiments, the compound is further screened to determine whether it is capable of inhibiting de novo NiRAN-independent initiation of RNA synthesis comprising:

i) contacting the compound with nsp12, nsp7, nsp8, a poly(A) template, and pppGpU;

ii) measuring the production of poly(U) RNA;

wherein an inhibition or reduction in the production of poly(U) RNA is indicative of a compound that can inhibit de novo NiRAN-independent RNA synthesis. Assays suitable for determining inhibition or reduction in the production of poly(U) RNA are described, for example, in Examples 6 and 15.

V. Methods of Treatment

The present invention includes a method for treating a host, typically a human, with or at risk of getting a mutant or resistant form of SARS-CoV-2 infection that includes identifying an optimal compound as described herein and administering an effective amount of the compound to the host in need thereof. In certain embodiments, the treatment is prophylactic or preventative. In some embodiments, a NiRAN interfering compound or a pharmaceutically acceptable salt thereof, is administered to a host who has been exposed to and thus is at risk of infection or at risk of reinfection from a SARS-CoV such as SARS-CoV-2.

In another alternative embodiment, a method to prevent transmission is provided that includes administering an effective amount of a NiRAN interfering compound to a human for a sufficient length of time prior to exposure to crowds that can be infected, including during travel or public events or meetings, including for example, up to 3, 5, 7, 10, 12, 14 or more days prior to a communicable situation, either because the human is infected or to prevent infection from an infected person in the communicable situation.

In some embodiments, a NiRAN interfering compound is administered in an effective amount for at least two weeks, three weeks, one month, two months, three months, four months, five months, or six months or more after infection.

The invention includes NiRAN interfering compounds and methods of treatment of a SARS-CoV infection, including drug resistant and multidrug resistant forms of the virus and related disease states, conditions, or complications of the viral infection, including pneumonia, such as 2019 novel coronavirus-infected pneumonia (NCIP), acute lung injury (ALI), and acute respiratory distress syndrome (ARDS). Additional non-limiting complications include hypoxemic respiratory failure, acute respiratory failure (ARF), acute liver injury, acute cardiac injury, acute kidney injury, septic shock, disseminated intravascular coagulation, blood clots, multisystem inflammatory syndrome, chronic fatigue, rhabdomyolysis, and cytokine storm.

The method also comprises administering to a host in need thereof, typically a human, an effective amount of a NiRAN interfering compound or a pharmaceutically acceptable salt thereof, optionally in combination with at least one additional bioactive agent, for example, an additional antiviral agent, further optionally in combination with a pharmaceutically acceptable carrier additive and/or excipient.

In some embodiments, the administration of a NiRAN interfering compound to a patient in need thereof results in a reduction in the incidence of progressive respiratory insufficiency (PRI) as measured by greater than or equal to a 1-tier or even 2-tier or more increase in respiratory support methods required to maintain satisfactory oxygenation ($SpO_2 \geq 93\%$) using the 6-tier hierarchical levels of respiratory support methods described below.

The scale of increasing respiratory support levels includes:

Level 1: Normal oxygenation on room air ($SpO_2 \geq 93\%$), no need for supplemental $O_2$ Level 2: Persistent hypoxemia on room air ($SpO_2 \geq 93$) with requirement for low-level supplemental $O_2$ by nasal cannular or mask (up to 2 L/min) to maintain $SpO_2 \geq 93$ Level 3: Requirement for higher levels of passive supplemental $O_2$ by nasal cannular or mask (up to 2 L/min) to maintain $SpO_2 \geq 93$ Level 4: Requirement for oxygenation by positive-pressure devices, e.g., Continuous Positive Airway Pressure (CPAP) or Bi-level Positive Airway Pressure (BiPAP) or other non-invasive positive-pressure respiratory support methods to main satisfactory oxygenation and/or ventilation Level 5: Requires invasive respiratory support (intubated mechanical ventilation or ECMO)

Level 6: Death

In some embodiments, the reduction in PRI results in a decrease from level 5 to level 3, level 5 to level 2, or level 5 to level 1. In some embodiments, the reduction in PRI results in a decrease from level 4 to level 2 or level 4 to level 1. In some embodiments, the reduction in PRI results in a decrease from level 3 to level 1.

In some embodiments, the administration of a NiRAN interfering compound or a pharmaceutically acceptable salt thereof reduces the median time to Clinical Recovery (status 6, 7, or 8 in the NIAID Clinical Status scale using an adapted National Institute of Allergy and Infectious Diseases (NIAID) ordinal scale of Clinical Status) by at least 3, 4, 5 or more days. In some embodiments, the administration of a NiRAN interfering compound or a pharmaceutically acceptable salt thereof results in an improvement as measured by the adapted ordinal scale of Clinical Status.

From most severe disease to progressively less severe disease, the stages of the adapted ordinal scale of overall Clinical Status are defined as follows:

1. Death
2. Hospitalized, on invasive mechanical ventilation or ECMO
3. Hospitalized, on non-invasive ventilation or high flow oxygen devices
4. Hospitalized, requiring supplemental oxygen
5. Hospitalized, not requiring supplemental oxygen—requiring ongoing medical care (COVID-19 related or otherwise)
6. Hospitalized, not requiring supplemental oxygen; no longer requires close medical care for COVID-19
7. Not hospitalized, but with limitation on activities and needing close outpatient care for COVID-19 manifestations
8. Not hospitalized, no limitations on activities, no need for continued close medical care In some embodiments, the administration of a NiRAN interfering compound or a pharmaceutically acceptable salt thereof reduces the median time to Clinical Recovery (status 6, 7, or 8 in the NIAID Clinical Status scale using an adapted National Institute of Allergy and Infectious Diseases (NIAID) ordinal scale of Clinical Status) by at least 5 days, at least 6 days, at least 7 days, at least 8 days, at least 9 days, or at least 10 days.

In some embodiments, the administration of a NiRAN interfering compound or a pharmaceutically acceptable salt thereof reduces the duration of hospitalization for a patient infected with a SARS-CoV infection.

In some embodiments, the administration of a NiRAN interfering compound or a pharmaceutically acceptable salt thereof reduces the time to sustained non-detectable SARS-CoV in the nose and/or throat in a patient infected with a SARS-CoV infection.

In some embodiments, the administration of a NiRAN interfering compound or a pharmaceutically acceptable salt thereof reduces respiratory failure or death.

In some embodiments, the administration of a NiRAN interfering compound of or a pharmaceutically acceptable salt thereof reduces the proportion of patients in a hospital population who are SARS-CoV positive after at least about 5, 6, 7, 8, 9, 10, 11, 12, 13, or 14 days of treatment.

VI. Pharmaceutical Compositions and Dosage Forms

A compound of Formula I, Formula II, Formula III, Formula IV, Formula V, Formula VI, Formula VII, Formula VIII or a pharmaceutically acceptable salt thereof, can be administered in an effective amount for the treatment of mutant or resistant forms of the SARS-CoV-1 or SARS-CoV-2 virus in a host, typically a human, in need thereof. In some embodiments the compound is Compound 1A or Compound 3A or a pharmaceutically acceptable salt thereof, for example Compound 2A or Compound 4A. In some embodiments the compound is Compound 1B or Compound 3B or a pharmaceutically acceptable salt thereof, for example Compound 2B or Compound 4B.

In some embodiments, the disclosure provides pharmaceutical compositions comprising an effective amount of a compound of Formula I, Formula II, Formula III, Formula IV, Formula V, Formula VI, Formula VII, or Formula VIII, or a pharmaceutically acceptable salt thereof, with at least one pharmaceutically acceptable carrier for the treatment of mutant or resistant forms of the SARS-CoV-1 or SARS-CoV-2 virus. The pharmaceutical composition may contain a compound of Formula I, Formula II, Formula III, Formula IV, Formula V, Formula VI, Formula VII, or Formula VIII, or a pharmaceutically acceptable salt thereof, as the only active agent, or, in an alternative embodiment, in combination with at least one additional active agent.

A compound of Formula I (including but not limited to Compound 1, 1A or 1B), Formula II (including but not limited to Compound 3, 3A or 3B), Formula III, Formula IV, Formula V, Formula VI, Formula VII, or Formula VIII, or a pharmaceutically acceptable salt thereof, can be formulated with one or more pharmaceutically acceptable carriers. Oral dosage forms are sometimes selected due to ease of administration and prospective favorable patient compliance. In some embodiments, a compound of Formula I, Formula II, Formula III, Formula IV, Formula V, Formula VI, Formula VII, or Formula VIII, or a pharmaceutically acceptable salt thereof, is provided in a solid dosage form, such as a tablet or pill, which are well known in the art and described further below. Enteric coated oral tablets may also be used to enhance bioavailability of the compounds for an oral route of administration. Pharmaceutical compositions (formulations) may be administered via oral, parenteral, intravenous, inhalation, intramuscular, topical, transdermal, buccal, subcutaneous, suppository, or other route, including intranasal spray routes of delivery.

In some embodiments, a compound of Formula I, Formula II, Formula III, Formula IV, Formula V, Formula VI, Formula VII, or Formula VIII, or a pharmaceutically acceptable salt thereof is administered intravenously. In one non-limiting embodiment, a compound of the present invention is administered intravenously at a loading dose of 550 mg/day and a maintenance dose of 275 mg/day. In some embodiments, the loading dose is administered once and the maintenance dose is administered twice a day for at least 3, 4, 5, 6, 7, 8, 9, 10, 11, or 12 days. In one non-limiting embodiment, an intravenous loading dose is 550 mg/day of Compound 1 (i.e., 600 mg/day hemisulfate salt of Compound 1), and a maintenance dose is 275 mg/day (i.e., 300 mg/day of hemisulfate salt)).

Effective dosage form will depend upon the bioavailability/pharmacokinetic of the particular agent chosen as well as the severity of disease in the patient. A compound of Formula I, Formula II, Formula III, Formula IV, Formula V, Formula VI, Formula VII, or Formula VIII, or a pharmaceutically acceptable salt thereof, can be administered, for example, in one or more tablets, capsules, injections, intravenous formulations, suspensions, liquids, emulsions, implants, particles, spheres, creams, ointments, suppositories, inhalable forms, transdermal forms, buccal, sublingual, topical, gel, mucosal, and the like.

Intravenous and intramuscular formulations are often administered in sterile saline. One of ordinary skill in the art may modify the formulations to render them more soluble in water or another vehicle, for example, this can be easily accomplished by minor modifications (salt formulation, esterification, etc.).

The pharmaceutical compositions contemplated here optionally include a carrier, as described further below. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Representative carriers include solvents, diluents, pH modifying agents, preservatives, antioxidants, suspending agents, wetting agent, viscosity agents, tonicity agents, stabilizing agents, and combinations thereof. In some embodiments, the carrier is an aqueous carrier.

One or more viscosity agents may be added to the pharmaceutical composition to increase the viscosity of the composition as desired. Examples of useful viscosity agents include, but are not limited to, hyaluronic acid, sodium hyaluronate, carbomers, polyacrylic acid, cellulosic derivatives, polycarbophil, polyvinylpyrrolidone, gelatin, dextin, polysaccharides, polyacrylamide, polyvinyl alcohol (including partially hydrolyzed polyvinyl acetate), polyvinyl acetate, derivatives thereof and mixtures thereof.

Solutions, suspensions, or emulsions for administration may be buffered with an effective amount of buffer necessary to maintain a pH suitable for the selected administration. Suitable buffers are well known by those skilled in the art. Some examples of useful buffers are acetate, borate, carbonate, citrate, and phosphate buffers.

To prepare the pharmaceutical compositions according to the present invention, a therapeutically effective amount of a compound of Formula I, Formula II, Formula III, Formula IV, Formula V, Formula VI, Formula VII, or Formula VIII, or a pharmaceutically acceptable salt thereof may be admixed with a pharmaceutically acceptable carrier according to conventional pharmaceutical compounding techniques to produce a dose. A carrier may take a wide variety of forms depending on the form of preparation desired for administration, e.g., oral or parenteral.

In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, mannitol, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersions, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleotide compounds according to the present invention.

Amounts and weights mentioned in this disclosure typically refer to the free form (i.e., non-salt, hydrate or solvate form). The typically values described herein represent free-form equivalents, i.e., quantities as if the free form would be administered. If salts are administered the amounts need to be calculated in function of the molecular weight ratio between the salt and the free form.

The amount of a compound of Formula I, Formula II, Formula III, Formula IV, Formula V, Formula VI, Formula VII, or Formula VIII, or a pharmaceutically acceptable salt thereof, in the pharmaceutically acceptable formulation according to the present invention is an effective amount to achieve the desired outcome of treating the mutant or resistant forms of the SARS-CoV-1 or SARS-CoV-2 virus, reducing the likelihood of with a mutant or resistant form of the SARS-CoV-1 or SARS-CoV-2 virus, or the inhibition, reduction, and/or elimination of mutant or resistant forms of the SARS-CoV-1 or SARS-CoV-2 virus or its secondary effects, including disease states, conditions, and/or complications which occur secondary to the virus. As non-limiting embodiments, a therapeutically effective amount of the present compounds in a pharmaceutical dosage form may range, for example, from about 0.001 mg/kg to about 100 mg/kg per day or more. A compound of Formula I, Formula II, Formula III, Formula IV, Formula V, Formula VI, Formula VII, or Formula VIII, or a pharmaceutically acceptable salt thereof, may for example in non-limiting embodiments be administered in amounts ranging from about 0.1 mg/kg to about 15 mg/kg per day of the patient, depending upon the pharmacokinetics of the agent in the patient.

The weight of active compound in the dosage form described herein is with respect to either the free form or the salt form of the compound unless otherwise specifically indicated. For example, approximately 600 mg of Compound 2 is the equivalent of approximately 550 mg of Compound 1.

In certain embodiments, the pharmaceutical composition is in a dosage form that contains from about 1 mg to about 2000 mg, from about 10 mg to about 1000 mg, from about 100 mg to about 800 mg, from about 200 mg to about 600 mg, from about 300 mg to about 500 mg, or from about 400 mg to about 450 mg of a compound of Formula I, Formula II, Formula III, Formula IV, Formula V, Formula VI, Formula VII, or Formula VIII, or a pharmaceutically acceptable salt thereof, in a unit dosage form.

In certain embodiments, the pharmaceutical composition is in a dosage form, for example in a solid dosage form, that contains up to about 10, about 50, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg or more of a compound of Formula I, Formula II, Formula III, Formula IV, Formula V, Formula VI, Formula VII, or Formula VIII, or a pharmaceutically acceptable salt thereof, in a unit dosage form.

In certain embodiments, a compound of Formula I, Formula II, Formula III, Formula IV, Formula V, Formula VI, Formula VII, or Formula VIII, or a pharmaceutically acceptable salt thereof, for example Compound 1 or Compound 2, is administered at an initial dose (or loading dose) followed by a maintenance dose of at least about 300 mg, at least about 350 mg, at least about 400 mg, at least about 450 mg, at least about 500 mg, at least about 550 mg, at least about 650, or at least about 750 and the dose is taken once or twice a day. In some embodiments, the loading dose is about 1.5 times greater, about 2 times greater, about 2.5 times greater, or 3-fold times greater than the maintenance dose. In some embodiments, the loading dose is administered once, twice, three, four, or more times before the first maintenance dose.

In some embodiments, the pharmaceutical composition is in a dosage form, for example in a solid dosage form, that contains at least 500 mg, at least 550 mg, 600 mg, at least 700 mg, at least 800 mg, at least 900 mg, at least 1000 mg, at least 1100 mg, at least 1200, at least 1300 mg, at least 1400 mg, or at least 1500 mg of a compound of Formula I, Formula II, Formula III, Formula IV, Formula V, Formula VI, Formula VII, or Formula VIII, or a pharmaceutically acceptable salt thereof, in a unit dosage form.

In certain embodiments, the pharmaceutical composition, for example, a solid dosage form, contains at least about 450 mg, 550 mg, 650 mg, 750 mg or 850 mg of Compound 1 or Compound 3. In some embodiments, the pharmaceutical composition contains at least about 500 mg, at least about 550 mg, or at least about 600 mg of Compound 1 or Compound 3 and the composition is administered twice a day. In some embodiments, the pharmaceutical composition contains at least about 550 mg of Compound 1 and the pharmaceutical composition is administered twice a day. In some embodiments, the pharmaceutical composition is administered at an initial dose (or loading dose) of at least about 900 mg, 1000 mg, 1100 mg, 1100 mg, or 1200 mg of Compound 1 followed by a dose of at least about 400 mg, at least about 450 mg, at least about 500 mg, at least about 550, at least about 600 mg, or at least about 650 mg of Compound 1 twice a day. In some embodiments, the pharmaceutical composition is administered at an initial dose (or loading dose) of at least about 1100 mg of Compound 1 followed by a dose of at least about 450 mg, 550 mg, 650 mg, 750 mg, or 850 mg of Compound 1 twice a day. In some embodiments, the pharmaceutical composition is administered at an initial dose (or loading dose) of at least about 1100 mg of Compound 1 followed by a dose of at least about 550 mg of Compound 1 twice a day. In some embodiments, the maintenance dose is administered for at about 4, 5, 6, 7, 8, 9, 10, or more days. In some embodiments, Compound 1 is Compound 1A. In some embodiments, Compound 1 is Compound 1B.

In some embodiments, an effective amount of a compound of Formula I:

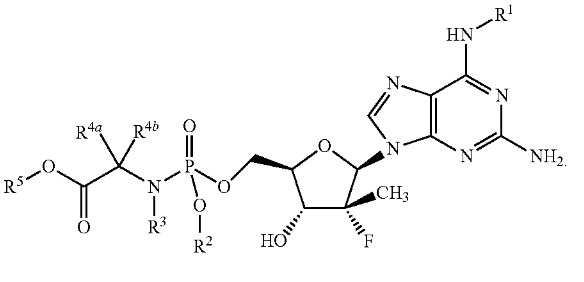

or a pharmaceutically acceptable salt thereof, optionally in a pharmaceutically acceptable carrier, is administered for the treatment of a mutant or resistant form of the SARS-CoV-2 virus in a human in need thereof wherein the compound is administered according to the following schedule:

(i) a single loading dose of 1100 mg of free base in one day; followed by (ii) a maintenance dose of 550 mg of free base per day.

In some embodiments, an effective amount of a compound of the Formula:

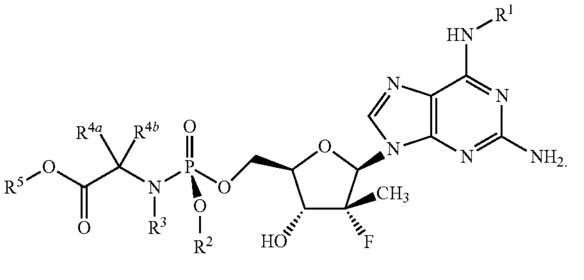

or a pharmaceutically acceptable salt thereof, optionally in a pharmaceutically acceptable carrier, is administered for the treatment of a mutant or resistant form of the SARS-CoV-2 virus in a human in need thereof wherein the compound is administered according to the following schedule:

(iii) a single loading dose of 1100 mg of free base in one day; followed by (iv) a maintenance dose of 550 mg of free base per day.

In some embodiments, an effective amount of a compound of the Formula:

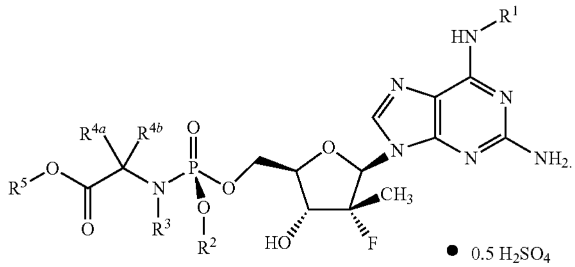

optionally in a pharmaceutically acceptable carrier, is administered for the treatment of a mutant or resistant form of the SARS-CoV-2 virus in a human in need thereof wherein the compound is administered according to the following schedule:

(i) a single loading dose of 1200 mg of salt in one day; followed by (ii) a maintenance dose of 600 mg of salt per day.

In certain embodiments, the pharmaceutical composition, for example, a solid dosage form, contains at least about 400 mg, at least about 500 mg, 600 mg, 700 mg, or 800 mg of Compound 2 or Compound 4. In some embodiments, the pharmaceutical composition contains at least about 500 mg, at least about 600 mg, or at least about 700 mg of Compound 2 or Compound 4 and the composition is administered twice a day. In some embodiments, the pharmaceutical composition contains at least about 600 mg of Compound 2 and the pharmaceutical composition is administered twice a day. In some embodiments, the pharmaceutical composition is administered at an initial dose (or loading dose) of at least about 900 mg, 1000 mg, 1100 mg, 1200 mg, or 1300 mg of Compound 2 followed by a dose of at least about 400 mg, 500 mg, 600 mg, 700 mg, or 800 mg of Compound 2 once, twice, or three times a day. In some embodiments, the pharmaceutical composition is administered at an initial dose (or loading dose) of at least about 1000 mg, 1200 mg, or 1400 mg of Compound 2 followed by a dose of at least about 600 mg of Compound 2 twice a day. In some embodiments, the pharmaceutical composition is administered at an initial dose (or loading dose) of at least about 1200 mg of Compound 2 followed by a dose of at least about 400 mg, 500 mg, 600 mg, 700 mg, or 800 mg of Compound 2 twice a day. In some embodiments, the pharmaceutical composition is administered at an initial dose (or loading dose) of at least about 1200 mg of Compound 2 followed by a dose of at least about 600 mg of Compound 2 twice a day. In some embodiments, the maintenance dose is administered for at about 4, 5, 6, 7, 8, 9, 10, or more days. In some embodiments, Compound 2 is Compound 2A. In some embodiments, Compound 2 is Compound 2B.

In certain embodiments, a compound of Formula I, Formula II, Formula III, Formula IV, Formula V, Formula VI, Formula VII, or Formula VIII, or a pharmaceutically acceptable salt thereof, is administered for at least five days, six days, seven days, eight days, nine days, ten days, two weeks, three weeks, one month, at least two months, at least three months, at least four months, at least five months, at least six months or more. In some embodiments, a compound of Formula I, Formula II, Formula III, Formula IV, Formula V, Formula VI, Formula VII, or Formula VIII, or a pharmaceutically acceptable salt thereof, is administered once, twice, three, or more times a day. In some embodiments, it is administered orally twice a day.

For purposes of the present invention, a prophylactically or preventive effective amount of the compositions according to the present invention may generally fall within the ranges set out above, and can be determined in the best judgement of the health care provider. In some embodiments, a compound of the present invention is administered seasonally as the risk of the virus increases to prevent infection, or can be administered, for example, before, during and/or after travel or exposure.

One of ordinary skill in the art will recognize that a therapeutically effective amount will vary with the infection or condition to be treated, its severity, the treatment regimen to be employed, the pharmacokinetic of the agent used, as well as the patient or subject (animal or human) to be treated, and such therapeutic amount can be determined by the attending physician or specialist.

Solid Dosage Forms

An aspect of the invention is a solid dosage form that includes an effective amount of a compound of Formula I (including but not limited to Compound 1, 1A, 1B, 2, 2A or 2B), Formula II (including but not limited to Compound 3), Formula III, Formula IV, Formula V, Formula VI, Formula VII, or Formula VIII, or a pharmaceutically acceptable salt thereof, optionally in a pharmaceutically acceptable carrier.

In some embodiments, the solid dosage form includes a spray dried solid dispersion of a compound of Formula I, Formula II, Formula III, Formula IV, Formula V, Formula VI, Formula VII, or Formula VIII, or a pharmaceutically acceptable salt thereof, and the composition is suitable for oral delivery. In another embodiment, the solid dosage form is a granulo layered solid dispersion of a compound of Formula I, Formula II, Formula III, Formula IV, Formula V, Formula VI, Formula VII, or Formula VIII, or a pharmaceutically acceptable salt thereof, and the composition is suitable for oral delivery.

In other embodiments, the solid dispersion also contains at least one excipient selected from copovidone, poloxamer and HPMC-AS. In some embodiments the poloxamer is Poloxamer 407 or a mixture of poloxamers that may include Poloxamer 407. In some embodiments HPMC-AS is HPMC-AS-L.

In other embodiments, a solid dosage form prepared from a compound of Formula I, Formula II, Formula III, Formula IV, Formula V, Formula VI, Formula VII, or Formula VIII, or a pharmaceutically acceptable salt thereof, also comprises one or more of the following excipients: a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, silicified microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g., poly(1,3-dioxan-2one)), polyanhydride (e.g., poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g., poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), or hydroxypropylmethyl cellulose acetate succinate (HPMCAS).

In other embodiments, a solid dosage form prepared from a compound of Formula I, Formula II, Formula III, Formula IV, Formula V, Formula VI, Formula VII, or Formula VIII, or a pharmaceutically acceptable salt thereof, also comprises one or more of the following surfactants: polyoxyethylene glycol, polyoxypropylene glycol, decyl glucoside, lauryl glucoside, octyl glucoside, polyoxyethylene glycol octylphenol, Triton X-100, glycerol alkyl ester, glyceryl laurate, cocamide MEA, cocamide DEA, dodecyldimethylamine oxide, and poloxamers. Examples of poloxamers include, poloxamers 188, 237, 338 and 407. These poloxamers are available under the trade name Pluronic® (available from BASF, Mount Olive, N.J.) and correspond to Pluronic® F-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,700 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about E101 P56 E101 to about E106 P70 E106, or about E101 P56E101, or about E106 P70 E106, with an average molecular mass of about 10,000 to about 15,000 Da, or about 12,000 to about 14,000 Da, or about 12,000 to about 13,000 Da, or about 12,600 Da.

In yet other embodiments, a solid dosage form prepared from a compound of Formula I, Formula II, Formula III, Formula IV, Formula V, Formula VI, Formula VII, or Formula VIII, or a pharmaceutically acceptable salt thereof, also comprises one or more of the following surfactants: polyvinyl acetate, cholic acid sodium salt, dioctyl sulfosuccinate sodium, hexadecyltrimethyl ammonium bromide, saponin, sugar esters, Triton X series, sorbitan trioleate, sorbitan mono-oleate, polyoxyethylene (20) sorbitan monolaurate, polyoxyethylene (20) sorbitan monooleate, oleyl polyoxyethylene (2) ether, stearyl polyoxyethylene (2) ether, lauryl polyoxyethylene (4) ether, block copolymers of oxyethylene and oxypropylene, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, cetylpyridinium chloride, benzalkonium chloride, olive oil, glyceryl monolaurate, corn oil, cotton seed oil, and sunflower seed oil.

In alternative embodiments, a solid dosage form prepared from a compound of Formula I, Formula II, Formula III, Formula IV, Formula V, Formula VI, Formula VII, or Formula VIII, or a pharmaceutically acceptable salt thereof, is prepared by a process that includes solvent or dry granulation optionally followed by compression or compaction, spray drying, nano-suspension processing, hot melt extrusion, extrusion/spheronization, molding, spheronization, layering (e.g., spray layering suspension or solution), or the like. Examples of such techniques include direct compression, using appropriate punches and dies, for example wherein the punches and dies are fitted to a suitable tableting press; wet granulation using suitable granulating equipment such as a high shear granulator to form wetted particles to be dried into granules; granulation followed by compression using appropriate punches and dies, wherein the punches and dies are fitted to a suitable tableting press; extrusion of a wet mass to form a cylindrical extrudate to be cut into desire lengths or break into lengths under gravity and attrition; extrusion/spheronization where the extrudate is rounded into spherical particles and densified by spheronization; spray layering of a suspension or solution onto an inert core using a technique such as a convention pan or Wurster column; injection or compression molding using suitable molds fitted to a compression unit; and the like.

Exemplary disintegrants include alginic acid, carboxymethylcellulose calcium, carboxymethylcellulose sodium, cross-linked sodium carboxymethylcellulose (sodium croscarmellose), powdered cellulose, chitosan, croscarmellose sodium, crospovidone, guar gum, low substituted hydroxypropyl cellulose, methyl cellulose, microcrystalline cellulose, sodium alginate, sodium starch glycolate, partially pregelatinized starch, pregelatinized starch, starch, sodium carboxymethyl starch, and the like, or a combination thereof.

Exemplary lubricants include calcium stearate, magnesium stearate, glyceryl behenate, glyceryl palmitostearate, hydrogenated castor oil, light mineral oil, sodium lauryl sulfate, magnesium lauryl sulfate, sodium stearyl fumarate, stearic acid, zinc stearate, silicon dioxide, colloidal silicon dioxide, dimethyldichlorosilane treated with silica, talc, or a combination thereof.

The dosage form cores described herein may be coated to result in coated tablets. The dosage from cores can be coated with a functional or non-functional coating, or a combination of functional and non-functional coatings. "Functional coating" includes tablet coatings that modify the release properties of the total composition, for example, a sustained-release or delayed-release coating. "Non-functional coating" includes a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition. A non-functional coating can also mask the taste of the uncoated composition including the active pharmaceutical ingredient. A coating may comprise a light blocking material, a light absorbing material, or a light blocking material and a light absorbing material.

Exemplary polymethacrylates include copolymers of acrylic and methacrylic acid esters, such as a. an aminomethacrylate copolymer USP/NF such as a poly(butyl methacrylate, (2-dimethyl aminoethyl)methacrylate, methyl methacrylate) 1:2:1 (e.g., EUDRAGIT E 100, EUDRAGIT EPO, and EUDRAGIT E 12.5; CAS No. 24938-16-7); b. a poly(methacrylic acid, ethyl acrylate) 1:1 (e.g., EUDRAGIT L30 D-55, EUDRAGIT L100-55, EASTACRYL 30D, KOLLICOAT MAE 30D AND 30DP; CAS No. 25212-88-8); c. a poly(methacrylic acid, methyl methacrylate) 1:1 (e.g., EUDRAGIT L 100, EUDRAGIT L 12.5 and 12.5 P; also known as methacrylic acid copolymer, type ANF; CAS No. 25806-15-1); d. a poly(methacrylic acid, methyl methacrylate) 1:2 (e.g., EUDRAGIT S 100, EUDRAGIT S 12.5 and 12.5P; CAS No. 25086-15-1); e. a poly(methyl acrylate, methyl methacrylate, methacrylic acid) 7:3:1 (e.g., Eudragit FS 30 D; CAS No. 26936-24-3); f. a poly(ethyl acrylate, methylmethacrylate, trimethylammonioethyl methacrylate chloride) 1:2:0.2 or 1:2:0.1 (e.g., EUDRAGITS RL 100, RL PO, RL 30 D, RL 12.5, RS 100, RS PO, RS 30 D, or RS 12.5; CAS No. 33434-24-1); g. a poly(ethyl acrylate, methyl methacrylate) 2:1 (e.g., EUDRAGIT NE 30 D, Eudragit NE 40D, Eudragit NM 30D; CAS No. 9010-88-2); and the like, or a combination thereof.

Suitable alkylcelluloses include, for example, methylcellulose, ethylcellulose, and the like, or a combination thereof. Exemplary water based ethylcellulose coatings include AQUACOAT, a 30% dispersion further containing sodium lauryl sulfate and cetyl alcohol, available from FMC, Philadelphia, PA; SURELEASE a 25% dispersion further containing a stabilizer or other coating component (e.g., ammonium oleate, dibutyl sebacate, colloidal anhydrous silica, medium chain triglycerides, etc.) available from Colorcon, West Point, PA; ethyl cellulose available from Aqualon or Dow Chemical Co (Ethocel), Midland, MI. Those skilled in the art will appreciate that other cellulosic polymers, including other alkyl cellulosic polymers, can be substituted for part or all of the ethylcellulose.

Other suitable materials that can be used to prepare a functional coating include hydroxypropyl methylcellulose acetate succinate (HPMCAS); cellulose acetate phthalate (CAP); a polyvinylacetate phthalate; neutral or synthetic waxes, fatty alcohols (such as lauryl, myristyl, stearyl, cetyl or specifically cetostearyl alcohol), fatty acids, including fatty acid esters, fatty acid glycerides (mono-, di-, and tri-glycerides), hydrogenated fats, hydrocarbons, normal waxes, stearic acid, stearyl alcohol, hydrophobic and hydrophilic materials having hydrocarbon backbones, or a combination thereof. Suitable waxes include beeswax, glycowax, castor wax, carnauba wax, microcrystalline wax, candelilla, and wax-like substances, e.g., material normally solid at room temperature and having a melting point of from about 30° C. to about 100° C., or a combination thereof.

In other embodiments, a functional coating may include digestible, long chain (e.g., C8-C50, specifically C12-C40), substituted or unsubstituted hydrocarbons, such as fatty acids, fatty alcohols, glyceryl esters of fatty acids, mineral and vegetable oils, waxes, or a combination thereof. Hydrocarbons having a melting point of between about 25° C. and about 90° C. may be used. Specifically, long chain hydrocarbon materials, fatty (aliphatic) alcohols can be used.

The coatings can optionally contain additional pharmaceutically acceptable excipients such as a plasticizer, a stabilizer, a water-soluble component (e.g., pore formers), an anti-tacking agent (e.g., talc), a surfactant, and the like, or a combination thereof.

A functional coating may include a release-modifying agent, which affects the release properties of the functional coating. The release-modifying agent can, for example, function as a pore-former or a matrix disrupter. The release-modifying agent can be organic or inorganic, and include materials that can be dissolved, extracted or leached from the coating in the environment of use. The release-modifying agent can comprise one or more hydrophilic polymers including cellulose ethers and other cellulosics, such as hydroxypropyl methylcellulose, hydroxypropylcellulose, hydroxyethylcellulose, methyl cellulose, cellulose acetate phthalate, or hydroxypropyl methylcellulose acetate phthalate; povidone; polyvinyl alcohol; an acrylic polymer, such as gastric soluble Eudragit FS 30D, pH sensitive Eudragit L30D 55, L 100, S 100, or L 100-55; or a combination thereof. Other exemplary release-modifying agents include a povidone; a saccharide (e.g., lactose, and the like); a metal stearate; an inorganic salt (e.g., dibasic calcium phosphate, sodium chloride, and the like); a polyethylene glycol (e.g., polyethylene glycol (PEG) 1450, and the like); a sugar alcohol (e.g., sorbitol, mannitol, and the like); an alkali alkyl sulfate (e.g., sodium lauryl sulfate); a polyoxyethylene sorbitan fatty acid ester (e.g., polysorbate); or a combination thereof. Exemplary matrix disrupters include water insoluble organic or inorganic material. Organic polymers including but not limited to cellulose, cellulose ethers such as ethylcellulose, cellulose esters such as cellulose acetate, cellulose acetate butyrate and cellulose acetate propionate; and starch can function as matrix disrupters. Examples or inorganic disrupters include many calcium salts such as mono-, di- and tri calcium phosphate; silica and, talc.

The coating may optionally contain a plasticizer to improve the physical properties of the coating. For example, because ethylcellulose has a relatively high glass transition temperature and does not form flexible films under normal coating conditions, it may be advantageous to add plasticizer to the ethylcellulose before using the same as a coating material. Generally, the amount of plasticizer included in a coating solution is based on the concentration of the polymer, e.g., can be from about 1% to about 200% depending on the polymer but is most often from about 1 wt % to about 100 wt % of the polymer. Concentrations of the plasticizer, however, can be determined by routine experimentation.

Examples of plasticizers for ethylcellulose and other celluloses include plasticizers such as dibutyl sebacate, diethyl phthalate, triethyl citrate, tributyl citrate, triacetin, or a combination thereof, although it is possible that other water-insoluble plasticizers (such as acetylated monoglycerides, phthalate esters, castor oil, etc.) can be used.

Examples of plasticizers for acrylic polymers include citric acid esters such as triethyl citrate NF, tributyl citrate, dibutyl phthalate, 1,2-propylene glycol, polyethylene glycols, propylene glycol, diethyl phthalate, castor oil, triacetin, or a combination thereof, although it is possible that other plasticizers (such as acetylated monoglycerides, phthalate esters, castor oil, etc.) can be used.

Suitable methods can be used to apply the coating material to the surface of the dosage form cores. Processes such as simple or complex coacervation, interfacial polymerization, liquid drying, thermal and ionic gelation, spray drying, spray chilling, fluidized bed coating, pan coating, or electrostatic deposition may be used.

In certain embodiments, an optional intermediate coating is used between the dosage form core and an exterior coating. Such an intermediate coating can be used to protect the active agent or other component of the core subunit from the material used in the exterior coating or to provide other properties. Exemplary intermediate coatings typically include water-soluble film forming polymers. Such intermediate coatings may include film forming polymers such as hydroxyethyl cellulose, hydroxypropyl cellulose, gelatin, hydroxypropyl methylcellulose, polyethylene glycol, polyethylene oxide, and the like, or a combination thereof; and a plasticizer. Plasticizers can be used to reduce brittleness and increase tensile strength and elasticity. Exemplary plasticizers include polyethylene glycol propylene glycol and glycerin.

Combination and Alternation Therapy

The compounds or their pharmaceutically acceptable salts as described herein can be administered on top of the current standard of care for COVID patients, or in combination or alternation with any other compound or therapy that the healthcare provider deems beneficial for the patient. The combination and/or alternation therapy can be therapeutic, adjunctive, or palliative.

It has been observed that COVID patients can pass through various stages of disease, and that the standard of care can differ based on what stage of illness the patient presents with or advances to. COVID is noteworthy for the development of "cross-talk" between the immune system and the coagulation system. As the disease progresses, the patient can mount an overreaction by the immune system, which can lead to a number of serious implications, including a cytokine storm. Via the cross-talk between the immune system and the coagulation system, the patient can begin clotting in various areas of the body, including the respiratory system, brain, heart and other organs. Multiple clots throughout the body have been observed in COVID patients, requiring anticoagulant therapy. It is considered that these clots may cause long term, or even permanent damage if not treated and disease alleviated.

More specifically, COVID-19 has been described as progressing through three general stages of illness: stage 1 (early infection), stage 2 (pulmonary phase), and stage 3 (hyperinflammation phase/cytokine storm).

Stage 1 is characterized by non-specific, and often mild, symptoms. Viral replication is occurring, and it is appropriate to begin immediate treatment with the compounds described herein and perhaps in combination or alternation with another anti-viral therapy. Interferon-0 may also be administered to augment the innate immune response to the virus. In one embodiment, therefore, a compound of Formula I, Formula II, Formula III, Formula IV, Formula V, Formula VI, Formula VII, or Formula VIII, or a pharmaceutically acceptable salt thereof is used in an effective amount in combination or alternation with interferon-0 and or an additional anti-viral drug. Zinc supplements and or Vitamin C is also sometimes administered at this stage or as the illness progresses.

Stage 2 of COVID-19 is the pulmonary phase where patients may experience acute hypoxemic respiratory failure. In fact, the primary organ failure of COVID-19 is hypoxemic respiratory failure. It has been shown that moderate immunosuppression via a steroid, for example, dexamethasone, can be beneficial to patients with acute hypoxemic respiratory failure and/or patients on mechanical ventilation. In one embodiment, a compound of Formula I, Formula II, Formula III, Formula IV, Formula V, Formula VI, Formula VII, or Formula VIII, in combination with a corticosteroid which may be a glucocorticoid. Non-limiting examples are budesonide (Entocort EC), bethamethasone, (Celestone), prednisone (Prednisone Intensol), prednisolone (Orapred, Prelone), triamcinolone (Aristospan Intra-Articular, Aristospan Intralesional, Kenalog), methylprednisolone (Medrol, Depo-Medrol, Solu-Medrol), hydrocortisone, or dexamethasone (Dexamethasone Intensol, DexPak 10 Day, DexPak 13 Day, DexPak 6 Day).

The NS5B inhibitor remdesivir has provided mixed results when given to COVID-19 patients. In one embodiment, a compound of Formula I, Formula II, Formula III, Formula IV, Formula V, Formula VI, Formula VII, or Formula VIII, or a pharmaceutically acceptable salt thereof, is administered in combination or in alternation with Remdesivir to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with molnupiravir to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with PF-07304814 to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with PF-07321332 to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with EDP-235 to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with PBI-0451 to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with ALG-097111 to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with GC376 to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with sofosbuvir to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with ivermectin to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with nitazoxanide to amplify the overall antiviral effect.

In one embodiment, a compound of Formula I, Formula II, Formula III, Formula IV, Formula V, Formula VI, Formula VII, or Formula VIII, or a pharmaceutically acceptable salt thereof, is administered in combination or in alternation with the anti-inflammatory baricitinib. In some embodiments, a compound of Formula I, Formula II, Formula III, Formula IV, Formula V, Formula VI, Formula VII, or Formula VIII, or a pharmaceutically acceptable salt thereof, is administered in combination or in alternation with the anti-inflammatory baricitinib and dexamethasone.

Stage 3, the final stage of the disease, is characterized by progressive disseminated intravascular coagulation (DIC), a condition in which small blood clots develop throughout the bloodstream. This stage also can include multi-organ failure (e.g., vasodilatory shock, myocarditis). It has also been observed that many patients respond to this severe stage of COVID-19 infection with a "cytokine storm." There does appear to be a bi-directional, synergistic relationship between DIC and cytokine storm. To combat DIC, patients are often administered an anti-coagulant agent, which may, for example, be an indirect thrombin inhibitor or a direct oral anticoagulant ("DOAC"). Non-limiting examples are low-molecular weight heparin, warfarin, bivalirudin (Angiomax), rivaroxaban (Xarelto), dabigatran (Pradaxa), apixaban (Eliquis), or edoxaban (Lixiana). In one embodiment, a compound of Formula I, Formula II, Formula III, Formula IV, Formula V, Formula VI, Formula VII, or Formula VIII, or a pharmaceutically acceptable salt thereof, is administered in combination or in alternation with anti-coagulant therapy. In some severe cases of clotting in COVID patients, TPA can be administered (tissue plasminogen activator).

It has been observed that high levels of the cytokine interleukin-6 (IL-6) are a precursor to respiratory failure and death in COVID-19 patients. To treat this surge of an immune response, which may constitute a cytokine storm, patients can be administered an IL-6-targeting monoclonal antibody, pharmaceutical inhibitor or protein degrader such as a bispecific compound that binds to IL-6 and also to a protein that mediates degradation. Examples of antibodies include tocilizumab, sarilumab, siltuximab, olokizumab and clazakizumab. In one embodiment, a compound of Formula I, Formula II, Formula III, Formula IV, Formula V, Formula VI, Formula VII, or Formula VIII, or a pharmaceutically acceptable salt thereof, is administered in combination or in alternation with tocilizumab or sarilumab. Additional non-limiting examples of immunosuppressant drugs used to treat the overreacting immune system include Janus kinase inhibitors (tofacitinib (Xeljanz)); calcineurin inhibitors (cyclosporine (Neoral, Sandimmune, SangCya)), tacrolimus (Astagraf XL, Envarsus XR, Prograf)); mTOR inhibitors (sirolimus (Rapamune), everolimus (Afinitor, Zortress)); and, IMDH inhibitors (azathioprine (Azasan, Imuran), leflunomide (Arava), mycophenolate (CellCept, Myfortic)). Additional antibodies and biologics include abatacept (Orencia), adalimumab (Humira), anakinra (Kineret), certolizumab (Cimzia), etanercept (Enbrel), golimumab (Simponi), infliximab (Remicade), ixekizumab (Taltz), natalizumab (Tysabri), rituximab (Rituxan), secukinumab (Cosentyx), tocilizumab (Actemra), ixekizumab (Taltz), natalizumab (Tysabri), rituximab (Rituxan), tocilizumab (Actemra), ustekinumab (Stelara), vedolizumab (Entyvio), basiliximab (Simulect), and daclizumab (Zinbryta)).

IL-1 blocks the production of IL-6 and other proinflammatory cytokines. COVID patients are also sometimes treated with anti-IL-1 therapy to reduce a hyperinflammatory response, for example, an intravenous administration of anakinra. Anti-IL-1 therapy generally may be for example, a targeting monoclonal antibody, pharmaceutical inhibitor or protein degrader such as a bispecific compound that binds to IL-1 and also to a protein that mediates degradation.

Patients with COVID often develop viral pneumonia, which can lead to bacterial pneumonia. Patients with severe COVID-19 can also be affected by sepsis or "septic shock". Treatment for bacterial pneumonia secondary to COVID or for sepsis includes the administration of antibiotics, for example a macrolide antibiotic, including azithromycin, clarithromycin, erythromycin, or roxithromycin. Additional antibiotics include amoxicillin, doxycycline, cephalexin, ciprofloxacin, clindamycin, metronidazole, sulfamethoxazole, trimethoprim, amoxicillin, clavulanate, or levofloxacin. In one embodiment, thus a compound of Formula I, Formula II, Formula III, Formula IV, Formula V, Formula VI, Formula VII, or Formula VIII, or a pharmaceutically acceptable salt thereof, is administered in combination or in alternation with an antibiotic, for example, azithromycin. Some of these antibiotics such as azithromycin have independent anti-inflammatory properties. Such drugs may be used both as anti-inflammatory agents for COVID patients and have a treatment effect on secondary bacterial infections.

A unique challenge in treating patients infected with COVID-19 is the relatively long-term need for sedation if patients require mechanical ventilation which might last up to or greater than 5, 10 or even 14 days. For ongoing pain during this treatment, analgesics can be added sequentially, and for ongoing anxiety, sedatives can be added sequentially. Non-limiting examples of analgesics include acetaminophen, ketamine, and PRN opioids (hydromorphone, fentanyl, and morphine). Non-limiting examples of sedatives include melatonin, atypical antipsychotics with sedative-predominant properties (olanzapine, quetiapine), propofol or dexmedetomidine, haloperidol, and phenobarbital. In one embodiment, a compound of Formula I, Formula II, Formula III, Formula IV, Formula V, Formula VI, Formula VII, or Formula VIII, or a pharmaceutically acceptable salt thereof, is administered in combination or in alternation with a pain reliever, such as acetaminophen, ketamine, hydromorphone, fentanyl, or morphine. In one embodiment, a compound of Formula I, Formula II, Formula III, Formula IV, Formula V, Formula VI, Formula VII, or Formula VIII, or a pharmaceutically acceptable salt thereof, is administered in combination or in alternation with a sedative, such as melatonin, olanzapine, quetiapine, propofol, dexmedetomidine, haloperidol, or phenobarbital.

Investigational drugs for COVID-19 include chloroquine and hydroxychloroquine. In one embodiment, a compound of Formula I, Formula II, Formula III, Formula IV, Formula V, Formula VI, Formula VII, or Formula VIII, or a pharmaceutically acceptable salt thereof, is administered in combination or in alternation with chloroquine or hydroxychloroquine.

A protease inhibitor such as lopinavir or ritonavir, previously approved for HIV, may also be administered in combination with a compound of Formula I, Formula II, Formula III, Formula IV, Formula V, Formula VI, Formula VII, or Formula VIII, or a pharmaceutically acceptable salt thereof.

Additional drugs that may be used in combination with compound of Formula I, Formula II, Formula III, Formula IV, Formula V, Formula VI, Formula VII, or Formula VIII, or a pharmaceutically acceptable salt thereof, for the treatment of a COVID patient include, but are not limited to favipiravir, fingolimod (Gilenya), methylprednisolone, bevacizumab (Avastin), Actemra (tocilizumab), umifenovir, losartan and the monoclonal antibody combination of REGN3048 and REGN3051 or ribavirin. Any of these drugs or vaccines can be used in combination or alternation with an active compound provided herein to treat a viral infection susceptible to such.

In one embodiment, a compound of the present invention is used in an effective amount in combination with anti-coronavirus vaccine therapy, including but not limited to mRNA-1273 (Moderna, Inc.), AZD-1222 (AstraZeneca and University of Oxford), BNT162 (Pfizer and BioNTech), CoronaVac (Sinovac), NVX-CoV 2372 (NovoVax), SCB-2019 (Sanofi and GSK), ZyCoV-D (Zydus Cadila), and CoVaxin (Bharat Biotech). In another embodiment, a compound of the present invention is used in an effective amount in combination with passive antibody therapy or convalescent plasma therapy.

Additional drugs that may be used in combination with compound of Formula I, Formula II, Formula III, Formula IV, Formula V, Formula VI, Formula VII, or Formula VIII, or a pharmaceutically acceptable salt thereof, include, but are not limited to, mavrilimumab, remdesivir, baricitinib, dexamethasone, prednisone, methylprednisolone, hydrocortisone, tocilizumab, siltuximab, sarilumab, casirivimab, imdevimab, canakinumab, azithromycin, chloroquine/hydroxychloroquine, amodiaquine, artesunate, lopinavir, ritonavir, favipiravir, ribavirin, EIDD-2801, niclosamide, nitazoxanide, oseltamivir, ivermectin, molnupiravir, recombinant ACE-2, sotrovimab, budesonide, AZD7442, doxycycline; interferons, regdanvimab, anakinra, ruxolitinib, tofacitinib, acalabrutinib, imatinib, brensocatib, ravulizumab, namilumab, infliximab, adalimumab, otilimab, medi3506, bamlanivimab, etesevimab, sotrovimab, leronlimab, Risankizumab, lenzilumab, IMU-838, fluvoxamine, lenzilumab, EXO-CD24, leronlimab, colchicine, dimethyl fumarate, angiotensin-converting-enzyme inhibitors/angiotensin II receptor blockers, statins, clopidogrel, anticoagulants, bemcentinib, omeprazole, famotidine, zilucoplan, ascorbic acid/vitamin C, vitamin D3, aviptadi, tradipitant, nitric oxide, fluvoxamine, proxalutamide, ruconest, TRV027, fluvoxamine, isoflurane, sevoflurane, sotrovimab/VIR-7831 (GSK4182136), VIR-7832, ADG20, ADG10, LSALT Peptide, BRII-196/BRII-198, AZD7442 (IV), SNG001, AZD7442 (IM), camostat, C135-LS+C144-LS, SAB-185, NP-120 (fenprodil), losartan, omalizumab, ruxolitinib, Allogeneic Bone Marrow Mesenchymal Stromal Cells (BM-MSCs), Allogeneic Umbilical Cord Mesenchymal Stromal Cells (UC-MSCs), ixekizumab/apremilast, CPI-006, cadesartan, valsartan, ramipril, perindopril, irbesartan, losartan, enalapril, captopril, remestemcel-L, dapagliflozin, alcetrapid, pulmozyme (dornase alfa), EB05, perflenapent (NANO2), furosemide, peginterferon Lambda-1A, novaferon (chimeric interferon $\alpha$), LAU-7B (fenretinide), BLES (bovine lipid extract surfactant suspension), ciclesonide, MK-4482, ozanimol, hiltonol (Polyriboinosinic acid-polyribocytidylic acid (Poly-ICLC)), innohep (tinzaparin sodium), lovenox (enoxaparin sodium), fragmin (dalteparin sodium), heparin sodium, dapsone, rivaroxaban, cholecalciferol, fondaparinux, innohep, fragmin, SY-005 (Recombinant Human Annexin A5), simvastatin, ticagrelor, ramipril, lisinopril, perindopril erbumine, enalapril, trandolapril, captopril, valsatan, candesartan cilexetil, irbesartan, telmisartan, olmesartan medoxomil, RVX000222 (Apabetalone), S-1226 (Carbon-Dioxide Perflubron), placenta derived decidual stromal cells (DSC), ozempic (semaglutide), (Vascepa™) (icosapent) REGN-COV2, an anti-SARS-CoV-2 antibody cocktail, and VIR-7831, or a combination thereof. In some embodiments, the additional agent is combined with Compound 1, or a pharmaceutically acceptable salt thereof. In some embodiments, the additional agent is combined with Compound 1A, or a pharmaceutically acceptable salt thereof. In some embodiments, the additional agent is combined with Compound 1B, or a pharmaceutically acceptable salt thereof. In some embodiments, the additional agent is combined with Compound 2A. In some embodiments, the additional agent is combined with Compound 2B. In some embodiments, the additional agent is combined with Compound 3A, or a pharmaceutically acceptable salt thereof. In some embodiments, the additional agent is combined with Compound 3B, or a pharmaceutically acceptable salt thereof. In some embodiments, the additional agent is combined with Compound 4A. In some embodiments, the additional agent is combined with Compound 4B. In some embodiments, the additional agent is combined with a compound of Formula I, or pharmaceutically acceptable salt thereof. In some embodiments, the additional agent is combined with a compound of Formula II, or pharmaceutically acceptable salt thereof. In some embodiments, the additional agent is combined with a compound of Formula III, or pharmaceutically acceptable salt thereof. In some embodiments, the additional agent is combined with a compound of Formula IV, or pharmaceutically acceptable salt thereof. In some embodiments, the additional agent is combined with a compound of Formula V, or pharmaceutically acceptable salt thereof. In some embodiments, the additional agent is combined with a compound of Formula VI, or pharmaceutically acceptable salt thereof. In some embodiments, the additional agent is combined with a compound of Formula VII, or pharmaceutically acceptable salt thereof. In some embodiments, the additional agent is combined with a compound of Formula VIII, or pharmaceutically acceptable salt thereof.

SARS-CoV-2 is constantly mutating, which many increase virulence and transmission rates. Drug-resistant variants of viruses may emerge after prolonged treatment with an antiviral agent. Drug resistance may occur by mutation of a gene that encodes for an enzyme used in viral replication. The efficacy of a drug against an RNA virus infection in certain cases can be prolonged, augmented, or restored by administering the compound in combination or alternation with another, and perhaps even two or three other, antiviral compounds that induce a different mutation or act through a different pathway, from that of the principal drug.

Alternatively, the pharmacokinetics, bio distribution, half-life, or other parameter of the drug can be altered by such combination therapy (which may include alternation therapy if considered concerted). Since the disclosed purine nucleotides are polymerase inhibitors, it may be useful to administer the compound to a host in combination with, for example a:

(1) Protease inhibitor (including both 3CLpro/Mpro and PLpro inhibitor);
(2) Another polymerase inhibitor;
(3) Allosteric polymerase inhibitor;

(4) Interferon alfa-2a, which may be pegylated or otherwise modified, and/or ribavirin;
(5) Non-substrate-based inhibitor;
(6) Helicase inhibitor;
(7) Inhibitors of other viral non-structural proteins, including nsp14 exoribonuclease/methyltransferase, nsp15 endoribonuclease, nsp16 methyltransferase;
(8) Inhibitors of viral structural proteins, such as nucleocapsid protein;
(9) Antisense oligodeoxynucleotide (S-ODN);
(10) Aptamer;
(11) Nuclease-resistant ribozyme;
(12) small RNA, including microRNA and SiRNA;
(13) Antibody, partial antibody or domain antibody to the virus; or
(14) Viral antigen or partial antigen that induces a host antibody response.

In some embodiments, Compound 1A, or a pharmaceutically acceptable salt thereof, is administered to a patient with a SARS-CoV-2 variant infection in combination or alternation with PF-07304814:

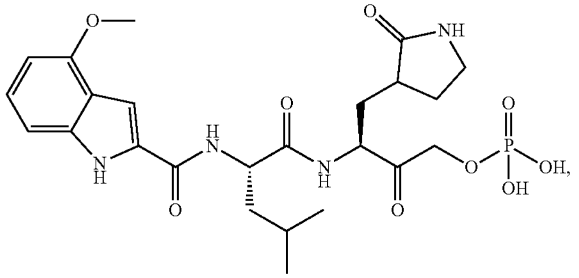 [SMILES: COc1cccc2[nH]c(C(=O)N[C@@H](CC(C)C)C(=O)N[C@@H](CC3CCNC3=O)C(=O)COP(=O)(O)O)cc12]

or a pharmaceutically acceptable salt thereof. In some embodiments, Compound 1B, or a pharmaceutically acceptable salt thereof, is administered in combination or alternation with PF-07304814. In some embodiments, Compound 2A is administered in combination or alternation with PF-07304814. In some embodiments, Compound 2B, or a pharmaceutically acceptable salt thereof, is administered in combination or alternation with PF-07304814. In some embodiments, Compound 3A, or a pharmaceutically acceptable salt thereof, is administered in combination or alternation with PF-07304814. In some embodiments, Compound 3B, or a pharmaceutically acceptable salt thereof, is administered in combination or alternation with PF-07304814. In some embodiments, Compound 4A is administered in combination or alternation with PF-07304814. In some embodiments, Compound 4B is administered in combination or alternation with PF-07304814. In some embodiments, a compound of Formula I, or a pharmaceutically acceptable salt thereof, is administered in combination or alternation with PF-07304814. In some embodiments, a compound of Formula II, or a pharmaceutically acceptable salt thereof, is administered in combination or alternation with PF-07304814. In some embodiments, a compound of Formula III, or a pharmaceutically acceptable salt thereof, is administered in combination or alternation with PF-07304814. In some embodiments, a compound of Formula IV, or a pharmaceutically acceptable salt thereof, is administered in combination or alternation with PF-07304814. In some embodiments, a compound of Formula V, or a pharmaceutically acceptable salt thereof, is administered in combination or alternation with PF-07304814. In some embodiments, a compound of Formula VI, or a pharmaceutically acceptable salt thereof, is administered in combination or alternation with PF-07304814. In some embodiments, a compound of Formula VII, or a pharmaceutically acceptable salt thereof, is administered in combination or alternation with PF-07304814. In some embodiments, a compound of Formula VIII, or a pharmaceutically acceptable salt thereof, is administered in combination or alternation with PF-07304814. In some embodiments, the patient has a SARS-CoV-2 variant selected from Alpha, Beta, Gamma, Delta, Lambda, or Mu. In some embodiments, the patient has a SARS-CoV-2 Delta variant. In some embodiments, the patient has a SARS-CoV-2 Lambda variant. In some embodiments, the patient has a SARS-CoV-2 Mu variant.

In some embodiments, Compound 1A, or a pharmaceutically acceptable salt thereof, is administered to a patient with a SARS-CoV-2 variant infection in combination or alternation with PF-07321332:

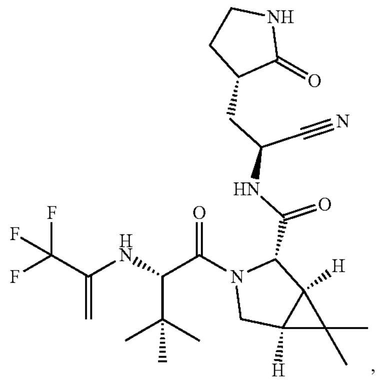

or a pharmaceutically acceptable salt thereof. In some embodiments, Compound 1B, or a pharmaceutically acceptable salt thereof, is administered in combination or alternation with PF-07321332. In some embodiments, Compound 2A is administered in combination or alternation with PF-07321332. In some embodiments, Compound 2B, or a pharmaceutically acceptable salt thereof, is administered in combination or alternation with PF-07321332. In some embodiments, Compound 3A, or a pharmaceutically acceptable salt thereof, is administered in combination or alternation with PF-07321332. In some embodiments, Compound 3B, or a pharmaceutically acceptable salt thereof, is administered in combination or alternation with PF-07321332. In some embodiments, Compound 4A is administered in combination or alternation with PF-07321332. In some embodiments, Compound 4B is administered in combination or alternation with PF-07321332. In some embodiments, a compound of Formula I, or a pharmaceutically acceptable salt thereof, is administered in combination or alternation with PF-07321332. In some embodiments, a compound of Formula II, or a pharmaceutically acceptable salt thereof, is administered in combination or alternation with PF-07321332. In some embodiments, a compound of Formula III, or a pharmaceutically acceptable salt thereof, is administered in combination or alternation with PF-07321332. In some embodiments, a compound of Formula IV, or a pharmaceutically acceptable salt thereof, is administered in combination or alternation with PF-07321332. In some embodiments, a compound of Formula V, or a pharmaceutically acceptable salt thereof, is administered in combination or alternation with PF-07321332. In some embodiments, a compound of Formula VI, or a pharmaceutically acceptable salt thereof, is administered in combination or alternation with PF-07321332. In some embodiments, a compound of Formula VII, or a pharmaceutically acceptable salt thereof, is administered in combination or alternation with PF-07321332. In some embodiments, a compound of Formula VIII, or a pharmaceutically acceptable salt thereof, is administered in combination or alternation with PF-07321332. In some embodiments, the patient has a SARS-CoV-2 variant selected from Alpha, Beta, Gamma, Delta, Lambda, or Mu. In some embodiments, the patient has a SARS-CoV-2 Delta variant. In some embodiments, the patient has a SARS-CoV-2 Lambda variant. In some embodiments, the patient has a SARS-CoV-2 Mu variant.

In some embodiments, Compound 1A, or a pharmaceutically acceptable salt thereof, is administered to a patient with a SARS-CoV-2 variant infection in combination or alternation with GC-376:

GC376

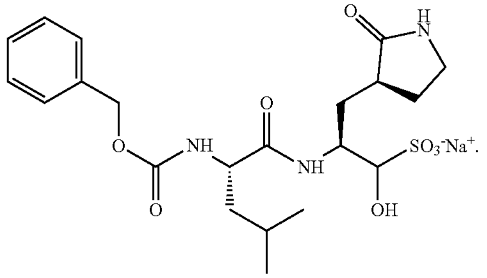

In some embodiments, Compound 1B, or a pharmaceutically acceptable salt thereof, is administered in combination or alternation with GC-376. In some embodiments, Compound 2A is administered in combination or alternation with GC-376. In some embodiments, Compound 2B, or a pharmaceutically acceptable salt thereof, is administered in combination or alternation with GC-376. In some embodiments, Compound 3A, or a pharmaceutically acceptable salt thereof, is administered in combination or alternation with GC-376. In some embodiments, Compound 3B, or a pharmaceutically acceptable salt thereof, is administered in combination or alternation with GC-376. In some embodiments, Compound 4A is administered in combination or alternation with GC-376. In some embodiments, Compound 4B is administered in combination or alternation with GC-376. In some embodiments, a compound of Formula I, or a pharmaceutically acceptable salt thereof, is administered in combination or alternation with GC-376. In some embodiments, a compound of Formula II, or a pharmaceutically acceptable salt thereof, is administered in combination or alternation with GC-376. In some embodiments, a compound of Formula III, or a pharmaceutically acceptable salt thereof, is administered in combination or alternation with GC-376. In some embodiments, a compound of Formula IV, or a pharmaceutically acceptable salt thereof, is administered in combination or alternation with GC-376. In some embodiments, a compound of Formula V, or a pharmaceutically acceptable salt thereof, is administered in combination or alternation with GC-376. In some embodiments, a compound of Formula VI, or a pharmaceutically acceptable salt thereof, is administered in combination or alternation with GC-376. In some embodiments, a compound of Formula VII, or a pharmaceutically acceptable salt thereof, is administered in combination or alternation with GC-376. In some embodiments, a compound of Formula VIII, or a pharmaceutically acceptable salt thereof, is administered in combination or alternation with GC-376. In some embodiments, the patient has a SARS-CoV-2 variant selected from Alpha, Beta, Gamma, Delta, Lambda, or Mu. In some embodiments, the patient has a SARS-CoV-2 Delta variant. In some embodiments, the patient has a SARS-CoV-2 Lambda variant. In some embodiments, the patient has a SARS-CoV-2 Mu variant.

In some embodiments, Compound 1A, or a pharmaceutically acceptable salt thereof, is administered to a patient with a SARS-CoV-2 variant infection in combination or alternation with molnupiravir. In some embodiments, Compound 1B, or a pharmaceutically acceptable salt thereof, is administered in combination or alternation with molnupiravir. In some embodiments, Compound 2A is administered in combination or alternation with molnupiravir. In some embodiments, Compound 2B is administered in combination or alternation with molnupiravir. In some embodiments, Compound 3A, or a pharmaceutically acceptable salt thereof, is administered in combination or alternation with molnupiravir. In some embodiments, Compound 3B, or a pharmaceutically acceptable salt thereof, is administered in combination or alternation with molnupiravir. In some embodiments, Compound 4A is administered in combination or alternation with molnupiravir. In some embodiments, Compound 4B is administered in combination or alternation with molnupiravir. In some embodiments, a compound of Formula I, or a pharmaceutically acceptable salt thereof, is administered in combination or alternation with molnupiravir. In some embodiments, a compound of Formula II, or a pharmaceutically acceptable salt thereof, is administered in combination or alternation with molnupiravir. In some embodiments, a compound of Formula III, or a pharmaceutically acceptable salt thereof, is administered in combination or alternation with molnupiravir. In some embodiments, a compound of Formula IV, or a pharmaceutically acceptable salt thereof, is administered in combination or alternation with molnupiravir. In some embodiments, a compound of Formula V, or a pharmaceutically acceptable salt thereof, is administered in combination or alternation with molnupiravir. In some embodiments, a compound of Formula VI, or a pharmaceutically acceptable salt thereof, is administered in combination or alternation with molnupiravir. In some embodiments, a compound of Formula VII, or a pharmaceutically acceptable salt thereof, is administered in combination or alternation with molnupiravir. In some embodiments, a compound of Formula VIII, or a pharmaceutically acceptable salt thereof, is administered in combination or alternation with molnupiravir. In some embodiments, the patient has a SARS-CoV-2 variant selected from Alpha, Beta, Gamma, Delta, Lambda, or Mu. In some embodiments, the patient has a SARS-CoV-2 Delta variant. In some embodiments, the patient has a SARS-CoV-2 Lambda variant. In some embodiments, the patient has a SARS-CoV-2 Mu variant.

In some embodiments, Compound 1A, or a pharmaceutically acceptable salt thereof, is administered to a patient with a SARS-CoV-2 variant infection in combination or alternation with REGN-COV2. In some embodiments, Compound 1B, or a pharmaceutically acceptable salt thereof, is administered in combination or alternation with REGN-COV2. In some embodiments, Compound 2A is administered in combination or alternation with REGN-COV2. In some embodiments, Compound 2B is administered in combination or alternation with REGN-COV2. In some embodiments, Compound 3A, or a pharmaceutically acceptable salt thereof, is administered in combination or alternation with REGN-COV2. In some embodiments, Compound 3B, or a pharmaceutically acceptable salt thereof, is administered in combination or alternation with REGN-COV2. In some embodiments, Compound 4A is administered in combination or alternation with REGN-COV2. In some embodiments, Compound 4B is administered in combination or alternation with REGN-COV2. In some embodiments, a compound of Formula I, or a pharmaceutically acceptable salt thereof, is administered in combination or alternation with REGN-COV2. In some embodiments, a compound of Formula II, or a pharmaceutically acceptable salt thereof, is administered in combination or alternation with REGN-COV2. In some embodiments, a compound of Formula III, or a pharmaceutically acceptable salt thereof, is administered in combination or alternation with REGN-COV2. In some embodiments, a compound of Formula IV, or a pharmaceutically acceptable salt thereof, is administered in combination or alternation with REGN-COV2. In some embodiments, a compound of Formula V, or a pharmaceutically acceptable salt thereof, is administered in combination or alternation with REGN-COV2. In some embodiments, a compound of Formula VI, or a pharmaceutically acceptable salt thereof, is administered in combination or alternation with REGN-COV2. In some embodiments, a compound of Formula VII, or a pharmaceutically acceptable salt thereof, is administered in combination or alternation with REGN-COV2. In some embodiments, a compound of Formula VIII, or a pharmaceutically acceptable salt thereof, is administered in combination or alternation with REGN-COV2. In some embodiments, the patient has a SARS-CoV-2 variant selected from Alpha, Beta, Gamma, Delta, Lambda, or Mu. In some embodiments, the patient has a SARS-CoV-2 Delta variant. In some embodiments, the patient has a SARS-CoV-2 Lambda variant. In some embodiments, the patient has a SARS-CoV-2 Mu variant.

In some embodiments, Compound 1A, or a pharmaceutically acceptable salt thereof, is administered to a patient with a SARS-CoV-2 variant infection in combination or alternation with sofosbuvir. In some embodiments, Compound 1B, or a pharmaceutically acceptable salt thereof, is administered in combination or alternation with sofosbuvir. In some embodiments, Compound 2A is administered in combination or alternation with sofosbuvir. In some embodiments, Compound 2B is administered in combination or alternation with sofosbuvir. In some embodiments, Compound 3A, or a pharmaceutically acceptable salt thereof, is administered in combination or alternation with sofosbuvir. In some embodiments, Compound 3B, or a pharmaceutically acceptable salt thereof, is administered in combination or alternation with sofosbuvir. In some embodiments, Compound 4A is administered in combination or alternation with sofosbuvir. In some embodiments, Compound 4B is administered in combination or alternation with sofosbuvir. In some embodiments, a compound of Formula I, or a pharmaceutically acceptable salt thereof, is administered in combination or alternation with sofosbuvir. In some embodiments, a compound of Formula II, or a pharmaceutically acceptable salt thereof, is administered in combination or alternation with sofosbuvir. In some embodiments, a compound of Formula III, or a pharmaceutically acceptable salt thereof, is administered in combination or alternation with sofosbuvir. In some embodiments, a compound of Formula IV, or a pharmaceutically acceptable salt thereof, is administered in combination or alternation with sofosbuvir. In some embodiments, a compound of Formula V, or a pharmaceutically acceptable salt thereof, is administered in combination or alternation with sofosbuvir. In some embodiments, a compound of Formula VI, or a pharmaceutically acceptable salt thereof, is administered in combination or alternation with sofosbuvir. In some embodiments, a compound of Formula VII, or a pharmaceutically acceptable salt thereof, is administered in combination or alternation with sofosbuvir. In some embodiments, a compound of Formula VIII, or a pharmaceutically acceptable salt thereof, is administered in combination or alternation with sofosbuvir. In some embodiments, the patient has a SARS-CoV-2 variant selected from Alpha, Beta, Gamma, Delta, Lambda, or Mu. In some embodiments, the patient has a SARS-CoV-2 Delta variant. In some embodiments, the patient has a SARS-CoV-2 Lambda variant. In some embodiments, the patient has a SARS-CoV-2 Mu variant.

In some embodiments, Compound 1A, or a pharmaceutically acceptable salt thereof, is administered to a patient with a SARS-CoV-2 variant infection in combination or alternation with remdesivir. In some embodiments, Compound 1B, or a pharmaceutically acceptable salt thereof, is administered in combination or alternation with remdesivir. In some embodiments, Compound 2A is administered in combination or alternation with remdesivir. In some embodiments, Compound 2B is administered in combination or alternation with remdesivir. In some embodiments, Compound 3A, or a pharmaceutically acceptable salt thereof, is administered in combination or alternation with remdesivir. In some embodiments, Compound 3B, or a pharmaceutically acceptable salt thereof, is administered in combination or alternation with remdesivir. In some embodiments, Compound 4A is administered in combination or alternation with remdesivir. In some embodiments, Compound 4B is administered in combination or alternation with remdesivir. In some embodiments, a compound of Formula I, or a pharmaceutically acceptable salt thereof, is administered in combination or alternation with remdesivir. In some embodiments, a compound of Formula II, or a pharmaceutically acceptable salt thereof, is administered in combination or alternation with remdesivir. In some embodiments, a compound of Formula III, or a pharmaceutically acceptable salt thereof, is administered in combination or alternation with remdesivir. In some embodiments, a compound of Formula IV, or a pharmaceutically acceptable salt thereof, is administered in combination or alternation with remdesivir. In some embodiments, a compound of Formula V, or a pharmaceutically acceptable salt thereof, is administered in combination or alternation with remdesivir. In some embodiments, a compound of Formula VI, or a pharmaceutically acceptable salt thereof, is administered in combination or alternation with remdesivir. In some embodiments, a compound of Formula VII, or a pharmaceutically acceptable salt thereof, is administered in combination or alternation with remdesivir. In some embodiments, a compound of Formula VIII, or a pharmaceutically acceptable salt thereof, is administered in combination or alternation with remdesivir. In some embodiments, the patient has a SARS-CoV-2 variant selected from Alpha, Beta, Gamma, Delta, Lambda, or Mu. In some embodiments, the patient has a SARS-CoV-2 Delta variant. In some embodiments, the patient has a SARS-CoV-2 Lambda variant. In some embodiments, the patient has a SARS-CoV-2 Mu variant.

In some embodiments, Compound 1A, or a pharmaceutically acceptable salt thereof, is administered to a patient with a SARS-CoV-2 variant infection in combination or alternation with casirivimab and imdevimab. In some embodiments, Compound 1B, or a pharmaceutically acceptable salt thereof, is administered in combination or alternation with casirivimab and imdevimab. In some embodiments, Compound 2A is administered in combination or alternation with casirivimab and imdevimab. In some embodiments, Compound 2B is administered in combination or alternation with casirivimab and imdevimab. In some embodiments, Compound 3A, or a pharmaceutically acceptable salt thereof, is administered in combination or alternation with casirivimab and imdevimab. In some embodiments, Compound 3B, or a pharmaceutically acceptable salt thereof, is administered in combination or alternation with casirivimab and imdevimab. In some embodiments, Compound 4A is administered in combination or alternation with casirivimab and imdevimab. In some embodiments, Compound 4B is administered in combination or alternation with casirivimab and imdevimab. In some embodiments, a compound of Formula I, or a pharmaceutically acceptable salt thereof, is administered in combination or alternation with casirivimab and imdevimab. In some embodiments, a compound of Formula II, or a pharmaceutically acceptable salt thereof, is administered in combination or alternation with casirivimab and imdevimab. In some embodiments, a compound of Formula III, or a pharmaceutically acceptable salt thereof, is administered in combination or alternation with casirivimab and imdevimab. In some embodiments, a compound of Formula IV, or a pharmaceutically acceptable salt thereof, is administered in combination or alternation with casirivimab and imdevimab. In some embodiments, a compound of Formula V, or a pharmaceutically acceptable salt thereof, is administered in combination or alternation with casirivimab and imdevimab. In some embodiments, a compound of Formula VI, or a pharmaceutically acceptable salt thereof, is administered in combination or alternation with casirivimab and imdevimab. In some embodiments, a compound of Formula VII, or a pharmaceutically acceptable salt thereof, is administered in combination or alternation with casirivimab and imdevimab. In some embodiments, a compound of Formula VIII, or a pharmaceutically acceptable salt thereof, is administered in combination or alternation with casirivimab and imdevimab. In some embodiments, the patient has a SARS-CoV-2 variant selected from Alpha, Beta, Gamma, Delta, Lambda, or Mu. In some embodiments, the patient has a SARS-CoV-2 Delta variant. In some embodiments, the patient has a SARS-CoV-2 Lambda variant. In some embodiments, the patient has a SARS-CoV-2 Mu variant.

EMBODIMENTS

At least the following non-limiting embodiments are provided herein:

1. A method for the treatment or prevention of a mutant or resistant form of the SARS-CoV-2 virus in a human in need thereof comprising administering an effective amount of a compound of Formula I or a pharmaceutically acceptable salt thereof:

Formula I

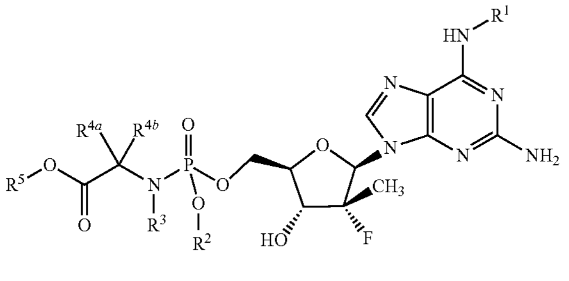

wherein $R^1$ is selected from $C_1$-$C_6$alkyl, $C_3$-$C_6$cycloalkyl, and —$C(O)C_1$-$C_6$alkyl;

$R^2$ is hydrogen, $C_{1-6}$alkyl (including methyl, ethyl, propyl, and isopropyl), $C_{3-7}$cycloalkyl, aryl (including phenyl and napthyl), aryl($C_1$-$C_4$alkyl)-, heteroaryl, or heteroalkyl;

$R^3$ is hydrogen or $C_{1-6}$alkyl (including methyl, ethyl, propyl, and isopropyl);

$R^{4a}$ and $R^{4b}$ are independently selected from hydrogen, $C_{1-6}$alkyl (including methyl, ethyl, propyl, and isopropyl), and $C_{3-7}$cycloalkyl; and $R^5$ is hydrogen, $C_{1-6}$alkyl (including methyl, ethyl, propyl, and isopropyl), $C_{1-6}$haloalkyl, $C_{3-7}$cycloalkyl, aryl($C_1$-$C_4$alkyl)-, aryl, heteroaryl, or heteroalkyl.

2. The method of embodiment 1, wherein the compound is (Compound 1)

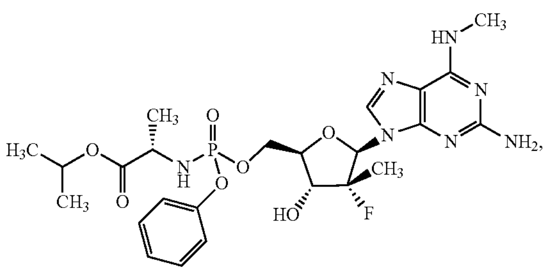

or a pharmaceutically acceptable salt thereof.

3. The method of embodiment 1, wherein the compound is (Compound 2)

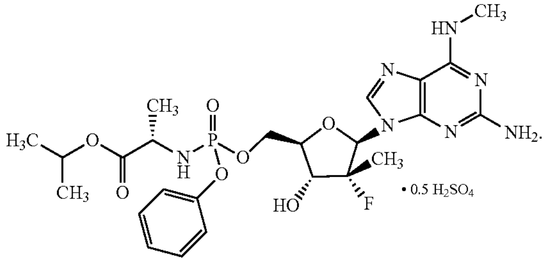

4. The method of embodiment 1, wherein the compound is (Compound 1A)

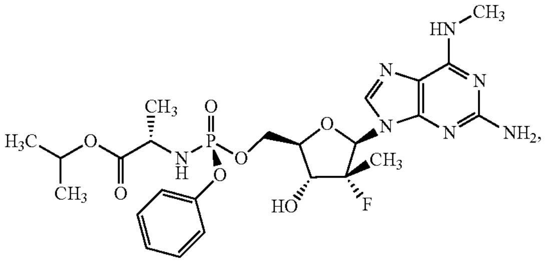

or a pharmaceutically acceptable salt thereof.

5. The method of embodiment 1, wherein the compound is (Compound 1B)

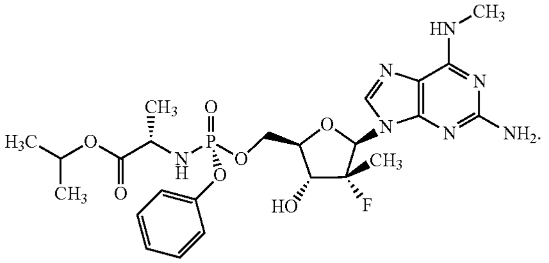

6. The method of embodiment 1, wherein the compound is (Compound 2A)

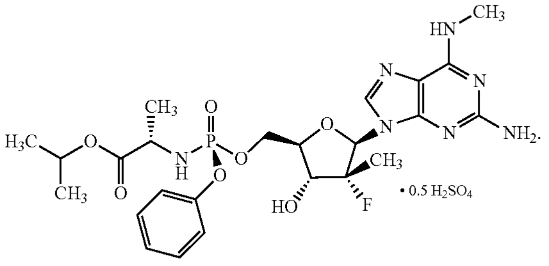

7. The method of embodiment 1, wherein the compound is (Compound 2B)

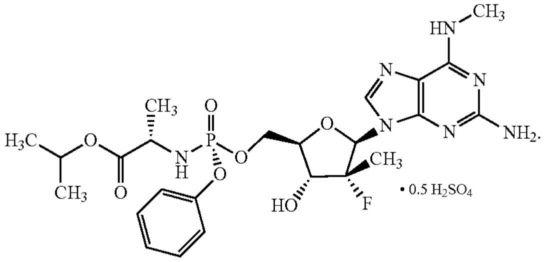

8. A method for the treatment or prevention of a mutant or resistant form of the SARS-CoV-2 virus in a human in need thereof comprising administering an effective amount of a compound of Formula II or a pharmaceutically acceptable salt thereof:

(Formula II)

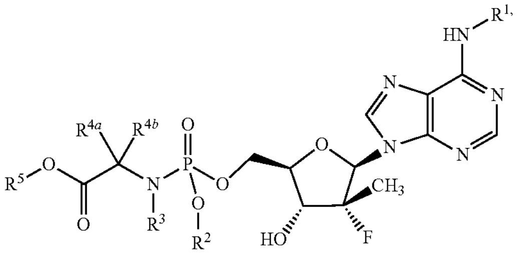

wherein:

$R^1$ is selected from $C_1$-$C_6$alkyl, $C_3$-$C_6$cycloalkyl, and —C(O)$C_1$-$C_6$alkyl;

$R^2$ is hydrogen, $C_{1-6}$alkyl (including methyl, ethyl, propyl, and isopropyl), $C_{3-7}$cycloalkyl, aryl (including phenyl and napthyl), aryl($C_1$-$C_4$alkyl)-, heteroaryl, or heteroalkyl;

$R^3$ is hydrogen or $C_{1-6}$alkyl (including methyl, ethyl, propyl, and isopropyl);

$R^{4a}$ and $R^{4b}$ are independently selected from hydrogen, $C_{1-6}$alkyl (including methyl, ethyl, propyl, and isopropyl), and $C_{3-7}$cycloalkyl; and $R^5$ is hydrogen, $C_{1-6}$alkyl (including methyl, ethyl, propyl, and isopropyl), $C_{1-6}$haloalkyl, $C_{3-7}$cycloalkyl, aryl($C_1$-$C_4$alkyl)-, aryl, heteroaryl, or heteroalkyl.

9. The method of embodiment 8, wherein the compound is:

(Compound 3)

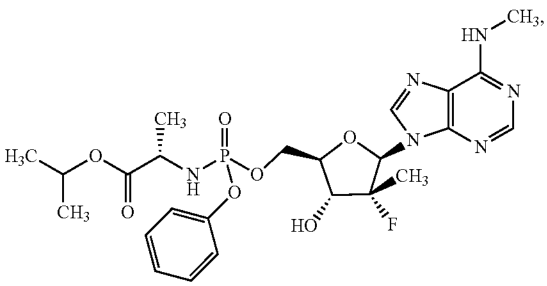

or a pharmaceutically acceptable salt thereof.

10. The method of embodiment 8, wherein the compound is:

(Compound 4)

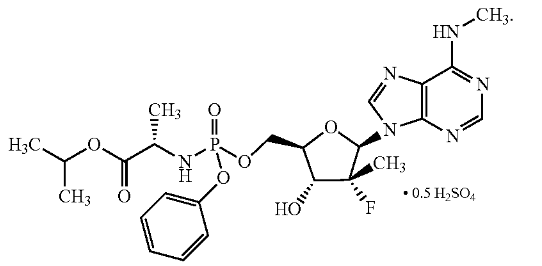

11. The method of embodiment 8, wherein the compound is:

(Compound 3A)

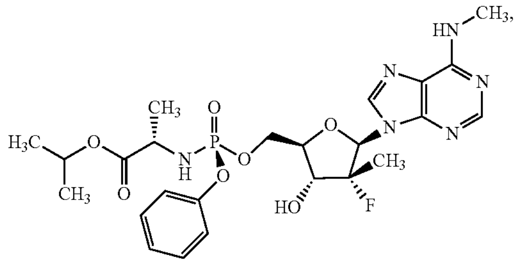

or a pharmaceutically acceptable salt thereof.

12. The method of embodiment 8, wherein the compound is:

(Compound 3B)

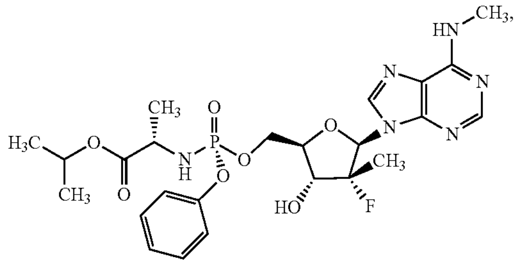

or a pharmaceutically acceptable salt thereof.

13. The method of embodiment 8, wherein the compound is:

(Compound 4A)

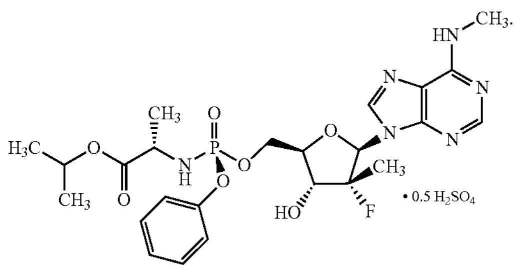

14. The method of embodiment 8, wherein the compound is:

(Compound 4B)

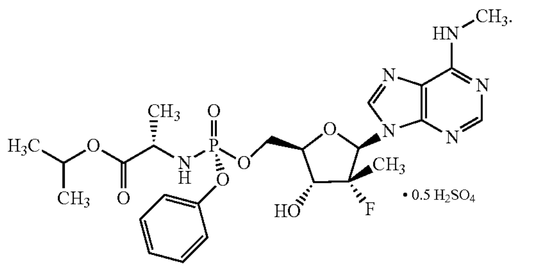

15. A method for the treatment or prevention of a mutant or resistant form of the SARS-CoV-2 virus in a human in need thereof comprising administering an effective amount of a compound of Formula III or a pharmaceutically acceptable salt thereof:

(Formula III)

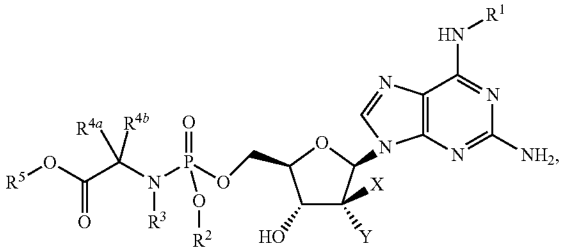

or a pharmaceutically acceptable salt thereof, wherein:

$R^1$ is selected from $C_1$-$C_6$alkyl, $C_3$-$C_6$cycloalkyl, and —C(O)$C_1$-$C_6$alkyl;

$R^2$ is hydrogen, $C_{1-6}$alkyl (including methyl, ethyl, propyl, and isopropyl), $C_{3-7}$cycloalkyl, aryl (including phenyl and napthyl), aryl($C_1$-$C_4$alkyl)-, heteroaryl, or heteroalkyl;

$R^3$ is hydrogen or $C_{1-6}$alkyl (including methyl, ethyl, propyl, and isopropyl);

$R^{4a}$ and $R^{4b}$ are independently selected from hydrogen, $C_{1-6}$alkyl (including methyl, ethyl, propyl, and isopropyl), and $C_{3-7}$cycloalkyl; and $R^5$ is hydrogen, $C_{1-6}$alkyl (including methyl, ethyl, propyl, and isopropyl), $C_{1-6}$haloalkyl, $C_{3-7}$cycloalkyl, aryl($C_1$-$C_4$alkyl)-, aryl, heteroaryl, or heteroalkyl;

X is selected from F, $C_1$, $C_1$-$C_3$haloalkyl (including $C_{1-3}$fluoroalkyl and $C_{1-3}$chloroalkyl, such as $CH_2F$, $CHF_2$, $CF_3$, $CH_2CF_3$, $CH_2CHF_2$, $CH_2CH_2F$, $CF_2CH_3$, $CF_2CF_3$, and $CH_2C_1$), $C_2$-$C_4$alkenyl, $C_2$-$C_4$alkynyl, and $C_1$-$C_3$hydroxyalkyl; and Y is Cl or F.

16. A method for the treatment or prevention of a mutant or resistant form of the SARS-CoV-2 virus in a human in need thereof comprising administering an effective amount of a compound of Formula IV or a pharmaceutically acceptable salt thereof:

(Formula IV)

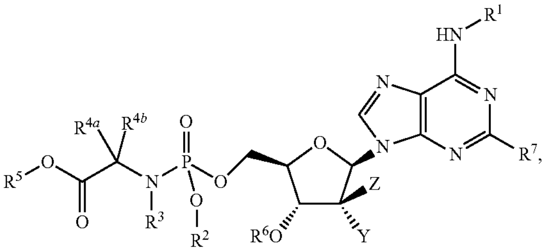

wherein $R^6$ is selected from hydrogen, —C(O)$R^{6A}$, —C(O)O$R^{6A}$, $C_{1-6}$alkyl, —$CH_2$—O—$R^{6A}$;

$R^{6A}$ is selected from hydrogen, $C_{1-6}$alkyl, $C_1$-$C_6$haloalkyl (for example, —$CHCl_2$, —$CCl_3$, —$CH_2Cl$, —$CF_3$, —$CHF_2$, —$CH_2F$), aryl, aryl($C_{1-6}$alkyl)- wherein the aryl group is optionally substituted with a substituent selected from alkoxy, hydroxy, nitro, bromo, chloro, fluoro, azido, and haloalkyl;

$R^7$ is $NH_2$, H, or —$NR^8R^9$; $R^8$ and $R^9$ are independently selected from hydrogen, $C_{1-6}$alkyl, —C(O)$R^{6A}$, and —C(O)O$R^{6A}$;

Y is selected from F and Cl;

Z is selected from methyl, $C_1$-$C_3$haloalkyl (including $C_{1-3}$fluoroalkyl and $C_{1-3}$chloroalkyl, such as $CH_2F$, $CHF_2$, $CF_3$, $CH_2CF_3$, $CH_2CHF_2$, $CH_2CH_2F$, $CF_2CH_3$, $CF_2CF_3$, and $CH_2C_1$), $C_2$-$C_4$alkenyl, $C_2$-$C_4$alkynyl, $C_1$-$C_3$hydroxyalkyl, and halogen (including Cl and F); and $R^1$, $R^2$, $R^3$, $R^{4a}$, $R^{4b}$, and $R^5$ are as defined herein.

17. A method for the treatment or prevention of a mutant or resistant form of the SARS-CoV-2 virus in a human in need thereof comprising administering an effective amount of a compound of Formula V, Formula VI, or Formula VII, or a pharmaceutically acceptable salt thereof:

(Formula V)

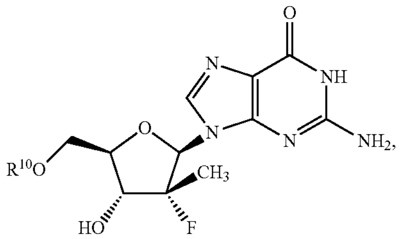

(Formula VI)

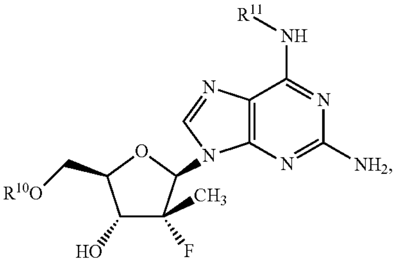

-continued (Formula VII)

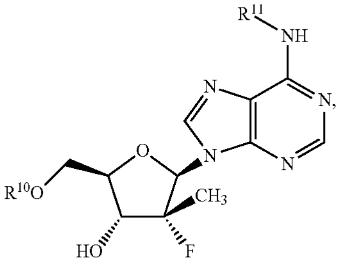

Wherein:

$R^{10}$ is selected from

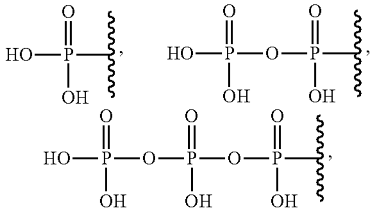

and $R^{10A}$;

$R^{10A}$ is a stabilized phosphate prodrug that metabolizes in vivo to a monophosphate, diphosphate, or triphosphate;

$R^{11}$ is selected from hydrogen and $R^1$; and $R^1$ is selected from $C_1$-$C_6$alkyl, $C_3$-$C_6$cycloalkyl, and —C(O)$C_1$-$C_6$alkyl.

18. A method for the treatment or prevention of a SARS-CoV-2 viral infection in a human in need thereof comprising administering an effective amount of a compound of Formula VIII:

(Formula VIII)

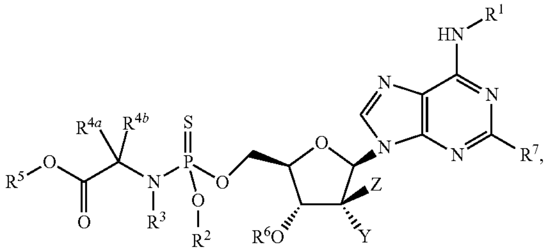

or a pharmaceutically acceptable salt thereof:

wherein $R^1$ is selected from $C_1$-$C_6$alkyl, $C_3$-$C_6$cycloalkyl, and —C(O)$C_1$-$C_6$alkyl;

$R^2$ is hydrogen, $C_{1-6}$alkyl (including methyl, ethyl, propyl, and isopropyl), $C_{3-7}$cycloalkyl, aryl (including phenyl and napthyl), aryl($C_1$-$C_4$alkyl)-, heteroaryl, or heteroalkyl;

$R^3$ is hydrogen or $C_{1-6}$alkyl (including methyl, ethyl, propyl, and isopropyl);

$R^{4a}$ and $R^{4b}$ are independently selected from hydrogen, $C_{1-6}$alkyl (including methyl, ethyl, propyl, and isopropyl), and $C_{3-7}$cycloalkyl; and $R^5$ is hydrogen, $C_{1-6}$alkyl (including methyl, ethyl, propyl, and isopropyl), $C_{1-6}$haloalkyl, $C_{3-7}$cycloalkyl, aryl($C_1$-$C_4$alkyl)-, aryl, heteroaryl, or heteroalkyl.

$R^6$ is selected from hydrogen, —C(O)$R^{6A}$, —C(O)O$R^{6A}$, $C_{1-6}$alkyl, —$CH_2$—O—$R^{6A}$;

$R^{6A}$ is selected from hydrogen, $C_{1-6}$alkyl, $C_1$-$C_6$haloalkyl (for example, —$CHCl_2$, —$CCl_3$, —$CH_2Cl$, —$CF_3$, —$CHF_2$, —$CH_2F$), aryl, aryl($C_{1-6}$alkyl)- wherein the aryl group is optionally substituted with a substituent selected from alkoxy, hydroxy, nitro, bromo, chloro, fluoro, azido, and haloalkyl;

$R^7$ is $NH_2$, H, or —$NR^8R^9$;

$R^8$ and $R^9$ are independently selected from hydrogen, $C_{1-6}$alkyl, —C(O)$R^{6A}$, and —C(O)O$R^{6A}$; Y is selected from F and Cl; and Z is selected from methyl, $C_1$-$C_3$haloalkyl (including $C_{1-3}$fluoroalkyl and $C_{1-3}$chloroalkyl, such as $CH_2F$, $CHF_2$, $CF_3$, $CH_2CF_3$, $CH_2CHF_2$, $CH_2CH_2F$, $CF_2CH_3$, $CF_2CF_3$, and $CH_2C_1$), $C_2$-$C_4$alkenyl, $C_2$-$C_4$alkynyl, $C_1$-$C_3$hydroxyalkyl, and halogen (including Cl and F).

19. The method of embodiment 18, wherein the SARS-CoV-2 virus is a mutant strain of SARS-CoV-2.

20. The method of embodiments 1-19, wherein the virus is a SARS-CoV-2 variant strain selected from: B.1.1.207 lineage variant, B.1.1.7 lineage variant, B.1.427/B.1.428 lineage variant, and B.1.351 lineage variant, or viral variants related thereto.

21. The method of embodiments 1-19, wherein the virus is a SARS-CoV-2 B.1.1.207 lineage variant, or a virus related thereto.

22. The method of embodiments 1-19, wherein the virus is a SARS-CoV-2 B.1.1.7 lineage variant, or a virus related thereto.

23. The method of embodiments 1-19, wherein the virus is a SARS-CoV-2 B.1.427/B.1.428 lineage variant, or a virus related thereto.

24. The method of embodiments 1-19, wherein the virus is a SARS-CoV-2 B.1.351 lineage variant, or a virus related thereto. lineage variant, or viral variants related thereto.

25. The method of embodiments 1-19, wherein the virus is a SARS-CoV-2 B.1.177 lineage variant, or a virus related thereto. lineage variant, or viral variants related thereto.

26. The method of embodiments 1-19, wherein the virus is a SARS-CoV-2 P.1 lineage variant, or a virus related thereto. lineage variant, or viral variants related thereto.

27. The method of embodiments 1-19, wherein the virus is a SARS-CoV-2 variant strain selected from: mink cluster 5 variant strain, Nexstrain cluster 20A.EU1 variant strain, Nexstrain cluster 20A.EU2 variant strain, "Cluster 5" variant strain, SARS-CoV-2 clade 19A, 19B, 20A, or 20C variant strain; SARS-CoV-2 clade G614, S84, V251, 1378 or D392 variant strain; or SARS-CoV-2 clade O, S, L, V, G, GH, or GR variant strain.

28. The method of embodiment 1-19, wherein the virus is a SARS-CoV-2 variant strain selected from: Alpha (Pango lineage: B.1.1.7), Beta (Pango lineages: B.1.351, B.1.351.2, B.1.351.3), Gamma (Pango Lineages: P.1, P.1.1, P.1.2), Delta (Pango Lineages: B.1.617.2, AY.1, AY.2, AY.3), Eta (Pango Lineages: B.1.525), Iota (Pango Lineage: B.1.526), Kappa (Pango Lineage: B.1.617.1), Lambda (Pango Lineage: C.37), Epsilon (Pango Lineages: B.1.427, B.1.429), Zeta (Pango Lineage: P.2), Theta (Pango Lineage: P.3) or Mu (Pango Lineage B.1.621).

29. The method of embodiment 1-19, wherein the virus is a SARS-CoV-2 variant strain selected from Pango Lineages P.2, P.3, R.1, R.2, B.1.466.2, B.1.621, B.1.1.318, B.1.1.519, C.36.3, C.36.3.1, B.1.214.2, B.1.1.523, B.1.617.3, B.1.619, B.1.620, B.1.621, A.23.1 (+E484K), A.27, A.28, C.16, B.1.351 (+P384L), B.1351 (+E516Q), B.1.1.7 (+L452R), B.1.1.7 (+S494P), C.36 (+L452R), AT.1, B.1.526.1, B.1.526.2, B.1.1.318, B.1.1.519, AV.1, P.1 (+P681H), B.1.671.2 (+K417N), or C.1.2.

30. The method of embodiment 1-19, wherein the virus is a SARS-CoV-2 Alpha variant (Pango lineage: B.1.1.7).

31. The method of embodiment 1-19, wherein the virus is a SARS-CoV-2 Beta variant (Pango lineages: B.1.351, B.1.351.2, B.1.351.3).

32. The method of embodiment 1-19, wherein the virus is a SARS-CoV-2 Gamma variant (Pango Lineages: P.1, P.1.1, P.1.2).

33. The method of embodiment 1-19, wherein the virus is a SARS-CoV-2 Delta variant (Pango Lineages: B.1.617.2, AY.1, AY.2, AY.3).

34. The method of embodiment 1-19, wherein the virus is a SARS-CoV-2 Eta variant (Pango Lineages: B.1.525).

35. The method of embodiment 1-19, wherein the virus is a SARS-CoV-2 Iota variant (Pango Lineage: B.1.526).

36. The method of embodiment 1-19, wherein the virus is a SARS-CoV-2 Kappa variant (Pango Lineage: B.1.617.1).

37. The method of embodiment 1-19, wherein the virus is a SARS-CoV-2 Lambda variant (Pango Lineage: C.37).

38. The method of embodiment 1-19, wherein the virus is a SARS-CoV-2 Epsilon variant (Pango Lineages: B.1.427, B.1.429).

39. The method of embodiment 1-19, wherein the virus is a SARS-CoV-2 Zeta variant (Pango Lineage: P.2).

40. The method of embodiment 1-19, wherein the virus is a SARS-CoV-2 Theta variant (Pango Lineage: P.3).

41. The method of embodiment 1-19, wherein the virus is a SARS-CoV-2 Mu variant (Pango Lineage: B.1.621).

42. The method of embodiment 1-19, wherein the virus is a SARS-CoV-2 comprising at least the following mutations in the spike (S) protein: N501Y, D614G, and P681H.

43. The method of embodiment 1-19, wherein the virus is a SARS-CoV-2 comprising at least the following mutations in the spike (S) protein: E484K, N501Y, D614G, and P681H.

44. The method of embodiment 1-19, wherein the virus is a SARS-CoV-2 comprising at least the following mutations in the spike (S) protein: K417N, E484K, N501Y, D614G, and A701V.

45. The method of embodiment 1-19, wherein the virus is a SARS-CoV-2 comprising at least the following mutations in the spike (S) protein: K417T, E484K, N501Y, D614G, and H655Y.

46. The method of embodiment 1-19, wherein the virus is a SARS-CoV-2 comprising at least the following mutations in the spike (S) protein: L452R, T478K, D614G, and P681R.

47. The method of embodiment 1-19, wherein the virus is a SARS-CoV-2 comprising at least the following mutations in the spike (S) protein: E484K, D614G, and Q677H.

48. The method of embodiment 1-19, wherein the virus is a SARS-CoV-2 comprising at least the following mutations in the spike (S) protein: E484K, N501Y, D614G, and P681H.
49. The method of embodiment 1-19, wherein the virus is a SARS-CoV-2 comprising at least the following mutations in the spike (S) protein: L452R, E484Q, D614G, and P681R.
50. The method of embodiment 1-19, wherein the virus is a SARS-CoV-2 comprising at least the following mutations in the spike (S) protein: S477N, E484K, D614G, and P681H.
51. The method of embodiment 1-19, wherein the virus is a SARS-CoV-2 comprising at least the following mutations in the spike (S) protein: R346K, E484K, N501Y, D614G, and P681H.
52. The method of embodiment 1-19, wherein the virus is a SARS-CoV-2 comprising at least the following mutations in the spike (S) protein: L452Q, F490S, and D614G.
53. The method of embodiment 1-19, wherein the virus is a SARS-CoV-2 comprising at least the following mutations in the spike (S) protein: L452R, E484Q, D614G, and P681R.
54. The method of embodiment 1-19, wherein the virus is a SARS-CoV-2 comprising at least the following mutations in the spike (S) protein: Q414K, N450K, ins214TDR, and D614G.
55. The method of embodiment 1-19, wherein the virus is a SARS-CoV-2 comprising at least the following mutations in the spike (S) protein: V367F, E484K, and Q613H.
56. The method of embodiment 1-19, wherein the virus is a SARS-CoV-2 comprising at least the following mutations in the spike (S) protein: L452R, N501Y, A653V, and H655Y.
57. The method of embodiment 1-19, wherein the virus is a SARS-CoV-2 comprising at least the following mutations in the spike (S) protein: E484K, N501T, and H655Y.
58. The method of embodiment 1-19, wherein the virus is a SARS-CoV-2 comprising at least the following mutations in the spike (S) protein: L452R, and D614G.
59. The method of embodiment 1-19, wherein the virus is a SARS-CoV-2 comprising at least the following mutations in the spike (S) protein: P384L, K417N, E484K, N501Y, D614G, and A701V.
60. The method of embodiment 1-19, wherein the virus is a SARS-CoV-2 comprising at least the following mutations in the spike (S) protein: K417N, E484K, N501Y, E516Q, D614G, and A701V.
61. The method of embodiment 1-19, wherein the virus is a SARS-CoV-2 comprising at least the following mutations in the spike (S) protein: L452R, N501Y, D614G, and P681H.
62. The method of embodiment 1-19, wherein the virus is a SARS-CoV-2 comprising at least the following mutations in the spike (S) protein: S494P, N501Y, D614G, and P681H.
63. The method of embodiment 1-19, wherein the virus is a SARS-CoV-2 comprising at least the following mutations in the spike (S) protein: L452R, D614G, and Q677H.
64. The method of embodiment 1-19, wherein the virus is a SARS-CoV-2 comprising at least the following mutations in the spike (S) protein: E484K, D614G, N679K, and ins679GIAL.
65. The method of embodiment 1-19, wherein the virus is a SARS-CoV-2 comprising at least the following mutations in the spike (S) protein: E484K, D614G, and A701V.
66. The method of embodiment 1-19, wherein the virus is a SARS-CoV-2 comprising at least the following mutations in the spike (S) protein: L452R, and D614G.
67. The method of embodiment 1-19, wherein the virus is a SARS-CoV-2 comprising at least the following mutations in the spike (S) protein: S477N, and D614G.
68. The method of embodiment 1-19, wherein the virus is a SARS-CoV-2 comprising at least the following mutations in the spike (S) protein: E484K, D614G, and P681H.
69. The method of embodiment 1-19, wherein the virus is a SARS-CoV-2 comprising at least the following mutations in the spike (S) protein: E484K, and D614G.
70. The method of embodiment 1-19, wherein the virus is a SARS-CoV-2 comprising at least the following mutations in the spike (S) protein: T478K, and D614G.
71. The method of embodiment 1-19, wherein the virus is a SARS-CoV-2 comprising at least the following mutations in the spike (S) protein: N439K, E484K, D614G, and P681H.
72. The method of embodiment 1-19, wherein the virus is a SARS-CoV-2 comprising at least the following mutations in the spike (S) protein: D614G, E484K, H655Y, K417T, N501Y, and P681H.
73. The method of embodiment 1-19, wherein the virus is a SARS-CoV-2 comprising at least the following mutations in the spike (S) protein: L452R, T478K, D614G, P681R, and K417N.
74. The method of embodiment 1-19, wherein the virus is a SARS-CoV-2 comprising at least the following mutations in the spike (S) protein: D614G, E484K, H655Y, N501Y, N679K, and Y449H.
75. The method of embodiments 1-19, wherein the virus is a SARS-CoV-2 virus which has a deletion of the spike protein amino acids H69 and V70.
76. The method of embodiments 1-19, wherein the virus is a SARS-CoV-2 virus which has a spike protein amino acid substitution D614G.
77. The method of embodiments 1-19, wherein the virus is a SARS-CoV-2 virus which has a deletion of the spike protein amino acid Y144.
78. The method of embodiments 1-19, wherein the virus is a SARS-CoV-2 virus which has a spike protein amino acid substitution N501Y.
79. The method of embodiments 1-19, wherein the virus is a SARS-CoV-2 virus which has a spike protein amino acid substitution A570D.
80. The method of embodiments 1-19, wherein the virus is a SARS-CoV-2 virus which has a spike protein amino acid substitution P681H.
81. The method of embodiments 1-19, wherein the virus is a SARS-CoV-2 virus which has a spike protein amino acid substitution T716I.
82. The method of embodiments 1-19, wherein the virus is a SARS-CoV-2 virus which has a spike protein amino acid substitution S982A.
83. The method of embodiments 1-19, wherein the virus is a SARS-CoV-2 virus which has a spike protein amino acid substitution D1118H.
84. The method of embodiments 1-19, wherein the virus is a SARS-CoV-2 virus which has a premature stop codon mutation Q27stop in the protein product of ORFS.

85. The method of embodiments 1-19, wherein the virus is a SARS-CoV-2 virus which has a spike protein amino acid substitution K417N.

86. The method of embodiments 1-19, wherein the virus is a SARS-CoV-2 virus which has a spike protein amino acid substitution E484K.

87. The method of embodiments 1-19, wherein the virus is a SARS-CoV-2 virus which has a spike protein amino acid substitution K417N.

88. The method of embodiments 1-19, wherein the virus is a SARS-CoV-2 virus which has a spike protein amino acid substitution D215G.

89. The method of embodiments 1-19, wherein the virus is a SARS-CoV-2 virus which has a spike protein amino acid substitution A701V.

90. The method of embodiments 1-19, wherein the virus is a SARS-CoV-2 virus which has a spike protein amino acid substitution L18F.

91. The method of embodiments 1-19, wherein the virus is a SARS-CoV-2 virus which has a spike protein amino acid substitution R246I.

92. The method of embodiments 1-19, wherein the virus is a SARS-CoV-2 virus which has a spike protein deletion at amino acids 242-244

93. The method of embodiments 1-19, wherein the virus is a SARS-CoV-2 virus which has a spike protein amino acid substitution Y453F.

94. The method of embodiments 1-19, wherein the virus is a SARS-CoV-2 virus which has a spike protein amino acid substitution I692V.

95. The method of embodiments 1-19, wherein the virus is a SARS-CoV-2 virus which has a spike protein amino acid substitution M1229I.

96. The method of embodiments 1-19, wherein the virus is a SARS-CoV-2 virus which has a spike protein amino acid substitution N439K.

97. The method of embodiments 1-19, wherein the virus is a SARS-CoV-2 virus which has a spike protein amino acid substitution A222V.

98. The method of embodiments 1-19, wherein the virus is a SARS-CoV-2 virus which has a spike protein amino acid substitution S477N.

99. The method of embodiments 1-19, wherein the virus is a SARS-CoV-2 virus which has a spike protein amino acid substitution A376T.

100. The method of embodiments 1-19, wherein the virus is a SARS-CoV-2 virus which has a nsp12 protein amino acid substitution P323L.

101. The method of embodiments 1-19, wherein the virus is a SARS-CoV-2 virus which has a nsp12 protein amino acid substitution Y455I.

102. The method of embodiments 1-19, wherein the virus is a SARS-CoV-2 virus which has a Orf8 protein amino acid substitution $R^{52I}$.

103. The method of embodiments 1-19, wherein the virus is a SARS-CoV-2 virus which has an ORF8 protein amino acid substitution Y73C.

104. The method of embodiments 1-19, wherein the virus is a SARS-CoV-2 virus which has a nucleocapsid (N) protein amino acid substitution D3L.

105. The method of embodiments 1-19, wherein the virus is a SARS-CoV-2 virus which has a nucleocapsid (N) protein amino acid substitution S235F.

106. The method of embodiments 1-19, wherein the virus is a SARS-CoV-2 virus which has a ORF1ab protein amino acid substitution T1001I.

107. The method of embodiments 1-19, wherein the virus is a SARS-CoV-2 virus which has a ORF1ab protein amino acid substitution A1708D.

108. The method of embodiments 1-19, wherein the virus is a SARS-CoV-2 virus which has a ORF1ab protein amino acid substitution 12230T.

109. The method of embodiments 1-19, wherein the virus is a SARS-CoV-2 virus which has a ORF1ab protein amino acid SGF 3675-3677 deletion.

110. The method of embodiments 1-19, wherein the virus is a SARS-CoV-2 virus which has a nsp12 protein amino acid substitution S861X, wherein X is any amino acid.

111. The method of embodiments 1-19, wherein the virus is a SARS-CoV-2 virus which has a nsp12 protein amino acid substitution F480V.

112. The method of embodiments 1-19, wherein the virus is a SARS-CoV-2 virus which has a nsp12 protein amino acid substitution V557L.

113. The method of embodiments 1-19, wherein the virus is a SARS-CoV-2 virus which has a nsp12 protein amino acid substitution D484Y.

114. The method of embodiments 1-19, wherein the virus is a SARS-CoV-2 virus which has a nsp12 protein amino acid substitution F480X, wherein X=any amino acid.

115. The method of embodiments 1-19, wherein the virus is a SARS-CoV-2 virus which has a nsp12 protein amino acid substitution V557X, wherein X=any amino acid.

116. The method of embodiments 1-19, wherein the virus is a SARS-CoV-2 virus which has a nsp12 protein amino acid substitution D484X, wherein X=any amino acid.

117. The method of embodiments 1-19, wherein the virus is a SARS-CoV-2 virus which has a nsp12 protein amino acid substitution P323L and a spike protein amino acid substitution D614G.

118. The method of embodiments 1-19, wherein the virus is a SARS-CoV-2 virus which has a nsp2 protein amino acid substitution T85I and a ORF3a amino acid substitution Q57H.

119. The method of embodiments 1-19, wherein the virus is a SARS-CoV-2 virus which has a nsp13 protein amino acid substitution P504L and Y541C.

120. The method of embodiments 1-19, wherein the virus is a SARS-CoV-2 virus which has a K417T, E484K, and N501Y mutation in the spike protein.

121. The method of embodiments 1-19, wherein the virus is a SARS-CoV-2 virus which has a deletion of the spike protein amino acids 69-70, deletion of the spike protein amino acid Y144, the the spike protein amino acid substitution D614G, the spike protein amino acid substitution P681H, the spike protein amino acid substitution T716I, the spike protein amino acid substitution S982A, the spike protein amino acid substitution D1118H, and a premature stop codon mutation (Q27stop) in the protein product of ORFS.

122. The method of embodiments 1-19, wherein the virus is a SARS-CoV-2 virus which has amino acid substitutions in the spike protein of N501Y, K417N, E484K, D80A, D215G, L18F, and R246I in the spike protein, and amino acid deletion at amino acids 242-244 of the spike protein.

123. The method of embodiments 1-19, wherein the virus is a SARS-CoV-2 virus which has a mutation in the receptor binding domain of the spike protein.

124. The method of embodiments 1-19, wherein the virus is a SARS-CoV-2 virus which has a mutation in the nsp12 protein.

125. The method of embodiments 1-19, wherein the virus is a SARS-CoV-2 virus which has a mutation in the active site of the RdRp domain of the nsp12 protein.

126. The method of embodiments 1-19, wherein the virus is a SARS-CoV-2 virus which has an amino acid substitution P323L in the nsp12 protein.

127. The method of embodiments 1-19, wherein the virus is a SARS-CoV-2 virus which has an amino acid substitution Y455I in the nsp12 protein.

128. The method of embodiments 1-19, wherein the virus is a SARS-CoV-2 virus which has a nsp12 protein amino acid substitution P323L and a spike protein amino acid substitution D614G.

129. The method of embodiments 1-19, wherein the virus is a SARS-CoV-2 virus which has a nsp12 protein amino acid substitution S861X, wherein X is any amino acid.

130. The method of embodiments 1-19, wherein the virus is a SARS-CoV-2 virus which has a nsp12 protein amino acid substitution F480V.

131. The method of embodiments 1-19, wherein the virus is a SARS-CoV-2 virus which has a nsp12 protein amino acid substitution V557L.

132. The method of embodiments 1-19, wherein the virus is a SARS-CoV-2 virus which has a nsp12 protein amino acid substitution D484Y.

133. The method of embodiments 1-19, wherein the virus is a SARS-CoV-2 virus which has a nsp12 protein amino acid substitution F480X, wherein X=any amino acid.

134. The method of embodiments 1-19, wherein the virus is a SARS-CoV-2 virus which has a nsp12 protein amino acid substitution V557X, wherein X=any amino acid.

135. The method of embodiments 1-19, wherein the virus is a SARS-CoV-2 virus which has a nsp12 protein amino acid substitution D484X, wherein X=any amino acid.

136. The method of embodiments 1-19, wherein the virus is a SARS-CoV-2 virus which has one or more of the following mutations in the nsp12 protein: P323L; T1411; A449V; S434F; M666I; H613Y; S647I; M380I; E922D; M629I; G774S; M6011; E436G; N491S; Q822H; A443V; T85I; A423V; M463I; T26I; A656T; M668I; T8061; T276M; T801N; V588L; K267N; V880I; K718R; L514F; F415S; T252N; Y38H; E744D; H752Q; I171V; S913L; A526V; A382V; G228C; P94L; E84K; K59N; P830S; T9081; P21S; D879Y; G108D; K780N; R279S; D258Y; T259I; K263N; D284Y; Q292H; T293I; N297S; V299F; D304Y; T319I; F321L; P328S; V330E; I333T; G337C; T344I; Y346H; L351P; V354L; Q357H; E370G; L372F; A400S; T4021; V405F; V410I; D418N; K426N; K430N; V435F; Q444H; D445G; A448V; R457C; P461T; C464F; I466V; V473F; K478N; D481G; D517G; D523N; A529V; P537S; S549N; A555V; C563F; M566I; A581T; G584V; A585T; G596S; T6041; S6071; D608G; V6091; M615V; W617L; M629V; I632V; L636F; L638F; A639V; T643I; T644M; L648F; V667I; A699S; N713S; H725; N734T; D736N; V737F; T739I; V742M; N743S; M756I; L758I; A771V; L775V; A777T; K780T; F793L; T801I; T803A; H810Y; G823C; D825Y; V827A; Y828H; V848L; T870I; K871R; N874D; Q875R; E876D; H882Y; H892Y; D901Y; M9061; N909D; T912N; P918S; E919D; A923T; F480V; V557L; D484Y; E802D; E802A; or S433G; or combinations thereof.

137. The method of embodiments 1-136, wherein the method further comprises administering an effective amount of at least one additional active agent.

138. The method of embodiments 1-137, wherein the additional active agent is selected from mavrilimumab, remdesivir, baricitinib, dexamethasone, prednisone, methylprednisolone, hydrocortisone, tocilizumab, siltuximab, sarilumab, casirivimab, imdevimab, canakinumab, azithromycin, chloroquine/hydroxychloroquine, amodiaquine, artesunate, lopinavir, ritonavir, favipiravir, ribavirin, EIDD-2801, niclosamide, nitazoxanide, oseltamivir, ivermectin, molnupiravir, recombinant ACE-2, sotrovimab, budesonide, AZD7442, doxycycline; interferons, regdanvimab, anakinra, ruxolitinib, tofacitinib, acalabrutinib, imatinib, brensocatib, ravulizumab, namilumab, infliximab, adalimumab, otilimab, medi3506, bamlanivimab, etesevimab, sotrovimab, leronlimab, Risankizumab, lenzilumab, IMU-838, fluvoxamine, lenzilumab, EXO-CD24, leronlimab, colchicine, dimethyl fumarate, angiotensin-converting-enzyme inhibitors/angiotensin II receptor blockers, statins, clopidogrel, anticoagulants, bemcentinib, omeprazole, famotidine, zilucoplan, ascorbic acid/vitamin C, vitamin D3, aviptadi, tradipitant, nitric oxide, fluvoxamine, proxalutamide, ruconest, TRV027, fluvoxamine, isoflurane, sevoflurane, VIR-7831 (GSK4182136), LSALT Peptide, BRII-196/BRII-198, AZD7442 (IV), SNG001, AZD7442 (IM), camostat, C135-LS+C144-LS, SAB-185, NP-120 (fenprodil), losartan, omalizumab, ruxolitinib, Allogeneic Bone Marrow Mesenchymal Stromal Cells (BM-MSCs), Allogeneic Umbilical Cord Mesenchymal Stromal Cells (UC-MSCs), ixekizumab/apremilast, CPI-006, cadesartan, valsartan, ramipril, perindopril, irbesartan, losartan, enalapril, captopril, remestemcel-L, dapagliflozin, alcetrapid, pulmozyme (dornase alfa), EB05, perflenapent (NANO2), furosemide, peginterferon Lambda-1A, novaferon (chimeric interferon α), LAU-7B (fenretinide), BLES (bovine lipid extract surfactant suspension), ciclesonide, MK-4482, ozanimol, hiltonol (Polyriboinosinic acid-polyribocytidylic acid (Poly-ICLC)), innohep (tinzaparin sodium), lovenox (enoxaparin sodium), fragmin (dalteparin sodium), heparin sodium, dapsone, rivaroxaban, cholecalciferol, fondaparinux, innohep, fragmin, SY-005 (Recombinant Human Annexin A5), simvastatin, ticagrelor, ramipril, lisinopril, perindopril erbumine, enalapril, trandolapril, captopril, valsatan, candesartan cilexetil, irbesartan, telmisartan, olmesartan medoxomil, RVX000222 (Apabetalone), S-1226 (Carbon-Dioxide Perflubron), placenta derived decidual stromal cells (DSC), ozempic (semaglutide), (Vascepa™) (icosapent), PF-07304814, PF-07321332, EDP-235, PBI-0451, ALG-097111, sotrovimab (VIR-7831), VIR-7832, BRII-196, BRII-198, ADG20, ADG10, REGN-COV2, an anti-SARS-CoV-2 antibody cocktail, or VIR-7831, or a combination thereof. 139. The method of embodiments 1-137, wherein the additional active agent is remdesivir.

140. The method of embodiments 1-137, wherein the additional active agent is a corticosteroid.

141. The method of embodiments 1-137, wherein the additional active agent is dexamethasone.

142. The method of embodiments 1-137, wherein the additional active agent is prednisone, methylprednisolone, or hydrocortisone.
143. The method of embodiments 1-137, wherein the additional active agent is baricitinib.
144. The method of embodiments 1-137, wherein the additional active agent is tocilizumab.
145. The method of embodiments 1-137, wherein the additional active agent is molnupiravir.
146. The method of embodiments 1-137, wherein the additional active agent is sofosbuvir.
147. The method of embodiments 1-137, wherein the additional active agent is GC376.
148. A method of treating or preventing a SARS-CoV infection in a human comprising the steps of (a) identifying a compound capable of inhibiting nidovirus RdRp-associated nucleotidyltransferase (NiRAN)-domain mediated activity of non-structural protein (nsp) 12 of a severe acute respiratory syndrome (SARS)-related coronavirus comprising determining the compound's ability to inhibit a NiRAN-domain mediated activity, wherein the NiRAN-domain mediated activity is selected from (i) the UMPylation of non-structural protein 8 (nsp8) with native uridine triphosphate (UTP); ii) the nucleotidylation of nsp8 with native uridine triphosphate (UTP); (iii) the nucleotidylation of nsp8 with native guanosine-triphosphate (GTP) by the NiRAN-domain; (iv) the transfer of native GTP to non-structural protein (nsp) 8; (v) the transfer of native UTP to nsp 8; and (vi) the initiation or completion of protein primed RNA synthesis; or a combination thereof; wherein a compound capable of inhibiting one or more NiRAN-domain mediated activities selected from (i)-(vi) by at least 25% or more as measured in an in vitro assay and compared to the same assay without the compound is identified as a compound capable of inhibiting a NiRAN-domain mediated activity; and
(b) if the compound inhibits the NiRAN-domain mediated activity of the virus, administering an effective amount of the compound to a human in need thereof.
149. The method of embodiment 148, wherein the compound identified as capable of inhibiting a NiRAN-domain mediated activity prevents the initiation or completion of protein primed RNA synthesis.
150. The method of embodiments 148 or 149, wherein the compound also acts to inhibit de novo dinucleotide synthesis in NiRAN-independent RNA synthesis or chain termination of RNA-dependent RNA synthesis.
151. The method of any of embodiments 148-150, wherein the compound is a nucleotide.
152. The method of any of embodiments 148-151, wherein the nucleotide is a guanosine-based nucleotide.
153. The method of any of embodiments 148-152, wherein the compound identified as a compound capable of inhibiting NiRAN-domain mediated activity is administered to a human having a SARS-CoV infection.
154. The method of embodiments 148-153, wherein the SARS-CoV is SARS-CoV-2.
155. A method for treating or preventing a SARS-CoV infection in a human in need thereof, comprising the steps of (a) identifying a compound capable of inhibiting NiRAN-domain mediated activity of nsp 12 of a SARS-related coronavirus comprising:
i. contacting the compound with a nsp12 protein of a SARS-related coronavirus; and,
ii. determining in vitro whether the compound binds to (i) the invariant lysine residue K73 in the NiRAN-domain of nsp12 or (ii) the active site of the NiRAN-domain; wherein a compound that binds to the invariant lysine residue K73 or the active site of the NiRAN-domain is indicative of a compound capable of inhibiting NiRAN-domain mediated activity; and (b) if the compound inhibits the NiRAN-domain mediated activity of the virus administering an effective amount of the compound to the human in need thereof.
156. The method of embodiment 155, wherein the active site of the NiRAN-domain is lined with the following residues: K73, R74, H75, N79, E83, R116, N209, G214, D218, F219, and F222.
157. The method of embodiment 155, wherein the active site of the NiRAN-domain is lined with the following residues: K50, R55 T120, N, 209, and Y217.
158. The method of embodiments 155-157, wherein the compound identified as a compound capable of inhibiting NiRAN-domain mediated activity is administered to a human that has a SARS-CoV-2 infection.
159. A method of treating or preventing a SARS-CoV infection in a human comprising: (a) identifying a compound capable of inhibiting NiRAN-domain mediated activity of nsp 12 of a SARS-CoV comprising:
i. contacting the compound with the nsp12 protein in the presence of UTP and/or GTP in vitro; and,
ii. measuring the binding of the compound, GTP, and/or UTP to the NiRAN-domain;
wherein the binding by the compound of at least about 1.5 times greater than that of GTP and or UTP is indicative of a compound capable of inhibiting NiRAN-domain mediated activity; and (b) if the compound inhibits the NiRAN-domain mediated activity of the virus, administering an effective amount of the compound to the human in need thereof.
160. The method of embodiment 159, wherein the compound contacts nsp12 in the presence of UTP.
161. The method of embodiment 159-160, wherein the compound contacts nsp12 in the presence of GTP.
162. The method of embodiment 159, wherein the compound contacts nsp12 in the presence of both UTP and GTP.
163. The method of any of embodiments 159-162, wherein GTP and/or UTP are present in a greater concentration than the compound.
164. The method of any of embodiments 159-163, wherein GTP and/or UTP are in equimolar concentrations with the compound.
165. The method of any of embodiments 159-164, wherein a compound is capable of inhibiting NiRAN-domain mediated activity if the compound binds the NiRAN-domain at about 2.0 times or greater than UTP and/or GTP compared to a control wherein the compound is not present.
166. The method of any of embodiments 159, 161-165, wherein a compound is capable of inhibiting NiRAN-domain mediated activity if the compound binds the NiRAN-domain at about 1.5 times greater than GTP.
167. The method of any of embodiments 159-160, 162-165, wherein a compound is capable of inhibiting NiRAN-domain mediated activity if the compound binds the NiRAN-domain at about 2.0 times greater than UTP.

168. The method of any of embodiments 159-167, wherein the compound identified as a compound capable of inhibiting NiRAN-domain mediated activity is administered to a human having or at risk of contracting a SARS-CoV infection.
169. A method of identifying a compound capable of inhibiting NiRAN-domain mediated activity of nsp 12 of a SARS-CoV comprising:
   i. contacting the compound with a nsp12 and nsp8 protein of a SARS-related coronavirus in the presence of UTP in vitro; and,
   ii. determining whether the compound inhibits the UMPylation of nsp8 by nsp12;
   wherein inhibition of UMPylation of nsp8 by the NiRAN-domain by at least 25% or more as measured in an in vitro assay and compared to the same assay without the compound is indicative of a compound capable of inhibiting NiRAN-domain mediated activity.
170. A method of identifying a compound capable of inhibiting NiRAN-domain mediated activity of nsp 12 of a SARS-CoV comprising:
   i. contacting the compound with a nsp12 and nsp8 protein of a SARS-related coronavirus in the presence of UTP and/or GTP in vitro; and,
   ii. determining whether the compound inhibits the nucleotidylation of nsp8;
   wherein inhibition of nucleotidylation of nsp8 by the NiRAN-domain by at least 25% or more as measured in an in vitro assay and compared to the same assay without the compound is indicative of a compound capable of inhibiting NiRAN-domain mediated activity.
171. The method of embodiment 170, wherein the method provides contacting nsp12 and nsp8 in the presence of UTP.
172. The method of embodiments 170, wherein the method provides contacting nsp12 and nsp8 in the presence of GTP.
173. The method of embodiments 169-170, wherein the method provides contacting nsp12 and nsp8 in the presence of both UTP and GTP.
174. The method of embodiments 169-173, wherein GTP and/or UTP are present in a greater concentration than the compound.
175. The method of embodiments 169-173, wherein GTP and/or UTP are in equimolar concentrations with the compound.
176. The method of embodiments 169-175, wherein a compound capable of inhibiting NiRAN-domain mediated activity reduces nucleotidylation of nsp8 by at least 50% or more compared to a control wherein the compound is not present.
177. The method of embodiments 169-175, wherein a compound capable of inhibiting NiRAN-domain mediated activity reduces nucleotidylation of nsp8 by at least 90% or more compared to a control wherein the compound is not present.
178. The method of any of embodiments 169-177, wherein the compound identified as a compound capable of inhibiting NiRAN-domain mediated activity is administered to a human having or at risk of contracting a SARS-CoV infection.
179. A method of identifying a compound capable of inhibiting NiRAN-domain mediated activity of nsp 12 of a SARS-CoV comprising:
   i. contacting the compound with a nsp12 and nsp8 protein of a SARS-related coronavirus in the presence of UTP and/or GTP in vitro; and,
   ii. determining whether the compound inhibits the transfer of UTP and/or GTP from nsp12 to nsp8;
   wherein inhibition of the transfer of UTP and/or GTP by the NiRAN-domain by at least 25% or more as measured in an in vitro assay and compared the same assay without the compound is indicative of a compound capable of inhibiting NiRAN-domain mediated activity.
180. The method of embodiment 179, wherein the compound contacts nsp12 and nsp8 in the presence of UTP.
181. The method of embodiments 179-180, wherein the compound contacts nsp12 and nsp8 in the presence of GTP.
182. The method of embodiments 179-181, wherein the compound contacts nsp12 and nsp8 in the presence of both UTP and GTP.
183. The method of embodiments 179-182, wherein GTP and/or UTP are present in a greater concentration than the compound.
184. The method of embodiments 179-182, wherein GTP and/or UTP are in equimolar concentrations with the compound.
185. The method of embodiments 179-184, wherein a compound capable of inhibiting NiRAN-domain mediated activity reduces transfer of GTP and/or UTP from nsp12 to nsp8 by at least 50% or more compared to a control wherein the compound is not present.
186. The method of embodiment 179-184, wherein a compound capable of inhibiting NiRAN-domain mediated activity reduces transfer of GTP and/or UTP from nsp12 to nsp8 by at least 90% or more compared to control wherein the compound is not present.
187. The method of any of embodiments 179-186, wherein the compound identified as a compound capable of inhibiting NiRAN-domain mediated activity is administered to a human having or at risk of contracting a SARS-CoV infection.
188. A method for identifying a compound capable of inhibiting protein primed RNA synthesis in a SARS-related coronavirus comprising:
   i. contacting the compound with a nsp12, nsp7, and nsp8 protein of a SARS-related coronavirus in the presence of UTP and a poly(A) RNA template in vitro; and
   ii. determining whether the compound inhibits de novo RNA synthesis on the poly(A) RNA template in the presence of UTP;
   wherein the inhibition of protein primed RNA synthesis on the poly(A) RNA template in the presence of UTP by at least 25% or more as measured in an in vitro assay as compared to the same assay without the compound is indicative of a compound capable of inhibiting protein-primed RNA synthesis.
189. The method of embodiment 188, wherein the nsp12, nsp7, and nsp8 is provided as a nsp12:7L8:8 polymerase complex.
190. The method of embodiments 188-189, wherein nsp12:7L8:8 polymerase complex is in a 1:3:3 molar ratio or a 1:3:6 molar ratio.
191. The method of embodiments 188-190, wherein a compound is identified as capable of inhibiting protein primed RNA synthesis if the compound reduces primer independent RNA synthesis of the poly(A) RNA template by at least 50% or more compared to a control wherein the compound is not present.

192. The method of embodiments 188-190, wherein the compound reduces protein primed RNA synthesis of the poly(A) RNA template by at least 90% or more compared to a control wherein the compound is not present.

193. The method of any of embodiments 188-192, wherein the compound identified as a compound capable of inhibiting protein primed RNA synthesis is administered to a human having or at risk of contracting a SARS-CoV-2 infection.

194. A method of treating or preventing a SARS-CoV infection in a human comprising identifying a compound capable of inhibiting SARS-CoV replication in a human, comprising (a):

i. selecting a nucleotide;

ii. screening the nucleotide in vitro to determine whether the compound inhibits NiRAN-domain mediated activity of the virus;

wherein the compound is determined to inhibit NiRAN-domain mediated activity if it: (i) prevents or decreases the binding of native UTP and/or GTP to the active region of NiRAN by at least 25% or more as measured in an in vitro assay and compared to the same assay without the compound; (ii) prevents or decreases the binding of native UTP to the active UMPylation site of NiRAN by at least 25% or more as measured in an in vitro assay and compared to the same assay without the compound; iii) prevents or decreases the binding of native NTP to the active NMPylation site of NiRAN by at least 25% or more as measured in an in vitro assay and compared to the same assay without the compound; iv) prevents or decreases the binding of native UTP and/or GTP to the invariant lysine residue K73 in the NiRAN-domain by at least 25% or more as measured in an in vitro assay and compared to the same assay without the compound; (v) prevents or decreases native UTP and/or GTP from accessing the active site of the NiRAN-domain; (vi) prevents or decreases native UTP and/or GTP from accessing the active site of the NiRAN-domain by at least 25% or more as measured in an in vitro assay and compared to the same assay without the compound, wherein the active site is a pocket lined with the following residues: K73, R74, H75, N79, E83, R116, N209, G214, D218, F219, and F222; (vii) prevents or decreases native UTP and/or GTP from accessing the active site of the NiRAN-domain by at least 25% or more as measured in an in vitro assay and compared to the same assay without the compound, wherein the active site is a pocket lined with the following residues: K50, R55 T120, N, 209, Y217; (viii) binds to the invariant lysine residue K73; (ix) binds to the active site pocket of the NiRAN-domain; (x) binds to the active site pocket of the NiRAN-domain, wherein the active site pocket is lined with the following residues: K73, R74, H75, N79, E83, R116, N209, G214, D218, F219, and F222; (xi) binds to the active site pocket of the NiRAN-domain, wherein the active site pocket is lined with the following residues: K50, R55 T120, N, 209, Y217; (xii) prevents the transfer of native UTP and/or GTP by the NiRAN-domain by at least 25% or more as measured in an in vitro assay and compared to the same assay without the compound; (xiii) prevents the transfer of native GTP and/or UTP to nsp8 by at least 25% or more as measured in an in vitro assay and compared to the same assay without the compound; or (xiv) prevents the initiation or completion of protein primed RNA synthesis by at least 25% or more as measured in an in vitro assay and compared to the same assay without the compound; or combinations thereof; and (b) if the compound inhibits the NiRAN-domain mediated activity of the virus, administering the compound to the human in need thereof.

195. The method of embodiment 194, wherein the nucleotide is a guanosine-based nucleotide.

196. The method of embodiments 194-195, wherein the nucleotide is a stabilized phosphate prodrug.

197. The method of embodiments 194-196, wherein the compound identified as a compound capable of inhibiting SARS-CoV replication is administered to a human having or at risk of contracting a SARS-CoV-2 infection.

198. A method for treating or preventing a SARS-CoV infection in a human comprising:

i. determining whether the human has a SARS-CoV infection;

ii. identifying a compound having NiRAN-domain mediated inhibitory activity; and, iii. if the compound has NiRAN-domain mediated inhibitory activity, administering to the human an effective amount of the compound.

199. The method of embodiment 194-198, wherein the compound inhibits NiRAN-domain mediated nsp8 UMPylation by at least 25% or more as measured in an in vitro assay and compared to the same assay without the compound.

200. The method of embodiment 194-198, wherein the compound inhibits NiRAN-domain mediated nsp8 nucleotidylation by at least 25% or more as measured in an in vitro assay and compared to the same assay without the compound.

201. The method of embodiment 194-198, wherein the compound inhibits transfer of a nucleotide from the NiRAN-domain of nsp12 to nsp8 by at least 25% or more as measured in an in vitro assay and compared to the same assay without the compound.

202. The method of embodiment 194-198, wherein the compound inhibits protein primed and/or primer independent RNA synthesis by at least 25% or more as measured in an in vitro assay and compared to the same assay without the compound.

203. The method of embodiment 194-198, wherein the compound inhibits protein primed and/or primer independent RNA synthesis and RNA-dependent RNA chain extension by at least 25% or more as measured in an in vitro assay and compared to the same assay without the compound.

204. The method of embodiment 194-198, wherein the compound preferentially binds to the NiRAN-domain of nsp12 over native UTP and GTP.

205. The method of embodiment 194-198, wherein the compound preferentially binds to the NiRAN-domain at least about 3× over native UTP when assayed in a 1:1 ratio.

206. The method of embodiment 194-198, wherein the compound preferentially binds to the NiRAN-domain at least about 1.5× over native GTP when assayed in a 1:1 ratio.

207. The method of embodiment 194-198, wherein the compound binds the invariant lysine residue K73 in the NiRAN-domain.
208. The method of embodiment 194-198, wherein the compound is a guanine-based or uridine-based nucleotide.
209. The method of embodiment 194-198, wherein the compound is a guanosine-based nucleotide.
210. The method of embodiment 194-198, wherein the compound is a stabilized phosphate prodrug.
211. The method of any of embodiments 148-210, wherein the SARS-related coronavirus viral infection is SARS-CoV-2.
212. The method of embodiment 211, wherein the compound is administered in combination or alternation with one or more additional active agents.
213. The method of embodiment 211, wherein the additional active agent is selected from mavrilimumab, remdesivir, baricitinib, dexamethasone, prednisone, methylprednisolone, hydrocortisone, tocilizumab, siltuximab, sarilumab, casirivimab, imdevimab, canakinumab, azithromycin, chloroquine/hydroxychloroquine, amodiaquine, artesunate, lopinavir, ritonavir, favipiravir, ribavirin, EIDD-2801, niclosamide, nitazoxanide, oseltamivir, ivermectin, molnupiravir, recombinant ACE-2, sotrovimab, budesonide, AZD7442, doxycycline; interferons, regdanvimab, anakinra, ruxolitinib, tofacitinib, acalabrutinib, imatinib, brensocatib, ravulizumab, namilumab, infliximab, adalimumab, otilimab, medi3506, bamlanivimab, etesevimab, sotrovimab, leronlimab, Risankizumab, lenzilumab, IMU-838, fluvoxamine, lenzilumab, EXO-CD24, leronlimab, colchicine, dimethyl fumarate, angiotensin-converting-enzyme inhibitors/angiotensin II receptor blockers, statins, clopidogrel, anticoagulants, bemcentinib, omeprazole, famotidine, zilucoplan, ascorbic acid/vitamin C, vitamin D3, aviptadi, tradipitant, nitric oxide, fluvoxamine, proxalutamide, ruconest, TRV027, fluvoxamine, isoflurane, sevoflurane, VIR-7831 (GSK4182136), LSALT Peptide, BRII-196/BRII-198, AZD7442 (IV), SNG001, AZD7442 (IM), camostat, C135-LS+C144-LS, SAB-185, NP-120 (fenprodil), losartan, omalizumab, ruxolitinib, Allogeneic Bone Marrow Mesenchymal Stromal Cells (BM-MSCs), Allogeneic Umbilical Cord Mesenchymal Stromal Cells (UC-MSCs), ixekizumab/apremilast, CPI-006, cadesartan, valsartan, ramipril, perindopril, irbesartan, losartan, enalapril, captopril, remestemcel-L, dapagliflozin, alcetrapid, pulmozyme (dornase alfa), EB05, perflenapent (NANO2), furosemide, peginterferon Lambda-1A, novaferon (chimeric interferon α), LAU-7B (fenretinide), BLES (bovine lipid extract surfactant suspension), ciclesonide, MK-4482, ozanimol, hiltonol (Polyriboinosinic acid-polyribocytidylic acid (Poly-ICLC)), innohep (tinzaparin sodium), lovenox (enoxaparin sodium), fragmin (dalteparin sodium), heparin sodium, dapsone, rivaroxaban, cholecalciferol, fondaparinux, innohep, fragmin, SY-005 (Recombinant Human Annexin A5), simvastatin, ticagrelor, ramipril, lisinopril, perindopril erbumine, enalapril, trandolapril, captopril, valsatan, candesartan cilexetil, irbesartan, telmisartan, olmesartan medoxomil, RVX000222 (Apabetalone), S-1226 (Carbon-Dioxide Perflubron), placenta derived decidual stromal cells (DSC), ozempic (semaglutide), (Vascepa™) (icosapent), PF-07304814, PF-07321332, EDP-235, PBI-0451, ALG-097111, or VIR-7832, BRII-196, BRII-198, ADG20, ADG10, VIR-7831, or a combination thereof.
214. The method of embodiment 212, wherein the additional active agent is remdesivir.
215. The method of embodiment 212, wherein the additional active agent is a corticosteroid.
216. The method of embodiment 212, wherein the additional active agent is dexamethasone.
217. The method of embodiment 212, wherein the additional active agent is prednisone, methylprednisolone, or hydrocortisone.
218. The method of embodiment 212, wherein the additional active agent is baricitinib.
219. The method of embodiment 212, wherein the additional active agent is tocilizumab.
220. The method of embodiment 212, wherein the additional active agent is molnupiravir.
221. The method of embodiment 212, wherein the additional active agent is sofosbuvir.
222. The method of embodiment 212, wherein the additional active agent is GC376.
223. The method of any of embodiments 148-222, wherein the compound is not a compound of Formula I.
224. The method of embodiments 148-223, wherein the virus is a mutant strain of SARS-CoV-2.
225. The method of embodiments 148-223, wherein the virus is a SARS-CoV-2 variant strain selected from: B.1.1.207 lineage variant, B.1.1.7 lineage variant, B.1.427/B.1.428 lineage variant, and B.1.351 lineage variant, or viral variants related thereto.
226. The method of embodiments 148-223, wherein the virus is a SARS-CoV-2 B.1.1.207 lineage variant, or a virus related thereto.
227. The method of embodiments 148-223, wherein the virus is a SARS-CoV-2 B.1.1.7 lineage variant, or a virus related thereto.
228. The method of embodiments 148-223, wherein the virus is a SARS-CoV-2 B.1.427/B.1.428 lineage variant, or a virus related thereto.
229. The method of embodiments 148-223, wherein the virus is a SARS-CoV-2 B.1.351 lineage variant, or a virus related thereto. lineage variant, or viral variants related thereto.
230. The method of embodiments 148-223, wherein the virus is a SARS-CoV-2 B.1.177 lineage variant, or a virus related thereto. lineage variant, or viral variants related thereto.
231. The method of embodiments 148-223, wherein the virus is a SARS-CoV-2 P.1 lineage variant, or a virus related thereto. lineage variant, or viral variants related thereto.
232. The method of embodiments 148-223, wherein the virus is a SARS-CoV-2 variant strain selected from: mink cluster 5 variant strain, Nexstrain cluster 20A.EU1 variant strain, Nexstrain cluster 20A.EU2 variant strain, “Cluster 5” variant strain, SARS-CoV-2 clade 19A, 19B, 20A, or 20C variant strain; SARS-CoV-2 clade G614, S84, V251, 1378 or D392 variant strain; or SARS-CoV-2 clade O, S, L, V, G, GH, or GR variant strain.
233. The method of embodiments 148-223, wherein the virus is a SARS-CoV-2 virus which has a deletion of the spike protein amino acids H69 and V70.

234. The method of embodiments 148-223, wherein the virus is a SARS-CoV-2 virus which has a spike protein amino acid substitution D614G.

235. The method of embodiments 148-223, wherein the virus is a SARS-CoV-2 virus which has a deletion of the spike protein amino acid Y144.

236. The method of embodiments 148-223, wherein the virus is a SARS-CoV-2 virus which has a spike protein amino acid substitution N501Y.

237. The method of embodiments 148-223, wherein the virus is a SARS-CoV-2 virus which has a spike protein amino acid substitution A570D.

238. The method of embodiments 148-223, wherein the virus is a SARS-CoV-2 virus which has a spike protein amino acid substitution P681H.

239. The method of embodiments 148-223, wherein the virus is a SARS-CoV-2 virus which has a spike protein amino acid substitution T716I.

240. The method of embodiments 148-223, wherein the virus is a SARS-CoV-2 virus which has a spike protein amino acid substitution S982A.

241. The method of embodiments 148-223, wherein the virus is a SARS-CoV-2 virus which has a spike protein amino acid substitution D1118H.

242. The method of embodiments 148-223, wherein the virus is a SARS-CoV-2 virus which has a premature stop codon mutation Q27stop in the protein product of ORFS.

243. The method of embodiments 148-223, wherein the virus is a SARS-CoV-2 virus which has a spike protein amino acid substitution K417N.

244. The method of embodiments 148-223, wherein the virus is a SARS-CoV-2 virus which has a spike protein amino acid substitution E484K.

245. The method of embodiments 148-223, wherein the virus is a SARS-CoV-2 virus which has a spike protein amino acid substitution K417N.

246. The method of embodiments 148-223, wherein the virus is a SARS-CoV-2 virus which has a spike protein amino acid substitution D215G.

247. The method of embodiments 148-223, wherein the virus is a SARS-CoV-2 virus which has a spike protein amino acid substitution A701V.

248. The method of embodiments 148-223, wherein the virus is a SARS-CoV-2 virus which has a spike protein amino acid substitution L18F.

249. The method of embodiments 148-223, wherein the virus is a SARS-CoV-2 virus which has a spike protein amino acid substitution R246I.

250. The method of embodiments 148-223, wherein the virus is a SARS-CoV-2 virus which has a spike protein deletion at amino acids 242-244

251. The method of embodiments 148-223, wherein the virus is a SARS-CoV-2 virus which has a spike protein amino acid substitution Y453F.

252. The method of embodiments 148-223, wherein the virus is a SARS-CoV-2 virus which has a spike protein amino acid substitution I692V.

253. The method of embodiments 148-223, wherein the virus is a SARS-CoV-2 virus which has a spike protein amino acid substitution M1229I.

254. The method of embodiments 148-223, wherein the virus is a SARS-CoV-2 virus which has a spike protein amino acid substitution N439K.

255. The method of embodiments 148-223, wherein the virus is a SARS-CoV-2 virus which has a spike protein amino acid substitution A222V.

256. The method of embodiments 148-223, wherein the virus is a SARS-CoV-2 virus which has a spike protein amino acid substitution S477N.

257. The method of embodiments 148-223, wherein the virus is a SARS-CoV-2 virus which has a spike protein amino acid substitution A376T.

258. The method of embodiments 148-223, wherein the virus is a SARS-CoV-2 virus which has a nsp12 protein amino acid substitution P323L.

259. The method of embodiments 148-223, wherein the virus is a SARS-CoV-2 virus which has a nsp12 protein amino acid substitution Y455I.

260. The method of embodiments 148-223, wherein the virus is a SARS-CoV-2 virus which has a Orf8 protein amino acid substitution $R^{52I}$.

261. The method of embodiments 148-223, wherein the virus is a SARS-CoV-2 virus which has an ORF8 protein amino acid substitution Y73C.

262. The method of embodiments 148-223, wherein the virus is a SARS-CoV-2 virus which has a nucleocapsid (N) protein amino acid substitution D3L.

263. The method of embodiments 148-223, wherein the virus is a SARS-CoV-2 virus which has a nucleocapsid (N) protein amino acid substitution S235F.

264. The method of embodiments 148-223, wherein the virus is a SARS-CoV-2 virus which has a ORF1ab protein amino acid substitution T1001I.

265. The method of embodiments 148-223, wherein the virus is a SARS-CoV-2 virus which has a ORF1ab protein amino acid substitution A1708D.

266. The method of embodiments 148-223, wherein the virus is a SARS-CoV-2 virus which has a ORF1ab protein amino acid substitution 12230T.

267. The method of embodiments 148-223, wherein the virus is a SARS-CoV-2 virus which has a ORF1ab protein amino acid SGF 3675-3677 deletion.

268 The method of embodiments 148-223, wherein the virus is a SARS-CoV-2 virus which has a nsp12 protein amino acid substitution S861X, wherein X is any amino acid.

269. The method of embodiments 148-223, wherein the virus is a SARS-CoV-2 virus which has a nsp12 protein amino acid substitution F480V.

270. The method of embodiments 148-223, wherein the virus is a SARS-CoV-2 virus which has a nsp12 protein amino acid substitution V557L.

271. The method of embodiments 148-223, wherein the virus is a SARS-CoV-2 virus which has a nsp12 protein amino acid substitution D484Y.

272. The method of embodiments 148-223, wherein the virus is a SARS-CoV-2 virus which has a nsp12 protein amino acid substitution F480X, wherein X=any amino acid.

273. The method of embodiments 148-223, wherein the virus is a SARS-CoV-2 virus which has a nsp12 protein amino acid substitution V557X, wherein X=any amino acid.

274. The method of embodiments 148-223, wherein the virus is a SARS-CoV-2 virus which has a nsp12 protein amino acid substitution D484X, wherein X=any amino acid.

275. The method of embodiments 148-223, wherein the virus is a SARS-CoV-2 virus which has a nsp12 protein amino acid substitution P323L and a spike protein amino acid substitution D614G.

276. The method of embodiments 148-223, wherein the virus is a SARS-CoV-2 virus which has a nsp2 protein amino acid substitution T85I and a ORF3a amino acid substitution Q57H.

277. The method of embodiments 148-223, wherein the virus is a SARS-CoV-2 virus which has a nsp13 protein amino acid substitution P504L and Y541C.

278. The method of embodiments 148-223, wherein the virus is a SARS-CoV-2 virus which has a K417T, E484K, and N501Y mutation in the spike protein.

279. The method of embodiments 148-223, wherein the virus is a SARS-CoV-2 virus which has a deletion of the spike protein amino acids 69-70, deletion of the spike protein amino acid Y144, the spike protein amino acid substitution N501Y, the spike protein amino acid substitution A570D, the spike protein amino acid substitution D614G, the spike protein amino acid substitution P681H, the spike protein amino acid substitution T716I, the spike protein amino acid substitution S982A, the spike protein amino acid substitution D1118H, and a premature stop codon mutation (Q27stop) in the protein product of ORFS.

280. The method of embodiments 148-223, wherein the virus is a SARS-CoV-2 virus which has amino acid substitutions in the spike protein of N501Y, K417N, E484K, D80A, D215G, L18F, and R246I in the spike protein, and amino acid deletion at amino acids 242-244 of the spike protein.

281. The method of embodiments 148-223, wherein the virus is a SARS-CoV-2 virus which has a mutation in the receptor binding domain of the spike protein.

282. The method of embodiments 148-223, wherein the virus is a SARS-CoV-2 virus which has a mutation in the nsp12 protein.

283. The method of embodiments 148-223, wherein the virus is a SARS-CoV-2 virus which has a mutation in the active site of the RdRp domain of the nsp12 protein.

284. The method of embodiments 148-223, wherein the virus is a SARS-CoV-2 virus which has an amino acid substitution P323L in the nsp12 protein.

285. The method of embodiments 148-223, wherein the virus is a SARS-CoV-2 virus which has an amino acid substitution Y455I in the nsp12 protein.

286. The method of embodiments 148-223, wherein the virus is a SARS-CoV-2 virus which has a nsp12 protein amino acid substitution P323L and a spike protein amino acid substitution D614G.

287. The method of embodiments 148-223, wherein the virus is a SARS-CoV-2 virus which has a nsp12 protein amino acid substitution S861X, wherein X is any amino acid.

288. The method of embodiments 148-223, wherein the virus is a SARS-CoV-2 virus which has a nsp12 protein amino acid substitution F480V.

289. The method of embodiments 148-223, wherein the virus is a SARS-CoV-2 virus which has a nsp12 protein amino acid substitution V557L.

290. The method of embodiments 148-223, wherein the virus is a SARS-CoV-2 virus which has a nsp12 protein amino acid substitution D484Y.

291. The method of embodiments 148-223, wherein the virus is a SARS-CoV-2 virus which has a nsp12 protein amino acid substitution F480X, wherein X=any amino acid.

292. The method of embodiments 148-223, wherein the virus is a SARS-CoV-2 virus which has a nsp12 protein amino acid substitution V557X, wherein X=any amino acid.

293. The method of embodiments 148-223, wherein the virus is a SARS-CoV-2 virus which has a nsp12 protein amino acid substitution D484X, wherein X=any amino acid.

294. The method of embodiments 148-223, wherein the virus is a SARS-CoV-2 virus which has one or more of the following mutations in the nsp12 protein: P323L; T1411; A449V; S434F; M666I; H613Y; S647I; M380I; E922D; M629I; G774S; M6011; E436G; N491S; Q822H; A443V; T85I; A423V; M463I; T26I; A656T; M668I; T8061; T276M; T801N; V588L; K267N; V880I; K718R; L514F; F415S; T252N; Y38H; E744D; H752Q; I171V; S913L; A526V; A382V; G228C; P94L; E84K; K59N; P830S; T9081; P21S; D879Y; G108D; K780N; R279S; D258Y; T259I; K263N; D284Y; Q292H; T293I; N297S; V299F; D304Y; T319I; F321L; P328S; V330E; I333T; G337C; T344I; Y346H; L351P; V354L; Q357H; E370G; L372F; A400S; T4021; V405F; V410I; D418N; K426N; K430N; V435F; Q444H; D445G; A448V; R457C; P461T; C464F; I466V; V473F; K478N; D481G; D517G; D523N; A529V; P537S; S549N; A555V; C563F; M566I; A581T; G584V; A585T; G596S; T6041; S6071; D608G; V6091; M615V; W617L; M629V; I632V; L636F; L638F; A639V; T643I; T644M; L648F; V667I; A699S; N713S; H725; N734T; D736N; V737F; T739I; V742M; N743S; M756I; L758I; A771V; L775V; A777T; K780T; F793L; T801I; T803A; H810Y; G823C; D825Y; V827A; Y828H; V848L; T870I; K871R; N874D; Q875R; E876D; H882Y; H892Y; D901Y; M9061; N909D; T912N; P918S; E919D; A923T; F480V; V557L; D484Y; E802D; E802A; or S433G; or combinations thereof.

295. The method of embodiments 148-223, wherein the virus is a SARS-CoV-2 variant strain selected from: Alpha (Pango lineage: B.1.1.7), Beta (Pango lineages: B.1.351, B.1.351.2, B.1.351.3), Gamma (Pango Lineages: P.1, P.1.1, P.1.2), Delta (Pango Lineages: B.1.617.2, AY.1, AY.2, AY.3), Eta (Pango Lineages: B.1.525), Iota (Pango Lineage: B.1.526), Kappa (Pango Lineage: B.1.617.1), Lambda (Pango Lineage: C.37), Epsilon (Pango Lineages: B.1.427, B.1.429), Zeta (Pango Lineage: P.2), Theta (Pango Lineage: P.3) or Mu (Pango Lineage: B.1.621).

296. The method of embodiments 148-223, wherein the virus is a SARS-CoV-2 variant strain selected from Pango Lineages P.2, P.3, R.1, R.2, B.1.466.2, B.1.621, B.1.1.318, B.1.1.519, C.36.3, C.36.3.1, B.1.214.2, B.1.1.523, B.1.617.3, B.1.619, B.1.620, B.1.621, A.23.1 (+E484K), A.27, A.28, C.16, B.1.351 (+P384L), B.1351 (+E516Q), B.1.1.7 (+L452R), B.1.1.7 (+S494P), C.36 (+L452R), AT.1, B.1.526.1, B.1.526.2, B.1.1.318, B.1.1.519, AV.1, P.1 (+P681H), B.1.671.2 (+K417N), or C.1.2.

297. The method of embodiments 148-223, wherein the virus is a SARS-CoV-2 Alpha variant (Pango lineage: B.1.1.7).

298. The method of embodiments 148-223, wherein the virus is a SARS-CoV-2 Beta variant (Pango lineages: B.1.351, B.1.351.2, B.1.351.3).

299. The method of embodiments 148-223, wherein the virus is a SARS-CoV-2 Gamma variant (Pango Lineages: P.1, P.1.1, P.1.2).

300. The method of embodiments 148-223, wherein the virus is a SARS-CoV-2 Delta variant (Pango Lineages: B.1.617.2, AY.1, AY.2, AY.3).
301. The method of embodiments 148-223, wherein the virus is a SARS-CoV-2 Eta variant (Pango Lineages: B.1.525).
302. The method of embodiments 148-223, wherein the virus is a SARS-CoV-2 Iota variant (Pango Lineage: B.1.526).
303. The method of embodiments 148-223, wherein the virus is a SARS-CoV-2 Kappa variant (Pango Lineage: B.1.617.1).
304. The method of embodiments 148-223, wherein the virus is a SARS-CoV-2 Lambda variant (Pango Lineage: C.37).
305. The method of embodiments 148-223, wherein the virus is a SARS-CoV-2 Epsilon variant (Pango Lineages: B.1.427, B.1.429).
306. The method of embodiments 148-223, wherein the virus is a SARS-CoV-2 Zeta variant (Pango Lineage: P.2).
307. The method of embodiments 148-223, wherein the virus is a SARS-CoV-2 Theta variant (Pango Lineage: P.3).
308. The method of embodiments 148-223, wherein the virus is a SARS-CoV-2 Mu variant (Pango Lineage: B.1.621).
309. The method of embodiments 148-223, wherein the virus is a SARS-CoV-2 comprising at least the following mutations in the spike (S) protein: N501Y, D614G, and P681H.
310. The method of embodiments 148-223, wherein the virus is a SARS-CoV-2 comprising at least the following mutations in the spike (S) protein: E484K, N501Y, D614G, and P681H.
311. The method of embodiments 148-223, wherein the virus is a SARS-CoV-2 comprising at least the following mutations in the spike (S) protein: K417N, E484K, N501Y, D614G, and A701V.
312. The method of embodiments 148-223, wherein the virus is a SARS-CoV-2 comprising at least the following mutations in the spike (S) protein: K417T, E484K, N501Y, D614G, and H655Y.
313. The method of embodiments 148-223, wherein the virus is a SARS-CoV-2 comprising at least the following mutations in the spike (S) protein: L452R, T478K, D614G, and P681R.
314. The method of embodiments 148-223, wherein the virus is a SARS-CoV-2 comprising at least the following mutations in the spike (S) protein: E484K, D614G, and Q677H.
315. The method of embodiments 148-223, wherein the virus is a SARS-CoV-2 comprising at least the following mutations in the spike (S) protein: E484K, N501Y, D614G, and P681H.
316. The method of embodiments 148-223, wherein the virus is a SARS-CoV-2 comprising at least the following mutations in the spike (S) protein: L452R, E484Q, D614G, and P681R.
317. The method of embodiments 148-223, wherein the virus is a SARS-CoV-2 comprising at least the following mutations in the spike (S) protein: S477N, E484K, D614G, and P681H.
318. The method of embodiments 148-223, wherein the virus is a SARS-CoV-2 comprising at least the following mutations in the spike (S) protein: R346K, E484K, N501Y, D614G, and P681H.
319. The method of embodiments 148-223, wherein the virus is a SARS-CoV-2 comprising at least the following mutations in the spike (S) protein: L452Q, F490S, and D614G.
320. The method of embodiments 148-223, wherein the virus is a SARS-CoV-2 comprising at least the following mutations in the spike (S) protein: L452R, E484Q, D614G, and P681R.
321. The method of embodiments 148-223, wherein the virus is a SARS-CoV-2 comprising at least the following mutations in the spike (S) protein: Q414K, N450K, ins214TDR, and D614G.
322. The method of embodiments 148-223, wherein the virus is a SARS-CoV-2 comprising at least the following mutations in the spike (S) protein: V367F, E484K, and Q613H.
323. The method of embodiments 148-223, wherein the virus is a SARS-CoV-2 comprising at least the following mutations in the spike (S) protein: L452R, N501Y, A653V, and H655Y.
324. The method of embodiments 148-223, wherein the virus is a SARS-CoV-2 comprising at least the following mutations in the spike (S) protein: E484K, N501T, and H655Y.
325. The method of embodiments 148-223, wherein the virus is a SARS-CoV-2 comprising at least the following mutations in the spike (S) protein: L452R, and D614G.
326. The method of embodiments 148-223, wherein the virus is a SARS-CoV-2 comprising at least the following mutations in the spike (S) protein: P384L, K417N, E484K, N501Y, D614G, and A701V.
327. The method of embodiments 148-223, wherein the virus is a SARS-CoV-2 comprising at least the following mutations in the spike (S) protein: K417N, E484K, N501Y, E516Q, D614G, and A701V.
328. The method of embodiments 148-223, wherein the virus is a SARS-CoV-2 comprising at least the following mutations in the spike (S) protein: L452R, N501Y, D614G, and P681H.
329. The method of embodiments 148-223, wherein the virus is a SARS-CoV-2 comprising at least the following mutations in the spike (S) protein: S494P, N501Y, D614G, and P681H.
330. The method of embodiments 148-223, wherein the virus is a SARS-CoV-2 comprising at least the following mutations in the spike (S) protein: L452R, D614G, and Q677H.
331. The method of embodiments 148-223, wherein the virus is a SARS-CoV-2 comprising at least the following mutations in the spike (S) protein: E484K, D614G, N679K, and ins679GIAL.
332. The method of embodiments 148-223, wherein the virus is a SARS-CoV-2 comprising at least the following mutations in the spike (S) protein: E484K, D614G, and A701V.
333. The method of embodiments 148-223, wherein the virus is a SARS-CoV-2 comprising at least the following mutations in the spike (S) protein: L452R, and D614G.
334. The method of embodiments 148-223, wherein the virus is a SARS-CoV-2 comprising at least the following mutations in the spike (S) protein: S477N, and D614G.

335. The method of embodiments 148-223, wherein the virus is a SARS-CoV-2 comprising at least the following mutations in the spike (S) protein: E484K, D614G, and P681H.
336. The method of embodiments 148-223, wherein the virus is a SARS-CoV-2 comprising at least the following mutations in the spike (S) protein: E484K, and D614G.
337. The method of embodiments 148-223, wherein the virus is a SARS-CoV-2 comprising at least the following mutations in the spike (S) protein: T478K, and D614G.
338. The method of embodiments 148-223, wherein the virus is a SARS-CoV-2 comprising at least the following mutations in the spike (S) protein: N439K, E484K, D614G, and P681H.
339. The method of embodiments 148-223, wherein the virus is a SARS-CoV-2 comprising at least the following mutations in the spike (S) protein: D614G, E484K, H655Y, K417T, N501Y, and P681H.
340. The method of embodiments 148-223, wherein the virus is a SARS-CoV-2 comprising at least the following mutations in the spike (S) protein: L452R, T478K, D614G, P681R, and K417N.
341. The method of embodiments 148-223, wherein the virus is a SARS-CoV-2 comprising at least the following mutations in the spike (S) protein: D614G, E484K, H655Y, N501Y, N679K, and Y449H.
342. The method of embodiments 148-223, wherein the virus is a SARS-CoV-2 comprising at least the following mutations in the spike (S) protein: T19R, T951, G142D, E156del, F157del, R158G, L452R, T478K, D614G, P681R, and D950N.
343. The method of embodiments 148-223, wherein the virus is a SARS-CoV-2 comprising at least the following mutations in the spike (S) protein: T19R, V70F, T951, G142D, E156del, F157del, R158G, A222V, W258L, K417N, L452R, T478K, D614G, P681R, and D950N.
344. The method of embodiments 1-147, wherein the compound for administration does not drive or induce further mutations in the SARS-CoV virus compared to the mutational rate observed in the native viral population.
345. The method of embodiments 148-344, wherein the identified compound for administration does not drive or induce further mutations in the SARS-CoV virus compared to the mutational rate observed in the native viral population.
346. The method of embodiments 1-19 or 294, wherein the virus is a SARS-CoV-2 virus which has a E802D mutation in the nsp12 protein.
347. The method of embodiments 1-19 or 294, wherein the virus is a SARS-CoV-2 virus which has a E802A mutation in the nsp12 protein.
348. The method of embodiments 137 or 212, wherein the additional active agent is PF-07304814.
349. The method of embodiments 137 or 212, wherein the additional active agent is PF-07321332.
350. The method of embodiments 137 or 212, wherein the additional active agent is EDP-235.
351. The method of embodiments 137 or 212, wherein the additional active agent is PBI-0451.
352. The method of embodiments 137 or 212, wherein the additional active agent is ALG-097111.
353. The method of embodiments 137 or 212, wherein the additional active agent is sotrovimab (VIR-7831).
354. The method of embodiments 137 or 212, wherein the additional active agent is VIR-7832.
355. The method of embodiments 137 or 212, wherein the additional active agent is BRII-196.
356. The method of embodiments 137 or 212, wherein the additional active agent is BRII-198.
357. The method of embodiments 137 or 212, wherein the additional active agent is ADG20.
358. The method of embodiments 137 or 212, wherein the additional active agent is ADG10.
359. The method of embodiments 155-187, wherein the NiRAN-domain mediated activity is protein primed RNA synthesis.
360. The method of embodiments 1-359, wherein the SARS-CoV virus has developed resistance to one or more anti-viral treatments.
361. The method of embodiment 360, wherein the SARS-CoV virus is resistant to mavrilimumab, remdesivir, baricitinib, dexamethasone, prednisone, methylprednisolone, hydrocortisone, tocilizumab, siltuximab, sarilumab, casirivimab, imdevimab, canakinumab, azithromycin, chloroquine/hydroxychloroquine, amodiaquine, artesunate, lopinavir, ritonavir, favipiravir, ribavirin, EIDD-2801, niclosamide, nitazoxanide, oseltamivir, ivermectin, molnupiravir, recombinant ACE-2, sotrovimab, budesonide, AZD7442, doxycycline; interferons, regdanvimab, anakinra, ruxolitinib, tofacitinib, acalabrutinib, imatinib, brensocatib, ravulizumab, namilumab, infliximab, adalimumab, otilimab, medi3506, bamlanivimab, etesevimab, sotrovimab, leronlimab, Risankizumab, lenzilumab, IMU-838, fluvoxamine, lenzilumab, EXO-CD24, leronlimab, colchicine, dimethyl fumarate, angiotensin-converting-enzyme inhibitors/angiotensin II receptor blockers, statins, clopidogrel, anticoagulants, bemcentinib, omeprazole, famotidine, zilucoplan, ascorbic acid/vitamin C, vitamin D3, aviptadi, tradipitant, nitric oxide, fluvoxamine, proxalutamide, ruconest, TRV027, fluvoxamine, isoflurane, sevoflurane, VIR-7831 (GSK4182136), LSALT Peptide, BRII-196/BRII-198, AZD7442 (IV), SNG001, AZD7442 (IM), camostat, C135-LS+C144-LS, SAB-185, NP-120 (fenprodil), losartan, omalizumab, ruxolitinib, Allogeneic Bone Marrow Mesenchymal Stromal Cells (BM-MSCs), Allogeneic Umbilical Cord Mesenchymal Stromal Cells (UC-MSCs), ixekizumab/apremilast, CPI-006, cadesartan, valsartan, ramipril, perindopril, irbesartan, losartan, enalapril, captopril, remestemcel-L, dapagliflozin, alcetrapid, pulmozyme (dornase alfa), EB05, perflenapent (NANO2), furosemide, peginterferon Lambda-1A, novaferon (chimeric interferon α), LAU-7B (fenretinide), BLES (bovine lipid extract surfactant suspension), ciclesonide, MK-4482, ozanimol, hiltonol (Polyriboinosinic acid-polyribocytidylic acid (Poly-ICLC)), innohep (tinzaparin sodium), lovenox (enoxaparin sodium), fragmin (dalteparin sodium), heparin sodium, dapsone, rivaroxaban, cholecalciferol, fondaparinux, innohep, fragmin, SY-005 (Recombinant Human Annexin A5), simvastatin, ticagrelor, ramipril, lisinopril, perindopril erbumine, enalapril, trandolapril, captopril, valsatan, candesartan cilexetil, irbesartan, telmisartan, olmesartan medoxomil, RVX000222 (Apabetalone), S-1226 (Carbon-Dioxide Perflubron), placenta derived decidual stromal cells (DSC), ozempic (semaglutide), (Vascepa™) (icosapent), PF-07304814, PF-07321332, EDP-235, PBI-0451, ALG-097111, or VIR-7832, BRII-196, BRII-198, ADG20, ADG10, VIR-7831, or a combination thereof.

362. The method of embodiment 360, wherein the agent is remdesivir.

363. The method of embodiment 360, wherein the agent is a corticosteroid.

364. The method of embodiment 360, wherein the agent is dexamethasone.

365. The method of embodiment 360, wherein agent is prednisone, methylprednisolone, or hydrocortisone.

366. The method of embodiment 360, wherein the agent is baricitinib.

367. The method of embodiment 360, wherein the is tocilizumab.

368. The method of embodiment 360, wherein the agent is molnupiravir.

369. The method of embodiment 360, wherein the agent is sofosbuvir.

370. The method of embodiment 360, wherein the agent is GC376.

371. The method of embodiment 360, wherein the agent is PF-07304814.

372. The method of embodiment 360, wherein the agent is PF-07321332.

373. The method of embodiment 360, wherein the agent is EDP-235.

374. The method of embodiment 360, wherein the agent is PBI-0451.

375. The method of embodiment 360, wherein the agent is ALG-097111.

376. The method of embodiment 360, wherein the agent is sotrovimab (VIR-7831).

377. The method of embodiment 360, wherein the agent is VIR-7832.

378. The method of embodiment 360, wherein the agent is BRII-196.

379. The method of embodiment 360, wherein the agent is BRII-198.

380. The method of embodiment 360, wherein the agent is ADG20.

381. The method of embodiment 360, wherein the agent is ADG10.

382 A method of identifying a compound capable of inhibiting or preventing a SARS-CoV infection comprising:

i. contacting the compound with a nsp12, nsp7, and nsp8 protein of a SARS-related coronavirus in the presence of UTP and a poly(A) RNA template in vitro; and ii. determining whether the compound inhibits de novo RNA synthesis on the poly(A) RNA template in the presence of UTP;

wherein the inhibition of protein primed RNA synthesis on the poly(A) RNA template in the presence of UTP by at least 25% or more as measured in an in vitro assay as compared to the same assay without the compound is indicative of a compound capable of inhibiting protein-primed RNA synthesis.

383. The method of embodiment 382, wherein the nsp12, nsp7, and nsp8 is provided as a nsp12:7L8:8 polymerase complex.

384. The method of embodiment 382, wherein nsp12: 7L8:8 polymerase complex is in a 1:3:3 molar ratio or a 1:3:6 molar ratio.

385. The method of embodiments 382-384, wherein a compound is identified as capable of inhibiting protein primed RNA synthesis if the compound reduces primer independent RNA synthesis of the poly(A) RNA template by at least 50% or more compared to a control wherein the compound is not present.

386. The method of embodiments 382-384, wherein the compound reduces protein primed RNA synthesis of the poly(A) RNA template by at least 90% or more compared to a control wherein the compound is not present.

387. The method of embodiments 382-386, wherein the SARS-CoV infection is a SARS-CoV-2 infection.

388. A method for the treatment or prevention of a SARS-CoV infection in a human in need thereof comprising (i) selecting a nucleotide drug that exhibits a mechanism of action which is the disruption of NiRAN-mediated protein primed RNA synthesis and (ii) administering an effective amount of the drug to the host to treat or prevent the infection.

389. The method of embodiment 388, wherein the SARS-CoV infection is a SARS-COV-2 infection.

390. The method of embodiments 148-343 or 388-389, wherein the compound remains stably bound to the active site of the NiRAN-domain and is not transferred to nsp8.

391. The method of embodiments 1-137, wherein the additional active agent is casirivimab and imdevimab.

392. The method of embodiments 1-137, wherein the additional active agent is REGN-COV2.

393. The method of embodiment 360, wherein the agent is casirivimab and imdevimab.

394. The method of embodiment 360, wherein the agent is REGN-COV2.

395. The method of embodiments 1-137, wherein the administration of the compound provides a reduction in the time to alleviate symptoms associated with SARS-CoV-2, compared to the time to alleviate symptoms without the administration of the compound.

396. The method of embodiments 1-137, wherein the administration of the compound provides a reduction in one or more of hospitalizations, medically attended visits, and/or death.

397. The method of embodiments 1-137, wherein the compound is administered in 2-275 mg doses two times or three times a day.

398. The method of embodiments 1-137, wherein the compound is administered in 3-275 mg doses two or three times a day.

399. The method of embodiments 1-137, wherein the compound is administered in 4-275 mg doses two times or three times a day.

400. The method of embodiments 1-137, wherein the compound is administered in 5-275 mg doses two times or three times a day.

401. The method of embodiments 1-137, wherein the compound is administered in 3-275 mg doses two or three times a day.

402. The method of embodiments 1-137, wherein the compound is administered in about a 550 mg dose two times or three times a day.

403. The method of embodiments 1-137, wherein the compound is administered in about a 825 mg dose two times or three times a day.

404. The method of embodiments 1-137, wherein the compound is administered in about a 1100 mg dose two times or three times a day 405. The method of embodiments 397-404, wherein the compound is Compound 2A.

EXAMPLES

Example 1. Activity of Compound 1A Against Coronavirus in Huh7 Cells

The activity of Compound 1A was tested against the human coronaviruses alpha-229E and beta-OC43 in Huh7 cells. Huh7 cells were seeded in 96-well plates at a concentration that yielded 80-100% confluent monolayers in each well after overnight incubation. Compound 1A was dissolved in DMSO to 10 mg/mL and 8 half-log serial dilutions in test medium (modified Eagle's medium containing 5% fetal bovine serum and 50 μL gentamicin) were prepared with the highest concentration of 50 μg/mL. 100 μL of each concentration were added to 5 test wells on the 96-well plate and 3 wells were infected with test virus in test medium (≤100 $CCID_{50}$ per well). An equivalent amount of test medium was added to the remaining test wells to assess toxicity to uninfected cells. Six wells were infected to serve as untreated virus controls. Media only was added to 6 wells to serve as cell controls. Plates were incubated at 37° C. in a humidified 5% $CO_2$ atmosphere until cytopathic effect (CPE) was observed microscopically.

To obtain the CPE endpoint, wells were stained with 0.011% neutral red dye for approximately 2 hours. The dye was siphoned off and wells were rinsed once with phosphate-buffered saline to remove residual, unincorporated dye. 200 μL of 50:50 Sorensen citrate buffer/ethanol was added for >30 min with agitation and then light absorbance at 540 nm was measured on a spectrophotometer.

To obtain the virus yield reduction (VYR) endpoint, supernatant fluid from 3 replicate wells of each compound concentration were pooled and virus titer was measured using a standard endpoint dilution $CCID_{50}$ assay and titer calculations using the Reed Muench (1948) equation (Reed, L J and Muench, H. Am. *J Hygiene* 27:493-497 (1948)). The concentration of compound required to reduce virus yield by 1 $log_{10}$ ($EC_{90}$) was determined using regression analysis.

As shown in Table 1, Compound 1A is potent against both the alpha-229E coronavirus and the beta-OC43 coronavirus. Compound 1A exhibits an $EC_{90}$ value of 0.71 μM against alpha-229E in the virus yield reduction assay and an $EC_{90}$ value of 0.29 μM against beta-OC43. Additionally, Compound 1A exhibits high $CC_{50}$ values and selectivity indexes (SI) against both the alpha and beta coronaviruses. For example, against the beta coronavirus, Compound 1A has a selectivity index of greater than 170 when measured using the viral yield reduction assay and a $CC_{50}$ value of greater than 50 μM when measured in neutral red assay.

TABLE 1

Activity of Compound 1A against Coronaviruses Alpha-229E and Beta-OC43

| | Visual | | | Neutral Red | | | VYR | |
|---|---|---|---|---|---|---|---|---|
| Virus in Huh7 cells | $EC_{50}$ (μM) | $CC_{50}$ (μM) | SI | $EC_{50}$ (μM) | $CC_{50}$ (μM) | SI | $EC_{90}$ (μM) | SI |
| Alpha-229E | 1 | >50 | >50 | 1 | >50 | >50 | 0.71 | >70 |
| Beta-OC43 | NT | >50 | NT | NT | >50 | NT | 0.29 | >170 |

Visual and neutral red SI: $CC_{50}/EC_{50}$

VYR SI: $CC_{50}/EC_{90}$

NT: not tested

Example 2. Activity of Compound 1A and 1B Against Coronavirus in BHK-21 and MES-21 Cells Compound 1A and Compound 1B were tested for activity against human coronavirus in BHK-21 cells (Table 2A and Table 2B) and IVIES-1 cells (Table 3A and Table 3B). The $EC_{50}$ and the $CC_{50}$ was determined and compared to Sofosbuvir, an uracil-based nucleotide.

Compound activity against coronavirus was based on inhibition of virus induced cytopathogenicity acutely infected with a multiplicity of infection (m.o.i.) of 0.01. After a 3-day incubation at 37° C. cell viability was determined by the MTT method as described by Pauwels et al. (J. Virol. Methods 1988, 20, 309-321).

To determine the cytotoxicity, cells were seeded at an initial density of $1\times10^6$ cells/mL in 96 well plates containing Minimum Essential Medium with Earles's salts (MEM-E), L-glutamine, 1 mM sodium pyruvate and 25 mg/L kanamycin, supplemented with 10% fetal bovine serum. Cell cultures were then incubated at 37° C. in a humidified 5% $CO_2$ atmosphere in the absence or presence of serial dilutions of test compounds. Cell viability was determined by the MTT method.

TABLE 2A

Activity of Select Compounds against HCoV in BHK-21 Cells

| Compound | $CC_{50}$ [uM][a] | $EC_{50}$ [uM][b] |
|---|---|---|
| 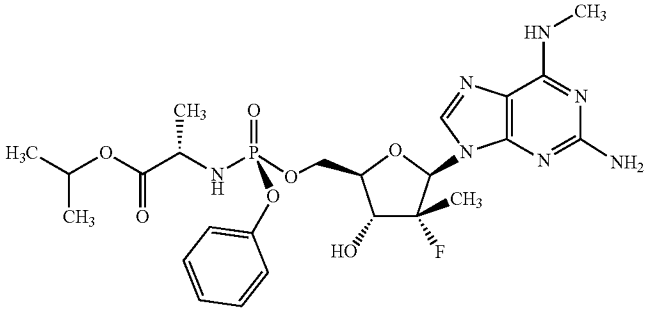 Compound 1A | >100 | 1.6 |

TABLE 2A-continued
| Activity of Select Compounds against HCoV in BHK-21 Cells | | |
|---|---|---|
| Compound | $CC_{50}$ [uM][a] | $EC_{50}$ [uM][b] |
| 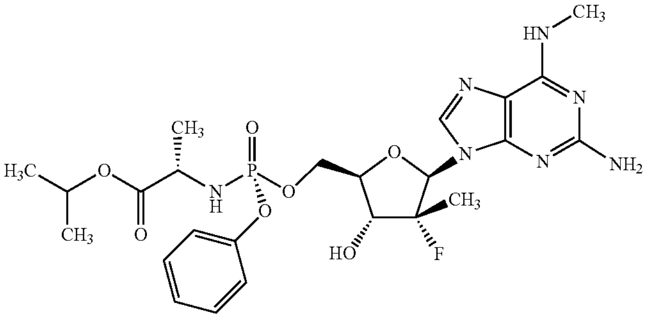 Compound 1B | >100 | 2.5 |
| 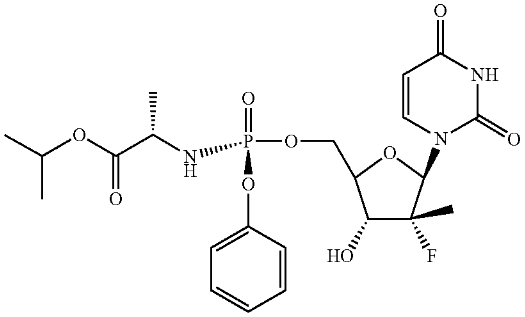 Sofosbuvir | >100 | >100 |
| 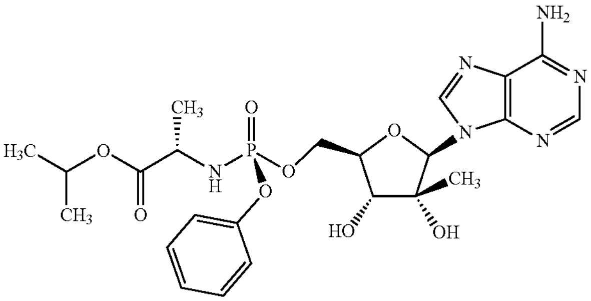 2'-$CH_3$/OH Adenosine | 53 | 6.1 |
| 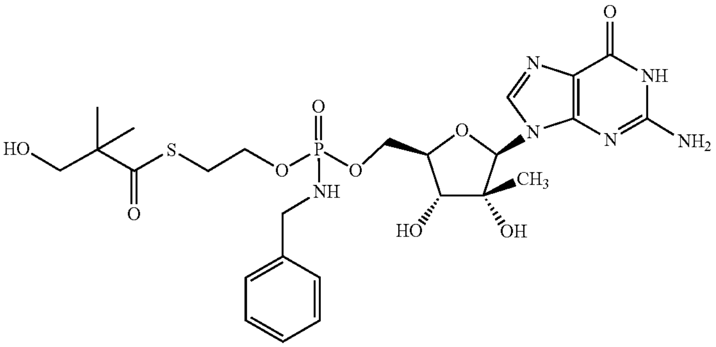 2'-$CH_3$/OH Guanosine$_{(IDX-184)}$ | 65 | 1.7 |

TABLE 2A-continued

| Activity of Select Compounds against HCoV in BHK-21 Cells | | |
|---|---|---|
| Compound | $CC_{50}$ [uM][a] | $EC_{50}$ [uM][b] |
| 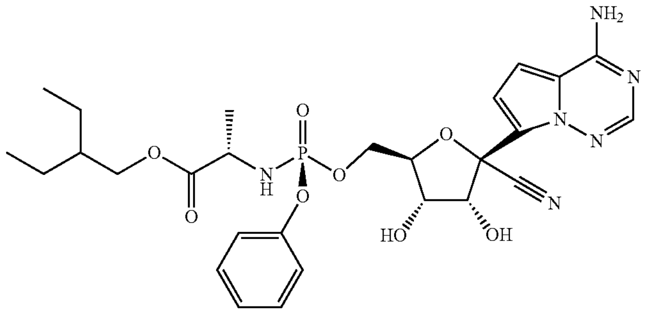 Remdesivir | >100 | 7.2 |
| 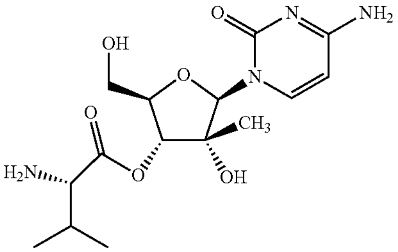 2′-$CH_3$/OH Cytidine (IDX-283) | >100 | >100 |

[a]Compd conc. (μM) required to reduce the viability of mock infected BHK cells by 50% as determined by the MTT method after 3 days of incubation
[b]Compd conc. (μM) required to achieve 50% protection of BHK cells from virus-induced cytopathogenicity as determined by the MTT method at day 3 post-infection

TABLE 2B

| Activity of Select Compounds against HCoV in BHK-21 Cells | | |
|---|---|---|
| Compound | $CC_{50}$ [uM][a] | $EC_{50}$ [uM][b] |
| 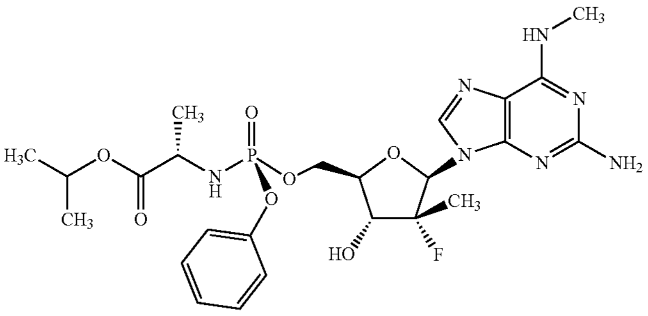 Compound 1A | >100 | 2.0 |

TABLE 2B-continued
| Activity of Select Compounds against HCoV in BHK-21 Cells | | |
|---|---|---|
| Compound | $CC_{50}$ [uM][a] | $EC_{50}$ [uM][b] |
| 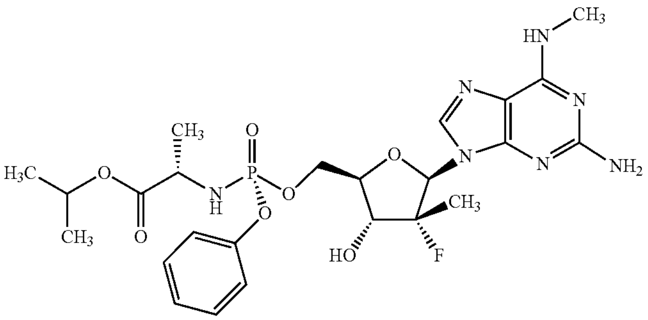 Compound 1B | >100 | 2.9 |
| 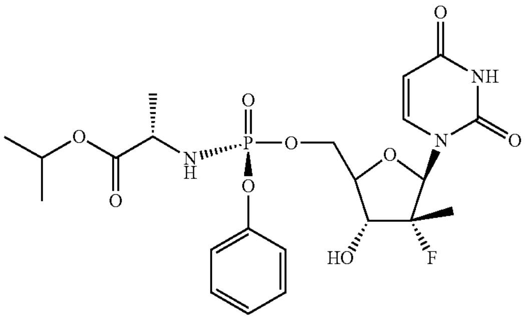 Sofosbuvir | >100 | >100 |
| 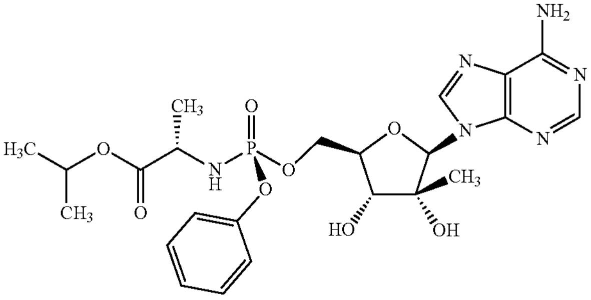 2'-$CH_3$/OH Adenosine | 53 | 5.9 |
| 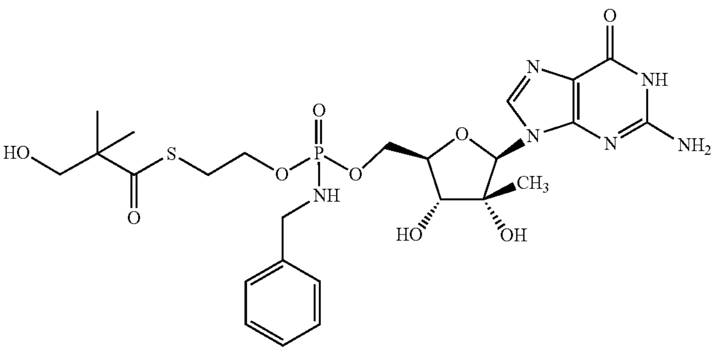 2'-$CH_3$/OH Guanosine (IDX-184) | 65 | 1.9 |

TABLE 2B-continued

Activity of Select Compounds against HCoV in BHK-21 Cells

| Compound | $CC_{50}$ [uM][a] | $EC_{50}$ [uM][b] |
|---|---|---|
| 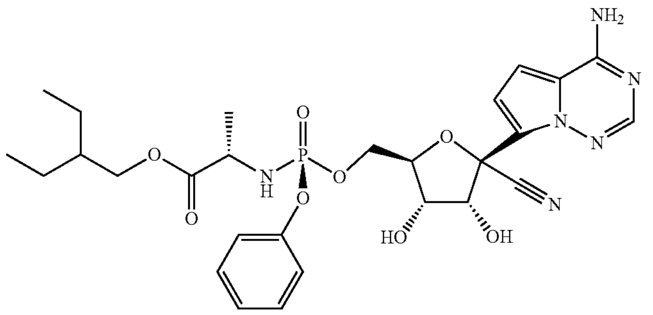 Remdesivir | >100 | 7.0 |
| 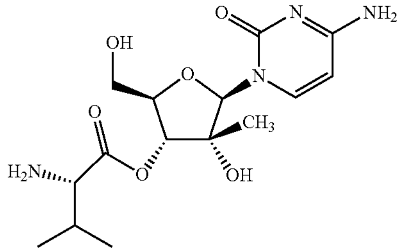 2'-$CH_3$/OH Cytidine (IDX-283) | >100 | >100 |

[a]Compd conc. (μM) required to reduce the viability of mock infected BHK cells by 50% as determined by the MTT method after 3 days of incubation

[b]Compd conc. (μM) required to achieve 50% protection of BHK cells from virus-induced cytopathogenicity as determined by the MTT method at day 3 post-infection

TABLE 3A

Activity of Select Compounds against HCoV in MES-1 Cells

| | $CC_{50}$ [uM][c] | $EC_{50}$ [uM][d] |
|---|---|---|
| 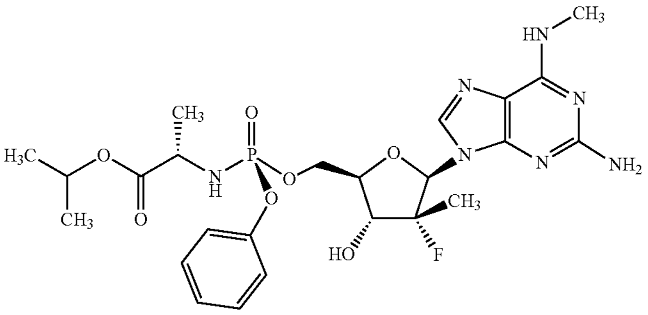 Compound 1A | >100 | 1.6 |

TABLE 3A-continued
| Activity of Select Compounds against HCoV in MES-1 Cells | $CC_{50}$ [uM][c] | $EC_{50}$ [uM][d] |
|---|---|---|
| 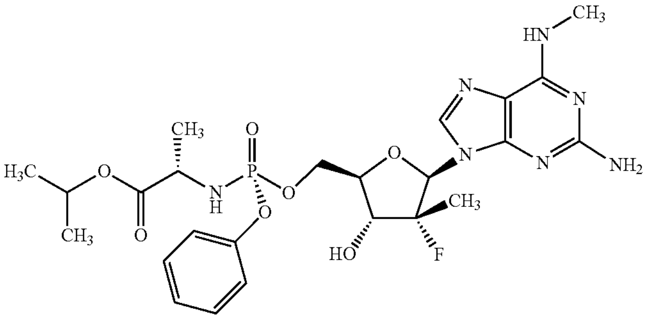 Compound 1B | >100 | 2.0 |
| 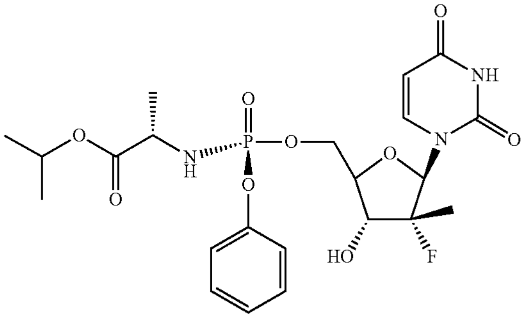 Sofosbuvir | >100 | >100 |
| 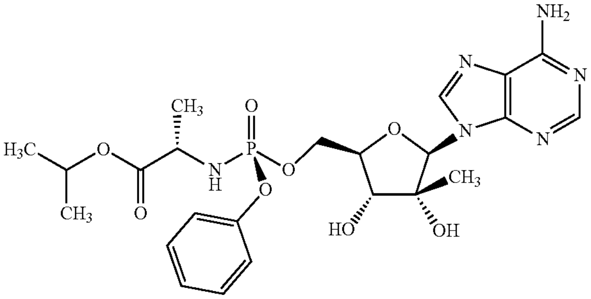 2'-$CH_3$/OH Adenosine | 65 | 5.5 |
| 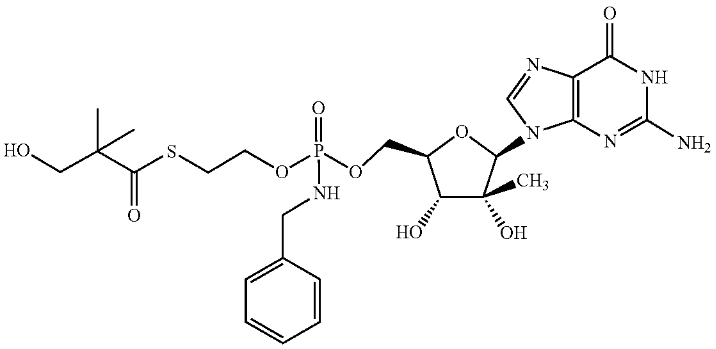 2'-$CH_3$/OH Guanosine (IDX-184) | 82 | 1.9 |

TABLE 3A-continued

| Activity of Select Compounds against HCoV in MES-1 Cells | $CC_{50}$ [uM][c] | $EC_{50}$ [uM][d] |
|---|---|---|
| 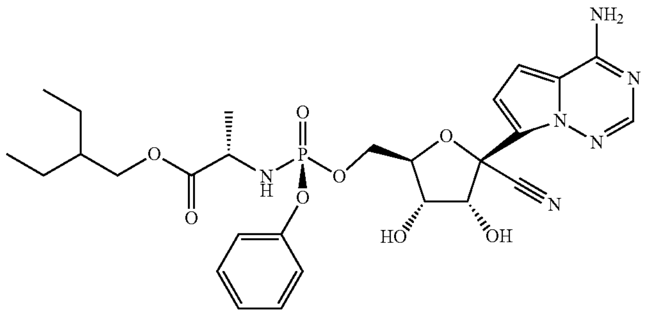 Remdesivir | >100 | 6.0 |
| 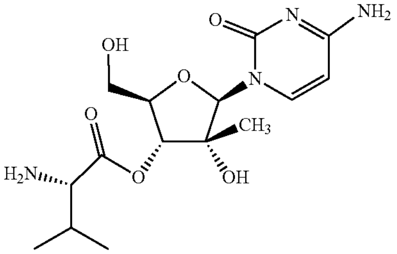 2′-$CH_3$/OH Cytidine (IDX-283) | >100 | >100 |

[c]Compd conc. (μM) required to reduce viability of mock infected MES-1 cells by 50% as determined by the MTT method after 3 days of incubation
[d]Compd conc. (μM) required to achieve 50% protection of MES-1 cells from virus-induced cytopathogenicity as determined by the MTT method at day 3 post-infection

TABLE 3B

| Activity of Select Compounds against HCoV in MES-1 Cells | $CC_{50}$ [uM][c] | $EC_{50}$ [uM][d] |
|---|---|---|
| 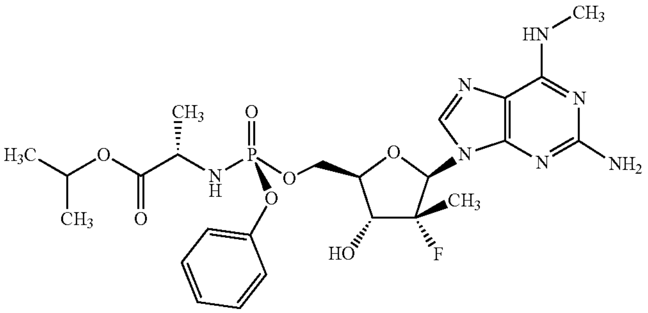 Compound 1A | >100 | 2.0 |

TABLE 3B-continued
| Activity of Select Compounds against HCoV in MES-1 Cells | $CC_{50}$ [uM][c] | $EC_{50}$ [uM][d] |
|---|---|---|
| 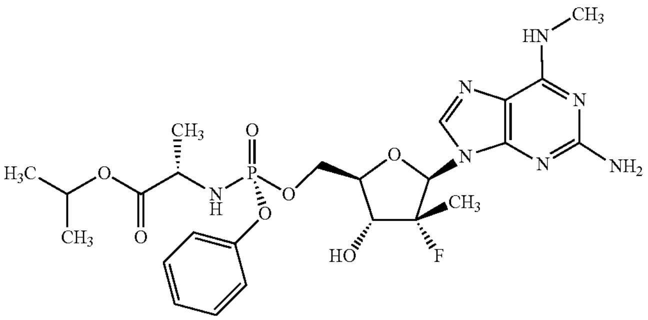 Compound 1B | >100 | 2.2 |
| 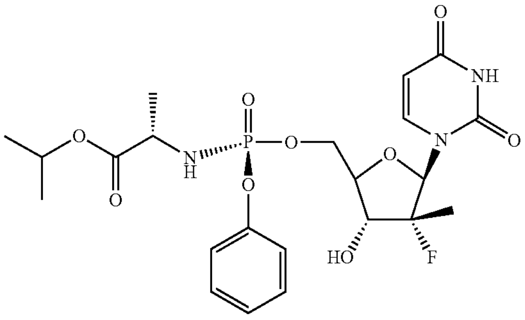 Sofosbuvir | >100 | >100 |
| 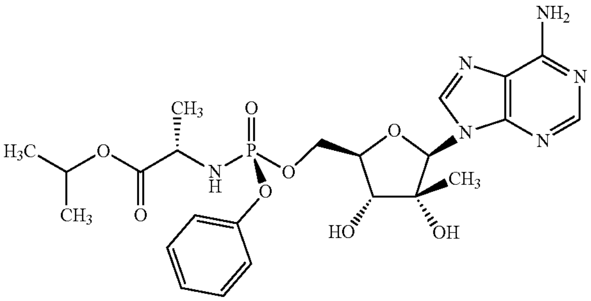 2'-$CH_3$/OH Adenosine | 65 | 5.3 |
| 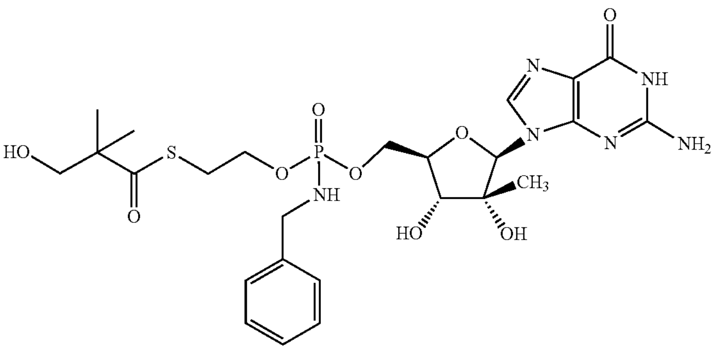 2'-$CH_3$/OH Guanosine (IDX-184) | 82 | 1.7 |

TABLE 3B-continued

| Activity of Select Compounds against HCoV in MES-1 Cells | CC$_{50}$ [uM][c] | EC$_{50}$ [uM][d] |
|---|---|---|
| 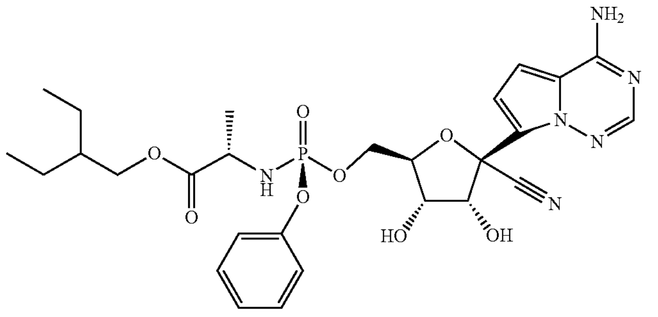 Remdesivir | >100 | 5.5 |
| 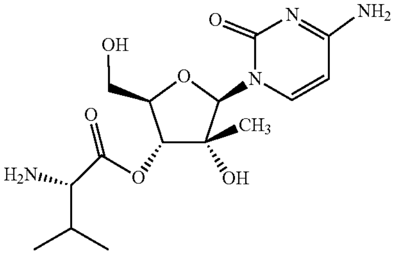 2′-CH$_3$/OH Cytidine (IDX-283) | >100 | >100 |

[c]Compd conc. (μM) required to reduce viability of mock infected MES-1 cells by 50%, as determined by the MTT method after 3 days of incubation.
[d]Compd conc. (μM) required to achieve 50% protection of MES-1 cells from virus-induced cytopathogenicity as determined by the MTT method at day 3 post-infection

Example 3. Activity of Compound 1A Against SARS-CoV and SARS-CoV-2

Compound 1A was tested against SARS-CoV in Huh7 cells and SARS-CoV-2 in differentiated normal human bronchial epithelial (dNHBE, also referred to as HAE (human airway epithelial)) cells and the results are provided in Table 4. The CC$_{50}$ was determined using the neutral red assay and the EC$_{90}$ and SI were determined using the virus yield reduction assay. The EC$_{90}$ is provided in μg/mL and μM. Compound 1A exhibits an EC$_{90}$ of 0.34 μM against SARS-CoV and an EC$_{90}$ of 0.64 μM against SARS-CoV-2.

TABLE 4

Activity of Compound 1A Against SARS-COV and SARS-COV-2

| HuCoV | | Neutral Red Assay | Virus Yield Reduction Assay | | |
|---|---|---|---|---|---|
| Virus (strain) | Cell Line | CC$_{50}$ (μg/mL) | EC$_{90}$ (μg/mL) | EC$_{90}$ (μM) | Selectivity Index |
| SARS-CoV (Urbani) | Huh7 | >50 | 0.2 | 0.34 | >250 |
| SARS-CoV-2 (WA1) | dNHBE | >50[1] | 0.37[2] | 0.64 | >135 |

[1]CC$_{50}$ was estimated by visual inspection of the cells
[2]Value represents the mean of two replicate EC$_{90}$ determinations, 0.33 and 0.41 μg/mL The activity of Compound 1A was evaluated in Huh-7 cells infected with SARS-CoV (Urbani) in a neutral red (NR) assay to assess cytotoxicity and then tested using a virus yield reduction (VYR) assay to assess antiviral activity.

Neutral red assay: Compound 1A was dissolved in 100% DMSO at a concentration of 10 mg/mL and serially diluted using eight half-log dilutions in test medium (Minimum Essential Medium supplemented with 5% FBS and 50 μg/mL gentamicin). The starting (high) test concentration was 50 μg/mL. Each dilution was added to 5 wells of a 96-well plate with 80-100% confluent Huh? or RD cells (hCoV beta OC43 only). Three wells of each dilution were infected with virus and two wells remained uninfected as toxicity controls. Six untreated wells were infected as virus controls and six untreated wells were left uninfected to use as cell controls. Viruses were diluted to a specific 50% cell culture infectious dose (CCID$_{50}$) per mL to achieve the lowest possible multiplicity of infection (MOI) that would yield >80% toxicity within 5-7 days. The MOI was 0.03 CCID$_{50}$/cell. Plates were incubated at 37±2° C., 5% $CO_2$.

On day 7 post-infection (p.i.), the plates were stained with neutral red dye for approximately 2 hours (±15 minutes). Supernatant dye was removed, wells were rinsed with PBS, and the incorporated dye was extracted in 50:50 Sorensen citrate buffer/ethanol for >30 minutes and the optical density was read on a spectrophotometer at 540 nm. Optical densities were converted to percent of cell controls and the concentration of Compound 1A required to cause 50% cell death in the absence of virus was calculated (CC$_{50}$). The selective index (SI) is the CC$_{50}$ divided by the EC$_{50}$.

Virus yield reduction assay: Vero76 cells were seeded in 96-well plates and grown overnight (37° C.) to 80% confluency. A sample of the supernatant fluid from each compound concentration was collected on day 3 post-infection (3 wells pooled) and tested for virus titer using a standard endpoint dilution $CCID_{50}$ assay and titer calculations using the Reed-Muench (1948) equation (Reed, L J and Muench, H. Am. *J Hygiene* 27:493-497 (1948)). The concentration of compound required to reduce virus yield by 1 log 10 ($EC_{90}$) was calculated by regression analysis.

The antiviral activity of Compound 1A was next evaluated against SARS-CoV-2 (WA1) using differentiated normal human bronchial epithelial (dNHBE, also referred to as HAE (human airway epithelial)) cells made to order by MatTek Corporation (Ashland, MA).

Cell Culture: dNHBE cells were grown on 6 mm mesh disks and arrived in kits with either 12- or 24-well transwell inserts. During transportation the tissues were stabilized on a sheet of agarose, which was removed upon receipt. One insert was estimated to consist of approximately 1.2×106 cells. Kits of cell inserts (EpiAirway™ AIR-100, AIR-112) originated from a single donor, #9831, a 23-year-old, healthy, non-smoking, Caucasian male. The cells have unique properties in forming layers, the apical side of which is exposed only to air and that creates a mucin layer. Upon arrival, the cell transwell inserts were immediately transferred to individual wells of a 6-well plate according to manufacturer's instructions, and 1 mL of MatTek's proprietary culture medium (AIR-100-MM) was added to the basolateral side, whereas the apical side was exposed to a humidified 5% $CO_2$ environment. Cells were cultured at 37° C. for one day before the start of the experiment. After the 24-hour equilibration period, the mucin layer, secreted from the apical side of the cells, was removed by washing with 400 μL pre-warmed 30 mM HEPES buffered saline solution 3×. Culture medium was replenished following the wash steps.

Viruses: Virus was diluted in AIR-100-MM medium before infection, yielding a multiplicity of infection (MOI) of approximately 0.0015 $CCID_{50}$ per cell.

Experimental design: Each compound treatment (120 μL) and virus (120 μL) were applied to the apical side. At the same time, the compound treatment (1 mL) was applied to the basal side for a 2-h incubation. As a virus control, some of the cells were treated with placebo (cell culture medium only). Following the 2-h infection, the apical medium was removed, and the basal side was replaced with fresh compound or medium (1 mL). The cells were maintained at the air-liquid interface. On day 5, cytotoxicity ($CC_{50}$ values) in the placebo-treated inserts was estimated by visual inspection, and the medium was removed from all inserts and discarded from the basal side. Virus released into the apical compartment of the dNHBE cells was harvested by the addition of 400 μL of culture medium that was pre-warmed at 37° C. The contents were incubated for 30 minutes, mixed well, collected, thoroughly vortexed and plated on Vero 76 cells for VYR titration. Duplicate wells were used for virus control and cell controls.

Determination of virus titers from each treated cell culture: Vero 76 cells were seeded in 96-well plates and grown overnight (37° C.) to confluence. Samples containing virus were diluted in 10-fold increments in infection medium and 200 μL of each dilution transferred into respective wells of a 96-well microtiter plate. Four microwells were used for each dilution to determine 50% viral endpoints. After 5 days of incubation, each well was scored positive for virus if any cytopathic effect (CPE) was observed as compared with the uninfected control and counts were confirmed for endpoint on days 6 and 7. The virus dose that was able to infect 50% of the cell cultures ($CCID_{50}$ per 0.1 mL) was calculated by the Reed-Muench method (1948) (Reed, L J and Muench, H. Am. *J. Hygiene* 27:493-497 (1948)) and the 90% effective concentration ($EC_{90}$; concentration to reduce virus yield by 1 $\log_{10}$) was determined by regression analysis. The day 5 values were reported. Untreated, uninfected cells were used as the cell controls.

Example 4. In Vitro Activity of Compound 1A and Other Oral Antiviral Drugs Against Various Human Coronaviruses Compound 1A and other oral antiviral drugs were tested against various human coronaviruses (Table 5) in various cell lines. The data demonstrate the potent in vitro activity of Compound 1A against several CoVs, with individual $EC_{90}$ values ranging from 0.34 to 1.2 against HCoV-229E, HCoV-OC43, SARS-CoV-1 and SARS-CoV-2 and less activity against MERS-CoV (average $EC_{90}$=36 μM).

TABLE 5

Activity of Compound 1A and Other Oral Antiviral Drugs Against Human Coronaviruses

| Virus | | | Neutral Red Assay | | Virus Yield Reduction Assay | Selectivity Index |
|---|---|---|---|---|---|---|
| (genus) | Cell line | Compound | $EC_{50}$ (μM) | $CC_{50}$ (μM) | $EC_{90}$ (μM) | ($CC_{50}/EC_{90}$) |
| HCOV-229E (alpha) | BHK-21 | Compound 1A | 1.8[a,b] | >100 | | >58[c] |
| | | sofosbuvir | >100[b] | >100 | | N/A |
| | Huh-7 | Compound 1A | 1.7/1.6 | >86 | 1.0 | >75 |
| | | chloroquine | 8.1 | 21 | <0.050 | 2.6[c] |
| | | hydroxychloroquine | 7.4 | 26 | <0.048 | 3.5[c] |
| HCoV-OC43 | Huh-7 | Compound 1A | ND[d] | >86 | 0.5/<0.03 | >170/>3100 |
| (beta) | RD | Compound 1A | 2.8 | >86 | 2.2 | >39 |
| MERS-COV (beta) | Huh-7 | Compound 1A | 15/36 | >86 | 17/56 | >5/>1.5 |
| SARS-COV-1 (beta) | Huh-7 | Compound 1A | ND | >86 | 0.34 | >250 |

TABLE 5-continued

Activity of Compound 1A and Other Oral Antiviral Drugs Against Human Coronaviruses

| Virus | | | Neutral Red Assay | | Virus Yield Reduction Assay | Selectivity Index |
|---|---|---|---|---|---|---|
| (genus) | Cell line | Compound | $EC_{50}$ (μM) | $CC_{50}$ (μM) | $EC_{90}$ (μM) | ($CC_{50}/EC_{90}$) |
| SARS-COV-2 (beta) | HAE | Compound 1A | ND | >86[e]/>8.6[e] | 0.64[f]/0.47[g] | >130/>18 |
| | | N4-hydroxycytidine | | >19[e] | 3.9[h] | >5.1 |

[a]Average of 2 experiments (1.6 and 2.0 μM)
[b]EC50 determined by dye staining (virus yield reduction substantially overestimates antiviral potency of cytotoxic compounds)
[c]$CC_{50}/EC_{50}$
[d]Not determined (no cytopathic effect with this virus in this cell line)
[e]Cytotoxicity assessed by visual inspection of cell monolayers
[f]Average of two replicates (0.57 and 0.70 μM)
[g]Average of two replicates (0.52 and 0.42 μM)
[h]Average of two replicates (4.7 and 3.1 μM)
BHK-21, baby hamster kidney cell line
Huh-7, human hepatocyte carcinoma cell line (established ability to form triphosphate from Compound 1A)
RD, human rhabdomyosarcoma cell line (unknown ability to form triphosphate from Compound 1A)
HAE, human airway epithelial cell culture (established ability to form triphosphate from Compound 1A) (established ability to form triphosphate from Compound 1A)

In an initial screening, BHK-21 cells acutely infected with a seasonal human alpha coronavirus, HCoV-229E, were exposed to serial dilutions of Compound 1A. After a 3-day incubation, the effective concentration of Compound 1A required to achieve 50% inhibition ($EC_{50}$) of the virus-induced cytopathic effect (CPE) from two independent experiments averaged 1.8 μM.

In contrast, the 2'-fluoro-2'-methyl uridine nucleotide prodrug sofosbuvir did not inhibit HCoV-229E replication at concentrations as high as 100 μM (Table 5). No toxicity was detected from either drug.

The in vitro potency of Compound 1A against HCoV-229E, HCoV-OC43 (another seasonal human coronavirus strain), MERS-CoV and SARS-CoV-1 was then evaluated in Huh-7 cell-based assays. This human hepatocarcinoma cell line was selected based on its ability to activate Compound 1A intracellularly to its triphosphate metabolite, unlike MRC-5 cells in which Compound 1A lacked activity against HCoV-229E ($EC_{50}$>100 μM) as reported in Good, S. S. et al. *PLoS One* 15(1), e0227104 (2020)). Antiviral activity was assessed by two different methods after exposure of Huh-7 cells to virus and serial dilutions of test compound by determining 1) the $EC_{50}$ for virus-induced CPE by neutral red dye staining after a 5-day (229E and OC43) or 7-day (MERS and SARS) incubation and 2) the effective concentration required to reduce secretion of infectious virus into the culture medium by 90% ($EC_{90}$) after a 3-day incubation using a standard endpoint dilution $CCID_{50}$ assay to determine virus yield reduction (VYR). Half-maximal cytotoxicity ($CC_{50}$) was measured by neutral red staining of compound-treated duplicates in the absence of virus. Although a robust VYR endpoint was obtained in Huh-7 cells infected with HCoV-OC43 or SARS-CoV-1, CPE was not observed and $EC_{50}$ values using neutral red staining were not obtained with these viruses. Individual determinations of $EC_{90}$ values for Compound 1A against HCoV-229E, HCoV-OC43 and SARS-CoV-1 ranged from 0.34 to 1.2 μM, whereas the value against MERS-CoV averaged 37 μM (Table 5). No cytotoxicity was detected with Compound 1A up to 86 μM, the highest concentration tested.

Chloroquine and hydroxychloroquine appeared to be quite potent against HCoV-229E and HCoV-OC43 based on their $EC_{90}$ values of <0.05 μM obtained using VYR measurements (Table 5). The respective $EC_{50}$ values for these two drugs (8.1 and 7.4 μM), obtained using the neutral red assay, were substantially higher and only 2.6- to 3.6-fold less than the corresponding $CC_{50}$ values, indicating considerably lower potencies and poor selectivity indices. These differences illustrate an inherent error in assessing antiviral activities of cytotoxic compounds using only measurements of VYR. When cells are poisoned by toxic drugs and are progressing toward death, their ability to support viral replication and propagation in addition to their own health likely is greatly diminished. At the point when cell death is detected by staining, viral yield reduction measurements likely reflect a combination of antiviral activity and cytotoxicity, thus overestimating antiviral potencies.

In contrast to data published in Wang, M. et al. (*Cell Research* 2020, 30, 269), Huh-7 cells were not permissive for replication of SARS-CoV-2. An assay was developed using human airway epithelial (HAE) cell preparations, a highly relevant in vitro model of the lung, which has been established as a more representative system than cell lines for SARS-CoV-2 replication (Jomsdottir, H. R., *Virol. J.* 13, 24 (2016)). These primary cells form polarized monolayers, the apical side of which is exposed to air and produces a mucin layer, consistent with the physiology of the human airways (Jomsdottir, H. R., *Virol. J.* 13, 24 (2016)). Average $EC_{90}$ and $CC_{50}$ values for Compound 1A against SARS-CoV-2 from two separate HAE assays (0.5 and >86 μM, respectively) were in the same range as those obtained for HCoV-OC43 and SARS-CoV-1 (Table 5).

In the second HAE assay, the activity of Compound 1A was tested in parallel with N4-hydroxycytidine with recently reported in vitro and in vivo activity against SARS-CoV-2 (Sheahan, T. P. et al. *Sci. Transl. Med.* 12, eabb5883 (2020)). The potency of $N^4$-hydroxycytidine against SARS-CoV-2 ($EC_{90}$=3.9 μM) was 8 times less than that of Compound 1A in the same experiment.

A 30-fold difference of Compound 1A activity between MERS-CoV and other CoVs was observed. The nucleotide selection is achieved at the CoVRdRp active site, the nsp12 gene product activated by its processivity co-factors nsp7 and nsp8 (Subissi, L., Proc. Natl. Acad. Sci. USA 111 (37) 3900-9 (2014)). Conserved amino acid motifs A and C are involved in phosphodiester bond formation, whereas motifs F and B participate in nucleotide channeling and binding at the active site, respectively. No significant structural differences are apparent between MERS-CoV and other CoVs in these essential motifs. With a similar ribose modification between Compound 1A and sofosbuvir, it is unlikely that the selective lack of activity of sofosbuvir would be due to excision by the CoV exonuclease carried by nsp14 (Ferron, F., *Proc. Natl. Acad. Sci. USA* 115 (2) 162-171 (2018)). Rather, the results suggest that the triphosphate formed from Compound 1A most likely targets another nsp12 domain, whose inhibition would account for both the antiviral effect and the MERS-CoV differential sensitivity pattern.

Cells, Antivirals and Viruses

BHK-21 (baby hamster kidney) cells, Huh-7 (human hepatocarcinoma) cells, RD (human rhabdomyosarcoma) cells and the seasonal human coronaviruses (HCoV-229E and HCoV-OC43) were obtained from American Type Culture Collection, Manassas, VA. MERS-CoV (EMC), SARS-CoV-1 (Urbani) and SARS-CoV-2 (USA-WA1/2020) were supplied by The Centers for Disease Control and Prevention, Atlanta, GA. The HAE cell preparations (EpiAirway™ AIR-100 or AIR-112) were purchased from MatTek Corporation, Ashland, MA. Compound 1A and N4-hydroxycytidine were prepared for Atea Pharmaceuticals by Topharman Shanghai Co., Ltd., Shanghai, China and Oxeltis, Montpellier, France, respectively. Chloroquine and hydroxychloroquine were purchased from Mason-Chem, Palo Alto, CA and sofosbuvir was purchased from Pharma Sys, Inc., Cary, NC.

Antiviral Assays

BHK-21 cells: Test compounds were dissolved in DMSO at 100 mM and then diluted in Minimum Essential Medium with Earle's salts (MEM-E) containing 1 mM sodium pyruvate and 25 μg/mL kanamycin, supplemented with 10% FBS (growth medium) to final concentrations of 100, 20, 4 and 0.8 μM (two 24-well replica plates each). After BHK-21 cells were grown to confluency in 96-well plates, growth medium was replaced with fresh maintenance medium (growth medium with 1% inactivated FBS in place of 10% FBS) containing serially diluted test compound and HCoV-229E at a multiplicity of infection (MOI) of 0.01. Uninfected cells in the presence of serially diluted compound were used to assess the cytotoxicity of compounds. After a 3-day incubation at 37° C. in a humidified 5% $CO_2$ atmosphere, cell viability was determined by the MTT method (Pauwels, R et al. J. Virol. Methods 20(4):309-321 (1988)). The effective concentration of test compound required to prevent virus-induced cytopathic effect (CPE) by 50% ($EC_{50}$) and to cause 50% cell death in the absence of virus ($CC_{50}$) were calculated by regression analysis.

Huh-7 and RD cells: The antiviral activities of test compounds were evaluated against human coronaviruses alpha (229E), beta (OC43), MERS (EMC) and SARS (Urbani) using a neutral red assay to determine inhibition of virus-induced and compound-induced CPE and using a virus yield reduction (VYR) assay as a second, independent determination of the inhibition of virus-induced CPE.

Neutral red assay: Test compounds were dissolved in DMSO at a concentration of 10 mg/mL and serially diluted using eight half-log dilutions in test medium (Minimum Essential Medium supplemented with 5% FBS and 50 μg/mL gentamicin) so that the highest test concentration was 50 μg/mL. Each dilution was added to 5 wells of a 96-well plate with 80-100% confluent Huh-7 or RD cells (OC43 only). Three wells of each dilution were infected with virus, and two wells remained uninfected as toxicity controls. Six untreated wells were infected as virus controls and six untreated wells were left uninfected to use as virus controls. Viruses were diluted to achieve MOIs of 0.003, 0.002, 0.001 and 0.03 $CCID_{50}$ per cell for 229E, OC43, MERS and SARS, respectively. Plates were incubated at 37±2° C. in a humidified atmosphere containing 5% $CO_2$.

On day 5 (229E and OC43) or day 7 (MERS and SARS) post-infection, when untreated virus control wells reached maximum CPE, the plates were stained with neutral red dye for approximately 2 hours (±15 minutes). Supernatant dye was removed, wells were rinsed with PBS, and the incorporated dye was extracted in 50:50 Sorensen citrate buffer/ethanol for >30 minutes and the optical density was read on a spectrophotometer at 540 nm. Optical densities were converted to percent of controls and the concentrations of test compound required to prevent virus-induced CPE by 50% ($EC_{50}$) and to cause 50% cell death in the absence of virus ($CC_{50}$) were calculated.

Virus yield reduction assay: Vero 76 cells were seeded in 96-well plates and grown overnight (37° C.) to confluence. A sample of the supernatant fluid from each compound concentration was collected on day 3 post infection (3 wells pooled) and tested for virus titer using a standard endpoint dilution $CCID_{50}$ assay and titer calculations using the Reed-Muench equation (1948) (Reed, L J and Muench, H. Am. *J. Hygiene* 27:493-497 (1948)) and the concentration of compound required to reduce virus yield by 90% ($EC_{90}$) was determined by regression analysis.

HAE Cell Preparations

The antiviral activities of test compounds were evaluated against SARS-CoV-2 (USA-WA1/2020) using made to order human airway epithelial (HAE) cells.

Cell Culture: HAE cells were grown on 6 mm mesh disks and arrived in kits with either 12- or 24-$_w$ell transwell inserts. During transportation the tissues were stabilized on a sheet of agarose, which was removed upon receipt. One insert was estimated to consist of approximately $1.2\times10^6$ cells. Kits of cell inserts (EpiAirway™ AIR-100 or AIR-112) originated from a single donor, #9831, a 23-year-old, healthy, non-smoking, Caucasian male. The cells form polarized monolayers, the apical side of which is exposed to air and creates a mucin layer. Upon arrival, the cell transwell inserts were immediately transferred to individual wells of a 6-well plate according to the manufacturer's instructions, and 1 mL of MatTek's proprietary culture medium (AIR-100-MM) was added to the basolateral side, whereas the apical side was exposed to a humidified 5% $CO_2$ environment. Cells were cultured at 37° C. in a humidified atmosphere containing 5% $CO_2$ for one day before the start of the experiment. After the 24-h equilibration period, the mucin layer, secreted from the apical side of the cells, was removed by washing with 400 μL pre-warmed 30 mM HEPES buffered saline solution 3×. Culture medium was replenished following the wash steps.

Viruses: Virus was diluted in AIR-100-MM medium before infection to yield a MOI when added to cultures of approximately 0.0015 $CCID_{50}$ per cell.

Experimental design: Each compound treatment (120 μL) and virus (120 μL) was applied to the apical side, and the compound treatment (1 mL) was applied to the basal side. As a virus control, some of the cells were treated with cell culture medium only. After a 2-h infection incubation, the apical medium was removed, and the basal medium was replaced with fresh compound or medium (1 mL). The cells were maintained at the air-liquid interface. On day 5, cytotoxicity ($CC_{50}$ values) in the uninfected, compound-treated inserts was estimated by visual inspection, and the basal medium was removed from all inserts and discarded. Virus released into the apical compartment of the HAE cells was harvested by the addition of 400 μL of culture medium that was pre-warmed at 37° C. The contents were incubated for 30 min, mixed well, collected, thoroughly vortexed and plated on Vero 76 cells for VYR titration. Separate wells were used for virus control and duplicate wells were used for untreated cell controls. Virus titers from each treated culture were determined as described above.

Example 5: Measurement of Inhibition of N7-Mtase Activity of SARS CoV1 Nsp14 with AT9010 and 2'-Me-GTP In order to determine the mechanistic action accounting for the 30-fold difference of Compound 1A activity between MERS-CoV and other CoVs, additional inhibitory targets were examined.

Initially, N7-Mtase inhibitory activity of the metabolite AT-9010, and 2'-C-Methyl-GTP on nsp14 was examined.

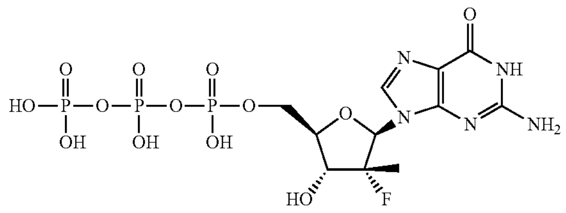

AT-9010

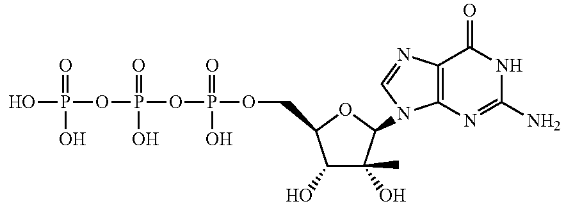

2'-C-Methyl-GTP

Figure 2A:
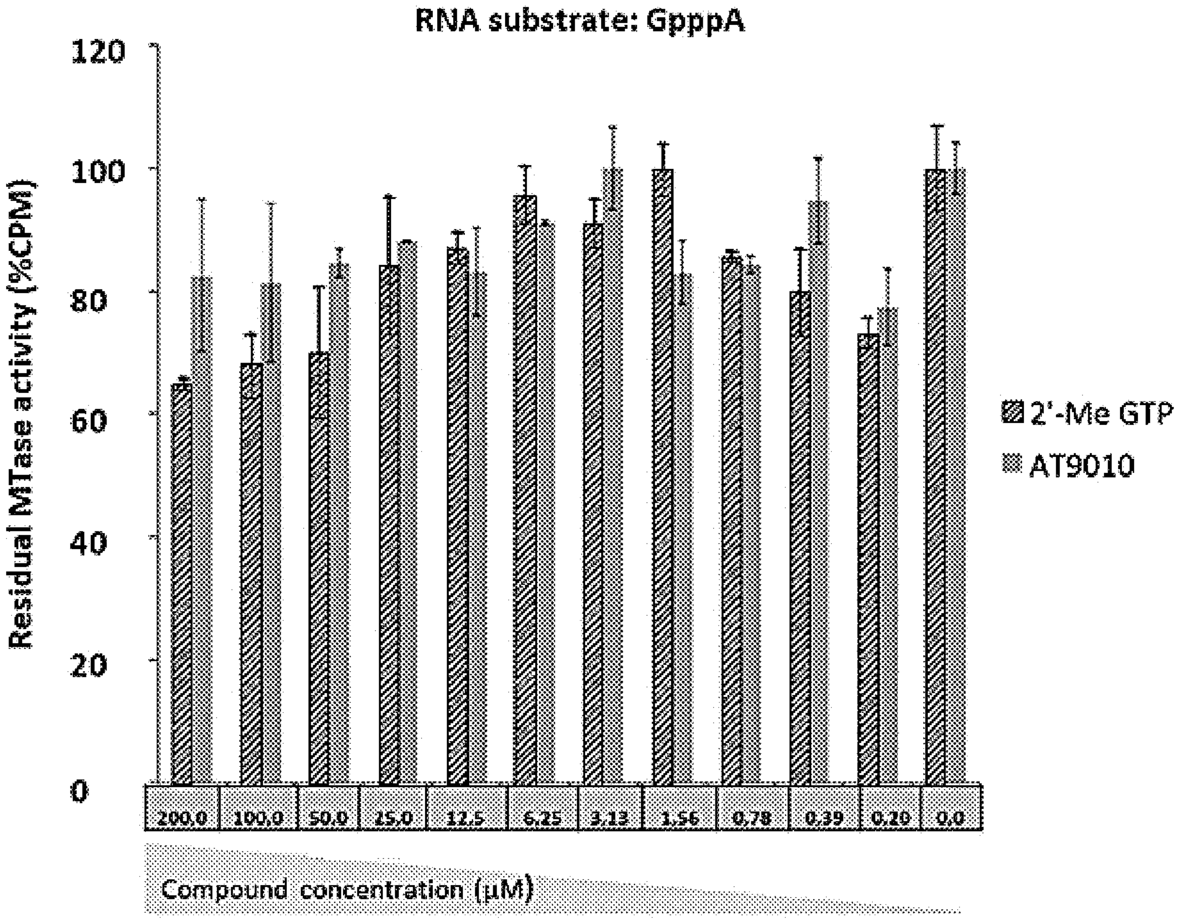
FIG. 2A Bar graph showing the results of a filter binding assay measuring the inhibition of N7-Mtase activity of SARS CoV1 nsp14 with increasing concentrations of AT9010 and 2'-Me-GTP using the RNA substrate GpppA. The x-axis shows the concentration of AT9010 and 2'-Me-GTP as measured in μM. The y-axis shows the residual MTase activity as measured in percentage of counts per minute (CPM) measured by a scintillation counter.
Figure 2B:
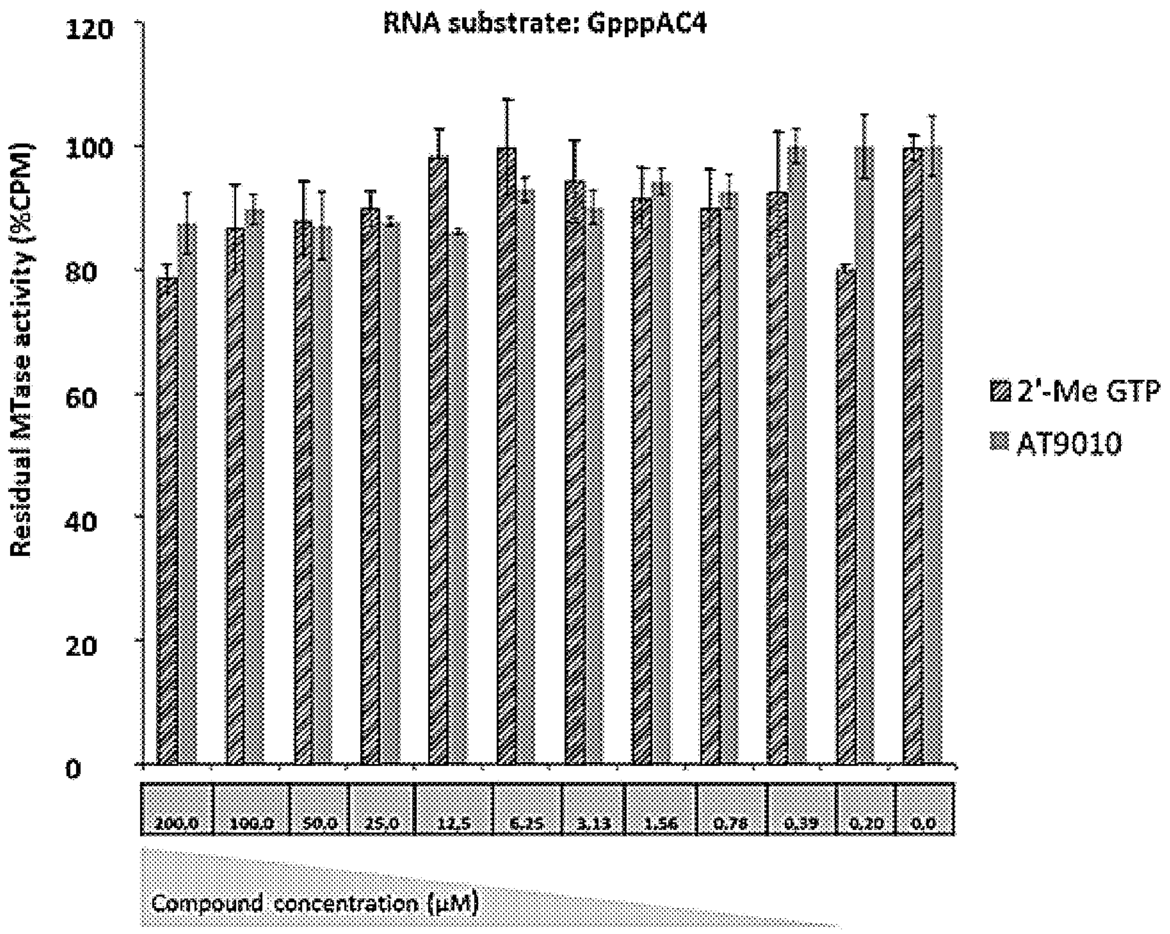
FIG. 2B Bar graph showing the results of a filter binding assay measuring the inhibition of N7-Mtase activity of SARS CoV1 nsp14 with increasing concentrations of AT9010 and 2'-Me-GTP using the RNA substrate $GpppAC_4$. The x-axis shows the concentration of AT9010 and 2'-Me-GTP as measured in μM. The y-axis shows the residual MTase activity as measured in percentage of counts per minute (CPM) measured by a scintillation counter.

Nsp14 can methylate GpppA or GpppAC$_4$ by transferring the [$^3$H]CH$_3$ moiety provided by [$^3$H] S-adenosyl-L-methionine (SAM). The resulting radio-labelled m7GpppA or m7 GpppAC$_4$ product can be quantified using a DEAE filter-binding assay, followed by liquid scintillation counting. The inhibitor specificity assays were carried out in reaction mixture [40 mM Tris-HCl (pH 8.0), 1 mM DTT, 1 mM MgCl$_2$, 2 μM SAM, and 0.33 μM 3H-SAM (Perkin Elmer)] in the presence of 0.7 μM GpppA or GpppAC$_4$ synthetic RNAs and Purified SARS-nsp14 (50 nM). The enzymes were mixed first with increasing concentrations (0-200 μm) of AT9010 or 2'-C-Methyl-GTP before the addition of RNA substrate and SAM and then incubated at 30° C. The final concentration of DMSO was 5%, and control reactions were performed in the presence of 5% DMSO. Reaction mixtures were stopped after 30 min by their 10-fold dilution in ice-cold 100 μM S-adenosyl-L-homocysteine (SAH). Samples were transferred to Diethylaminoethyl cellulose filters (DEAE) (Perkin Elmer) using a Filtermat Harvester apparatus (Packard Instruments). The unincorporated $^3$H SAM was removed from the filter by several washings with 0.01 M ammonium formate pH (8.0), H$_2$O, then absolute ethanol, before drying of the DEAE filters. The filters were incubated with BetaplateScint (Wallac) scintillation fluid before quantification of 3H methylation transferred onto RNA substrates using a Wallac 1450 MicroBetaTriLux liquid scintillation counter in counts per minute (cpm). The IC$_{50}$ of AT9010 and 2'-C-Me-GTP on the N7-MTase activity of SARS-CoV-1 nsp14 (50 nM) using the RNA substrate GpppA is shown in FIG. 2A, which shows no inhibition on SARS-CoV1 nsp14 N-7 guanine MTase with either AT9010 or 2'-C-Me-GTP. The IC$_{50}$ of AT9010 and 2'-Me-GTP on the N7-MTase activity of SARS nsp14 (50 nM) using the RNA substrate GpppAC$_4$ is shown in FIG. 2B, which shows no inhibition on SARS-CoV1 nsp14 N-7 guanine MTase with either AT9010 or 2'-C-Me-GTP.

Based on this experiment, it is unlikely that the anti-viral effect of Compound 1A is mediated through the inhibition of nsp14 activity.

Example 6: 5'Triphosphate Nucleotides, Dinucleotides and Synthetic Oligonucleotides 5'-Triphosphate Nucleosides and Dinucleosides AT-9010, 5'-triphosphate 2'-fluoro-2'-C-methyl uridine, and Remdesivir 5'-triphosphate were from NuBlocks LLC, Oceanside, CA, USA.

Other NTPs were purchased from GE Healthcare. Poly (N)$_{27}$ and oligonucleotide substrates corresponding to the 3' end of the SARS-CoV genome (with or without a poly(A)$_{15}$ tail) were purchased from Biomers (HPLC grade).

Chemical synthesis of 5'-triphosphate (TP) dinucleotides pppUpU, pppUpG, pppGpU and pppApU were performed on an ABI 394 synthesizer (Applied Biosystems) from long chain alkylamine controlled-pore glass (LCAA-CPG) solid support with a pore size of 1000 Å derivatized through the succinyl linker with 5'-O-dimethoxytrityl-2'-O-acetyl-[uridine or N2-isopropylphenoxyacetyl guanosine] (Link Technologies). Dinucleotides were assembled on a 1-μmole scale in Twist oligonucleotide synthesis columns (Glen Research) using the 5'-O-DMTr-2'-O-pivaloyloxymethyl-3'-O-(Ocyanoethyl-N,N-diisopropylphosphoramidite)-[uridine or N2-isopropylphenoxyacetyl guanosine or N6-phenoxyacetyl adenosine] (Chemgenes). After assembly, the CPG beads were dried under a stream of argon. A solution (2 mL) of 1 M diphenyl phosphite (0.4 mL) in dry pyridine (1.6 mL) was passed manually with a plastic syringe through the Twist column and left to stand for 30 min at 40° C. The CPG was then washed with acetonitrile and a 0.1 M solution of triethylammonium bicarbonate (TEAB, pH 7.5) was applied to the column and left to react for 45 min at 40° C. After several washings, an oxidation solution containing imidazole (150 mg) in N,O-bis-trimethylsilylacetamide (0.4 mL), acetonitrile (0.8 mL), bromotrichloromethane (0.8 mL) and triethylamine (0.1 mL) was added under argon and left to react for 2 h at 40° C. After washing and drying the support, a solution containing bis(tri-n-butylammonium) pyrophosphate (88 mg, 0.15 mmol) in dry DMF (0.5 mL) was applied to the column and left to react for 18 h at 40° C. The solution was removed, and the support was washed with dry acetonitrile. The CPG beads were dried by blowing argon through them for 1 min. 5'-TP dinucleotides were deprotected and released from the solid-support using a 1 M solution of 1,8-diazadicyclo-[5,4,0]undec-7-ene (DBU) (0.3 mL) in anhydrous acetonitrile (1.7 mL) for 3 min then the CPG beads were transferred into a glass vial and a 30% aqueous ammonia solution (2 mL) was applied for 3 h at 40° C. The ammonia solution was collected in a 100 mL round bottomed flask and was evaporated and co-evaporated with water under reduced pressure with a bath at 30° C. maximum. The residue was dissolved in water (1.8 mL divided into four portions for flask rinse: 0.6 mL, 0.4 mL, 0.4 mL, 0.4 mL), transferred to 2 mL Eppendorf-vials and then lyophilized from water.

5'-TP dinucleotides were purified by semi-preparative IEX-HPLC with a UHPLC Thermoscientific Ultimate 3000 system equipped with an HPG-3200 BX pump, a DAD 3000 detector, an WPS-3000TBRS Autosampler, a fraction collector F, using a DNAPac PA200 column (22×250 mm). Elution was performed with buffer A: 5% CH3CN in 25 mM Tris-HCl pH 8 and buffer B: 5% CH3CN containing 400 mM LiClO4 in 25 mM Tris-HCl pH 8 at a 9 mL·min-1 flow rate. The crude dinucleotides were purified using a 0-15% linear gradient of buffer B in buffer A in 25 min at 25° C. The pure fractions were pooled in a 100 mL round bottomed flask and were evaporated under reduced pressure with a bath at 30° C. maximum. The residue was desalted using a C18 cartridge Sep-Pak® Classic. The residue was dissolved in 1.2 mL water (divided in 3 portions of 0.4 mL for flask rinse), transferred to a 2 mL Eppendorf-vial and lyophilized from water.

Pure 5'-TP dinucleotides were characterized by MALDI-TOF mass spectrometry using a Axima Assurance spectrometer equipped with 337 nm nitrogen laser (Shimadzu Biotech, UK) using a 10:1 (m/m) mixture of 2,4,6-trihydroxyacetophenone/ammonium citrate as a saturated solution in acetonitrile/water (1:1, v/v) for the matrix. Analytical samples were mixed with the matrix in a 1:1 (v/v) ratio, crystallized on a 100-well stainless-steel plate and analyzed. UV quantification of 5'-TP dinucleotides was performed on a UV-1600 PC spectrometer (VWR) by measuring absorbance at 260 nm.

Synthetic Oligonucleotides

For primer-dependent incorporation assays, primer-template pairs were annealed at a molar ratio of 1:1.5 in 110 mM KCl at 70° C. for 10 min, then cooled slowly to room temperature over several hours. Hairpin RNAs were synthesized by Integrated DNA Technologies (Coralville, IA).

Example 7: Expression and Purification of SARS-CoV Proteins

SARS-CoV cofactor proteins nsp7(TEV)6His, 6His(TEV)nsp8 and nsp7L8(TEV)6His were expressed under the control of a T5-promoter in pQE30 vectors in *Escherichia coli* (*E. coli*) NEB Express C2523 cells (New England Biolabs) carrying the pRARE2LacI (Novagen) plasmid. Protein was expressed overnight at 17° C. in the presence of Ampicillin (100 µg/mL) and Chloramphenicol (17 µg/mL), following induction with 100 µM IPTG at an OD600=0.5-0.6. Cells were lysed by sonication in lysis buffer (50 mM Tris-HCl pH 8, 300 mM NaCl, 10 mM Imidazole, supplemented with 20 mM $MgSO_4$, 0.25 mg/mL Lysozyme, 10 µg/mL DNase and 1 mM PMSF) and protein was purified through affinity chromatography with TALON® Superflow™ cobalt-based IMAC resin (Cytiva). A wash step was performed before elution, with buffer supplemented with 500 mM NaCl. Protein was eluted in buffer supplemented with 200 mM imidazole. The affinity tag was removed via overnight cleavage with TEV protease (1:10 w/w ratio to TEV:protein) in a dialysis buffer containing no Imidazole and supplemented with 1 mM DTT.

Cleaved protein was re-purified through a second cobalt column to remove the histidine-labelled TEV protease, and further purified with size exclusion chromatography (Cytiva Superdex S200) in a final buffer of 25 mM HEPES pH 8, 150 mM NaCl, 5 mM $MgCl_2$ and 5 mM TCEP. SARS-CoV nsp12-8His was expressed from a pJ404 vector in *E. coli* strain BL21/pG-Tf2 (Takara 9124), in the presence of Ampicillin (100 µM/mL) and Chloramphenicol (17 µg/mL). Expression was induced at $OD_{600}$=0.5-0.6 with 250 µM IPTG and 5 ng/ml of tetracycline for induction of chaperones proteins (groES-groEL-tig), and left overnight at 23° C. at 220 rpm. After a passage at 80° C., cells were resuspended and lysed over 45-60 mins with stirring at 4° C., in a buffer containing 50 mM Tris pH 8, 300 mM NaCl, 5 mM $MgSO_4$, 10% glycerol, 1% CHAPS, supplemented with 5 mM 2-mercaptoethanol, 0.5 mg/mL Lysozyme, 10m/mL DNase and 1 mM PMSF and 0.2 mM Benzamidine.

A second lysis-step, for precipitation of nucleic acid, was carried out through the gradual addition of NaCl to a final concentration of 1 M. This step was performed for 45-60 min with stirring at 4° C. Following centrifugation at 30000×g for 30 min, the supernatant was diluted to reduce NaCl concentration to a final concentration of 300 mM. Protein was allowed to bind to cobalt-based IMAC resin TALON® Superflow™ (Cytiva) for 1 hr. at 4° C. Resin was washed 3 times with wash buffer (50 mM Tris pH 8, 10% glycerol) with a difference in NaCl concentration (300 mM, 1 M, 300 mM) before elution in the same buffer supplemented with 200 mM Imidazole. Protein was further purified through size exclusion chromatography (Cytiva Superdex 5200) in a final buffer of 25 mM HEPES pH 8, 150 mM NaCl, 5 mM $MgCl_2$, glycerol 10% and 5 mM TCEP.

Concentrated aliquots of nsp12, 7, 8 and 7L8 were flash-frozen in liquid nitrogen and stored at −80° C. SARS-CoV cofactor protein nsp10 was expressed under the control of a Tet-promoter in a pASK vector in *E. coli* NEB Express C2523 cells (New England Biolabs) carrying the pRare2LacI (Novagen) plasmid. Protein was expressed overnight at 17° C. in the presence of kanamycin (50 µM/mL) and Chloramphenicol (17 µg/mL), following induction with 200 µg/L Tetracycline at an $OD_{600}$=0.6-0.7. Cells were incubated in lysis buffer (50 mM HEPES pH 7.5, 300 mM NaCl, 10 mM Imidazole, 5 mM $MgSO_4$, 1 mM of β-mercaptoethanol supplemented with 0.25 mg/mL Lysozyme, 10 µg/mL Dnase, 0.1% triton and 1 mM PMSF) for 30 min at 4° C. with gentle rocking, then lysed by sonication. The protein was purified through affinity chromatography with HisPur Cobalt resin (Thermo Scientific) and eluted in buffer supplemented with 100 mM imidazole. Protein was further purified through size exclusion chromatography (GE Superdex S200) in a final buffer of 50 mM HEPES pH 7.5, 300 mM NaCl, 5 mM $MgCl_2$ and 1 mM of β-mercaptoethanol. SARS-CoV nsp14 was expressed from a pDEST14 vector in *E. coli* strain NEB Express C2566 cells (New England Biolabs) carrying the pRare2, in the presence of Ampicillin (100 µM/mL) and Chloramphenicol (17 µg/mL). Protein expression was induced at an $OD_{600}$=0.8 with 2 µM IPTG, and left overnight at 17° C. with shaking.

Cells were lysed by sonication in a buffer containing 50 mM HEPES pH 7.5, 500 mM NaCl, 20 mM Imidazole, supplemented with 0.25 mg/mL Lysozyme, 10m/mL Dnase and 1 mM PMSF. The protein was purified through affinity chromatography with HisPur Cobalt resin (Thermo Scientific). After washing with an increased concentration of salt (1 M NaCl), the nsp14 was eluted in buffer supplemented with 250 mM imidazole. The protein was further purified by a size exclusion chromatography (GE Superdex 5200) in a final buffer of 10 mM HEPES pH 7.5, 150 mM NaCl. SARS-CoV-2 proteins were either purchased from Biortus (en.wuxibiortus.com) or purified for cryoEM using the protocol described in Example 23. The gene of the full-length SARS-CoV-2 nsp12 (residues 1-932) was synthesized with codon optimization (General Biosystems). and cloned into pFastBacl baculovirus expression vector. An additional peptide (HHHHHHHHWSHPQFEKENLYFQG) (SEQ ID NO:1) was added to the N-terminus of nsp12.

*Spodoptera frugiperda* (Sf21) cells expressing the target protein were collected 48 h after infection at 27° C. and were centrifugation at 4,500 rpm for 10 min. Pellets were resuspended in lysis buffer (50 mM Tris-HCl (pH 8.0), 500 mM NaCl, 5% glycerol, 2 mM $MgCl_2$, cOmplete Protease Inhibitor Tablet) and homogenized with High Pressure Homogenizer at 4° C. Cell lysate was centrifuged at 18,000 rpm for 60 min at 4° C. The fusion protein was first purified by Strep-Tactin (Strep-Tactin®XT) affinity chromatography and the tag was removed by incubation of TEV protease overnight at 4° C. after elution. The protein was reloaded onto a Heparin HP column after buffer exchanged to buffer A (50 mM Tris-HCl, pH8.0, 150 mM NaCl, 5% glycerol, 2 mM $MgCl_2$). Flow through was collected and loaded on to a HiLoad 16/600 Superdex 200 pg column (GE healthcare) equilibrated in 10 mM Tris-HCl, pH 8.0, 500 mM NaCl, 2 mM $MgCl_2$. Purified nsp12 was concentrated to 6.86 mg/ml and stored at −80° C. The gene of SARS-CoV-2 nsp7 (residues 1-83) possessing a C-terminal Avi-6Histag (GLNDIFEAQKIEWHEHHHHHH) (SEQ ID NO:2) was cloned into a modified pET-32a vector. BL21(*E. coli*, T7 Express) containing the plasmid were grown to an $OD_{600}$ of 0.6 at 37° C., and protein was expressed at 15° C. for 16 h after the addition of isopropyl β-D-1-thiogalactopyranoside (IPTG) to a final concentration of 0.5 mM. The cells were harvested then resuspended in buffer B (50 mM Tris-HCl (pH 8.0), 500 mM NaCl, 5% glycerol, 10 mM imidazole). Cells were disrupted by a High-Pressure Homogenizer at 4° C. The insoluble material was removed by centrifugation at 18,000 rpm, 60 min at 4° C. The fusion protein was purified by Ni-NTA (Novagen, USA) affinity chromatography followed by a Superdex HiLoad 16/600 Superdex 75 pg column (GE Healthcare, USA) in buffer C (10 mM Tris-HCl (pH 8.0), 150 mM NaCl). Purified nsp7 was concentrated to 7.27 mg/ml and stored at −80° C.

The gene of SARS-CoV-2 nsp8 (residues 1-198) was cloned into a modified pET-28a vector containing an N-terminal His6-flag-tag with a TEV cleavage site (HHHHHHDYK DDDDKENLYFQG) (SEQ ID NO:3) for expression in *E. coli*. Nsp8 was expressed in the same way as that for nsp7. Cells were harvested then resuspended in buffer D (50 mM Tris-HCl, pH 8.0, 500 mM NaCl, 5% glycerol). Cells were lysed using a High-Pressure Homogenizer at 4° C. Cell lysate was clarified by centrifugation at 18,000 rpm, 60 min at 4° C. Supernatant was applied onto a Talon affinity chromatography column and tag was removed by on-column cleavage overnight using TEV protease. The mixture was buffer exchanged to buffer D and reloaded onto a His FF column again to remove the His tag and TEV protease. Target protein was further purified by passage through a HiLoad 16/600 Superdex 75 pg (GE Healthcare, USA) in buffer E (20 mM Tris-HCl, pH 8.0, 200 mM NaCl, 5% glycerol). The fractions near the maximum height of the peak were combined and further purified by a Mono Q 10/100 GL column (GE Healthcare, USA). Buffer exchange to buffer E. Purified nsp8 was buffer exchanged to buffer E, then concentrated to 11.63 mg/ml and stored at −80° C.

Example 8: NiRAN-Transfer Inhibition

In this experiment, the impact of guanosine analog inhibitors was tested in a NiRAN competition assay to measure the impact on labelling of nsp8 by nsp12-NiRAN with [$\alpha^{32}$P] GTP or UTP in the presence of increasing concentrations of AT9010 or 2'-C-Me-GTP (ranging from 1.2-1280 which compete with the native NTP for labelling. Transfer assays were performed in a total volume of 10 μl containing 50 mM Tris, pH 8.5, 6 mM $MnCl_2$, 5 mM DTT, up to 2.5 nsp8 and nsp12-NiRan and 5 μM [$\alpha^{32}$P] UTP (Perkin Elmer, 3000 Ci/mmol) or 504 [$\alpha^{32}$P] GTP (Perkin Elmer, 3000 Ci/mmol) and increasing concentrations of AT9010 or 2'-C-Me-GTP (ranging from 1.2-1280 μM). 12.5% glycerol (v/v), 25 mM NaCl, 5 mM HEPES, pH 7.5, and 0.5 mM DTT were carried over from the protein storage buffer. Samples were incubated for 30 min at 30° C. Reactions were stopped by addition of 5 μl gel loading buffer (62.5 mM Tris, pH 6.8, 100 mM dithiothreitol (DTT), 2.5% sodium dodecyl sulphate (SDS), 10% glycerol, 0.005% bromophenol blue) and denaturing of the proteins by heating at 95° C. for 5 min. 12% sodium dodecyl sulphate-polyacrylamide gel electrophoresis (SDS-PAGE) gels were run, stained with Coomassie G-250, and de-stained overnight. After drying, phosphorimager screens were exposed to gels for 5 h and scanned on a variable mode scanner, after which band intensities were analyzed with ImageQuant TL software (GE healthcare).

Figure 3A:
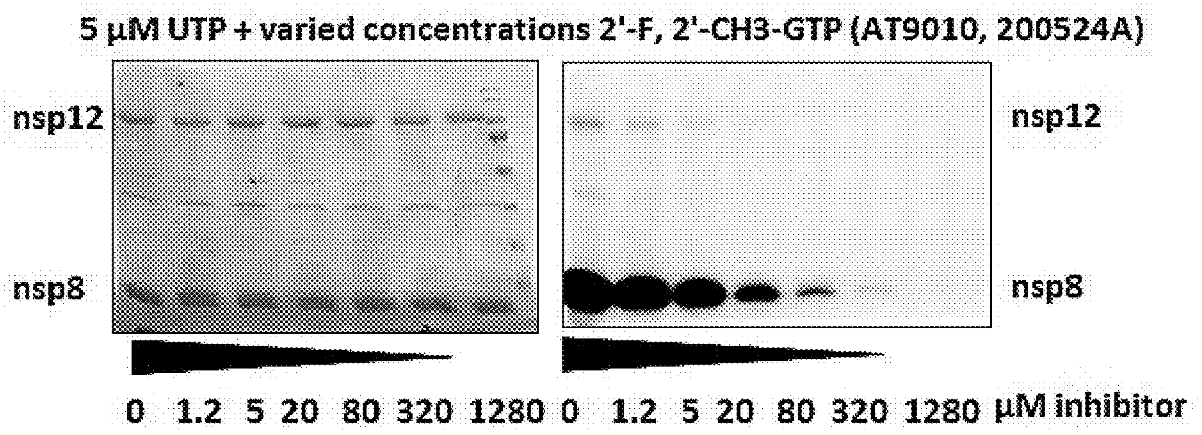
FIG. 3A is a Coomassie blue stained SDS-PAGE gel on the left and the same gel following exposure for radioactivity on the right. These show the results of a NiRAN Competition assay using 5 μM UTP+increasing concentrations of 2'F,2'CH3-GTP (AT9010, 200524A) to determine whether AT9010 inhibits the labelling of nsp8 by nsp12-NiRAN with radio-labelled UTP. The upper band of the gel represents the amount of nsp12 and the lower band represents the amount of nsp8. Each lane represents a concentration of AT9010 from 0-12.80 μM.
Figure 3B:
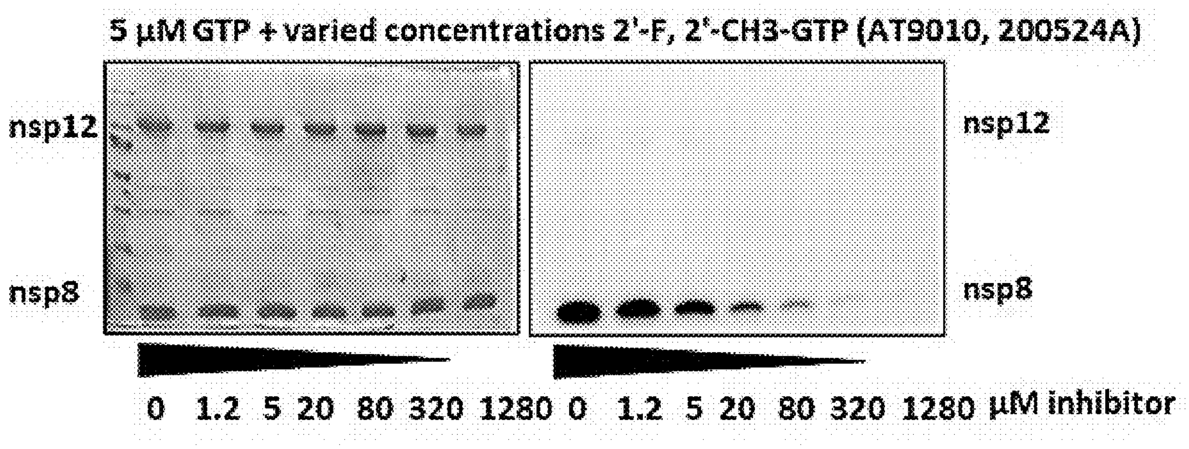
FIG. 3B is a Coomassie blue stained SDS-PAGE gel on the left and the same gel following exposure for radioactivity on the right. These show the results of a NiRAN Competition assay using 5 μM GTP+increasing concentrations of 2'F,2'CH3-GTP (AT9010, 200524A) to determine whether AT9010 inhibits the labelling of nsp8 by nsp12-NiRAN with radio-labelled GTP. The upper band of the gel represents the amount of nsp12 and the lower band represents the amount of nsp8. Each lane represents a concentration of AT9010 from 0-12.80 μM.
Figure 3C:
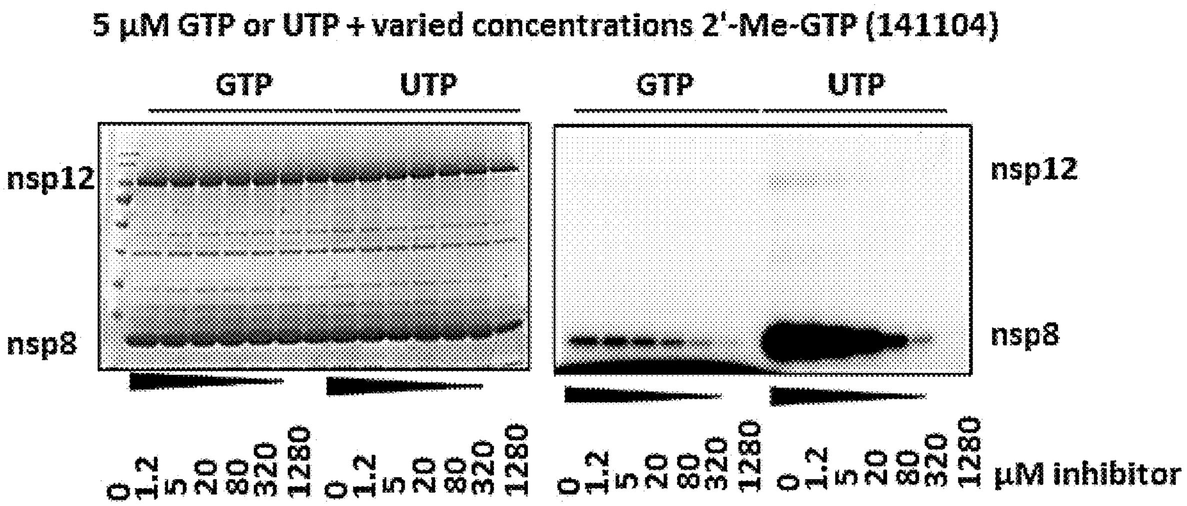
FIG. 3C is a Coomassie blue stained SDS-PAGE gel on the left and the same gel following exposure for radioactivity on the right. These show the results of a NiRAN Competition assay using 5 μM GTP and UTP+increasing concentrations of 2'Me-GTP to determine whether 2'Me-GTP inhibits the labelling of nsp8 by nsp12-NiRAN with radio-labelled GTP or UTP. The upper band of the gel represents the amount of nsp12 and the lower band represents the amount of nsp8. Each lane represents a concentration of 2'Me-GTP from 0-12.80 μM.
Figure 3D:
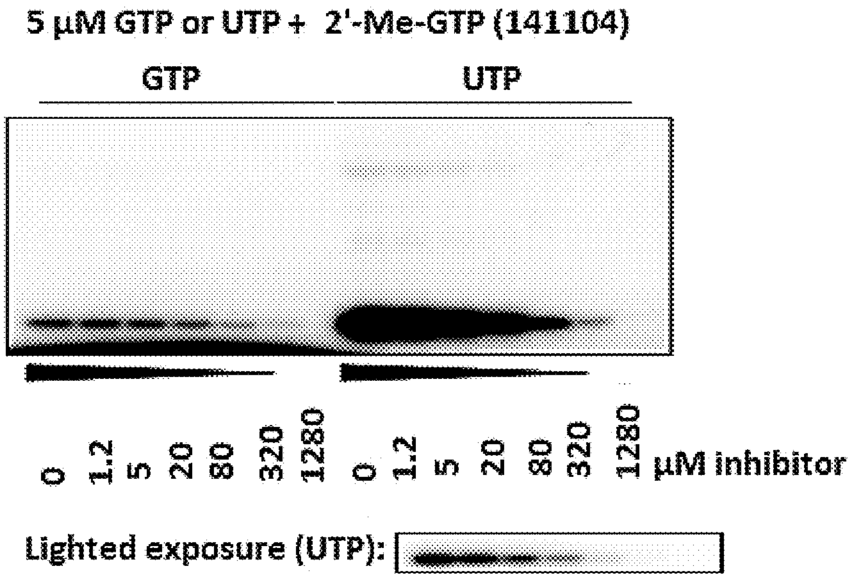
FIG. 3D is the same SDS-PAGE gel following exposure for radioactivity see in FIG. 3C. Included is a lighter exposure of the UTP lanes. These show the results of a NiRAN Competition assay using 504 GTP and UTP+increasing concentrations of 2'Me-GTP to determine whether 2'Me-GTP inhibits the labelling of nsp8 by nsp12-NiRAN with radio-labelled GTP or UTP. The upper band of the gel represents the amount of nsp12 and the lower band represents the amount of nsp8. Each lane represents a concentration of 2'Me-GTP from 0-12.80 μM.
Figure 3E:
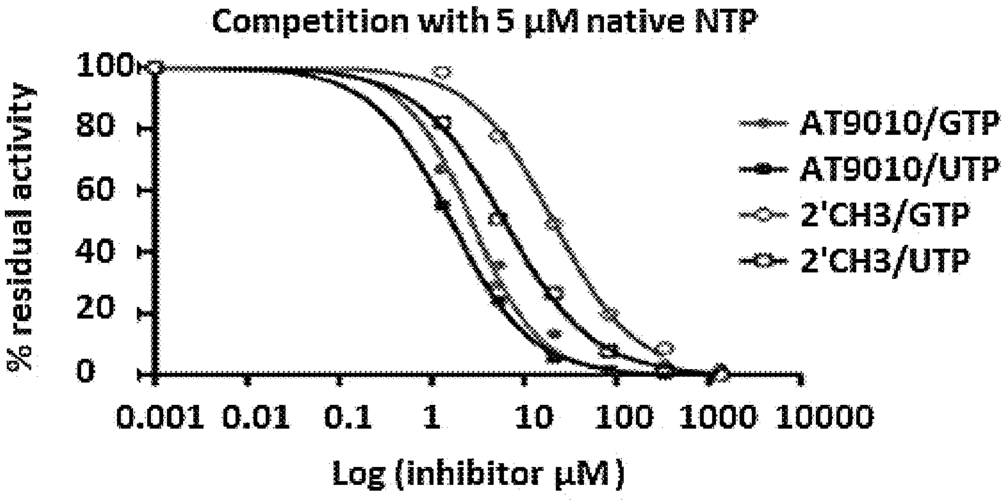
FIG. 3E is a graphical illustration of the $IC_{50}$ curves of the competition between AT9010 and GTP and UTP as well as 2'Me-GTP and GTP and UTP. The x-axis shows a log scale of the inhibitor concentration measured in μM and the y-axis shows the percentage of residual activity with the $IC_{50}$ of each combination shown below.

The image results of the assay using 5 μM UTP plus increasing concentrations of AT9010 are shown in FIG. 3A. The image results of the assay using 5 μM GTP plus increasing concentrations of AT9010 are shown in FIG. 3B. The image results of the assay using 5 μM GTP and 5 μM UTP plus increasing concentrations of 2'-C-Me-GTP are shown in FIG. 3C and with reduced exposure in FIG. 3D. In this experiment the image intensity is converted to a percentage to measure the level of inhibition. At an inhibitor concentration of 0 the intensity is 100%. The relative intensities of the remaining bands are determined at each concentration level of the inhibitor with the results shown in Table 6.

TABLE 6

| Percent Inhibition | | | | | |
|---|---|---|---|---|---|
| conc | AT9010 | | 2'CH3 | | inhibitor |
| inhibitor | GTP | UTP | GTP | UTP | Native NTP |
| 0.0 | 0.0 | 0.0 | 0.0 | 0.0 | ~1:1 ratio with native NTP |
| 1.3 | 32.5 | 44.8 | 1.4 | 17.9 | |
| 5.3 | 64.2 | 75.8 | 22.2 | 49.2 | |
| 21.1 | 86.6 | 94.4 | 50.8 | 73.5 | |
| 84.2 | 92.6 | 98.6 | 80.2 | 92.3 | |
| 336.8 | 96.3 | 99.6 | 91.4 | 98.4 | |
| 1347.4 | 97.8 | 99.8 | 100.0 | 99.9 | |

At ~equimolar proportions of native NTP and AT9010, activity is reduced by 64% and 75% when competing with GTP and UTP respectively. These results were then shown graphically in FIG. 3E where sigmoidal curves were generated and $IC_{50}$ was determined for each inhibitor and the native nucleotide. This corresponds to a fold preference of ~1.7 AT9010: GTP and ~3.2 for AT9010: UTP. This was determined by dividing the NTP concentration of 5 μM/$IC_{50}$.

Example 9: Labelling of Nsp8 Requires the Presence of $MnC_2$

Figure 4A:
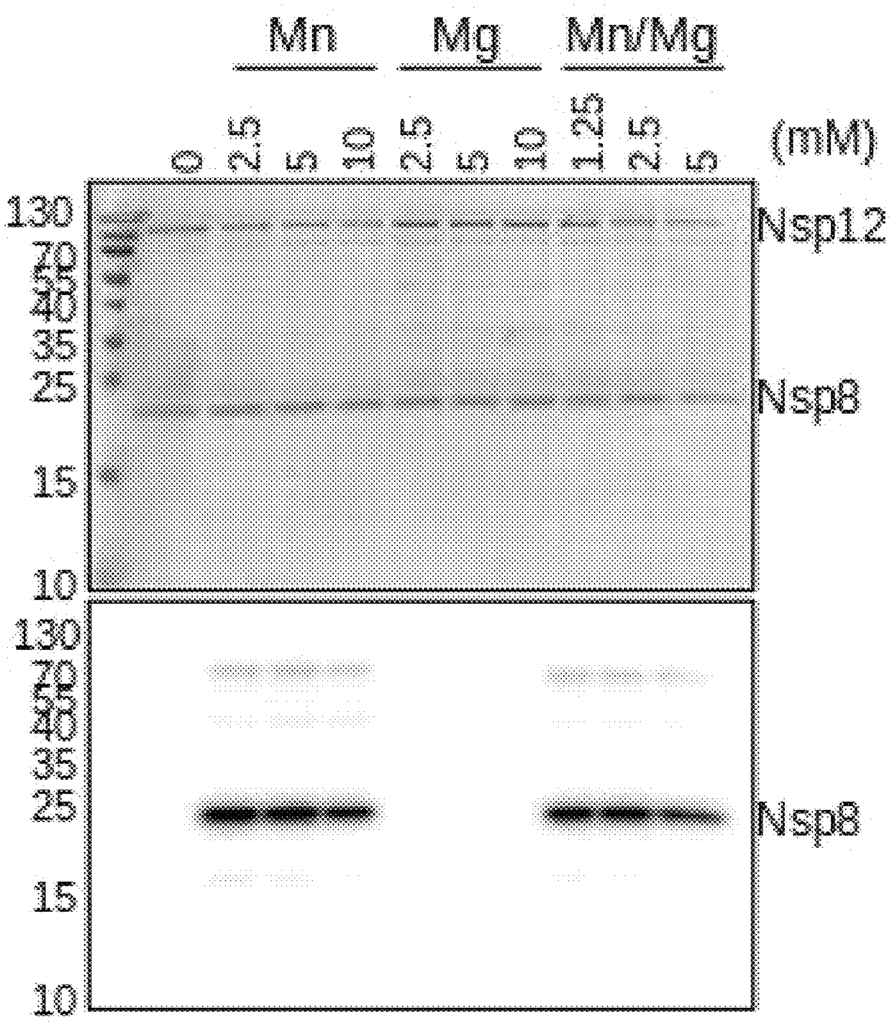
FIG. 4A is 15% SDS PAGE gel showing the labeling of nsp8 by the NiRAN-domain of nsp12 in the presence of varied concentrations of $MnCl_2$, $MgCl_2$, or both ions without RNA. The bottom gel was exposed overnight to reveal radioactive UMP.
Figure 4B:
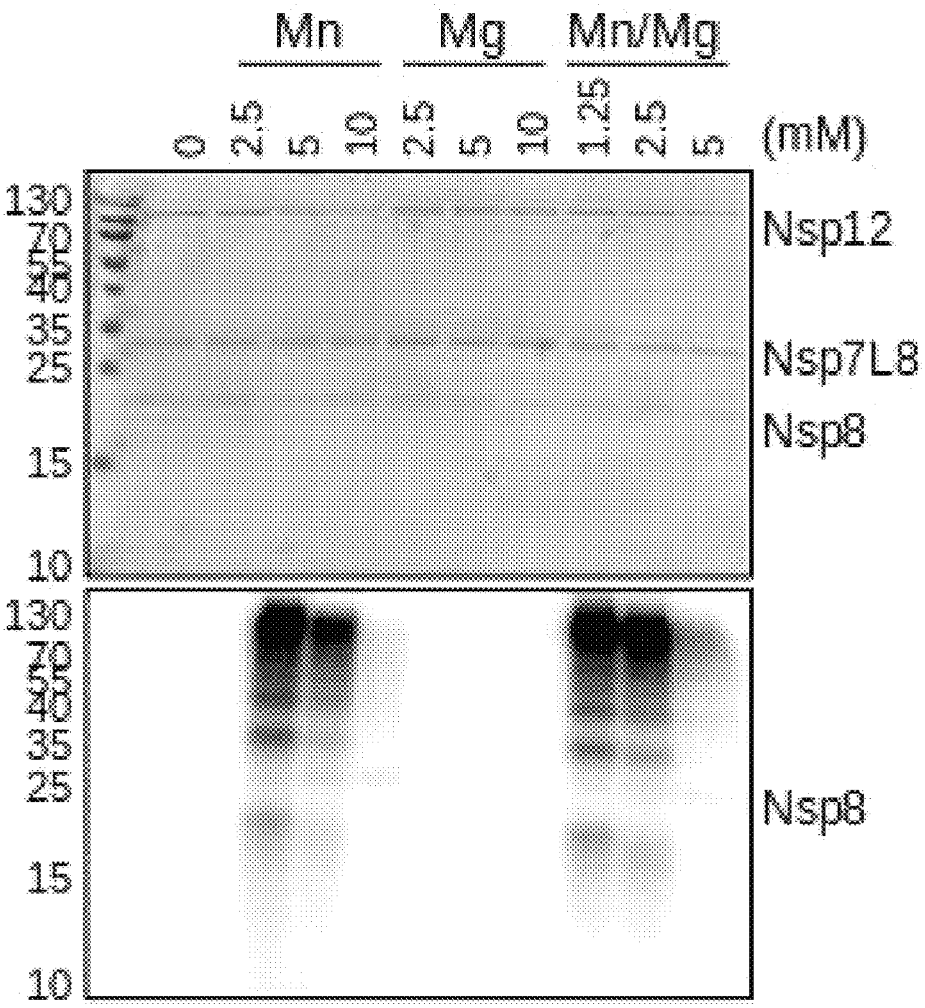
FIG. 4B is 15% SDS PAGE gel showing reactions performed with nsp12:7L8:8 RTC in the presence of varied concentrations of $MnCl_2$, $MgCl_2$, or both ions with $poly(A)_{27}$ RNA. The bottom gel was exposed overnight to reveal radioactive poly(U)n products.
Figure 4C:
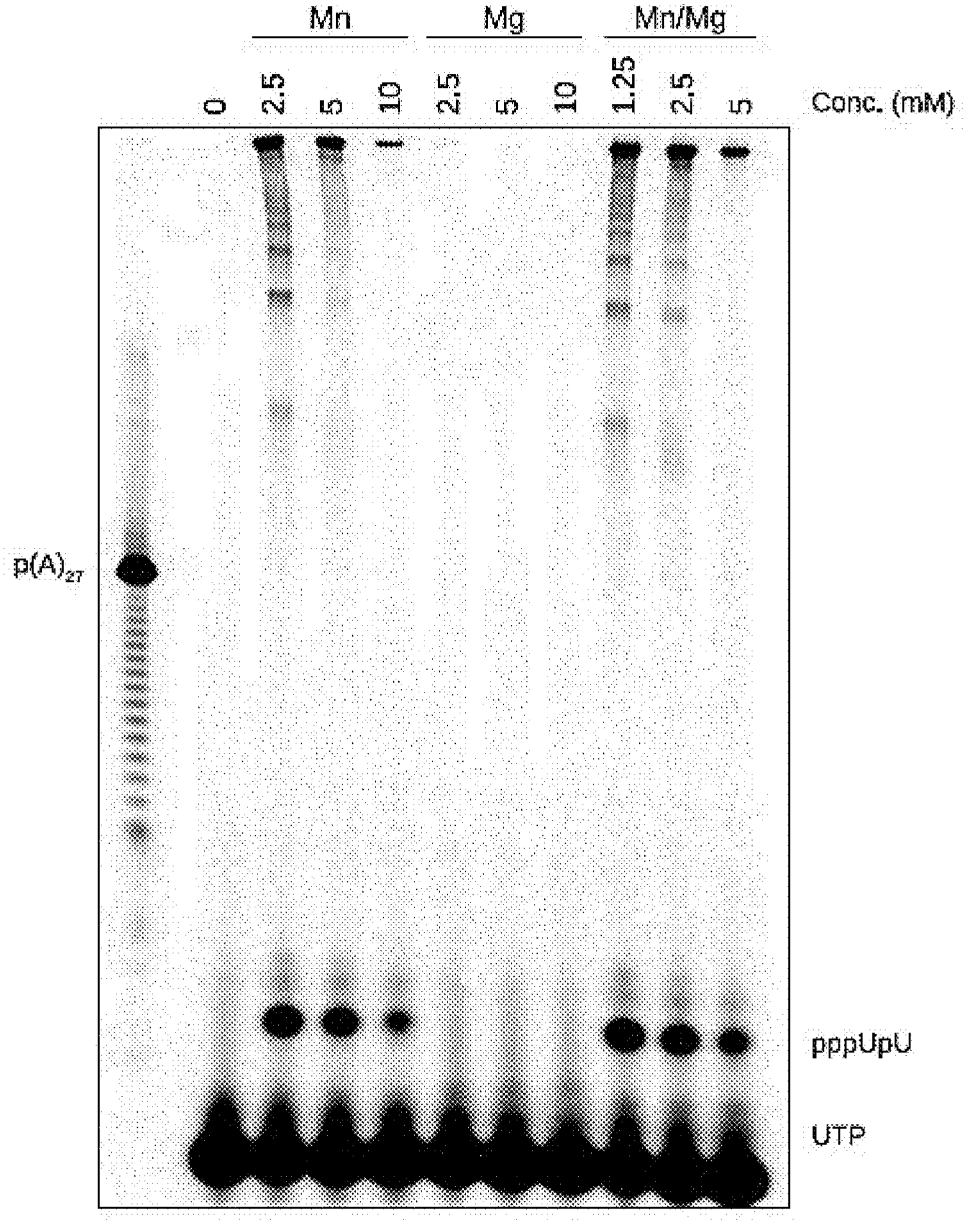
FIG. 4C is a 14% acrylamide UREA-PAGE gel showing reactions performed with nsp12:7L8:8 RTC in the presence of varied concentrations of $MnCl_2$, $MgCl_2$, or both ions with $poly(A)_{27}$ RNA. The gel was exposed overnight to reveal radioactive poly(U)n products.

Labelling of nsp8 with $\alpha^{32}$P-UTP by the NiRAN-domain of nsp12 was assessed using varied concentrations (0-10 mM for individual ions and 1.25-5 mM for both ions together) of $MnCl_2$, $MgCl_2$ or both ions together. Standard nucleotide transfer reactions were performed at 37° C. for reaction times ranging from 2-60 min, in a buffer containing 20 mM HEPES pH 7.5, 1 mM DTT, (0-10 mM $MnCl_2$, $MgCl_2$, or 1.25-5 mM $MnCl_2$/$MgCl_2$), 1-5 μCi $\alpha^{32}$P-NTP and 30 mM NaCl with final protein concentrations of 1 μM nsp12:8 or nsp12:7L8:8 RTC and/or 3 μM cofactors either with or without poly$(A)_{27}$ RNA. For analysis of labeling only, samples were stopped in a 2× concentration of SDS-loading dye and heated at 95° C. for 5 mins, to ensure only covalently-bound NMP remained bound to protein. Proteins were analyzed on 15% SDS PAGE gels, stained with InstantBlue for total protein and exposed for 2 hrs.—overnight to reveal radiolabeled proteins. FIG. 4A shows the results of reactions performed with nsp12 and nsp8 in the absence of RNA. FIG. 4B shows the results of reactions performed with nsp12:7L8:8 RTC in the presence of poly $(A)_{27}$ RNA. FIG. 4C shows the results of reactions performed with nsp12:7L8:8 RTC in the presence of poly$(A)_{27}$ RNA, but analyzed on 14% acrylamide UREA-PAGE gel exposed overnight to reveal poly(U) products. Importantly, it was found that labelling and synthesis of poly(U) products was seen only in the presence of MnC12.

Example 10: The SARS-CoV Nsp12 NiRAN-Domain Mediates Transfer of NMPs to Viral Cofactor Nsp8

To elucidate the specifics behind SARS-CoV nsp12 nucleotidyl transferase activity, different combinations of SARS-CoV enzymes nsp12, nsp7 and nsp8, constituting the minimal RTC required for RNA synthesis (Subissi), were incubated at 37° C. for reaction times ranging from 2-60 minutes in a buffer composed of 20 mM HEPES pH 7.5, 1 mM DTT, 0.5-2 mM MnC12, 30 mM NaCl with 1-5 μCi $\alpha^{32}$P-UTP with final protein concentrations of 1 μM nsp12 and/or 3 μM cofactors. For analysis of labeling only, samples were stopped in a 2× concentration of SDS loading dye and heated at 95° C. for 5 minutes, to ensure only covalently-bound NMP remained bound to protein.

Following incubation, proteins were analyzed on 15% SDS PAGE electrophoresis gels, stained with Instant Blue dye for total protein and exposed for 2 hours overnight to reveal radio-labelled proteins. As shown in FIGS. 4A-C and 5A, UMP is efficiently and specifically transferred to nsp8 and a small amount of contaminating protein (*) in a reaction dependent on nsp12 and $MnCl_2$. Furthermore, a linked version of nsp7 and 8 (nsp7L8) is unable to be labeled by the NiRAN indicating the authentic N-terminus of nsp8 is likely required. In contrast to the related equine arteritis virus, no covalent intermediate with nsp12 is formed.

Figure 5A:
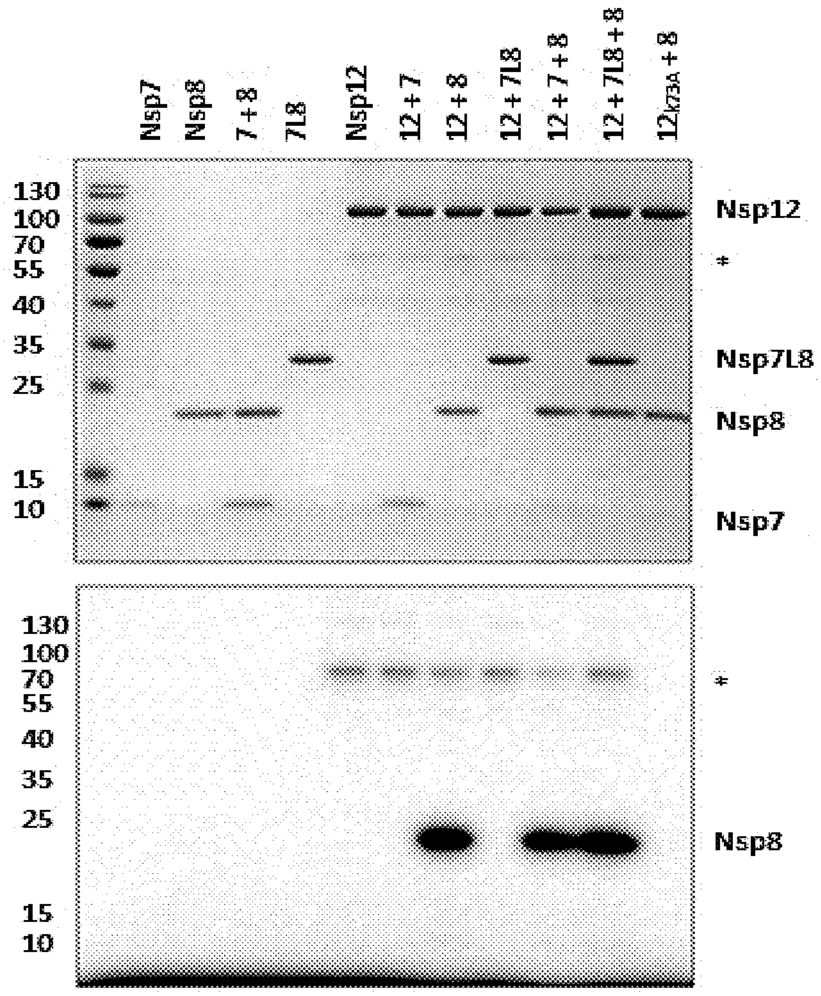
FIG. 5A is a 15% SDS PAGE gel. Various combinations of nsp12, nsp7 and nsp8, as well as a covalently linked version of nsp7 and 8 (nsp7L8) were incubated for 1 hr at 37° C. with $\alpha^{32}$P-UTP. Samples were separated on a 15% SDS PAGE gel to remove non-covalently bound nucleotides and stained for total protein (top), then exposed to reveal radioactivity (bottom). Nsp8 and a small amount of contaminating protein (*) is labeled in a nsp12-dependent fashion.
Figure 5B:
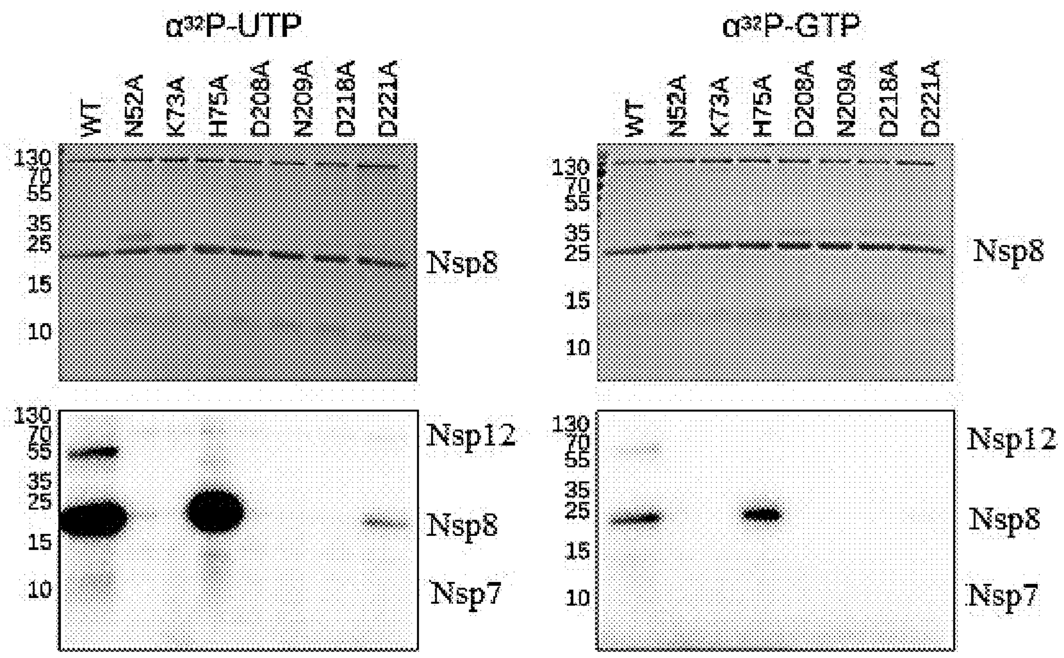
FIG. 5B is a 15% SDS PAGE gel showing the labelling of nsp8 by NiRAN active-site mutants. Labelling of nsp8 with $\alpha^{32}$P-UTP (left) and $\alpha^{32}$P-GTP (right) was performed with the nsp12:7:8 complex with various single NiRAN alanine mutants.
Figure 5C:
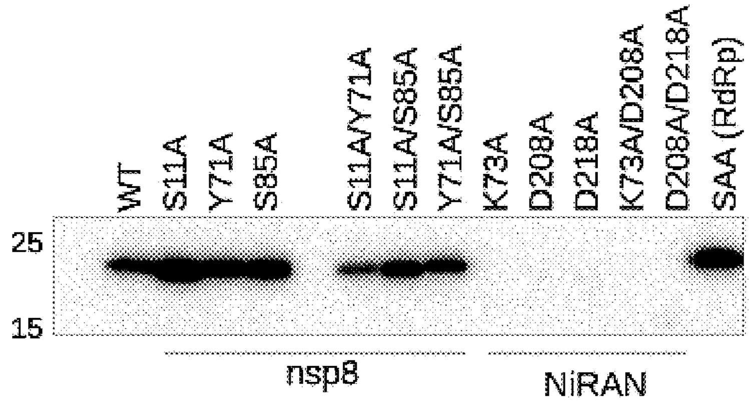
FIG. 5C is a 15% SDS PAGE gel exposed overnight showing the labeling of various nsp8 mutants by nsp12, and of nsp8 WT by various nsp12 NiRAN mutants. Final lane shows RdRp SAA active site mutant.
Figure 5D:
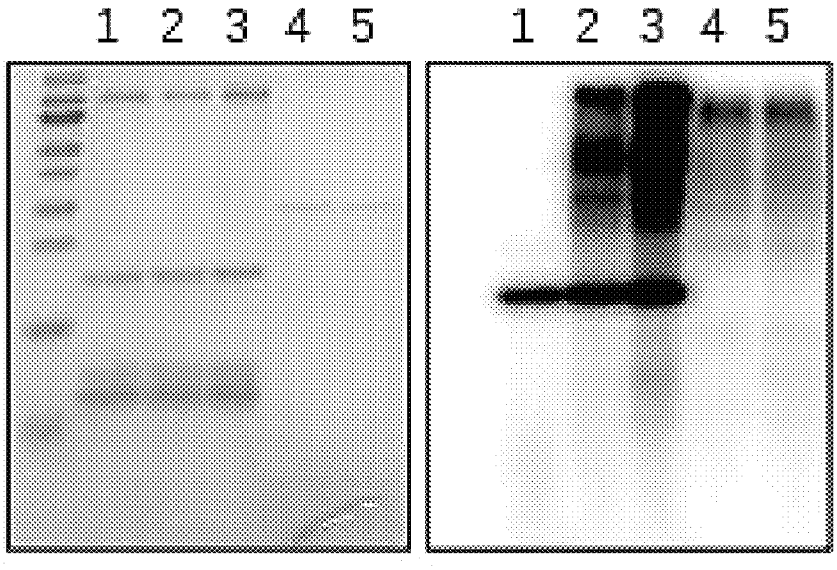
FIG. 5D is a denaturing SDS-PAGE gel showing the analysis of activity of SARS-CoV-2 nsp12:7:8 complex with $\alpha^{32}$P-UTP. Lane 1; without RNA, lane 2; protein complex pre-incubated with UTP+$\alpha^{32}$P-UTP prior to addition of $poly(A)_{27}$ RNA, lane 3; protein complex pre-incubated with $poly(A)_{27}$ RNA prior to addition of UTP+$\alpha^{32}$P-UTP, lanes 4-5; as in lane 2 and 3 but digested with proteinase K (PK) after completion of reaction.

As shown in FIGS. 5A-C, various NiRAN mutants, including k73A, abolish labeling of nsp8 confirming that nucleotide transfer activity is provided by the NiRAN-domain and not by nsp8 itself. As shown in FIG. 5D, the same specificity for nsp8-labeling was observed for the SAR-CoV-2 RTC.

Figure 5E:
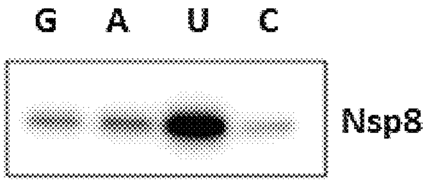
FIG. 5E is a 15% SDS PAGE gel exposed overnight showing the labeling of nsp8 by nsp12 with the four $\alpha^{32}$P radiolabeled nucleotides.

Next, a complex of nsp12: nsp8 was incubated in the same conditions as described above, but with the four different radio-labelled NTPs. As shown in FIG. 5E, incubation with different nucleotides shows UTP is the preferred substrate, albeit with a structural flexibility which allows the binding and transfer of GTP, CTP, and ATP to a lesser extent.

Figure 5F:
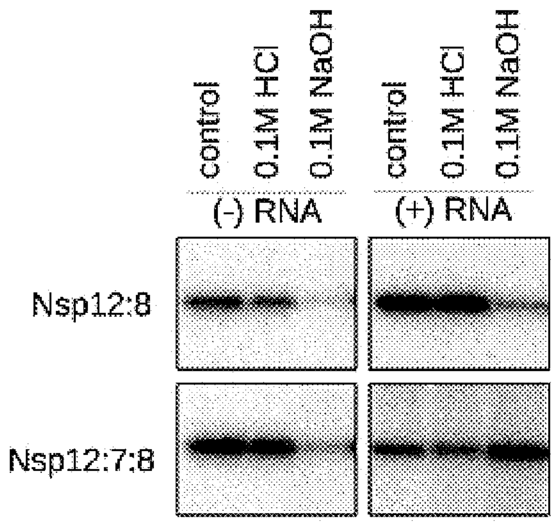
FIG. 5F is a 15% SDS PAGE gel exposed overnight, which shows the stability of the nsp8-UMP bond was assessed through treatment at low or high pH. The labeling reaction was performed with either nsp12+8 alone (top gels) or with the nsp12:7:8 RTC (bottom gels) in the absence (left gels) or presence of $poly(A)_{27}$ RNA (right gels).
Figure 5G:
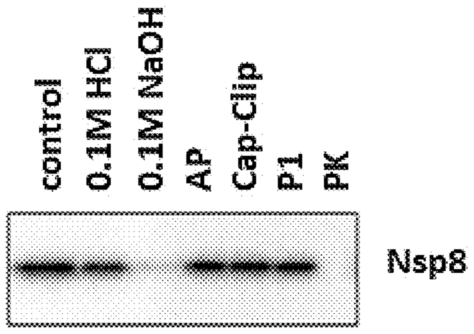
FIG. 5G is a 15% SDS PAGE gel exposed overnight, which shows the results of treatment of the nsp12: nsp8 complex either chemically (HCl or NaOH) or enzymatically with alkaline phosphatase (AP), CapClip enzyme, nuclease P1 (P1) or proteinase K (PK).

To determine the labeling site, stability of the UMP-nsp8 bond was assessed at high or low pH. Nsp8 was first labelled in a reaction containing only nsp12 protein, or with the full replication/transcription complex comprised of nsp12: nsp7L8: nsp8 in the presence or absence of a poly$(A)_{27}$ oligoribonucleotide. Reactions were heat inactivated at 70° C. for 10 minutes, then incubated with either 0.1M HCl or 0.1M NaOH for 1 hour at 30° C. Following incubation, the pH was neutralized with an equivalent concentration of acid or base, and samples were analyzed by SDS PAGE as described above. As shown in the left panel of FIG. 5F, UMP-nsp8 is stable in 0.1M HCL, but alkali labile, indicating that most of the UMP is bound to the hydroxyl group of either a serine or threonine residue. Interestingly, when the nsp8 labeling reaction is performed in the presence of a poly$(A)_{27}$ oligoribonucleotide and nsp7 (i.e., the nsp12-nsp7-$(nsp8)_2$ RTC), the UMP-nsp8 bond is stable at both high and low pH, indicative of a phosphodiester bond with a tyrosine hydroxyl group (FIG. 5F, right panel). Only two serines (S11 and S85) and one tyrosine (Y71) are highly conserved in CoV nsp8 (Subissi). Additionally, the nsp12: nsp8 complex was treated either chemically (HCl or NaOH), or enzymatically with Alkaline phosphatase (AP), CapClip enzyme, nuclease P1 or proteinase K (PK) for 2 hours at 37° C. to gauge bond type and stability followed by incubation in the same conditions as described above (FIG. 5G). As shown in FIG. 5C, single and double mutants to alanine reduce, but do not completely eliminate, labeling, although a notable increase in labeling efficiency is noted for Ser11A suggesting that this residue to be involved in the selectivity of the labeling site.

Between these two experiments, it therefore appears that several residues of nsp8 are able to be labelled by the NiRAN, and that this is depended on the conformation of the RTC dictated by the presence or absence of RNA. This is consistent with recent Cryo-EM structures, which show nsp8 to form "molecular sliding poles" stabilizing the RNA exiting from the polymerase active site (Hillen, Cramer 2020). In the absence of RNA, these flexible N-terminal extensions of nsp8 would likely be in alternative conformation, varying the tropism of the nucleotidylation site, and potentially serving as a mechanism to regulate NiRAN activity.

Example 11: Primer-Independent RNA Polymerization Assay

To perform primer independent RNA polymerization assays, the active nsp12:7:8 complex (RTC) was formed by first incubating nsp7 and 8 together at equimolar concentrations (100 μM) for 30 mins at room temperature. Nsp12, extra nsp8 and protein gel filtration buffer were added to form a final complex consisting of nsp12:7:8 at a 1:3:6 ratio, with 10 μM nsp12. The complex was further incubated for 10 mins at room temperature, and used at a final concentration of 1 μM nsp12. Primer-independent assays were performed in the same conditions used for nucleotidyl transferase reactions, but supplemented with 100-200 μM cold NTP and 0.7 μM final concentration of RNA. Reactions were stopped at indicated timepoints in either 2× concentration of SDS loading buffer for protein analysis, or a 2×-4× volume of FBD stop solution (formamide, 10 mM EDTA) for analysis on 14% acrylamide, 7M UREA sequencing gels. For proteinase K digestions, reactions were first stopped by heat-inactivation at 10 mins at 70° C. Digestion was performed for 2 hours at 37° C. in a buffer containing 20 mM HEPES pH 7.5 and X % SDS. Nuclease P1 (NEB) were performed as per manufacturer's instructions. De novo assays, using 0.35 μM poly$(A)_{27}$ RNA as template, were started by adding 200 μM [$\alpha$-$^{32}$P] UTP (0.5 μCi/μL).

For order of addition experiments, protein was pre-incubated in reaction buffer for 30 min at 37° C. with either UTP or RNA. Following incubation, the inverse reagent was added to start the reaction. AT-9010 and SOF inhibition was tested with a constant concentration of 200 μM cold NTP and varied concentrations of inhibitor. Inhibitor, NTP and RNA were incubated together in assay buffer, and reactions were started via addition of the protein complex. For analysis of covalent binding to nsp8 with western blotting, polymerase assays were performed in the buffer described above. Nsp12:7:8 complex was preincubated with 200 μM UTP for 30 min at 37° C. prior to addition of 2 μM poly$(A)_{27}$, ST20poly$(A)_{15}$ or ST20 RNA. Reactions were either stopped immediately after RNA addition (time 0), or after 60 min incubation at 37° C. in 2×SDS loading buffer. Samples were separated on 15% SDS-PAGE gels, transferred to nitrocellulose membranes and blocked in TBS-Tween (0.1%) containing 5% skim milk powder overnight. Nsp8 was probed with mouse monoclonal anti-nsp8 (5A10) from GeneTex (GTX632696), and HRP-conjugated rabbit anti-mouse secondary (Agilent Dako), washing 3× in PBS.T between each antibody. Nsp8 was revealed with Immobilon Crescendo Western HRP Substrate (Millipore).

Figure 6A:
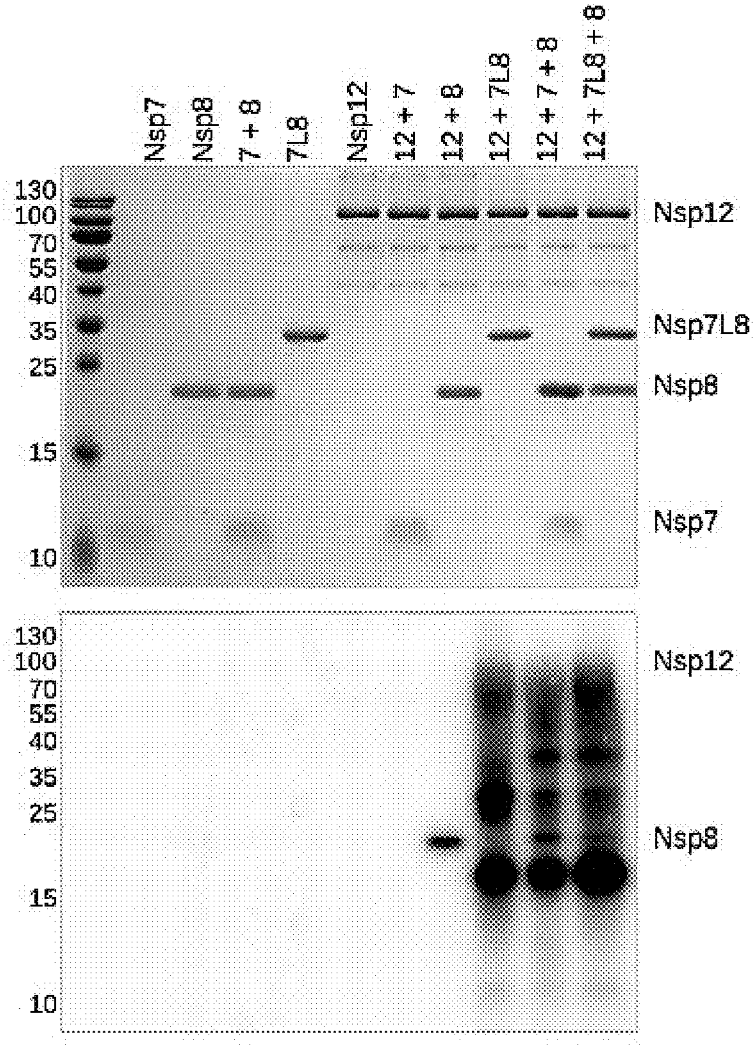
FIG. 6A is a 15% SDS PAGE gel stained for protein with Instant Blue (top) and exposed overnight (bottom) showing the results of various combinations of nsp12, nsp7, nsp8, as well as covalently linked version nsp7L8 incubated with $\alpha^{32}$P-UTP and $poly(A)_{27}$ RNA.
Figure 6B:
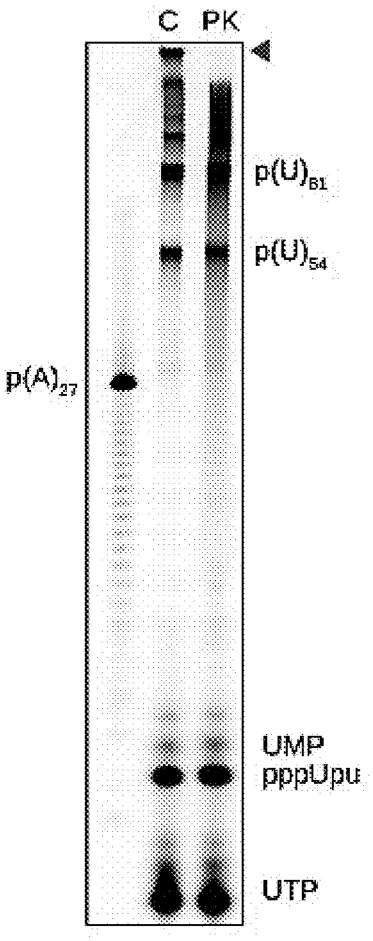
FIG. 6B is the results of a synthesis reaction run as described above measuring the activity of the nsp12:7:8 complex separated on a 14% acrylamide 7M UREA gel. Size of input template RNA shown as $p(A)_{27}$, with $p(U)_{54}$ and $p(U)_{81}$ showing multimeric poly(U) synthesis products. C represents reaction control, while PK shows same sample following protein digestion with proteinase K.
Figure 6C:
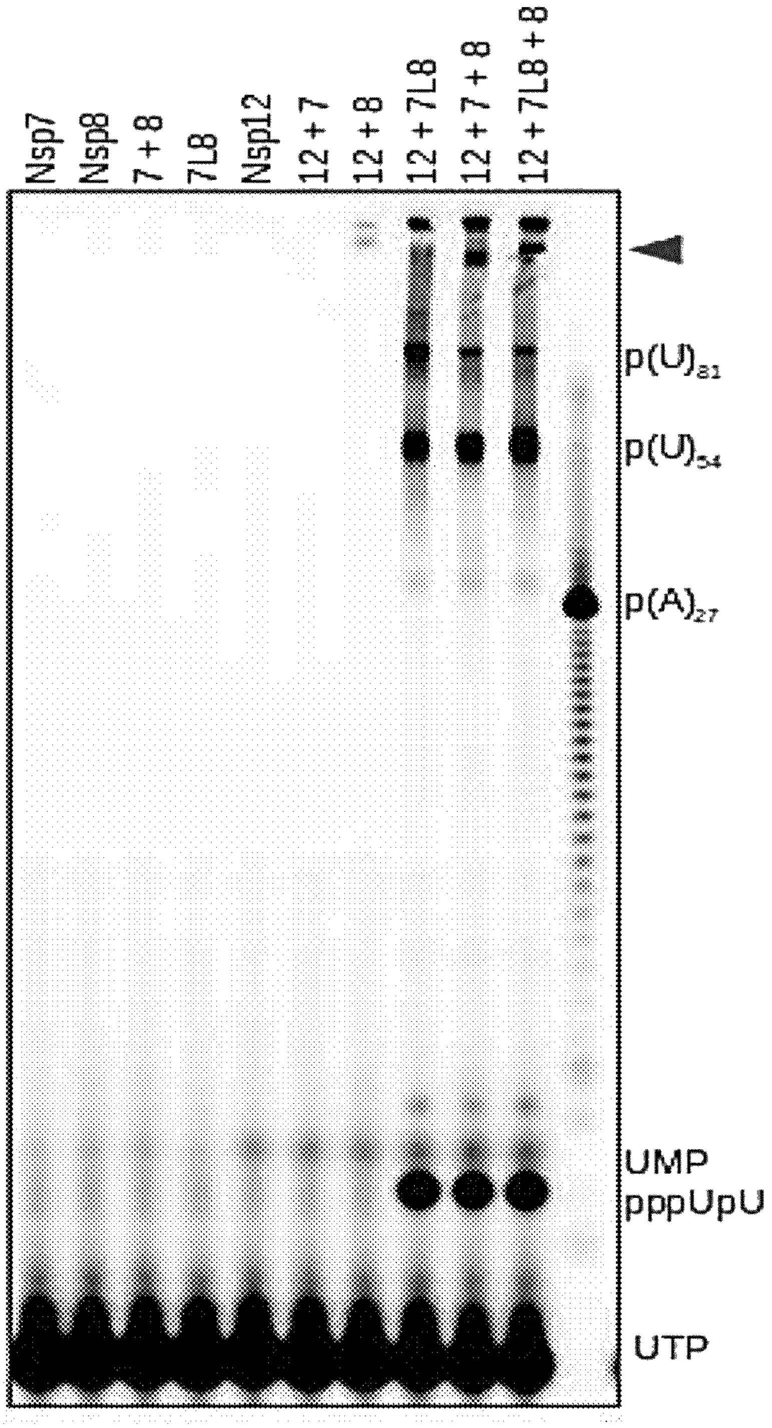
FIG. 6C is a 14% acrylamide 7M UREA-PAGE sequencing gel exposed overnight, which shows a synthesis reaction run using various combinations of SARS-CoV nsp12, nsp7 and nsp8, as well as a covalently linked version of nsp7 and 8 (nsp7L8) incubated for 1 hr at 37° C. with UTP (supplemented with $\alpha^{32}$P-UTP) and $poly(A)_{27}$ RNA. These samples correspond to samples shown in FIG. 6*a*.
Figure 6D:
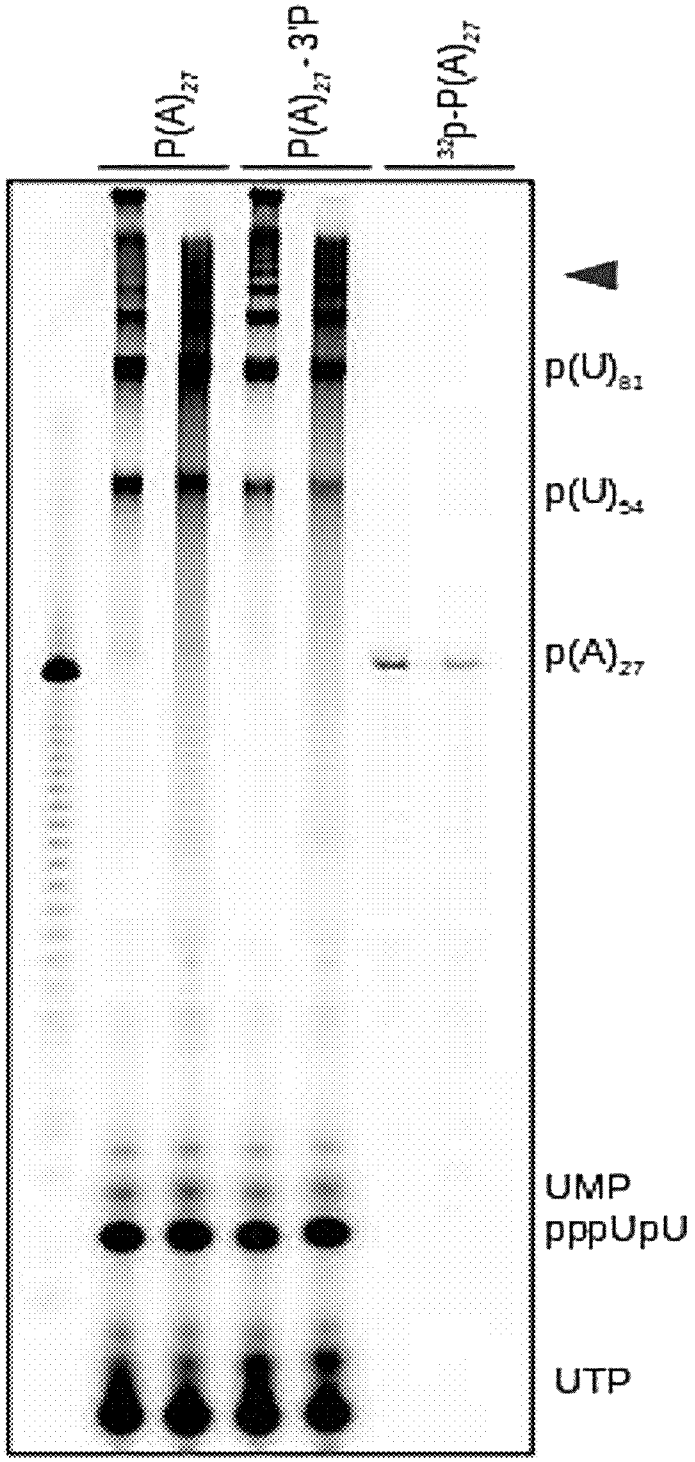
FIG. 6D is a 14% acrylamide 7M UREA-PAGE sequencing gel exposed overnight, which shows a synthesis reaction run with the nsp12:7:8 complex with three RNA substrates; i) $poly(A)_{27}$ template RNA, ii) $poly(A)_{27}$ template RNA blocked at the 3' end via replacement of the 3'OH with a phosphate group ($poly(A)_{27}$-P), and iii) $poly(A)_{27}$ template labeled at the 5' end with $^{32}$P ($^{32}$P-$poly(A)_{27}$). Synthesis was measured via addition of UTP supplemented with $\alpha^{32}$P-UTP for the first two RNAs, and with cold UTP only for $^{32}$P-$poly(A)_{27}$. C represents reaction control, while PK shows same sample following protein digestion with proteinase K.

Example 12: SARS-CoV Nsp8-UMP is Involved in a Unique Protein-Primed RNA Synthesis Step A high-throughput, fluorescent screening assay was established using the purified SARS-CoV RTC, which was able to synthesize poly(U) from a poly(A) template in the absence of a primer (Eydoux). RNA polymerization assays were run as described in Example 10. To gauge how synthesis is initiated in these assays, and whether UMPylation of nsp8 is involved, various combinations of nsp12, nsp7, and nsp8, as well as a covalently linked version of nsp7 and 8 (nsp7L8) were incubated for 1 hr. at 37° C. with UTP (supplemented with α-$^{32}$P-UTP and poly$(A)_{27}$ RNA. Samples were separated on a 15% SDS PAGE gel to remove non-covalently bound nucleotides/RNA and stained for total protein (FIG. 6A) and a high-resolution UREA-PAGE sequencing gels (FIG. 6B). The RTC efficiently synthesizes labeled RNA in the presence of $MnCl_2$ (FIGS. 4B-C), with the majority of products longer than the expected poly$(U)_{27}$ size (FIG. 6B-C). Modification of either the 5' or 3' end of the poly$(A)_{27}$ template does not affect synthesis, demonstrating that these products are not a result of nsp8 terminal-transferase activity (Tvarogova, 2019), or another template modification (FIG. 6D). Rather, once a full-length poly$(U)_{27}$ product is synthesized, the complex is able to switch to a new poly$(A)_{27}$ acceptor template and continue synthesis, resulting in products that are multimeric in length to the input poly$(A)_{27}$ template.

Figure 6E:
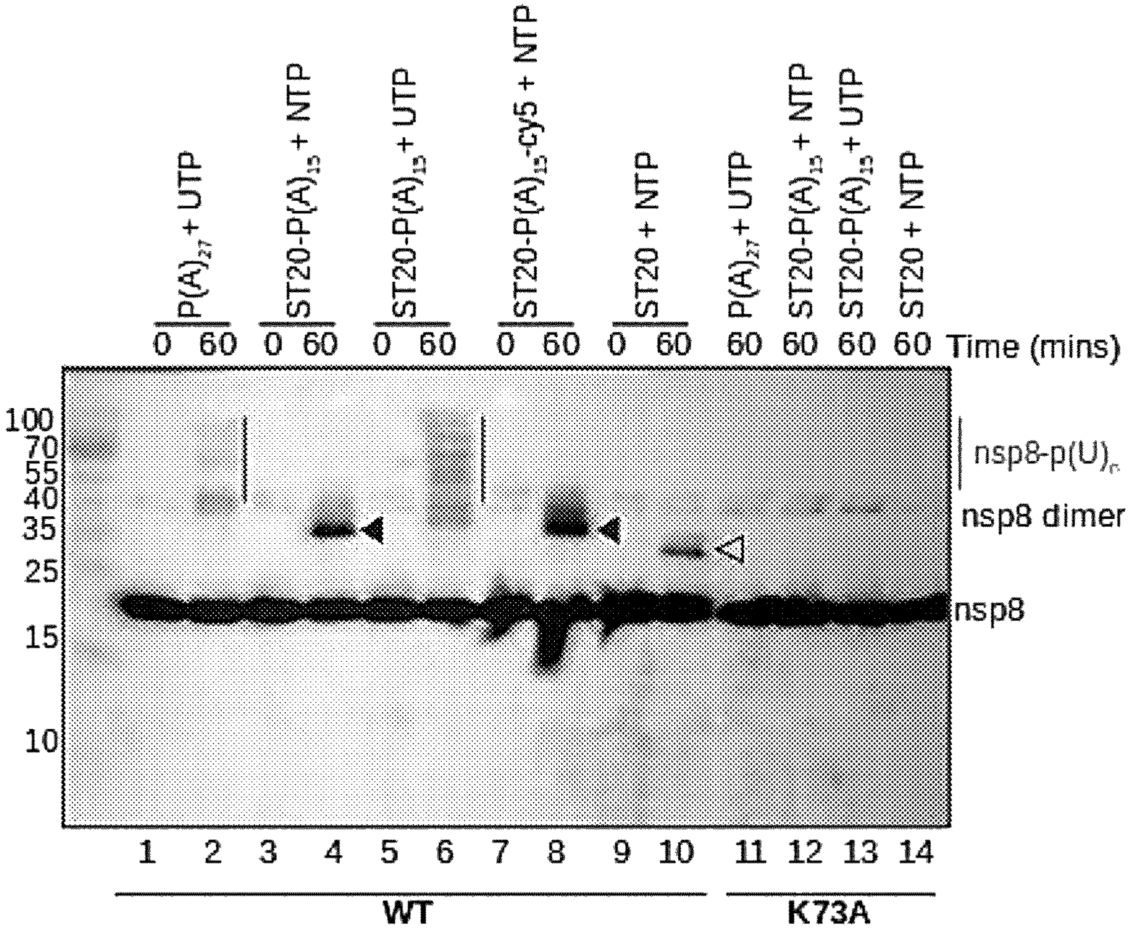
FIG. 6E is a denaturing SDS-PAGE western blot analysis with anti-nsp8 (5A10). The nsp12:7:8 complex was preincubated for 30 mins with UTP prior to addition of different RNAs and remaining NTPs (if indicated); $poly(A)_{27}$ (lanes 1, 2, 11), $ST20poly(A)_{15}$ (lanes 3-6, 12, 13), $ST20poly(A)_{15}$ 3' blocked with cy3 (lanes?-8), ST20 (lanes 9, 10, 14). Reactions were stopped immediately after RNA addition (time 0) or after 60 mins incubation. When only UTP is given with $ST20poly(A)_{15}$, synthesis occurs in a similar fashion to that of the poly(A) template (red line, nsp8-$p(U)_n$).

Similar template-switching activity has been previously described for other viral RdRps (Woodman; Menendez-Arias). Despite the previously reported primase (Imbert, 2006), poly(A) polymerase (Tvarogova), and primer-extension (Te Velthuis) activities of nsp8, activity of nsp8 alone or in combination with nsp7 was not observed in this context (FIGS. 6A & 6C). Importantly, a large amount of radiolabeled product is also seen to remain either in the wells, or with very limited migration down the gel (FIG. 6B, arrow). Proteinase K (PK) hydrolysis of the polymerase complexes lead to the digestion of these products and results in the further release of poly(U) synthesized RNA, consistent with a nsp8-primed synthesis event. Western blot analysis with anti-nsp8 confirms that the higher products (>40 kDa on SDS PAGE) are covalently linked with nsp8, and not another protein (FIG. 6E, lanes 1-2). Furthermore, these products are not seen with the NiRAN K73A mutant, showing this reaction is NiRAN-dependent (FIG. 6E, lane 11).

Figure 6F:
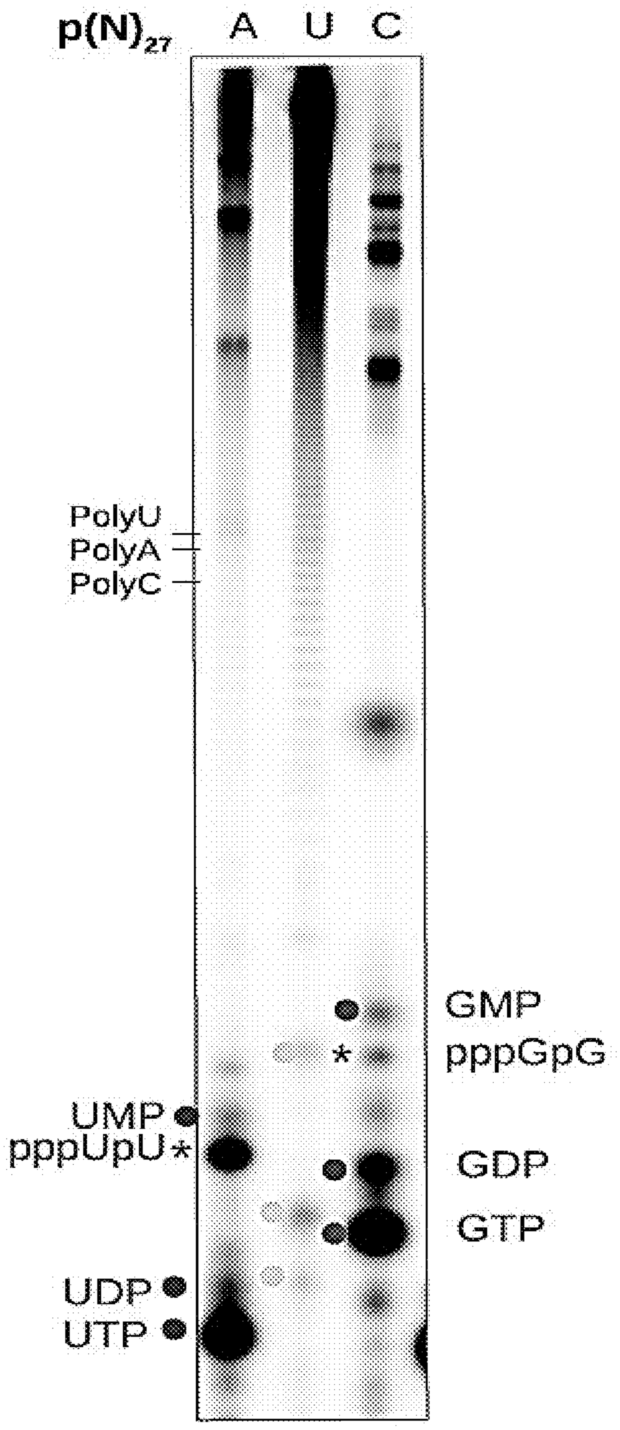
FIG. 6F is a 7M UREA-PAGE, which shows the activity of the nsp12:7:8 complex with $poly(A)_{27}$, $poly(U)_{27}$ or $poly(C)_{27}$ RNA templates, with UTP, ATP or GTP (supplemented with the corresponding $\alpha^{32}$P-NTP), respectively. From the bottom up, solid dots show tri-, di- and monophosphates of uridine (red), adenosine (yellow) and guanosine (green), respectively. Asterix's show pppNpN dinucleotide products with same color scheme.
Figure 6G:
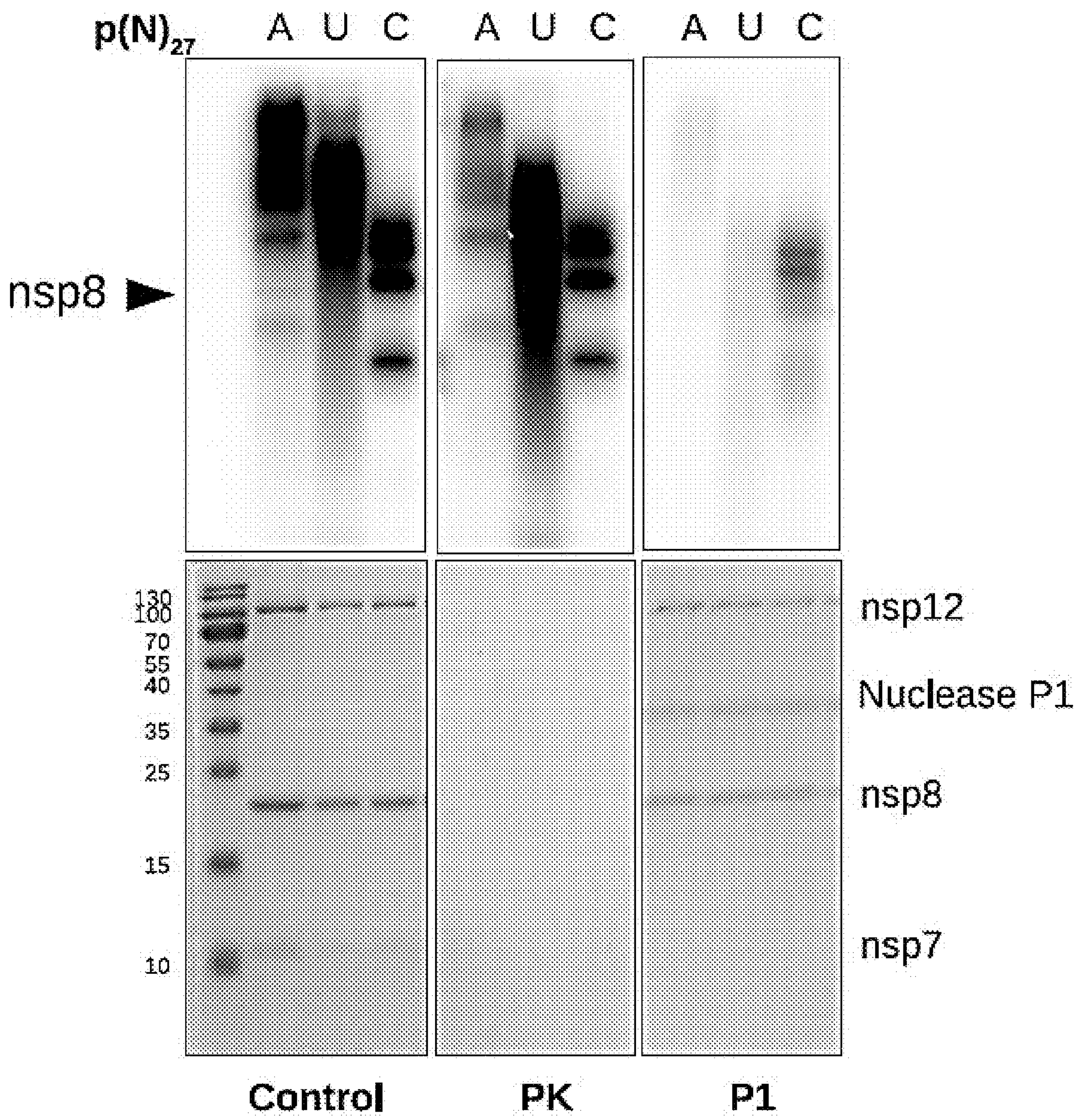
FIG. 6G is 3 15% SDS PAGE gels which shows the activity of the nsp12:7:8 complex with $poly(A)_{27}$, $poly(U)_{27}$ or $poly(C)_{27}$ RNA templates, with UTP, ATP or GTP (supplemented with the corresponding $\alpha^{32}$P-NTP), respectively before (left panel) and after treatment with proteinase K (middle panel), or nuclease P1 (right panel). Top panels show gels following exposure for radioactivity, bottom panels are same gels stained for total protein.

Interestingly, polymerization can also be initiated on poly(U) and poly(C) templates through the addition of ATP and GTP, respectively (FIGS. 6F-G). However, in contrast to poly(U) synthesis, poly(A) and poly(G) products are not retained in the wells, and furthermore are not sensitive to proteinase K digestion. Thus, protein-primed RNA synthesis is UTP-specific, consistent with the preference for UMP-nsp8 labeling by the NiRAN-domain. Therefore, the RTC complex transfers UMP to one of its presumably bound nsp8, which serves as an uridylated primer to initiate poly $(U)_n$ synthesis.

Example 13: Two Independent Pathways of Primer Synthesis in SARS-CoV Co-Exist to Initiate RNA Synthesis For the Picornaviridae family, the VPg protein is used to prime both plus and minus strand synthesis. Its covalent attachment to the 5' end of the RNA additionally substitutes for the RNA-cap, protecting the viral RNA from host cell degradation. In contrast, the CoV genome presumably contains a conventional m7Gppp$A_{2'Om}$ RNA cap (Bouvet). This difference suggests that for CoVs, the nsp8-UMP protein-primed strategy is specific to minus strand synthesis, templated from the poly(A) tail.

Figure 7A:
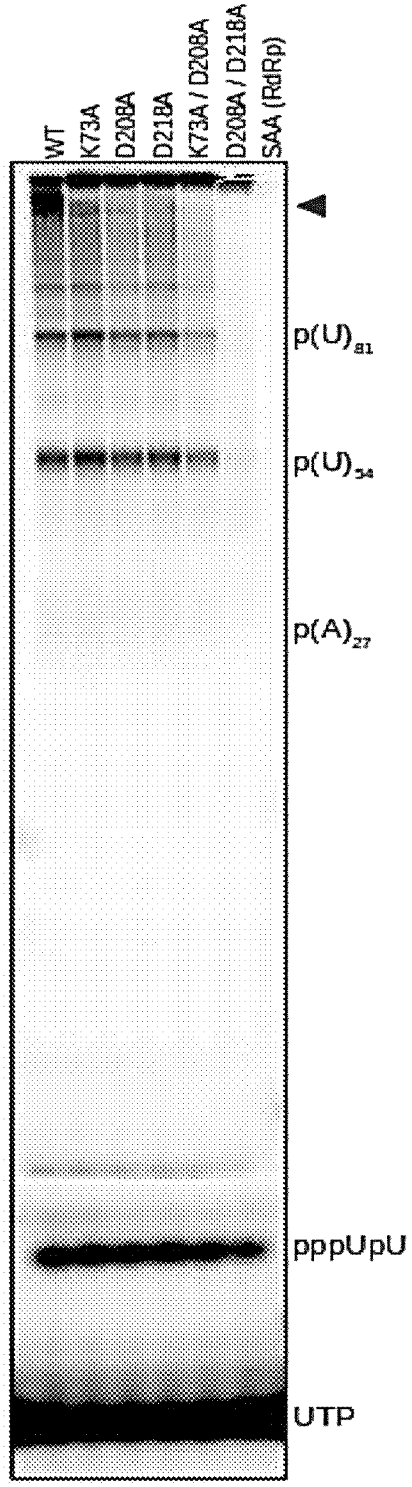
FIG. 7A is a denaturing SDS PAGE gel exposed overnight showing the activity of the 12:7:8 complex on poly$(A)_{27}$ template RNA with either wild-type (WT) nsp12, or various NiRAN active-site mutants. Arrow at the top of the gel shows protein-primed product.

It was noted that NiRAN mutants that completely eliminate nsp8 labeling with UMP are still able to synthesize poly(U) RNA, although notably with a loss in high-molecular weight products (FIG. 7A). To address this, an order-of-addition experiment was set up. The nsp12:7:8 complex (RTC) was incubated for 30 minutes at 37° C. with either UTP or poly$(A)_{27}$ RNA first, prior to addition of the inverse/complementary reagent. Following incubation, the inverse reagent was added to start the reaction and reactions were stopped at the indicated timepoints between 0.5 and 60 minutes. Reactions run for 60 minutes were additionally treated with proteinase K (PK) or nuclease P1 (P1) for protein and RNA digestion respectively. Nuclease P1 (NEB) was performed as per the manufacturer's instructions.

Figure 7B:
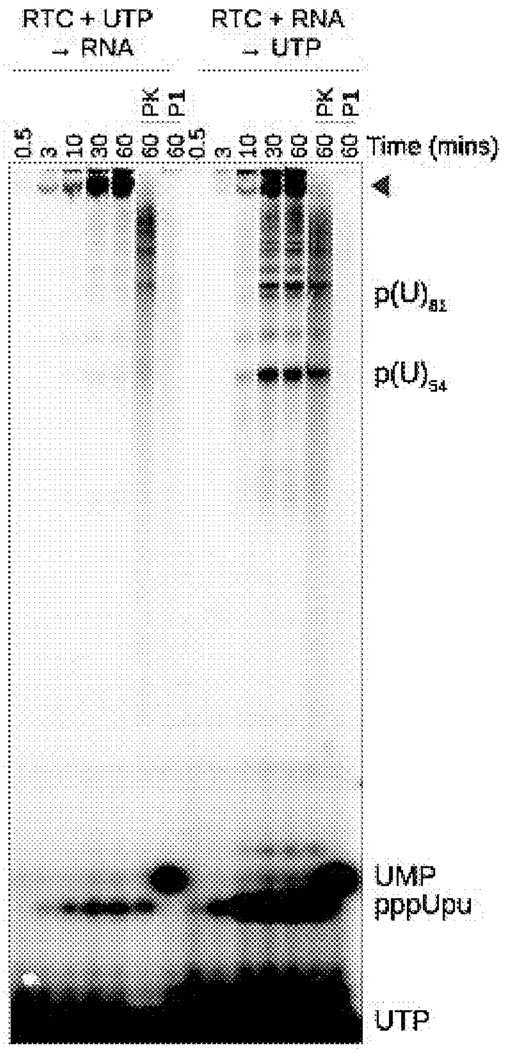
FIG. 7B is a denaturing SDS PAGE gel exposed overnight showing the activity following a time course order of addition experiment with the RTC+UTP followed by poly $(A)_{27}$ RNA (left) and the RTC+poly$(A)_{27}$ RNA followed by UTP addition. Proteinase K (PK) addition releases the protein-primed products.
Figure 7C:
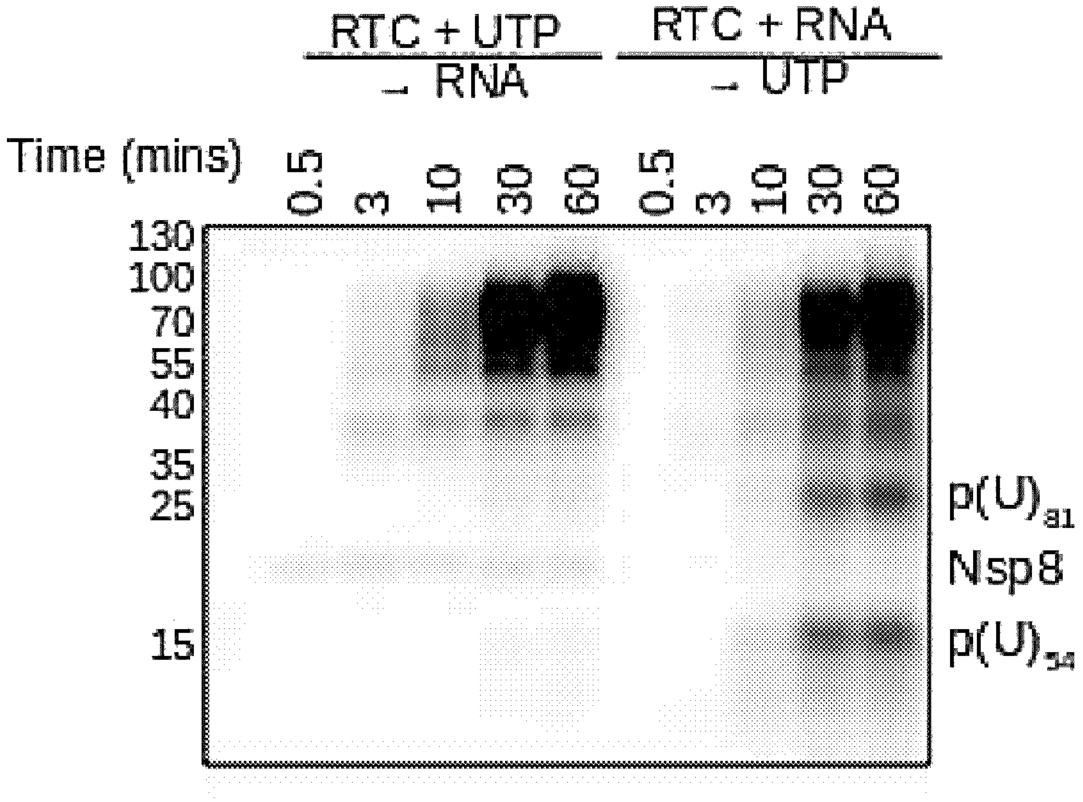
FIG. 7C is a denaturing SDS PAGE gel exposed overnight showing analysis of the order of addition experiment shown in FIG. 7B. The nsp12:7:8 complex was incubated for 30 min at 37° C. with either UTP or RNA. Following incubation, the complementary reagent was added and reactions were stopped at indicated timepoints.
Figure 7D:
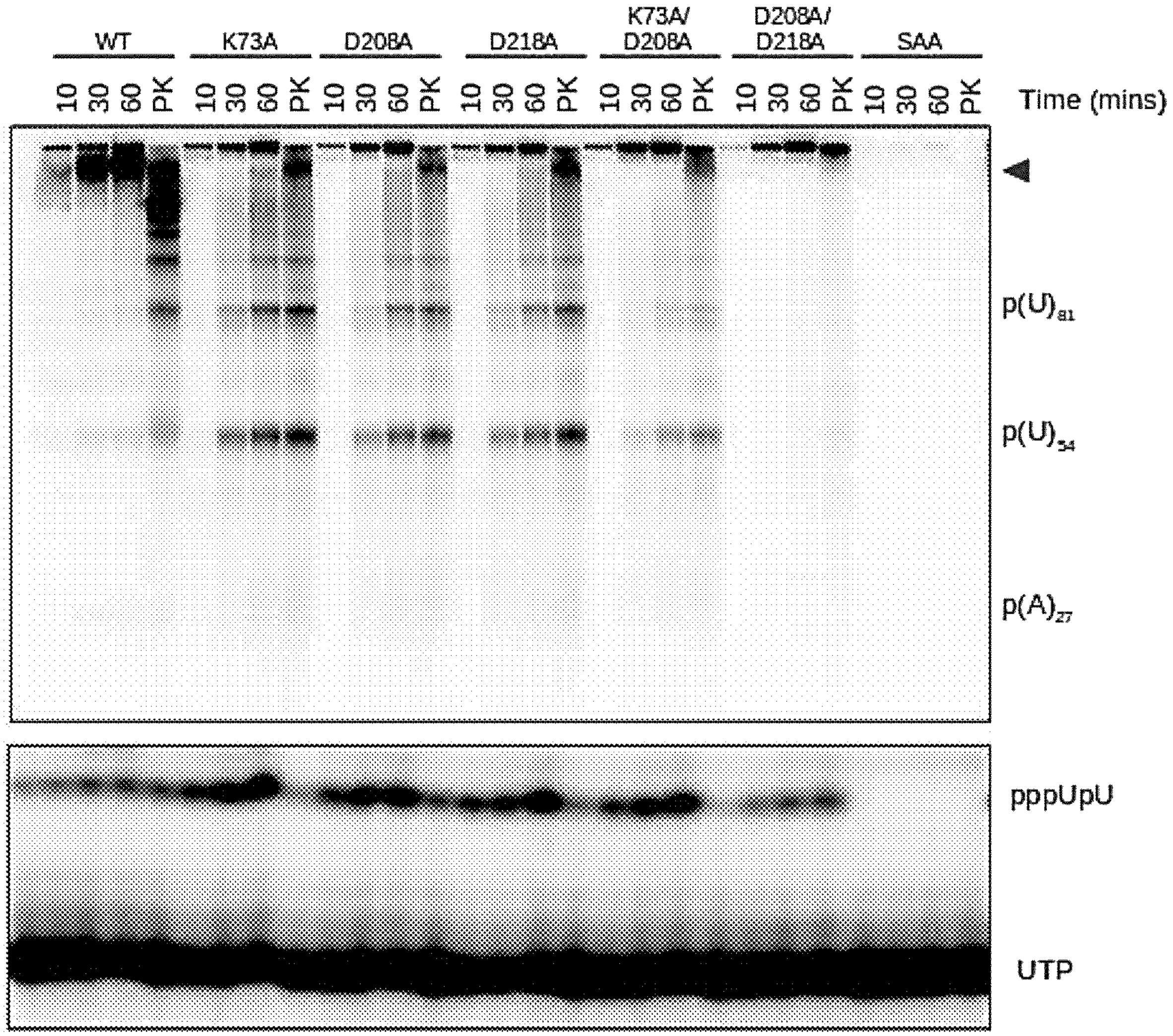
FIG. 7D is a denaturing SDS PAGE gel exposed overnight showing the activity following a time course order of addition experiment showing activity of various NiRAN mutant 12:7:8 complexes, in addition to SAA RdRp mutant. Complexes were preincubated with UTP prior to RNA addition. PK represents 60 min timepoint, digested with proteinase K.
Figure 7E:
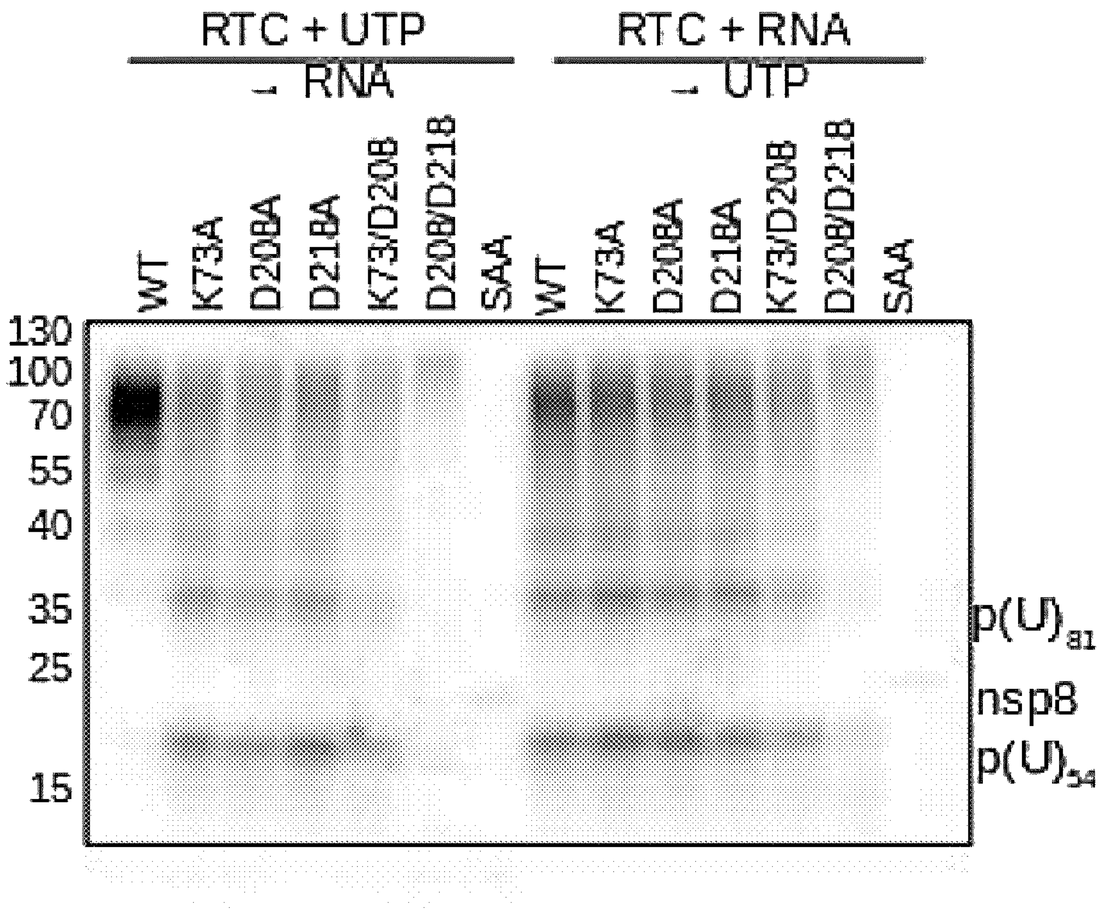
FIG. 7E is a denaturing SDS PAGE gel exposed overnight showing the activity following an order of addition experiment showing activity of various NiRAN mutant 12:7:8 complexes, in addition to SAA RdRp mutant. Activity of the 12:7:8 complex on poly$(A)_{27}$ template RNA with either wild-type (WT) nsp12, or various NiRAN active-site mutants. The nsp12:7:8 complex was incubated for 30 min at 37° C. with either UTP or RNA. Following incubation, the complementary reagent was added.
Figure 7F:
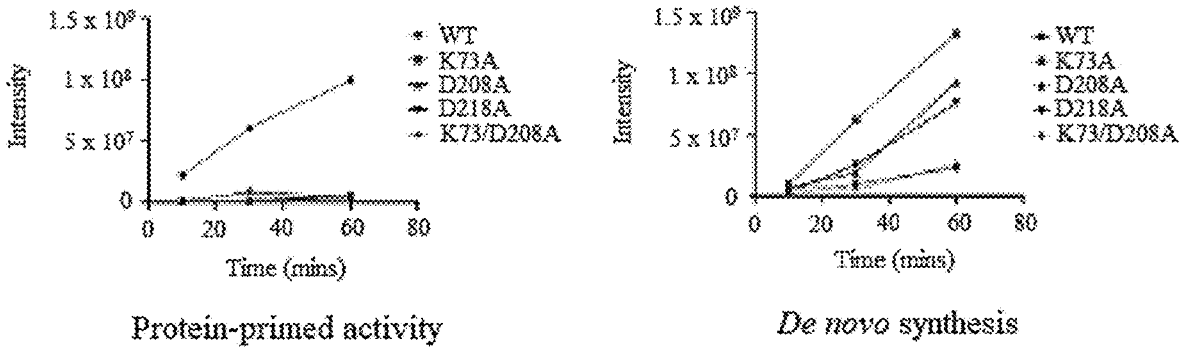
FIG. 7F is two-line graphs showing the quantification of protein-primed activity (left panel) and de novo synthesis activity (right panel) over time with WT RTC and various mutants. The x-axis is time measured in minutes and the y-axis is a log of fluorescent intensity.
Figure 7G:
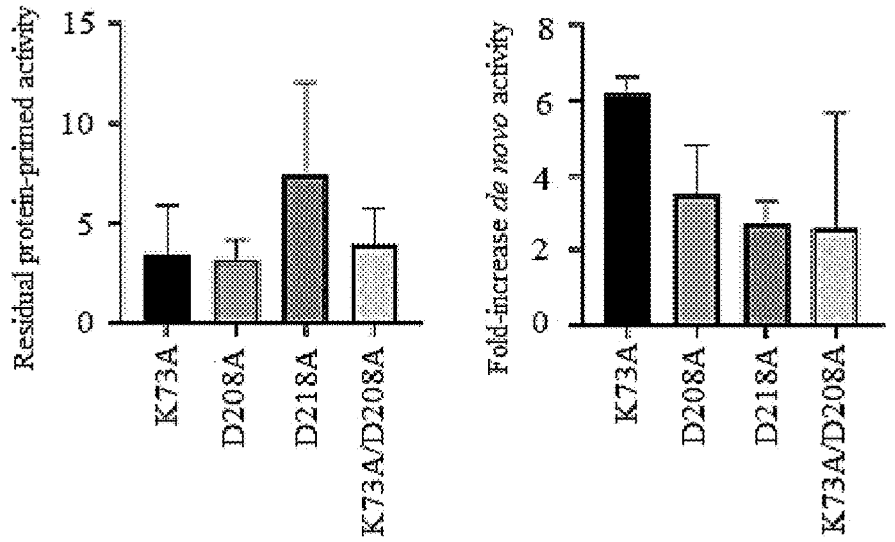
FIG. 7G is two bar graphs residual protein-primed activity of NiRAN mutants compared to WT (left panel) and quantification of de novo synthesis activity (right panel), based on $p(U)_{54}$ product in FIG. 7D.
Figure 7H:
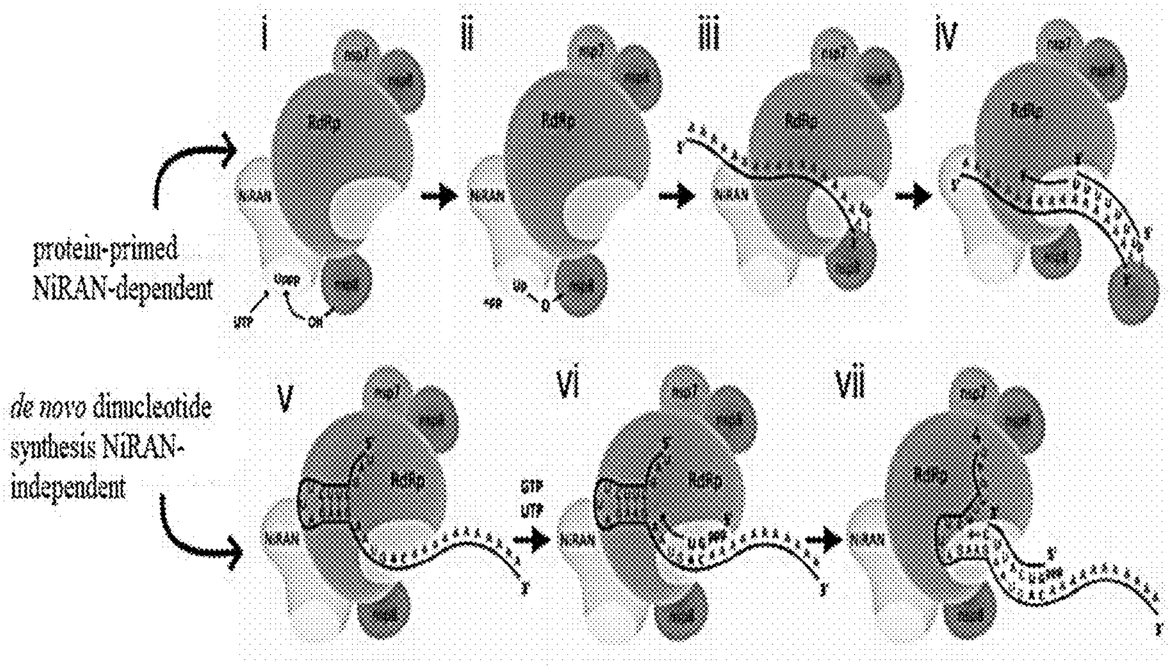
FIG. 7H is a cartoon representation of two RNA synthesis initiation pathways by the SARS-CoV RTC. In pathway 1, NiRAN-bound UTP (i) is transferred to nsp8 to yield UMP-nsp8 (ii), further positioned to the poly(A) 3'-end (iii) to prime RNA synthesis (iv). In pathway 2, the ST20p$(A)_{15}$ sequence drives nsp12 RdRp active site binding at the heteropolymeric—polyA junction (v) to synthesize a pppGpU dinucleotide primer (vi) able to prime RNA synthesis of the complementary strand (vii). ST20p(A)15 secondary structure based on RNAfold WebServer.

Pre-incubation with UTP, promoting NiRAN-domain mediated nsp8-UMP labeling, yields exclusively high-molecular weight poly$(U)_n$ products covalently bound to Nsp8 (FIG. 7B, arrow, FIG. 7C). In contrast, pre-incubation of the RTC with poly$(A)_{27}$ results in production of both protein-bound RNA (released by PK digestion), and long poly$(U)_n$ products not bound to Nsp8 (FIG. 7B). NiRAN mutants which eliminate nsp8-UMP labeling also eliminate higher molecular-weight protein-primed products, but do not abolish the synthesis of polyU products (FIGS. 7D-G). This indicates that two distinct priming mechanisms coexist: one NiRAN dependent promoted by Nsp8-UMP (pathway 1; FIG. 7H,top), and the other NiRAN independent (pathway 2; FIG. 7H, bottom).

Figure 8A:
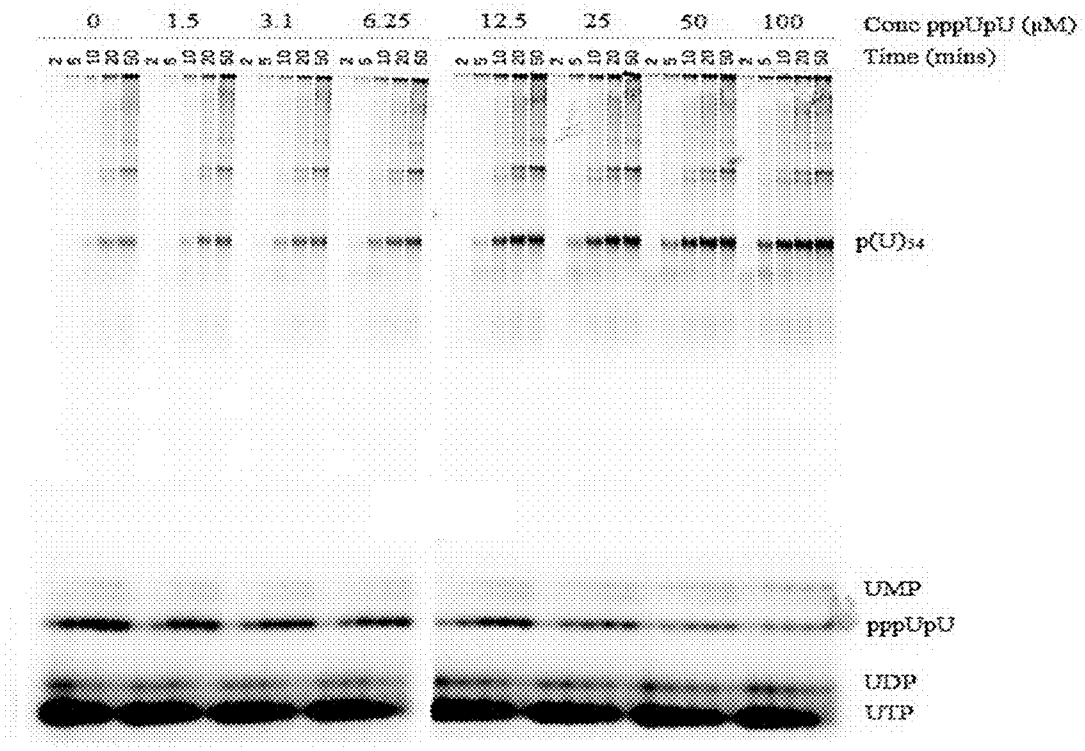
FIG. 8A is a SDS denaturing gel showing the synthesis of poly$(U)_{54}$ RNA by the nsp12:7:8 complex from a poly$(A)_{27}$ template assessed in the presence of varied concentrations of pppUpU (0-100 μM) over time (0-50 mins).
Figure 8B:
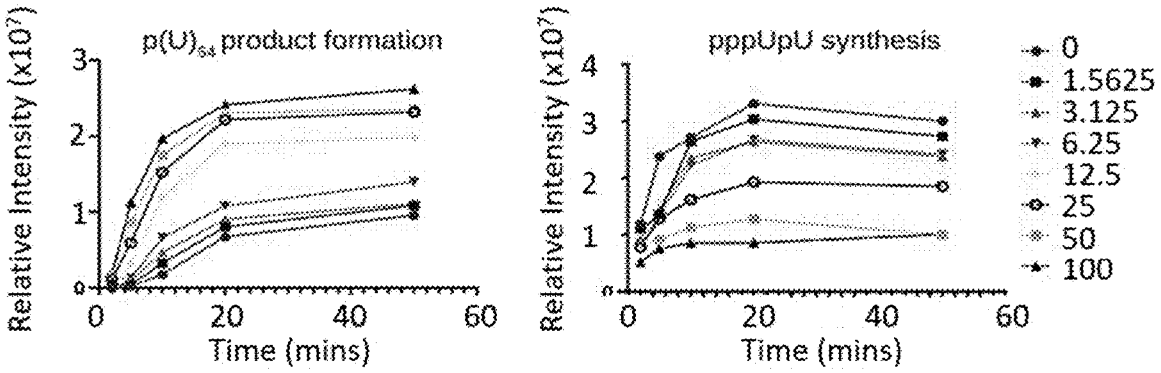
FIG. 8B is 2-line graphs plotting the quantification of p(U)54 (left) and pppUpU (right) products performed with ImageQuant analysis software measuring intensity (y-axis) and plotted as a function of time measured in minutes (x-axis).

Example 14: SARS-CoV RTC Synthesizes 5'-Triphosphate Dinucleotide Primers in a NiRAN-Independent Manner It was noted that for NiRAN mutant RTCs, polymerization through the NiRAN-independent pathway (pathway 2) was actually increased, indicating that the two initiation mechanisms occur simultaneously and in competition (FIG. 7D). NiRAN mutant RTCs also produced higher quantities of a small molecular-weight UMP-containing product, suggesting it to play a role in the second priming pathway. This product was identified as pppUpU based on its sensitivity to Calf Alkaline phosphatase and nuclease P1, as well as co-migration with chemically synthesized pppUpU. Addition of free pppUpU to the RTC increases synthesis of unbound poly$(U)_n$ RNA products, and decreases the lag time of the reaction in a concentration dependent manner, showing that synthesis of a dinucleotide pppUpU is a prerequisite for pathway 2 (FIGS. 8A-B). To show this, synthesis of poly$(U)_n$ RNA by the nsp12:7:8 complex from a poly$(A)_{27}$ template was assessed in the presence of varied concentrations of pppUpU (0-100 μM) over time (0-50 mins).

As expected, an RdRp active site mutant of nsp12 (SDD SAA) abolishes poly(U) synthesis, and additionally eliminates synthesis of pppUpU (FIG. 7D). This confirms that it is the RdRp domain of nsp12, in conjunction with nsp7 and 8, that drives production of this dinucleotide primer, and not the NiRAN.

Figure 9A:
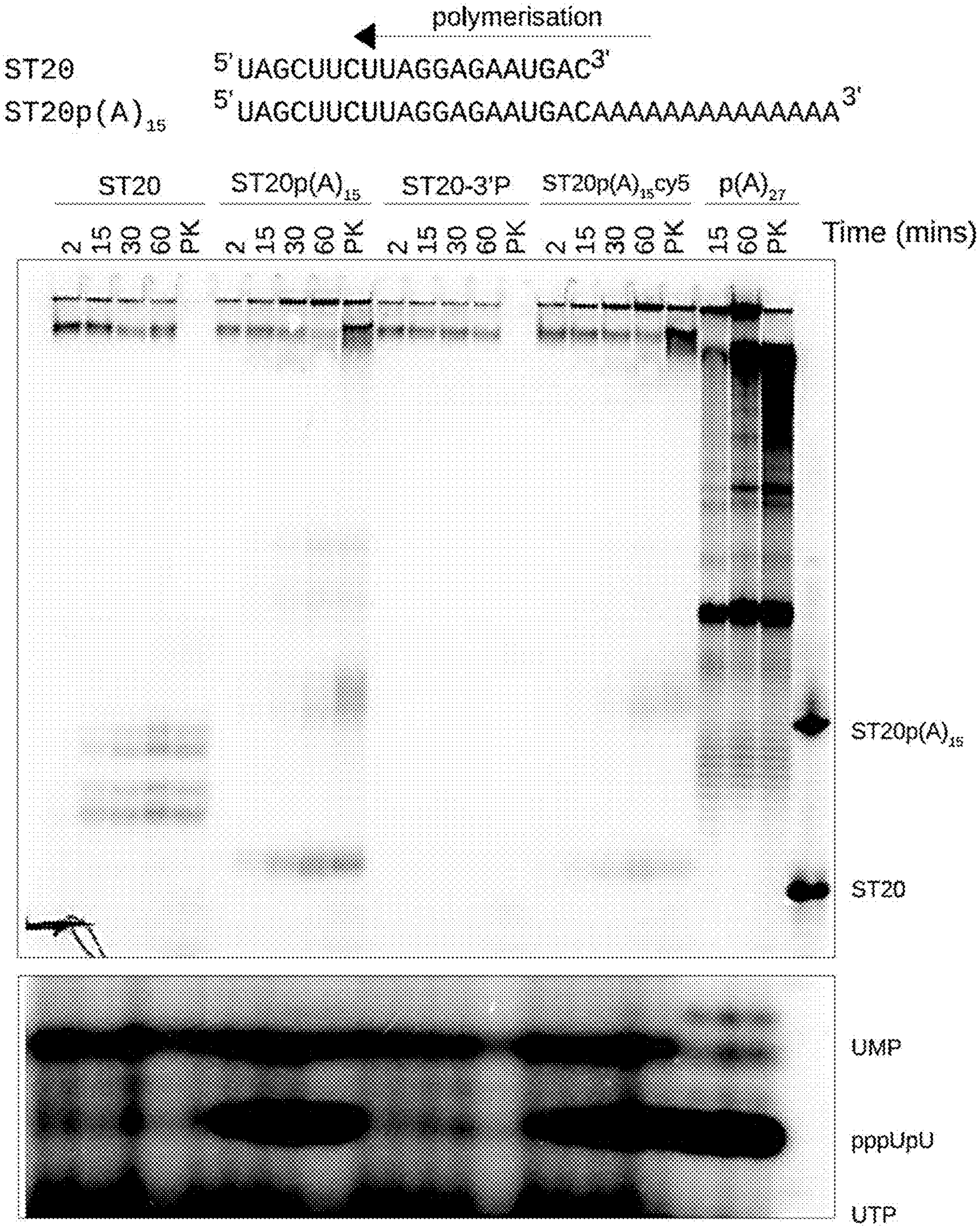
FIG. 9A is a 20% acrylamide 7M UREA-PAGE gel visualized using a Typhoon FluorImager. The gel shows synthesis heteropolymeric RNA from templates with and without a poly(A) tail. An RNA template mimicking the SARS-CoV-1 or 2 3'-end of the genome (ST20) extended by a poly$(A)_{14}$ sequence (ST20 $pA_{14}$) was incubated with the RTC and NTPs supplemented with $\alpha^{32}$P-UTP (left 10 lanes). The same templates were 3'-blocked with a phosphate group (ST20-3'P) or a cy5 fluorescent dye (STP20p$(A)_{14}$cy5, respectively. A control using a p$(A)_{27}$ template is shown on 3 lanes at the right part of gel. Size markers are shown as ST20 and ST20p$(A)_{15}$ (rightmost lane). UMP, pppUpU, and UTP separated at the bottom of the gel are shown in correspondence to the top part of the gel.
Figure 9B:
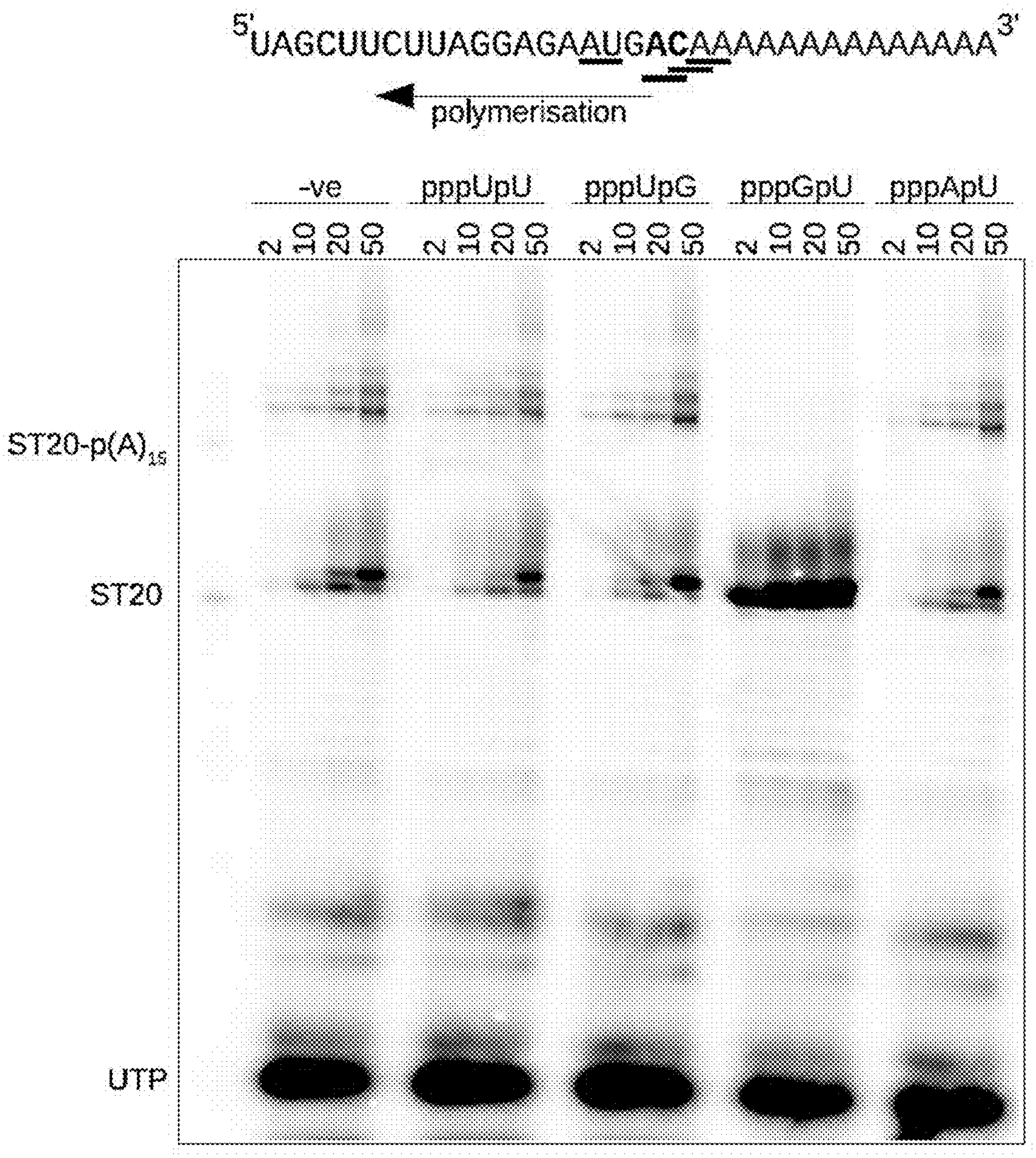
FIG. 9B is a 20% acrylamide 7M UREA-PAGE gel visualized using a Typhoon FluorImager. At top is an RNA template mimicking the SARS-CoV-1 or 2 genome-poly(A) junction sequence which was incubated with the RTC, NTPs (supplemented with $\alpha^{32}$P-UTP), and 10 μM of chemically synthesized, authentic dinucleotide 5'-triphosphates as indicated.

Example 15: Nsp12-Mediated pppGpU Synthesis Directs the Precise Start of Primer Elongation on (−) ssRNA Sequence To better understand how the two pathways are regulated during minus strand synthesis, hetero-polymeric RNA corresponding to the last 20 nucleotides of the 3'-end of the genome (ST20) was used with or without a poly$(A)_{15}$ tail. In the absence of the poly(A) sequence, spurious, self-primed products are synthesized, and can be eliminated by blocking the 3' end of the template (FIG. 9A). Strikingly, it was observed that in the presence of the poly$(A)_{15}$ tail, the majority of synthesis is initiated in the vicinity of the RNA-poly(A) junction, rather than from the end of the poly(A) sequence (FIG. 9B-ye panel). This indicates that the poly(A) tail and 3' genomic RNA sequence elements guide the positioning of the RTC to the true 3' end of the genome, i.e., at its junction with the poly(A) tail for initiation of synthesis. Pre-incubation of the complex with UTP can additionally promote low-level synthesis of the full-length template (ST20+poly$(A)_{15}$) through the protein-primed pathway 1, which is released following proteinase K digestion (FIG. 9A). Western blot analysis with anti-nsp8 confirms that the full-length RNA product is covalently attached to nsp8, and that this is dependent on the NiRAN-domain (FIG. 6E, filled arrows). These protein-primed ST20-Poly $(A)_{15}$ products are not seen with the NiRAN K37A mutant (FIG. 6E, lanes 12-13).

To determine the precise sequence initiation site, the reaction was supplemented with various chemically synthesized pppNpN dinucleotide primers. Addition of pppGpU, the sequence complementary to the last two bases immediately adjacent to the poly(A) tail, greatly increased both the reaction rate and level of product formation (FIG. 9B). In contrast, pppUpU, pppUpG and pppApU dinucleotides had a minimal effect on the reaction. It has been concluded that the polymerase complex (RTC) preferably initiates synthesis with a pppGpU dinucleotide, templated from the precise 3' end of the genome-poly(A) junction, immediately upstream of the poly(A) tail. Synthesis of this dinucleotide is presumed to be the rate-limiting step, and can be surpassed through the addition of free pppGpU.

Interestingly, in contrast to pppUpU, free pppGpU is not readily observed, indicating that it remains bound in the polymerase active site and is rapidly extended upon production. In contrast, pppUpU appears to be synthesized more efficiently, however it is released by the polymerase RTC, indicating that it is sub-optimal to start (−) RNA synthesis. FIG. 7H recapitulates both pathways operating in parallel at the 3'-end of the SARS-CoV genome. Altogether, the results show that the SARS-CoV RTC promotes RNA synthesis initiation through two distinct pathways: Pathway 1 is through protein-priming reminiscent of Picornaviridae, and Pathway 2 is by means of de novo synthesis of pppNpN primers, pppGpU being preferred to start at the genome-poly(A) junction.

Example 16: AT-9010 and STP Terminate RNA Synthesis, but are Excised by SARS-CoV Nsp14 Exonuclease Given the specific role of UTP and GTP in the (−) RNA priming event, it was investigated whether uracil- or guanine-nucleoside/tide can inhibit priming activity. Since most NAs generally exert an antiviral effect by targeting the viral RdRp for incorporation into viral RNA (Pruij ers and Denison), it was of particular interest to establish whether the NiRAN-domain would additionally constitute an antiviral target.

To measure primer-dependent polymerization and excision assays, the nsp12:7:8 complex was formed as for the primer-independent polymerase assays, using a nsp12 final concentration of 0.5 μM. Nucleotide incorporation assays were as described in Shannon et al. 2020. For nucleotide excision, polymerization reactions were stopped by heating at 70° C. for 10 min, the primer: template was re-annealed at 30° C. for >30 min, and 50 nM nsp14/nsp10(1:5) were added for time-course reactions. Aliquots were analyzed using denaturing polyacrylamide gel electrophoresis (20% acrylamide, 7M urea) and visualized using a Typhoon FluorImager.

The inhibition potential of the active metabolites of two NAs were investigated; the uracil analog Sofosbuvir (SOF) and its guanosine equivalent AT-511. SOF is clinically approved for the treatment of hepatitis C Virus (HCV) (Dousson, https://doi.org/10.1038/s41598-017-09797-8m). However, it has shown limited efficacy against SARS-CoV-2 infection (Good 2020b, Han 2021). In contrast, AT-527 (the hemi-sulfate salt of AT-511) was recently shown to act as a potent broad-spectrum anti-CoV inhibitor in a variety of cell lines (Good 2020b). It is now in phase II clinical trials for the treatment of both HCV infection (Good 2020a) and COVID-19 (Good 2020b).

Figure 10A:
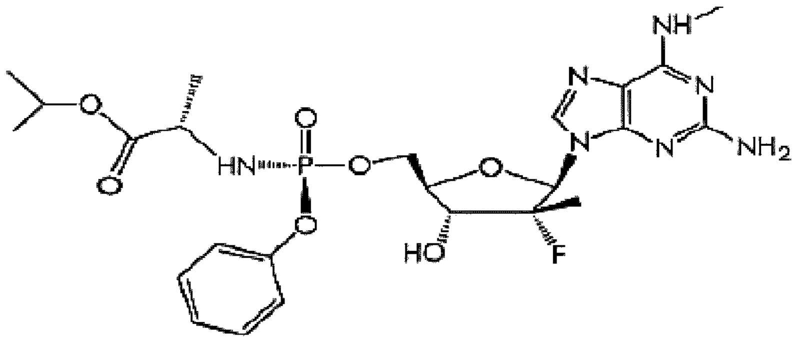
FIG. 10A is table showing the structural differences between the guanosine nucleotide prodrug AT-511, and active metabolite AT-9010, in comparison to STP
Figure 10A:
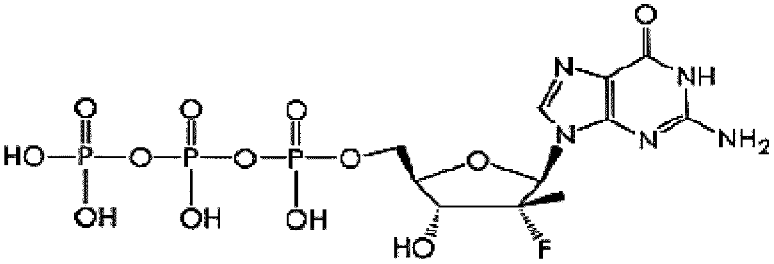
Figure 10A:
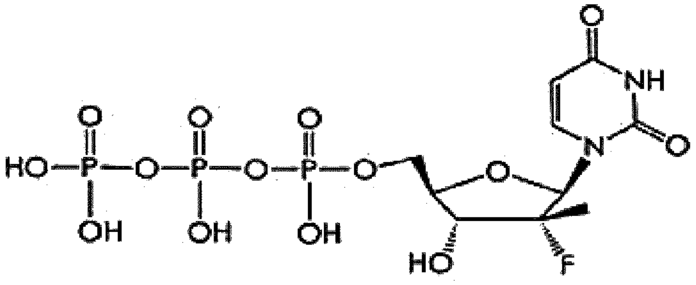
Figure 10B:
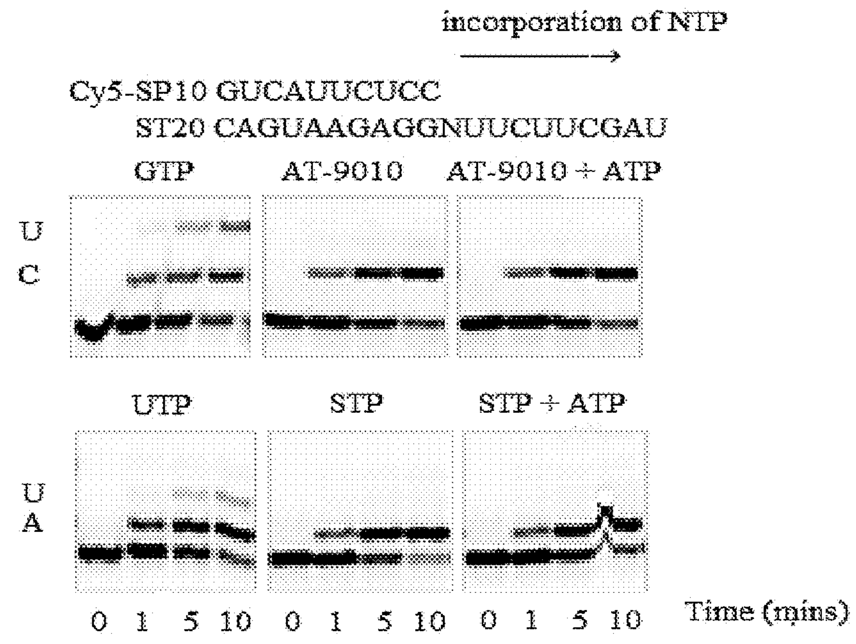
FIG. 10B is a phosphorimage of a 20% (wt/vol) polyacrylamide/7 M urea gel showing RNA extension products that measures the incorporation products of AT-9010 and STP relative to GTP and UTP as the first nucleotide (left panel), with (right panel) and without (middle panel) following NTP.
Figure 10C:
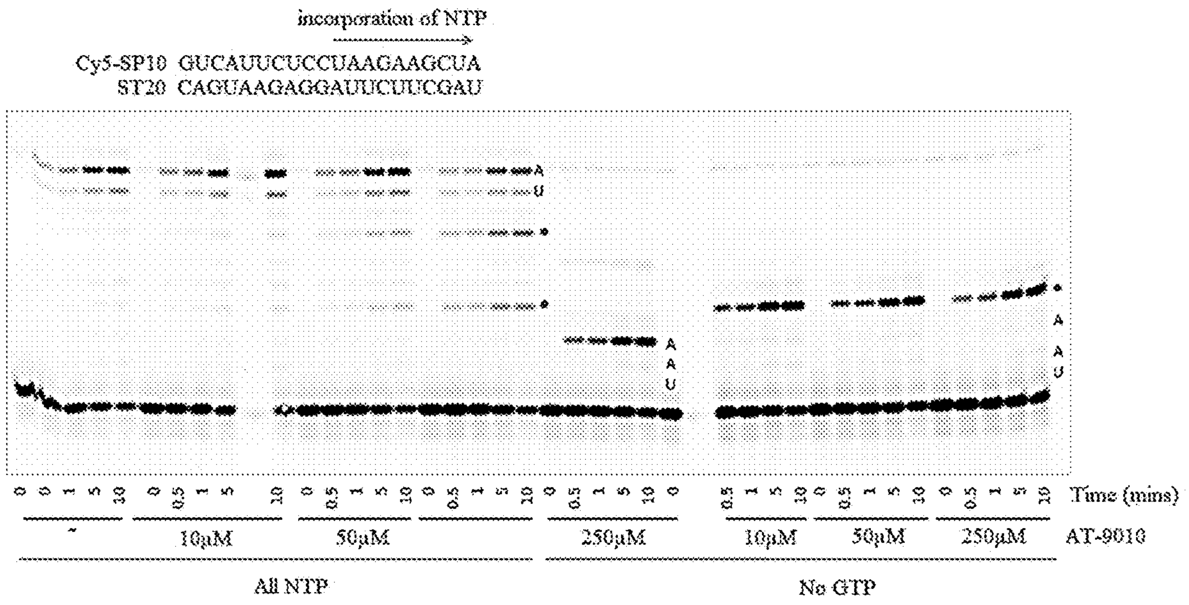
FIG. 10C is a phosphorimage of a 20% (wt/vol) polyacrylamide/7 M urea gel showing RNA extension products, which represent the incorporation of NTPs versus AT9010 in a primer extension assay.
Figure 10D:
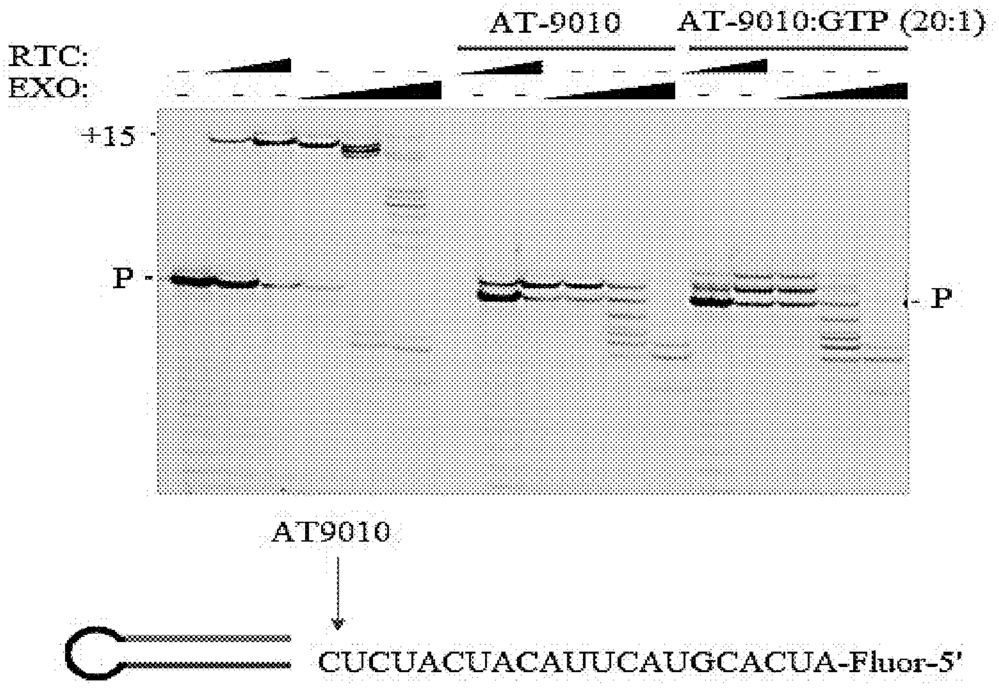
FIG. 10D is a phosphorimage of a 20% (wt/vol) polyacrylamide/7 M urea gel showing RNA extension products in the presence of AT-9010 and AT-9010 and GTP. In the presence of GTP, AT-9010 is a competitive guanosine substrate, discriminated 22-fold against GTP.
Figure 10E:
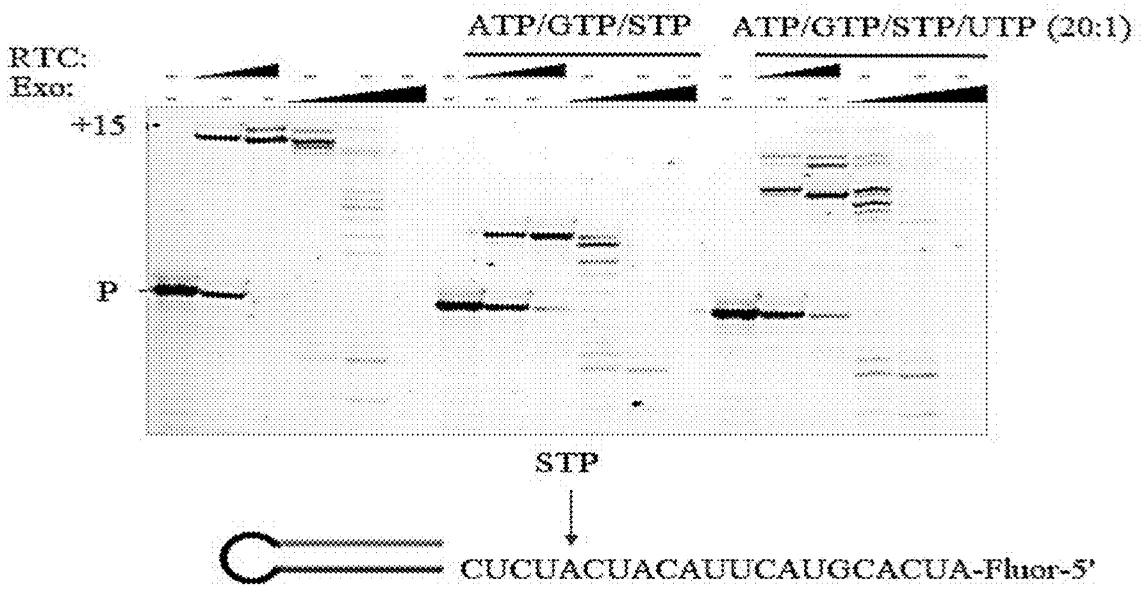
FIG. 10E is a phosphorimage of a 20% (wt/vol) polyacrylamide/7 M urea gel showing RNA extension products in the presence of STP and UTP (20:1) show STP is not competitive at this ratio.

Both SOF and AT-511 are phosphoramidate prodrugs containing a 2'-fluoro-2'-C-methyl modified ribose, with the only difference being the nucleobase (FIG. 10A). In cells, these prodrugs are metabolized by cellular kinases into active 5'-triphosphate forms (AT-9010 and STP, respectively), which presumably act as substrates for the viral RdRp for incorporation into viral RNA, as has been shown for HCV (reviewed in Dousson). RdRp selectivity for these two NAs was compared using the nsp12:7:8 RTC and a hetero-polymeric RNA primer/template pair (Shannon). Both AT-9010 and STP are incorporated into RNA by the RdRp as a substitute for GTP or UTP, respectively, causing immediate chain termination (FIG. 10B). In the presence of GTP, AT-9010 is a competitive guanosine substrate, discriminated 22-fold against GTP (FIGS. 10C and 10E and Table 8). In contrast, STP: UTP competition experiments (20:1) show STP is not competitive at this ratio (FIG. 13D). However, it was found that following incorporation, both drugs are sensitive to SARS-CoV ExoN-mediated excision (FIGS. 10D-E), indicating that the SARS-CoV RTC proofreading activity potentially jeopardizes their efficacy. It therefore seems unlikely that the potent anti-CoV activity of AT-527 would solely be provided by RdRp-mediated incorporation of AT-9010 into RNA.

Example 17: RdRp Inhibition: Primer Extension and Chain Termination

Figure 11A:
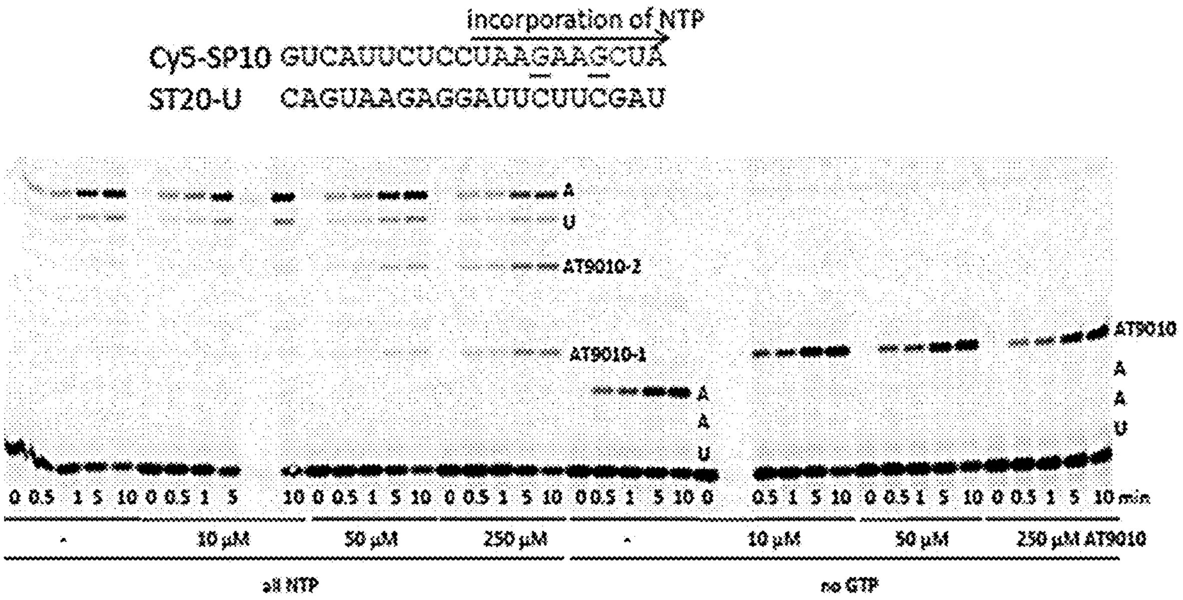
FIG. 11A is a phosphorimage of a 20% (wt/vol) polyacrylamide/7 M urea gel showing RNA extension products, which represent the incorporation of NTPs versus AT9010 in a primer extension assay. The gel on the left shows the results of the experiment where AT9010 was used with all NTPs and the gel on the right shows the results of the experiment where AT9010 was used with ATP/CTP/UTP (no GTP). Each lane is a time point measured in seconds and each gel shows the results from different concentrations of AT9010 (0, 50, 250 μM).

Polymerase elongation assays were performed in polymerase assay buffer (20 mM Tris, pH 8; 10 mM KCl; 1 mM DTT; 2 mM $MgCl_2$) with 0.5 μM SARS-Cov-1 nsp12:7L8:8 polymerase complex (1:3:3 molar ratio), 0.2 μM primer (Cy-5-SP10) and 0.2 μM template (ST20-U) RNA, 50 μM NTP or CTP/ATP/UTP (no GTP) with 10, 50, or 250 μM of AT9010. Cy-5-SP10 was radiolabeled at the 5' end using [γ-$^{32}$P] ATP and PNK. Cy-5-SP10 was then annealed to the complementary template ST20-U by heating at 70° C. for 10 min and then cooling down to room temperature (with a primer/template ratio of 1:1). Primer extension assays were always performed with ST20-U as template, and reactions were started by adding 50 μM NTP or CTP/ATP/UTP (no GTP) mix. After incubation at 30° C., reactions were quenched by the addition of an equal volume of loading buffer (formamide with 10 mM EDTA). RNA polymerization products of primer extension assays were analyzed in 20% (wt./vol) polyacrylamide/7 M urea gels. RNA products were visualized using photo-stimulated plates and a phosphorimager. The results are shown in FIG. 11A, which shows that AT9010 is incorporated as a GTP analog in the growing chain and incorporation of AT9010 causes chain termination.

Figure 11B:
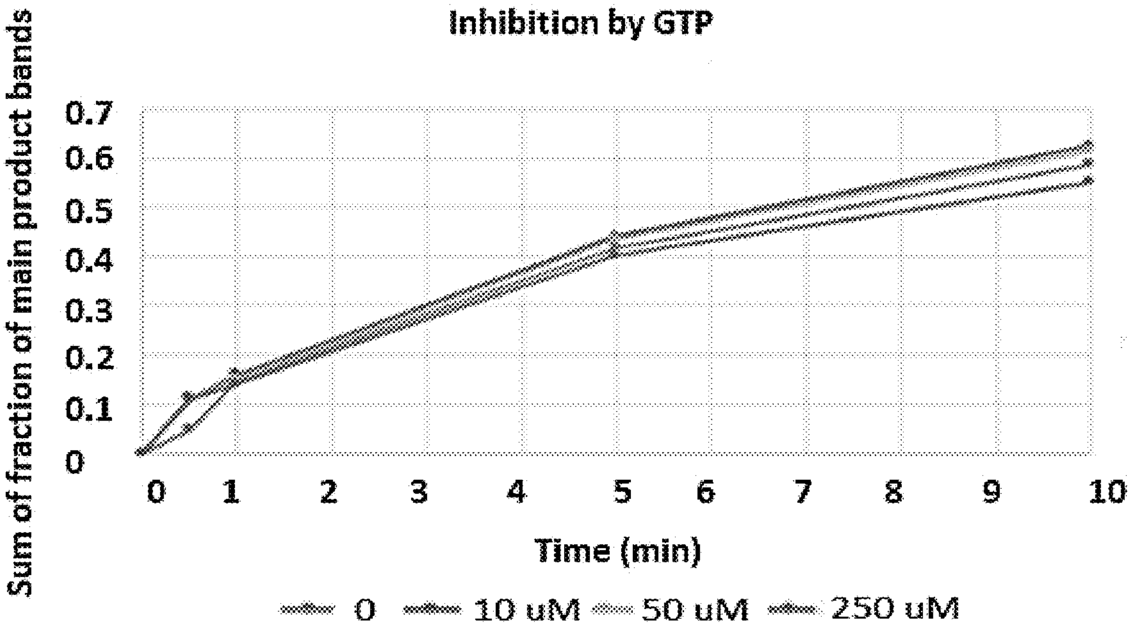
FIG. 11B is a graph comparing the sum of the RNA extension product bands measured in FIG. 11A. The x-axis is time measured in minutes and the y-axis is the sum of product bands measured numerically.

AT9010 is incorporated even in the presence of GTP, thus it can compete with GTP. To quantify these results relative intensities were measured and graphed as shown in FIG. 11B which shows a comparison of the sum of product bands to the sum of all bands in order to see if AT9010 is a competitive (or allosteric—NIRAN site) inhibitor of polymerization=sum of fractions of product bands over time. This shows that there is no inhibition of primer elongation by AT9010. The comparison of fraction of AT9010 product band 1 (AT9010-1) to sum of fractions of product bands derived from GTP incorporation at position 14 (AT9010-2+U19+A2) was measured and is shown in Table 7.

TABLE 7

| Time | 50 μM AT9010 | | 250 μM AT9010 | |
|---|---|---|---|---|
| (min) | 14 G | 17 G → 19 → 20 | 14 G | 17 G → 19 → 20 |
| 0.500 | 0.003 | 0.110 | 0.004 | 0.090 |
| 1.000 | 0.005 | 0.147 | 0.005 | 0.115 |
| 5.000 | 0.022 | 0.418 | 0.017 | 0.319 |
| 10.000 | 0.029 | 0.587 | 0.022 | 0.442 |

This allows for the calculation of the discrimination of AT9010 (only for 50 and 250 μM AT9010 with correction by 5 at 250 GTP always 50 μM) versus the native GTP, which is shown in Table 8.

TABLE 8

| Discrimination of ATEA-GTP | | |
|---|---|---|
| Time (min) | 50 μM | 250 μM |
| 0.5 | 37.4 | 22.8 |
| 1 | 31.8 | 21.8 |
| 5 | 18.5 | 19.1 |
| 10 | 20.1 | 20.1 |
| average | 27.0 | 21.0 |
| stdew | 7.9 | 1.5 |

The results show a fold discrimination of AT9010: GTP at 50 μM=27.0+/−7.9 and a fold discrimination of AT9010: GTP at 250 μM=21.0+/−1.5.

Figure 11C:
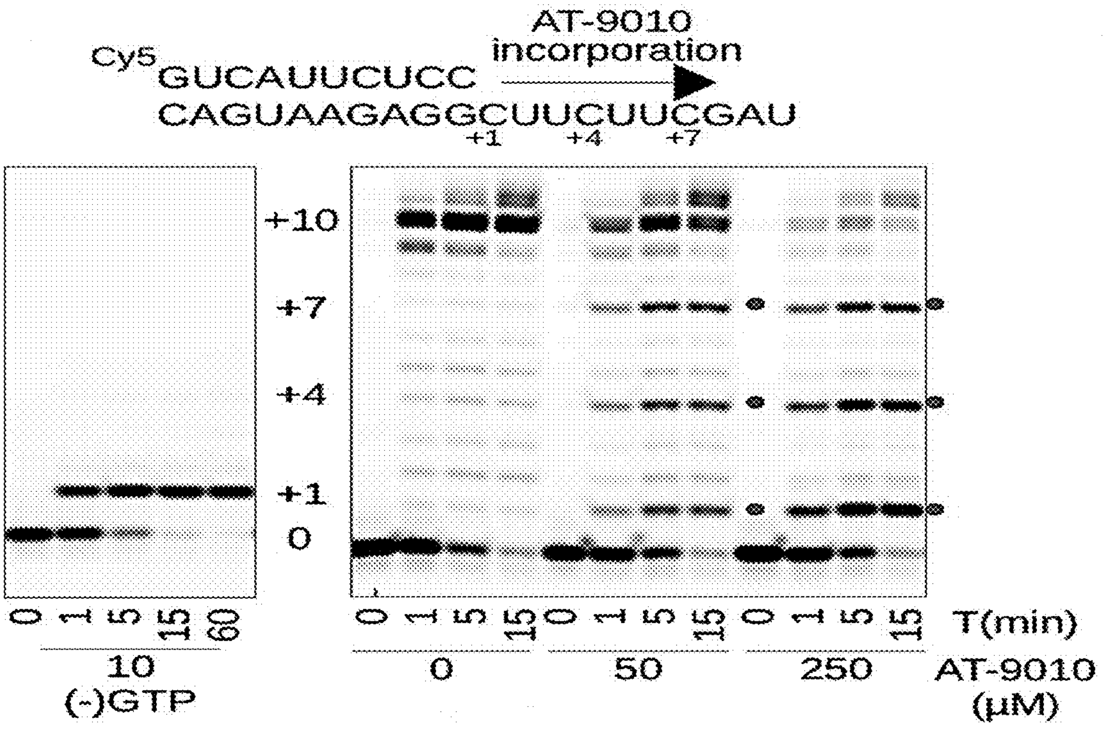
FIG. 11C is a 20% acrylamide 7M UREA-PAGE gel visualized using a Typhoon FluorImager, showing the incorporation of AT-9010 alone (10 left) or in the presence of NTPs (50 μM each) at indicated concentrations. Fold preference for GTP over AT-9010 incorporation is calculated by comparing the amount of AT-9010 insertion relative to full-length product at two concentrations and at three timepoints.
Figure 11D:
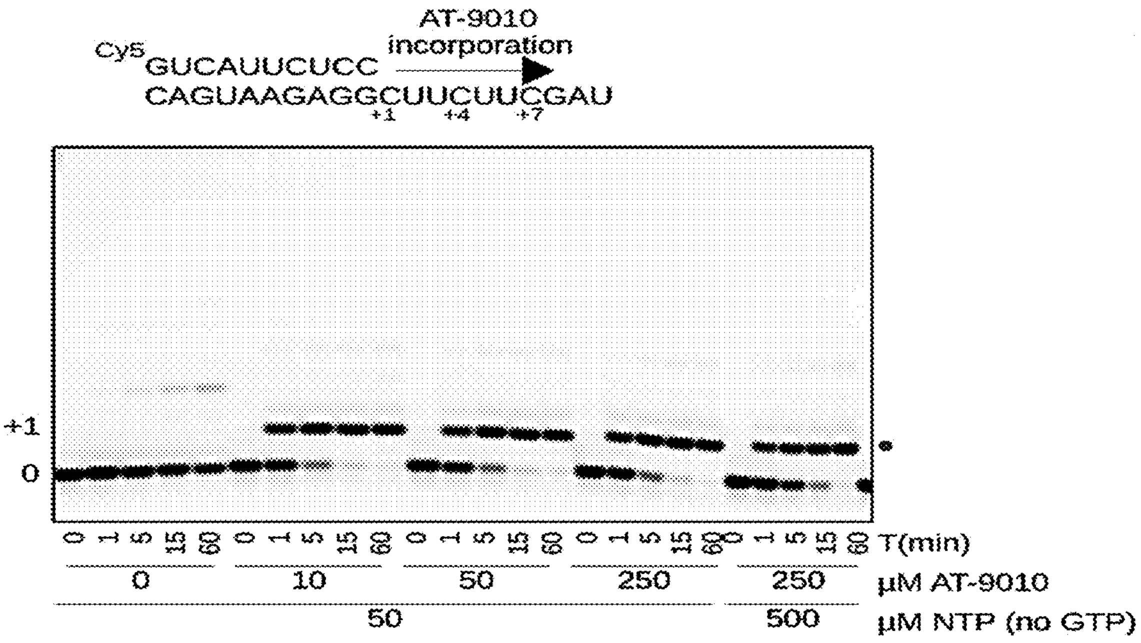
FIG. 11D is a 20% acrylamide 7M UREA-PAGE gel visualized using a Typhoon FluorImager, showing the incorporation of AT-9010 in the presence of NTPs at indicated concentrations, showing RNA chain termination. Fold preference for GTP over AT-9010 incorporation is calculated by comparing the amount of AT-9010 insertion relative to full-length product at two concentrations and at three time-points.
Figure 11E:
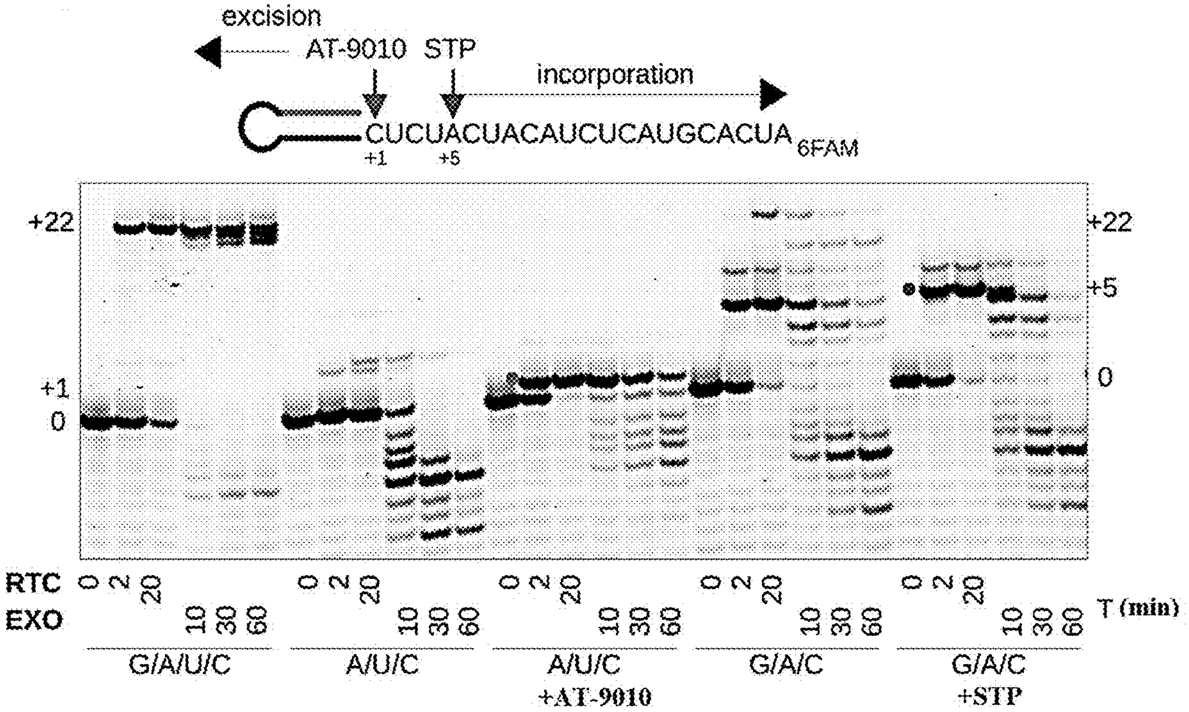
FIG. 11E is a 20% acrylamide 7M UREA-PAGE gel visualized using a Typhoon FluorImager, showing an incorporation time-course of AT-9010 and STP by the RTC, followed by excision time-course with ExoN (labelled EXO).
Figure 11F:
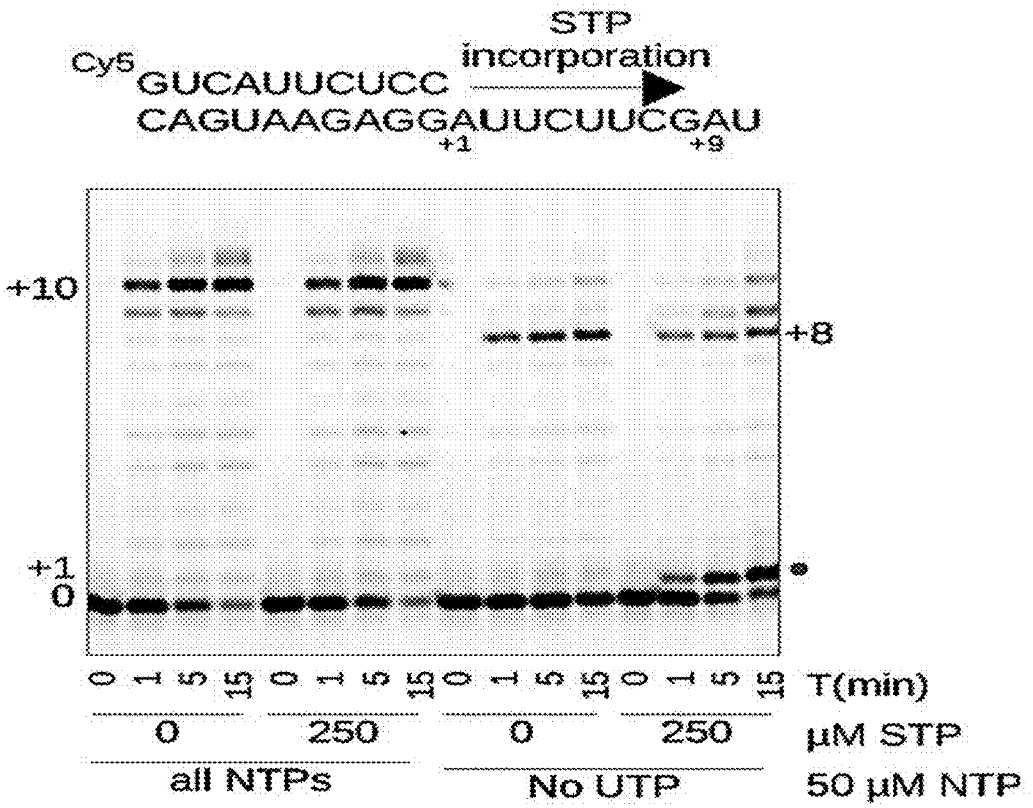
FIG. 11F is a 20% acrylamide 7M UREA-PAGE gel visualized using a Typhoon FluorImager, showing incorporation of STP in the presence of NTPs at indicated concentrations, showing no significant TNA chain termination.

Next, the incorporation and (non)elongation of AT9010 by the purified, recombinant SARS-CoV and SARS-CoV-2 RTCs using a heteropolymeric RNA primer:template pair was assessed. Primer-template (10:20) pairs, corresponding to the 3' end of the SARS-CoV genome, were annealed at a molar ratio of 1:1.5 in 110 mM KCl at 70° C. for 10 min, then cooled slowly to room temperature over several hours. Hairpin RNAs were synthesized by Integrated DNA Technologies (Coralville, IA). The active RTC was formed by first incubating nsp7 and 8 together at equimolar concentrations (100 μM) for 30 mins at room temperature. Nsp12, extra nsp8 and protein gel filtration buffer were added to form a final complex consisting of nsp12:7:8 at a 1:3:6 ratio, with 10 μM nsp12. The complex was further incubated for 10 mins at room temperature, then preincubated with RNA in a pre-mix containing 20 mM HEPES pH 7.5, 50 mM NaCl, 5 mM $MgCl_2$. For single nucleotide incorporation assays, reactions were initiated with 50 μM (final concentration) of all AT-9010 or STP, with or without the following nucleotide (ATP). Final reaction concentrations were 0.5 μM nsp12, 0.4 μM RNA. Reactions were quenched after indicated time-points with 5× volume of FBD stop solution (formamide, 10 mM EDTA). As shown in FIG. 11C, in the absence of GTP, even at low concentrations AT-9010 is rapidly incorporated into viral RNA. As shown in FIG. 11D, even at concentrations of 500 μM of the next correct nucleotide (ATP), elongation past the incorporated AT-9010 is not observed, suggesting that misalignment of the incoming NTP is due to the 2'-C-Me of the terminated primer. As shown in FIG. 11E, in the presence of equimolar concentrations of GTP, AT-9010 acts as a competitive guanosine substrate, discriminated against only ~5-fold compared with its natural GTP counterpart. AT-9010 incorporation was additionally compared with the structurally-related STP. As shown in FIG. 11F, although acting as a substrate when present alone, STP is not competitive with UTP, even at 5-fold higher concentrations.

For AT-9010—GTP competition experiments, protein-RNA complexes were preincubated as described above, and initiated with either all four NTPs, or with only CTP, UTP and ATP (50 μM each NTP), supplemented with various concentrations of AT-9010 (10-250 μM). To calculate the discrimination between AT-9010 and GTP, the AT-9010 product band (from 50 or 250 μM concentrations) was compared with the sum of fractions of product bands derived from GTP incorporation at three timepoints. Discrimination was corrected to account for concentration difference between AT-9010 and GTP. For analogue excision, polymerization reactions were performed on hairpin RNAs in the same conditions as described above (labelled RTC, 2' and 20'), then stopped by heating at 70° C. for 10 min. The hairpin was re-annealed at 30° for >30 min, and 50 nM nsp14/nsp10 (1:5) were added for time-course reactions (labelled Exo, 2', 10', and 60'). Aliquots were analyzed using denaturing polyacrylamide gel electrophoresis (20% acrylamide, 7M urea) and visualized using a Typhoon FluorImager.

Figure 11G:
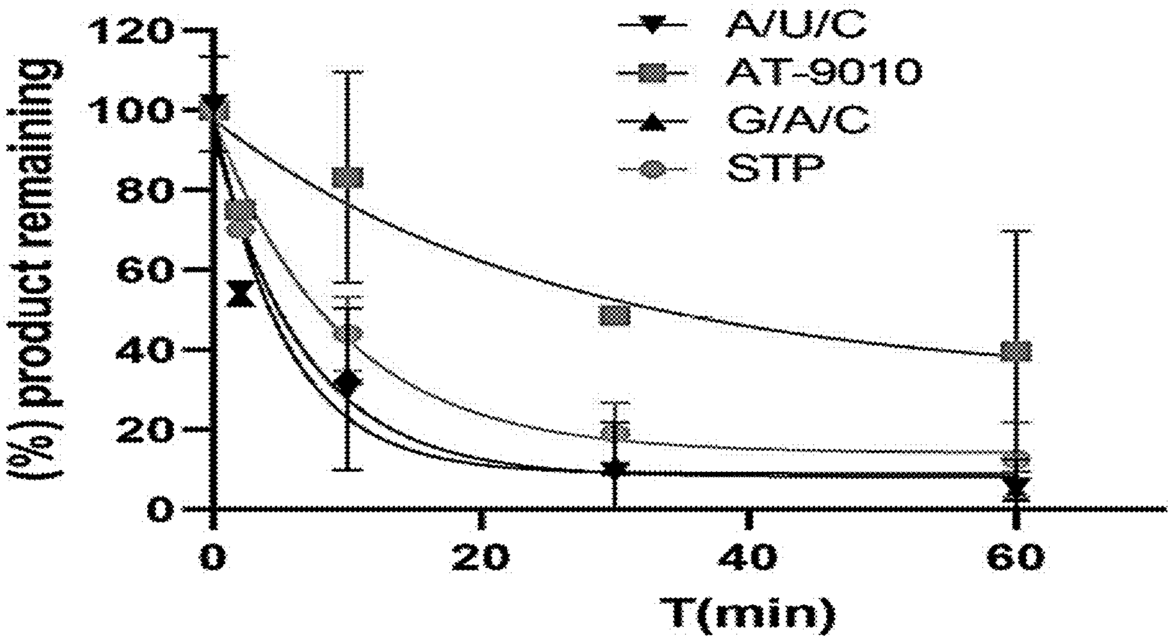
FIG. 11G is a line graph showing the quantitation of remaining product after ExoN excision shown in FIG. 11E. The x-axis is time and the y-axis is % of product remaining.

The stalling of the polymerase following insertion of a chain-terminating NA may allow excision by the proofreading 3'-to-5' exonuclease nsp14/nsp10 (Ferron et al., Structural and molecular basis of mismatch correction and ribavirin excision from coronavirus RNA. Proc. Natl. Acad. Sci. U.S.A. 115, E162-E171 (2018)), however, potentially dampening AT-9010 efficacy. As shown in FIGS. 11E and 11G, following incorporation into RNA, both AT-9010 and STP are excised by the SARS-CoV-2 ExoN. Additionally, AT-9010 and STP show ~4.8-fold and ~1.2-fold resistance to SARS-CoV-2 ExoN mediated excision relative to an unmodified RNA 3'-end, respectively.

Example 18: Comparative Study with 2'-C-Me 2'F-UTP

Polymerase elongation assays were performed in polymerase assay buffer (20 mM Tris, pH 8; 10 mM KCl; 1 mM DTT; 2 mM $MgCl_2$) with 0.5 μM SARS-Cov-1 nsp12:7L8:8 polymerase complex (1:3:3 molar ratio), 0.2 μM primer (Cy-5-SP10) and 0.2 μM template (ST20-U) RNA, 50 μM GTP/ATP/CTP (no UTP) with 10 or 50 μM of SofosbuvirTP (2'C-Me 2'F-UTP) (STP).

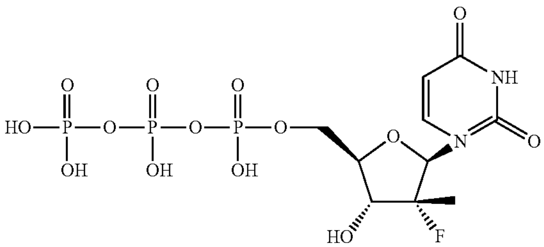

2'-C-Me 2'F-UTP (STP)

Figure 12A:
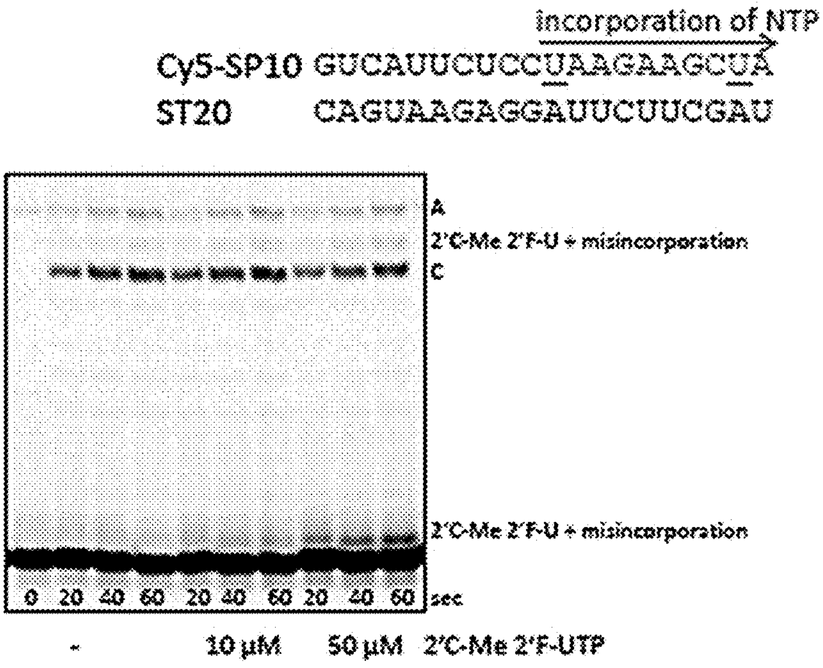
FIG. 12A is a phosphorimage of a 20% (wt/vol) polyacrylamide/7 M urea gel showing RNA extension products, which represent the incorporation of NTPs versus 2'C-Me 2'F-UTP (Sofosbuvir) in a primer extension assay. The gel shows the results of the experiment where 2'C-Me 2'F-UTP was used with ATP/CTP/GTP (no UTP). Each lane is a time point measured in seconds and each gel shows the results from different concentrations of 2'C-Me 2'F-UTP (0, 10, 50 μM).
Figure 12B:
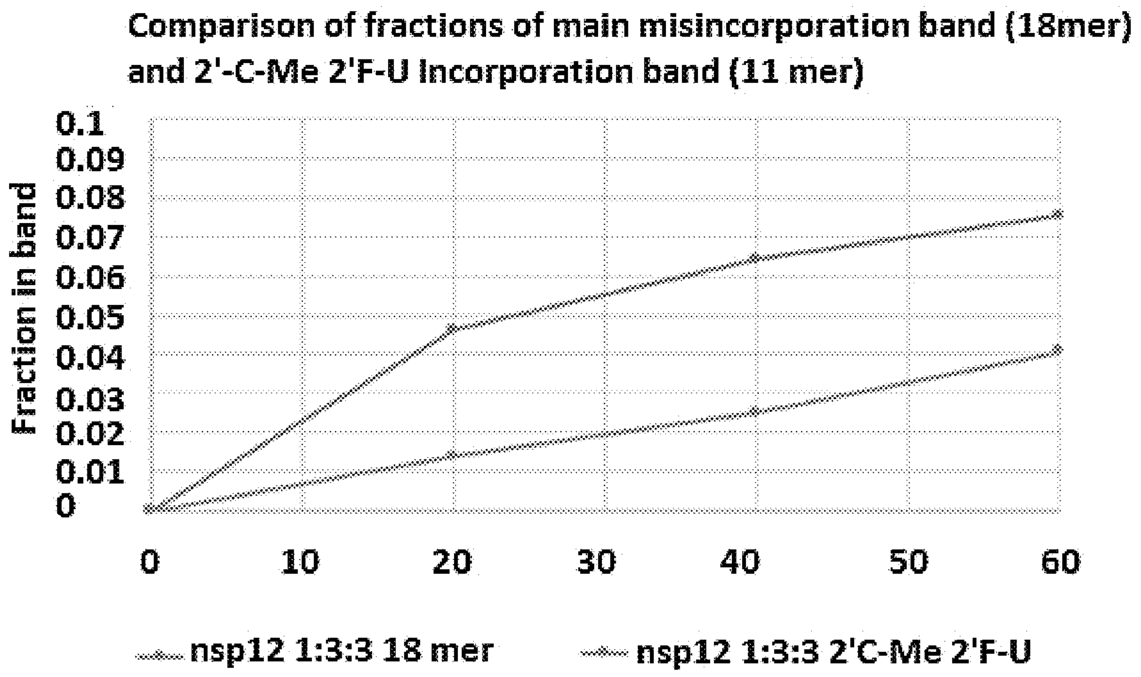
FIG. 12B is a graph comparing the sum of the RNA extension product bands measured in FIG. 12A. The x-axis is time measured in minutes and the y-axis is the sum of product bands measured numerically.

Cy-5-SP10 was radiolabeled at the 5' end using [γ-$^{32}$P] ATP and PNK. Cy-5-SP10 was then annealed to the complementary template ST20-U by heating at 70° C. for 10 min and then cooling down to room temperature (with a primer/template ratio of 1:1). Primer extension assays were always performed with ST20-U as template, and reactions were started by adding 50 μM GTP/ATP/CTP (no UTP) mix. After incubation at 30° C., reactions were quenched by the addition of an equal volume of loading buffer (formamide with 10 mM EDTA). RNA polymerization products of primer extension assays were analyzed in 20% (wt./vol) polyacrylamide/7 M urea gels. RNA products were visualized using photo-stimulated plates and a phosphorimager. As shown in FIG. 12A, 2'C-Me 2'F-UTP is incorporated as UTP analog in the growing chain and incorporation of 2'C-Me 2'F-UTP causes chain termination. As shown in FIG. 12B, 2'C-Me 2'F-UTP is incorporated with around 40% efficacy compared to misincorporation at a U position. Competition with UTP was not studied since a mismatch is already discriminated >250-fold. Unlike AT9010, 2'F-2'-C-methyl UTP is not a substrate for the SARS-CoV RDRP (discriminated >250-fold).

Example 19: AT-9010 Binds to the NiRAN Active-Site, Inhibiting Nsp8 and Nsp9-UMPylation (Pathway 1)

Figure 13A:
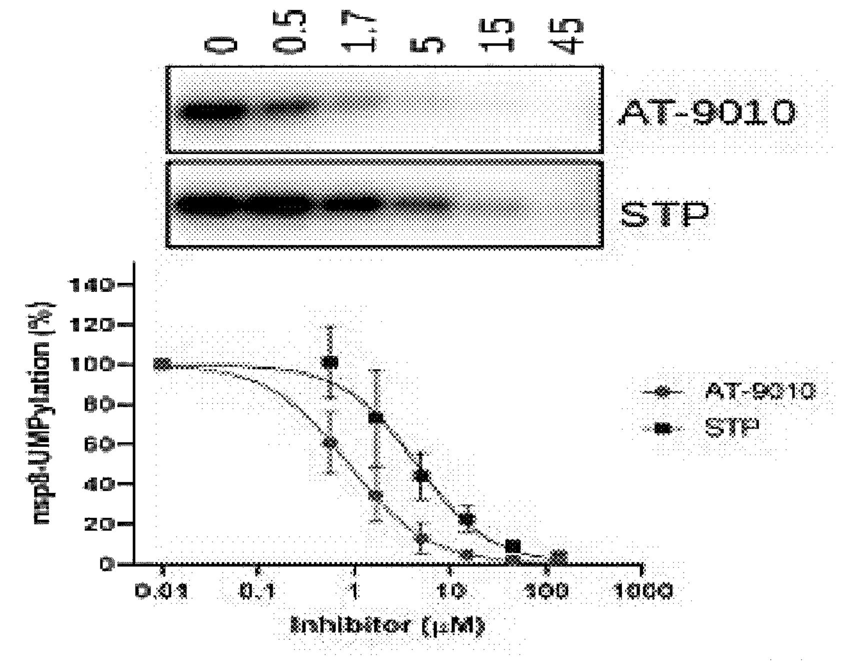
FIG. 13A is a phosphorimage of a 20% (wt/vol) polyacrylamide/7 M urea gel showing labeling of nsp8 by nsp12 with a 5 μM constant concentration of UTP (supplemented with $\alpha^{32}$P-NTP), in competition with increasing concentrations of AT-9010 or STP (n=3, SD shown). Gel shows representation of 3 individual data sets. Total intensity was quantified with ImageQuant, and plotted at % residual activity (y-axis). Calculated $IC_{50}$ values using 5 μM nsp12 with 5-fold molar excess of nsp8 were 0.87±0.1 for AT-9010 and 4.6±0.2 for STP (5-fold difference). The x-axis is a log scale of inhibitor measured in 04.
Figure 13B:
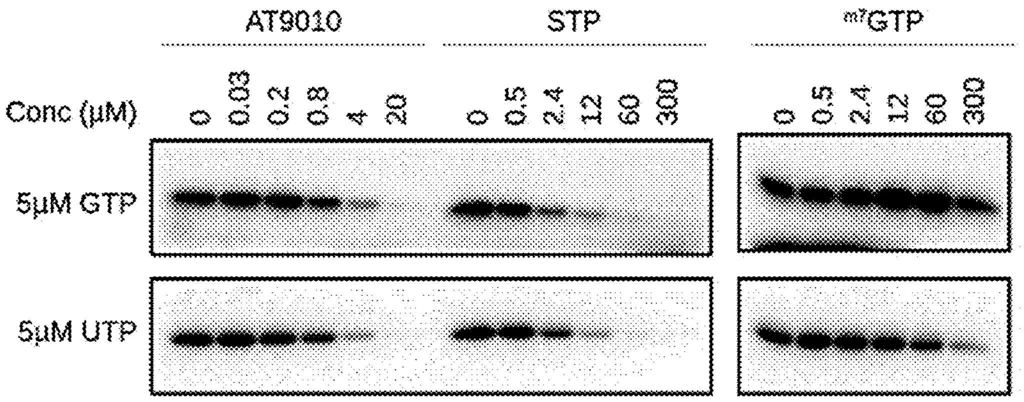
FIG. 13B is a phosphorimage of a 20% (wt/vol) polyacrylamide/7 M urea gel showing labeling of 5-fold molar excess of nsp8 by nsp12 (5 μM) was performed with a constant concentration of GTP (top) or UTP (bottom) supplemented with $\alpha^{32}$P-NTP (5 μM total), in competition with increasing concentrations of inhibitor (AT-9010, STP, or $^{m7}$GTP).
Figure 13C:
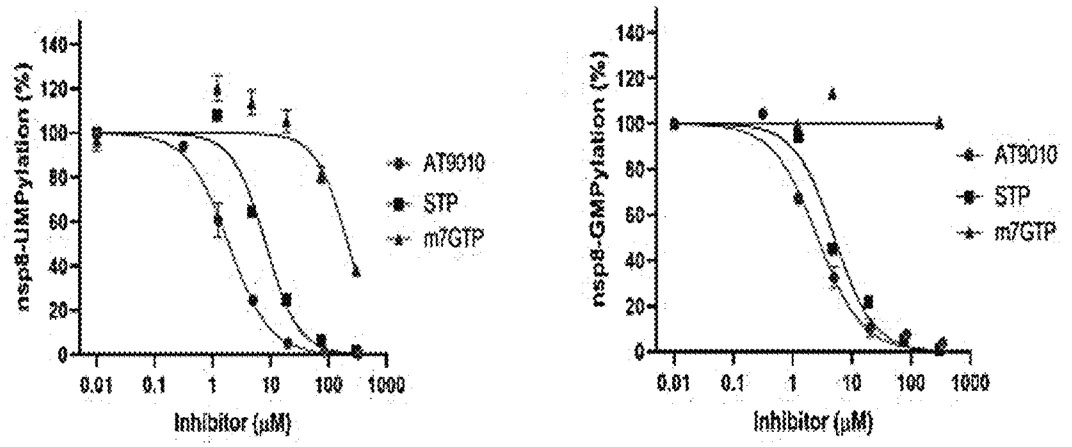
FIG. 13C shows a line graph measuring the total intensity of labeling quantified with ImageQuant software, and plotted at % residual activity (y-axis). Calculated $IC_{50}$ values were 2.7±0.3 and 1.9±0.1 for AT-9010 against GTP and UTP, respectively, and 5±0.8 and 8.2±1.4 for STP against GTP and UTP, respectively. Data was calculated from two individual replicates, with a minimum of 6-points per replicate. The x-axis is a log scale of inhibitor measured in μM.
Figure 13D:
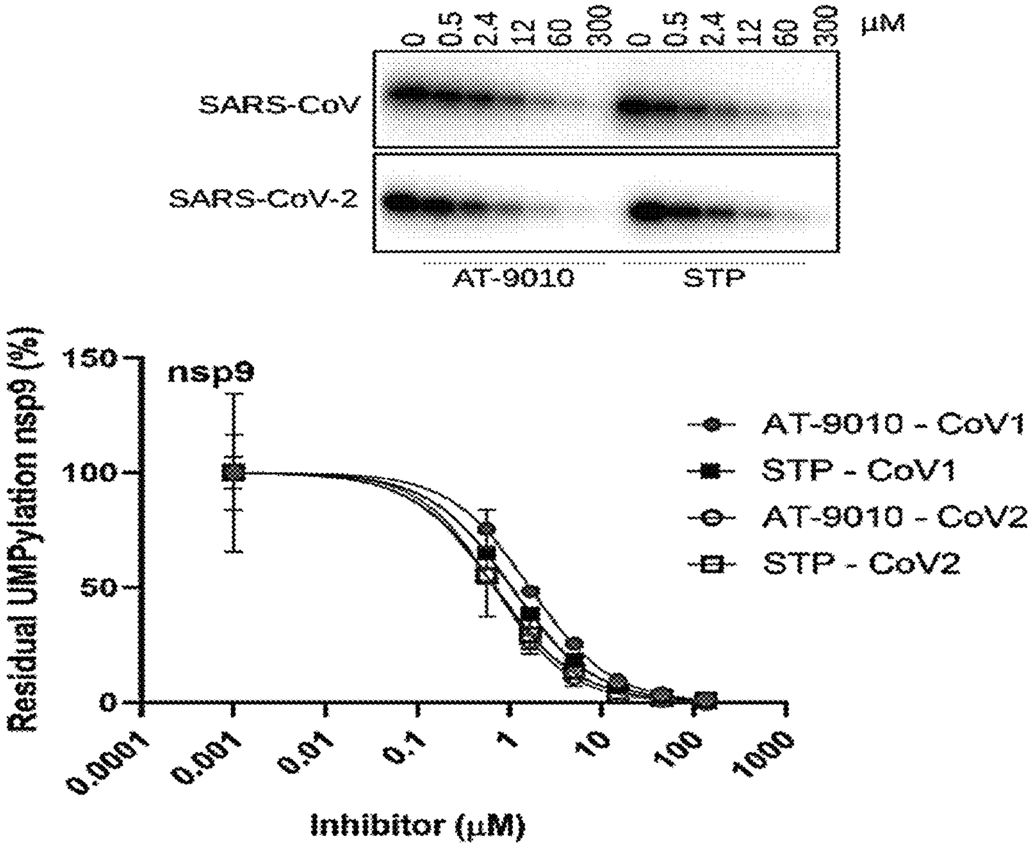
FIG. 13D shows a radiolabeled gel in the inset, which shows the labeling of Sars-CoV-2 nsp9 by nsp12 in the presence of increasing concentrations of AT-9010 or STP. Quantitation of radiolabel is plotted as a function of inhibitor concentration. Total intensity of labeling was quantified with ImageQuant software, and plotted at % residual activity (y-axis) compared with inhibitor concentration (x-axis).

To determine whether either drug was able to additionally target the NiRAN transfer activity, competition experiments measuring the labeling of nsp8 were performed with either UTP or GTP, with increasing concentrations of AT-9010 or STP (FIGS. 13A-C). Both drugs were able to inhibit labeling, in contrast to $^{m7}$GTP, used as a control. Interestingly, despite the preferential labeling of nsp8 with UMP, the uracil analog STP is ~5-fold less efficient at blocking nsp8-labeling than AT-9010, consistent at two enzyme concentrations (1 μM and 5 μM nsp12, with 5-fold excess nsp8) (FIG. 13B). The calculated $IC_{50}$ (half maximal inhibitory concentration) of inhibition of nsp8-UMP labeling by AT-9010 gives $IC_{50}$ values of approximately half the concentration of nsp12 (0.87 and 1.9 respectively), indicating that AT-9010 binds to the NiRAN-domain at a roughly 1:1 stoichiometry, strongly outcompeting UTP. Furthermore, given the excess of nsp8 in the reaction, these results suggest that AT-9010 remains stably bound in the NiRAN active-site, rather than being transferred to nsp8. Both STP and AT-9010 were additionally shown to inhibit GMPylation of nsp8 (FIG. 13C).

Figure 13E:
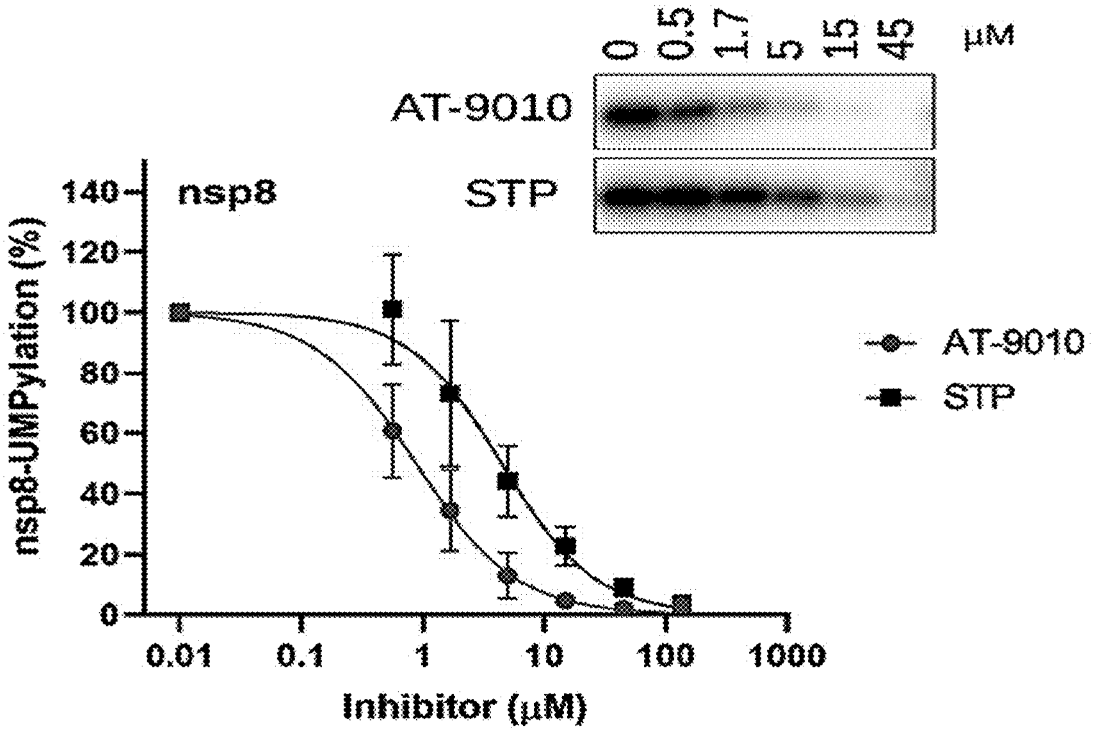
FIG. 13E shows a radiolabeled gel in the inset, which shows the labeling of Sars-CoV-2 nsp8 by nsp12 in the presence of increasing concentrations of AT-9010 or STP. Quantitation of radiolabel is plotted as a function of inhibitor concentration. Total intensity of labeling was quantified with ImageQuant software, and plotted at % residual activity (y-axis) compared with inhibitor concentration (x-axis).

Additionally, competition experiments measuring the efficiency of nsp9-UMPylation by both SARS-CoV and SARS-CoV-2 RTCs in the presence of increasing concentrations of AT-9010, or its uracil equivalent STP were performed with the results shown in FIG. 13D. Both drugs inhibit nsp9 labeling at comparable levels for SARS-CoV and SARS-CoV-2 RTCs. When provided at equimolar concentrations to UTP, nsp9-UMPylation is inhibited ~85-90% by both STP and AT-9010 for the SARS-CoV-2 complex, showing both drugs outcompete UTP for NiRAN-binding. Additional competition experiments measuring the efficiency of nsp8-UMPylation by both SARS-CoV and SARS-CoV-2 RTCs in the presence of increasing concentrations of AT-9010, or its uracil equivalent STP were performed. As shown in FIG. 13E, AT-9010 is ~4-5-fold more efficient at blocking nsp8 labeling than the uracil equivalent STP. This provides additional confirmation that AT-9010 remains stably bound into the NiRAN active site, rather than being transferred to nsp8 and cycled.

Figure 13F:
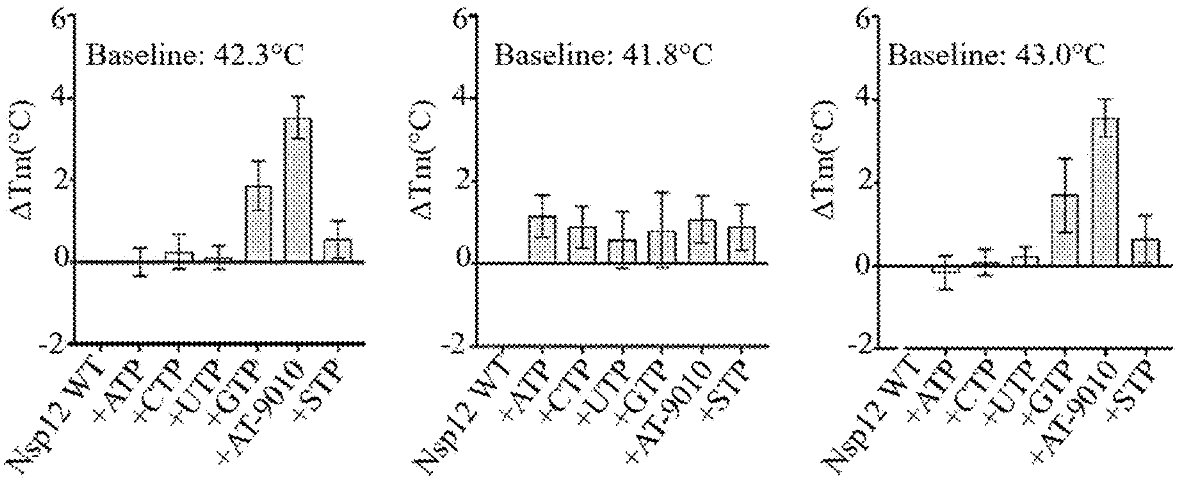
FIG. 13F is a group of bar graphs measuring the thermal stability of Sars-CoV-1 nsp12 WT (left), NiRAN mutant K73A (middle) and RdRp mutant SAA (right) in the presence of different native NTPs or inhibitors (x-axis). Reactions were run with 5 mM $MgCl_2$, and 0.5 mM $MnCl_2$ in triplicate, SD shown. The y-axis is measured in $\Delta T_m$ (° C.).
Figure 13G:
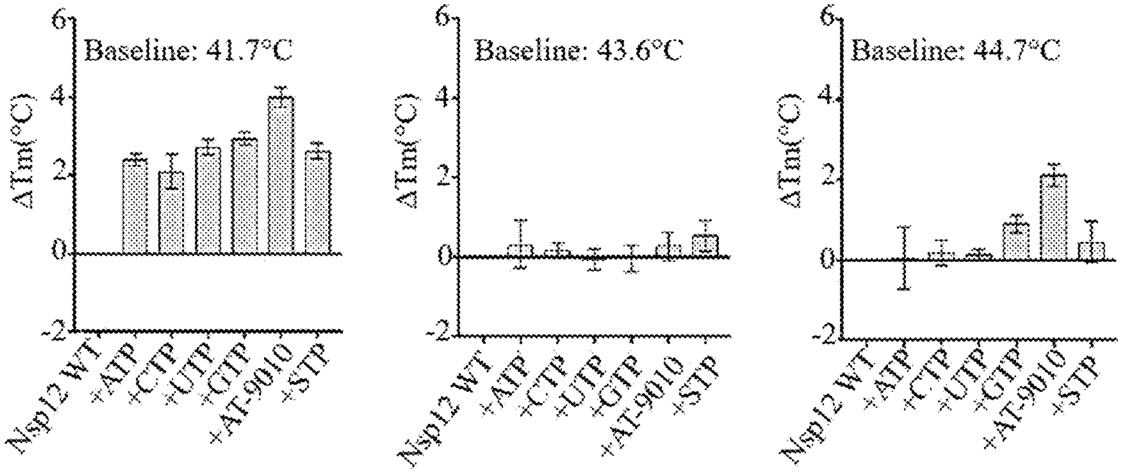
FIG. 13G is a group of bar graphs measuring the thermal stability of Sars CoV-1 nsp12 WT (left), NiRAN mutant K73A (middle) and RdRp mutant SAA (right) in the presence of different native NTPs or inhibitors (x-axis). Reactions were run with 5 mM $MgCl_2$ in triplicate, SD shown. The y-axis is measured in $\Delta T_m$ (° C.).
Figure 13H:
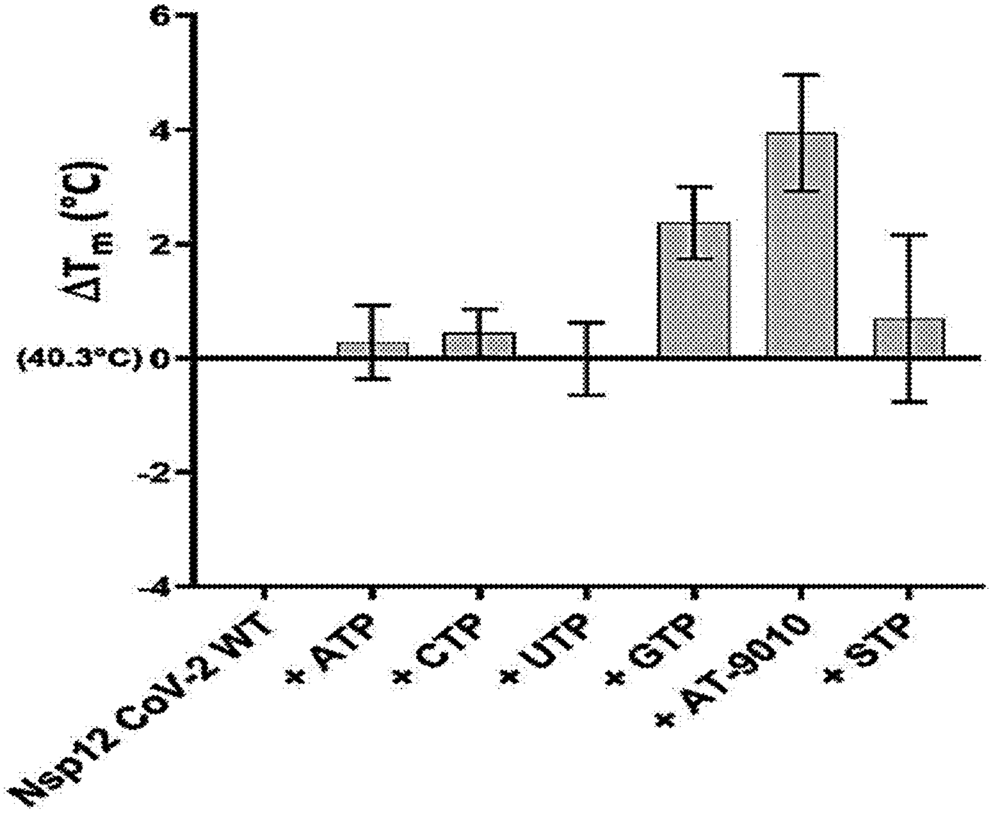
FIG. 13H is a bar graph measuring the thermal stability of Sars CoV-2 nsp12 WT in the presence of different native NTPs or inhibitors (x-axis). Reactions were run with 5 mM $MgCl_2$ in triplicate, SD shown. The y-axis is measured in $\Delta T_m$ (° C.).

Example 20: Thermal Shift Analysis Demonstrates that AT-9010 Preferentially Binds to Nsp12 NiRAN Active-Site The influence of compound binding on protein stability was measured by Thermofluor assay, using a CFX Connect BioRad real-time PCR machine, at a protein concentration of 2 (Nsp12 WT and Mutants) in a buffer composed of 10 mM HEPES pH 7.4, 150 mM NaCl and 5 mM $MgCl_2$ supplemented or not by 0.5 mM $MnCl_2$ freshly prepared. Compounds and dNTPs concentration were fixed at 100 μM. In 96-well thin-walled PCR plates, 2 μL of inhibitors or dNTPs were added to 16 μL of buffer follow by the addition of 2 μL of protein. Finally, 2 μL of the fluorescent dye SYPRO Orange was added (5-fold final). Melting-temperature ($T_m$) values given are the average and standard deviation of three independent experiments. Thermal shift assays with nsp12 in the presence of $MnCl_2$ confirms that AT-9010 provides more thermodynamic stability than any other native nucleotide (FIG. 13F). Comparison of NiRAN and RdRp active-site mutants (K73A and SAA, respectively), shows that this stability increase is provided by AT-9010 binding preferentially into the NiRAN active-site, rather than the RdRp active-site (FIGS. 13F-G). Both GTP- and AT-9010-nsp12 complexes show an increase in stability compared with UTP or STP-bound complexes. Consistent with inhibition results, these results indicate that guanosine is the preferred base of the NiRAN active-site, and the 2'-fluoro-2'-C-methyl ribose modification of AT-9010 provides additional stability. Similar results were seen using the Sars-CoV-2 WT Nsp12, which are shown in FIG. 13H.

Example 21: AT-9010 Inhibits RNA Synthesis Through Pathway 2

Figure 14A:
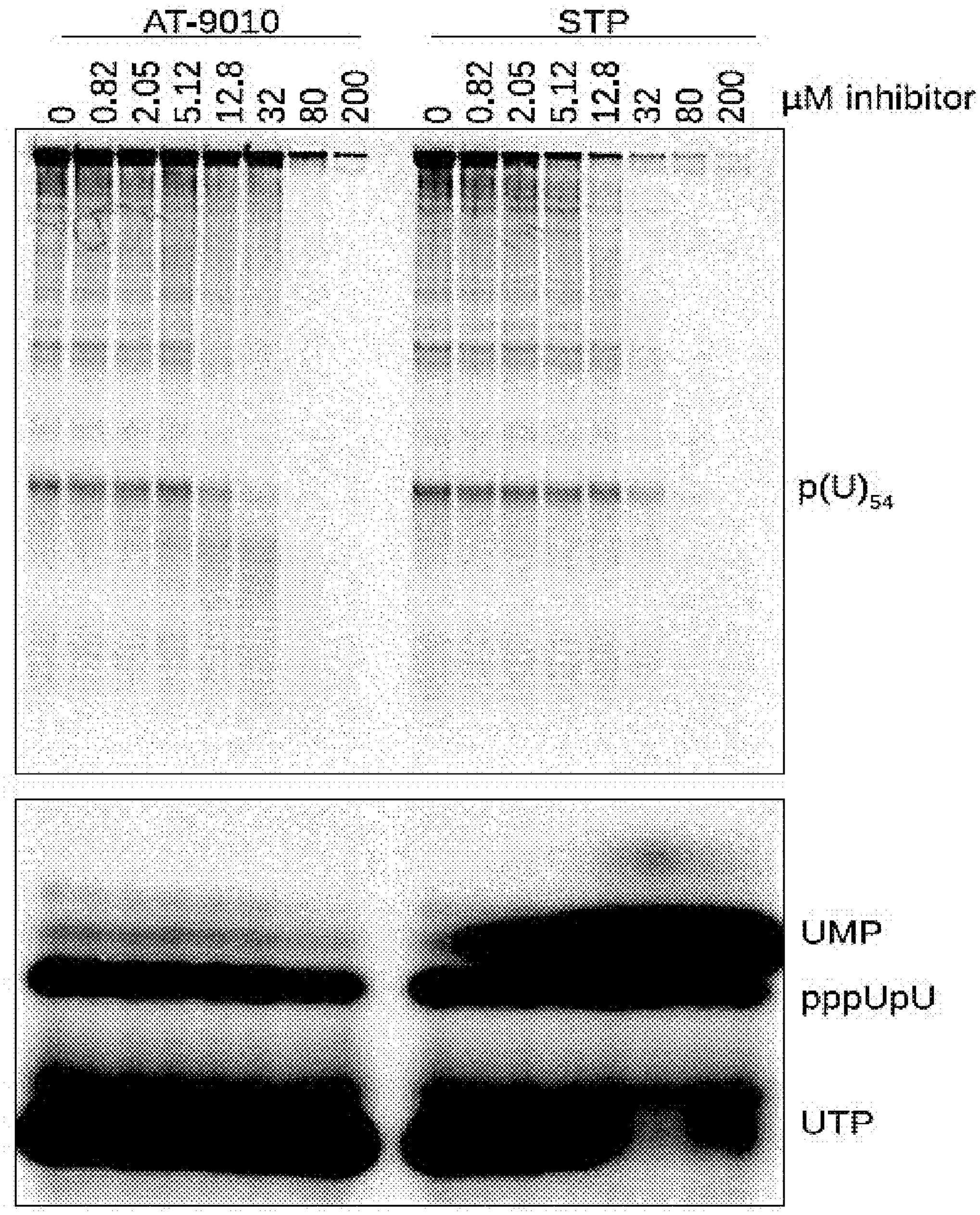
FIG. 14A is a phosphorimage of a 20% (wt/vol) polyacrylamide/7 M urea gel showing inhibition of nsp12:7:8 RTC synthesis from $poly(A)_{27}$ templates with AT-9010 and STP. Gel is representation of 2 independent experiments.
Figure 14B:
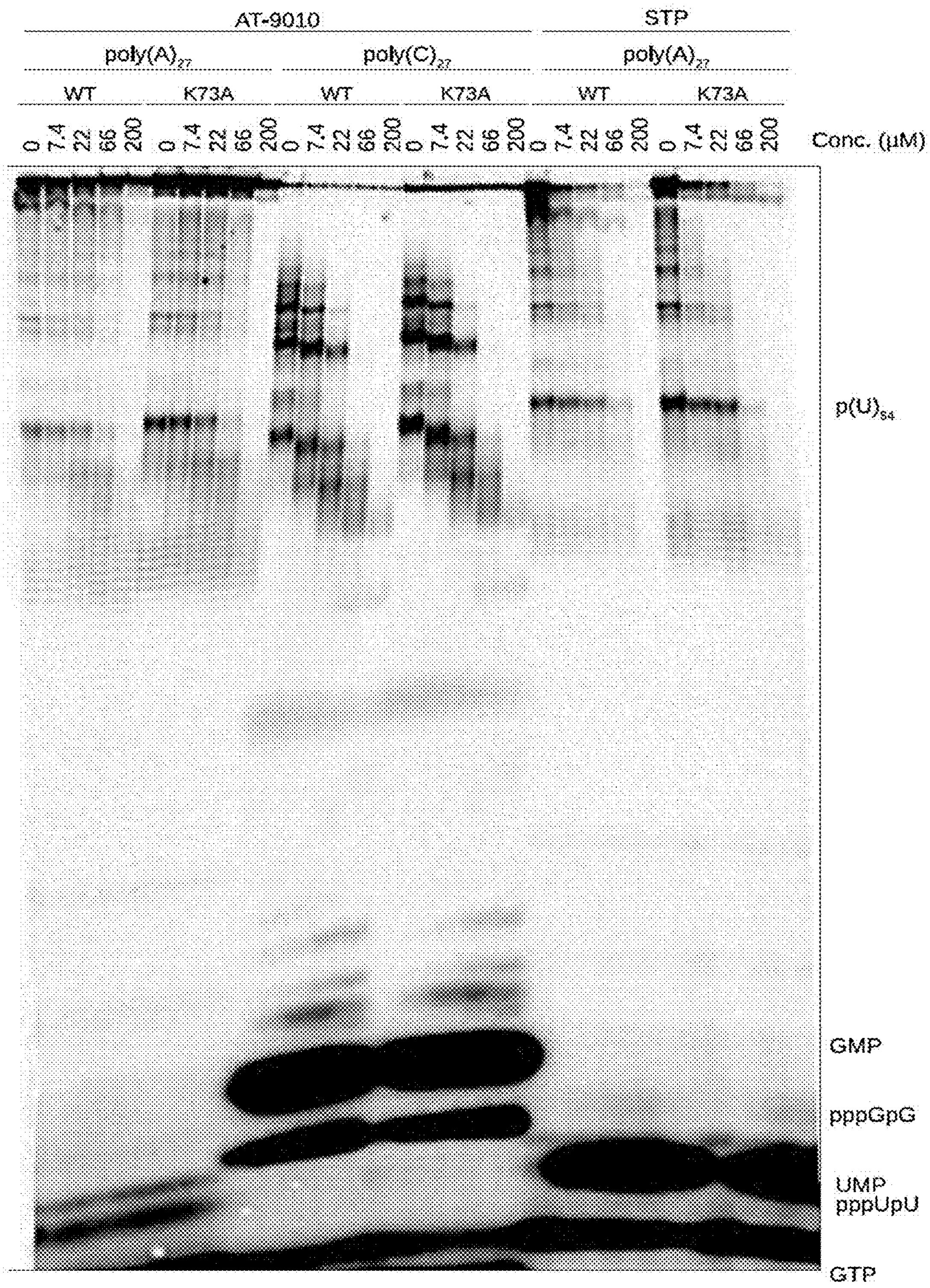
FIG. 14B is a phosphorimage of a 20% (wt/vol) polyacrylamide/7 M urea gel showing inhibition of RNA synthesis with varied concentrations of AT-9010 or STP, comparing WT and NiRAN mutant complexes, was run on both $poly(A)_{27}$ and $poly(C)_{27}$ templates in the presence of UTP and GTP, (200 supplemented with $\alpha^{32}$P-NTP).
Figure 14C:
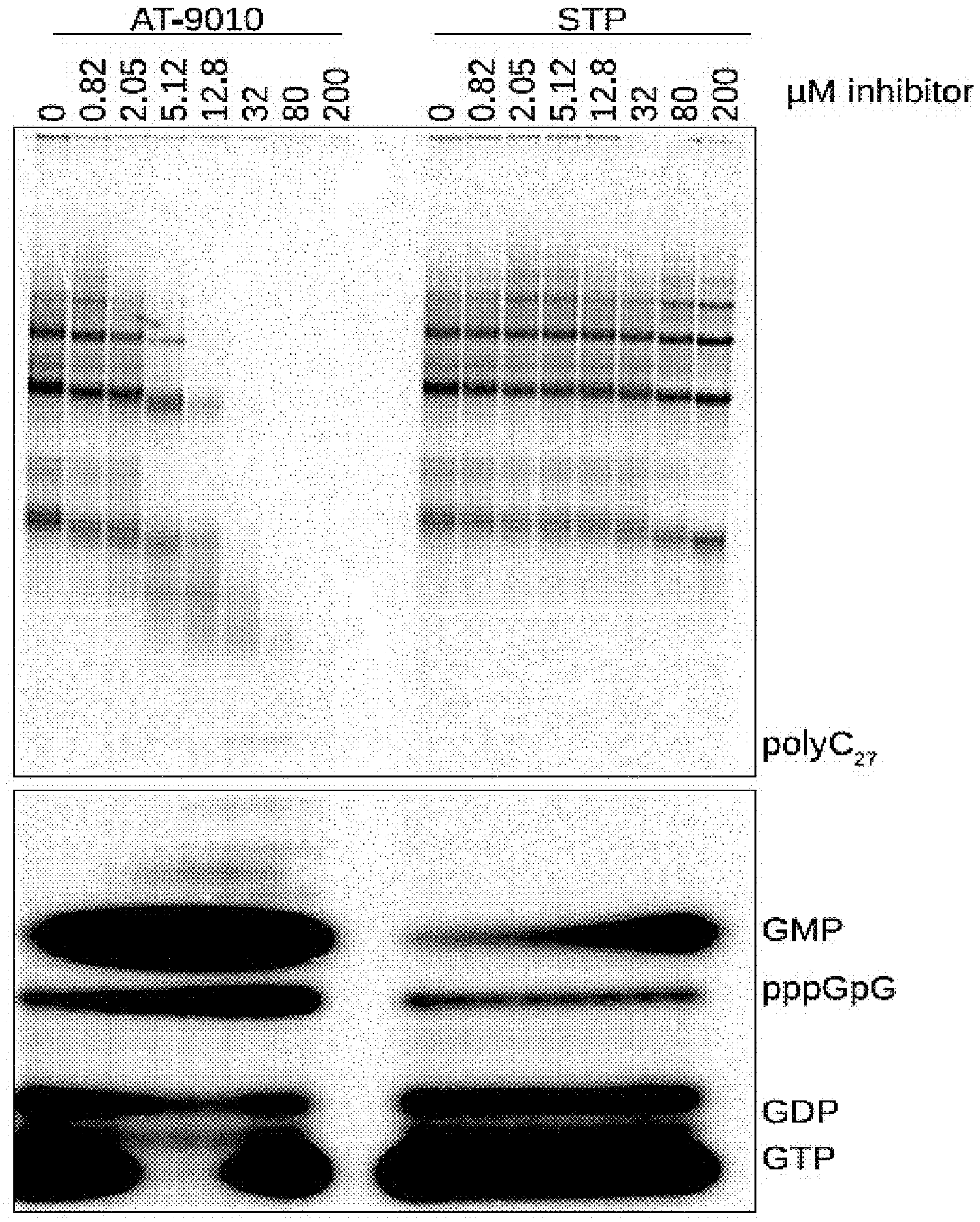
FIG. 14C is a phosphorimage of a 20% (wt/vol) polyacrylamide/7 M urea gel showing inhibition of nsp12:7:8 RTC synthesis from $poly(C)_{27}$ templates with AT-9010 and STP. Gel is representation of 3 independent experiments.
Figure 14D:
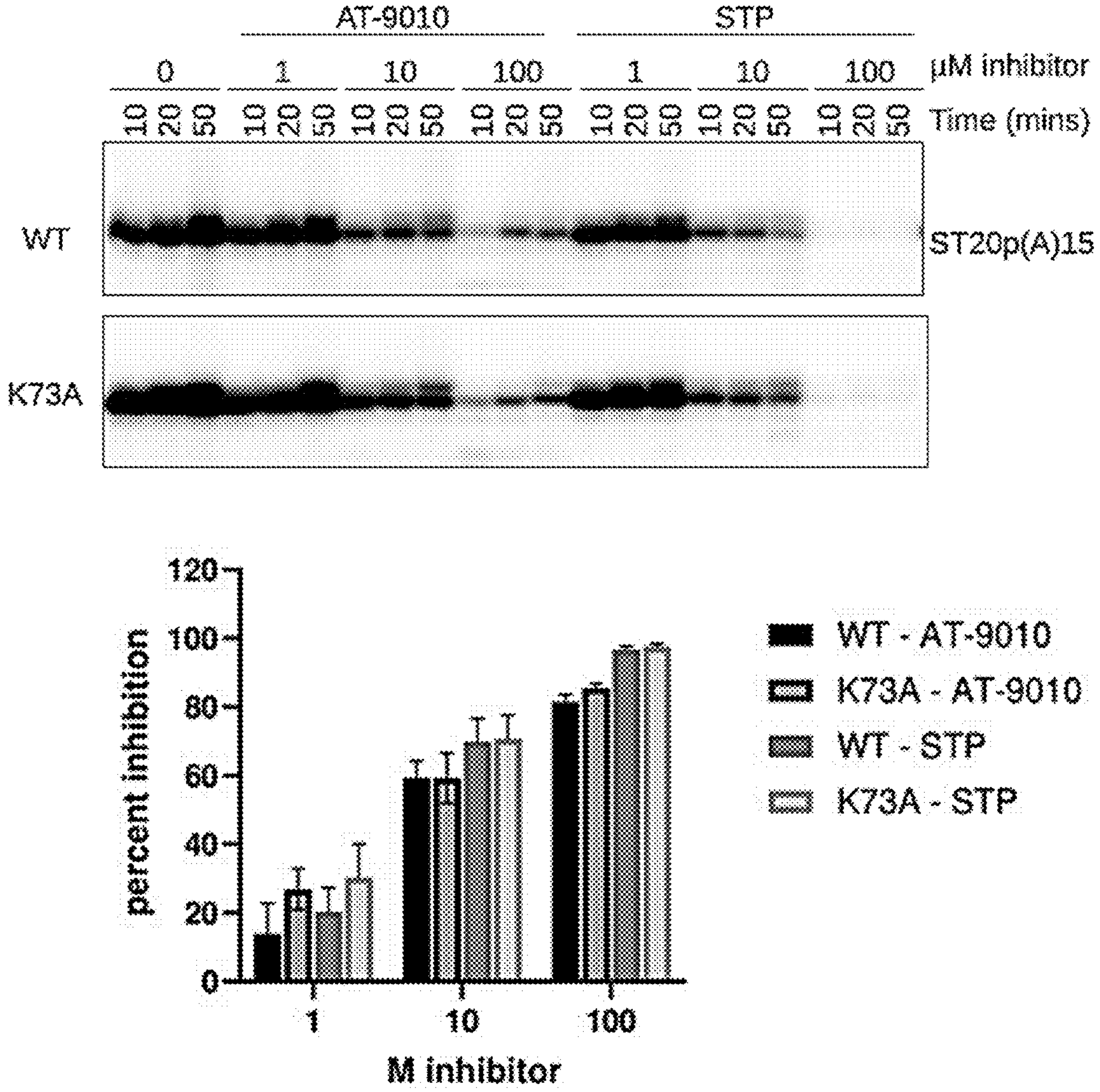
FIG. 14D is a phosphorimage of a 20% (wt/vol) polyacrylamide/7 M urea gel showing inhibition of synthesis from $ST20p(A)_{15}$ template by nsp12:7:8 RTCs with either WT (top gel) or NiRAN mutant (K73A) nsp12 (bottom gel). Graph below represents average activity from two independent experiments, with calculated difference from three time-points compared to no-inhibitor control. The x-axis is M inhibitor and the y-axis is percent inhibition.

The ability of the two drugs to inhibit initiation of RNA synthesis from a poly$(A)_{27}$ template was tested. Despite the fact that AT-9010 is a guanosine nucleotide, it inhibits synthesis of poly$(U)_n$ RNA equally as well as STP (FIG. 14A). The inhibition by AT-9010 shows that the majority of its inhibitory activity might not be due to RdRp-mediated incorporation, as purine-purine mismatches (in this case AT-9010: A, equivalent to G: A) would be significantly disfavored over the native UTP: A. Inhibition of RNA synthesis is comparable with the nsp12 K73A mutant, indicating that inhibition cannot be allosteric via binding to the NiRAN-domain (FIG. 14B). Rather, inhibition occurs through blocking RNA synthesis initiation at the RdRp active-site. The equivalent experiment with a poly(C) template, theoretically favoring AT-9010, shows STP to be virtually inactive, while AT-9010 significantly reduces activity (FIG. 14C). It therefore appears that while both drugs are able to inhibit de novo, NiRAN-independent initiation of RNA synthesis, AT-9010 inhibition is template-independent. Preincubation of the complexes with either STP or AT-9010, prior to addition of pppGpU and other NTPs inhibits synthesis of $ST20p(A)_{15}$ RNA at similar levels; Again, inhibition is comparable with WT and K73A NiRAN mutant complexes, showing that both drugs are additionally able to bind in the RdRp active-site and prevent synthesis and/or binding of dinucleotide primers (FIG. 14D).

Figure 15A:
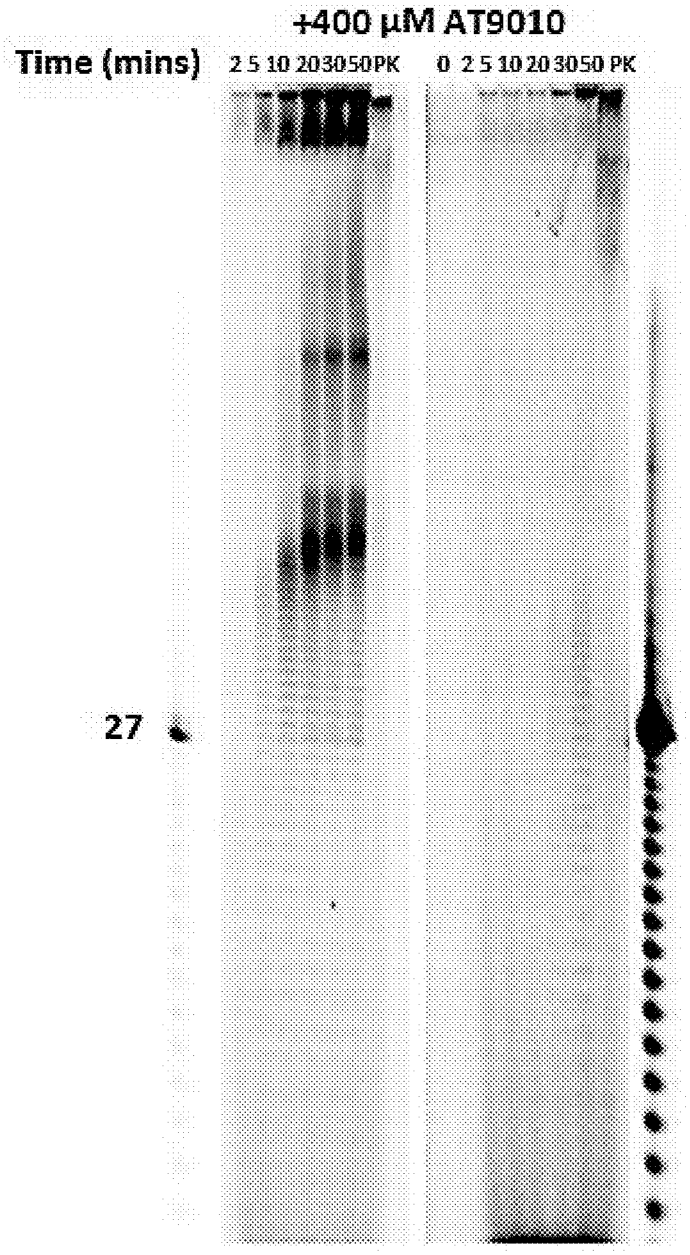
FIG. 15A is a 1% agarose-formaldehyde gel of the radiolabeled RNA polymerization products from de novo assays with and without AT9010. The gel on the left shows the radiolabeled RNA polymerization products without AT9010 over a time course of 50 mins. The gel on the left shows the radiolabeled RNA polymerization products with 400 μM AT9010 over a time course of 50 mins.

Example 22: AT-9010 Inhibits NiRAN-Dependent and NiRAN-Independent Pathways Better than SOF RNA polymerization assays were run as described in Example 10. De novo assays, using 0.35 μM $poly(A)_{27}$ RNA as template, were started by adding 200 μM $\alpha$-$^{32}$P-UTP (0.5 μCi/μL). Reactions were run either with 400 μM AT9010 or without. After incubation at 30° C., reactions were quenched by the addition of an equal volume of loading buffer (formamide with 10 mM EDTA). RNA polymerization products from de novo assays were analyzed in 1% agarose-formaldehyde gels. RNA products were visualized using photo-stimulated plates and a phosphorimager. As shown in FIG. 15A with 2-fold excess of AT9010 over UTP there is almost complete inhibition of de novo synthesis on poly(A) template, indicating AT9010's ability to inhibit protein-primed RNA polymerization.

Figure 15B:
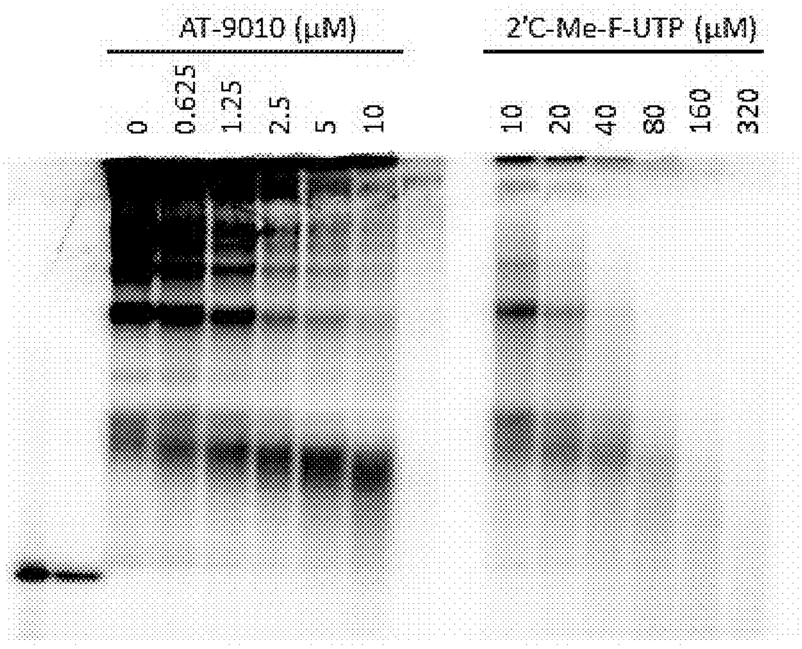
FIG. 15B is a 1% agarose-formaldehyde gel of the radiolabeled RNA polymerization products from protein primed RNA synthesis assays with increasing concentrations of AT9010 and 2'C-Me 2'F-UTP (Sofosbuvir). The gel on the left shows the results of the experiment where AT9010 was used. Each lane represents the results at rising concentrations of AT9010 (0, 0.625, 1.25, 2.5, 5 and 10 μM). The gel on the right shows the results of the experiment where 2' C-Me 2'F-UTP was used. Each lane represents the results at rising concentrations of 2'C-Me 2'F-UTP (10, 20, 40, 80, 160, and 320 μM).

Next primer-independent RNA synthesis assays were performed as described above where reactions were run with a dose escalation from 0 to 10 μM of AT9010 or 10 to 320 μM of 2'C-Me 2'F-UTP. The results for AT9010 are shown in the left panel of FIG. 15B which shows that AT9010 inhibits NiRAN mediated protein primed RNA synthesis with a $EC_{50}$ of ~1.5-2 μM. This shows that AT9010 very potently inhibits NiRAN mediated protein primed synthesis at physiologic doses. Alternatively, the results for 2'C-Me 2'F-UTP are shown on the right panel of FIG. 15B. This shows that the $EC_{50}$ of 2'C-Me 2'F-UTP is ~20-40 μM. This drug concentration level cannot be achieved with a physiologic dose of 2'C-Me 2'F-UTP so it is not effective at inhibiting NiRAN mediated protein primed RNA synthesis.

Figure 15C:
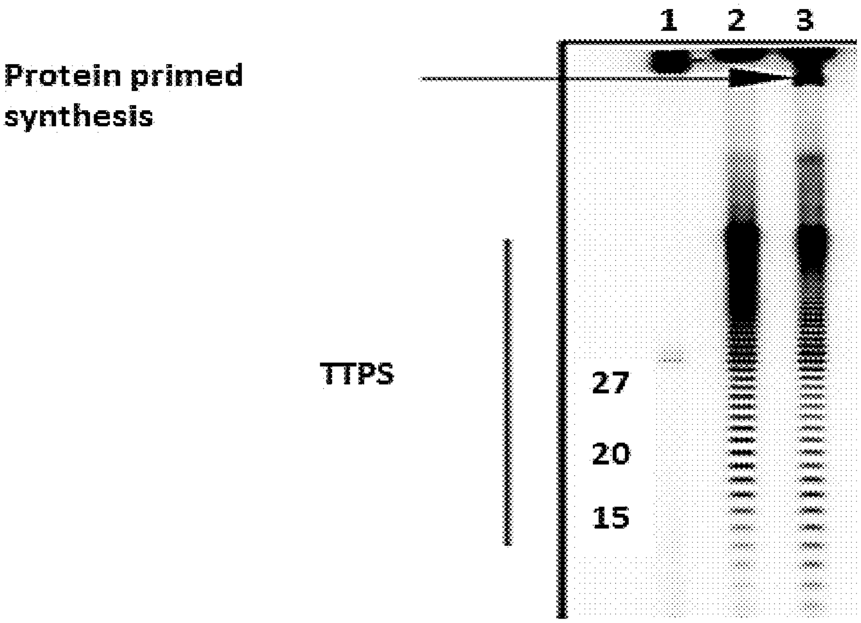
FIG. 15C is a 1% agarose-formaldehyde gel of the radiolabeled RNA polymerization products from RNA synthesis assays testing different polymerase complex components. Lane 1 shows no primer independent synthesis. Lane 2 shows primer-independent synthesis. Lane 3 shows primer independent synthesis as well as protein-primed synthesis.

Additional de novo synthesis assays were performed in polymerase assay buffer (20 mM Tris, pH 8; 10 mM KCl; 1 mM DTT; 2 mM $MgCl_2$) with either 0.5 μM SARS-Cov-1 nsp12:8 polymerase complex (1:3 molar ratio); 0.5 μM SARS-Cov-1 nsp12:7L8 polymerase complex (1:3 molar ratio); or 0.5 μM SARS-Cov-1 nsp12:7L8:8 polymerase complex (1:3:3 molar ratio) with 0.35 μM $poly(A)_{27}$ RNA. De novo assays, using 0.35 μM $poly(A)_{27}$ RNA as template, were started by adding 200 μM [$\alpha$-$^{32}$P] UTP (0.5 μCi/μL). After incubation at 30° C., reactions were quenched by the addition of an equal volume of loading buffer (formamide with 10 mM EDTA). RNA polymerization products from de novo assays were analyzed on 1% agarose-formaldehyde gels. RNA products were visualized using photo-stimulated plates and a phosphorimager. The results are shown in FIG. 15C. Lane 1 is the assay utilizing 0.5 μM SARS-Cov-1 nsp12:8 polymerase complex, which shows no primer-independent synthesis. Lane 2 is the assay utilizing 0.5 μM SARS-Cov-1 nsp12:7L8 polymerase complex, which shows primer-independent synthesis. Lane 3 is the assay utilizing 0.5 μM SARS-Cov-1 nsp12:7L8:8 polymerase complex, which shows primer-independent synthesis as well as protein-primed synthesis in the top band.

This ability to inhibit SARS primer independent RNA polymerization through the SARS NiRAN-domain by AT9010 may also explain the difference in effectiveness of Compound 1A in inhibiting SARS viral replication, while being less effective in inhibiting MERS viral replication (see Example 3), as the MERS and SARS NiRAN-domain are significantly more heterologous than the MERS and SARS RdRp domain (see Lehmann et al., Nucleic Acids Res. 2015 Sep. 30; 43(17): 8416-8434).

Example 23: Use of Cryo-EM to Better Visualize Binding

Assembly of the Extended Nsp12-Nsp7-Nsp8-RNA Complex for cryoEM

To assemble the extended RdRp complex, nsp12 was incubated with nsp7 and nsp8 at 4° C. for 3 h with a molar ratio of 1:3:6 in a buffer containing 25 mM Tris-HCl (pH 8.0), 50 mM NaCl, mM $MgCl_2$, 4 mM DTT. Then the mixture was purified by Mono Q 5/50 GL ion-exchange chromatography (GE Healthcare, USA), resulting in a stable nsp7-nsp8-nsp12 complex. The protein complex was desalted to buffer F (25 mM Tris-HCl (pH 8.0), 100 mM NaCl, 5 mM $MgCl_2$, 4 mM DTT). Purified RdRp complex were buffer exchanged to 25 mM Tris-HCl, pH 8.0, 100 mM NaCl, 5 mM $MgCl_2$, 4 mM DTT and concentrated to 10 mg/ml for cryo-EM experiments. A 30-mer oligoribonucleotide template and a 20-mer oligoribonucleotide primer were chemically synthesized by GenScript. The template and primer oligoribonucleotides were annealed by heating the solution to 95° C. and gradually cooling to 4° C. The annealed RNA scaffold was incubated with nsp12-nsp7-nsp8 complex for 30 min at 4° C. with a molar ratio of 2:1 to form the nsp12-nsp7-nsp8-RNA complex. AT9010 was added subsequently for compound incorporation.

Cryo-EM Sample Preparation and Data Collection

In total, 3 μL of protein solution at 5 mg/mL (with 0.025% DDM) was applied onto a glow-discharged holey carbon grid (Quantifoil, 300 mesh, R1.2/1.3). Excess samples were blotted for 5.0 s with a blotting force of 3, then the remaining solution was vitrified by plunging into liquid ethane using a Vitrobot Mark IV (Thermo Fischer Scientific) at 4° C. and 100% humidity. Cryo-EM data were collected with a 300 keV Titan Krios electron microscope (Thermo Fisher Scientific, USA) equipped with a K3 direct electron detector (Gatan, USA) operating in a super-resolution counting mode. All movies were automatically recorded using SerialEM (Mastronarde, 2005) at a magnification of 105K, with a physical pixel size of 0.83 Å. A total dose of 80.5 e–/Å2 was fractionated into 50 frames. 7,459 movie micrographs were collected with a defocus range from −1.5 μm to −2.5 μm, and the slit width of Gatan Quantum GIF energy filter (Gatan, USA) was set to be 20 eV. Statistics for data collection and refinement are shown in Table 51.

Cryo-EM Image Processing

All dose-fractioned movies were motion-corrected with Relion's own implementation. CTF estimation, 2D classification, 3D classification and refinements were all performed in cryoSPARC. A total of 2,410,466 particles were auto-picked using blob picker and extracted with a box size of 320 pixels. 248,401 particles were selected after three rounds of 2D classification based on the complex integrity. This particle set was used for Ab-Initio reconstruction with three classes, which were then used as 3D volume templates for heterogeneous refinement. The 3D volume corresponding to the intact nsp12-nsp7-nsp8-RNA complex was used for creating 100 2D projections which were then used as templates for template-based particle picking. Approximately 3,640,595 particles were picked from a set of 3,622 micrographs filtered based on fitted resolution better than 5 Å as estimated by CTFFIND4, using template picker. Particles were extracted with a box size of 360 pixels. A total of 234,421 particles were selected after four rounds of 2D classification based on the complex integrity. This particle set was used for Ab-Initio reconstruction with three classes, followed by heterogeneous refinement. A subset of 181,669 particles from the class with good features was subjected to Homogeneous Refinement, Local Refinement and Non-uniform Refinement, resulting in a 2.98 Å map.

Model Building and Refinement

To build the model of nsp12-nsp7-nsp8-RNA complex, the structure of SARS-CoV-2 nsp12-nsp7-nsp8-RNA complex (from PDB 7CYQ with one nsp9 and nsp13 removed) was placed and rigid-body fitted into the cryo-EM map using UCSF Chimera. The model was manually built in Coot (Emsley et al., 2010) with the guidance of the cryo-EM map, and in combination with real space refinement using Phenix (Afonine et al., 2018). The model validation statistics are shown in Table 9.

TABLE 9

Cryo-EM data collection, refinement, and validation statistics

| Nsp12-nsp7-nsp8 complex | RNA and AT9010 bound (PDB ID:) (EMDB ID:) |
|---|---|
| Data collection and Processing (for each dataset) | |
| Microscope | Titan Krios |
| Voltage (keV) | 300 |
| Camera | Gatan K3 Summit |
| Magnification | 105,000 |
| Pixel size at detector (Å/pixel) | 0.83 |
| Total electron exposure ($e^-/Å^2$) | 80.5 |
| Number of frames collected during exposure | 50 |
| Defocus range (μm) | −1.5∼−2.5 |
| Phase plate (if used) | N/A |
| phase shift range (in degrees) | N/A |
| number of images per phase plate position | N/A |
| Automation software | SerialEM |
| Tilt angle | 0 |
| Energy filter slit width (eV) | 20 |
| Micrographs collected (no.) | 7,459 |
| Micrographs used (no.) | 5,609 |
| Total extracted particles (no.) | 3,640,595 |
| For each reconstruction: | |
| Refined particles (no.) | 181,669 |
| Final particles (no.) | 181,669 |
| Point-group or helical symmetry parameters | C1 |
| Resolution (FSC 0.143, Å) | 2.98 |
| Resolution range (local, Å) | 2.7-3.3 |
| Map sharpening B factor ($Å^2$) | 82.7 |
| Map sharpening methods | cryoSPARC v2.15.0 |
| Model composition | |
| Protein | 1302 |
| Ligands | 8 |
| RNA | 44 |

TABLE 9-continued

Cryo-EM data collection, refinement, and validation statistics

| Nsp12-nsp7-nsp8 complex | RNA and AT9010 bound (PDB ID:) (EMDB ID:) |
|---|---|
| Model Refinement | |
| Refinement package | PHENIX-1.19_4085 |
| real or reciprocal space | real space |
| Model-Map CC | 0.84 |
| Model resolution (Å) | 3.14 |
| FSC threshold | 0.5 |
| B factors ($Å^2$) | |
| Protein residues | 69.09 |
| Ligands | 67.51 |
| RNA | 134.15 |
| R.m.s. deviations from ideal values | |
| Bond lengths (Å) | 0.002 |
| Bond angles (°) | 0.538 |
| Validation | |
| MolProbity score | 1.9 |
| CaBLAM outliers | 5.13 |
| Clashscore | 7.89 |
| Poor rotamers (%) | 0.09 |
| C-beta deviations | 0.00 |
| EMRinger score (if better than 4 Å resolution) | 3.32 |
| Ramachandran plot | |
| Favored (%) | 92.5 |
| Outliers (%) | 0.31 |

Example 24: Structural Basis for Nsp12 Inhibition by AT-9010

Figure 16A:
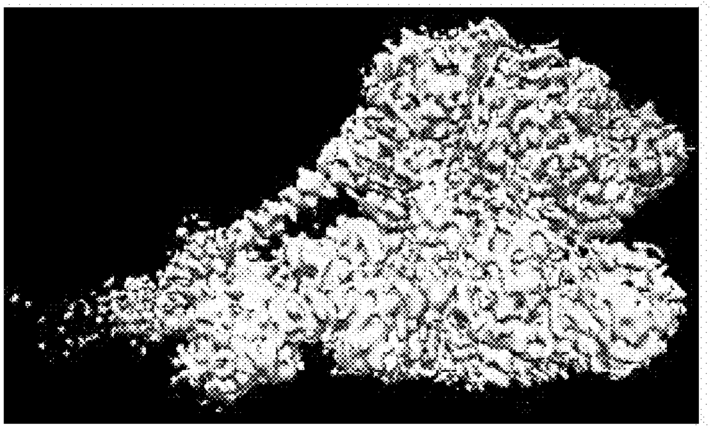
FIG. 16A is a 2.98 Å resolution Cryo-EM structure of the SARS-CoV-2 nsp7-$(nsp8)_2$-nsp12/RNA/NTP quaternary complex.
Figure 16B:
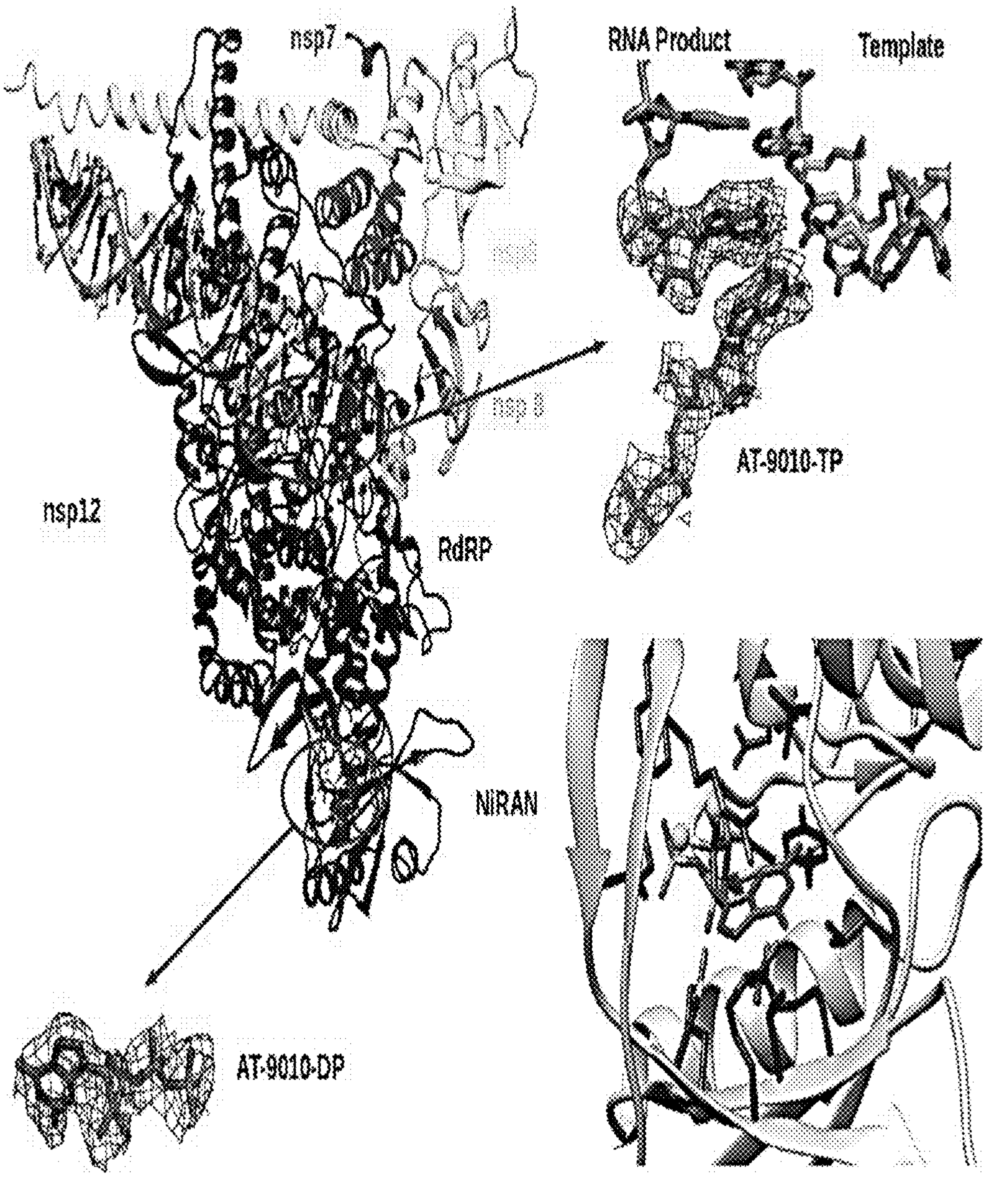
FIG. 16B is a ribbon representation of the Cryo-EM structure of nsp7-$(nsp8)_2$-nsp12:AT-9010-terminated-RNA: $(AT9010)_2$ complex. Circular regions are highlighted and enlarged showing density map and stick representation of two AT9010 molecules in the RdRp active site (lower left) and one AT-9010 is covalently incorporated into the RNA strand (upper right).
Figure 16C:
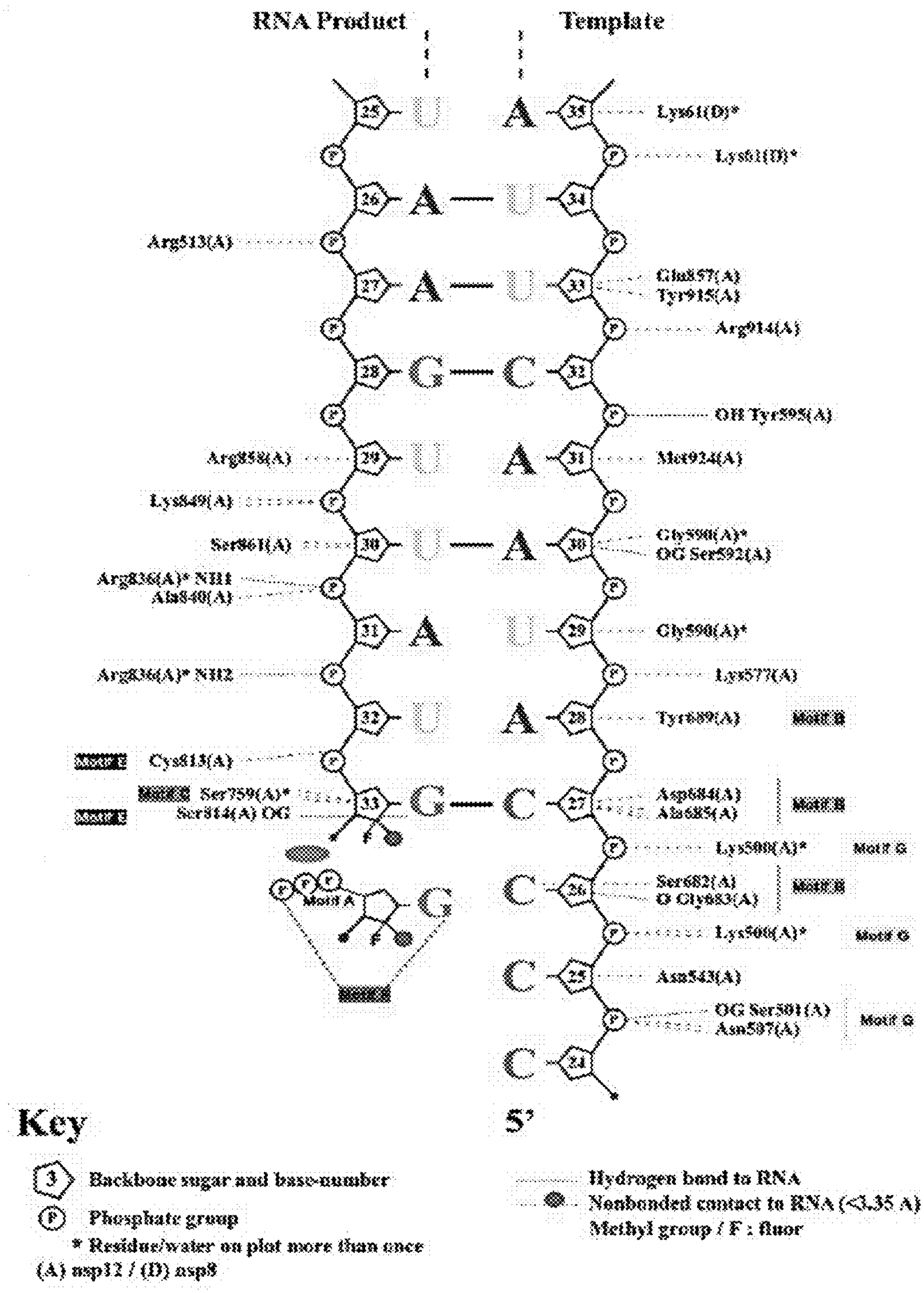
FIG. 16C is a Nucplot molecular analysis between RNA AT-9010 and nsp12.
Figure 16D:
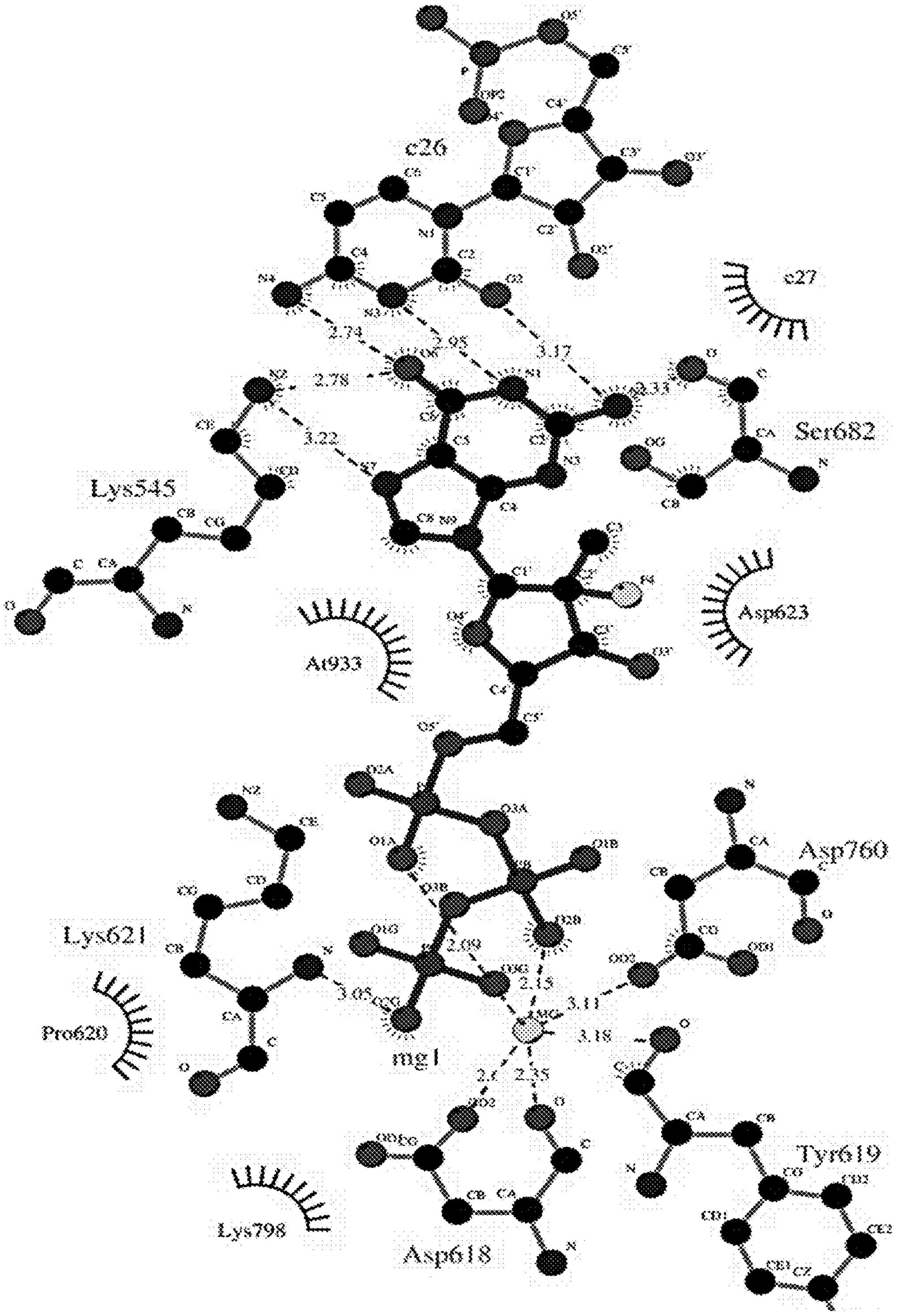
FIG. 16D shows a ligplot 2D analysis of the contacts of AT-9010 molecules.
Figure 16E:
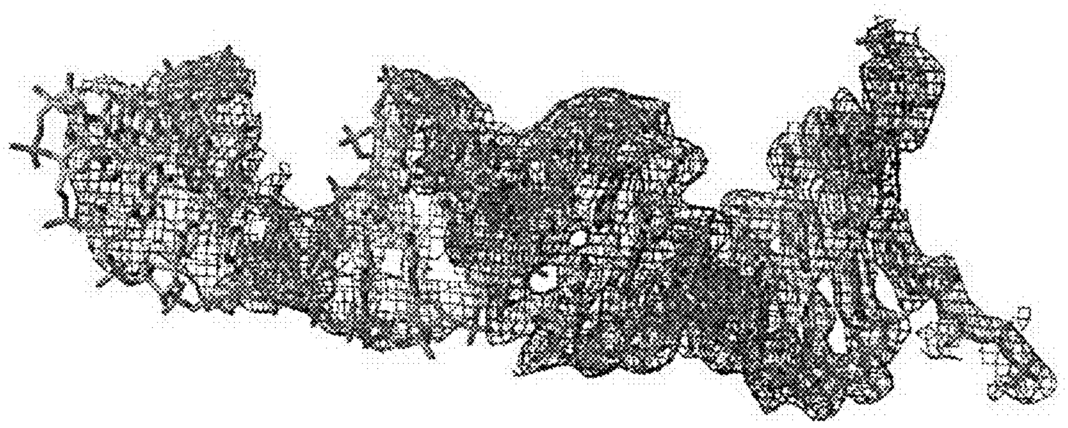
FIG. 16E shows AT-9010 (sticks) bound to the NiRAN-domain with density map.

Previously reported structures of the SARS-CoV-2 RTC in the presence and absence of RNA (Gao 2020; Wang 2020) have paved the way to understand inhibition at a structural level (Yin 2020). To investigate the binding and incorporation into RNA of AT-9010, and in particular the relationship between the RdRp and NiRAN active sites in its presence, Cryo-EM studies were performed using a dsRNA-bound to the SARS-CoV-2 RTC in the presence of AT-9010. Image processing of single particles allowed to reconstruct an RTC/RNA/AT-9010 quaternary assembly at 2.98 Å resolution (FIG. 16A), showing AT-9010 simultaneously binding to both NiRAN and RdRp active site of nsp12 (FIG. 16B). The overall structure resembles previously reported structures, with one nsp12, one nsp7 and two nsp8 proteins (FIG. 16B). The RdRp domain is bound to a primer-template dsRNA pair, with the 5'-monophosphate of AT-9010 incorporated at the 3' end of the RNA primer (FIG. 16B). A second, free AT-9010 triphosphate is present, being loaded into the polymerase at the NTP binding site (framed from left by motif C, bottom by motifs A, D, and top by motif F) (FIGS. 16C-D). This structure therefore represents the first snapshot of a SARS-CoV-2 polymerase in a post-translocation state, with the incoming NTP poised for incorporation. Residues Asp618 and Asp760 of motifs A and C, respectively, coordinate a single catalytic magnesium ion, which interacts with the phosphates of the second AT-9010 (FIGS. 16C-D). Finally, the structure also shows AT-9010 in its diphosphate form, bound in the active-site of the NiRAN-domain (FIG. 16E).

Example 25: The Nsp12 Active-Site Incorporates AT-9010 into RNA and Terminates Synthesis The visible 5' end of the RNA templates is composed of 4 consecutive cytidine bases (C24-C27) designed to favor the incorporation of AT-9010 into the RNA product strand. AT-9010 is incorporated at position −1 of the RNA product, pairing with C27 of the template strand. A second AT-9010 is observed in a pre-incorporation state pairing with C26 of the template. As a result, the RdRp-RNA complex is in a post-translocation state, with the +1 site is occupied by the second AT-9010, preventing other NTPs from being loaded (FIG. 16C).

Figure 16F:
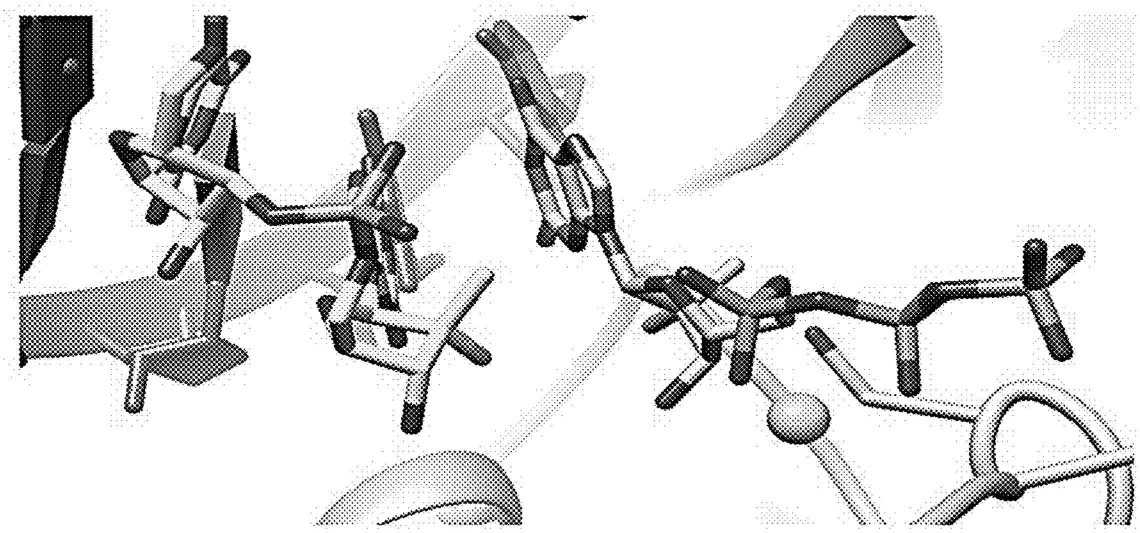
FIG. 16F shows one AT9010 molecule is incorporated into the primer RNA strand under a 5'-monophosphate form, and terminates RNA elongation. In NTP binding site in stick representation of an AT-9010 molecule coordinated by one ion.
Figure 16G:
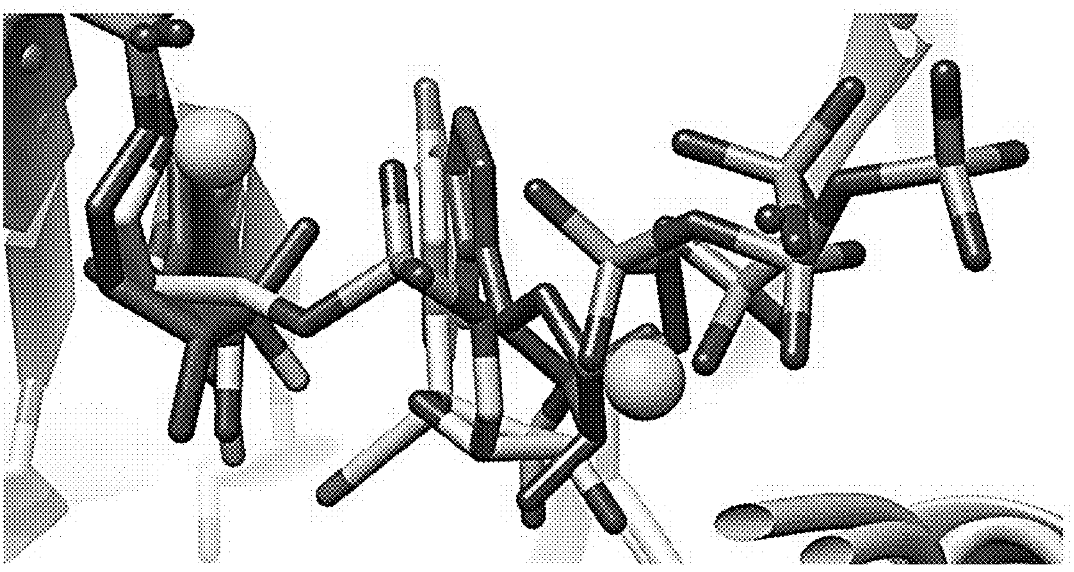
FIG. 16G shows Superimposition of AT-9010 molecule with remdesivir. The position of the ribose is shifted up by 45° and phosphates are in a post-incorporation position.

The guanine of the incorporated AT-9010 is canonically base-paired with the cytosine (C27) of the template (FIGS. 16B-C). The ribose forms hydrogen bonds with Ser814 and the 5' phosphate, coordinated by Cys813. The effect of the 2'-fluoro-2'-C-methyl ribose modification is two-fold. Firstly, the replacement of the 2' hydroxyl by a fluoro group eliminates the interaction between Ser759 (motif C) and the 2'-OH, which usually stabilizes the ribose. This sterically displaces the catalytic ions that are normally coordinated by residues of motif C and the RNA product. This observation is corroborated by the lack of a second catalytic Mg2+ in the structure, the latter ion usually coordinated by the catalytic Asp760 in motif C and with the 3'-OH and phosphate of the last incorporated nucleotide of the RNA product. This ion plays a critical role in the positioning of the 3' end of the RNA product and the incoming NTP. Secondly, the hydrophobic methyl group of the AT-9010 ribose amplifies the inhibitory effect by creating a hydrophobic hindrance that prevents correct positioning of the ribose of the incoming NTP. This prevents further elongation of the product strand, irrespective of the presence of a 3'-OH, explaining why AT-9010 acts as a chain terminator. As a result, the second triphosphate AT-9010 is stalled at the +1-site position. The guanine is correctly base-paired with the cytosine (C26) of the template strand, and is further stabilized by residues Lys545 (motif F) and Ser682 (motif B), two residues important during the fidelity check, prior to incorporation (FIGS. 16C-D). The ribose group is shifted by 45° compared to its theoretical position due to hydrophobic repulsion, mostly driven by the methyl group of the incorporated AT-9010 (FIGS. 16D and 16F-G). As a result, the side chain of Asp623 (motif A), usually responsible for stabilizing the pyrophosphate after incorporation, is pushed away.

The α- and β-phosphates are coordinated by the Mg2+ and the γ-phosphate is stabilized by the Lys621 also in motif A and Lys798 in motif D. The distances between the α-phosphate and the 3'-OH necessary to allow metal coordination and the bonding event (for incorporation) are not respected, preventing incorporation. Rather it is observed that AT-9010 is in a varied structural position where the α- and β-phosphates are spatially overlapping the position of a pyrophosphate (β- and γ-phosphates) (FIGS. 16D and 16F-G).

Example 26: The NiRAN-Domain Binds AT-9010 at the UMPylation Active Site

Figure 17A:
FIG. 17A shows sequence conservation (outlined in chart) plotted onto NiRAN structure. Sequence alignment derived from structural superimposition of several pseudokinase structure and NiRAN. Conserved residues are the darkest shade.
Figure 17B:
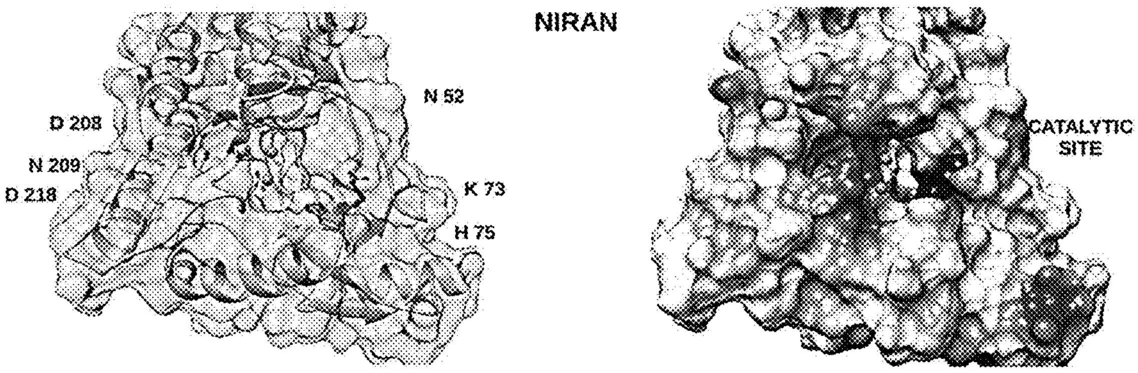
FIG. 17B shows a ribbon and surface representation of the NiRAN structure. Catalytic residues are labelled numerically and shown in sticks (left figure). Electrostatic representations of NiRAN ions are in dark shaded spheres (right figure). Catalytic site goes from the ions toward the flat opening. Below the ions is the entry of the cavity.
Figure 17C:
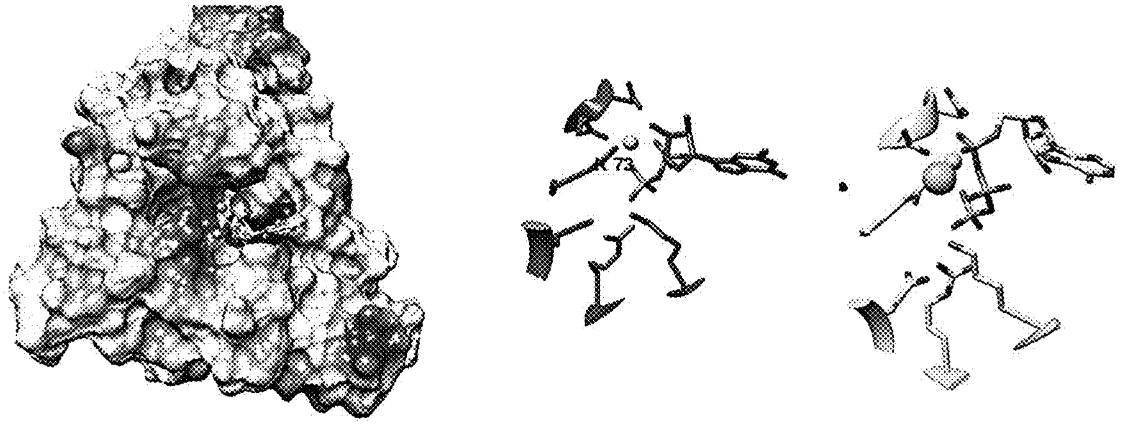
FIG. 17C shows an electrostatic representation of the NiRAN: GDP complex and detailed representation of the interaction between GDP, K73, and Mg2+ ion. The pseudo kinase SelO complex with ATP (non-hydrolysable analog) is shown for comparative purposes. The overall position is similar except for the flipped ribose.
Figure 17D:
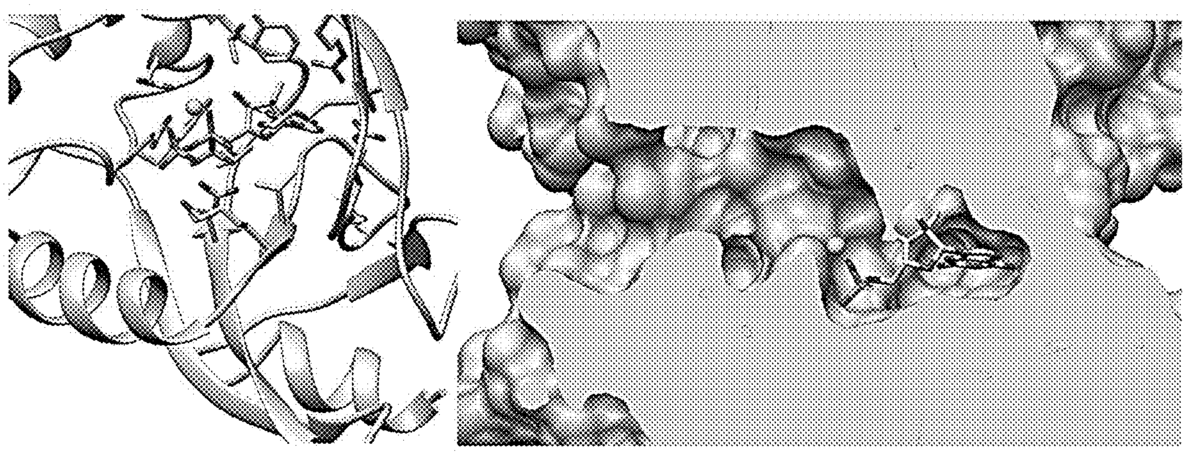
FIG. 17D shows a detailed stick representation of the AT-9010 binding at the NiRAN, and its sliced representation in the cavity.
Figure 17E:
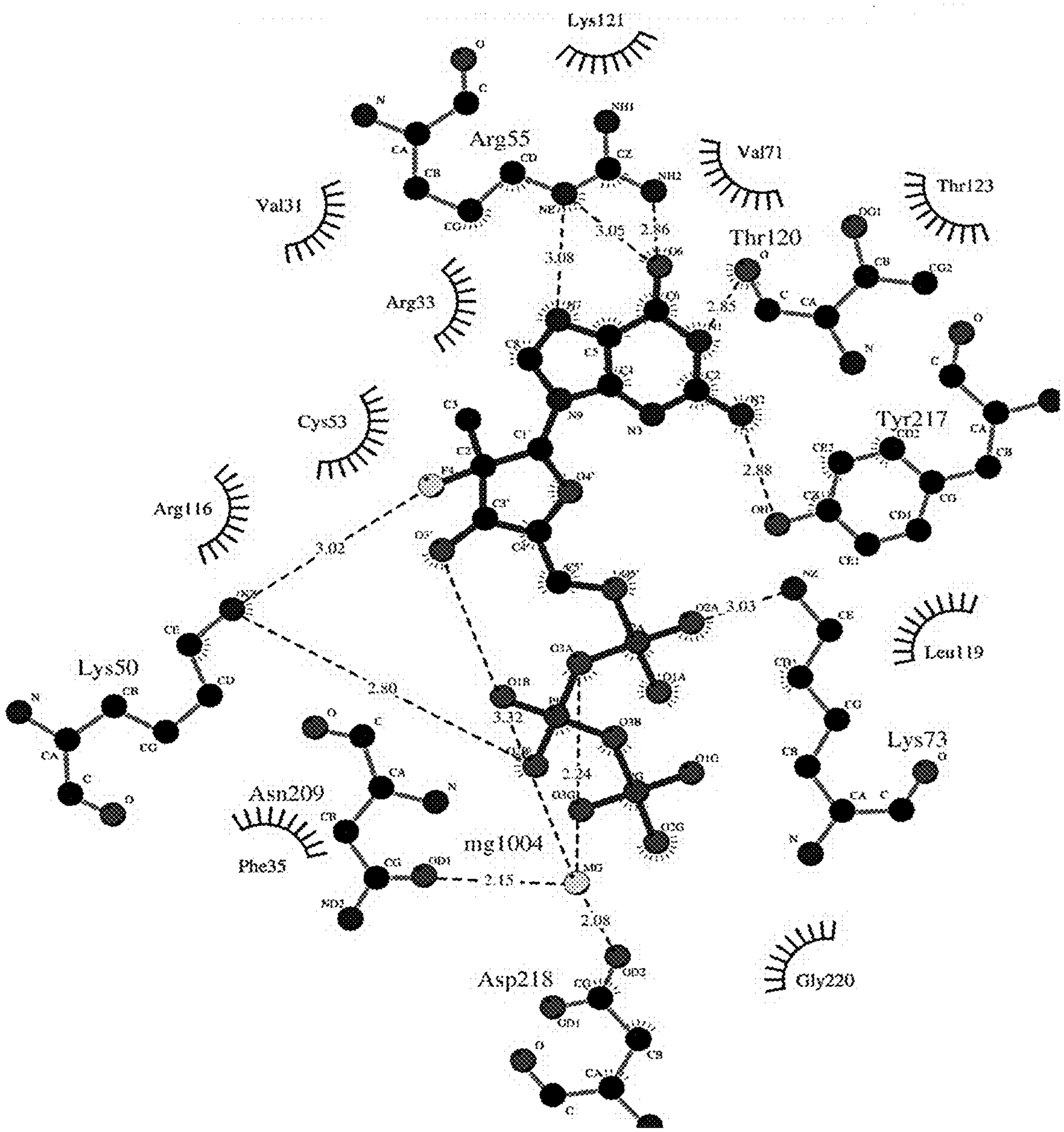
FIG. 17E shows a Ligplot 2D representation of the detailed interactions of AT-9010 binding in the cavity of the NiRAN.

The NiRAN-domain is structurally related to the pseudokinase family of enzymes (Slanina), allowing delineation of the catalytic residues of the enzyme (FIG. 17A). However, CoV-unique sequence and structural elements can also be identified for the NiRAN-domain. The structure shows AT-9010 in its diphosphate form, bound to the NiRAN-domain. The binding site is made of a closed cavity, which opens into a groove harboring two catalytic ions coordinated by the conserved Asn209 and Asp218 (see below). The groove further widens to a flat surface formed by the 2 β-strands (β2-β3 residues 33-48) (FIGS. 17B-C). The base and the modified ribose of AT-9010 fits snuggly in the cavity (FIG. 17D), while the α and β phosphates are coordinated in the groove by the two catalytic ions and Lys73. The guanine base is intensively stabilized by hydrophobic interaction and through hydrogen bonding with residues Arg55, Thr120 and Tyr217, residues which are conserved in CoV-NiRAN sequences (FIG. 17E), but are not present in other pseudokinases (FIG. 17A). The 2'-fluoro group of the modified ribose additionally stabilizes the nucleotide in the binding pocket through interaction with Lys50 (FIG. 17E). The binding mode of AT-9010 is reminiscent of the orientation of ATP bound to the casein kinase (Xu 1995) but strikingly different from the position of the nucleotide in the pseudokinase structures (Sreelatha, Yang) and a recently published GDP-bound NiRAN structure (Yan 2021). In contrast to the AT-9010-bound NiRAN reported here, the diphosphate moiety of GDP was buried in the closed cavity formed by Lys50, Asn52, Lys73, and Arg 116, and was coordinated by a single Mg2+ ion (FIG. 17E). Similarly, the pseudokinase structures with a non-hydrolysable NTP show the γ-phosphate binding in a cavity formed by equivalent residues, with the ribose stabilized along a wide surface close to the groove (FIG. 17C). It is thus reasonable to propose that AT-9010 has a unique binding mode, driven by both the hydrophobic nature of the cavity and the modified ribose. The base and ribose are stabilized in the cavity by conserved residues, accounting for a potent inhibition of the NiRAN function, consistent with enzymatic inhibition and thermal shift data.

Example 27. AT-511 (Compound 1A) does not Induce Mutations in the Viral Genome The mutagenic effect of AT-511 (Compound 1A) was compared to three reference compounds: Remdesivir, Molnupiravir, and GC 376.

Cell Line

HUH 7.5 cells were grown in Dulbecco's Modified Eagle's Medium High glucose (4500 mg/1) (Life Technologies) with 7.5% heat-inactivated fetal calf serum (FCS; Life Technologies), at 37° C. with 5% $CO_2$ with 1% penicillin/streptomycin (PS, 5000 U·mL-1 and 5000 μg·mL-1 respectively; Life Technologies), supplemented with 1% non-essential amino acids (Life Technologies) and L-Glutamine (Life Technologies).

Virus Strain

SARS-CoV-2 strain BavPatl was obtained from Pr. C. Drosten through EVA GLOBAL (https://www.european-virus-archive.com/).

To prepare the virus working stock, a 25 cm2 culture flask of confluent VeroE6 TMRPS S2 cells growing with MEM medium with 2.5% FCS was inoculated at a multiplicity of infection (MOI) of 0.001. Cell supernatant medium was harvested at the peak of replication and supplemented with 25 mM HEPES (Sigma-Aldrich) before being stored frozen in aliquots at −80° C. All experiments with infectious virus were conducted in a biosafety level 3 laboratory.

$EC_{50}$ and $CC_{50}$ Determination

One day prior to infection, $5\times10^4$ HUH7.5 cells −2 per well were seeded in 100 μL assay medium (containing 2.5% FCS) in 96 well culture plates. The next day, eight 2-fold serial dilutions of compounds in triplicate were added to the cells (25 μL/well, in assay medium) from 0.16 μM to 20 μM. On the culture plate, a control compound (G376, Medchemexpress) was added in duplicate with eight 2-fold serial dilutions (0.16 μM to 20 μM). Four virus control wells were supplemented with 25 μL of assay medium. After 15 min, 25 μL of a virus mix diluted in medium was added to the wells.

The amount of virus working stock used was calibrated prior to the assay, based on a replication kinetics, so that the viral replication was still in the exponential growth phase for the readout as previously described (Delang et al., 2016; Touret et al., 2020, 2019). In this experiment this corresponded to 300 $TCID_{50}$/well. Four cell control wells (i.e., with no virus) were supplemented with 50 μL of assay medium. Plates were incubated for 2 days at 37° C. prior to quantification of the viral genome by real-time RT-PCR. To do so, 100 μL of viral supernatant was collected in S-Block (Qiagen) previously loaded with VXL lysis buffer containing proteinase K and RNA carrier. RNA extraction was performed using the Qiacube HT automat and the QIAamp 96 DNA kit HT following manufacturer instructions. Viral RNA was quantified by real-time RT-qPCR (GoTaq 1-step qRt-PCR, Promega) using 3.8 μL of extracted RNA and 6.2 μL of RT-qPCR mix and standard fast cycling parameters, i.e., 10 min at 50° C., 2 min at 95° C., and 40 amplification cycles (95° C. for 3 sec followed by 30 sec at 60° C.). Quantification was provided by four 2 log serial dilutions of an appropriate T7-generated synthetic RNA standard of known quantities (102 to 108 copies/reaction). RT-qPCR reactions were performed on QuantStudio 12K Flex Real-Time PCR System (Applied Biosystems) and analyzed using QuantStudio 12K Flex Applied Biosystems software v1.2.3. Primers and probe sequences, which target SARS-CoV-2 N gene, were: Fw: GGCCGCAAATTGCACAAT (SEQ ID NO: 4); Rev: CCAATGCGCGACATTCC (SEQ ID NO: 5); Probe: FAM-CCCCCAGCGCTTCAGCGTTCT-BHQ1 (SEQ ID NO: 6). Viral inhibition was calculated as follows:

100*(quantity mean VC−sample quantity)/quantity mean VC

The 50% and 90% effective concentrations ($EC_{50}$, $EC_{90}$; compound concentration required to inhibit viral RNA replication by 50% and 90%) were determined using logarithmic interpolation as previously described (Touret et al., 2019/2020). For the evaluation of the 50% cytotoxic concentrations ($CC_{50}$), the same culture conditions as for the determination of the $EC_{50}$ were used, without addition of the virus, and cell viability was measured using CellTiter Blue® (Promega) following manufacturer's instructions. $CC_{50}$ was determined using logarithmic interpolation. All data obtained were analyzed using GraphPad Prism 7 software (Graphpad software).

Implementation of the Antiviral Assay

Figure 18:
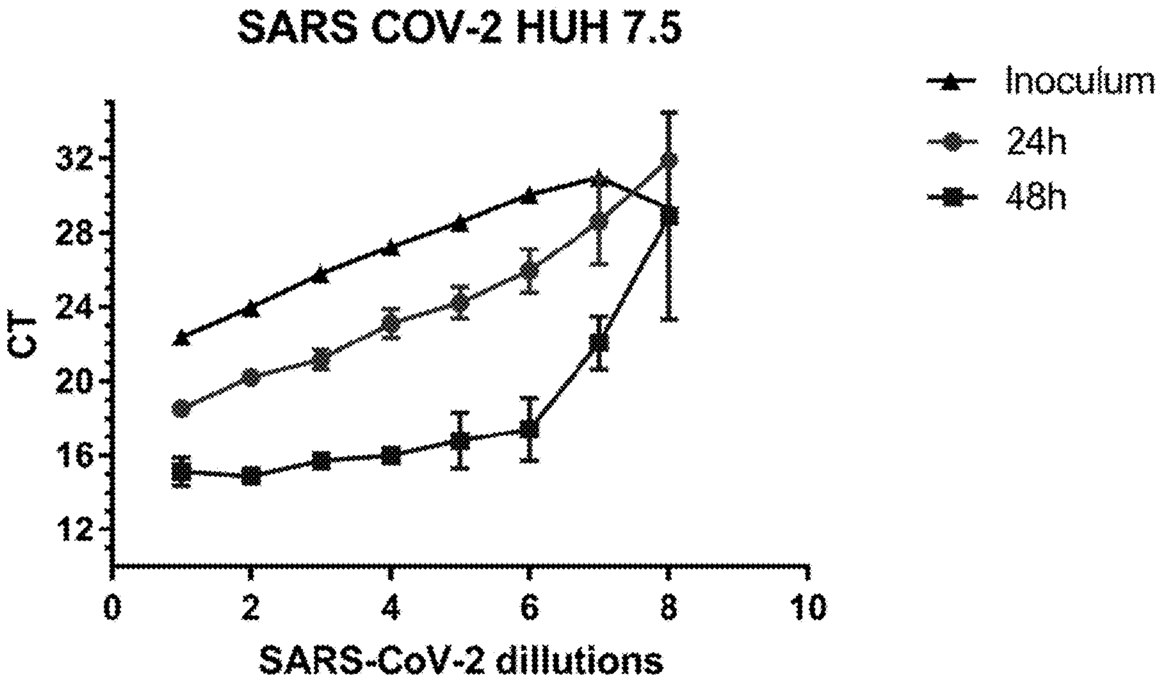
FIG. 18 is a graph showing the SARS-CoV-2 replication in HUH 7.5 cells at 24- and 48-hours post-infection as described in Example 27. The x-axis is the cycle threshold (CT) and the y-axis is the SARS-CoV-2 dilution.

In order to set-up an antiviral assay in HUH 7.5 cells, the viral replication of SARS-COV-2 was first evaluated in the cells. HUH7.5 cells were infected with ⅓-fold dilutions of SARS-CoV-2 in triplicate and the cell supernatant was collected at 24- and 48-hours post-infection. In order to evaluate the viral replication (de novo viral particles production), the final viral production was compared to the inoculum: the same virus quantity but with no cell in the well (FIG. 18). The different dilutions were analyzed to assess reproducibility of our triplicates and the phase of the viral replication. Finally, to choose the right dilution, the following criteria were identified: i) be at the end of the exponential phase/beginning of the plateau, ii) with a sufficient replication (6CT corresponding to −2 log) iii) as well as low variability between experiments. Results are presented in FIG. 18. At 24-hour post-infection, viral replication is not sufficient for an antiviral assay as replication inhibition effect would produce faint differences in CT (cycle threshold) in comparison with the inoculum, actually less than 5 CT. At 48 h post-infection, the viral replication led to more than 2 logs/6 CT for the six first dilutions. The third dilution is at the beginning of the plateau/end of exponential phase, shows more than 3 log of difference with the inoculum, and almost no variability in the triplicates. Thus dilution 3, corresponding to 300 $TCID_{50}$/well, meets all the criteria for the optimal conditions of the antiviral assay, and was selected for the determination of the $EC_{50}$.

Antiviral Assay with AT-511

Figure 19:
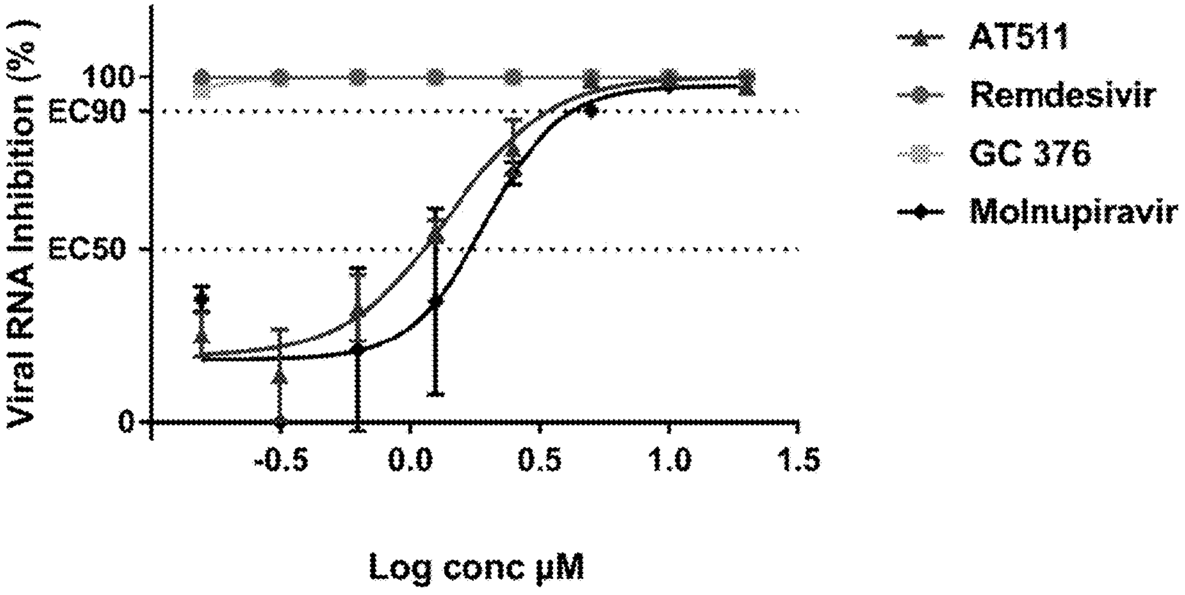
FIG. 19 shows the viral inhibition of AT-511, Remdesivir, GC 376, and Molnupiravir as discussed in Example 27 and shown in Table 10. The x-axis is the viral RNA inhibition measured in percent and the y-axis is the log concentration measured in μM.
Figure 20A:
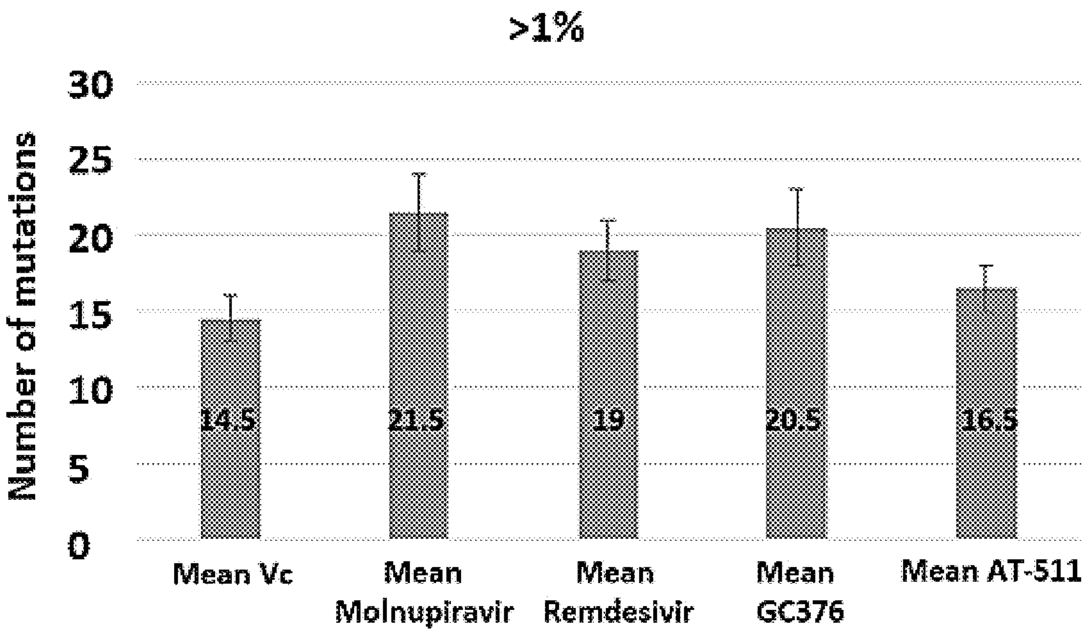
FIG. 20A is the number of mutations observed in the presence of AT-511, Remdesivir, GC 376, and Molnupiravir when a frequency threshold of >1% is applied as described in Example 27. The "frequency threshold" is defined as the presence of a mutation at a position of the genome observed in at least 0.1% of reads covering the given position. The x-axis is labelled with the compound and the y-axis the number of mutations.
Figure 20B:
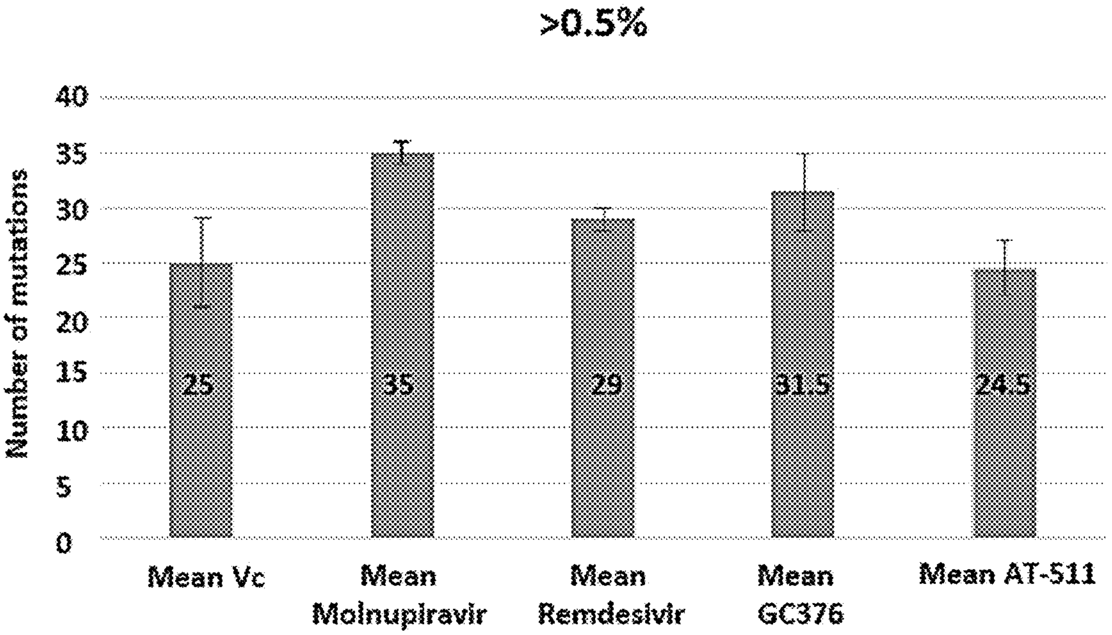
FIG. 20B is the number of mutations observed in the presence of AT-511, Remdesivir, GC 376, and Molnupiravir when a frequency threshold of >0.5% is applied as described in Example 27. The "frequency threshold" is defined as the presence of a mutation at a position of the genome observed in at least 0.1% of reads covering the given position. The x-axis is labelled with the compound and the y-axis the number of mutations.
Figure 20C:
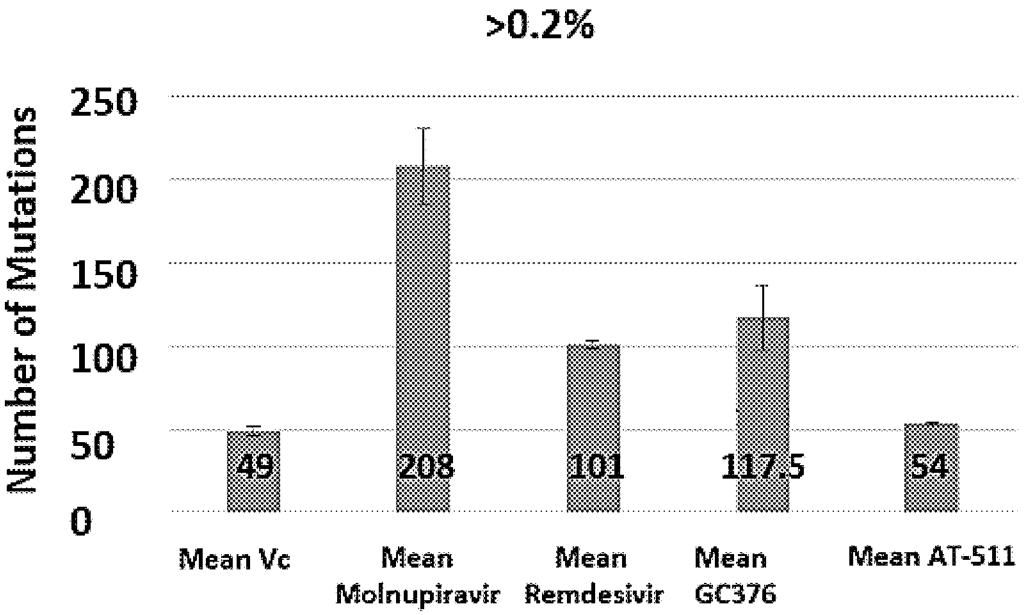
FIG. 20C is the number of mutations observed in the presence of AT-511, Remdesivir, GC 376, and Molnupiravir when a frequency threshold of >0.2% is applied as described in Example 27. The "frequency threshold" is defined as the presence of a mutation at a position of the genome observed in at least 0.1% of reads covering the given position. The x-axis is labelled with the compound and the y-axis the number of mutations.
Figure 20D:
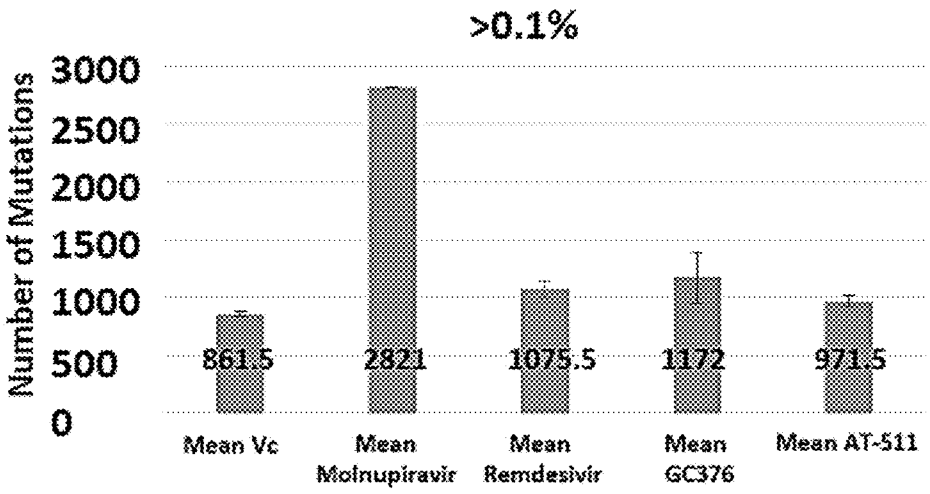
FIG. 20D is the number of mutations observed in the presence of AT-511, Remdesivir, GC 376, and Molnupiravir when a frequency threshold of >0.1% is applied as described in Example 27. The "frequency threshold" is defined as the presence of a mutation at a position of the genome observed in at least 0.1% of reads covering the given position. The x-axis is labelled with the compound and the y-axis the number of mutations.

AT-511 antiviral activity in HUH7.5 was evaluated and compared to three reference antiviral compounds: Remdesivir, Molnupiravir and GC376. All compounds were assessed in the same conditions and at the same concentrations: starting from 20 μM to 0.16 μM. (FIG. 19). We also evaluated the compound cytotoxicity in the same conditions (Table 10). No cytotoxicity was observed at these concentrations in HUH 7.5 cells (Table 10). Remdesivir and GC376 showed potent inhibition of the viral replication in this cell line with $EC_{50}$ values below 0.15 μM (FIG. 19; Table 10). AT-511 and Molnupiravir also have antiviral activity with an $EC_{50}$ of 1.1 and 1.7 μM, respectively (FIG. 19; Table 10).

TABLE 10

Antiviral Activity and Cytotoxicity of Certain Compounds in HUH7.5 Cells

| μM | AT-511 | Remdesivir | Molnupiravir | GC376 |
|---|---|---|---|---|
| $EC_{50}$ | 1.13 | <0.15 | 1.71 | <0.15 |
| $EC_{90}$ | 3.39 | <0.15 | 4.21 | <0.15 |
| $CC_{50}$ | >20 | >20 | >20 | >20 |

Evaluation of the Mutagenic Effect of the Four Antivirals

The mutagenic effect of the four compounds was determined by comparing the viral RNA after the end-point of the antiviral assay with the viral RNA obtained in the same culture conditions but with no antiviral (Virus control, hereafter named Vc). Viral RNA was extracted from the cell culture supernatant in the condition of the antiviral assay where compounds were tested at 5 μM, so all the compounds are at a concentration higher than their $EC_{90}$.

Thirteen overlapping amplicons were produced from the extracted viral RNA using the SuperScript IV One-Step RT-PCR System (Thermo Fisher Scientific) and specific primers (Table 11).

TABLE 11

List of Primers for Genome Amplification

| SEQ ID NO. | Name | Sequence | Start | End | Tm | GC% |
|---|---|---|---|---|---|---|
| 7 | 1F | ACCAACCAACTTTCGATCTCTTGT | 31 | 54 | 60.69 | 41.67 |
| 8 | 1R | TTTCGAGCAACATAAGCCCGTT | 2621 | 2642 | 61.13 | 45.45 |
| 9 | 2F | AACAACCTACTAGTGAAGCTGTTGA | 2565 | 2598 | 60.16 | 40.00 |

TABLE 11-continued

| List of Primers for Genome Amplification | | | | | | |
|---|---|---|---|---|---|---|
| SEQ ID NO. | Name | Sequence | Start | End | Tm | GC% |
| 10 | 2R | TTGACATGTCCACAACTTGCGT | 5006 | 5027 | 61.26 | 45.45 |
| 11 | 3F | CTTCTTTCTTTGAGAGAAGTGAGGACT | 4940 | 4966 | 60.69 | 40.74 |
| 12 | 3R | TGCCAAAAACCACTCTGCAACT | 7234 | 7255 | 61.47 | 45.45 |
| 13 | 4F | GTGGTTTAGATTCTTTAGACACCTATCCT | 7143 | 7171 | 60.59 | 37.93 |
| 14 | 4R | AGGTGTGAACATAACCATCCACTG | 9644 | 9667 | 60.81 | 45.83 |
| 15 | 5F | ACTCATTCTTACCTGGTGTTTATTCTGT | 9558 | 9585 | 60.69 | 35.71 |
| 16 | 5R | CTGGACACATTGAGCCCACAAT | 11923 | 11944 | 61.14 | 50.00 |
| 17 | 6F | TGCACATCAGTAGTCTTACTCTCAGT | 11864 | 11889 | 61.25 | 42.31 |
| 18 | 6R | TGTGACTCTGCAGTTAAAGCCC | 14186 | 14207 | 60.81 | 50.00 |
| 19 | 7F | AGACGGTGACATGGTACCACAT | 13758 | 13779 | 61.41 | 50.00 |
| 20 | 7R | ACACGTTGTATGTTTGCGAGCA | 15354 | 15375 | 61.63 | 45.45 |
| 21 | 8F | TGATTGTTACGATGGTGGCTGT | 14880 | 14901 | 60.29 | 45.45 |
| 22 | 8R | GTGCAGGTAATTGAGCAGGGTC | 17437 | 17458 | 61.52 | 54.55 |
| 23 | 9F | TGATTTGAGTGTTGTCAATGCCAG | 17382 | 17405 | 60.26 | 41.67 |
| 24 | 9R | ATTAGCAGCAATGTCCACACCC | 19845 | 19886 | 61.21 | 50.00 |
| 25 | 10F | AATGTAGCATTTGAGCTTTGGGC | 19774 | 19796 | 60.37 | 43.48 |
| 26 | 10R | ACCAGCTGTCCAACCTGAAGAA | 22324 | 22345 | 61.82 | 50.00 |
| 27 | 11F | ACATCACTAGGTTTCAAACTTTACTTGC | 22263 | 22290 | 60.68 | 35.71 |
| 28 | 11R | ATGAGGTGCTGACTGAGGGAAG | 24715 | 24736 | 61.74 | 54.55 |
| 29 | 12F | GTCAGAGTGTGTACTTGGACAATCA | 24649 | 24673 | 60.74 | 44.00 |
| 30 | 12R | ACTGCTACTGGAATGGTCTGTGT | 27142 | 27164 | 61.58 | 47.83 |
| 31 | 13F | GGTGACTCAGGTTTTGCTGCAT | 27087 | 27108 | 61.65 | 50.00 |
| 32 | 13R | CGTAAACGGAAAAGCGAAAACGT | 29571 | 29593 | 61.08 | 43.48 |

PCR products were pooled at equimolar proportions and fragmented by sonication in ~200 bp long fragments. Libraries were built by adding barcodes for sample identification to the fragmented DNA using AB Library Builder System (ThermoFisher Scientific). Quantification step by real-time PCR using Ion Library TaqMan™ Quantitation Kit (Thermo Fisher Scientific) was performed. An emulsion PCR of the pools and loading on 530 chip was done using the automated Ion Chef instrument (ThermoFisher). Sequencing was performed on the S5 Ion torrent technology v5.12 (Thermo Fisher Scientific). Consensus sequences were obtained after trimming of reads (reads with quality score <0.99, and length <100 pb were removed and the 30 first and 30 last nucleotides were removed from the reads) mapping of the reads on a reference (determined following Blast of De Novo contigs) using CLC genomics workbench software v.20 (Qiagen). A de novo contig was also produced to ensure that the consensus sequence was not affected by the reference sequence. Quasi species with frequency over 1, 0.5, 0.2 and 0.1% were analyzed.

Raw Sequencing Results

Results of the sequencing are presented in Table 12.

TABLE 12

| Assessment of Sequencing Data | | | | |
|---|---|---|---|---|
| Assay | Number of reads after trimming | Number of matching reads | Average coverage (Number of reads per position) | Average Median coverage (Number of reads per position) |
| Molnupiravir 1 | 20 768 161 | 16 322 335 | 99 408 | 92 264 |
| Molnupiravir 2 | 16 324 258 | 1 632 258 | 95 108 | 89 143 |
| Vc 1 | 17 821 405 | 17 815 993 | 109 753 | 106 058 |
| Vc 2 | 14 971 419 | 14 911 091 | 87 359 | 85 334 |
| AT 511 1 | 21 424 942 | 21 359 545 | 136 907 | 131 919 |
| AT 511 2 | 18 294 504 | 18 223 771 | 108 465 | 102 679 |
| Remdesivir 1 | 14 720 155 | 14 406 008 | 86 700 | 69 146 |
| Remdesivir 2 | 20 379 943 | 19 786 728 | 118 267 | 94 419 |
| GC 376 1 | 19 588 783 | 18 927 046 | 110 631 | 106 566 |
| GC 376 2 | 18 454 730 | 18 149 803 | 99 101 | 102 344 |

The average coverage is >80 000 and suitable for a statistical analysis of the sub-population as low as 0.1% at each position.

The consensus sequence of the 10 samples was determined and as expected, no difference with the reference sequence and between each other (no mutation with frequency >50% at a given position).

Frequency of Mutations

The frequency of mutations observed for the virus grown in HUH 7.5 is slightly higher compared to VeroE6 (Shannon et al., 2020). The "frequency threshold" is defined as the presence of a mutation at a position of the genome observed in at least 0.1% of reads covering the given position.

The number of mutations was defined for each experiment (Vc, Molnupiravir, Remdesivir, AT511, and GC376) applying a frequency threshold at 1, 0.5, 0.2 and 0.1% as presented below and in FIG. 20A-FIG. 20D. Table 13A and Table 13B show the number of mutations and type of transitions with frequency >0.1% for the virus control. Table 14A-17B shown the number of mutations and the type of transitions for Molnupiravir, Remdesivir, AT511, and GC376.

No significant difference in the number of mutations was observed between the genomic data from all the conditions with frequency threshold >0.5%. As expected, the genomic RNA in presence of effective concentrations of Molnupiravir showed a significant increase in the number of mutations compared to Vc at 0.2 and 0.1% threshold (Table 14A and Table 14B). The mutations were mainly transitions (transversions not shown).

TABLE 13A

Number of Mutations for Virus Control

| Frequency Threshold | Vc 1 Number of Mutations Detected | Vc 2 Number of Mutations Detected | Mean Number of Mutations Detected |
|---|---|---|---|
| >1% | 16 | 13 | 14.5 |
| >0.5% | 29 | 21 | 25 |
| >0.2% | 46 | 52 | 49 |
| >0.1% | 842 | 881 | 861.5 |

TABLE 13B

Type of Transitions with Frequency >0.1% for Virus Control

| Type of Mutation | Number of Mutations Vc 1 | Number of Mutations Vc 2 | Mean |
|---|---|---|---|
| T > C | 412 | 437 | 206 |
| A > G | 369 | 386 | 184.5 |
| C > T | 19 | 18 | 9.5 |
| G > A | 6 | 5 | 3 |

TABLE 14A

Number of Mutations for Molnupiravir

| Frequency Threshold | Molnupiravir 1 Number of Mutations Detected | Molnupiravir 2 Number of Mutations Detected | Mean Number of Mutations Detected |
|---|---|---|---|
| >1% | 24 | 19 | 21.5 |
| >0.5% | 36 | 34 | 35 |
| >0.2% | 231 | 185 | 208 |
| >0.1% | 2818 | 2824 | 2821 |

TABLE 14B

Type of Transitions with Frequency >0.1% for Molnupiravir

| Type of Mutation | Number of Mutations Molnupiravir 1 | Number of Mutations Molnupiravir 2 | Mean |
|---|---|---|---|
| T > C | 932 | 889 | 910.5 |
| A > G | 813 | 871 | 842 |
| C > T | 602 | 582 | 592 |
| G > A | 385 | 385 | 385 |

Remdesivir and GC376 may induce a slight increase of the number of mutations when compared to the virus control when the threshold is set at 0.2%. The trend is less visible at 0.1%, suggesting the direct or indirect mutagenic is limited.

TABLE 15A

Number of Mutations for Remdesivir

| Frequency Threshold | Remdesivir 1 Number of Mutations Detected | Remdesivir 2 Number of Mutations Detected | Mean Number of Mutations Detected |
|---|---|---|---|
| >1% | 21 | 17 | 19 |
| >0.5% | 30 | 28 | 29 |
| >0.2% | 99 | 103 | 101 |
| >0.1% | 1137 | 1014 | 1075.5 |

TABLE 15B

Type of Transitions with Frequency >0.1% for Remdesivir

| Type of Mutation | Number of Mutations Remdesivir 1 | Number of Mutations Remdesivir 2 | Mean |
|---|---|---|---|
| T > C | 535 | 425 | 480 |
| A > G | 438 | 412 | 425 |
| C > T | 77 | 68 | 72.5 |
| G > A | 12 | 15 | 13.5 |

TABLE 16A

Number of Mutations for GC 376

| Frequency Threshold | GC 376 1 Number of Mutations Detected | GC 376 2 Number of Mutations Detected | Mean Number of Mutations Detected |
|---|---|---|---|
| >1% | 23 | 18 | 20.5 |
| >0.5% | 35 | 28 | 31.5 |
| >0.2% | 137 | 98 | 117.5 |
| >0.1% | 1395 | 949 | 1172 |

TABLE 16B

Type of Transitions with Frequency >0.1% for GC 376

| Type of Mutation | Number of Mutations GC 376 1 | Number of Mutations GC 376 2 | Mean |
|---|---|---|---|
| T > C | 662 | 403 | 532.5 |
| A > G | 545 | 368 | 465.5 |
| C > T | 51 | 73 | 62 |
| G > A | 9 | 20 | 14.5 |

The viral RNAs in presence of AT-511 at effective concentration did not show an increased number of mutations compared to Vc at both 0.2 and 0.1% frequency threshold.

TABLE 17A

| Number of Mutations for AT-511 | | | |
|---|---|---|---|
| Frequency Threshold | AT-511 1 Number of Mutations Detected | AT-511 2 Number of Mutations Detected | Mean Number of Mutations Detected |
| >1% | 15 | 18 | 16.5 |
| >0.5% | 22 | 27 | 24.5 |
| >0.2% | 53 | 55 | 54 |
| >0.1% | 1020 | 923 | 971.5 |

TABLE 17B

| Type of Transitions with Frequency >0.1% for AT-511 | | | |
|---|---|---|---|
| Type of Mutation | Number of Mutations AT-511 1 | Number of Mutations AT-511 2 | Mean |
| T > C | 489 | 457 | 473 |
| A > G | 454 | 404 | 429 |
| C > T | 22 | 27 | 24.5 |
| G > A | 7 | 5 | 6 |

Example 28

Interim data from an ongoing clinical trial in hospitalized patients with COVID-19 showed that 550 mg AT-527 (Compound 2A) twice a day (BID) resulted in rapid and sustained reduction of viral replication. Dosing of AT-527 was informed by predicted lung exposure of its active triphosphate metabolite AT-9010 using plasma level of its surrogate nucleoside metabolite AT-273, to exceed the in vitro 90% effective concentration ($EC_{90}$=0.5 μM) of AT-527 for inhibiting SARS-CoV-2 replication. However, direct assessment of drug disposition in the lung is necessary to ensure attainment of antiviral drug levels at the primary site of SARS-CoV-2 infection.

Methods

Two cohorts of 8 healthy participants have been enrolled to receive AT-527 at 275 or 550 mg BID orally for 2.5 days. At 4 and 12 h following the last dose, each participant (4/timepoint/cohort) underwent a single bronchoalveolar lavage (BAL) via a standard bronchoscope. Intensive plasma PK sampling was also performed after the last dose. BAL and plasma samples were assayed for AT-273. AT-273 levels in lung epithelial lining fluid (ELF) were calculated by correcting for urea levels in the BAL and the corresponding plasma samples. Safety assessments included adverse events (AEs), vital signs, electrocardiograms (ECGs), and standard laboratory tests.

Results

Figure 21:
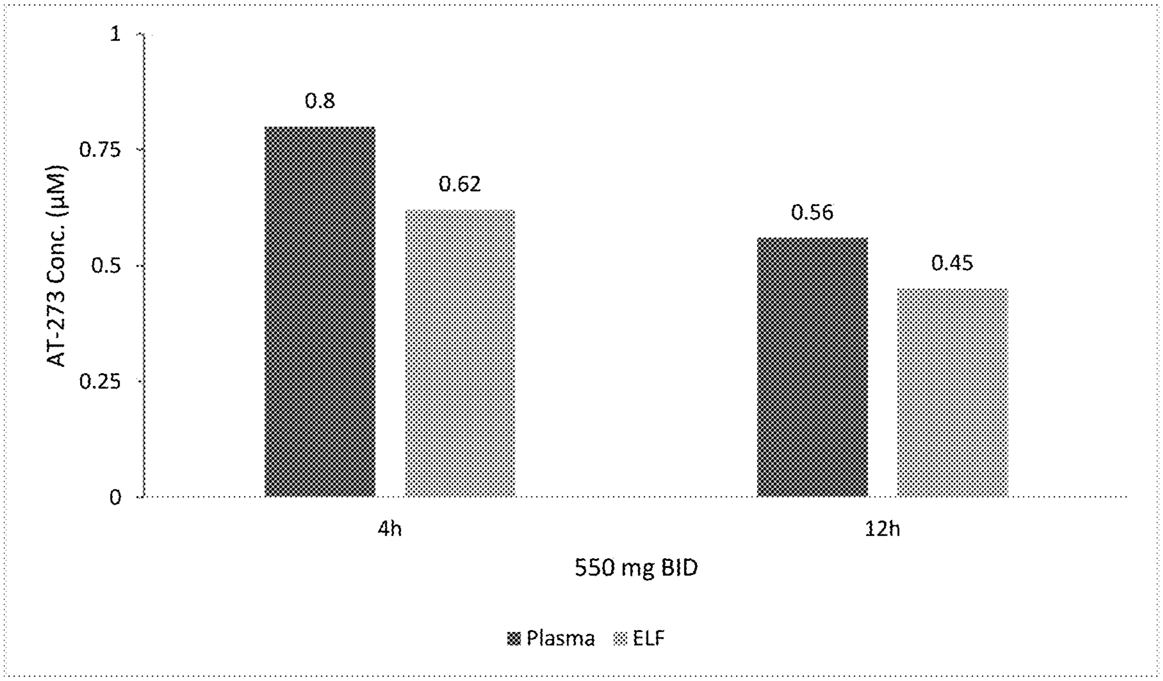
FIG. 21 is a graph showing the concentration (μM) of AT-527 (Compound 2A) metabolite AT-273 in plasma and lung epithelial lining fluid (ELF) at 4 and 12 h following the last administration of AT-527 at 550 mg BID orally for 2.5 days.

AT-527 was well tolerated with few self-limiting AEs which were nonserious and non-drug related. Mean AT-273 levels in plasma and lung ELF were dose-related and achieved the target level of 0.5 μM with AT-527 550 mg BID (FIG. 21). These results suggest higher AT-273 levels in ELF could be achieved with higher doses of AT-527. ELF and plasma levels of AT-273 were significantly correlated (r=0.86, P<0.001), allowing for reliable prediction of ELF levels from the more commonly available plasma samples.

CONCLUSIONS

Antivirally relevant drug exposure was achieved in the lungs with AT-527 550 mg BID, and higher AT-527 doses likely provide ELF AT-273 levels more consistently above the target level. These results further confirm the efficacy of treatment and prophylaxis with Compound 2A (AT-527) for SARS-CoV-2 infection, using doses from 550 mg/day to up to 1100-mg or more twice a day.

This specification has been described with reference to embodiments of the invention. Given the teaching herein, one of ordinary skill in the art will be able to modify the invention for a desired purpose and such variations are considered within the scope of the invention.

We claim:

1. A method for the treatment of an infection with a remdesivir-resistant strain of SARS-COV-2 virus in a human in need thereof, comprising administering an effective amount of a compound of Formula I:

Formula I

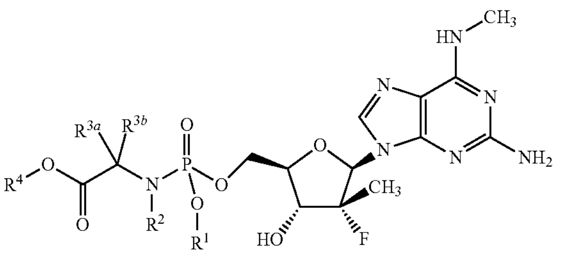

or a pharmaceutically acceptable salt thereof, optionally in a pharmaceutically acceptable carrier, wherein:

$R^1$ is hydrogen, $C_{1-6}$alkyl, $C_{3-7}$cycloalkyl, aryl or aryl-$C_{1-4}$alkyl;

$R^2$ is hydrogen or $C_{1-6}$alkyl;

$R^{3a}$ and $R^{3b}$ are independently selected from hydrogen, $C_{1-6}$alkyl, and $C_{3-7}$cycloalkyl; and $R^4$ is hydrogen, $C_{1-6}$alkyl, $C_{1-6}$haloalkyl, $C_{3-7}$cycloalkyl, or aryl-$C_{1-4}$alkyl.

2. The method of claim 1, wherein $R^1$ is aryl.

3. The method of claim 1, $R^2$ is hydrogen.

4. The method of claim 1, wherein $R^{3a}$ is $C_{1-6}$alkyl and $R^{3b}$ is hydrogen.

5. The method of claim 1, wherein $R^{3a}$ is methyl and $R^{3b}$ is hydrogen.

6. The method of claim 1, wherein $R^4$ is $C_{1-6}$alkyl.

7. The method of claim 1, wherein $R^4$ is methyl, ethyl or isopropyl.

8. The method of claim 7, wherein $R^4$ is isopropyl.

9. The method of claim 1, wherein the pharmaceutically acceptable carrier is in a dosage form suitable for oral administration.

10. The method of claim 9, wherein the dosage form is a solid dosage form.

11. The method of claim 10, wherein the solid dosage form is a tablet.

12. The method of claim 10, wherein the solid dosage form is a capsule.

13. The method of claim 9, wherein the dosage form is a liquid dosage form.

14. The method of claim 13, wherein the liquid dosage form is a solution or a suspension.

15. A method for the treatment of an infection with a remdesivir-resistant strain of SARS-COV-2 virus in a human in need thereof, comprising administering an effective amount of Compound 1:

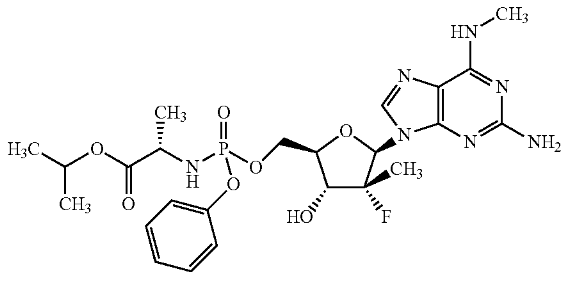 [SMILES: CNc1nc(N)nc2c1ncn2[C@@H]1O[C@H](COP(=O)(N[C@@H](C)C(=O)OC(C)C)Oc2ccccc2)[C@@H](O)[C@@]1(C)F]

or a pharmaceutically acceptable salt thereof, optionally in a pharmaceutically acceptable carrier.

16. The method of claim 15, comprising administering an effective amount of Compound 1A

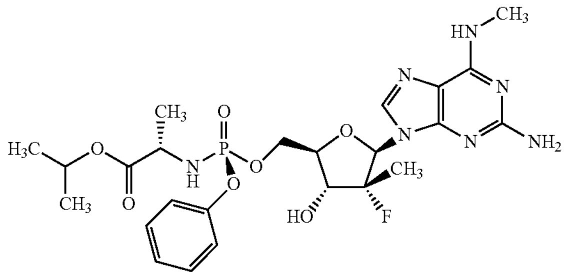 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

or a pharmaceutically acceptable salt thereof, optionally in a pharmaceutically acceptable carrier.

17. The method of claim 15, comprising administering an effective amount of Compound 1B

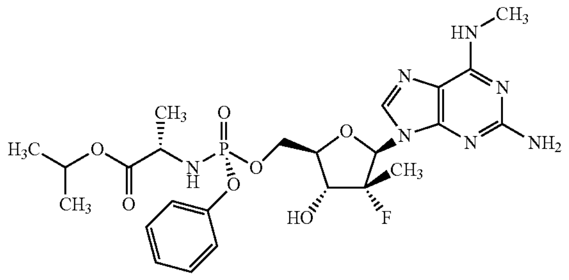 [SMILES: CNc1nc(N)nc2c1ncn2[C@@H]1O[C@H](CO[P@](=O)(N[C@@H](C)C(=O)OC(C)C)Oc2ccccc2)[C@@H](O)[C@@]1(C)F]

or a pharmaceutically acceptable salt thereof, optionally in a pharmaceutically acceptable carrier.

18. The method of claim 16, comprising administering an effective amount of Compound 1A

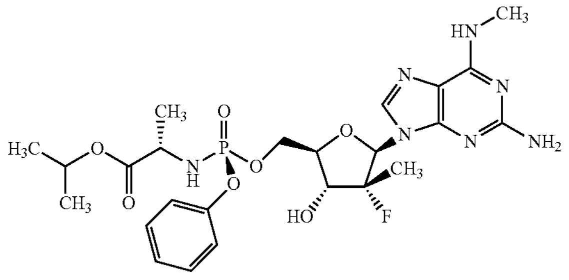 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

in an oral dosage of about 550 mg of Compound 1A twice a day to a human in need thereof.

19. The method of claim 18, wherein the oral dosage form is a tablet, gelcap, pill, or capsule.

20. The method of claim 15, comprising administering an effective amount of Compound 2

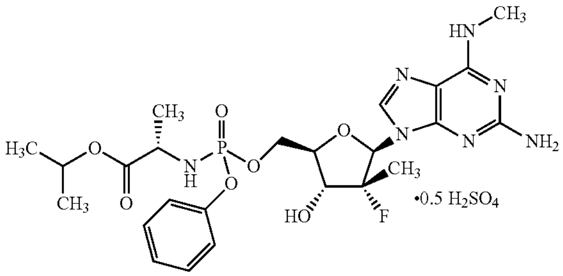 [SMILES: CNc1nc(N)nc2c1ncn2[C@@H]1O[C@H](COP(=O)(N[C@@H](C)C(=O)OC(C)C)Oc2ccccc2)[C@@H](O)[C@@]1(C)F]

optionally in a pharmaceutically acceptable carrier.

21. The method of claim 20, comprising administering an effective amount of Compound 2A

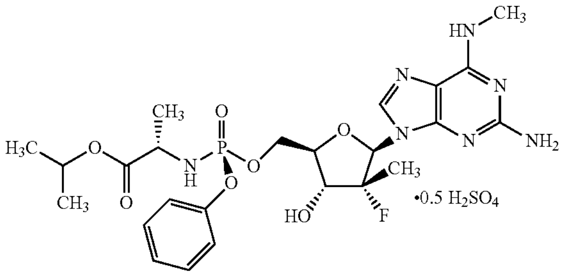 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

optionally in a pharmaceutically acceptable carrier.

22. The method of claim 20, comprising administering an effective amount of Compound 2B

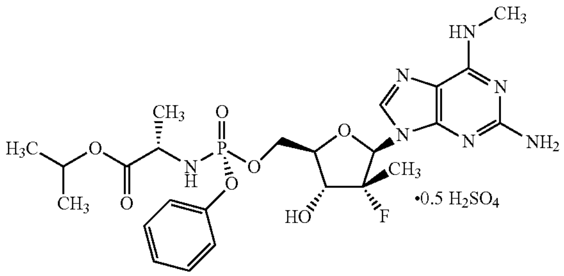 [SMILES: CNc1nc(N)nc2c1ncn2[C@@H]1O[C@H](CO[P@](=O)(N[C@@H](C)C(=O)OC(C)C)Oc2ccccc2)[C@@H](O)[C@@]1(C)F]

optionally in a pharmaceutically acceptable carrier.

23. The method of claim 21, wherein the pharmaceutically acceptable carrier is in a dosage form suitable for oral administration.

24. The method of claim 23, wherein the dosage form is a solid dosage form.

25. The method of claim 24, wherein the solid dosage form is a tablet.

26. The method of claim 24, wherein the solid dosage form is a capsule.

27. The method of claim 23, wherein the dosage form is a liquid dosage form.

28. The method of claim 27, wherein the liquid dosage form is a solution or a suspension.

* * * * *

SEQUENCE LISTING

```
Sequence total quantity: 32
SEQ ID NO: 1            moltype = AA  length = 23
FEATURE                 Location/Qualifiers
source                  1..23
                        mol_type = protein
                        organism = synthetic construct
SEQUENCE: 1
HHHHHHHHWS HPQFEKENLY FQG                                    23

SEQ ID NO: 2            moltype = AA  length = 21
FEATURE                 Location/Qualifiers
source                  1..21
                        mol_type = protein
                        organism = synthetic construct
SEQUENCE: 2
GLNDIFEAQK IEWHEHHHHH H                                      21

SEQ ID NO: 3            moltype = AA  length = 21
FEATURE                 Location/Qualifiers
source                  1..21
                        mol_type = protein
                        organism = synthetic construct
SEQUENCE: 3
HHHHHHDYKD DDDKENLYFQ G                                      21

SEQ ID NO: 4            moltype = DNA  length = 18
FEATURE                 Location/Qualifiers
source                  1..18
                        mol_type = other DNA
```

-continued

```
                        organism = synthetic construct
SEQUENCE: 4
ggccgcaaat tgcacaat                                                18

SEQ ID NO: 5            moltype = DNA  length = 17
FEATURE                 Location/Qualifiers
source                  1..17
                        mol_type = other DNA
                        organism = synthetic construct
SEQUENCE: 5
ccaatgcgcg acattcc                                                 17

SEQ ID NO: 6            moltype = DNA  length = 21
FEATURE                 Location/Qualifiers
source                  1..21
                        mol_type = other DNA
                        organism = synthetic construct
SEQUENCE: 6
cccccagcgc ttcagcgttc t                                            21

SEQ ID NO: 7            moltype = DNA  length = 24
FEATURE                 Location/Qualifiers
source                  1..24
                        mol_type = other DNA
                        organism = synthetic construct
SEQUENCE: 7
accaaccaac tttcgatctc ttgt                                         24

SEQ ID NO: 8            moltype = DNA  length = 22
FEATURE                 Location/Qualifiers
source                  1..22
                        mol_type = other DNA
                        organism = synthetic construct
SEQUENCE: 8
tttcgagcaa cataagcccg tt                                           22

SEQ ID NO: 9            moltype = DNA  length = 25
FEATURE                 Location/Qualifiers
source                  1..25
                        mol_type = other DNA
                        organism = synthetic construct
SEQUENCE: 9
aacaacctac tagtgaagct gttga                                        25

SEQ ID NO: 10           moltype = DNA  length = 22
FEATURE                 Location/Qualifiers
source                  1..22
                        mol_type = other DNA
                        organism = synthetic construct
SEQUENCE: 10
ttgacatgtc cacaacttgc gt                                           22

SEQ ID NO: 11           moltype = DNA  length = 27
FEATURE                 Location/Qualifiers
source                  1..27
                        mol_type = other DNA
                        organism = synthetic construct
SEQUENCE: 11
cttctttctt tgagagaagt gaggact                                      27

SEQ ID NO: 12           moltype = DNA  length = 22
FEATURE                 Location/Qualifiers
source                  1..22
                        mol_type = other DNA
                        organism = synthetic construct
SEQUENCE: 12
tgccaaaaac cactctgcaa ct                                           22

SEQ ID NO: 13           moltype = DNA  length = 29
FEATURE                 Location/Qualifiers
source                  1..29
                        mol_type = other DNA
                        organism = synthetic construct
SEQUENCE: 13
gtggtttaga ttctttagac acctatcct                                    29

SEQ ID NO: 14           moltype = DNA  length = 24
FEATURE                 Location/Qualifiers
source                  1..24
```

```
                        mol_type = other DNA
                        organism = synthetic construct
SEQUENCE: 14
aggtgtgaac ataaccatcc actg                                            24

SEQ ID NO: 15           moltype = DNA  length = 28
FEATURE                 Location/Qualifiers
source                  1..28
                        mol_type = other DNA
                        organism = synthetic construct
SEQUENCE: 15
actcattctt acctggtgtt tattctgt                                        28

SEQ ID NO: 16           moltype = DNA  length = 22
FEATURE                 Location/Qualifiers
source                  1..22
                        mol_type = other DNA
                        organism = synthetic construct
SEQUENCE: 16
ctggacacat tgagcccaca at                                              22

SEQ ID NO: 17           moltype = DNA  length = 26
FEATURE                 Location/Qualifiers
source                  1..26
                        mol_type = other DNA
                        organism = synthetic construct
SEQUENCE: 17
tgcacatcag tagtcttact ctcagt                                          26

SEQ ID NO: 18           moltype = DNA  length = 22
FEATURE                 Location/Qualifiers
source                  1..22
                        mol_type = other DNA
                        organism = synthetic construct
SEQUENCE: 18
tgtgactctg cagttaaagc cc                                              22

SEQ ID NO: 19           moltype = DNA  length = 22
FEATURE                 Location/Qualifiers
source                  1..22
                        mol_type = other DNA
                        organism = synthetic construct
SEQUENCE: 19
agacggtgac atggtaccac at                                              22

SEQ ID NO: 20           moltype = DNA  length = 22
FEATURE                 Location/Qualifiers
source                  1..22
                        mol_type = other DNA
                        organism = synthetic construct
SEQUENCE: 20
acacgttgta tgtttgcgag ca                                              22

SEQ ID NO: 21           moltype = DNA  length = 22
FEATURE                 Location/Qualifiers
source                  1..22
                        mol_type = other DNA
                        organism = synthetic construct
SEQUENCE: 21
tgattgttac gatggtggct gt                                              22

SEQ ID NO: 22           moltype = DNA  length = 22
FEATURE                 Location/Qualifiers
source                  1..22
                        mol_type = other DNA
                        organism = synthetic construct
SEQUENCE: 22
gtgcaggtaa ttgagcaggg tc                                              22

SEQ ID NO: 23           moltype = DNA  length = 24
FEATURE                 Location/Qualifiers
source                  1..24
                        mol_type = other DNA
                        organism = synthetic construct
SEQUENCE: 23
tgatttgagt gttgtcaatg ccag                                            24

SEQ ID NO: 24           moltype = DNA  length = 22
FEATURE                 Location/Qualifiers
```

```
source                 1..22
                       mol_type = other DNA
                       organism = synthetic construct
SEQUENCE: 24
attagcagca atgtccacac cc                                           22

SEQ ID NO: 25          moltype = DNA  length = 23
FEATURE                Location/Qualifiers
source                 1..23
                       mol_type = other DNA
                       organism = synthetic construct
SEQUENCE: 25
aatgtagcat ttgagctttg ggc                                          23

SEQ ID NO: 26          moltype = DNA  length = 22
FEATURE                Location/Qualifiers
source                 1..22
                       mol_type = other DNA
                       organism = synthetic construct
SEQUENCE: 26
accagctgtc caacctgaag aa                                           22

SEQ ID NO: 27          moltype = DNA  length = 28
FEATURE                Location/Qualifiers
source                 1..28
                       mol_type = other DNA
                       organism = synthetic construct
SEQUENCE: 27
acatcactag gtttcaaact ttacttgc                                     28

SEQ ID NO: 28          moltype = DNA  length = 22
FEATURE                Location/Qualifiers
source                 1..22
                       mol_type = other DNA
                       organism = synthetic construct
SEQUENCE: 28
atgaggtgct gactgaggga ag                                           22

SEQ ID NO: 29          moltype = DNA  length = 25
FEATURE                Location/Qualifiers
source                 1..25
                       mol_type = other DNA
                       organism = synthetic construct
SEQUENCE: 29
gtcagagtgt gtacttggac aatca                                        25

SEQ ID NO: 30          moltype = DNA  length = 23
FEATURE                Location/Qualifiers
source                 1..23
                       mol_type = other DNA
                       organism = synthetic construct
SEQUENCE: 30
actgctactg gaatggtctg tgt                                          23

SEQ ID NO: 31          moltype = DNA  length = 22
FEATURE                Location/Qualifiers
source                 1..22
                       mol_type = other DNA
                       organism = synthetic construct
SEQUENCE: 31
ggtgactcag gttttgctgc at                                           22

SEQ ID NO: 32          moltype = DNA  length = 23
FEATURE                Location/Qualifiers
source                 1..23
                       mol_type = other DNA
                       organism = synthetic construct
SEQUENCE: 32
cgtaaacgga aaagcgaaaa cgt                                          23
```